US008193238B2

(12) United States Patent
Martin et al.

(10) Patent No.: US 8,193,238 B2

(45) Date of Patent: Jun. 5, 2012

(54) INHIBITION OF MICROTUBULE PROTRUSION IN CANCER CELLS

(75) Inventors: Stuart Martin, Severna Park, MD (US); Rebecca Whipple-Bettes, Columbia, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 599 days.

(21) Appl. No.: 12/282,014

(22) PCT Filed: Mar. 8, 2007

(86) PCT No.: PCT/US2007/063566

§ 371 (c)(1), (2), (4) Date: Dec. 18, 2008

(87) PCT Pub. No.: WO2007/104011

PCT Pub. Date: Sep. 13, 2007

(65) Prior Publication Data

US 2009/0137473 A1 May 28, 2009

Related U.S. Application Data

(60) Provisional application No. 60/780,468, filed on Mar. 8, 2006.

(51) Int. Cl.
*A61K 31/335* (2006.01)
*A61K 43/16* (2006.01)
*A61K 31/167* (2006.01)

(52) U.S. Cl. ......................... 514/449; 514/456; 514/626

(58) Field of Classification Search ........................ None
See application file for complete search history.

(56) References Cited

U.S. PATENT DOCUMENTS

| | | | | |
|---|---|---|---|---|
| 5,622,986 | A | 4/1997 | Greenwald et al. | 514/449 |
| 6,114,397 | A | 9/2000 | Flack et al. | |
| 6,239,167 | B1 * | 5/2001 | Bissery | 514/449 |
| 6,391,888 | B1 | 5/2002 | Gleich | |
| 7,300,943 | B2 | 11/2007 | Wager | 514/303 |

FOREIGN PATENT DOCUMENTS

FR 2 766 572 1/1999

OTHER PUBLICATIONS

Momiyama et al. Gan to Kagaku Ryoho, vol. 28, No. 9, pp. 1287-1289 (Abstract attached).*

Murakami et al. Gan to Kagaku Ryoho, 2002, vol. 29, No. 11, pp. 1963-1966 (Abstract attached).*

International Search Report issued Jul. 25, 2008, during the prosecution of International Application No. PCT/US07/63566.

Kao et al., "Concomitant radiation therapy and paclitaxel for unresectable locally advanced breast cancer: results from two consecutive phase I/II trials," Int J Radiat Oncol Biol Phys. Mar. 15, 2005;61(4):1045-53.

Lî et al., "Phase I and pharmacokinetic study of fostriecin given as an intravenous bolus daily for five consecutive days," Invest New Drugs. Apr. 2004;22(2):159-67.

Written Opinion issued Jul. 25, 2008, during the prosecution of International Application No. PCT/US07/63566.

Balzer et al., "Antimitotic chemotherapeutics promote adhesive responses in detached and circulating tumor cells," *Breast Cancer Res. Treat.*, 121(1):65-78, 2010. Epub. Jul. 11, 2009.

Balzer et al., "c-Src differentially regulates the functions of microtentacles and invadopodia," *Oncogene*, 29(48):6402-8, 2010. Epub Oct. 18, 2010.

Cho et al., "Delocalization of gamma-tubulin due to increased solubility in human breast cancer cell lines," *Cancer Biol. Ther.*, 9(1):66-76, 2010. Epub Jan 28, 2010.

Coghlan et al., "Selective small molecule inhibitors of glycogen synthase kinase-3 modulate glycogen metabolism and gene transcription," *Chemistry and Biology*, 7:793-803, 2000.

Contin et al., "Inhibitors of protein phosphatase 1 and 2A decrease the level of tublin carboxypeptidase activity associated with microtubules," *Eur. J. Biochem.*, 270:4921-4929, 2003.

DeBonis et al., "In vitro screening for inhibitors of the human mitotic kinesin Eg5 with antimitotic and antitumor activities," *Molecular Cancer Therapeutics*, 3(9):1079-1090, 2004.

Dokken et al., "Acute elective blycogen synthase kinase-3 inhibition enhances insulin singaling in prediabetic insulin-resistant rat skeletal muscle," *Am. J. Physiol. Endocrinol. Metab.*, 288:E1188-E1194, 2005.

Extended European Search Report, issued in European Patent application No. 07758146.0, dated Jan. 25, 2010.

Ghosh and Altieri, "Activation of p53-dependent apoptosis by acute ablation of glycogen synthase kinase-3-beta in colorectal cancer cells," *Clin. Cancer Res.*, 11912):4580-4588, 2005.

Infante et al., "Detyrosinated (Glu) microtubules are stabilized by an ATP-sensitive plus-end cap," *Journal of Cell Science*, 113:3907-3919, 2000.

Ingber, "Cancer as a disease of epithelial-mesenchymal interactions and extracellular matrix regulation," *Differentiation*, 70:547-560, 2002.

MacAulay et al., "Use of lithium and SB-415286 to expore the role of glycogen synthase kinase-3 in the regulation of glucose transport and glycogen synthase," *Eur. J. Biochem.*, 270:3829-3838, 2003.

Malaguti and Rossini et al., "Recovery of cellular E-cadherin precedes replenishment of estrogen receptor and estrogen-dependent proliferation of breast cancer cells rescued from a death stimulus," *Journal of Cellular Physiology*, 192:171-181, 2002.

Martin, Stuart, Ph.D., "Using functional genomics to identify determinants of breast tumor dormancy and metastasis," University of Maryland—Baltimore School of Medicine Department of Physiology Seminar Series, Nov. 17, 2005.

Martinez et al., "Glycogen synthase kinase 3 (GSK-3) inhibitors as new promising drugs for diabetes, neurodegeneration, cancer, and inflammation," *Medicinal Research Reviews*, 22(4):373-384, 2002.

(Continued)

*Primary Examiner* — James D Anderson

(74) *Attorney, Agent, or Firm* — Fulbright & Jaworski L.L.P.

(57) ABSTRACT

The present invention generally concerns microtubule protrusions in cancer cells, including detached cancer cells, and inhibition of the protrusions. In particular aspects, the inhibition of the protrusions interferes with attachment of the cell to a vessel wall, and in further aspects the cell is killed by forcing it to enter capillaries and be destroyed, for example by shearing. Inhibition by a variety of agents and methods is contemplated.

21 Claims, 40 Drawing Sheets

OTHER PUBLICATIONS

Matrone et al., "Metastatic breast tumors express increased tau, which promotes microtentacle formation and reattachment of detached breast tumor cells," *Oncogene*, 29(22):3217-27, 2010. Epub Mar. 15, 2010.

Matrone et al., "Microtentacles tip the balance of cytoskeletal forces in circulating tumor cells," *Cancer Res.*, 70(20):7737-41, 2010. Epub Oct. 5, 2010.

Miahle et al., "Tubulin detrosination is a frequent occurrence in breast cancers of poor prognosis," *Cancer Research*, 61:5024-2027, 2001.

Mistry et al., "Anti-angiogenesis therapy: targeting vascular endothelial cells by anti-stathmin adenovirus," Database Biosis [online] Biosciences Information Service; Nov. 2003; vol. 102(11); pp. 495-496b. Database accesson No. PREV200400182156 *abstract* & Blood.

Reddig et al., "Clinging to life: cell matrix adhesion and cell survival," *Cancer Metastasis Rev.*, 24:425-439, 2005.

Reed, "Dysregulation of apoptosis in cancer," *J. Clin. Oncol.*, 17(9):2941-2953, 1999.

Rodriguez de la Vega et al., "Nnal-like proteins are active metallocarboxypeptidases of a new and diverse M14 subfamily," *The FASEB Journal*, 20:851-865, 2007.

Shen et al., "Phospholipase D2 stimulates cell protrusion in v-Src-transformed cells," *Biochemical and Biophysical Research Communication*, 293:201-206, 2002.

Sugiura and Berditchevski, "Function of alpha-3-beta-l-tetraspanin protein complexes in tumor cell invasion. Evidence for the role of the complexes in production of matrix metalloproteinase 2 (MMP-2)," *The Journal f Cell Biology*, 146(6):1375-1389, 1999.

Supplementary European Search Report, issued in European Patent application No. 07758146.0, dated Feb. 11, 2010.

Valentijn et al., "Anoikis," *Biochem. Soc. Trans.*, 32:421-425, 2004.

Wang et al., "Mechanical behavior in living cells consistent with the tensegrity model," *Proc. Natl. Acad. Sci USA*, 98:7765-7770, 2001.

Whipple et al., "Detyrosinated microtube protrusions in suspended mammary epithelial cells promote reattachment," *Experimental Cell Research*, 313:1326-1336, 2007.

Whipple et al., "Epithelial-to-mesenchymal transition promotes tublin detyrosination and microtentacles that enhance endothelial engagement," *Cancer Res.*, 70(20):8127-8137, 2010. Epub Oct. 5, 2010.

Whipple et al., "Persistent stress responses in "dormant" breast tumor cells," Poster Session presented at the Membrane Biology Training Grant Retreat. University of Maryland—Baltimore, Nov. 3, 2005.

Whipple et al., "Vimentin filaments support extension of tubulni-based microtentacles in detached breast tumor cells," *Cancer Res.*, 68(14):5678-88, 2008.

Yoon et al., "Local anesthetics inhibit kinesin motility and microtentacle protrusions in human epithelial and breast tumor cells," *Breast Cancer Res. Treat*, Nov. 11, 2010 [Epub ahead of print].

Zhu et al., "Functional analysis of human microtubule-based motor proteins, the kinesins and dyneins, in mitosis/cytokinesis using RNA interference," *Molecular Biology of the Cell*, 16:3187-3199, 2005.

* cited by examiner

Brief:
- Human Cells (10A, MCF7, MDA231, Bt474) attached, treated with LA, or suspended
    - Cells were washed in PBS and suspended cells were centrifuged for 5min at 2000rpm at RT
- Lysis Buffer: RIPA
- Load = 15ug
- Gel Type = 1mm 4-12% Tris-Bis Gel
- Running Buffer = Invitrogen Mes Running Buffer
    - @130V for 2h
- Transfer
    - Semi-Dry @25V for 1h
    - NuPage Transfer Buffer
- ECL expose for 3min Hs578t/Bt474 timecourse for siRNA Vim4 1.23.07

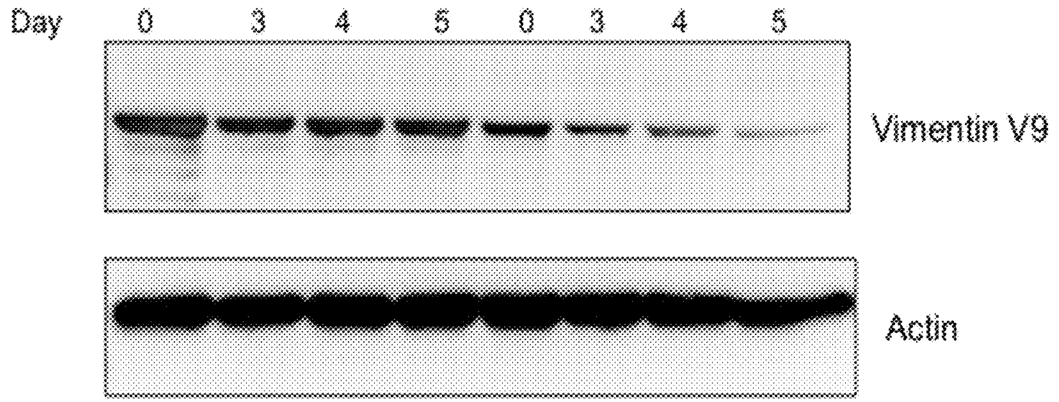

Brief:
Hs578t and Bt474 were split into a 12 well (~40% confluency)
On day 0- cells were transfected with siRNA Vim4 (5nM) with 6ul HiPerfect according to protocol
At Day3, 4 and 5 after transfection, cells were lysed in RIPA buffer with PIC and PMSF
20ug of protein was loaded on 10% gel
5% block @RT for 1h
2.5% overnight with 1:1000 Vimentin V9
Ecl+ to expose
Acetic Acid strip
1:2500 Ms Actin

FIG. 33

SEQUENCE LISTING

```
<160> NUMBER OF SEQ ID NOS: 160

<210> SEQ ID NO 1
<211> LENGTH: 1847
<212> TYPE: DNA
<213> ORGANISM: Human

<400> SEQUENCE: 1

gtccccgcgc cagagacgca gccgcgctcc caccacccac acccaccgcg ccctcgttcg      60
```

cctcttctcc gggagccagt ccgcgccacc gccgccgccc aggccatcgc caccctccgc 120
agccatgtcc accaggtccg tgtcctcgtc ctcctaccgc aggatgttcg gcggcccggg 180
caccgcgagc cggccgagct ccagccggag ctacgtgact acgtccaccc gcacctacag 240
cctgggcagc gcgctgcgcc ccagcaccag ccgcagcctc tacgcctcgt ccccgggcgg 300
cgtgtatgcc acgcgctcct ctgccgtgcg cctgcggagc agcgtgcccg ggtgcggct 360 cctgcaggac tcggtggact tctcgctggc cgacgccatc aacaccgagt tcaagaacac 420
ccgcaccaac gagaaggtgg agctgcagga gctgaatgac cgcttcgcca actacatcga 480
caaggtgcgc ttcctggagc agcagaataa gatcctgctg gccgagctcg agcagctcaa 540
gggccaaggc aagtcgcgcc tgggggacct ctacgaggag gagatgcggg agctgcgccg 600
gcaggtggac cagctaacca acgacaaagc ccgcgtcgag gtggagcgcg acaacctggc 660
cgaggacatc atgcgcctcc gggagaaatt gcaggaggag atgcttcaga gagaggaagc 720
cgaaaacacc ctgcaatctt tcagacagga tgttgacaat gcgtctctgg cacgtcttga 780
ccttgaacgc aaagtggaat ctttgcaaga agagattgcc tttttgaaga aactccacga 840
agaggaaatc caggagctgc aggctcagat tcaggaacag catgtccaaa tcgatgtgga 900
tgtttccaag cctgacctca cggctgccct gcgtgacgta cgtcagcaat atgaaagtgt 960
ggctgccaag aacctgcagg aggcagaaga atggtacaaa tccaagtttg ctgacctctc 1020
tgaggctgcc aaccggaaca atgacgccct gcgccaggca aagcaggagt ccactgagta 1080
ccggagacag gtgcagtccc tcacctgtga agtggatgcc cttaaaggaa ccaatgagtc 1140
cctggaacgc cagatgcgtg aaatggaaga gaactttgcc gttgaagctg ctaactacca 1200
agacactatt ggccgcctgc aggatgagat tcagaatatg aaggaggaaa tggctcgtca 1260
ccttcgtgaa taccaagacc tgctcaatgt taagatggcc cttgacattg agattgccac 1320
ctacaggaag ctgctggaag gcgaggagag caggatttct ctgcctcttc caaacttttc 1380
ctccctgaac ctgagggaaa ctaatctgga ttcactccct ctggttgata cccactcaaa 1440
aaggacactt ctgattaaga cggttgaaac tagagatgga caggttatca acgaaacttc 1500
tcagcatcac gatgaccttg aataaaaatt gcacacactc agtgcagcaa tatattacca 1560
gcaagaataa aaaagaaatc catatcttaa agaaacagct ttcaagtgcc tttctgcagt 1620
ttttcaggag cgcaagatag atttggaata ggaataagct ctagttctta acaaccgaca 1680
ctcctacaag atttagaaaa aagtttacaa cataatctag tttacagaaa aatcttgtgc 1740
tagaatactt tttaaaaggt attttgaata ccattaaaac tgcttttttt tttccagcaa 1800
gtatccaacc aacttggttc tgcttcaata aatctttgga aaaactc 1847

<210> SEQ ID NO 2
<211> LENGTH: 1938
<212> TYPE: DNA
<213> ORGANISM: Human

<400> SEQUENCE: 2
aacggtttcc cctaaaccgc taggagccct caatcggcgg gacagcaggg cgcgtcctct 60
gccactctcg ctccgaggtc cccgcgccag agacgcagcc gcgctcccac cacccacacc 120
caccgcgccc tcgttcgcct cttctccggg agccagtccg cgccaccgcc gccgcccagc 180
ccatcgccac cctccgcagc catgtccacc aggtccgtgt cctcgtcctc ctaccgcagg 240
atgttcggcg gcccgggcac cgcgagccgg ccgagctcca gccggagcta cgtgactacg 300
tccacccgca cctacagcct gggcagcgcg ctgcgcccca gcaccagccg cagcctctac 360

```
gcctcgtccc cgggcggcgt gtatgccacg cgctcctctg ccgtgcgcct gcggagcagc    420
gtgcccgggg tgcggctcct gcaggactcg gtggacttct cgctggccga cgccatcaac    480
accgagttca agaacacccg caccaacgag aaggtggagc tgcaggagct gaatgaccgc    540
ttcgccaact acatcgacaa ggtgcgcttc ctggagcagc agaataagat cctgctggcc    600
gagctcgagc agctcaaggg ccaaggcaag tcgcgcctgg gggacctcta cgaggaggag    660
atgcgggagc tgcgccggca ggtggaccag ctaaccaacg acaaagcccg cgtcgaggtg    720
gagcgcgaca acctggccga ggacatcatg cgcctccggg agaaattgca ggaggagatg    780
cttcagagag aggaagccga aaacaccctg caatctttca gacaggatgt tgacaatgcg    840
tctctggcac gtcttgacct tgaacgcaaa gtggaatctt tgcaagaaga gattgccttt    900
ttgaagaaac tccacgaaga ggaaatccag gagctgcagg ctcagattca ggaacagcat    960
gtccaaatcg atgtggatgt ttccaagcct gacctcacgg ctgccctgcg tgacgtacgt   1020
cagcaatatg aaagtgtggc tgccaagaac ctgcaggagg cagaagaatg gtacaaatcc   1080
aagtttgctg acctctctga ggctgccaac cggaacaatg acgccctgcg ccaggcaaag   1140
caggagtcca ctgagtaccg gagacaggtg cagtccctca cctgtgaagt ggatgccctt   1200
aaaggaacca atgagtccct ggaacgccag atgcgtgaaa tggaagagaa ctttgccgtt   1260
gaagctgcta actaccaaga cactattggc cgcctgcagg atgagattca gaatatgaag   1320
gaggaaatgg ctcgtcacct tcgtgaatac caagacctgc tcaatgttaa gatggccctt   1380
gacattgaga ttgccaccta caggaagctg ctggaaggcg aggagagcag gatttctctg   1440
cctcttccaa acttttcctc cctgaacctg agggaaacta atctggattc actccctctg   1500
gttgataccc actcaaaaag gacacttctg attaagacgg ttgaaactag agatggacag   1560
gttatcaacg aaacttctca gcatcacgat gaccttgaat aaaaattgca cacactcagt   1620
gcagcaatat attaccagca agaataaaaa agaaatccat atcttaaaga aacagctttc   1680
aagtgccttt ctgcagtttt tcaggagcgc aagatagatt tggaatagga ataagctcta   1740
gttcttaaca accgacactc ctacaagatt tagaaaaaag tttacaacat aatctagttt   1800
acagaaaaat cttgtgctag aatacttttt aaaaggtatt ttgaatacca ttaaaactgc   1860
ttttttttt ccagcaagta tccaaccaac ttgtttctgc ttcaataaat ctttggaaaa   1920
actaaaaaaa aaaaaaaa                                                 1938
```

<210> SEQ ID NO 3
<211> LENGTH: 1591
<212> TYPE: DNA
<213> ORGANISM: Human

<400> SEQUENCE: 3

```
gtccccgcgc cagagacgca gccgcgctcc caccacccac acccaccgcg ccctcgttcg     60
cctcttctcc gggagccagt ccgcgccacc gccgccgccc aggccatcgc caccctccgc    120
agccatgtcc accaggtccg tgtcctcgtc ctcctaccgc aggatgttcg gcggcccggg    180
caccgcgagc cggccgagct ccagccggag ctacgtgact acgtccaccc gcacctacag    240
cctgggcagc gcgctgcgcc ccagcaccag ccgcagcctc tacgcctcgt ccccgggcgg    300
cgtgtatgcc acgcgctcct ctgccgtgcg cctgcggagc agcgtgcccg gggtgcggct    360
cctgcaggac tcggtggact tctcgctggc cgacgccatc aacaccgagt tcaagaacac    420
ccgcaccaac gagaaggtgg agctgcagga gctgaatgac cgcttcgcca actacatcga    480
caaggtgcgc ttcctggagc agcagaataa gatcctgctg gccgagctcg agcagctcaa    540
```

-continued

```
gggccaaggc aagtcgcgcc tgggggacct ctacgaggag gagatgcggg agctgcgccg    600

gcaggtggac cagctaacca acgacaaagc ccgcgtcgag gtggagcgcg acaacctggc    660

cgaggacatc atgcgcctcc gggagaaatt gcaggaggag atgcttcaga gagaggaagc    720

cgaaaacacc ctgcaatctt tcagacagga tgttgacaat gcgtctctgg cacgtcttga    780

ccttgaacgc aaagtggaat ctttgcaaga agagattgcc tttttgaaga aactccacga    840

agaggaaatc caggagctgc aggctcagat tcaggaacag catgtccaaa tcgatgtgga    900

tgtttccaag cctgacctca cggctgccct gcgtgacgta cgtcagcaat atgaaagtgt    960

ggctgccaag aacctgcagg aggcagaaga atggtacaaa tccaagtttg ctgacctctc   1020

tgaggctgcc aaccggaaca atgacgccct gcgccaggca aagcaggagt ccactgagta   1080

ccggagacag gtgcagtccc tcacctgtga agtggatgcc cttaaaggaa ccaatgagtc   1140

cctggaacgc cagatgcgtg aaatggaaga gaactttgcc gttgaagctg ctaactacca   1200

agacactatt ggccgcctgc aggatgagat tcagaatatg aaggaggaaa tggctcgtca   1260

ccttcgtgaa taccaagacc tgctcaatgt taagatggcc cttgacattg agattgccac   1320

ctacaggaag ctgctggaag gcgaggagag caggatttct ctgcctcttc caaacttttc   1380

ctccctgaac ctgagggaaa ctaatctgga ttcactccct ctggttgata cccactcaaa   1440

aaggacactt ctgattaaga cggttgaaac tagagatgga caggttatca acgaaacttc   1500

tcagcatcac gatgaccttg aataaaaatt gcacacactc agtgcagcaa tatattacca   1560

gcaaaaaaaa aaaaaaaaaa aaaaaaaaaa a                                  1591
```

<210> SEQ ID NO 4
<211> LENGTH: 1862
<212> TYPE: DNA
<213> ORGANISM: Human

<400> SEQUENCE: 4

```
gtccccgcgc cagagacgca gccgcgctcc caccacccac acccaccgcg ccctcgttcg     60

cctcttctcc gggagccagt ccgcgccacc gccgccgccc aggccatcgc caccctccgc    120

agccatgtcc accaggtccg tgtcctcgtc ctcctaccgc aggatgttcg gcggcccggg    180

caccgcgagc cggccgagct ccagccggag ctacgtgact acgtccaccc gcacctacag    240

cctgggcagc gcgctgcgcc ccagcaccag ccgcagcctc tacgcctcgt ccccgggcgg    300

cgtgtatgcc acgcgctcct ctgccgtgcg cctgcggagc agcgtgcccg gggtgcggct    360

cctgcaggac tcggtggact tctcgctggc cgacgccatc aacaccgagt tcaagaacac    420

ccgcaccaac gagaaggtgg agctgcagga gctgaatgac cgcttcgcca actacatcga    480

caaggtgcgc ttcctggagc agcagaataa gatcctgctg gccgagctcg agcagctcaa    540

gggccaaggc aagtcgcgcc tgggggacct ctacgaggag gagatgcggg agctgcgccg    600

gcaggtggac cagctaacca acgacaaagc ccgcgtcgag gtggagcgcg acaacctggc    660

cgaggacatc atgcgcctcc gggagaaatt gcaggaggag atgcttcaga gagaggaagc    720

cgaaaacacc ctgcaatctt tcagacagga tgttgacaat gcgtctctgg cacgtcttga    780

ccttgaacgc aaagtggaat ctttgcaaga agagattgcc tttttgaaga aactccacga    840

agaggaaatc caggagctgc aggctcagat tcaggaacag catgtccaaa tcgatgtgga    900

tgtttccaag cctgacctca cggctgccct gcgtgacgta cgtcagcaat atgaaagtgt    960

ggctgccaag aacctgcagg aggcagaaga atggtacaaa tccaagtttg ctgacctctc   1020

tgaggctgcc aaccggaaca atgacgccct gcgccaggca aagcaggagt ccactgagta   1080
```

ccggagacag gtgcagtccc tcacctgtga agtggatgcc cttaaaggaa ccaatgagtc 1140
cctggaacgc cagatgcgtg aaatggaaga gaactttgcc gttgaagctg ctaactacca 1200
agacactatt ggccgcctgc aggatgagat tcagaatatg aaggaggaaa tggctcgtca 1260
ccttcgtgaa taccaagacc tgctcaatgt taagatggcc cttgacattg agattgccac 1320
ctacaggaag ctgctggaag gcgaggagag caggatttct ctgcctcttc caaacttttc 1380
ctccctgaac ctgagggaaa ctaatctgga ttcactccct ctggttgata cccactcaaa 1440
aaggacactt ctgattaaga cggttgaaac tagagatgga caggttatca acgaaacttc 1500
tcagcatcac gatgaccttg aataaaaatt gcacacactc agtgcagcaa tatattacca 1560
gcaagaataa aaaagaaatc catatcttaa agaaacagct ttcaagtgcc tttctgcagt 1620
ttttcaggag cgcaagatag atttggaata ggaataagct ctagttctta acaaccgaca 1680
ctcctacaag atttagaaaa aagtttacaa cataatctag tttacagaaa aatcttgtgc 1740
tagaatactt tttaaaaggt attttgaata ccattaaaac tgcttttttt tttccagcaa 1800
gtatccaacc aacttggttc tgcttcaata aatctttgga aaaactcaaa aaaaaaaaaa 1860
aa 1862

<210> SEQ ID NO 5
<211> LENGTH: 1639
<212> TYPE: DNA
<213> ORGANISM: Human

<400> SEQUENCE: 5
atcatctata tgttaaatat ccgtgccgat ctgtcttgaa ggagaaatat atcgcttgtt 60
ttgtttttta tagtatacaa aaggagtgaa aagccaagag gacgaagtct ttttcttttt 120
cttctgtggg agaacttaat gctgcattta tcgttaacct aacaccccaa cataaagaca 180
aaaggaagaa aaggaggaag gaaggaaaag gtgattcgcg aagagagtga tcatgtcagg 240
gcggcccaga accacctcct ttgcggagag ctgcaagccg gtgcagcagc cttcagcttt 300
tggcagcatg aaagttagca gagacaagga cggcagcaag gtgacaacag tggtggcaac 360
tcctgggcag ggtccagaca ggccacaaga agtcagctat acagacacta aagtgattgg 420
aaatggatca tttggtgtgg tatatcaagc caaactttgt gattcaggag aactggtcgc 480
catcaagaaa gtattgcagg acaagagatt taagaatcga gagctccaga tcatgagaaa 540
gctagatcac tgtaacatag tccgattgcg ttatttcttc tactccagtg gtgagaagaa 600
agatgaggtc tatcttaatc tggtgctgga ctatgttccg gaaacagtat acagagttgc 660
cagacactat agtcgagcca aacagacgct ccctgtgatt tatgtcaagt tgtatatgta 720
tcagctgttc cgaagtttag cctatatcca ttcctttgga atctgccatc gggatattaa 780
accgcagaac ctcttgttgg atcctgatac tgctgtatta aaactctgtg actttggaag 840
tgcaaagcag ctggtccgag gagaacccaa tgtttcgtat atctgttctc ggtactatag 900
ggcaccagag ttgatctttg gagccactga ttatacctct agtatagatg tatggtctgc 960
tggctgtgtg ttggctgagc tgttactagg acaaccaata tttccagggg atagtggtgt 1020
ggatcagttg gtagaaataa tcaaggtcct gggaactcca acaagggagc aaatcagaga 1080
aatgaaccca aactacacag aatttaaatt ccctcaaatt aaggcacatc cttggactaa 1140
ggattcgtca ggaacaggac atttcacctc aggagtgcgg gtcttccgac cccgaactcc 1200
accggaggca attgcactgt gtagccgtct gctggagtat acaccaactg cccgactaac 1260
accactggaa gcttgtgcac attcattttt tgatgaatta cgggacccaa atgtcaaact 1320

-continued accaaatggg cgagacacac ctgcactctt caacttcacc actcaagaac tgtcaagtaa 1380
tccacctctg gctaccatcc ttattcctcc tcatgctcgg attcaagcag ctgcttcaac 1440
ccccacaaat gccacagcag cgtcagatgc taatactgga gaccgtggac agaccaataa 1500
tgctgcttct gcatcagctt ccaactccac ctgaacagtc ccgagcagcc agctgcacag 1560
gaaaaaccac cagttacttg agtgtcactc agcaacactg gtcacgtttg gaaagaatat 1620
taaaaaaaaa aaaaaaaaa 1639

<210> SEQ ID NO 6
<211> LENGTH: 2143
<212> TYPE: DNA
<213> ORGANISM: Human

<400> SEQUENCE: 6
ctctttgtac cgcacccccct gaccgcatgg accgtcccgc aggccgctga tgccgcccgc 60
ggcgaggtgg cccggaccgc agtgccccaa gagagctcta atggtaccaa gtgacaggtt 120
ggctttactg tgactcgggg acgccagagc tcctgagaag atgtcagcaa tacaggccgc 180
ctggccatcc ggtacagaat gtattgccaa gtacaacttc cacggcactg ccgagcagga 240
cctgcccttc tgcaaaggag acgtgctcac cattgtggcc gtcaccaagg accccaactg 300
gtacaaagcc aaaaacaagg tgggccgtga gggcatcatc ccagccaact acgtccagaa 360
gcgggagggc gtgaaggcgg gtaccaaact cagcctcatg ccttggttcc acggcaagat 420
cacacgggag caggctgagc ggcttctgta cccgccggag acaggcctgt tcctggtgcg 480
ggagagcacc aactaccccg gagactacac gctgtgcgtg agctgcgacg gcaaggtgga 540
gcactaccgc atcatgtacc atgccagcaa gctcagcatc gacgaggagg tgtactttga 600
gaacctcatg cagctggtgg agcactacac ctcagacgca gatggactct gtacgcgcct 660
cattaaacca aaggtcatgg agggcacagt ggcggcccag gatgagttct accgcagcgg 720
ctgggccctg aacatgaagg agctgaagct gctgcagacc atcgggaagg gggagttcgg 780
agacgtgatg ctgggcgatt accgagggaa caaagtcgcc gtcaagtgca ttaagaacga 840
cgccactgcc caggccttcc tggctgaagc ctcagtcatg acgcaactgc ggcatagcaa 900
cctggtgcag ctcctgggcg tgatcgtgga ggagaagggc gggctctaca tcgtcactga 960
gtacatggcc aaggggagcc ttgtggacta cctgcggtct aggggtcggt cagtgctggg 1020
cggagactgt ctcctcaagt tctcgctaga tgtctgcgag gccatggaat acctggaggg 1080
caacaatttc gtgcatcgag acctggctgc ccgcaatgtg ctggtgtctg aggacaacgt 1140
ggccaaggtc agcgactttg gtctcaccaa ggaggcgtcc agcacccagg acacgggcaa 1200
gctgccagtc aagtggacag cccctgaggc cctgagagag aagaaattct ccactaagtc 1260
tgacgtgtgg agtttcggaa tccttctctg ggaaatctac tcctttgggc gagtgcctta 1320
tccaagaatt cccctgaagg acgtcgtccc tcgggtggag aagggctaca agatggatgc 1380
ccccgacggc tgcccgcccg cagtctatga agtcatgaag aactgctggc acctggacgc 1440
cgccatgcgg ccctccttcc tacagctccg agagcagctt gagcacatca aaacccacga 1500
gctgcacctg tgacggctgg cctccgcctg ggtcatgggc ctgtggggac tgaacctgga 1560
agatcatgga cctggtgccc ctgctcactg ggcccgagcc tgaactgagc cccagcgggc 1620
tggcgggcct ttttcctgcg tcccagcctg cacccctccg gccccgtctc tcttggaccc 1680
acctgtgggg cctggggagc ccactgaggg gccagggagg aaggaggcca cggagcggga 1740
ggcagcgccc caccacgtcg ggcttccctg gcctcccgcc actcgccttc ttagagtttt 1800

-continued

```
attcctttcc tttttgaga tttttttcc gtgtgtttat tttttattat ttttcaagat   1860

aaggagaaag aaagtaccca gcaaatgggc attttacaag aagtacgaat cttatttttc   1920

ctgtcctgcc cgtgagggtg gggggaccg ggcccctctc tagggacccc tcgccccagc   1980

ctcattcccc attctgtgtc ccatgtcccg tgtctcctcg gtcgccccgt gtttgcgctt   2040

gaccatgttg cactgtttgc atgcgcccga ggcagacgtc tgtcaggggc ttggatttcg   2100

tgtgccgctg ccacccgccc acccgccttg tgagatggaa tcg                    2143
```

<210> SEQ ID NO 7
<211> LENGTH: 2000
<212> TYPE: DNA
<213> ORGANISM: Human

<400> SEQUENCE: 7

```
cagcgcaggt ctgaggagct gagaagggag gcttacgtga agggaattta gataatgggc     60

tgtgtgcaat gtaaggataa agaagcaaca aaactgacgg aggagaggga cggcagcctg    120

aaccagagct ctgggtaccg ctatggcaca gaccccaccc ctcagcacta ccccagcttc    180

ggtgtgacct ccatccccaa ctacaacaac ttccacgcag ccgggggcca aggactcacc    240

gtctttggag gtgtgaactc ttcgtctcat acggggacct tgcgtacgag aggaggaaca    300

ggagtgacac tctttgtggc cctttatgac tatgaagcac ggacagaaga tgacctgagt    360

tttcacaaag gagaaaaatt tcaaatattg aacagctcgg aaggagattg gtgggaagcc    420

cgctccttga caactggaga gacaggttac attcccagca attatgtggc tccagttgac    480

tctatccagg cagaagagtg gtactttgga aaacttggcc gaaaagatgc tgagcgacag    540

ctattgtcct ttggaaaccc aagaggtacc tttcttatcc gcgagagtga aaccaccaaa    600

ggtgcctatt cactttctat ccgtgattgg gatgatatga aaggagacca tgtcaaacat    660

tataaaattc gcaaacttga caatggtgga tactacatta ccacccgggc ccagtttgaa    720

acacttcagc agcttgtaca acattactca ggtacctgga atggaaacac aaaagtagcc    780

ataaagactc ttaaaccagg cacaatgtcc cccgaatcat tccttgagga agcgcagatc    840

atgaagaagc tgaagcacga caagctggtc cagctctatg cagtggtgtc tgaggagccc    900

atctacatcg tcaccgagta tatgaacaaa ggaagtttac tggatttctt aaaagatgga    960

gaaggaagag ctctgaaatt accaaatctt gtggacatgg cagcacaggt ggctgcagga   1020

atggcttaca tcgagcgcat gaattatatc catagagatc tgcgatcagc aaacattcta   1080

gtggggaatg gactcatatg caagattgct gacttcggat tggcccgatt gatagaagac   1140

aatgagtaca cagcaagaca aggtgcaaag ttccccatca agtggacggc ccccgaggca   1200

gccctgtacg ggaggttcac aatcaagtct gacgtgtggt cttttggaat cttactcaca   1260

gagctggtca ccaaaggaag agtgccatac ccaggcatga acaaccggga ggtgctggag   1320

caggtggagc gaggctacag gatgccctgc ccgcaggact gccccatctc tctgcatgag   1380

ctcatgatcc actgctggaa aaaggaccct gaagaacgcc ccacttttga gtacttgcag   1440

agcttcctgg aagactactt taccgcgaca gagccccagt accaacctgg tgaaaacctg   1500

taaggcccgg gtctgcggag agaggccttg tcccagaggc tgccccaccc ctccccatta   1560

gctttcaatt ccgtagccag ctgctcccca gcagcggaac cgcccaggat cagattgcat   1620

gtgactctga agctgacgaa cttccatggc cctcattaat gacacttgtc cccaaatccg   1680

aacctcctct gtgaagcatt cgagacagaa ccttgttatt tctcagactt tggaaaatgc   1740

attgtatcga tgttatgtaa aaggccaaac ctctgttcag tgtaaatagt tactccagtg   1800
```

ccaacaatcc tagtgctttc cttttttaaa aatgcaaatc ctatgtgatt ttaactctgt 1860
cttcacctga ttcaactaaa aaaaaaaaag tattattttc caaaagtggc ctctttgtct 1920
aaaacaataa aattttttttt catgttttaa caaaaaccaa aaaaaaaaaa aaaaaaaaaa 1980
aaaaaaaaaa aaaaaaaaaa 2000

<210> SEQ ID NO 8
<211> LENGTH: 2073
<212> TYPE: DNA
<213> ORGANISM: Human

<400> SEQUENCE: 8
gaatttagat aatgggctgt gtgcaatgta aggataaaga agcaacaaaa ctgacggagg 60
agagggacgg cagcctgaac cagagctctg ggtaccgcta tggcacagac cccacccctc 120
agcactaccc cagcttcggt gtgacctcca tccccaacta caacaacttc cacgcagccg 180
ggggccaagg actcaccgtc tttggaggtg tgaactcttc gtctcatacg ggaccttgc 240 gtacgagagg aggaacagga gtgacactct ttgtggccct ttatgactat gaagcacgga 300
cagaagatga cctgagtttt cacaaaggag aaaaatttca aatattgaac agctcggaag 360
gagattggtg ggaagcccgc tccttgacaa ctggagagac aggttacatt cccagcaatt 420
atgtggctcc agttgactct atccaggcag aagagtggta ctttggaaaa cttggccgaa 480
aagatgctga gcgacagcta ttgtcctttg gaaacccaag aggtaccttt cttatccgcg 540
agagtgaaac caccaaaggt gcctattcac tttctatccg tgattgggat gatatgaaag 600
gagaccatgt caaacattat aaaattcgca aacttgacaa tggtggatac tacattacca 660
cccgggccca gtttgaaaca cttcagcagc ttgtacaaca ttactcagag aaagctgatg 720
gtttgtgttt taacttaact gtgattgcat cgagttgtac ccccacaaact tctggattgg 780 ctaaagatgc ttgggaagtt gcacgtcgtt cgttgtgtct ggagaagaag ctgggtcagg 840
ggtgtttcgc tgaagtgtgg cttggtacct ggaatggaaa cacaaaagta gccataaaga 900
ctcttaaacc aggcacaatg tcccccgaat cattccttga ggaagcgcag atcatgaaga 960
agctgaagca cgacaagctg gtccagctct atgcagtggt gtctgaggag cccatctaca 1020
tcgtcaccga gtatatgaac aaaggaagtt tactggattt cttaaaagat ggagaaggaa 1080
gagctctgaa attaccaaat cttgtggaca tggcagcaca ggtggctgca ggaatggctt 1140
acatcgagcg catgaattat atccatagag atctgcgatc agcaaacatt ctagtgggga 1200
atggactcat atgcaagatt gctgacttcg gattggcccg attgatagaa gacaatgagt 1260
acacagcaag acaaggtgca aagttcccca tcaagtggac ggcccccgag gcagccctgt 1320
acgggaggtt cacaatcaag tctgacgtgt ggtcttttgg aatcttactc acagagctgg 1380
tcaccaaagg aagagtgcca tacccaggca tgaacaaccg ggaggtgctg gagcaggtgg 1440
agcgaggcta caggatgccc tgcccgcagg actgccccat ctctctgcat gagctcatga 1500
tccactgctg gaaaaaggac cctgaagaac gccccacttt tgagtacttg cagagcttcc 1560
tggaagacta ctttaccgcg acagagcccc agtaccaacc tggtgaaaac ctgtaaggcc 1620
cgggtctgcg gagagaggcc ttgtcccaga ggctgcccca cccctcccca ttagctttca 1680
attccgtagc cagctgctcc ccagcagcgg aaccgcccag gatcagattg catgtgactc 1740
tgaagctgac gaacttccat ggccctcatt aatgacactt gtccccaaat ccgaacctcc 1800
tctgtgaagc attcgagaca gaaccttgtt atttctcaga ctttggaaaa tgcattgtat 1860
cgatgttatg taaaaggcca aacctctgtt cagtgtaaat agttactcca gtgccaacaa 1920

-continued

```
tcctagtgct ttccttttttt aaaaatgcaa atcctatgtg attttaactc tgtcttcacc   1980

tgattcaact aaaaaaaaaa aagtattatt ttccaaaagt ggcctctttg tctaaaacaa   2040

taaaattttt tttcatgttt taacaaaaac caa                                 2073
```

<210> SEQ ID NO 9
<211> LENGTH: 2650
<212> TYPE: DNA
<213> ORGANISM: Human

<400> SEQUENCE: 9

```
gccgcgctgg tggcggcggc gcgtcgttgc agttgcgcca tctgtcagga gcggagccgg     60

cgaggagggg gctgccgcgg gcgaggagga ggggtcgccg cgagccgaag gccttcgaga    120

cccgcccgcc gcccggcggc gagagtagag gcgaggttgt tgtgcgagcg gcgcgtcctc    180

tcccgcccgg gcgcgccgcg cttctcccag cgcaccgagg accgcccggg cgcacacaaa    240

gccgccgccc gcgccgcacc gcccggcggc cgccgcccgc gccagggagg gattcggccg    300

ccgggccggg gacaccccgg cgccgccccc tcggtgctct cggaaggccc accggctccc    360

gggcccgccg gggacccccc ggagccgcct cggccgcgcc ggaggagggc ggggagagga    420

ccatgtgagt gggctccgga gcctcagcgc cgcgcagttt ttttgaagaa gcaggatgct    480

gatctaaacg tggaaaaaga ccagtcctgc ctctgttgta gaagacatgt ggtgtatata    540

aagtttgtga tcgttggcgg acattttgga atttagataa tgggctgtgt gcaatgtaag    600

gataaagaag caacaaaact gacggaggag agggacggca gcctgaacca gagctctggg    660

taccgctatg gcacagaccc caccccctcag cactacccca gcttcggtgt gacctccatc    720

cccaactaca acaacttcca cgcagccggg ggccaaggac tcaccgtctt tggaggtgtg    780

aactcttcgt ctcatacggg gaccttgcgt acgagaggag gaacaggagt gacactcttt    840

gtggcccttt atgactatga agcacggaca gaagatgacc tgagttttca caaaggagaa    900

aaatttcaaa tattgaacag ctcggaagga gattggtggg aagcccgctc cttgacaact    960

ggagagacag gttacattcc cagcaattat gtggctccag ttgactctat ccaggcagaa   1020

gagtggtact ttggaaaact tggccgaaaa gatgctgagc gacagctatt gtcctttgga   1080

aacccaagag gtacctttct tatccgcgag agtgaaacca ccaaaggtgc ctattcactt   1140

tctatccgtg attgggatga tatgaaagga gaccatgtca aacattataa aattcgcaaa   1200

cttgacaatg gtggatacta cattaccacc cgggcccagt ttgaaacact tcagcagctt   1260

gtacaacatt actcagagag agctgcaggt ctctgctgcc gcctagtagt tccctgtcac   1320

aaagggatgc caaggcttac cgatctgtct gtcaaaacca aagatgtctg ggaaatccct   1380

cgagaatccc tgcagttgat caagagactg ggaaatgggc agtttgggga agtatggatg   1440

ggtacctgga atggaaacac aaaagtagcc ataaagactc ttaaaccagg cacaatgtcc   1500

cccgaatcat tccttgagga agcgcagatc atgaagaagc tgaagcacga caagctggtc   1560

cagctctatg cagtggtgtc tgaggagccc atctacatcg tcaccgagta tatgaacaaa   1620

ggaagtttac tggatttctt aaaagatgga gaaggaagag ctctgaaatt accaaatctt   1680

gtggacatgg cagcacaggt ggctgcagga atggcttaca tcgagcgcat gaattatatc   1740

catagagatc tgcgatcagc aaacattcta gtggggaatg gactcatatg caagattgct   1800

gacttcggat tggcccgatt gatagaagac aatgagtaca cagcaagaca aggtgcaaag   1860

ttccccatca agtggacggc ccccgaggca gccctgtacg ggaggttcac aatcaagtct   1920

gacgtgtggt cttttggaat cttactcaca gagctggtca ccaaaggaag agtgccatac   1980
```

ccaggcatga acaaccggga ggtgctggag caggtggagc gaggctacag gatgccctgc 2040
ccgcaggact gccccatctc tctgcatgag ctcatgatcc actgctggaa aaaggaccct 2100
gaagaacgcc ccacttttga gtacttgcag agcttcctgg aagactactt taccgcgaca 2160
gagccccagt accaacctgg tgaaaacctg taaggcccgg gtctgcggag agaggccttg 2220
tcccagaggc tgccccaccc ctccccatta gctttcaatt ccgtagccag ctgctcccca 2280
gcagcggaac cgcccaggat cagattgcat gtgactctga agctgacgaa cttccatggc 2340
cctcattaat gacacttgtc cccaaatccg aacctcctct gtgaagcatt cgagacagaa 2400
ccttgttatt tctcagactt tggaaaatgc attgtatcga tgttatgtaa aaggccaaac 2460
ctctgttcag tgtaaatagt tactccagtg ccaacaatcc tagtgctttc ctttttttaaa 2520 aatgcaaatc ctatgtgatt ttaactctgt cttcacctga ttcaactaaa aaaaaaaaag 2580
tattattttc caaaagtggc ctctttgtct aaaacaataa aatttttttt catgttttaa 2640
caaaaaccaa 2650

<210> SEQ ID NO 10
<211> LENGTH: 2950
<212> TYPE: DNA
<213> ORGANISM: Human

<400> SEQUENCE: 10
gtcacaccct cgaataatga cgcataccta tcctactgtt actgatcacc tagtaataat 60
cttgtagttc acattactca tttttcacca aattcttttg gtgaaggacg cttcagaaac 120
ggccatcact gaagagcaga cccgtttggg ttctccacgc attctagact cccgaagagc 180
tcatgttttt tggctagacc tatgaccatt ttcgctagac ttcactgcac gttttctcaa 240
gtatcttctt tgtccctaat gtgtgacacc tcatcatgga cacgctactt tagctaaggc 300
atgaccagca atgaacagta gtaagatatg tgctgattag aaggctcact tgtgcagtgt 360
ggaggataac cagtgcctta caaaatgggg tttgggagtg acctgaagaa ttcacatgaa 420
gcagtgttaa aattgcaaga ctgggaatta cggttactgg aaacagtaaa gaaatttatg 480
gccctgagaa taaaaagtga taaagaatat gcatctactt tacagaacct ttgtaatcaa 540
gttgataagg aaagtactgt ccaaatgaat tatgtcagca acgtatccaa gtcttggcta 600
cttatgattc agcagacaga acaacttagt aggataatga agacacatgc agaggacttg 660
aactctggac ctttacacag gctcaccatg atgattaagg acaagcagca ggtgaagaaa 720
agttacatag gtgttcatca gcagatagag gcagagatga tcaaggttac caaaacagaa 780
ttggagaagt taaaatgcag ctatagacaa ttaataaaag aaatgaattc tgccaaagag 840
aaatataaag aagctttagc taaagggaag gaaactgaaa aggccaagga acgatacgac 900
aaagccacaa tgaaacttca tatgttgcac aatcagtatg tattggcgtt gaaaggggca 960
cagctccatc agaatcagta ttatgatatc acacttcccc tgcttctgga ctccttacaa 1020
aagatgcaag aagaaatgat aaaagcactc aaaggtatat ttgatgaata cagccagata 1080
accagtcttg tcacagagga aatagtgaat gtccataaag agattcaaat gtcggttgaa 1140
cagatagatc ctagtacaga atacaataat ttcatagatg ttcacagaac aacggctgct 1200
aaagaacaag aaatagagtt tgatacttcc ttactggaag aaaatgaaaa tcttcaggca 1260
aatgagatca tgtggaataa cttaacagca gaaagtttgc aagtaatgtt gaaaacgtta 1320
gcggaagaac ttatgcaaac acagcagatg cttttaaaca aggaggaggc tgttttggag 1380
ttagagaaga gaattgaaga atcttctgaa acttgtgaga agaagtctga tattgtgctt 1440
ctgctaagcc aaaaacaggc acttgaagaa ctgaaacagt cagtccagca gctgagatgc 1500
actgaagcaa agttttcagc acagaaggaa ttactagagc aaaaagtgca agaaaatgat 1560
gggaaagagc cacctccagt agtaaattat gaagaagatg cacgatcagt tacatctatg 1620
gaaagaaagg agaggctatc caaatttgaa tctattcgtc attcaattgc tggaataatt 1680
aggtctccaa aatctgcact gggctcttca gcactttctg atatgatctc catcagtgag 1740
aagcctttgg cagaacagga ctggtaccat ggtgcaattc ccagaataga agctcaagaa 1800
ctgttaaaaa aacaaggaga ctttttggtg cgagagagtc atgggaaacc tggtgaatat 1860
gtcctttctg tatattctga tggacagagg agacatttta tcatacaata tgttgataac 1920
atgtatcgat tcgagggcac tgggttttca aacattcctc aacttataga tcatcactat 1980
acaacaaaac aggtcatcac taagaaatca ggtgtagttc tgctgaatcc tattcctaag 2040
gacaagaaat ggattctcag tcatgaagat gtcatattgg gagaattact gggcaaggga 2100
aattttggtg aagtatataa gggcacatta aaggataaaa cttctgttgc tgttaaaaca 2160
tgtaaagaag atcttcctca ggaattgaaa ataaaatttt tacaagaagc caaaattctc 2220
aagcaatatg atcatcccaa tattgtcaaa cttataggag tttgcacaca aagacagcct 2280
gtctacatca ttatggaact ggtttcagga ggtgatttcc tcacctttct gagaaggaag 2340
aaggatgaac taaaactcaa acagttagtg aaattttcat tagacgctgc tgctggtatg 2400
ttgtatctcg agagtaaaaa ctgtatacac agggaccttg ctgcaagaaa ctgcctggta 2460
ggtgaaaata atgttctgaa aatcagtgac tttggaatgt ctcgtcaaga ggatggtgga 2520
gtgtattcat cttctggctt aaagcagatt cccattaaat ggacagcacc ggaagctctt 2580
aattatggga gatacagttc agagagtgac gtgtggagct ttggcatcct tctctgggag 2640
accttcagct taggggtttg tccgtaccct ggaatgacaa atcagcaagc aagagagcaa 2700
gtagaaagag gataccggat gtcagctccc cagcactgtc cagaggatat ttccaaaatc 2760
atgatgaagt gttgggatta taaacctgaa aatcgcccta agttcagtga acttcagaaa 2820
gagctcacta tcatcaagag aaaactcaca tagtgacagg atggcgccaa actcagcctt 2880
caggactctg tcctccagca gagtaacatt attgttctca ttaacaatga atttatacca 2940
cattaccttc 2950

<210> SEQ ID NO 11
<211> LENGTH: 2118
<212> TYPE: DNA
<213> ORGANISM: Human

<400> SEQUENCE: 11
gtgtgaattt acttgtagcc tgagggctca gagggagcac cggtttggag ctgggacccc 60
ctattttagc ttttctgtgg ctggtgaatg gggatcccag gatctcacaa tctcagggac 120
catgggctgt ggctgcagct cacacccgga agatgactgg atggaaaaca tcgatgtgtg 180
tgagaactgc cattatccca tagtcccact ggatggcaag ggcacgctgc tcatccgaaa 240
tggctctgag gtgcgggacc cactggttac ctacgaaggc tccaatccgc cggcttcccc 300
actgcaagac aacctggtta tcgctctgca cagctatgag ccctctcacg acggagatct 360
gggctttgag aagggggaac agctccgcat cctggagcag agcggcgagt ggtggaaggc 420
gcagtccctg accacgggcc aggaaggctt catccccttc aattttgtgg ccaaagcgaa 480
cagcctggag cccgaaccct ggttcttcaa gaacctgagc cgcaaggacg cggagcggca 540
gctcctggcg cccgggaaca ctcacggctc cttcctcatc cgggagagcg agagcaccgc 600

```
gggatcgttt tcactgtcgg tccgggactt cgaccagaac cagggagagg tggtgaaaca    660
ttacaagatc cgtaatctgg acaacggtgg cttctacatc tcccctcgaa tcacttttcc    720
cggcctgcat gaactggtcc gccattacac caatgcttca gatgggctgt gcacacggtt    780
gagccgcccc tgccagaccc agaagcccca gaagccgtgg tgggaggacg agtgggaggt    840
tcccagggag acgctgaagc tggtggagcg gctgggggct ggacagttcg gggaggtgtg    900
gatggggtac tacaacgggc acacgaaggt ggcggtgaag agcctgaagc agggcagcat    960
gtccccggac gccttcctgg ccgaggccaa cctcatgaag cagctgcaac accagcggct   1020
ggttcggctc tacgctgtgg tcacccagga gcccatctac atcatcactg aatacatgga   1080
gaatgggagt ctagtggatt ttctcaagac cccttcaggc atcaagttga ccatcaacaa   1140
actcctggac atggcagccc aaattgcaga aggcatggca ttcattgaag agcggaatta   1200
tattcatcgt gaccttcggg ctgccaacat tctggtgtct gacaccctga gctgcaagat   1260
tgcagacttt ggcctagcac gcctcattga ggacaacgag tacacagcca gggagggggc   1320
caagtttccc attaagtgga cagcgccaga agccattaac tacgggacat tcaccatcaa   1380
gtcagatgtg tggtcttttg ggatcctgct gacggaaatt gtcacccacg gccgcatccc   1440
ttacccaggg atgaccaacc cggaggtgat tcagaacctg gagcgaggct accgcatggt   1500
gcgccctgac aactgtccag aggagctgta ccaactcatg aggctgtgct ggaaggagcg   1560
cccagaggac cggcccacct ttgactacct gcgcagtgtg ctggaggact tcttcacggc   1620
cacagagggc cagtaccagc ctcagccttg agaggccttg agaggccctg gggttctccc   1680
cctttctctc cagcctgact tggggagatg gagttcttgt gccatagtca catggcctat   1740
gcacatatgg actctgcaca tgaatcccac ccacatgtga cacatatgca ccttgtgtct   1800
gtacacgtgt cctgtagttg cgtggactct gcacatgtct tgtacatgtg tagcctgtgc   1860
atgtatgtct tggacactgt acaaggtacc cctttctggc tctcccattt cctgagacca   1920
cagagagagg ggagaagcct gggattgaca gaagcttctg cccacctact tttctttcct   1980
cagatcatcc agaagttcct caagggccag gactttatct aatacctctg tgtgctcctc   2040
cttggtgcct ggcctggcac acatcaggag ttcaataaat gtctgttgat gactgttgta   2100
aaaaaaaaaa aaaaaaaa                                                 2118
```

<210> SEQ ID NO 12
<211> LENGTH: 2135
<212> TYPE: DNA
<213> ORGANISM: Human

<400> SEQUENCE: 12

```
aagtcagggt gggacgtggg cgcggggaga caggtggtgg ctacgacggc gaagggagct     60
gagactgtcc aggcagccag gttaggccag gaggaccatg tgaatggggc cagagggctc    120
ccgggctggg cagggaccat gggctgtggc tgcagctcac acccggaaga tgactggatg    180
gaaaacatcg atgtgtgtga gaactgccat tatcccatag tcccactgga tggcaagggc    240
acgctgctca tccgaaatgg ctctgaggtg cgggacccac tggttaccta cgaaggctcc    300
aatccgccgg cttccccact gcaagacaac ctggttatcg ctctgcacag ctatgagccc    360
tctcacgacg gagatctggg ctttgagaag gggggaacagc tccgcatcct ggagcagagc    420
ggcgagtggt ggaaggcgca gtccctgacc acgggccagg aaggcttcat ccccttcaat    480
tttgtggcca aagcgaacag cctggagccc gaaccctggt tcttcaagaa cctgagccgc    540
aaggacgcgg agcggcagct cctggcgccc gggaacactc acggctcctt cctcatccgg    600
```

```
gagagcgaga gcaccgcggg atcgttttca ctgtcggtcc gggacttcga ccagaaccag    660
ggagaggtgg tgaaacatta caagatccgt aatctggaca acggtggctt ctacatctcc    720
cctcgaatca cttttcccgg cctgcatgaa ctggtccgcc attacaccaa tgcttcagat    780
gggctgtgca cacggttgag ccgcccctgc cagacccaga agccccagaa gccgtggtgg    840
gaggacgagt gggaggttcc cagggagacg ctgaagctgg tggagcggct gggggctgga    900
cagttcgggg aggtgtggat ggggtactac aacgggcaca cgaaggtggc ggtgaagagc    960
ctgaagcagg gcagcatgtc cccggacgcc ttcctggccg aggccaacct catgaagcag   1020
ctgcaacacc agcggctggt tcggctctac gctgtggtca cccaggagcc catctacatc   1080
atcactgaat acatggagaa tgggagtcta gtggattttc tcaagacccc ttcaggcatc   1140
aagttgacca tcaacaaact cctggacatg gcagcccaaa ttgcagaagg catggcattc   1200
attgaagagc ggaattatat tcatcgtgac cttcgggctg ccaacattct ggtgtctgac   1260
accctgagct gcaagattgc agactttggc ctagcacgcc tcattgagga caacgagtac   1320
acagccaggg agggggccaa gtttcccatt aagtggacag cgccagaagc cattaactac   1380
gggacattca ccatcaagtc agatgtgtgg tcttttggga tcctgctgac ggaaattgtc   1440
acccacggcc gcatccctta cccagggatg accaacccgg aggtgattca gaacctggag   1500
cgaggctacc gcatggtgcg ccctgacaac tgtccagagg agctgtacca actcatgagg   1560
ctgtgctgga aggagcgccc agaggaccgg cccacctttg actacctgcg cagtgtgctg   1620
gaggacttct tcacggccac agagggccag taccagcctc agccttgaga ggccttgaga   1680
ggccctgggg ttctccccct ttctctccag cctgacttgg ggagatggag ttcttgtgcc   1740
atagtcacat ggcctatgca catatggact ctgcacatga atcccaccca catgtgacac   1800
atatgcacct tgtgtctgta cacgtgtcct gtagttgcgt ggactctgca catgtcttgt   1860
acatgtgtag cctgtgcatg tatgtcttgg acactgtaca aggtacccct ttctggctct   1920
cccatttcct gagaccacag agagagggga gaagcctggg attgacagaa gcttctgccc   1980
acctactttt ctttcctcag atcatccaga agttcctcaa gggccaggac tttatctaat   2040
acctctgtgt gctcctcctt ggtgcctggc ctggcacaca tcaggagttc aataaatgtc   2100
tgttgatgac tgttgtaaaa aaaaaaaaaa aaaaa                              2135
```

<210> SEQ ID NO 13
<211> LENGTH: 4685
<212> TYPE: DNA
<213> ORGANISM: Human

<400> SEQUENCE: 13

```
ggaggaggtg gagagtgagg ccgaggcgtg gggagcccgg gaactccctc ctcctgaagt     60
aacgcgtccc gggccggctc tgccgtcgtt gctgccgccg ggcgccccgg gacgaggagg    120
tggaggaggg agagggcccg cgggcctcgc ctccgccctc cgccacctcg agctgcggta    180
gcagcgactc atgagagcgc ggccggagga cagatttgat aatgggctgc attaaaagta    240
aagaaaacaa aagtccagcc attaaataca gacctgaaaa tactccagag cctgtcagta    300
caagtgtgag ccattatgga gcagaaccca ctacagtgtc accatgtccg tcatcttcag    360
caaagggaac agcagttaat ttcagcagtc tttccatgac accatttgga ggatcctcag    420
gggtaacgcc ttttggaggt gcatcttcct cattttcagt ggtgccaagt tcatatcctg    480
ctggtttaac aggtggtgtt actatatttg tggccttata tgattatgaa gctagaacta    540
cagaagacct ttcatttaag aagggtgaaa gatttcaaat aattaacaat acggaaggag    600
```

-continued

```
attggtggga agcaagatca atcgctacag gaaagaatgg ttatatcccg agcaattatg    660
tagcgcctgc agattccatt caggcagaag aatggtattt tggcaaaatg gggagaaaag    720
atgctgaaag attacttttg aatcctggaa atcaacgagg tattttctta gtaagagaga    780
gtgaaacaac taaaggtgct tattcccttt ctattcgtga ttgggatgag ataaggggtg    840
acaatgtgaa acactacaaa attaggaaac ttgacaatgg tggatactat atcacaacca    900
gagcacaatt tgatactctg cagaaattgg tgaaacacta cacagaacat gctgatggtt    960
tatgccacaa gttgacaact gtgtgtccaa ctgtgaaacc tcagactcaa ggtctagcaa   1020
aagatgcttg ggaaatccct cgagaatctt tgcgactaga ggttaaacta ggacaaggat   1080
gtttcggcga agtgtggatg ggaacatgga atggaaccac gaaagtagca atcaaaacac   1140
taaaaccagg tacaatgatg ccagaagctt tccttcaaga agctcagata atgaaaaaat   1200
taagacatga taaacttgtt ccactatatg ctgttgtttc tgaagaacca atttacattg   1260
tcactgaatt tatgtcaaaa ggaagcttat tagatttcct taaggaagga gatggaaagt   1320
atttgaagct tccacagctg gttgatatgg ctgctcagat tgctgatggt atggcatata   1380
ttgaaagaat gaactatatt caccgagatc ttcgggctgc taatattctt gtaggagaaa   1440
atcttgtgtg caaaatagca gactttggtt tagcaaggtt aattgaagac aatgaataca   1500
cagcaagaca aggtgcaaaa tttccaatca aatggacagc tcctgaagct gcactgtatg   1560
gtcggtttac aataaagtct gatgtctggt catttggaat tctgcaaaca gaactagtaa   1620
caaagggccg agtgccatat ccaggtatgg tgaaccgtga agtactagaa caagtggagc   1680
gaggatacag gatgccgtgc cctcagggct gtccagaatc cctccatgaa ttgatgaatc   1740
tgtgttggaa gaaggaccct gatgaaagac caacatttga atatattcag tccttcttgg   1800
aagactactt cactgctaca gagccacagt accagccagg agaaaattta taattcaagt   1860
agcctatttt atatgcacaa atctgccaaa atataaagaa cttgtgtaga ttttctacag   1920
gaatcaaaag aagaaaatct tctttactct gcatgttttt aatggtaaac tggaatccca   1980
gatatggttg cacaaaacca ctttttttc cccaagtatt aaactctaat gtaccaatga    2040
tgaatttatc agcgtatttc agggtccaaa caaaatagag ctaagatact gatgacagtg   2100
tgggtgacag catggtaatg aaggacagtg aggctcctgc ttatttataa atcatttcct   2160
ttcttttttt ccccaaagtc agaattgctc aaagaaaatt atttattgtt acagataaaa   2220
cttgagagat aaaaagctat accataataa aatctaaaat taaggaatat catgggacca   2280
aataattcca ttccagtttt ttaaagtttc ttgcatttat tattctcaaa agtttttct    2340
aagttaaaca gtcagtatgc aatcttaata tatgctttct tttgcatgga catgggccag   2400
gtttttcaaa aggaatataa acaggatctc aaacttgatt aaatgttaga ccacagaagt   2460
ggaatttgaa agtataatgc agtacattaa tattcatgtt catggaactg aaagaataag   2520
aactttttca cttcagtcct tttctgaaga gtttgactta gaataatgaa ggtaactaga   2580
aagtgagtta atcttgtatg aggttgcatt gattttttaa ggcaatatat aattgaaact   2640
actgtccaat caaaggggaa atgttttgat ctttagatag catgcaaagt aagacccagc   2700
attttaaaag cccttttaa aaactagact tcgtactgtg agtattgctt atatgtcctt    2760
atggggatgg gtgccacaaa tagaaaatat gaccagatca gggacttgaa tgcacttttg   2820
ctcatggtga atatagatga acagagagga aaatgtattt aaaagaaata cgagaaaaga   2880
aagtgaaagt tttacaagtt agagggatgg aaggtaatgt ttaatgttga tgtcatggag   2940
tgacagaatg gctttgctgg cactcagagc tcctcactta gctatattct gagactttga   3000
```

agagttataa agtataacta taaaactaat ttttcttaca cactaaatgg gtatttgttc 3060
aaaataatga agttatggct tcacattcat tgcagtggga tatggttttt atgtaaaaca 3120
tttttagaac tccagttttc aaatcatgtt tgaatctaca ttcacttttt tttgttttct 3180
tttttgagac ggagtctcgc tctgtcgccc aggctggagt gcagtggcgc gatctcggct 3240
cactgcaagc tctgcctccc aggttcacac cattctcctg cctcagcctc ccgagtagct 3300
gggactacag gtgcccacca ccacgcctgg ctagtttttt gtatttttag tagagacgca 3360
gtttcaccgt gttagccagg atggtctcga tctcctgacc ttgtgatctg cccgcctcgg 3420
cctcccaaag tgctgggatt acaggcgtga gccaccgcgc ccagcctaca ttcacttcta 3480
aagtctatgt aatggtggtc atttttttccc ttttagaata cattaaatgg ttgatttggg 3540
gaggaaaact tattctgaat attaacggtg gtgaaaaggg gacagttttt accctaaagt 3600
gcaaaagtga aacatacaaa ataagactaa tttttaagag taactcagta atttcaaaat 3660
acagatttga atagcagcat tagtggtttg agtgtctagc aaaggaaaaa ttgatgaata 3720
aaatgaaggt ctggtgtata tgttttaaaa tactctcata tagtcacact ttaaattaag 3780
ccttatatta ggcccctcta ttttcaggat ataattctta actatcatta tttacctgat 3840
tttaatcatc agattcgaaa ttctgtgcca tggcatatat gttcaaattc aaaccatttt 3900
taaaatgtga agatggactt catgcaagtt ggcagtggtt ctggtactaa aaattgtggt 3960
tgttttttct gtttacgtaa cctgcttagt attgacactc tctaccaaga gggtcttcct 4020
aagaagagtg ctgtcattat ttcctcttat caacaacttg tgacatgaga tttttttaagg 4080 gctttatgtg aactatgata ttgtaatttt tctaagcata ttcaaaaggg tgacaaaatt 4140
acgtttatgt actaaatcta atcaggaaag taaggcagga aaagttgatg gtattcatta 4200
ggttttaact gaatggagca gttccttata taataacaat tgtatagtag ggataaaaca 4260
ctaacttaat gtgtattcat tttaaattgt tctgtatttt taaattgcca agaaaaacaa 4320
ctttgtaaat ttggagatat tttccaacag cttttcgtct tcagtgtctt aatgtggaag 4380
ttaaccctta ccaaaaaagg aagttggcaa aaacagcctt ctagcacact tttttaaatg 4440
aataatggta gcctaaactt aatattttta taaagtattg taatattgtt ttgtggataa 4500
ttgaaataaa aagttctcat tgaatgcacc tattaatcgt tttagttgct attcatattc 4560
tcattcgttt tttaaaaact gatatattct gaatttattc ttccattgag aaaaaaatgt 4620
tcagttactt gtaactactg agcagaattt aatcaatcct ttattaaatt cagaacatta 4680
ttgaa 4685

<210> SEQ ID NO 14
<211> LENGTH: 2458
<212> TYPE: DNA
<213> ORGANISM: Human

<400> SEQUENCE: 14
aataagagaa gtccgaggcg gcttcctcct ccctgcccag caggggcggc ggtcagaggc 60
gggcagcacc ccagttctcc ccgcacgccg gcactcgcgg ctgctggagc cccggctggc 120
tcaccccggg gccgggcaga attgggctcc aggtctctga cccctcccaa ggatcatgcc 180
gcagccccac tgacccagga gtaggggcct aagggcaggg aacctggaat gggctgtgtg 240
ttctgcaaga aattggagcc ggtggccacg gccaaggagg atgctggcct ggaaggggac 300
ttcagaagct acggggcagc agaccactat gggcctgacc ccactaaggc ccggcctgca 360
tcctcatttg cccacatccc caactacagc aacttctcct ctcaggccat caaccctggc 420
ttccttgata gtggcaccat caggggtgtg tcagggattg gggtgaccct gttcattgcc 480
ctgtatgact atgaggctcg aactgaggat gacctcacct tcaccaaggg cgagaagttc 540
cacatcctga acaatactga aggtgactgg tgggaggctc ggtctctcag ctccggaaaa 600
actggctgca ttcccagcaa ctacgtggcc cctgttgact caatccaagc tgaagagtgg 660
tactttggaa agattgggag aaaggatgca gagaggcagc tgctttcacc aggcaacccc 720 caggggggcct ttctcattcg ggaaagcgag accaccaaag gtgcctactc cctgtccatc 780
cgggactggg atcagaccag aggcgatcat gtgaagcatt acaagatccg caaactggac 840
atgggcggct actacatcac cacacgggtt cagttcaact cggtgcagga gctggtgcag 900
cactacatgg aggtgaatga cgggctgtgc aacctgctca tcgcgccctg caccatcatg 960
aagccgcaga cgctgggcct ggccaaggac gcctgggaga tcagccgcag ctccatcacg 1020
ctggagcgcc ggctgggcac cggctgcttc ggggatgtgt ggctgggcac gtggaacggc 1080
agcactaagg tggcggtgaa gacgctgaag ccgggcacca tgtccccgaa ggccttcctg 1140
gaggaggcgc aggtcatgaa gctgctgcgg cacgacaagc tggtgcagct gtacgccgtg 1200
gtgtcggagg agcccatcta catcgtgacc gagttcatgt gtcacggcag cttgctggat 1260
tttctcaaga acccagaggg ccaggatttg aggctgcccc aattggtgga catggcagcc 1320
caggtagctg agggcatggc ctacatggaa cgcatgaact acattcaccg cgacctgagg 1380
gcagccaaca tcctggttgg ggagcggctg gcgtgcaaga tcgcagactt tggcttggcg 1440
cgtctcatca aggacgatga gtacaacccc tgccaaggtt ccaagttccc catcaagtgg 1500
acagccccag aagctgccct ctttggcaga ttcaccatca agtcagacgt gtggtccttt 1560
gggatcctgc tcactgagct catcaccaag ggccgaatcc cctacccagg catgaataaa 1620
cgggaagtgt tggaacaggt ggagcagggc taccacatgc cgtgccctcc aggctgccca 1680
gcatccctgt acgaggccat ggaacagacc tggcgtctgg acccggagga gaggcctacc 1740
ttcgagtacc tgcagtcctt cctggaggac tacttcacct ccgctgaacc acagtaccag 1800
cccggggatc agacatagcc tgtccgggca tcaaccctct ctggcggtgg ccaccagtcc 1860
ttgccaatcc ccagagctgt tcttccaaag cccccaggct ggcttagaac cccatagagt 1920
cctagcatca ccgaggacgt ggctgctctg acaccaccta gggcaaccta cttgttttac 1980
agatggggca aaaggaggcc cagagctgat ctctcatccg ctctggcccc aagcactatt 2040
tcttcctttt ccacttaggc ccctacatgc ctgtagcctt tctcactcca tccccaccca 2100
aagtgctcag accttgtcta gttatttata aaactgtatg tacctccctc acttctctcc 2160
tatcactgct ttcctactct ccttttatct cactctagtc caggtgccaa gaatttccct 2220
tctaccctct attctcttgt gtctgtaagt tacaaagtca ggaaaagtct tggctggacc 2280
cctttcctgc tgggtggatg cagtggtcca ggactggggt ctgggcccag gtttgaggga 2340
gaaggttgca gagcacttcc cacctctctg aatagtgtgt atgtgttggt ttattgattc 2400
tgtaaataag taaaatgaca atatgaatcc tcaaaccatg aaaaaaaaaa aaaaaaaa 2458

<210> SEQ ID NO 15
<211> LENGTH: 2501
<212> TYPE: DNA
<213> ORGANISM: Human

<400> SEQUENCE: 15
ctctgagtgt tgcaatggca atgtttctgg cagggtgtgg gggacccttg ctcaatgacc 60
tcctgccctg ttgctcagag gataccgctg ccagaaaagg gttggctcat tgtggggctt 120

-continued

```
cccaaggtac tctggtagcc ccagcttctg acctggtcct ttctctggta tggggatagg    180
aggagagctc cggaggtctc tgacccctcc caaggatcat gccgcagccc cactgaccca    240
ggagtagggg cctaagggca gggaacctgg aatgggctgt gtgttctgca agaaattgga    300
gccggtggcc acggccaagg aggatgctgg cctggaaggg gacttcagaa gctacggggc    360
agcagaccac tatgggcctg accccactaa ggcccggcct gcatcctcat ttgcccacat    420
ccccaactac agcaacttct cctctcaggc catcaaccct ggcttccttg atagtggcac    480
catcaggggt gtgtcaggga ttggggtgac cctgttcatt gccctgtatg actatgaggc    540
tcgaactgag gatgacctca ccttcaccaa gggcgagaag ttccacatcc tgaacaatac    600
tgaaggtgac tggtgggagg ctcggtctct cagctccgga aaaactggct gcattcccag    660
caactacgtg gcccctgttg actcaatcca agctgaagag tggtactttg gaaagattgg    720
gagaaaggat gcagagaggc agctgctttc accaggcaac ccccaggggg cctttctcat    780
tcgggaaagc gagaccacca aaggtgccta ctccctgtcc atccgggact gggatcagac    840
cagaggcgat catgtgaagc attacaagat ccgcaaactg gacatgggcg gctactacat    900
caccacacgg gttcagttca actcggtgca ggagctggtg cagcactaca tggaggtgaa    960
tgacgggctg tgcaacctgc tcatcgcgcc ctgcaccatc atgaagccgc agacgctggg   1020
cctggccaag gacgcctggg agatcagccg cagctccatc acgctggagc gccggctggg   1080
caccggctgc ttcggggatg tgtggctggg cacgtggaac ggcagcacta aggtggcggt   1140
gaagacgctg aagccgggca ccatgtcccc gaaggccttc ctggaggagg cgcaggtcat   1200
gaagctgctg cggcacgaca agctggtgca gctgtacgcc gtggtgtcgg aggagcccat   1260
ctacatcgtg accgagttca tgtgtcacgg cagcttgctg gattttctca agaacccaga   1320
gggccaggat ttgaggctgc cccaattggt ggacatggca gcccaggtag ctgagggcat   1380
ggcctacatg gaacgcatga actacattca ccgcgacctg agggcagcca acatcctggt   1440
tggggagcgg ctggcgtgca agatcgcaga ctttggcttg gcgcgtctca tcaaggacga   1500
tgagtacaac ccctgccaag gttccaagtt ccccatcaag tggacagccc cagaagctgc   1560
cctctttggc agattcacca tcaagtcaga cgtgtggtcc tttgggatcc tgctcactga   1620
gctcatcacc aagggccgaa tcccctaccc aggcatgaat aaacgggaag tgttggaaca   1680
ggtggagcag ggctaccaca tgccgtgccc tccaggctgc ccagcatccc tgtacgaggc   1740
catggaacag acctggcgtc tggacccgga ggagaggcct accttcgagt acctgcagtc   1800
cttcctggag gactacttca cctccgctga accacagtac cagcccgggg atcagacata   1860
gcctgtccgg gcatcaaccc tctctggcgg tggccaccag tccttgccaa tccccagagc   1920
tgttcttcca aagcccccag gctggcttag aaccccatag agtcctagca tcaccgagga   1980
cgtggctgct ctgacaccac ctagggcaac ctacttgttt tacagatggg gcaaaaggag   2040
gcccagagct gatctctcat ccgctctggc cccaagcact atttcttcct tttccactta   2100
ggcccctaca tgcctgtagc ctttctcact ccatccccac ccaaagtgct cagaccttgt   2160
ctagttattt ataaaactgt atgtacctcc ctcacttctc tcctatcact gctttcctac   2220
tctcctttta tctcactcta gtccaggtgc caagaatttc ccttctaccc tctattctct   2280
tgtgtctgta agttacaaag tcaggaaaag tcttggctgg accccttcc tgctgggtgg    2340
atgcagtggt ccaggactgg ggtctgggcc caggtttgag ggagaaggtt gcagagcact   2400
tcccacctct ctgaatagtg tgtatgtgtt ggtttattga ttctgtaaat aagtaaaatg   2460
acaatatgaa tcctcaaacc atgaaaaaaa aaaaaaaaaa a                       2501
```

<210> SEQ ID NO 16
<211> LENGTH: 2442
<212> TYPE: DNA
<213> ORGANISM: Human

<400> SEQUENCE: 16

```
tacacacatg agagatcact tagagcaaag ggtgagaggg gcaggtgggg ctagggtgga     60
gaccaaagca ctgatgtgac ggaaccatca gccaggcaac tggacctggt ggatccagga    120
agactttctg gaagaggtct ctgacccctc ccaaggatca tgccgcagcc ccactgaccc    180
aggagtaggg gcctaagggc agggaacctg gaatgggctg tgtgttctgc aagaaattgg    240
agccggtggc cacggccaag gaggatgctg gcctggaagg ggacttcaga agctacgggg    300
cagcagacca ctatgggcct gaccccacta aggcccggcc tgcatcctca tttgcccaca    360
tccccaacta cagcaacttc tcctctcagg ccatcaaccc tggcttcctt gatagtggca    420
ccatcagggg tgtgtcaggg attggggtga ccctgttcat tgccctgtat gactatgagg    480
ctcgaactga ggatgacctc accttcacca agggcgagaa gttccacatc ctgaacaata    540
ctgaaggtga ctggtgggag gctcggtctc tcagctccgg aaaaactggc tgcattccca    600
gcaactacgt ggcccctgtt gactcaatcc aagctgaaga gtggtacttt ggaaagattg    660
ggagaaagga tgcagagagg cagctgcttt caccaggcaa cccccagggg gcctttctca    720
ttcgggaaag cgagaccacc aaaggtgcct actccctgtc catccgggac tgggatcaga    780
ccagaggcga tcatgtgaag cattacaaga tccgcaaact ggacatgggc ggctactaca    840
tcaccacacg ggttcagttc aactcggtgc aggagctggt gcagcactac atggaggtga    900
atgacgggct gtgcaacctg ctcatcgcgc cctgcaccat catgaagccg cagacgctgg    960
gcctggccaa ggacgcctgg gagatcagcc gcagctccat cacgctggag cgccggctgg   1020
gcaccggctg cttcggggat gtgtggctgg gcacgtggaa cggcagcact aaggtggcgg   1080
tgaagacgct gaagccgggc accatgtccc cgaaggcctt cctggaggag gcgcaggtca   1140
tgaagctgct gcggcacgac aagctggtgc agctgtacgc cgtggtgtcg gaggagccca   1200
tctacatcgt gaccgagttc atgtgtcacg gcagcttgct ggattttctc aagaacccag   1260
agggccagga tttgaggctg ccccaattgg tggacatggc agcccaggta gctgagggca   1320
tggcctacat ggaacgcatg aactacattc accgcgacct gagggcagcc aacatcctgg   1380
ttggggagcg gctggcgtgc aagatcgcag actttggctt ggcgcgtctc atcaaggacg   1440
atgagtacaa cccctgccaa ggttccaagt tccccatcaa gtggacagcc ccagaagctg   1500
ccctctttgg cagattcacc atcaagtcag acgtgtggtc ctttgggatc ctgctcactg   1560
agctcatcac caagggccga atcccctacc caggcatgaa taaacgggaa gtgttggaac   1620
aggtggagca gggctaccac atgccgtgcc ctccaggctg cccagcatcc ctgtacgagg   1680
ccatggaaca gacctggcgt ctggacccgg aggagaggcc taccttcgag tacctgcagt   1740
ccttcctgga ggactacttc acctccgctg aaccacagta ccagcccggg gatcagacat   1800
agcctgtccg ggcatcaacc ctctctggcg gtggccacca gtccttgcca atccccagag   1860
ctgttcttcc aaagccccca ggctggctta gaaccccata gagtcctagc atcaccgagg   1920
acgtggctgc tctgacacca cctagggcaa cctacttgtt ttacagatgg ggcaaaagga   1980
ggcccagagc tgatctctca tccgctctgg ccccaagcac tatttcttcc ttttccactt   2040
aggcccctac atgcctgtag cctttctcac tccatcccca cccaaagtgc tcagaccttg   2100
tctagttatt tataaaactg tatgtacctc cctcacttct ctcctatcac tgctttccta   2160
```

```
ctctcctttt atctcactct agtccaggtg ccaagaattt cccttctacc ctctattctc   2220

ttgtgtctgt aagttacaaa gtcaggaaaa gtcttggctg gaccccttc ctgctgggtg   2280

gatgcagtgg tccaggactg ggtctgggc ccaggtttga gggagaaggt tgcagagcac   2340

ttcccacctc tctgaatagt gtgtatgtgt tggtttattg attctgtaaa taagtaaaat   2400

gacaatatga atcctcaaac catgaaaaaa aaaaaaaaaa aa                      2442
```

<210> SEQ ID NO 17
<211> LENGTH: 2298
<212> TYPE: DNA
<213> ORGANISM: Human

<400> SEQUENCE: 17

```
tcggccgagc ccagagacag ccagttcctc tcccgccgcg ccgggccgcg tgccgctcgc     60

tccccggccg tggcgcctcc gggccagacg cgctgcagcc tccagcccgc ggcaagcggg    120

cggggcggcc gcgccacccc cggccccgcg ccagcagccc ctcgccgcgc gtccagcgtt    180

cccggccagc agcctcccca tacgcagtcc tgctggaccg ccccgtcgcg ccccccactc    240

tgaactcaag tcaccgtgga gctccgccgc cccgaaactt tcacgcgagc gggaaatatg    300

ggatgtataa aatcaaaagg gaaagacagc ttgagtgacg atggagtaga tttgaagact    360

caaccagtac gtaatactga aagaactatt tatgtgagag atccaacgtc caataaacag    420

caaaggccag ttccagaatc tcagctttta cctggacaga ggtttcaaac taaagatcca    480

gaggaacaag gagacattgt ggtagccttg taccccctatg atggcatcca cccggacgac    540

ttgtctttca agaaaggaga gaagatgaaa gtcctggagg agcatggaga atggtggaaa    600

gcaaagtccc ttttaacaaa aaaagaaggc ttcatcccca gcaactatgt ggccaaactc    660

aacaccttag aaacagaaga gtggttttc aaggatataa ccaggaagga cgcagaaagg    720

cagcttttgg caccaggaaa tagcgctgga gctttcctta ttagagaaag tgaaacatta    780

aaaggaagct tctctctgtc tgtcagagac tttgaccctg tgcatggtga tgttattaag    840

cactacaaaa ttagaagtct ggataatggg ggctattaca tctctccacg aatcactttt    900

ccctgtatca gcgacatgat taaacattac caaaagcagg cagatggctt gtgcagaaga    960

ttggagaagg cttgtattag tcccaagcca cagaagccat gggataaaga tgcctgggag   1020

atcccccggg agtccatcaa gttggtgaaa aggcttggcg ctgggcagtt tggggaagtc   1080

tggatgggtt actataacaa cagtaccaag gtggctgtga aaaccctgaa gccaggaact   1140

atgtctgtgc aagccttcct ggaagaagcc aacctcatga agaccctgca gcatgacaag   1200

ctcgtgaggc tctacgctgt ggtcaccagg gaggagccca tttacatcat caccgagtac   1260

atggccaagg gcagtttgct ggatttcctg aagagcgatg aaggtggcaa agtgctgctt   1320

ccaaagctca ttgacttttc tgctcagatt gcagagggaa tggcatacat cgagcggaag   1380

aactacattc accgggacct gcgagcagct aatgttctgg tctccgagtc actaatgtgc   1440

aaaattgcag attttggcct tgctagagta attgaagata atgagtacac agcaagggaa   1500

ggtgctaagt tccctattaa gtggacggct ccagaagcaa tcaactttgg atgtttcact   1560

attaagtctg atgtgtggtc ctttggaatc ctcctatacg aaattgtcac ctatgggaaa   1620

attccctacc cagggagaac taatgccgac gtgatgaccg ccctgtccca gggctacagg   1680

atgccccgtg tggagaactg cccagatgag ctctatgaca ttatgaaaat gtgctggaaa   1740

gaaaaggcag aagagagacc aacgtttgac tacttacaga gcgtcctgga tgatttctac   1800

acagccacgg aagggcaata ccagcagcag ccttagagca cagggagacc cgtccatttg   1860
```

```
gcaggggtgg ctgcctcatt tagagaggaa aagtaaccat cactggttgc acttatgatt   1920

tcatgtgcgg ggatcatctg ccgtgcctgg atcctgaaat agaggctaaa ttactcagga   1980

agaacaccct ctaaatggga aagtattctg tactcttaga tggattctcc actcagttgc   2040

aacttggact tgtcctcagc agctggtaat cttgctctgc ttgacaacat ctgagtgcag   2100

ccgtttgaga agaaaacatc tattctctcc aaaaatgcac ccaactagct ctatgtttac   2160

aaatggacat aggactcaaa gtttcagaga ccattgcaat gaatccccaa taattgcaga   2220

actaaactca tttataaagc taaaataacc ggatatatac atagcatgac atttctttgt   2280

gctttggctt acttgttt                                                 2298
```

<210> SEQ ID NO 18
<211> LENGTH: 2105
<212> TYPE: DNA
<213> ORGANISM: Human

<400> SEQUENCE: 18

```
gtcccagctc gggagcacat cagaggctta gaggcgagtg ggaagggact cagacagtgc     60

aggacgagaa acgcccgcgg caccaaagcc cctcagagcg tcgcccccgc ctctagttct    120

agaaagtcag tttcccggca ctggcacccc ggaacctcag gggctgccga gctggggggg    180

cgctcaagct gcgaggatcc gggctgcccg cgagacgagg agcgggcgcc caggatgggg    240

tgcatgaagt ccaagttcct ccaggtcgga ggcaatacat tctcaaaaac tgaaaccagc    300

gccagcccac actgtcctgt gtacgtgccg gatcccacat ccaccatcaa gccggggcct    360

aatagccaca acagcaacac accaggaatc agggaggcag gctctgagga catcatcgtg    420

gttgccctgt atgattacga ggccattcac cacgaagacc tcagcttcca gaagggggac    480

cagatggtgg tcctagagga atccggggag tggtggaagg ctcgatccct ggccacccgg    540

aaggagggct acatcccaag caactatgtc gcccgcgttg actctctgga gacagaggag    600

tggtttttca agggcatcag ccggaaggac gcagagcgcc aactgctggc tcccggcaac    660

atgctgggct ccttcatgat ccgggatagc gagaccacta aaggaagcta ctctttgtcc    720

gtgcgagact acgaccctcg gcagggagat accgtgaaac attacaagat ccggaccctg    780

gacaacgggg gcttctacat atcccccgga agcaccttca gcactctgca ggagctggtg    840

gaccactaca agaaggggaa cgacgggctc tgccagaaac tgtcggtgcc ctgcatgtct    900

tccaagcccc agaagccttg ggagaaagat gcctgggaga tccctcggga atccctcaag    960

ctggagaaga aacttggagc tgggcagttt ggggaagtct ggatggccac ctacaacaag   1020

cacaccaagg tggcagtgaa gacgatgaag ccagggagca tgtcggtgga ggccttcctg   1080

gcagaggcca acgtgatgaa aactctgcag catgacaagc tggtcaaact tcatgcggtg   1140

gtcaccaagg agcccatcta catcatcacg gagttcatgg ccaaaggaag cttgctggac   1200

tttctgaaaa gtgatgaggg cagcaagcag ccattgccaa aactcattga cttctcagcc   1260

cagattgcag aaggcatggc cttcatcgag cagaggaact acatccaccg agacctccga   1320

gctgccaaca tcttggtctc tgcatccctg gtgtgtaaga ttgctgactt tggcctggcc   1380

cgggtcattg aggacaacga gtacacggct cgggaagggg ccaagttccc catcaagtgg   1440

acagctcctg aagccatcaa ctttggctcc ttcaccatca agtcagacgt ctggtccttt   1500

ggtatcctgc tgatggagat cgtcacctac ggccggatcc cttacccagg gatgtcaaac   1560

cctgaagtga tccgagctct ggagcgtgga taccggatgc ctcgcccaga gaactgccca   1620

gaggagctct acaacatcat gatgcgctgc tggaaaaacc gtccggagga gcggccgacc   1680
```

```
ttcgaataca tccagagtgt gctggatgac ttctacacgg ccacagagag ccagtaccaa   1740

cagcagccat gatagggagg accagggcag ggccaggggg tgcccaggtg gtggctgcaa   1800

ggtggctcca gcaccatccg ccagggccca cacccccttc ctactcccag acacccaccc   1860

tcgcttcagc cacagtttcc tcatctgtcc agtgggtagg ttggactgga aaatctcttt   1920

ttgactcttg caatccacaa tctgacattc tcaggaagcc cccaagttga tatttctatt   1980

tcctggaatg gttggatttt agttacagct gtgatttgga agggaaactt tcaaaatagt   2040

gaaatgaata tttaaataaa agatataaat gccaaagtct ttaccaaaaa aaaaaaaaaa   2100

aaaaa                                                               2105

<210> SEQ ID NO 19
<211> LENGTH: 1518
<212> TYPE: DNA
<213> ORGANISM: Human

<400> SEQUENCE: 19

atggggtcga tgaagtccaa gttcctccag gtcggaggca atacattctc aaaaactgaa     60

accagcgcca gcccacactg tcctgtgtac gtgccggatc ccacatccac catcaagccg    120

gggcctaata gccacaacag caacacaccg ggaatcaggg aggcaggctc tgaggacatc    180

atcgtggttg ccctgtatga ttacgaggcc attcaccacg aagacctcag cttccagaag    240

ggggaccaga tggtggtcct agaggaatcc ggggagtggt ggaaggctcg atccctggcc    300

acccggaagg agggctacat cccaagcaac tatgtcgccc gcgttgactc tctggagaca    360

gaggagtggt ttttcaaggg catcagccgg aaggacgcag agcgccaact gctggctccc    420

ggcaacatgc tgggctcctt catgatccgg gatagcgaga ccactaaagg aagctactct    480

ttgtccgtgc gagactacga ccctcggcag ggagataccg tgaaacatta caagatccgg    540

accctggaca acgggggctt ctacatatcc ccccgaagca ccttcagcac tctgcaggag    600

ctggtggacc actacaagaa ggggaacgac gggctctgcc agaaactgtc ggtgccctgc    660

atgtcttcca agccccagaa gccttgggag aaagatgcct gggagatccc tcgggaatcc    720

ctcaagctgg agaagaaact tggagctggg cagtttgggg aagtctggat ggccacctac    780

aacaagcaca ccaaggtggc agtgaagacg atgaagccag ggagcatgtc ggtggaggcc    840

ttcctggcag aggccaacgt gatgaaaact ctgcagcatg acaagctggt caaacttcat    900

gcggtggtca ccaaggagcc catctacatc atcacggagt tcatggccaa aggaagcttg    960

ctggactttc tgaaaagtga tgagggcagc aagcagccat tgccaaaact cattgacttc   1020

tcagcccaga ttgcagaagg catggccttc atcgagcaga ggaactacat ccaccgagac   1080

ctccgagctg ccaacatctt ggtctctgca tccctggtgt gtaagattgc tgactttggc   1140

ctggcccggg tcattgagga caacgagtac acggctcggg aaggggccaa gttccccatc   1200

aagtggacag ctcctgaagc catcaacttt ggctccttca ccatcaagtc agacgtctgg   1260

tcctttggta tcctgctgat ggagatcgtc acctacggcc ggatccctta cccagggatg   1320

tcaaaccctg aagtgatccg agctctggag cgtggatacc ggatgcctcg cccagagaac   1380

tgcccagagg agctctacaa catcatgatg cgctgctgga aaaaccgtcc ggaggagcgg   1440

ccgaccttcg aatacatcca gagtgtgctg gatgatttct acacggccac agagagccag   1500

taccaacagc agccatga                                                 1518

<210> SEQ ID NO 20
<211> LENGTH: 2642
```

<212> TYPE: DNA
<213> ORGANISM: Human

<400> SEQUENCE: 20
cacacagatg gcacatggca gagcccaagc cctctccatg agatctgcag cgtttgtcca 60
cacggcaggg caaattacct tgtagagtca gcatggaggt ttgctaactc tgccggactt 120
ggtgcagaaa aaataccagc cgtgctgtta aaccaaaacc ccaggagaaa actttctggt 180
gacagaaggg cattgtgacc cacgttgccc agggccaggg acagggcagc tgctcatggt 240
ccttcctcac gagttttcct ggagcagagg gatacccca aacccaggga gcccacagga 300
gcttcagaag ggctcggctg gagggcgggg cccctgttgc acttgctcac tggggactgg 360
ggaggctctg atcgcagacc gggggtgctg ccacctctgt ctgctgccgg cagaaagcca 420
caagccatga aaactgattg agatgagaag aattcatctg ggactggctt ttgctttagg 480
atggtgttgg aagttgctcg ttgtcgctag gagcctgctc cactgtaagg gtgtcaggat 540
ctgaagagct atggtgaaac accactgaag cattgccaag gatggggctg gtaagtagca 600
aaaagccgga caaggaaaag ccgatcaaag agaaggacaa gggccaatgg agccccctga 660
aggtcagcgc ccaagacaag gacgccccgc cactgccgcc cctggttgtc ttcaaccacc 720
ttactcctcc accgcccgat gaacacctgg atgaagacaa gcatttcgtg gtggctctgt 780
atgactacac cgctatgaat gatcgggacc tgcagatgct gaagggggag aagctacagg 840
tcctgaaggg aactggagac tggtggctgg ccaggtcact cgtcacagga agagaaggct 900
atgtgcccag taactttgtg gcccgagtgg agagcctgga aatggaaagg tggttcttta 960
gatcacaggg tcggaaggag gctgagaggc agcttcttgc tccaatcaac aaggccggct 1020
cctttcttat cagagagagt gaaaccaaca aaggtgcctt ctccctgtct gtgaaggatg 1080
tcaccaccca gggggagctg atcaagcact ataagatccg ctgcctggat gaagggggct 1140
actacatctc cccccggatc accttcccct cgctccaggc cctggtgcag cactattcta 1200
agaaggggga tggtctatgc cagaggctga ccctgccctg tgtgcgcccg gccccgcaga 1260
atccctgggc ccaggatgaa tgggagatcc cccggcagtc tctcaggctg gtcaggaaac 1320
tcgggtctgg acaattcggc gaagtctgga tgggttacta caaaaacaac atgaaggtgg 1380
ccattaagac gctgaaggag ggaaccatgt ctccagaagc ctttctgggt gaggccaacg 1440
tgatgaaggc tctgcagcac gagcggctgg tccgactcta cgcagtggtc accaaggagc 1500
ccatctacat tgtcaccgag tacatggcca gaggatgcct gctggatttc ctgaagacag 1560
atgaagggag cagattgtca ctcccaaggc tgattgacat gtcggcgcag attgctgaag 1620
ggatggcata cattgagcgc atgaattcca tccaccgcga cctgcgggcg gccaacatcc 1680
tggtgtctga ggccttgtgc tgcaaaattg ctgattttgg cttggctcga atcatcgaca 1740
gtgaatacac ggcccaagag gggggccaagt tccccatcaa gtggacagcc ccggaagcca 1800
tccacttcgg ggtcttcacc atcaaagcag acgtgtggtc gtttggagtc ctcctgatgg 1860
aagttgtcac ttatgggcgg gtgccatacc cagggatgag caaccccgag gtcatccgca 1920
acctggagcg cggctaccgc atgccgcgcc ccgacacctg cccgcccgag ctgtaccgcg 1980
gcgtcatcgc cgagtgctgg cgcagccggc ccgaggagcg gcccaccttc gagttcctgc 2040
agtcggtgct ggaggacttc tacacggcca ccgagcggca gtacgagctg cagccctagc 2100
cggccgcgcc cgcctgcgcc ccgtgcccac ctctgcgcgg acgaccccga cttccgtgcc 2160
atcccagacg ggccgcgaag gcggggtgtc gcctgtgccc ttttctcaga cccggaatcc 2220
agtgggcaga ggcagcttcg caggggggtcc ccggacggac tccttcaccg actgcacccc 2280

-continued cgggcgagtt acgcggcctc tctgtgccgc ttcatttgta gagggctgta acagtgacct 2340
cgcacggtca tccggagtac taagccccag taaggtgttc aggactggta agcgactgtc 2400
atcaagtaag gcccccgtgc tgggcacccc ccgtgctggc cgcgtccccg cctctgcgcc 2460
ctgcgtggac cccgccctgc cccgctacag aagccagact gggtcccgcg gacgccagca 2520
ggggcagccc cagcctaggc tgcgctccag cactgcgggg cttttctgca ataaagtcac 2580
gagcgttcga aaaaaaaaaa aaaaaaaaaa aaaaaaaaaa aaaaaaaaaa aaaaaaaaaa 2640
aa 2642

<210> SEQ ID NO 21
<211> LENGTH: 2251
<212> TYPE: DNA
<213> ORGANISM: Human

<400> SEQUENCE: 21
cacctctgtc tgctgccggc agaaagccac aagccatgaa aactgattga gatgagaaga 60
attcatctgg gactggcttt tgctttagga tggtgttgga agttgctcgt tgtcgctagg 120
agcctgctcc actgtaaggg tgtcgggatc tgaagagcta tggtgaaaca ccactgaagc 180
attgccaagg atggggctgg taagtagcaa aaagccggac aaggaaaagc cgatcaaaga 240
gaaggacaag ggccaatgga gccccctgaa ggtcagcgcc caagacaagg acgccccgcc 300
actgccgccc ctggttgtct tcaaccacct tactcctcca ccgcccgatg aacacctgga 360
tgaagacaag catttcgtgg tggctctgta tgactacacc gctatgaatg atcgggacct 420
gcagatgctg aagggggaga agctacaggt cctgaaggga actggagact ggtggctggc 480
caggtcactc gtcacaggaa gagaaggcta tgtgcccagt aactttgtgg cccgagtgga 540
gagcctggaa atggaaaggt ggttctttag atcacagggt cggaaggagg ctgagaggca 600
gcttcttgct ccaatcaaca aggccggctc ctttcttatc agagagagtg aaaccaacaa 660
aggtgccttc tccctgtctg tgaaggatgt caccacccag ggggagctga tcaagcacta 720
taagatccgc tgcctggatg aagggggcta ctacatctcc ccccggatca ccttcccctc 780
gctccaggcc ctggtgcagc actattctaa gaagggggat ggtctatgcc agaggctgac 840
cctgccctgt gtgcgcccgg ccccgcagaa tccctgggcc caggatgaat gggagatccc 900
ccggcagtct ctcaggctgg tcaggaaact cgggtctgga caattcggcg aagtctggat 960
gggttactac aaaaacaaca tgaaggtggc cattaagacg ctgaaggagg gaaccatgtc 1020
tccagaagcc ttcctgggtg aggccaacgt gatgaaggct ctgcagcacg agcggctggt 1080
ccgactctac gcagtggtca ccaaggagcc catctacatt gtcaccgagt acatggccag 1140
aggatgcctg ctggatttcc tgaagacaga tgaagggagc agattgtcac tcccaaggct 1200
gattgacatg tcggcgcaga ttgctgaagg gatggcatac attgagcgca tgaattccat 1260
ccaccgcgac ctgcgggcgg ccaacatcct ggtgtctgag gccttgtgct gcaaaattgc 1320
tgattttggc ttggctcgaa tcatcgacag tgaatacacg gcccaagagg gggccaagtt 1380
ccccatcaag tggacagccc cggaagccat ccacttcggg gtcttcacca tcaaagcaga 1440
cgtgtggtcg tttggagtcc tcctgatgga agttgtcact tatgggcggg tgccataccc 1500
agggatgagc aaccccgagg tcatccgcaa cctggagcgc ggctaccgca tgccgcgccc 1560
cgacacctgc ccgcccgagc tgtaccgcgg cgtcatcgcc gagtgctggc gcagccggcc 1620
cgaggagcgg cccaccttcg agttcctgca gtcggtgctg gaggacttct acacggccac 1680
cgagcggcag tacgagctgc agccctagcc ggccgcgccc gcctgcgccc cgtgcccacc 1740

```
tctgcgcgga cgaccccgac ttccgtgcca tcccagacgg gccgcgaagg cggggtgtcg   1800

cctgtgccct tttctcagac ccggaatcca gtgggcagag gcagcttcgc agggggtccc   1860

cggacggact ccttcaccga ctgcaccccc gggcgagtta cgcggcctct ctgtgccgct   1920

tcatttgtag agggctgtaa cagtgacctc gcacggtcat ccggagtact aagccccagt   1980

aaggtgttca ggactggtaa gcgactgtca tcaagtaagg cccccgtgct gggcaccccc   2040

cgtgctggcc gcgtccccgc ctctgcgccc tgcgtggacc ccgccctgcc ccgctacaga   2100

agccagactg ggtcccgcgg acgccagcag gggcaacccc agcctaggct gcgctccagc   2160

actgcggggc ttttctgcaa taaagtcacg agcgttcgaa aaaaaaaaaa aaaaaaaaaa   2220

aaaaaaaaaa aaaaaaaaaa aaaaaaaaaa a                                  2251
```

<210> SEQ ID NO 22
<211> LENGTH: 2201
<212> TYPE: DNA
<213> ORGANISM: Human

<400> SEQUENCE: 22

```
ttgagatgag aagaattcat ctgggactgg cttttgcttt aggatggtgt tggaagttgc     60

tcgttgtcgc taggagcctg ctccactgta agggtgtcgg gatctgaaga gctatggtga    120

aacaccactg aagcattgcc aaggatgggg ctggtaagta gcaaaaagcc ggacaaggaa    180

aagccgatca aagagaagga caagggccaa tggagccccc tgaaggtcag cgcccaagac    240

aaggacgccc cgccactgcc gcccctggtt gtcttcaacc accttactcc tccaccgccc    300

gatgaacacc tggatgaaga caagcatttc gtggtggctc tgtatgacta caccgctatg    360

aatgatcggg acctgcagat gctgaagggg gagaagctac aggtcctgaa gggaactgga    420

gactggtggc tggccaggtc actcgtcaca ggaagagaag gctatgtgcc cagcaacttt    480

gtggcccgag tggagagcct ggaaatggaa aggtggttct ttagatcaca gggtcggaag    540

gaggctgaga ggcagcttct tgctccaatc aacaaggccg gctcctttct tatcagagag    600

agtgaaacca acaaaggtgc cttctccctg tctgtgaagg atgtcaccac ccagggggag    660

ctgatcaagc actataagat ccgctgcctg gatgaagggg gctactacat ctccccccgg    720

atcaccttcc cctcgctcca ggccctggtg cagcactatt ctaagaaggg ggatggtcta    780

tgccagaggc tgaccctgcc ctgtgtgcgc ccggccccgc agaatccctg ggcccaggat    840

gaatgggaga tcccccggca gtctctcagg ctggtcagga aactcgggtc tggacaattc    900

ggcgaagtct ggatgggtta ctacaaaaac aacatgaagg tggccattaa gacgctgaag    960

gagggaacca tgtctccaga agcctttctg ggtgaggcca acgtgatgaa ggctctgcag   1020

cacgagcggc tggtccgact ctacgcagtg gtcaccaagg agcccatcta cattgtcacc   1080

gagtacatgg ccagaggatg cctgctggat ttcctgaaga cagatgaagg gagcagattg   1140

tcactcccaa ggctgattga catgtcggcg cagattgctg aagggatggc atacattgag   1200

cgcatgaatt ccatccaccg cgacctgcgg gcggccaaca tcctggtgtc tgaggccttg   1260

tgctgcaaaa ttgctgattt tggcttggct cgaatcatcg acagtgaata cacggcccaa   1320

gagggggcca agttccccat caagtggaca gccccggaag ccatccactt cggggtcttc   1380

accatcaaag cagacgtgtg gtcgtttgga gtcctcctga tggaagttgt cacttatggg   1440

cgggtgccat acccagggat gagcaacccc gaggtcatcc gcaacctgga gcgcggctac   1500

cgcatgccgc gccccgacac ctgcccgccc gagctgtacc gcggcgtcat cgccgagtgc   1560

tggcgcagcc ggcccgagga gcggcccacc ttcgagttcc tgcagtcggt gctggaggac   1620
```

```
ttctacacgg ccaccgagcg gcagtacgag ctgcagccct agccggccgc gcccgcctgc   1680
gccccgtgcc cacctctgcg cggacgaccc cgacttccgt gccatcccag acgggccgcg   1740
aaggcggggt gtcgcctgtg ccctttttctc agacccggaa tccagtgggc agaggcagct   1800
tcgcaggggg tccccggacg gactccttca ccgactgcac ccccgggcga gttacgcggc   1860
ctctctgtgc cgcttcattt gtagagggct gtaacagtga cctcgcacgg tcatccggag   1920
tactaagccc cagtaaggtg ttcaggactg gtaagcgact gtcatcaagt aaggcccccg   1980
tgctgggcac cccccgtgct ggccgcgtcc ccgcctctgc gccctgcgtg gaccccgccc   2040
tgccccgcta cagaagccag actgggtccc gcggacgcca gcaggggcag ccccagccta   2100
ggctgcgctc cagcactgcg gggcttttct gcaataaagt cacgagcgtt aaaaaaaaaa   2160
aaaaaaaaaa aaaaaaaaaa aaaaaaaaaa aaaaaaaaaa a                       2201
```

<210> SEQ ID NO 23
<211> LENGTH: 5384
<212> TYPE: DNA
<213> ORGANISM: Human

<400> SEQUENCE: 23

```
aaaatgttgg agatctgcct gaagctggtg ggctgcaaat ccaagaaggg gctgtcctcg     60
tcctccagct gttatctgga agaagccctt cagcggccag tagcatctga ctttgagcct    120
cagggtctga gtgaagccgc tcgttggaac tccaaggaaa accttctcgc tggacccagt    180
gaaaatgacc ccaacctttt cgttgcactg tatgattttg tggccagtgg agataacact    240
ctaagcataa ctaaaggtga aaagctccgg gtcttaggct ataatcacaa tggggaatgg    300
tgtgaagccc aaaccaaaaa tggccaaggc tgggtcccaa gcaactacat cacgccagtc    360
aacagtctgg agaaacactc ctggtaccat gggcctgtgt cccgcaatgc cgctgagtat    420
ctgctgagca gcgggatcaa tggcagcttc ttggtgcgtg agagtgagag cagtcctggc    480
cagaggtcca tctcgctgag atacgaaggg agggtgtacc attacaggat caacactgct    540
tctgatggca agctctacgt ctcctccgag agccgcttca acaccctggc cgagttggtt    600
catcatcatt caacggtggc cgacgggctc atcaccacgc tccattatcc agccccaaag    660
cgcaacaagc ccactgtcta tggtgtgtcc cccaactacg acaagtggga gatggaacgc    720
acggacatca ccatgaagca caagctgggc gggggccagt acggggaggt gtacgagggc    780
gtgtggaaga aatacagcct gacggtggcc gtgaagacct tgaaggagga caccatggag    840
gtggaagagt tcttgaaaga agctgcagtc atgaaagaga tcaaacaccc taacctggtg    900
cagctccttg gggtctgcac ccgggagccc ccgttctata tcatcactga gttcatgacc    960
tacgggaacc tcctggacta cctgagggag tgcaaccggc aggaggtgaa cgccgtggtg   1020
ctgctgtaca tggccactca gatctcgtca gccatggagt acctggagaa gaaaaacttc   1080
atccacagag atcttgctgc ccgaaactgc ctggtagggg agaaccactt ggtgaaggta   1140
gctgattttg gcctgagcag gttgatgaca ggggacacct acacagccca tgctggagcc   1200
aagttcccca tcaaatggac tgcacccgag agcctggcct acaacaagtt ctccatcaag   1260
tccgacgtct gggcatttgg agtattgctt tgggaaattg ctacctatgg catgtcccct   1320
tacccgggaa ttgacctgtc ccaggtgtat gagctgctag agaaggacta ccgcatggag   1380
cgcccagaag gctgcccaga gaaggtctat gaactcatgc gagcatgttg gcagtggaat   1440
ccctctgacc ggccctcctt tgctgaaatc caccaagcct ttgaaacaat gttccaggaa   1500
tccagtatct cagacgaagt ggaaaaggag ctggggaaac aaggcgtccg tggggctgtg   1560
```

-continued

```
agtaccttgc tgcaggcccc agagctgccc accaagacga ggacctccag gagagctgca   1620
gagcacagag acaccactga cgtgcctgag atgcctcact ccaagggcca gggagagagc   1680
gatcctctgg accatgagcc tgccgtgtct ccattgctcc ctcgaaaaga gcgaggtccc   1740
ccggagggcg gcctgaatga agatgagcgc cttctcccca aagacaaaaa gaccaacttg   1800
ttcagcgcct tgatcaagaa gaagaagaag acagccccaa cccctcccaa acgcagcagc   1860
tccttccggg agatggacgg ccagccggag cgcagagggg ccggcgagga agagggccga   1920
gacatcagca acggggcact ggctttcacc cccttggaca cagctgaccc agccaagtcc   1980
ccaaagccca gcaatggggc tggggtcccc aatggagccc tccgggagtc cgggggctca   2040
ggcttccggt ctccccacct gtggaagaag tccagcacgc tgaccagcag ccgcctagcc   2100
accggcgagg aggagggcgg tggcagctcc agcaagcgct tcctgcgctc ttgctccgcc   2160
tcctgcgttc cccatggggc caaggacacg gagtggaggt cagtcacgct gcctcgggac   2220
ttgcagtcca cgggaagaca gtttgactcg tccacatttg gagggcacaa aagtgagaag   2280
ccggctctgc ctcggaagag ggcaggggag aacaggtctg accaggtgac ccgaggcaca   2340
gtaacgcctc cccccaggct ggtgaaaaag aatgaggaag ctgctgatga ggtcttcaaa   2400
gacatcatgg agtccagccc gggctccagc ccgcccaacc tgactccaaa acccctccgg   2460
cggcaggtca ccgtggcccc tgcctcgggc ctcccccaca aggaagaagc tggaaagggc   2520
agtgccttag ggacccctgc tgcagctgag ccagtgaccc ccaccagcaa agcaggctca   2580
ggtgcaccag gggcaccag caagggcccc gccgaggagt ccagagtgag gaggcacaag   2640
cactcctctg agtcgccagg gagggacaag ggaaattgt ccaggctcaa acctgccccg   2700
ccgcccccac cagcagcctc tgcagggaag gctggaggaa agccctcgca gagcccgagc   2760
caggaggcgg ccggggaggc agtcctgggc gcaaagacaa aagccacgag tctggttgat   2820
gctgtgaaca gtgacgctgc caagcccagc cagccgggag agggcctcaa aaagcccgtg   2880
ctcccggcca ctccaaagcc acagtccgcc aagccgtcgg ggacccccat cagcccagcc   2940
cccgttccct ccacgttgcc atcagcatcc tcggccctgg caggggacca gccgtcttcc   3000
accgccttca tccctctcat atcaacccga gtgtctcttc ggaaaacccg ccagcctcca   3060
gagcggatcg ccagcggcgc catcaccaag ggcgtggtcc tggacagcac cgaggcgctg   3120
tgcctcgcca tctctaggaa ctccgagcag atggccagcc acagcgcagt gctggaggcc   3180
ggcaaaaacc tctacacgtt ctgcgtgagc tatgtggatt ccatccagca aatgaggaac   3240
aagtttgcct tccgagaggc catcaacaaa ctggagaata atctccggga gcttcagatc   3300
tgcccggcga cagcaggcag tggtccagcg gccactcagg acttcagcaa gctcctcagt   3360
tcggtgaagg aaatcagtga catagtgcag aggtagcagc agtcaggggt caggtgtcag   3420
gcccgtcgga gctgcctgca gcacatgcgg gctcgcccat acccgtgaca gtggctgaca   3480
agggactagt gagtcagcac cttggcccag gagctctgcg ccaggcagag ctgagggccc   3540
tgtggagtcc agctctacta cctacgtttg caccgcctgc cctcccgcac cttcctcctc   3600
cccgctccgt ctctgtcctc gaattttatc tgtggagttc ctgctccgtg gactgcagtc   3660
ggcatgccag gacccgccag ccccgctccc acctagtgcc ccagactgag ctctccaggc   3720
caggtgggaa cggctgatgt ggactgtctt tttcattttt ttctctctgg agcccctcct   3780
cccccggctg ggcctccttc ttccacttct ccaagaatgg aagcctgaac tgaggccttg   3840
tgtgtcaggc cctctgcctg cactccctgg ccttgcccgt cgtgtgctga agacatgttt   3900
caagaaccgc atttcgggaa gggcatgcac gggcatgcac acggctggtc actctgccct   3960
```

```
ctgctgctgc ccggggtggg gtgcactcgc catttcctca cgtgcaggac agctcttgat   4020
ttgggtggaa aacagggtgc taaagccaac cagcctttgg gtcctgggca ggtgggagct   4080
gaaaaggatc gaggcatggg gcatgtcctt tccatctgtc cacatcccca gagcccagct   4140
cttgctctct tgtgacgtgc actgtgaatc ctggcaagaa agcttgagtc tcaagggtgg   4200
caggtcactg tcactgccga catccctccc ccagcagaat ggaggcaggg gacaagggag   4260
gcagtggcta gtggggtgaa cagctggtgc caaatagccc cagactgggc ccaggcaggt   4320
ctgcaagggc ccagagtgaa ccgtcctttc acacatctgg gtgccctgaa agggcccttc   4380
ccctccccca ctcctctaag acaaagtaga ttcttacaag gccctttcct ttggaacaag   4440
acagccttca cttttctgag ttcttgaagc atttcaaagc cctgcctctg tgtagccgcc   4500
ctgagagaga atagagctgc cactgggcac ctgcgcacag gtgggaggaa agggcctggc   4560
cagtcctggt cctggctgca ctcttgaact gggcgaatgt cttatttaat taccgtgagt   4620
gacatagcct catgttctgt gggggtcatc agggagggtt aggaaaacca caaacggagc   4680
ccctgaaagc ctcacgtatt tcacagagca cgcctgccat cttctccccg aggctgcccc   4740
aggccggagc ccagatacgg gggctgtgac tctgggcagg gacccggggt ctcctggacc   4800
ttgacagagc agctaactcc gagagcagtg ggcaggtggc cgcccctgag gcttcacgcc   4860
gggagaagcc accttcccac cccttcatac cgcctcgtgc cagcagcctc gcacaggccc   4920
tagctttacg ctcatcacct aaacttgtac tttatttttc tgatagaaat ggtttcctct   4980
ggatcgtttt atgcggttct tacagcacat cacctctttg cccccgacgg ctgtgacgca   5040
gccggaggga ggcactagtc accgacagcg gccttgaaga cagagcaaag cgcccaccca   5100
ggtcccccga ctgcctgtct ccatgaggta ctggtccctt ccttttgtta acgtgatgtg   5160
ccactatatt ttacacgtat ctcttggtat gcatctttta tagacgctct tttctaagtg   5220
gcgtgtgcat agcgtcctgc cctgccccct cgggggcctg tggtggctcc ccctctgctt   5280
ctcggggtcc agtgcatttt gtttctgtat atgattctct gtggtttttt ttgaatccaa   5340
atctgtcctc tgtagtattt tttaaataaa tcagtgttta catt                    5384
```

<210> SEQ ID NO 24
<211> LENGTH: 5881
<212> TYPE: DNA
<213> ORGANISM: Human

<400> SEQUENCE: 24

```
ggttggtgac ttccacagga aaagttctgg aggagtagcc aaagaccatc agcgtttcct     60
ttatgtgtga gaattgaaat gactagcatt attgaccctt ttcagcatcc cctgtgaata    120
tttctgttta ggtttttctt cttgaaaaga aattgttatt cagcccgttt aaaacaaatc    180
aagaaacttt tgggtaacat tgcaattaca tgaaattgat aaccgcgaaa ataattggaa    240
ctcctgcttg caagtgtcaa cctaaaaaaa gtgcttcctt ttgttatgga agatgtcttt    300
ctgtgattga cttcaattgc tgacttgtgg agatgcagcg aatgtgaaat cccacgtata    360
tgccatttcc ctctacgctc gctgaccgtt ctggaagatc ttgaaccctc ttctggaaag    420
gggtacctat tattacttta tggggcagca gcctggaaaa gtacttgggg accaaagaag    480
gccaagcttg cctgccctgc attttatcaa aggagcaggg aagaaggaat catcgaggca    540
tgggggtcca cactgcaatg tttttgtgga acatgaagcc cttcagcggc cagtagcatc    600
tgactttgag cctcagggtc tgagtgaagc cgctcgttgg aactccaagg aaaaccttct    660
cgctggaccc agtgaaaatg accccaacct tttcgttgca ctgtatgatt ttgtggccag    720
```

-continued

```
tggagataac actctaagca taactaaagg tgaaaagctc cgggtcttag gctataatca    780
caatggggaa tggtgtgaag cccaaaccaa aaatggccaa ggctgggtcc caagcaacta    840
catcacgcca gtcaacagtc tggagaaaca ctcctggtac catgggcctg tgtcccgcaa    900
tgccgctgag tatctgctga gcagcgggat caatggcagc ttcttggtgc gtgagagtga    960
gagcagtcct ggccagaggt ccatctcgct gagatacgaa gggagggtgt accattacag   1020
gatcaacact gcttctgatg gcaagctcta cgtctcctcc gagagccgct tcaacaccct   1080
ggccgagttg gttcatcatc attcaacggt ggccgacggg ctcatcacca cgctccatta   1140
tccagcccca aagcgcaaca agcccactgt ctatggtgtg tcccccaact acgacaagtg   1200
ggagatggaa cgcacggaca tcaccatgaa gcacaagctg ggcgggggcc agtacgggga   1260
ggtgtacgag ggcgtgtgga agaaatacag cctgacggtg gccgtgaaga ccttgaagga   1320
ggacaccatg gaggtggaag agttcttgaa agaagctgca gtcatgaaag agatcaaaca   1380
ccctaacctg gtgcagctcc ttggggtctg cacccgggag cccccgttct atatcatcac   1440
tgagttcatg acctacggga acctcctgga ctacctgagg gagtgcaacc ggcaggaggt   1500
gaacgccgtg gtgctgctgt acatggccac tcagatctcg tcagccatgg agtacctgga   1560
gaagaaaaac ttcatccaca gagatcttgc tgcccgaaac tgcctggtag gggagaacca   1620
cttggtgaag gtagctgatt ttggcctgag caggttgatg acaggggaca cctacacagc   1680
ccatgctgga gccaagttcc ccatcaaatg gactgcaccc gagagcctgg cctacaacaa   1740
gttctccatc aagtccgacg tctgggcatt tggagtattg ctttgggaaa ttgctaccta   1800
tggcatgtcc ccttacccgg gaattgacct gtcccaggtg tatgagctgc tagagaagga   1860
ctaccgcatg gagcgcccag aaggctgccc agagaaggtc tatgaactca tgcgagcatg   1920
ttggcagtgg aatccctctg accggccctc ctttgctgaa atccaccaag cctttgaaac   1980
aatgttccag gaatccagta tctcagacga agtggaaaag gagctgggga aacaaggcgt   2040
ccgtggggct gtgagtacct tgctgcaggc cccagagctg cccaccaaga cgaggacctc   2100
caggagagct gcagagcaca gagacaccac tgacgtgcct gagatgcctc actccaaggg   2160
ccagggagag agcgatcctc tggaccatga gcctgccgtg tctccattgc tccctcgaaa   2220
agagcgaggt cccccggagg gcggcctgaa tgaagatgag cgccttctcc ccaaagacaa   2280
aaagaccaac ttgttcagcg ccttgatcaa gaagaagaag aagacagccc caacccctcc   2340
caaacgcagc agctccttcc gggagatgga cggccagccg gagcgcagag ggccggcgga   2400
ggaagagggc cgagacatca gcaacggggc actggctttc acccccttgg acacagctga   2460
cccagccaag tccccaaagc ccagcaatgg ggctggggtc cccaatggag ccctccggga   2520
gtccgggggc tcaggcttcc ggtctcccca cctgtggaag aagtccagca cgctgaccag   2580
cagccgccta gccaccggcg aggaggaggg cggtggcagc tccagcaagc gcttcctgcg   2640
ctcttgctcc gcctcctgcg ttccccatgg ggccaaggac acggagtgga ggtcagtcac   2700
gctgcctcgg gacttgcagt ccacgggaag acagtttgac tcgtccacat ttggagggca   2760
caaaagtgag aagccggctc tgcctcggaa gagggcaggg gagaacaggt ctgaccaggt   2820
gacccgaggc acagtaacgc ctcccccag gctggtgaaa aagaatgagg aagctgctga   2880
tgaggtcttc aaagacatca tggagtccag cccgggctcc agcccgccca acctgactcc   2940
aaaacccctc cggcggcagg tcaccgtggc ccctgcctcg ggcctccccc acaaggaaga   3000
agctggaaag ggcagtgcct tagggacccc tgctgcagct gagccagtga cccccaccag   3060
caaagcaggc tcaggtgcac cagggggcac cagcaagggc cccgccgagg agtccagagt   3120
```

-continued

```
gaggaggcac aagcactcct ctgagtcgcc agggagggac aaggggaaat tgtccaggct   3180
caaacctgcc ccgccgcccc caccagcagc ctctgcaggg aaggctggag gaaagccctc   3240
gcagagcccg agccaggagg cggccgggga ggcagtcctg ggcgcaaaga caaaagccac   3300
gagtctggtt gatgctgtga acagtgacgc tgccaagccc agccagccgg gagagggcct   3360
caaaaagccc gtgctcccgg ccactccaaa gccacagtcc gccaagccgt cggggacccc   3420
catcagccca gcccccgttc cctccacgtt gccatcagca tcctcggccc tggcagggga   3480
ccagccgtct tccaccgcct tcatccctct catatcaacc cgagtgtctc ttcggaaaac   3540
ccgccagcct ccagagcgga tcgccagcgg cgccatcacc aagggcgtgg tcctggacag   3600
caccgaggcg ctgtgcctcg ccatctctag gaactccgag cagatggcca gccacagcgc   3660
agtgctggag gccggcaaaa acctctacac gttctgcgtg agctatgtgg attccatcca   3720
gcaaatgagg aacaagtttg ccttccgaga ggccatcaac aaactggaga ataatctccg   3780
ggagcttcag atctgcccgg cgacagcagg cagtggtcca gcggccactc aggacttcag   3840
caagctcctc agttcggtga aggaaatcag tgacatagtg cagaggtagc agcagtcagg   3900
ggtcaggtgt caggcccgtc ggagctgcct gcagcacatg cgggctcgcc catacccgtg   3960
acagtggctg acaagggact agtgagtcag caccttggcc caggagctct gcgccaggca   4020
gagctgaggg ccctgtggag tccagctcta ctacctacgt ttgcaccgcc tgccctcccg   4080
caccttcctc ctccccgctc cgtctctgtc ctcgaatttt atctgtggag ttcctgctcc   4140
gtggactgca gtcggcatgc caggacccgc cagccccgct cccacctagt gccccagact   4200
gagctctcca ggccaggtgg gaacggctga tgtggactgt ctttttcatt tttttctctc   4260
tggagcccct cctcccccgg ctgggcctcc ttcttccact tctccaagaa tggaagcctg   4320
aactgaggcc ttgtgtgtca ggccctctgc ctgcactccc tggccttgcc cgtcgtgtgc   4380
tgaagacatg tttcaagaac cgcatttcgg gaagggcatg cacgggcatg cacacggctg   4440
gtcactctgc cctctgctgc tgcccggggt ggggtgcact cgccatttcc tcacgtgcag   4500
gacagctctt gatttgggtg gaaaacaggg tgctaaagcc aaccagcctt tgggtcctgg   4560
gcaggtggga gctgaaaagg atcgaggcat ggggcatgtc ctttccatct gtccacatcc   4620
ccagagccca gctcttgctc tcttgtgacg tgcactgtga atcctggcaa gaaagcttga   4680
gtctcaaggg tggcaggtca ctgtcactgc cgacatccct cccccagcag aatggaggca   4740
ggggacaagg gaggcagtgg ctagtggggt gaacagctgg tgccaaatag ccccagactg   4800
ggcccaggca ggtctgcaag ggcccagagt gaaccgtcct ttcacacatc tgggtgccct   4860
gaaagggccc ttcccctccc ccactcctct aagacaaagt agattcttac aaggcccttt   4920
cctttggaac aagacagcct tcacttttct gagttcttga agcatttcaa agccctgcct   4980
ctgtgtagcc gccctgagag agaatagagc tgccactggg cacctgcgca caggtgggag   5040
gaaagggcct ggccagtcct ggtcctggct gcactcttga actgggcgaa tgtcttattt   5100
aattaccgtg agtgacatag cctcatgttc tgtgggggtc atcagggagg gttaggaaaa   5160
ccacaaacgg agcccctgaa agcctcacgt atttcacaga gcacgcctgc catcttctcc   5220
ccgaggctgc cccaggccgg agcccagata cgggggctgt gactctgggc agggacccgg   5280
ggtctcctgg accttgacag agcagctaac tccgagagca gtgggcaggt ggccgcccct   5340
gaggcttcac gccgggagaa gccaccttcc cacccccttca taccgcctcg tgccagcagc   5400
ctcgcacagg ccctagcttt acgctcatca cctaaacttg tactttattt ttctgataga   5460
aatggtttcc tctggatcgt tttatgcggt tcttacagca catcacctct ttgcccccga   5520
```

```
cggctgtgac gcagccggag ggaggcacta gtcaccgaca gcggccttga agacagagca   5580
aagcgcccac ccaggtcccc cgactgcctg tctccatgag gtactggtcc cttccttttg   5640
ttaacgtgat gtgccactat attttacacg tatctcttgg tatgcatctt ttatagacgc   5700
tcttttctaa gtggcgtgtg catagcgtcc tgccctgccc cctcgggggc ctgtggtggc   5760
tccccctctg cttctcgggg tccagtgcat tttgtttctg tatatgattc tctgtggttt   5820
tttttgaatc caaatctgtc ctctgtagta ttttttaaat aaatcagtgt ttacattaga   5880
a                                                                   5881
```

<210> SEQ ID NO 25
<211> LENGTH: 3543
<212> TYPE: DNA
<213> ORGANISM: Human

<400> SEQUENCE: 25

```
agaggtatgg tccttgggac agttctcctt ccacctaata cttatggcag agatcaggac     60
acttcacttt gctgcctgtg cactgaggcc tcagaatctg ctctacccga cttaacagaa    120
gctttgcatc gtccctatgg ttgtgatgtt gaaccccagg cactaaatga ggctatcagg    180
tggagctcca aggagaactt gctcggagcc actgagagtg accctaatct cttcgttgca    240
ctttatgatt ttgtagcaag tggtgataac acactcagca tcactaaagg tgaaaagcta    300
cgagtccttg gttacaacca gaatggtgag tggagtgaag ttcgctctaa gaatgggcag    360
ggctgggtgc caagcaacta catcacccca gtgaacagcc tggaaaaaca ctcctggtac    420
catggacctg tgtcacgcag tgcagctgag tatctgctca gcagtctaat caatggcagc    480
ttcctggtgc gagaaagtga gagtagccct gggcagctgt ccatctcgct caggtacgag    540
ggacgtgtgt atcactacag gatcaatacc actgcagatg gcaaggtgta tgtgactgct    600
gagagccgct tcagcacctt ggcagagctt gtacaccatc actccacagt ggctgatggg    660
ctggtgacaa cattacacta cccagcaccc aagtgtaata agcctacagt ctatggtgtg    720
tcccccatcc acgacaaatg ggaaatggag cgaacagata ttaccatgaa gcacaaactt    780
gggggcggtc agtatggaga ggtttacgtt ggcgtctgga agaaatacag ccttacagtt    840
gctgtgaaaa cattgaagga agataccatg gaggtagaag aattcctgaa agaagctgca    900
gtaatgaagg aaatcaagca tcctaatctg gtacaacttt taggtgtgtg tactttggag    960
ccaccatttt acattgtgac tgaatacatg ccatacggga atttgctgga ttacctccga   1020
gaatgcaacc gagaagaggt gactgcagtt gtgctgctct acatggccac tcagatttct   1080
tctgcaatgg agtacttaga gaagaagaat ttcatccata gagatcttgc agctcgtaac   1140
tgcctagtgg gagaaaacca tgtggtaaaa gtggctgact ttggcttaag tagattgatg   1200
actggagaca cttatactgc tcatgctgga gccaaatttc ctattaagtg gacagcacca   1260
gagagtcttg cctacaatac cttctcaatt aaatctgacg tctgggcttt tggggtattg   1320
ttgtgggaaa ttgctaccta tggaatgtca ccatatccag gtattgacct gtctcaggtc   1380
tatgacctac tagaaaaagg atatcgaatg gaacagcctg agggatgccc ccctaaggtt   1440
tatgaactta tgagagcatg ctggaagtgg agccctgccg ataggccctc ttttgctgaa   1500
acacaccaag cttttgaaac catgttccat gactccagca tttctgaaga ggtagctgag   1560
gagcttggga gagccgcctc ctcgtcatct gttgttccat acctgccccg gctacctata   1620
cttccttcca agactcggac actgaagaaa caggtggaga acaaggagaa cattgaaggg   1680
gcacaagatg ccacagaaaa ttctgcttcc agtttagcac cagggttcat cagaggtgca   1740
```

caggcctcta gtggatcccc agcactgcct cgaaagcaaa gagacaagtc acccagcagc 1800
ctcttggaag atgccaaaga gacatgcttc accagggata ggaagggggg cttcttcagc 1860
tccttcatga agaagagaaa tgctcctaca ccccccaaac gcagcagctc cttccgagaa 1920
atggagaatc agccccataa gaaatacgaa ctcacgggta acttctcatc tgttgcttct 1980
ctacagcatg ctgatgggtt ctctttcact cctgcccagc aagaggcgaa tctggtgcca 2040
cccaagtgct atggggggag ctttgcacag aggaacctct gtaatgacga cggtggtggg 2100
ggtgggggca gtggcactgc tgggggtggg tggtctggca tcacaggctt ctttacacca 2160
cgcttaatca aaaagacact gggcttacga gcaggtaaac ccacagccag tgatgacact 2220
tccaagcctt ttccaaggtc aaactctaca tcttccatgt cctcagggct tccagagcag 2280
gataggatgg caatgaccct tcccaggaac tgccagaggt ccaaactcca gctggaaagg 2340
acagtgtcca cctcttctca gccagaagag aatgtggaca gggccaatga catgcttcca 2400
aaaaaatcag aggaaagtgc tgctccaagc agggagagac caaaagccaa gttattgccc 2460
agaggagcca cagctcttcc tctcagaaca ccctctgggg atctagccat tacagagaag 2520
gaccctccag ggtgggagt ggctggagtg gcagctgccc ccaagggtaa agagaagaat 2580
ggtggggcac gacttgggat ggctggagtt ccagaggatg gagagcagcc gggctggcct 2640
tctccagcca aggctgcccc cgtcctccca accactcaca accacaaagt gccagtcctt 2700
atctcaccca ctctgaaaca cactccagct gacgtgcagc tcattggcac agactctcag 2760
gggaataaat tcaagctctt atctgagcat caggtcacat cctctggaga caaggaccga 2820
ccccgacggg taaaaccaaa gtgtgcccca cccccaccac cagtgatgag actactgcag 2880
catccgtcca tctgctcaga ccctacagaa gagccaactg ccctaactgc aggacagtcc 2940
acatcagaaa cacaggaagg aggaaagaag gcagctctgg gcgcagtgcc catcagtggg 3000
aaagctggga ggccagtgat gcctccacct caagtgcctc tgcccacatc ttccatctcg 3060
ccagccaaaa tggccaatgg cacagcaggt actaaagtgg ctctgagaaa aaccaaacag 3120
gccgctgaga aaatctcagc agacaaaatc agcaaagagg ccctgctgga atgtgctgac 3180
ctactgtcca gtgcactcac ggaacctgtg cccaacagcc agctggtaga cactggacac 3240
cagctgcttg actactgctc aggctatgtg gactgcatcc ctcaaactcg caacaaattt 3300
gccttccgag aggctgtgag caaactggaa ctcagcctgc aggagctaca ggtttcttca 3360
gcagctgctg gtgtgcccgg gacaaaccct gtccttaata acttattgtc atgtgtacag 3420
gaaatcagtg atgtggtgca gaggtagcca ctgttagcct ggtgggaaaa tgcacacatt 3480
tctgagggga gagggaaaag gacttgtttt cctgtgttct tgttttcaga aaatgaaaga 3540
ctc 3543

<210> SEQ ID NO 26
<211> LENGTH: 3840
<212> TYPE: DNA
<213> ORGANISM: Human

<400> SEQUENCE: 26
ggccttcccc ctgcgaggat cgccgttggc ccgggttggc tttggaaagc ggcggtggct 60
ttgggccggg ctcggcctcg ggaacgccag gggcccctgg gtgcggacgg gcgcggccag 120
gagggggtta aggcgcaggc ggcggcgggg cgggggcggg cctggcgggc gccctctccg 180 ggcccctttgt taacaggcgc gtcccggcca gcggagacgc ggccgccctg ggcgggcgcg 240
ggcggcgggc ggcggtgagg gcggcctgcg gggcggcgcc cgggggccgg gccgagccgg 300

-continued

```
gcctgagccg ggcccggacc gagctgggag aggggctccg gcccgatcgt tcgcttggcg    360
caaaatgttg gagatctgcc tgaagctggt gggctgcaaa tccaagaagg ggctgtcctc    420
gtcctccagc tgttatctgg aagaagccct tcagcggcca gtagcatctg actttgagcc    480
tcagggtctg agtgaagccg ctcgttggaa ctccaaggaa aaccttctcg ctggacccag    540
tgaaaatgac cccaaccttt tcgttgcact gtatgatttt gtggccagtg gagataacac    600
tctaagcata actaaaggtg aaaagctccg ggtcttaggc tataatcaca atggggaatg    660
gtgtgaagcc caaaccaaaa atggccaagg ctgggtccca agcaactaca tcacgccagt    720
caacagtctg gagaaacact cctggtacca tgggcctgtg tcccgcaatg ccgctgagta    780
tccgctgagc agcgggatca atggcagctt cttggtgcgt gagagtgaga gcagtcctag    840
ccagaggtcc atctcgctga gatacgaagg gagggtgtac cattacagga tcaacactgc    900
ttctgatggc aagctctacg tctcctccga gagccgcttc aacaccctgg ccgagttggt    960
tcatcatcat tcaacggtgg ccgacgggct catcaccacg ctccattatc cagccccaaa   1020
gcgcaacaag cccactgtct atggtgtgtc ccccaactac gacaagtggg agatggaacg   1080
cacggacatc accatgaagc acaagctggg cgggggccag tacggggagg tgtacgaggg   1140
cgtgtggaag aaatacagcc tgacggtggc cgtgaagacc ttgaaggagg acaccatgga   1200
ggtggaagag ttcttgaaag aagctgcagt catgaaagag atcaaacacc ctaacctagt   1260
gcagctcctt ggggtctgca cccgggagcc cccgttctat atcatcactg agttcatgac   1320
ctacgggaac ctcctggact acctgaggga gtgcaaccgg caggaggtga acgccgtggt   1380
gctgctgtac atggccactc agatctcgtc agccatggag tacctagaga agaaaaactt   1440
catccacaga gatcttgctg cccgaaactg cctggtaggg gagaaccact tggtgaaggt   1500
agctgatttt ggcctgagca ggttgatgac aggggacacc tacacagccc atgctggagc   1560
caagttcccc atcaaatgga ctgcacccga gagcctggcc tacaacaagt tctccatcaa   1620
gtccgacgtc tgggcatttg gagtattgct ttgggaaatt gctacctatg gcatgtcccc   1680
ttacccggga attgaccgtt cccaggtgta tgagctgcta gagaaggact accgcatgaa   1740
gcgcccagaa ggctgcccag agaaggtcta tgaactcatg cgagcatgtt ggcagtggaa   1800
tccctctgac cggccctcct ttgctgaaat ccaccaagcc tttgaaacaa tgttccagga   1860
atccagtatc tcagacgaag tggaaaagga gctggggaaa caaggcgtcc gtggggctgt   1920
gactaccttg ctgcaggccc cagagctgcc caccaagacg aggacctcca ggagagctgc   1980
agagcacaga gacaccactg acgtgcctga gatgcctcac tccaagggcc agggagagag   2040
cgatcctctg gaccatgagc ctgccgtgtc tccattgctc cctcgaaaag agcgaggtcc   2100
cccggagggc ggcctgaatg aagatgagcg ccttctcccc aaagacaaaa agaccaactt   2160
gttcagcgcc ttgatcaaga agaagaagaa gacagcccca acccctccca aacgcagcag   2220
ctccttccgg gagatggacg gccagccgga gcgcagaggg gccggcgagg aagagggccg   2280
agacatcagc aacggggcac tggctttcac cccccttggac acagctgacc cagccaagtc   2340
cccaaagccc agcaatgggg ctggggtccc caatggagcc ctccgggagt ccgggggctc   2400
aggcttccgg tctccccacc tgtggaagaa gtccagcacg ctgaccagca gccgcctagc   2460
caccggcgag gaggagggcg gtggcagctc cagcaagcgc ttcctgcgct cttgctccgt   2520
ctcctgcgtt ccccatgggg ccaaggacac ggagtggagg tcagtcacgc tgcctcggga   2580
cttgcagtcc acgggaagac agtttgactc gtccacattt ggagggcaca aaagtgagaa   2640
gccggctctg cctcggaaga gggcagggga gaacaggtct gaccaggtga cccgaggcac   2700
```

agtaacgcct ccccccaggc tggtgaaaaa gaatgaggaa gctgctgatg aggtcttcaa 2760
agacatcatg gagtccagcc cgggctccag cccgcccaac ctgactccaa aacccctccg 2820
gcggcaggtc accgtggccc ctgcctcggg cctcccccac aaggaagaag cctggaaagg 2880
cagtgcctta gggacccctg ctgcagctga gccagtgacc cccaccagca aagcaggctc 2940
aggtgcacca aggggcacca gcaagggccc cgccgaggag tccagagtga ggaggcacaa 3000
gcactcctct gagtcgccag ggagggacaa ggggaaattg tccaagctca aacctgcccc 3060
gccgccccca ccagcagcct ctgcagggaa ggctggagga aagccctcgc agaggcccgg 3120
ccaggaggct gccggggagg cagtcttggg cgcaaagaca aaagccacga gtctggttga 3180
tgctgtgaac agtgacgctg ccaagcccag ccagccggca gagggcctca aaaagcccgt 3240
gctcccggcc actccaaagc cacaccccgc caagccgtcg gggaccccca tcagcccagc 3300
ccccgttccc ctttccacgt tgccatcagc atcctcggcc ttggcagggg accagccgtc 3360
ttccactgcc ttcatccctc tcatatcaac ccgagtgtct cttcggaaaa cccgccagcc 3420
tccagagcgg gccagcggcg ccatcaccaa gggcgtggtc ttggacagca ccgaggcgct 3480
gtgcctcgcc atctctggga actccgagca gatggccagc cacagcgcag tgctggaggc 3540
cggcaaaaac ctctacacgt tctgcgtgag ctatgtggat tccatccagc aaatgaggaa 3600
caagtttgcc ttccgagagg ccatcaacaa actggagaat aatctccggg agcttcagat 3660
ctgcccggcg tcagcaggca gtggtccggc ggccactcag gacttcagca agctcctcag 3720
ttcggtgaag gaaatcagtg acatagtgca gaggtagcag cagtcagggg tcaggtgtca 3780
ggcccgtcgg agctgcctgc agcacatgcg ggctcgccca tacccatgac agtggctgag 3840

<210> SEQ ID NO 27
<211> LENGTH: 4220
<212> TYPE: DNA
<213> ORGANISM: Human

<400> SEQUENCE: 27
acgttgcccg ggatgcggac aggttccgcc gcctccagcg ccccatcctg agccgattat 60
ctgcaattat gaaatgaagt aactcaagat gagcaagtta aaagtgatac cagaaaaaag 120
ccttaccaat aattctagga tcgtaggact cctggctcaa ctggagaaga tcaatgctga 180
gccttcagaa tcagacactg cccgatatgt tacatcaaaa attcttcatc tggctcagag 240
tcaagaaaaa acaaggagag aaatgacagc caaaggttct acaggaatgg aaattctgct 300
gtcaacatta gagaacacaa aagatcttca aactacactt aatatcttaa gcattcttgt 360
tgagctggtg tcagctggtg gaggtcgaag agtgagtttc ttagtcacca aaggtggttc 420
acaaatattg ttgcagttac ttatgaatgc cagcaaagaa tctcccccac atgaggactt 480
aatggtacag attcattcta ttcttgcaaa gattggacca aaagataaaa aatttggagt 540
aaaggctaga attaatgggg ctctgaatat aaccctgaat ttggtcaagc agaatttgca 600
gaatcatcgc ttggttctac cttgccttca gcttttacga gtatattctg ccaactctgt 660
gaattcagta tccttaggga aaaatggagt tgtggaactg atgtttaaaa tcattggacc 720
atttagtaag aagaattcca gtcttataaa ggttgcttta gacactcttg ctgcattgct 780
aaaatcaaaa acaaatgcca ggagagctgt agacagagga tatgtccaag tgcttttaac 840
aatttatgta gattggcacc gccatgataa ccggcataga aacatgctca ttcggaaagg 900
aattttacgg agtttaaaaa gtgttacaaa catcaagttg ggaagaaaag catttattga 960
tgccaatggg atgaaaattc tgtataatac ttcgcaattg cctgttattc ctgtgactgg 1020

```
tcctgtggct cagctctaca gcttacctcc tgaagtggat gacgtagtag atgaaagtga   1080
tgacaacgat gatattgatg tagaagctga aaacgaaact gagaatgaag atgacctaga   1140
tcaaaatttt aagaatgatg atattgaaac agatattaac aaactaaaac cccagcaaga   1200
accgggacga acaatagaag atctaaaaat gtatgaacac cttttccctg agcttgttga   1260
tgattttcag gactatgatt taatctccaa agaaccaaag ccttttgtat ttgagggaaa   1320
agtacgtggt cctattgttg ttcctacggc aggcgaggga acatctggga attctggcaa   1380
tttaagaaaa gttgtaatga aggagaacat atcttctaaa ggagatgaag gtgaaaagaa   1440
gtctaccttt atggatctag caaaagaaga tattaaagat aatgatagaa cattacaaca   1500
gcagccaggt gatcaaaata gaactatttc atcagtccat ggtttaaaca atgatattgt   1560
aaaggccttg gaccgaatta cattgcagaa tattccttct caaacagccc caggttttac   1620
tgcagaaatg aagaaggact gcagtcttcc tcttactgtc cttacctgtg ctaaagcatg   1680
tccacacatg gctacttgtg gaaatgttct gtttgaggga agaacagttc agctagggaa   1740
gctttgctgc actggagttg gaactgaaga tgatgaagat actgagtcaa attcatcggt   1800
agaacaagca tcggttgaag tacctgatgg accaacactc catgacccag acctctatat   1860
tgagattgtg aaaaatacga agtctgtccc agaatattca gaggtggctt atcccgatta   1920
ttttggtcac attccgcctc cattcaaaga gcctatttta gaaaggcctt atggtgtaca   1980
aaggacaaaa attgctcaag atattgaaag gctaatacat cagagtgata tcatagatcg   2040
tgtggtatat gacttggata acccaaatta caccattcca gaagagggag atattttgaa   2100
atttaactcc aaatttgagt ctgggaatct gcgcaaagta attcaaatta gaaaaaatga   2160
atatgatctt attctgaact cagacataaa cagcaatcat tatcatcagt ggttttactt   2220
tgaagtcagt ggaatgcgac caggtgttgc ttacaggttt aacatcatta actgtgaaaa   2280
gtccaacagt cagtttaatt atggtatgca accactcatg tattcggttc aggaagcatt   2340
aaatgccaga ccatggtgga ttcgtatggg gactgacatt tgttactata aaaatcattt   2400
ctcaagaagt tcagttgctg caggtgggca aaagggaaaa tcctactata caattacatt   2460
tactgtcaat tttccacata aagatgatgt ttgctacttt gcttatcact atccatatac   2520
gtattcaact ttacagatgc atcttcaaaa attggaatca gcacacaatc ctcagcaaat   2580
ctattttcgg aaagatgtgt tatgtgaaac cctgtctgga aacagctgcc ccttggtgac   2640
tataacagca atgccagagt ctaattatta tgaacatatc tgccatttca gaaatcgccc   2700
ttacgttttc ttgtctgctc gggtacatcc tggagaaact aatgcaagtt gggttatgaa   2760
aggaacgttg gaatatctca tgagcaataa ccccactgct cagagcttac gagaatctta   2820
tatttttaaa attgtcccta tgttaaatcc agatggtgtc atcaatggaa atcatcgctg   2880
ttctttaagt ggagaggatt tgaataggca gtggcaaagt ccaagtccgg atttacatcc   2940
tacaatttac catgctaagg ggctgttgca atacttggct gcagtgaagc gtttaccctt   3000
ggtttattgt gattatcatg gccattcccg aaagaagaat gtatttatgt atggttgcag   3060
catcaaagag acagtgtggc ataccaatga taatgcaact tcatgtgatg ttgtggagga   3120
tacgggatac aggacattgc ctaagatact gagccatatc gccccagcat tttgcatgag   3180
cagctgtagc ttcgtagtgg aaaaatctaa agaatccaca gcacgtgttg tagtttggag   3240
ggaaatagga gtacaaagaa gttataccat ggagagtact ttatgtggct gtgatcaggg   3300
aaaatacaag ggtttacaga ttggtacccg agaactggaa gagatgggag caaaattttg   3360
tgttggtctt ttacgtttga aaagactgac ctctccattg gagtataatc tgccttccag   3420
```

cctgcttgac tttgaaaatg atttaattga atcaagctgc aaagtaacta gccctaccac 3480
ttatgtcttg gatgaagatg aacctcgatt ccttgaagaa gttgattaca gtgcagaaag 3540
taatgatgag ttagatattg agttggctga aaatgtagga gattatgaac cttctgctca 3600
agaagaagta ctttctgact ctgaattatc aagaacatac ctaccttgag cccgctgcca 3660
tctcttgtta actgcaaaga ataaatgaaa tatcttggtt tttatttccc aggaagcttg 3720
agagaaatga gtttatacag agctgactca aaaagacaaa aagtaacttg ggccagtttg 3780
gtttcaagat aataaatgtg ttattaatta atgataaaat tggcgcttgt tttattttcg 3840
atattcaatg cactttatgt agcattgaat gatcaaatat tggatttacc tttaaaaaaa 3900
aaaaacctga gtatcattgc atgaattttt atctccctat ggttatatcc tgcatcaagt 3960
ggataatttt gaagtgtgtt cagaatataa aattgaaatt ttagagttgt tgaaaatcct 4020
gacttgttga aaactaatat atatgtacat ggatttctat agatgtgttt gtttagaagt 4080
gggtagatat tgcagataag actgttcttc agaatcatgt taactattgg gttgtgactg 4140
aagtagtgca gggtttgcct tgaaaccatt acattctaca tttaccaaat taaacaaata 4200
aaaactgtat taaatgttgc 4220

<210> SEQ ID NO 28
<211> LENGTH: 3996
<212> TYPE: DNA
<213> ORGANISM: Human

<400> SEQUENCE: 28
gtgggcgggg cgccgcgctg acgttgcccg ggatgcggac aggttccgcc gcctccagcg 60
ccgccgccgc agctgccgcc gccgccgcct ccgcctcgcc tgccaccggg gtttgtatga 120
aaacaccggg cggcgggcgg cgagggatcc gccgtgatcc aggtgctgag ccgggtgctg 180
cggctctgcg cggtccccgc cagcgcccca tcctgagccg attatctgca attatgaaat 240
gaagtaactc aagatgagca agttaaaagt gataccagaa aaaagcctta ccaataattc 300
taggatcgta ggactcctgg ctcaactgga gaagatcaat gctgagcctt cagaatcaga 360
cactgcccga tatgttacat caaaaattct tcatctggct cagagtcaag aaaaaacaag 420
gagagaaatg acagccaaag gttctacagg aatggaaatt ctgctgtcaa cattagagaa 480
cacaaaagat cttcaaacta cacttaatat cttaagcatt cttgttgagc tggtgtcagc 540
tggtggaggt cgaagagtga gtttcttagt caccaaaggt ggttcacaaa tattgttgca 600
gttacttatg aatgccagca aagaatctcc cccacatgag gacttaatgg tacagattca 660
ttctattctt gcaaagattg gaccaaaaga taaaaaattt ggagtaaagg ctagaattaa 720
tggggctctg aatataaccc tgaatttggt caagcagaat ttgcagaatc atcgcttggt 780
tctaccttgc cttcagcttt tacgagtata ttctgccaac tctgtgaatt cagtatcctt 840
agggaaaaat ggagttgtgg aactgatgtt taaaatcatt ggaccattta gtaagaagaa 900
ttccagtctt ataaaggttg ctttagacac tcttgctgca ttgctaaaat caaaaacaaa 960
tgccaggaga gctgtagaca gaggatatgt ccaagtgctt ttaacaattt atgtagattg 1020
gcaccgccat gataaccggc atagaaacat gctcattcgg aaaggaattt tacagagttt 1080
aaaaagtgtt acaaacatca agttgggaag aaaagcattt attgatgcca atgggatgaa 1140
aattctgtat aatacttcgc aattgcctgt tattcctgtg actggtcctg tggctcagct 1200
ctacagctta cctcctgaag tggatgacgt agtagatgaa agtgatgaca acgatgatat 1260
tgatgtagaa gctgaaaacg aaactgagaa tgaagatgac ctagatcaaa attttaagaa 1320

-continued

```
tgatgatatt gaaacagata ttaacaaact aaaaccccag caagaaccgg gacgaacaat   1380
agaagatcta aaaatgtatg aacacctttt ccctgagctt gttgatgatt ttcaggacta   1440
tgatttaatc tccaaagaac caaagccttt tgtatttgag ggaaaagtac gtggtcctat   1500
tgttgttcct acggcaggcg aggaaacatc tgggaattct ggcaatttaa gaaaagttgt   1560
aatgaaggag aacatatctt ctaaaggaga tgaaggtgaa aagaagtcta cctttatgga   1620
tctagcaaaa gaagatatta aagataatga tagaacatta caacagcagc caggtgatca   1680
aaatagaact atttcatcag tccatggttt aaacaatgat attgtaaagg ccttggaccg   1740
aattacattg cagaatattc cttctcaaac agccccaggt tttactgcag aaatgaagaa   1800
ggactgcagt cttcctctta ctgtccttac ctgtgctaaa gcatgtccac acatggctac   1860
ttgtggaaat gttctgtttg agggaagaac agttcagcta gggaagcttt gctgcactgg   1920
agttgaaact gaagatgatg aagatactga gtcaaattca tcggtagaac aagcatcggt   1980
tgaagtacct gatggaccaa cactccatga cccagacctc tatattgaga ttgtgaaaaa   2040
tacgaagtct gtcccagaat attcagaggt ggcttatccc gattattttg gtcacattcc   2100
gcctccattc aaagagccta ttttagaaag gccttatggt gtacaaagga caaaaaattgc   2160
tcaagatatt gaaaggctaa tacatcagag tgatatcata gatcgtgtgg tatatgactt   2220
ggataaccca aattacacca ttccagaaga gggagatatt ttgaaattta actccaaatt   2280
tgagtctggg aatctgcgca aagtaattca aattagaaaa aatgaatatg atcttattct   2340
gaactcagac ataaacagca atcattatca tcagtggttt tactttgaag tcagtggaat   2400
gcgaccaggt gttgcttaca ggtttaacat cattaactgt gaaaagtcca acagtcagtt   2460
taattatggt atgcaaccac tcatgtattc ggttcaggaa gcattaaatg ccagaccatg   2520
gtggattcgt atggggactg acatttgtta ctataaaaat catttctcaa gaagttcagt   2580
tgctgcaggt gggcaaaagg gaaaatccta ctatacaatt acatttactg tcaattttcc   2640
acataaagat gatgtttgct actttgctta tcactatcca tatacgtatt caactttaca   2700
gatgcatctt caaaaattgg aatcagcaca caatcctcag caaatctatt ttcggaaaga   2760
tgtgttatgt gaaaccctgt ctggaaacag ctgccccttg gtgactataa cagcaatgcc   2820
agagtctaat tattatgaac atatctgcca tttcagaaat cgcccttacg ttttcttgtc   2880
tgctcgggta catcctggag aaactaatgc aagttgggtt atgaaaggaa cgttggaata   2940
tctcatgagc aataacccca ctgctcagag cttacgagaa tcttatattt ttaaaattgt   3000
ccctatgtta aatccagatg gtgtcatcaa tggaaatcat cgctgttctt taagtggaga   3060
ggatttgaat aggcagtggc aaagtccaag tccggattta catcctacaa tttaccatgc   3120
taaggggctg ttgcaatact tggctgcagt gaagcgttta cccttggttt attgtgatta   3180
tcatggccat tcccgaaaga agaatgtatt tatgtatggt tgcagcatca aagagacagt   3240
gtggcatacc aatgataatg caacttcatg tgatgttgtg gaggatacgg gatacaggac   3300
attgcctaag atactgagcc atatcgcccc agcattttgc atgagcagct gtagcttcgt   3360
agtggaaaaa tctaaagaat ccacagcacg tgttgtagtt tggagggaaa taggagtaca   3420
aagaagttat accatggaga gtactttatg tggctgtgat cagggaaaat acaagggttt   3480
acagattggt acccgagaac tggaagagat gggagcaaaa ttttgtgttg gtcttttacg   3540
tttgaaaaga ctgacctctc cattggagta taatctgcct tccagcctgc ttgactttga   3600
aaatgattta attgaatcaa gctgcaaagt aactagccct accacttatg tcttggatga   3660
agatgaacct cgattccttg aagaagttga ttacagtgca gaaagtaatg atgagttaga   3720
```

-continued

```
tattgagttg gctgaaaatg taggagatta tgaaccttct gctcaagaag aagtactttc   3780
tgactctgaa ttatcaagaa catacctacc ttgagcccgc tgccatctct tgttaactgc   3840
aaagaataaa tgaaatatct tggtttttat ttcccaggaa gcttgagaga aatgagttta   3900
tacagagctg actcaaaaag acaaaaagta acttgggcca gtttggtttc aagataataa   3960
atgtgttatt aattaatgat aaaaaaaaaa aaaaaa                             3996
```

<210> SEQ ID NO 29
<211> LENGTH: 3411
<212> TYPE: DNA
<213> ORGANISM: Human

<400> SEQUENCE: 29

```
cttctcttgt gtaatcagct gcctatttgg aaattgggca gggtttgcga ctggatgcta     60
atgtcactga ctagttttca gcctaccatc cagaagtaac atgttcccag ctttggaaac    120
gcacctaaag cagactattc ctgatcctta tgaagacttt atgtaccgtc acctccaata    180
ttatggctac tttaaagctc agagaggcag tttaccaaac tctgctacgc atcagcatgt    240
tcggaagaat aaccctcaat gcctgttgaa tggctctctt ggggaaaaag atgatttgat    300
accagacacc ctgcaaaagg agaagcttct atggcctatc agtttatctt cagctgtgca    360
cagacagata gaagccatca acagagactt tcactcttgc ctgggctgga tgcagtggcg    420
cggcctcagc tcactgcaac ctccacctcc cagattcaag gattctcctg cctcagcttt    480
ccgagtagct gggattacag attcacatat gctgagttta ccacatctta ggagcagaca    540
gcttctttat gatgagttgg atgaagtaaa cccacgtctt cgagaacccc aagagctctt    600
ttccattttg tctaccaaga ggccactgca ggctccaaga tggccaattg aatgtgaggt    660
catcaaggaa aacatccatc atattgagtg ggctccacct caaccagaat atttctatca    720
gcctaaagga aatgaaaagg taccagagat tgtaggagag aaaaaaggaa cagttgtcta    780
tcaattagat tcagtgccta tagaaggttc ctattttacc agttccagag tgggaggcaa    840
acgaggaatt gtcaaggaac ttgctgtcac gttgcaagga ccagaagata atactctact    900
gtttgaatca aggtttgaga gtgggaatct gcaaaaagct gtcagagtag acacctatga    960
gtatgaactc accttgcgaa ctgacctcta cactaacaaa cacactcagt ggttttattt   1020
tcgtgttcag aacaccagaa aagatgctac ctatcgcttc accattgtca acttgctaaa   1080
acccaagagt ctttatactg tagggatgaa gccactcttg tactcccaat tggatgccaa   1140
cacccgcaat attggctgga ggagagaagg aaatgaaatc aagtactaca agaacaacac   1200
ggatgatggg cagcagccct tctactgtct cacgtggacc attcagtttc catatgacca   1260
ggacacttgc ttctttgcac acttctaccc atatacatac actgatttgc aatgctacct   1320
cctgtcagtg gcaaacaacc ctatccagtc tcagttctgc aagctccaaa ctttatgcag   1380
gagcctagca ggaaataccg tttacttgct caccatcacc aacccatccc agaccccctca   1440
agaggcagct gcaaagaaag ctgtggtctt gagtgccaga gttcaccctg gagaaagtaa   1500
tggctcctgg gttatgaaag gcttttttgga cttcatcctt agcaactccc cagatgccca   1560
gctcctcaga gatatttttg tcttcaaggt gcttcccatg ttaaatccag atggtgtgat   1620
tgtggggaat tatcggtgtt ccttggccgg aagggatttg aacaggcatt ataaaaccat   1680
tctgaaggag tctttccctt gtatttggta caccaggaac atgatcaaaa gacttcttga   1740
agaaagagag gttctgttgt attgtgattt ccatggccac agtcgtaaga ataatatctt   1800
cctgtatggc tgtaataaca acaatcgcaa atactggctt catgaacgag tctttccttt   1860
```

aatgttatgc aaaaatgcac cagataagtt ctcttttcac agttgtaatt ttaaggtcca 1920
aaaatgcaaa gaaggaacag gacgagttgt tatgtggcgg atgggaatcc taaacagcta 1980
caccatggag tctacctttg gcgggtccac cctgggtaat aaaagagaca cccactttac 2040
catcgaagat ctgaagtcct taggttatca tgtctgtgac acccttctgg acttttgtga 2100
tcctgaccaa atgaagttca ctcagtgtct agcagagctt aaggagcttt tacgacagga 2160
aatccacaag aaattccatg aacttggaca agatgtagat ttagaaggaa gttggagtga 2220
catctctttg tctgacattg aatccagcac cagtggctct gacagttctc tctcagatgg 2280
tcttcctgtt cacctagcaa acatagcaga tgagctgact cagaaaaaga agatgtttaa 2340
gaagaaaaaa aagaagtcac ttcagactag gaaacagcga aatgagcagt atcagaaaaa 2400
aaatttgatg cagaagttaa agttaacaga agatacctca gaaaaggcag gatttgcttc 2460
tactctgcaa aagcagccaa cctttttcaa aaactcagag aattccagtt ttttaccaat 2520
gaaaaatgaa aacccaaggt taaatgagac aaatttaaat agaagagaca aagacacccc 2580
cctggaccca tcaatggcca ccctgattct gcctaagaat aaagggagaa tgcagaataa 2640
gaagccaggc tttacagtat catgctctcc aaagagaacc ataaactcca gccaagagcc 2700
agctccaggt atgaagccaa actggcctag gagcagatat cctgccacaa agagaggctg 2760
tgctgccatg gcggcatacc catccttgca catatacaca tacccgtagg tgagcctggg 2820
ctgtgccaca caagcacttc atcgggggtt ttgagattag acacatttta taatggggga 2880
gatgtatgac tgggaactgc atttacttgt ggtatactgt gttgtgcact catgcactga 2940
ccttacactt tgtacttaca ctgtgggcat gtggtcaaga tgcatacctc atgaattcaa 3000
ctattttttc ataaaatgaa attttattat gatgtgtaaa aatgctttat cagaaactga 3060
agtgtgttct catggcacac ttcatggcag cacagatata cctcatttta accaatagat 3120
attctctcta aaattatgtg caaatcaatt tttaaaaatc aaaatctatg ttaaacacat 3180
tttggcagtg tgctataata aaaaaaagtg ttgtgtcaaa gctttctagt gacggtcagt 3240
cctactgctg tatgtcaggt ttgctcacaa tgaggtattc ccacatagaa ataacaatgc 3300
atgtattacc cagaatttaa tgttgcgtac cttatgttca atgaggtttt gtaatttttt 3360
taggctgatg attaaaattc tttctctcta aaaaaaaaaa aaaaaaaaaa a 3411

<210> SEQ ID NO 30
<211> LENGTH: 3635
<212> TYPE: DNA
<213> ORGANISM: Human

<400> SEQUENCE: 30
ggggcctcac agaaggcggt ggcgggcggg tgcagcgagt ttgtcccctt gcccgcacac 60
tgcttggcct ctgtacttaa gtgcggtggc cgcctgcctc gctggagctt ctctgccgca 120
gccatccgtg ctgcttggga cgggccgggg cgcgaaggcg gtcgcatcca tcgctctgcc 180
ctcctgcttc tcttgtgtaa tcagctgcct atttggaaat tgggcagggt ttgcgactgg 240
atgctaatgt cactgactag ttttcagcct accatccaga agtaacatgt tcccagcttt 300
ggaaacgcac ctaaagcaga ctattcctga tccttatgaa gactttatgt accgtcacct 360
ccaatattat ggctacttta aagctcagag aggcagttta ccaaactctg ctacgcatca 420
gcatgttcgg aagaataacc ctcaatgcct gttgaatggc tctcttgggg aaaaagatga 480
tttgatacca gacaccctgc aaaaggagaa gcttctatgg cctatcagtt tatcttcagc 540
tgtgcacaga cagatagaag ccatcaacag agactttcac tcttgcctgg gctggatgca 600

-continued

```
gtggcgcggc ctcagctcac tgcaacctcc acctcccaga ttcaaggatt ctcctgcctc    660
agctttccga gtagctggga ttacagattc acatatgctg agtttaccac atcttaggag    720
cagacagctt ctttatgatg agttggatga agtaaaccca cgtcttcgag aaccccaaga    780
gctcttttcc attttgtcta ccaagaggcc actgcaggct ccaagatggc caattgaatg    840
tgaggtcatc aaggaaaaca tccatcatat tgagtgggct ccacctcaac cagaatattt    900
ctatcagcct aaaggaaatg aaaaggtacc agagattgta ggagagaaaa aaggaacagt    960
tgtctatcaa ttagattcag tgcctataga aggttcctat tttaccagtt ccagagtggg   1020
aggcaaacga ggaattgtca aggaacttgc tgtcacgttg caaggaccag aagataatac   1080
tctactgttt gaatcaaggt ttgagagtgg gaatctgcaa aaagctgtca gagtagacac   1140
ctatgagtat gaactcacct tgcgaactga cctctacact aacaaacaca ctcagtggtt   1200
ttattttcgt gttcagaaca ccagaaaaga tgctacctat cgcttcacca ttgtcaactt   1260
gctaaaaccc aagagtcttt atactgtagg gatgaagcca ctcttgtact cccaattgga   1320
tgccaacacc cgcaatattg gctggaggag agaaggaaat gaaatcaagt actacaagaa   1380
caacacggat gatgggcagc agcccttcta ctgtctcacg tggaccattc agtttccata   1440
tgaccaggac acttgcttct ttgcacactt ctacccatat acatacactg atttgcaatg   1500
ctacctcctg tcagtggcaa acaaccctat ccagtctcag ttctgcaagc tccaaacttt   1560
atgcaggagc ctagcaggaa ataccgttta cttgctcacc atcaccaacc catcccagac   1620
ccctcaagag gcagctgcaa agaaagctgt ggtcttgagt gccagagttc accctggaga   1680
aagtaatggc tcctgggtta tgaaaggctt tttggacttc atccttagca actccccaga   1740
tgcccagctc ctcagagata tttttgtctt caaggtgctt cccatgttaa atccagatgg   1800
tgtgattgtg gggaattatc ggtgttcctt ggccggaagg gatttgaaca ggcattataa   1860
aaccattctg aaggagtctt tcccttgtat ttggtacacc aggaacatga tcaaaagact   1920
tcttgaagaa agagaggttc tgttgtattg tgatttccat ggccacagtc gtaagaataa   1980
tatcttcctg tatggctgta ataacaacaa tcgcaaatac tggcttcatg aacgagtctt   2040
tcctttaatg ttatgcaaaa atgcaccaga taagttctct tttcacagtt gtaattttaa   2100
ggtccaaaaa tgcaaagaag gaacaggacg agttgttatg tggcggatgg gaatcctaaa   2160
cagctacacc atggagtcta cctttggcgg gtccaccctg ggtaataaaa gagacaccca   2220
ctttaccatc gaagatctga agtccttagg ttatcatgtc tgtgacaccc ttctggactt   2280
ttgtgatcct gaccaaatta agttcactca gtgtctagca gagcttaagg agcttttacg   2340
acaggaaatc cacaagaaat tccatgaact tggacaagat gtagatttag aaggaagttg   2400
gagtgacatc tctttgtctg acattgaatc cagcaccagt ggctctgaca gttctctctc   2460
agatggtctt cctgttcacc tagcaaacat agcagatgag ctgactcaga aaaagaagat   2520
gtttaagaag aaaaaaaaga agtcacttca gactaggaaa cagcgaaatg agcagtatca   2580
gaaaaaaaat ttgatgcaga agttaaagtt aacagaagat acctcagaaa aggcaggatt   2640
tgcttctact ctgcaaaagc agccaacctt tttcaaaaac tcagagaatt ccagtttttt   2700
accaatgaaa aatgaaaacc caaggttaaa tgagacaaat ttaaatagaa gagacaaaga   2760
caccccccctg gacccatcaa tggccaccct gattctgcct aagaataaag ggagaatgca   2820
gaataagaag ccaggcttta cagtatcatg ctctccaaag agaaccataa actccagcca   2880
agagccagct ccaggtatga agccaaactg gcctaggagc agatatcctg ccacaaagag   2940
aggctgtgct gccatggcgg catacccatc cttgcacata tacacatacc cgtaggtgag   3000
```

```
cctgggctgt gccacacaag cacttcatcg ggggttttga gattagacac attttataat   3060
gggggagatg tatgactggg aactgcattt acttgtggta tactgtgttg tgcactcatg   3120
cactgacctt acactttgta cttacactgt gggcatgtgg tcaagatgca tacctcatga   3180
attcaactat tttttcataa aatgaaattt tattatgatg tgtaaaaatg ctttatcaga   3240
aactgaagtg tgttctcatg gcacacttca tggcagcaca gatatacctc attttaacca   3300
atagatattc tctctaaaat tatgtgcaaa tcaattttta aaaatcaaaa tctatgttaa   3360
acacattttg gcagtgtgct ataataaaaa aaagtgttgt gtcaaagctt tctagtgacg   3420
gtcagtccta ctgctgtatg tcaggtttgc tcacaatgag gtattcccac atagaaataa   3480
caatgcatgt attacccaga atttaatgtt gcgtacctta tgttcaatga ggttttgtaa   3540
tttttttagg ctgatgatta aaattctttc tctctaaaaa aaaaaaaaaa aaaaaaaaaa   3600
aaaaaaaaaa aaaaaaaaga aaaaaaaaaa aaaaa                              3635
```

<210> SEQ ID NO 31
<211> LENGTH: 1869
<212> TYPE: DNA
<213> ORGANISM: Human

<400> SEQUENCE: 31

```
ctcaagaggc agctgcaaag aaagctgtgg tcttgagtgc cagagttcac cctggagaaa     60
gtaatggctc ctgggttatg aaaggctttt tggacttcat ccttagcaac tccccagatg    120
cccagctcct cagagatatt tttgtcttca aggtgcttcc catgttaaat ccagatggtg    180
tgattgtggg gaattatcgg tgttccttgg ccggaaggga tttgaacagg cattataaaa    240
ccattctgaa ggagtctttc ccttgtattt ggtacaccag gaacatgatc aaaagttctc    300
ttttcacagt tgtaatttta aggtccaaaa atgcaaagaa ggaacaggac gagttgttat    360
gtggcggatg ggaatcctaa acagctacac catggagtct acctttggcg ggtccaccct    420
gggtaataaa agagacaccc actttaccat cgaagatctg aagtccttag gttatcatgt    480
ctgtgacacc cttctggact tttgtgatcc tgaccaaatt aagttcactc agtgtctagc    540
agagcttaag gagcttctac gacaggaaat ccacaagaaa ttccatgaac ttggacaaga    600
tgtagattta gaaggaagtt ggagtgacat ctctttgtct gacattgaat ccagcaccag    660
tggctctgac agttctctct cagatggtct tcctgttcac ctagcaaaca tagcagatga    720
gctgactcag aaaaagaaga tgtttaagaa gaaaaaaaag aagtcacttc agactaggaa    780
acagcgaaat gagcagtatc agaaaaaaaa tttgatgcag aagttaaagt taacagaaga    840
tacctcagaa aaggcaggat ttgcttctac tctgcaaaag cagccaacct tttcaaaaa     900
ctcagagaat tccagttttt taccaatgaa aaatgaaaac ccaaggttaa atgagacaaa    960
tttaaataga agagacaaag acacccccct ggacccatca atggccaccc tgattctgcc   1020
taagaataaa gggagaatgc agaataagaa gccaggcttt acagtatcat gctctccaaa   1080
gagaaccata aactccagcc aagagccagc tccaggtatg aagccaaact ggcctaggag   1140
cagatatcct gccacaaaga gaggctgtgc tgccatggcg gcatacccat ccttgcacat   1200
atacacatac ccgtaggtga gcctgggctg tgccacacaa gcacttcatc gggggttttg   1260
agattagaca cattttataa tgggggagat gtatgactgg gaactgcatt tacttgtggt   1320
atactgtgtt gtgcactcat gcactgacct tacactttgt acttacactg tgggcatgtg   1380
gtcaagatgc atacctcatg aattcaacta tttttcata aaatgaaatt ttattatgat    1440
gtgtaaaaat gctttatcag aaactgaagt gtgttctcat ggcacacttc atggcagcac   1500
```

-continued agatatacct cattttaacc aatagatatt ctctctaaaa ttatgtgcaa atcaattttt 1560
aaaaatcaaa atctatgtta aacacatttt ggcagtgtgc tataataaaa aaaagtgttg 1620
tgtcaaagct ttctagtgac ggtcagtcct actgctgtat gtcaggtttg ctcacaatga 1680
ggtattccca catagaaata acaatgcatg tattacccag aatttaatgt tgcgtacctt 1740
atgttcaatg aggttttgta attttttag gctgatgatt aaaattcttt ctctctaaaa 1800
aaaaaaaaaa aaaaaaaaaa aaaaaaaaaa aaaaaaaaaa aaaaaaaaaa aaaaaaaaaa 1860
aaaaaaaaa 1869

<210> SEQ ID NO 32
<211> LENGTH: 2995
<212> TYPE: DNA
<213> ORGANISM: Human

<400> SEQUENCE: 32
ggctgatgac gagagttggg agtgtggctg gggctgcgga tctccagcag tggcgttact 60
tctagcggct ggataccggg ttctccgcga gatcccgaga tattctcccc gcacggaagc 120
gacgactggc ctggccagag gactcgcgtg ggagcgaggt gccggccccg acaggacggt 180
gagcctaccc gtatattaca agaaatctca agtcaaacac tggaaaagat gtcagaagat 240
tcagaaaagg aagactattc agacagaaca atcagtgatg aagatgaatc ggatgaggat 300
atgttcatga aatttgtaag tgaagatctt catcggtgtg cacttttaac agctgactct 360
tttggtgatc ccttcttccc ccggactaca cagatactat tagaatatca gctagggaga 420
tgggtgccac gtcttcgtga accaagggat ttatatggtg tctcttcttc tggtccattg 480
agcccaacac ggtggccata ccattgtgaa gtcatcgatg aaaaagtcca gcatattgat 540
tggactcctt cttgtcctga gccagtgtat atcccaacgg gcttagaaac gcaacccctt 600
tatccagact ccaaggaagc tactgtggtt tatctagctg aagatgctta caaagagccc 660
tgttttgtgt attcccgagt tgggggtaac cgaacacctt tgaagcagcc tgtggattac 720
cgtgacaata ctttgatgtt tgaagcaagg tttgagagtg gtaatctaca gaaggtagtc 780
aaagtggcag aatacgaata ccaattgact gtacgccctg acctcttcac aaataaacac 840
acccagtggt actatttcca agtcactaat atgcgagcag gaatagtcta cagattcact 900
attgtcaact tcaccaaacc tgctagtctt tacagtcggg gtatgcgccc actgttctat 960
tctgaaaaag aggccaaggc tcatcacatt ggctggcaga gaataggaga ccaaatcaag 1020
tattatagga acaacccagg ccaagatggg cgccattatt tctctcttac atggacattt 1080
caatttccac acaacaaaga tacctgctac tttgctcatt gctatccata cacttacacc 1140
aacctgcaag aataccttc tggcatcaat aatgatccag tacggtcaaa gttttgtaaa 1200
atacgtgttt tgtgccacac gcttgctagg aacatggtgt atattttaac aatcactacc 1260
cccttgaaga actctgactc aagaaagcgg aaggctgtga ttctgactgc aagggtccat 1320
ccaggggaaa ccaacagctc ttggatcatg aaaggcttcc tagattatat tttaggaaac 1380
tcaagtgatg cacagttgct tcgggacact tttgtcttca aggtggtacc catgctgaat 1440
ccagatggtg tgattgtggg aaattatcgc tgttccttag ctggacggga tttaaaccgt 1500
aattatacat ctctcctgaa ggaatctttt ccttctgtat ggtataccg gaacatggtt 1560 catagactga tggagaaacg agaggttata ttatactgtg atcttcatgg ccatagtagg 1620
aaagagaaca tcttcatgta tggctgtgat ggtagtgaca gatctaagac attatactta 1680
cagcaacgaa tcttcccact tatgctaagc aaaaattgtc cagataaatt ttcattctca 1740
gcttgcaagt ttaatgtcca gaagagcaaa gaaggaacag gaagggtggt aatgtggaaa 1800
atgggaatca ggaacagctt taccatggag gccaccttct gtggatctac tctgggtaac 1860
aaacgaggca ctcatttcag cacgaaagac ctggaatcaa tgggatatca tttttgtgat 1920
tctctcttgg attattgtga tcccgaccgg accaagtatt atcggtgcct gaaagaatta 1980
gaagaaatgg aaagacatat aaccctggaa aaagtctttg aggattcaga cacacctgtg 2040
atagacatta cattggatgt agagtctaga gaactgacat ttttattgag atgacacaaa 2100
agcagtataa taaaaggtaa tgaataataa ctggaaaatt caatgccaca ggaatatagt 2160
tggaagaaag aatgtactaa ttttataagc tcccacttat agtagccgag gctctgacag 2220
ttcagaatcc attgactctc tgacttacct tctcaagtta acttctcaga aaaaacattt 2280
gaaaacaaag aaggaaagga attctaccat agcaagccac caaaatgcca gaggacaaga 2340
ggtttatgat agagggcatt tgctgcaaag acacacacaa tcaaattctg atgtgaaaga 2400
tacaaggcca aatgaaccag atgattatat ggttgattat ttcagaagac aattacctaa 2460
tcaaggtttg gatctgcacc acaacttaaa aagcaaaata aaagaatgca tatctttcca 2520
aagcaagaag actggcataa attggacaga tgatgaaaaa agaagctaca aggataaagg 2580
aatagttcaa actcaagaaa tattgcagta tttgctcccc atcgtgcata gcactaaaaa 2640
catgcaaacc actcagataa aacagctatt caatccaaga accaacttcc aaatccaaca 2700
tcagtaagtc aatacaattt tatcactctt atctatttaa cacatctttt ttaaaaaagc 2760
agggcttatt aatttattat cctacgaaaa aaaaatctgc tcttgaaaat gatgtcagct 2820
ccatcacatt tggcaaagaa caaagaccca aagctgtcag aaaacactgg ataaatgaag 2880
gagtaagtta tcaggcctta tttaattgat tatttgcatg aaactactca ttaatttaga 2940
tctattaata aagtaggcat aaataaaaaa aaaaaaaaga aaaaaaaaaa aaaaa 2995

<210> SEQ ID NO 33
<211> LENGTH: 3938
<212> TYPE: DNA
<213> ORGANISM: Human

<400> SEQUENCE: 33
accgagaaga agatatttac cagtttgctt actgctaccc atatacatac actcgcttcc 60
aacattacct tgacagcctg caaaagagaa acatggatta cttctttcgg gagcagctgg 120
gccagagtgt gcaacaacga aagcttgacc tcctgacgat aaccagccct gacaatctcc 180
gggaaggggc agagcagaag gtggtattca tcacaggacg agtccaccca ggggaaacac 240
cctcatcatt tgtgtgccaa gggatcattg acttccttgt aagccagcac cctattgcct 300
gtgtcctccg ggaatacctg gtcttcaaga tcgcaccaat gctcaatcct gatggagtct 360
acctgggcaa ttacaggtgt tctctgatgg gatttgatct gaatcgtcac tggctggatc 420
cctctccatg ggtccatcct accctgcatg gagtgaaaca actcatcgtc cagatgtaca 480
acgacccaaa aacaagcctg gagttttata ttgacatcca tgcccactcc accatgatga 540
atggcttcat gtatggcaac atctttgagg atgaggaacg gttccagagg caggccattt 600
ttcccaagct cctctgccag aatgctgagg acttctccta ttccagcaca ccctttaacc 660
gggacgctgt gaaagcagga actggccgtc gcttcctcgg tggactcctg gaccacactt 720
cctattgcta caccctagag gtctccttct acagctacat catcagtggc accacggctg 780
ctgtgcccta cactgaagaa gcctgtatcc ttagtcccca cccagccttg ggccagccct 840
catccagccg agagtatcca agtctgacag gtcaggaatt aggcccccag ctcaggtaag 900

-continued

```
ggctgagact ctcaggtgag gatggaggtg cttcttcttc tggtggcgtc tttggattgt    960
ccagtttgcc tcagccctta gtatgatact cctaccccaa ttgccatgct ccaaatcttt   1020
cccaggccag ccggacccat ggcctgccca tatcttactc tgcttccatc tctctcccct   1080
ctcttctctc atgatgcagt gagtctcctg ccatctaagc tatgcaagtc cacaggctgg   1140
atgaccatcc ccagggttgc tgaggaagag cttgatgatc ttgactcctt ctaaccctga   1200
acatacaaaa acatatgttc tcttttcatc ttttgtctaa cctatcctct cccactttct   1260
cttccctcta ctcactattt ccccttctac ttacttttct caccccttgtt ccctctcctt   1320
ctatgccctc ctcctccctc ctcacctgtc ctgtgcttct ctttccttac ttctttttcc   1380
ccctcctccc ctcctttctg tcctctctct catcccatcc tcctttttctt tctctcctct   1440
ttgcctgtct tctgtcttcc ttgtctttcc cctctcatcc tctgtgcatc tttctctctg   1500
cctttgcatt tcctttgaca aattcctttt cctcttagtt tcttcataaa atttctctga   1560
aaactccaaa gccttccatg atgaaattag aagttatttt ctagtttgcc taattttta    1620
aggattaggt agtaactcta gtttcccgag tgttgatttt aatatcaagg tcactgcatc   1680
agagctgtaa cagatcgtgg cagattctgc tttccttgat cctttgtttt cgggttgatc   1740
tatgtctcct ttcctaacac ttagttttct cagagaagtg gagggaggag gaaggaactt   1800
tagatgaaat gaactctgta tttctgcaaa ttccccctcc ctggaggtag aagtgctctt   1860
ttagcatttt ttcaaccctt ggtgagtgtt tatggaattc ctctgtgcag ggaaacatct   1920
tttctgaacg tggcatgact tagggctagt cccaccagcc aactgcaact tagtggctct   1980
gtttgtatgt gtgtttggga gggttggggg tatggtgtcc aggtaccttg ccaggaacat   2040
cggaagtagg gcaatggccc tagaaggagg ggctgtcagg gggtaggcca ggtgttagag   2100
caatgttcca catcctgttg gacacagaga tattatgatt ggaactgaga gttccctatg   2160
tacagtcatc aagactgagg gtcatcttgc agtctgcttt aatacccacc tgactcagca   2220
aggccaaggg agtaggctct gctctgagga agagggtctg tgggttccaa agtcctggcc   2280
acctgttatg tgccacattg cccctcttca tgccccatac acaccttaga tgatgcatat   2340
ggcctatgcc ttctccagaa tctgctaact cctataacac atgcatatgc ttcattccac   2400
attgtacttg ctttgctctc ccataatatt atggcaaagg gacagagagc tgcctggaat   2460
aagagtttga gcttgtgcac taaaggggat tctgcaaccc ttattcatag tgagatgagg   2520
gtccctccag aggaggcctg cccttagttt gttgtttttt gctgtccaat ctgacaggct   2580
ctcctacctt ttcttagcac ttctgacatg cttctgtctt agaagaaaat gtgtttctta   2640
gtagaaagcc cacccttggt tcaggcccaa ggtttccacc cctcaacagc caacactcat   2700
ttatcaaaag taaacacagc attagtacat accaggaatc ataaaaggca cctagggtaa   2760
aatactgaat aaaaaggcat gattcctgac tcacagaact ttcagtctac ttggggagac   2820
agaaaaggga agagataatt acaatgtatg tgataaattc tggtggagga attccagaag   2880
gctctgggac attttcattt gacaagtata tattgagtgc ctgtcatagg tcaggtaaag   2940
ttctaggcac agggaatgta acagagaaca tactaaagac aagaatgtct ttacatgggg   3000
gaaagaggga actcacacgc agtcctagga gtcagggaag atttcccagg aaaagagaca   3060
tctaaactga gattttttgt ttgtttgttt ttgagatgga gtctcactct gttacccagg   3120
ctagagtgta gtggcatgat ctcagctcac tgcaacttct gcctcctggg ttcaagcgat   3180
tcccctgcct cagcctcctg agtagctggg attacaggtg tgcgccacca tgtccggcta   3240
atttttgtat ttttagcaga gatggggttt taccatgttg gtcaggctgg tctcaaactt   3300
```

ctgacctcgt gatccacctg cttcggcctc ccaaagtgct gagattacag gtgtaagcca 3360
ctgagcccgg cctaaactga gtttttaata tgaactagtc aaactgggtg agggtgttgt 3420
tgaagggagg atgtggtaga cagagggggg agtacagaag gtatgggcag aagctgtaag 3480
tggtccctta gggctgaagg acttcagact caatgataag tctgaagtgg aaagatgtaa 3540
gaagtttgat cttgaatgta gacaatggaa ggacagattc gagggggcca gtattgtaga 3600
cagggacatg cattaggagg ctgttataaa aatccaggtg agaaataatc caggccaaga 3660
ccagagtggt ggctgtagaa tacttagaat gtggaactga gaagacttgg taattgacta 3720
tttgggagtg gcgacaggga atgggagctc gtgattggaa ggggttaagg tgagtagaga 3780
ggctatgcac aagctgagca ggtcgtgata ctgatggacc taccctgcct tgttctgtcc 3840
tctagaggat gagaagagga aacaaactgc accagggaag ctcaggccga ttcaatgcat 3900
gcaagggtga tttaacctgg gttctgtttg aaatactt 3938

<210> SEQ ID NO 34
<211> LENGTH: 953
<212> TYPE: DNA
<213> ORGANISM: Human

<400> SEQUENCE: 34
ccttgacagc ctgcaaaaga gaaacatgga ttacttcttt cgggagcagc tgggccagag 60
tgtgcaacaa cgaaagcttg acctcctgac gataaccagc cctgacaatc tccgggaagg 120
ggcagagcag aaggtggtat tcatcacagg acgagtccac ccaggggaaa caccctcatc 180
atttgtgtgc caagggatca ttgacttcct tgtaagccag caccctattg cctgtgtcct 240
ccgggaatac ctggtcttca agatcgcacc aatgctcaat cctgatggag tctacctggg 300
caattacagg tgttctctga tgggatttga tctgaatcgt cactggctgg atccctctcc 360
atgggtccat cctaccctgc atggagtgaa acaactcatc gtccagatgt acaacgaccc 420
aaaaacaagc ctggagtttt atattgacat ccatgcccac tccaccatga tgaatggctt 480
catgtatggc aacatctttg aggatgagga acggttccag aggcaggcca tttttcccaa 540
gctcctctgc cagaatgctg aggacttctc ctattccagc acatccttta accgggacgc 600
tgtgaaagca ggaactggcc gtcgcttcct cggtggactc ctggaccaca cttcctattg 660
ctacacccta gaggtctcct tctacagcta catcatcagt ggcaccacgg ctgctgtgcc 720
ctacactgaa gaagcctgta tccttagtcc ccacccagcc ttgggccagc cctcatccag 780
ccgagagtat ccaagtctga caggtcagga attaggcccc cagctcaggt aagggctgag 840
actctcaggt gaggatggag gtgcttcttc ttctggtggc gtctttggat tgtccagttt 900
gcctcagccc ttagtatgat actcctaccc caattgccat gctccaaatc ttt 953

<210> SEQ ID NO 35
<211> LENGTH: 8843
<212> TYPE: DNA
<213> ORGANISM: Human

<400> SEQUENCE: 35
agccggcgag cggcagcagc tccgggctcg agagcccgcg cccatgccag tgcccatgcg 60
gggccgccgc cagtgacgcc ggagaggtgt tccccccaca ctggggctcc cactactgcg 120
aggagtgacc cacgaaggcc acagagatgg ccggggcttc ggtgaaggtg gcggtgcggg 180
tccgcccctt caattcccgg gaaatgagcc gtgactccaa gtgcatcatt cagatgtctg 240
gaagcaccac caccattgtt aaccccaaac agcccaagga gacgcccaaa agcttcagct 300

-continued

```
ttgactactc ctactggtcg cacacctcac ctgaggacat caactacgcg tcgcagaagc    360
aggtgtaccg ggacatcggc gaggagatgc tgcagcatgc ctttgaggga tacaacgtgt    420
gcatcttcgc ctatgggcag acgggtgccg gcaagtccta caccatgatg ggcaagcagg    480
agaaggacca gcagggcatc atcccacagc tctgcgagga cctcttctct cggatcaacg    540
acacgaccaa cgacaacatg tcctactccg tggaggtcag ctacatggag atttactgtg    600
agcgcgtccg tgacctcctg aaccccaaga acaagggcaa ccttcgcgtg agggagcacc    660
cactgctggg gccctacgtg gaggacctct ccaagctggc tgtcacctcc tacaatgaca    720
tccaggacct catggactca gggaacaagg ccaggaccgt ggcggccacc aacatgaatg    780
agaccagcag tcgctcccac gccgtcttca acatcatctt cacccagaag cgccatgacg    840
cagagaccaa tatcaccacg gagaaggtga gcaaaatcag cctggtggac ctggctggga    900
gcgagcgggc tgactccacg ggagccaagg gcacgcgcct caaggagggg gccaacatca    960
acaagtcgct gaccaccctg ggcaaggtca tctccgccct ggctgaaatg gactccggac   1020
ccaacaagaa caagaaaaag aagaagacag atttcattcc gtaccgagat tccgtgttga   1080
cctggctcct ccgggaaaac ctgggcggta actcaaggac agctatggtg gcagccttga   1140
gtcctgcaga catcaactac gatgagaccc ttagcacgct gaggtatgct gaccgggcca   1200
agcagatccg ctgcaatgct gtcatcaatg aggaccccaa caacaagctg atccgcgagc   1260
tgaaggatga ggtgacccgg ctgcgggacc ttctgtacgc ccagggtctt ggcgacatca   1320
ctgacatgac caatgccctg gtgggtatga gcccctcatc ctcgctctca gccctgtcca   1380
gccgcgcggc ctccgtgtcc agcctccacg agcgcatctt gtttgccccg ggcagcgagg   1440
aggccattga aagactgaag gaaacagaga agatcatagc tgagctcaat gagacctggg   1500
aggagaagct gcggcggaca gaagccatcc ggatggagag ggaagccctg ctggccgaga   1560
tgggtgtggc catgagggag gatggcggca ccttgggcgt attctctccc aaaaagacac   1620
cacacctcgt caacctgaac gaggacccgc tgatgtctga gtgcctgctc tactacatca   1680
aggatgggat caccagagtg ggcagggagg atggcgagag gcggcaggac attgttctga   1740
gtgggcactt catcaaggag gagcactgcg tcttccggag cgactccagg ggaggcagcg   1800
aagctgtggt gaccttggag ccctgtgagg gggcagacac ctacgtcaat ggcaagaaag   1860
tcacagagcc cagcatcctg cgttcaggaa accgcatcat catgggtaag agccatgtgt   1920
tccggttcaa ccaccccgag caggcccggc aggagcgtga gcgcacgcct tgtgcggaga   1980
cgccagctga gcctgtggac tgggccttcg cccagcgtga gctgctggag aagcagggca   2040
tcgacatgaa gcaggagatg gagcagaggc tccaggaact ggaggaccag taccgccgcg   2100
agcgggagga ggccacctac ctgctggagc agcagcggct ggactatgag agcaagctgg   2160
aggctctgca gaagcagatg gactccaggt actacccgga ggtgaacgag gaggaggagg   2220
agcccgagga tgaagtccag tggacagagc gggagtgtga gctggcgctc tgggccttcc   2280
ggaagtggaa gtggtaccag ttcacgtctc tgcgggacct gctgtggggc aacgccatct   2340
tcctcaagga ggccaatgcc atcagcgtgg agctgaaaaa gaaggtacaa ttccagtttg   2400
tcctcctgac ggacacactc tactcccctc tgccacccga cctgctgccc ccagaggccg   2460
ccaaagaccg agagacgcgg cccttccccc gcaccattgt ggccgtggag gtccaggacc   2520
agaagaacgg ggccacccac tactggacgc tggagaagct caggcagcgt ctggacctga   2580
tgcgggagat gtacgaccgc gctgcagagg tgccctccag tgtcatcgag gactgtgaca   2640
acgtggtgac cggcggagac cccttctatg accgcttccc ctggttccgg ctggtgggca   2700
```

```
gggccttcgt gtacctgagc aacctgctgt accccgttcc cctggtacac cgtgtggcaa   2760
tcgtcagcga gaagggcgag gtgaagggct tcctccgcgt ggccgtccag gccatctcag   2820
ccgatgaaga ggcccctgat tatggctctg gcgtccgcca gtcgggaact gctaaaatct   2880
cctttgatga ccagcatttt gaaaagttcc agtccgagtc ttgccccgtg gtggggatgt   2940
cccgctcggg aacctcccag gaagagcttc gcatcgtgga gggccagggc cagggtgcag   3000
acgtggggcc ctcagccgat gaagtcaaca acaacacctg ttcagcagtg cccccagaag   3060
gcctcctcct agacagctct gagaaagccg ccctggatgg gcccctggat gctgccctgg   3120
accacctccg cctgggcaac accttcacct tccgtgtgac agtcctgcag gcgtccagca   3180
tctctgccga atatgccgac atcttctgcc agttcaactt catccaccgc cacgacgagg   3240
ccttctccac agagcccctg aagaacacag gcagaggccc cccacttggc ttctaccacg   3300
tccagaacat cgcagtggag gtgaccaagt ccttcattga gtacatcaag agccagccca   3360
ttgttttcga ggtctttggc cactaccagc agcacccgtt cccgcccctc tgcaaggacg   3420
tgctcagccc cctgaggccc tcgcgccgcc acttccctcg ggtcatgcca ctgtccaagc   3480
cagtgcccgc caccaagctc agcacactga cgcggccctg tccgggaccc tgccactgca   3540
agtacgacct gctggtctac ttcgagatct gtgagctgga ggccaacggc gattacatcc   3600
cggccgtggt ggaccaccgt gggggcatgc catgcatggg gaccttcctc ctccaccagg   3660
gcatccagcg acggattacg gtgacactac tgcatgagac aggcagccat atccgctgga   3720
aggaagtgcg cgagctggtc gtgggccgca tccgaaacac tccagagacc gacgagtccc   3780
tgatcgaccc caacatcttg tctctcaaca tcctctcttc cggatacatc cacccagccc   3840
aagatgaccg gaccttttac caatttgagg ctgcgtggga cagctccatg cacaactctc   3900
tcctgctgaa ccgggtcacc ccttatcgag agaaaatcta catgacactc tccgcttata   3960
tcgagatgga gaactgcacc cagccggctg ttgtcaccaa ggacttctgc atggtcttct   4020
attcccgtga tgccaagctg ccagcctcgc gctccatccg caacctcttt ggcagtggga   4080
gccttcgggc ctcagagagt aaccgtgtga ctggtgtgta cgagctcagc ctgtgccacg   4140
tggctgacgc gggcagccca gggatgcagc gccggcgccg acgagtcctg gacacatctg   4200
tggcctatgt ccggggcgag gagaacctgg caggctggag gccccggagt gacagtctca   4260
ttctggacca ccagtgggag ctggagaagc tgagcctcct gcaggaggtg gagaagacta   4320
ggcactacct gctcctgcgg gagaagctgg agaccgccca gcggcctgtc ccggaggcac   4380
tgtccccggc cttcagcgag gactctgagt cccatggctc ctccagcgcc tcctccccgc   4440
tctcggctga gggccgccca tcacccctgg aggctcccaa cgagaggcag cgggagctgg   4500
ccgtcaagtg cttgcgcctg ctcacgcaca cattcaacag agagtacaca cacagccacg   4560
tctgcgtcag tgccagcgag agcaagctct ccgagatgtc tgtcaccctg ctccgggacc   4620
cgtcgatgtc ccctctaggg gtggccactc tcaccccctc ctccacttgc ccctctctgg   4680
ttgaagggcg gtacggtgcc actgacctga ggaccccgca gccctgctcc cggccagcca   4740
gcccagagcc cgagctgctg ccagaggccg actccaagaa gctcccttcc cctgcccggg   4800
caacagagac agacaaggag ccccagcgcc tgctggtccc tgacatccag gagatccgag   4860
tcagcccgat cgtttccaag aaggggtacc tgcacttcct ggagccgcac acgtcaggct   4920
gggccaggcg cttcgtggtg gtgcggcgcc cctatgccta catgtacaac agcgacaagg   4980
acaccgtgga gcggttcgtg ctcaacctgg ccactgccca ggtggagtac agtgaggacc   5040
agcaggctat gctcaagaca cccaacacat tcgcggtgtg cacggaacac cgcggcatcc   5100
```

```
tgctgcaggc cgccagcgac aaggacatgc atgactggct gtacgccttc aacccccctcc   5160
tggccgggac catacggtcc aagctctcca gaaggaggtc tgcccagatg cgggtctgaa   5220
cctgagccct cccgtgacag ccggcaggcc cagcccatcc cctccctcat cctcgtctgt   5280
cctgtcacct gccgcccagc ccctctcctg ccagacagcc cacgaccggg tcgacccccc   5340
aggggacgcc catgccaggc ccggggacct gtgccacacg accagctgtg ctcccagcag   5400
aggctgtgcg tgtcagttct tcttgcagaa tgtgctctgg tggaacaagt tgggagaggc   5460
tggggggggcc aagggcacag gttacggggg ttcttgctgc cgttctaata tttttttaag   5520
catagacaga cttataatta atatacgtta gttagtgaca ttgaaacagt caactcggaa   5580
attaactata agacttgttc tatttataag tatttatttc taatgcctcc acatagccct   5640
gtaatattca gatggaaccc ccaaccacct ccaccctgtt tgttcccaca tgtgtctccc   5700
aagcctgcta gggacaggca gggcagggac agccaccttg gaaggccgca gtgaggagct   5760
gtctggacca gtggggcacc ttggggctag cacacgggtg tatcgcctgg gccccaggct   5820
tctccatggc cacatgggtc ctgggtgtat gtgtgggaga gtggggggggt gtctttggtg   5880
cctgaagtct gcgcggcatg gagggtggtg tgagttcctc tggtgggagg gagaacgcac   5940
atctcttctg ggcggccacc tgaggagtga ctccaagaag agttccggca gctttcccca   6000
ggaaagggtg aggggtgaca ctcggctctg gctctgagat gaggcagacg gcacccaggc   6060
tgtgatctgt cctgggcggg gaccaggagg gagcggggtc gggatcacct gccagtgtgc   6120
agactctggg actgcgtgct gtctccggac catcagggta gggtggtggg ttgagaccag   6180
gaagtcaggg aagatcggaa ttcagggcga cggtctaggt gtcgagggct gtggcgcagc   6240
ctcttcagct gcggcgagaa atggagtgag tcaaggtagc ttctgggaag aaatgctgcc   6300
attagcaggt ttcttgcaaa gactttcctc tctttgttcc cagggcagag agtttctgtg   6360
agtcccactg agaaaatccc atggggtggg ggtatcctgg tcggtcggca atggagggtg   6420
gctggcttgg tggttattgt cttcaaggag ctcttcgctg ctgcatctgc ggtgtccctt   6480
tgttcttgtc ccatttcacc ccctctgcag acaccaatgt ccgagggcca cccaggacag   6540
gacgggggtc agccccaagc tgagagtctg gtcataggag tcatgtccag aggcctaggg   6600
aggttttagg gccctcccca cccacaccca caggtcgatt tggtctcttt ttagctcaag   6660
gaaagacagt agccaagcaa cagagcccct ctcccgccgt ggcccgtggg agcagttaca   6720
tcgggtctgg tgctccagac ctagggccca gcactttcat cagatcctgc ctcctggagt   6780
gggggaaacg cagcacccca ctggttctga ggcccctacc ctcccaggct gtcccacgtg   6840
atgctgacat gagcctcaga gaccccaatc ccatgcctgg gggagagaca gcggctcagg   6900
agtgggggag cacgggcctt ctacaccaca tgggaaggct ctggcatgag gttttccttt   6960
gggaaggttg tttgggcccc tgaagttcca tctccgagag tggtgtgcag ggcaggccag   7020
ggcccatgct ggctgcagtc tctgtggctg cctgcctggg ccagcctgtt tgggagctgg   7080
gactgtgggc tcgccttttc gtacctgggc tcaggtgcgg tgtggccacc gccaccctca   7140
tcccctgcct gggaggctct cccaggggct gatggggggg ttctgtgagg gagaatcagg   7200
gctcgggaag ccacgcctgg gaaggcagga cacaggacac agcagctttc tttggaaatc   7260
tcccaggtga ggattcacat cccaaaataa aattcagaag ccaggtggcc tgtgctcccc   7320
atgggtgacc tctggaggca gtggaccaag atgcagcaag gagaggatgc agaacagctt   7380
cttgcagaag cacctgctcc ggcatccagc gctgcctgga ggcaggaagg agaggcaggg   7440
caggacacgc tggtctgaga tgagggggag ccccacgggc cccaggcagg ctagaggagg   7500
```

cacaggccct gccacggcca actcaggtca gccagcctga ggctgtggcc tccaaagggt 7560
ctgggcgcac cccccaggtc gcaggtgtct gaggccagcc aacctgcaga gcactcgcgg 7620
cgtgggtggg ctgagtggag gtgcctggga gctgcctaaa ttcagaagcc tccactgcca 7680
tggagactgc ctggctgtgt cctctcagcc aggtgccgtg ttggccttgg ctaggaccca 7740
gagccacact gcagcctccg ccgactccct ccttccgggc ctgctctagt gaggagtgcc 7800
taagccagga cccagaaact cagagttgat ggtgagagga ggccgcctga gtcaggacac 7860
ctggcttctt gaaaagttcg ctctgccaga aaccacctag ggaccacgtt agctgccttc 7920
cttgagctcc ccaggagtcg gtttccacat ctgtgaggtg gagggctggt gtggaggtgc 7980
tcatggggtg cggtgcttgg gagacagcca ggcccagggt ggctgctgct tcctgctaag 8040
tgggggaggt gagacagatc tggaaagccg tctccctcag atggtttcat ttaatgcttt 8100
atactgccga gtctgggggc ttgttttggt ttgggggcag ccatcctcca ccagaaaggg 8160
ggagctcctt ccgctgcggc tccagataga tggggatgcc gggctccagg ccgaccagca 8220
cttgggatct gatgggacac ggccagtgcc taggggtgcc aagtccaagg cctcccactg 8280
ggagtcatcg ctgagaagat gccaatgttt catccaccgg ctgcacaggc acaaactccc 8340
ccacccagga cggctgtgat gaggtggccc tccctgtcaa ccctggtccc tggagtcccc 8400
agcacctggg gccctggtgg ggctgatgtc acaggtgttt actgtgctgc tgcactggtc 8460
ctatgccagc ctcacccatg tggggaccac ggaaggcaca ctcccttacc cccggtgccg 8520
ggccgtgcgg tcccccagac ggacagcagc tgtggcgacc tgcgtttctc cctgggcctg 8580
tgcttcctgt agttagtccg tcccctggtt cccctgtggc tcagaggccg cgtccctggc 8640
ttgtacatat gtgattgctg tgggcacacc ccagacccca tgtcatagct gccgtcccga 8700
cgtcacgacg cctgtcccga tgtcttacac ccgagtgtta gccctaggct cctgtactgt 8760
gcgtgcactt gaggctctgt ccaattaaga aataaatgtg gctcttactc aacacaaaaa 8820
aaaaaaaaaa aaaaaaaaaa aaa 8843

<210> SEQ ID NO 36
<211> LENGTH: 10551
<212> TYPE: DNA
<213> ORGANISM: Human

<400> SEQUENCE: 36
gcggccgctg ctcgcgctga ggtgcgtcgg tgcccggccc cccgcgcccc cgcgcgccgc 60
ggctcctgtt gacccggtcc gcccgtcggt ctgcagcgcg gctgaggaaa cttggctgta 120
acttcaaaag aagatttgat tctttatttc tggactgcat atatatatat aacaaggcca 180
ttaaaatgtc gggagcctca gtgaaggtgg ctgtccgggt aaggcccttc aattctcgag 240
agaccagcaa ggaatccaaa tgcatcattc agatgcaagg caactcgacc agtattatta 300
acccaaagaa tccaaaggaa gctccaaagt ccttcagctt cgactattcc tactggtctc 360
atacctcacc cgaagatccc tgttttgcat ctcaaaaccg tgtgtacaat gacattggca 420
aggaaatgct cttacacgcc tttgagggat ataatgtctg tatttttgcc tatgggcaga 480
ctggtgctgg aaaatcttat acaatgatgg gtaaacaaga agaaagccag gctggcatca 540
ttccacagtt atgtgaagaa ctttttgaga aaatcaatga caactgtaat gaagaaatgt 600
cttactctgt agaggtgagc tacatggaaa tttactgtga aagagtacga gatttgctga 660
atccaaaaaa caagggtaat ttgcgtgtgc gtgaacaccc acttcttgga ccctatgtgg 720
aggatctgtc caagttggca gttacttcct acacagacat tgctgacctc atggatgctg 780

```
ggaacaaagc caggacagtg gcagctacaa acatgaatga aacaagtagc cgttcccacg    840
ctgtgtttac gattgttttc acccagaaga aacacgataa tgagaccaac ctttccactg    900
agaaggtcag taaaatcagc ttggtggatc tagcaggaag tgaacgagct gattcaactg    960
gtgccaaagg gactcgatta aaggaaggag caaatattaa taagtctctt acaactttgg   1020
gcaaagtcat ttcagccttg gccgaggtga gtaaaaagaa gaagaaaaca gattttattc   1080
cctacaggga ttctgtactt acttggctcc ttcgagaaaa tttaggtggc aattctcgga   1140
ctgcaatggt tgctgctctg agccccgcgg atatcaacta cgatgagact ttgagcactc   1200
tgagatatgc agatcgtgca aaacaaatta aatgcaatgc tgttatcaat gaggacccca   1260
atgccaaact ggttcgtgaa ttaaaggagg aggtgacacg gctgaaggac cttcttcgtg   1320
ctcagggcct gggagatatt attgatacat ccatggggtc cctcacttca tccccatctt   1380
cctgctcact cagtagtcag gtgggcttga cgtctgtgac cagtattcaa gagaggatca   1440
tgtctacacc tggaggagag gaagctattg aacgtttaaa ggaatcagag aagatcattg   1500
ctgagttgaa tgaaacttgg gaagagaagc ttcgtaaaac agaggccatc agaatggaga   1560
gagaggcttt gttggctgag atgggagttg ccattcggga agatggagga accctagggg   1620
ttttctcacc taaaaagacc ccacatcttg ttaacctcaa tgaagaccca ctaatgtctg   1680
agtgcctact ttattacatc aaagatggaa ttacaagggt tggccaagca gatgctgagc   1740
ggcgccagga catagtgctg agcggggctc acattaaaga agagcattgt atcttccgga   1800
gtgagagaag caacagcggg gaagttatcg tgaccttaga gccctgtgag cgctcagaaa   1860
cctacgtaaa tggcaagagg gtgtcccagc ctgttcagct gcgctcagga aaccgtatca   1920
tcatgggtaa aaaccatgtt ttccgcttta accacccgga acaagcacga gctgagcgag   1980
agaagactcc ttctgctgag acccccctctg agcctgtgga ctggacattt gcccagaggg   2040
agcttctgga aaaacaagga attgatatga aacaagagat ggagaaaagg ctacaggaaa   2100
tggagatctt atacaaaaag gagaaggaag aagcagatct tcttttggag cagcagagac   2160
tggactatga gagtaaattg caggccttgc agaagcaggt tgaaacccga tctctggctg   2220
cagaaacaac tgaagaggag gaagaagagg aagaagttcc ttggacacag catgaatttg   2280
agttggccca atgggccttc cggaaatgga agtctcatca gtttacttca ttacgggact   2340
tactctgggg caatgccgtg tacctaaagg aggccaatgc catcagtgtg gaactgaaaa   2400
agaaggtgca gtttcagttt gttctgctga ctgacacact gtactcccct ttgcctcctg   2460
aattacttcc cactgagatg gaaaaaactc atgaggacag gcctttccct cgcacagtgg   2520
tagcagtaga agtccaggat ttgaagaatg gagcaacaca ctattggtct ttggagaaac   2580
tcaagcagag gctggatttg atgcgagaga tgtatgatag ggcaggggag atggcctcca   2640
gtgcccaaga cgaaagcgaa accactgtga ctggcagcga tcccttctat gatcggttcc   2700
actggttcaa acttgtgggg agctccccca ttttccacgg ctgtgtgaac gagcgccttg   2760
ccgaccgcac accctccccc actttttcca cggccgattc cgacatcact gagctggctg   2820
acgagcagca agatgagatg gaggattttg atgatgaggc attcgtggat gacgccggct   2880
ctgacgcagg gacggaggag ggatcagatc tcttcagtga cgggcatgac ccgttttacg   2940
accgatcccc ttggttcatt ttagtgggaa gggcatttgt ttacctgagc aatctgctgt   3000
atcccgtgcc cctgatccac agggtggcca tcgtcagtga gaaaggtgaa gtgcggggat   3060
ttctgcgtgt ggctgtacag gccatcgcag cggatgaaga agctcctgat tatggctctg   3120
gaattcgaca gtcaggaaca gctaaaatat cttttgataa tgaatacttt aatcagagtg   3180
```

actttttcgtc tgttgcaatg actcgttctg gtctgtcctt ggaggagttg aggattgtgg 3240
aaggacaggg tcagagttct gaggtcatca ctcctccaga agaaatcagt cgaattaatg 3300
acttggattt gaagtcaagc actttgctgg atggtaagat ggtaatggaa gggttttctg 3360
aagagattgg caaccacctg aaactgggca gtgccttcac tttccgagta acagtgttgc 3420
aggccagtgg aatcctccca gagtatgcag atatcttctg tcagttcaac tttttgcatc 3480
gccatgatga agcattctcc acggagcccc tcaaaaacaa tggcagagga agtcccctgg 3540
ccttttatca tgtgcagaat attgcagtgg agatcactga atcatttgtg gattacatca 3600
aaaccaagcc tattgtattt gaagtctttg ggcattatca gcagcaccca cttcatctgc 3660
aaggacagga gcttaacagt ccgcctcagc cgtgccgccg attcttccct ccacccatgc 3720
cactgtccaa gccagttcca gccaccaagt taaacacgat gagcaaaacc agccttggcc 3780
agagcatgag caagtatgac ctcctggttt ggtttgagat cagtgaactg gagcctacag 3840
gagagtatat cccagctgtg gttgaccaca cagcaggctt gccttgccag ggacattttt 3900
tgcttcatca gggcatccag cgaaggatca cagtgaccat tatccatgag aaggggagcg 3960
agctccattg gaaagatgtt cgtgaactgg tggtaggtcg tattcggaat aagcctgagg 4020
tggatgaagc tgcagttgat gccatcctct ccctaaatat tatttctgcc aagtacctga 4080
agtcttccca caactctagc aggaccttct accgctttga ggctgtgtgg gatagctctc 4140
tgcataactc ccttcttctg aaccgagtga caccctatgg agaaaagatc tacatgacct 4200
tgtcggccta cctagagctg gatcattgca tccagccggc tgtcatcacc aaggatgtgt 4260
gcatggtctt ctactcccga gatgccaaga tctcaccacc acgctctctg cgtagcctct 4320
ttggcagcgg ctactcaaag tcaccagatt cgaatcgagt cactggcatt tacgaactca 4380
gcttatgcaa aatgtcagac acaggtagtc caggtatgca gagaaggaga agaaaaatct 4440
tagatacgtc agtggcatat gtgcggggag aagagaactt agcaggctgg cggccccgtg 4500
gagacagcct catccttgag caccagtggg agctggagaa gctggagctc ctacatgagg 4560
tggaaaaaac ccgccacttt ttgctgctgc gtgagagact tggtgacagc atccccaaat 4620
ccctgagcga ctcgttatcc cccagcctca gcagtgggac cctcagcacc tccaccagta 4680
tctcctctca gatctcaacc actacctttg aaagcgccat cacacctagc gagagcagtg 4740
gctatgattc aggagacatc gaaagcctgg tggaccgaga gaaagagctg gctaccaagt 4800
gcctgcaact tctcacccac actttcaaca gagaattcag ccaggtgcac ggcagcgtca 4860
gtgactgtaa gttgtctgat atctctccaa ttggacggga tccctctgag tccagtttca 4920
gcagtgccac cctcactccc tcctccacct gtccctctct ggtagactct aggagcaact 4980
ctctggatca gaagacccca gaagccaatt cccgggcctc tagtccctgc ccagaatttg 5040
aacagtttca gattgtccca gctgtggaaa caccatattt ggcccgagca ggaaaaaacg 5100
aatttctcaa tcttgttcca gatattgaag aaattagacc aagctcagtg gtctctaaga 5160
aaggatacct tcatttcaag gagcctcttt acagtaactg ggctaaacat tttgttgtcg 5220
tccgtcggcc ttatgtcttc atctataaca gtgacaaaga ccctgtggag cgtggaatca 5280
ttaacctgtc cacagcacag gtggagtaca gtgaggacca gcaggccatg gtgaagacac 5340
caaacacctt tgctgtctgc acaaagcacc gtggggtcct tttgcaggcc ctcaatgaca 5400
aagacatgaa cgactggttg tatgccttca acccacttct agctggcaca atacggtcaa 5460
agctttcccg cagatgcccg agccagtcga aatactaagt gactctgccg agtgccctca 5520
ctcgccttcg agagataaag aaagcgttac ctctcatttc tctttgtgat tcttgacggt 5580
gactcttgta tgtaatcctg tggcttaact acttctccct ccttgtccag cacttttcta 5640
gctctcccgt tccccatctc cattgctctg tactcttttc tttttcttg tgctgagaat 5700
ctcgttagta gcatgtggcc taacaaaagg aaaaaatgtt tttaaacaca cacacacaca 5760
cacacacaca cacacacata cacagacaaa aacacaaaaa ctctgagggg atctggtgaa 5820
tctccaaatt attgtgggtg tactttggct tccttttgta tgataggtcc ccatcatgac 5880
cacctctgat gtctgtgctg ctgtcaccag gcacctttgt ttttcaagac aacatacttt 5940
tttttctttt tctctgtttg tgatatcact ttaatttttc ttgggtggct tagagactaa 6000
gggaggagac atctggcctt tttagaacct gagaggaaaa aaagagtctt tttttcccct 6060
ctgtctcttt ttgccatggc taatccctgc atttccattc agggaaaagg tggtagtgag 6120
catagaactg caacagttat attctgagtc aaagttgggg ctttttacgg cataattatg 6180
gaatttttat ttactggtag agaggagacg agaggctttt tcagtgggcc tgggacagtg 6240
gctgctcttg actttgtgtg aagggaaatg ccaaggatgc ttctggtgga cttcagggga 6300
ccccagggtt tggccgtggg ccgtgatggc agcaggcggt gggatgcttg tagctcctca 6360
cagcaggatt cctgcccact gtttttttctc tgttgggagg gaagctcttt tctaggagtg 6420
tctcagttct gcttttggca ttagtgatgg tggtggtaca gttggaatta gtgccatgtc 6480
atacacaaat gttccacaag gcgggagtgt ttcactttct ggtgataaac ttgatggtca 6540
ttgttatgat taagataatg ccgggcaggc cgggcacagt ggctcacgcc tgtaatccaa 6600
gcacttgggg aggccgaggc gggcagatca cgagatcagg agttcaagac cagcctggcc 6660
aatatgatga aaccccgtct ctactaaaaa tacaaaatta gtcgggtatg gtggcacatg 6720
cctgtaattc cagctgcttg ggagcctgag gcaggagaac tgcttgaacc caggaggcag 6780
aggttgcagt gagccaagat cgcgctattg cactccagcc tgggtgacag agcaagactc 6840
tgcctcagaa aaaaaaaaaa ataataatgc tgggtagtga ccttgtgatt gttacagctc 6900
cctttgatca aagaaatata gctttcaggc ataaacctgg aagtctccct ctgaatccag 6960
cagttgtttt cattgatgct tgtcaggttg aagatgcttt cagtgatgct ctctatactc 7020
ataaataagc aaatgtggca ggctttgctt tctggatccc aggattaaaa ctaaccgtga 7080
ccactactcc aaacaaaaca caatatgcct aggggcacgg atgaacgtcc agggagcccg 7140
ggccccaggc tttgttgcgt gttccctgct cctctccatc tggtgtggaa acactgccca 7200
gggagaaagg aggaagctca ctgtggacag tcttctttcc ttctgacaga ccaggtcatc 7260
tggcttccga gatcatcaga gaagataagt ctgtctcttt cagctgccag taagttttcc 7320
aggatgagag gggaaaaaga aagcctccag tgacttcagt tgctttgcca gttgtcttgg 7380
gattgtttta caccatcctt tacttccctt gctcagacct ctctgtttca ccattgctca 7440
ggcattcagg aaagtatctg ctcactccca cttggtgagt cctcggcctt gaggttgctg 7500
actctcaggc gttaggcagc tggatgactt cccgcttcac gcagcaaagg ccaggggctt 7560
gcgcgcctct gcagagttgt tgctagggag acttgtgtca tcatccacaa ccttgtttct 7620
cacttcctgg ttgggctcat ctctgaagaa caggtctccc agcttcgctc cttatcactg 7680
cattgtgaag aggaggaaaa gtgaatcacg gagagagaaa ggaaaggata gaatcacagg 7740
ctgcgtctgc acctgaaaag tgacccgcgg aaactctatg gcggattttt tttttaactt 7800
tcttcttcct gttaaaacat aggtcactaa ctgtgatgtt atttgttttc taagtggtat 7860
gtgagatttt ctaatgtagt tagaagtttc attgtctgat ggacacaata tgcccttccg 7920
gttctattca aaccagcagg atctgtcggt gcttagagat ggctgcctgg actggaatca 7980

-continued

```
aatctaattt cagggaaatg aagatggaat ttgaaggtca cttttaaaat taagtcattg   8040
atgctgctgt tacagagtgt gacagaggat ccatgtctgt gacacaggac ggtgggaagc   8100
ctgagagaga gtgaaattat gtgatacact gaaatgactt ttgtttttct tctaactcat   8160
acaaaactgg tttggaaagt ctttgctttg gaagcgtcag acattagaac aggccaaact   8220
ggactgtctg ttcatagcgt gcctgaataa gaaggcctct tagggagcca gagggagcag   8280
agtggtcgtg tcctgcgtgc tcttcaccct ctggggcgcc cctgctgcgg ctggcaggtg   8340
cagacagcct ttgctggtcc ccagcacgtc cagggtgggt gctcccttgc ccgacagaac   8400
catccccact gtgaggctgt gagagatttg tggcaggaac tgtttatgag gctctagttg   8460
ttgctgttgt ggcgggaaag ttaagaaaca tagcccttaa ggaaaccacc tttatgtatt   8520
ttcttaaagc acgcctttaa ataagcaaaa actttaaaag gcaggaaaga gaattcttag   8580
gcaaattcag agaaataagt gctagttaat actaatcacc tcctcctctg tctctcatcc   8640
tcctttctcc catcaaagca aaatatggcc tcaccaccag ccccaaatca gtgctcagac   8700
cctctctgtg tctgtgtgcc ctcctgggag tcagtcagcg ctcaggccag gactgtgcag   8760
ggccagccag cccatgcgct agtcaggagc acaggcaagg ggtgcttgtg gcagtggccg   8820
ggcacctgag ccccagctcg ttgttaaacg tgctgacggc aaggggcaat ggagtgagtt   8880
tcccaactaa gaaaccacta ttatatattt tttcccttca gtcacataga cttcagacaa   8940
ctctcctatt ttttatggat ttttcagctc atttcagatg aaggaactaa gtcattgtga   9000
actgtctctt gagatctaaa aacaagatga cttttcctgg cacatattcc aaagcaaaga   9060
ctttgttgcc tgctgcttat tgtctaattt acagggatat ttaattttgt caggtctatg   9120
tatatttatc cagctatact tacttgcaca gtggattgga gagaaaggat tctccagtgt   9180
gcacactcat cggtactctt tctgcatttc cctcgtgctg tgtcccgctc gggttccaat   9240
ggacagtatc agggcttgtt tgacttaggt ctttcagttt tcctttcggt tcccttttaa   9300
aaatgtgatt gttaacctgc ctcttgaaag attcaaccgg gtgtggtggc tcacgcctgt   9360
aatcccagca cattgggagg ccaaggcagg tggatcacct gaggtcagaa gtttgagacc   9420
agcctggcca acatggtgaa accccgtctc tactaaaaat acaaaaagta gccaggcgtg   9480
gtggcgtgtg cctgtagtcc cagctacttg ggaggctgag gcaggagaat agcttgaacc   9540
tgggaggtgg aggctgcagt gagttgagac tgcaccattg cactccagcc tgggtgacaa   9600
agcaggactc cgtctcaaaa aaaaagaaaa gattcatgat gctgctgctc ccagaaggtt   9660
tgctggatgt gtttacatag gactctaact tgtgtgcact acagttgttc accagggcca   9720
gtgattcacc ccagtgtgtg gccagaccat gactgtgtag caggaatgtt ttaatttgtg   9780
cttccttagt aaattgaaat atcagctgag agattatttg ctgctgttat tcaaaaggcc   9840
atttatgaag ttagtatttg agccccataa gatctttaaa aagcctccaa tcatttaaag   9900
gaagaaatca gagttgctat aaaattcagt aaaaagctca tagccaaacg gctgtgctca   9960
gatggaaagt ctgagctgag gttggtctct tgccaaaccg tggctgttgt gtgttgttct  10020
tcatgtcttc gagttcattt tttttcattc tgcctattct ggcatcagct cacttgagga  10080
gtccctcagc cttcttgtat ttaaggcatc gtcttagact ttgtggctct aaagtacctg  10140
tctgttgaga tttcaagtct cttgtcacca tcctcacaca tgacaacaaa acccataatg  10200
cataagtggc ctttttgaac caagactttg caaactgatc tctcccccgt gaaggagttg  10260
agcacattag caacaatgta cattaatttt ggattttcat tttcatgttt tattttgtaa  10320
atattatctg atgtttggag cttgagtata cagactgtaa atatagttct tgtatttgta  10380
```

ctaattctga ttcttttgct gtatagcctt agatgtgcaa tgcagacact atctaactgt 10440
gtgtggtaac cttgcgtcac ggagctgtta gtgaacgagg taaaaataat aaaggtacag 10500
ccagtgcaaa aaaaaaaaaa aaaaaaaaaa aaaaaaaaaa aaaaaaaaaa a 10551

<210> SEQ ID NO 37
<211> LENGTH: 4218
<212> TYPE: DNA
<213> ORGANISM: Human

<400> SEQUENCE: 37
ctcgcgctgc ccgggcgggc gccggccgct ggcgccgcta ctgctgccgc ccccggggcg 60
cgagtccgcc gcccgccgcc cgggcacccg gcgaggggcg ggggcagctc cgaaccggcc 120
ccagatcctt cccgcttccg cctcacgctt cccggaaagc ttgtccctct ccgccgagct 180
gctccgggag ccccgccgcg ccgagggtat ctcccagagc cccagctggt gtggccaggc 240
cccaggagta ggatggggct ccccctacga gggccggtgg cagccagaac tgatacagcc 300
cccctggtct ggggccagga cgccagctga ggagggcagg agtgtctgga gctatggctg 360
gtgcctcggt gaaagtggca gtgagggttc ggccctttaa cgcccgtgag accagccagg 420
atgccaagtg tgtggtcagc atgcagggca acaccacctc catcatcaat cctaaacaga 480
gcaaggatgc ccccaaaagc ttcacctttg actactccta ctggtcacac acttcgacgg 540
aggaccccca gtttgcatct cagcagcaag tgtatcggga catcggagaa gagatgctgc 600
tccacgcctt tgaaggctac aacgtgtgca tctttgccta tgggcagacc ggggctggga 660
aatcctatac catgatgggg cgacaggagc cagggcagca gggcatcgtg ccccagctct 720
gtgaggacct cttctctcgc gttagtgaga accagagtgc tcagctatcc tactctgtgg 780
aggtgagcta tatggagatc tactgtgagc gggtacgaga cctcttgaac cccaagagtc 840
ggggttctct gcgggtccgg gagcacccca tcctgggccc gtacgtgcag gacctgtcca 900
aattggctgt gacctcctac gcagacattg ctgacctcat ggactgtgga aataaagcac 960
ggactgtggc tgccaccaac atgaatgaga ccagcagccg ttcccatgcc gtctttacca 1020
tcgtcttcac acagcgctgc catgaccagc tcacggggct ggactcggag aaggtcagta 1080
agatcagttt ggtggacctt gctgggagtg agcgagccga ctcctcaggg gcccggggca 1140
tgcgcctgaa ggaaggagcc aacatcaata agtccctgac tacactaggg aaagtgatct 1200
cggcccttgc agatatgcaa tcaaagaagc gaaagtcgga ttttatcccc tacagggact 1260
ctgtgctcac ctggctgctc aaggaaaatt tgggggggaa ctcacgcaca gccatgattg 1320
cagccctgag ccctgctgac atcaattacg aggagactct cagcaccctc aggtatgctg 1380
accgcaccaa gcaaatccgc tgcaatgcca tcatcaacga ggaccctaat gcccggctga 1440
ttagagagct gcaggaggaa gtagcccggc tgcgggaact gctgatggct cagggactgt 1500
cagcctctgc tctggaaggc ctgaagacgg aagaagggag tgtcagaggc gccctgccag 1560
ctgtgtcatc tcccccagct ccagtttcac cctcatcacc caccacacat aatggggagc 1620
tggagccgtc attctccccc aacacggagt cccagattgg gcctgaggaa gccatggaga 1680
ggctgcagga gacagagaag attatagctg agctgaacga gacatgggag gagaagctac 1740
gcaagacaga agccctgagg atggagagag aagcattgct ggctgagatg ggggtggccg 1800
tccgggagga tgggggaact gtgggcgtct tctctccaaa gaagactccc cacctggtga 1860
acctgaacga agaccctctg atgtctgagt gtctgctcta ccacatcaaa gatggcgtca 1920
ccagggtcgg ccaagtagat atggacatca agctgaccgg acagttcatt cgggagcaac 1980

-continued

```
actgtctgtt ccggagcatc ccccagccag atggagaagt ggtggtcact ctggagcctt   2040
gtgaaggagc tgagacatat gtgaatggga agcttgtgac ggagccgctg gtgctgaagt   2100
cagggaatag gattgtgatg ggcaagaacc acgttttccg cttcaaccac ccggagcagg   2160
caaggctgga acgggaacga ggggtccccc cacccccagg accgccctct gagccagtcg   2220
actggaactt tgcccagaag gaactgctgg agcagcaagg catcgacata aagctggaaa   2280
tggagaagag gctgcaggat ctggagaatc agtaccggaa agaaaaggaa gaagccgatc   2340
ttctgctgga gcagcagcga ctgtatgcag actcggacag cggggatgac tctgacaagc   2400
gctcttgtga agagagctgg aggctcatct cctccttgcg ggagcagctg ccgcccacca   2460
cggtccagac cattgtcaaa cgctgtggtc tgcccagcag tggcaagcgc agggcccctc   2520
gcagggttta tcagatcccc cagcgacgca ggctgcaggg caaagacccc cgctgggcca   2580
ccatggctga cctgaagatg caggcggtga aggagatctg ctacgaggtg gccctggctg   2640
acttccgcca cgggcgggct gagattgagg ccctggccgc cctcaagatg cgggagctgt   2700
gtcgcaccta tggcaagcca gacggccccg gagacgcctg gagggctgtg gcccgggatg   2760
tctgggacac tgtaggcgag gaggaaggag gtggagctgg cagtggtggt ggcagtgagg   2820
agggagcccg aggggcggag gtggaggacc tccgggccca catcgacaag ctgacgggga   2880
ttctgcagga ggtgaagctg cagaacagca gcaaggaccg ggagctgcag gccctgcggg   2940
accgcatgct ccgcatggag agggtcatcc ccctggccca ggatcatgag gatgagaatg   3000
aagaaggtgg tgaggtcccc tgggccccgc ctgaaggatc agaggcagca gaggaggcag   3060
cccccagtga ccgcatgccg tcagcccggc ccccctcgcc accactgtca agctgggagc   3120
gggtgtcacg gctcatggag gaggaccctg ccttccgtcg tggtcgtctt cgctggctca   3180
agcaggagca gctacggctg cagggactgc agggctctgg gggccggggc ggggggctgc   3240
gcaggccccc agcccgcttt gtgccccctc acgactgcaa gctacgcttc cccttcaaga   3300
gcaaccccca gcaccgggag tcttggccag ggatggggag cggggaggct ccaactccgc   3360
tccaaccccc tgaggaggtc actccccatc cagccacccc tgcccgccgg cctccgagtc   3420
cccgaaggtc ccaccatccc cgcaggaact ccctggatgg agggggccga tcccggggag   3480
cgggttctgc acagcctgaa ccccagcact tccagcccaa aaagcacaac tcttatcccc   3540
agccacccca accctaccca gcccagcggc ccccagggcc ccgctacccc ccatacacta   3600
ctcccccacg aatgagacgg cagcgttctg cccctgacct caaggagagt ggggcagctg   3660
tgtgagtccc acatcctggg cagagggcct ggtggggccc cttgctagga gaagggaaga   3720
cgcccgagac gctgcttccc cagaagtgct ggggcaggga ggcccaggag atgagagaga   3780
aggtccgagt aggtgataga agacaagggg gagaccgagc cggaggctga ggaaaggaag   3840
agggcacgga gttgccagga gcaaaccaaa gtgaagagag agataggaag ctgcctcggg   3900
gccacccctt gcaaaggggg tgtgtcccac aaacgctgct atgggtgggg tggggggctg   3960
gggtgctgcg tagccagtgt ttgactttct tttcaagtgg gggaaagtgg gagaggactg   4020
agagtgaggc aagttctccc cagcccctgt ccgtctgtct gtctctgtct gtggtggttt   4080
ctgtttcttg ggaggcatgg taggatcata agtcattccc ctccccttcc aggcctcctg   4140
ctatatttgg gggacctgac tggtttggct ggagtcccat gaggatgtgg gccctttaat   4200
aaaggatagc aaacaggg                                                 4218
```

<210> SEQ ID NO 38
<211> LENGTH: 2905

<212> TYPE: DNA
<213> ORGANISM: Human

<400> SEQUENCE: 38

```
ggccgaatac atcaagcaat ggtaacatct ttaaatgaag ataatgaaag tgtaactgtt     60

gaatggatag aaaatggaga tacaaaaggc aaagagattg acctggagag catcttttca    120

cttaaccctg accttgttcc tgatgaagaa attgaaccca gtccagaaac acctccacct    180

ccagcatcct cagccaaagt aaacaaaatt gtaaagaatc gacggactgt agcttctatt    240

aagaatgacc ctccttcaag agataataga gtggttggtt cagcacgtgc acggcccagt    300

caatttcctg aacagtcttc ctctgcacaa cagaatggta gtgtttcaga tatatctcca    360

gttcaagctg caaaaaagga atttggaccc ccttcacgta gaaaatctaa ttgtgtgaaa    420

gaagtagaaa aactgcaaga aaaacgagag aaaaggagat tgcaacagca agaacttaga    480

gaaaaaagag cccaggacgt tgatgctaca aacccaaatt atgaaattat gtgtatgatc    540

agagacttta gaggaagttt ggattataga ccattaacaa cagcagatcc tattgatgaa    600

cataggatat gtgtgtgtgt aagaaaacga ccactcaata aaaaagaaac tcaaatgaaa    660

gatcttgatg taatcacaat tcctagtaaa gatgttgtga tggtacatga accaaaacaa    720

aaagtagatt taacaaggta cctagaaaac caaacatttc gttttgatta tgcctttgat    780

gactcagctc ctaatgaaat ggtttacagg tttactgcta aaccactagt ggaaactata    840

tttgaaaggg gaatggctac atgctttgct tatgggcaga ctggaagtgg aaaaactcat    900

actatgggtg gtgacttttc aggaaagaac caagattgtt ctaaaggaat ttatgcatta    960

gcagctcgag atgtcttttt aatgctaaag aagccaaact ataagaagct agaacttcaa   1020

gtatatgcaa ccttctttga aatttatagt ggaaaggtgt ttgacttgct aaacaggaaa   1080

acaaaattaa gagttctaga agatggaaaa cagcaggttc aagtggtggg attacaggaa   1140

cgggaggtca aatgtgttga agatgtactg aaactcattg acataggcaa cagttgcaga   1200

acatccggtc aaacatctgc aaatgcacat tcatctcgga gccatgcagt gtttcagatt   1260

attcttagaa ggaaaggaaa actacatggc aaattttctc tcattgattt ggctggaaat   1320

gaaagaggag ctgatacttc cagtgcggac aggcaaacta ggcttgaagg tgctgaaatt   1380

aataaaagcc ttttagcact caaggagtgc atcagagcct taggtagaaa taaacctcat   1440

actcctttcc gtgcaagtaa actcactcag gtgttaagag attctttcat aggtgaaaac   1500

tctcgtacct gcatgattgc cacaatctct ccaggaatgg catcctgtga aaatactctt   1560

aatacattaa gatatgcaaa tagggtcaaa gaattgactg tagatccaac tgctgctggt   1620

gatgttcgtc caataatgca ccatccacca aaccagattg atgacttaga gacacagtgg   1680

ggtgtgggga gttcccctca gagagatgat ctaaaacttc tttgtgaaca aaatgaagaa   1740

gaagtctctc cacagttgtt tactttccac gaagctgttt cacaaatggt agaaatggaa   1800

gaacaagttg tagaagatca cagggcagtg ttccaggaat ctattcggtg gttagaagat   1860

gaaaaggccc tcttagagat gactgaagaa gtagattatg atgtcgattc atatgctaca   1920

caacttgaag ctattcttga gcaaaaaata gacattttaa ctgaactgcg ggataaagtg   1980

aaatctttcc gtgcagctct acaagaggag gaacaagcca gcaagcaaat caacccgaag   2040

agaccccgtg ccctttaaac cggcatttgc tgctaaagga tacccagaac cctcactact   2100

gtaacataca acggttcagc tgtaagggcc atttgaaagt ttggaatttt aagtgtctgt   2160

ggaaaatgtt ttgtccttca cctgaattac atttcaattt tgtgaaacac tcttttgtct   2220

acaaaatgct tctagtccag gaggcacaac caagaactgg gattaatgaa gcattttgtt   2280
```

```
tcatttacac aaatagtgat ttacttttgg agatccttgt cagttttatt ttctatttga   2340

tgaagtaaga ctgtggactc aatccagagc cagatagtag gggaagccac agcatttcct   2400

tttaactcag ttcaattttt gtagtgagac tgagcagttt taaatccttt gcgtgcatgc   2460

atacctcatc agtgattgta catacettgc ccactcctag agacagctgt gctcactttt   2520

cctgctttgt gccttgatta aggctactga ccctaaattt ctgaagcaca gccaagaaaa   2580

attacattcc ttgtcattgt aaattacctt tgtgtgtaca tttttactgt atttgagaca   2640

tttttgtgt gtgactagtt aattttgcag gatgtgccat atcattgaac ggaactaaag   2700

tctgtgacag tggatatagc tgctggacca ttccatctta tatgtaaaga aatctggaat   2760

tattatttta aaaccatata acatgtgatt ataatttttc ttagcatttt ctttgtaaag   2820

aactacaata taaactagtt ggtgtataat aaaaagtaat gaaattctga agaaaaaaaa   2880

aaaaaaaaaa aaaaaaaaaa aaaaa                                         2905
```

<210> SEQ ID NO 39
<211> LENGTH: 2334
<212> TYPE: DNA
<213> ORGANISM: Human

<400> SEQUENCE: 39

```
ggcgcgctag gctcacaaag gcaggcacag actgcaaccc tgctcagtgc tccgggcgct     60

tcaggctggc ttgggtcctg ctgctccaac cccaagggcc ctggagcgct ccctgatacc    120

tccatcactc accatggcca gccagttctg cctccctgaa tccccatgtc tctcgcccct    180

gaaacccttg aagccacatt tcggagacat ccaagagggc atctacgtgg cgatccagcg    240

cagtgacaag cggatccacc tcgctgtggt cacggagatc aacagagaaa actattgggt    300

cacggtagag tgggtggaga aagcagtcaa aaaaggcaag aagattgacc tggagaccat    360

actcctgctg aatccagctc tggactctgc tgaacacccc atgccgcccc cgcccttatc    420

ccccttggct ctggcgccct cttcggccat cagggaccag cgtaccgcca cgaaatgggt    480

tgcgatgatc cccccagaaaa accaaacagc ctcaggggac agcctggatg tgagggtccc    540

cagcaaacct tgtctgatga agcagaaaaa gtctccctgc ctctgggaaa tccagaaact    600

gcaggagcag cgggaaaagc gcaggcggct gcagcaggag atccgagcta gacgcgccct    660

cgatgtcaat accagaaacc ccaactacga aatcatgcac atgatcgaag agtatcgcag    720

gcacctggac agcagcaaga tctcagtcct ggagcccccg caagaacatc gcatctgcgt    780

ctgcgtgagg aagcggcctc tcaaccagcg agagacaacc ttgaaggacc tggatatcat    840

caccgtcccc tcggacaatg tggttatggt gcatgagtcc aagcaaaagg tggacctcac    900

tcgctacctg cagaaccaga ccttctgctt cgaccatgcc ttcgatgaca aagcctccaa    960

cgagttggtg taccagttca ccgcccagcc actggtggag tccatcttcc gcaagggcat   1020

ggccacctgc tttgcctatg ggcagacggg aagtgggaag acgtacacca tgggtggaga   1080

cttttcagga acggcccaag attgttctaa gggcatttat gctctggtgg cacaggatgt   1140

ctttctcctg ctcagaaact ccacatatga gaagctggac ctcaaagtct atgggacatt   1200

ttttgagatt tatgggggca aggtgtatga tttgttgaac tggaagaaga agctgcaagt   1260

ccttgaggat ggcaatcagc aaatccaagt ggtcgggctg caggagaaag aggtgtgttg   1320

tgtggaggaa gtgctgaacc tggtggaaat agggaatagc tgtcggactt ccaggcaaac   1380

atctgtcaac gctcactcat ccaggagcca tgcagtgttc cagatcatcc tgaagtcagg   1440

agggataatg catggcaagt tttccctcgt tgatttagct gggaatgaaa gaggagcaga   1500
```

```
tacaaccaag gccagccgga aaaggcagct ggaaggggca gagattaaca agagtcttct   1560
agccctcaaa gaatgtattc tggctttggg tcagaacaag cctcacaccc cattcagagc   1620
cagcaaactc acactggtgc tccgggactc ctttataggc cagaactcct ccacttgcat   1680
gattgctacc atctctccgg ggatgacctc ttgtgaaaac actctcaaca ctttaagata   1740
tgcaaacaga gtaaaaaaat taaatgtaga tgtaaggccc taccatcgtg gccactatcc   1800
gattggacat gaggcaccaa ggatgttaaa aagtcacatc ggaaattcag aaatgtccct   1860
tcagagggat gaatttatta aaatacctta tgtacagagt gaggagcaga aagagattga   1920
agaggttgaa acattaccca ctctgttagg gaaggatacc acaatttcag ggaagggatc   1980
tagccaatgg ctggaaaaca tccaggagag agctggtgga gtacaccatg atattgattt   2040
ttgcattgcc cggtctttgt ccattttgga gcagaaaatt gatgctctga ccgagatcca   2100
aaagaaactg aaattattac tagctgacct ccacgtgaag agcaaggtag agtgaagcca   2160
atggcgagag atcaggtccg aaatgctgca ttgctgcagt ttccaccact cttatacagg   2220
aaaactgtcc aaattatcta aagatcctcc tgagaagctt aaaacatctt aaaatacact   2280
gatgggaaac atgctctttc ttctgcctct gttaaaaaaa aaaaaaaaaa aaaa         2334
```

<210> SEQ ID NO 40
<211> LENGTH: 2825
<212> TYPE: DNA
<213> ORGANISM: Human

<400> SEQUENCE: 40

```
gcgaaattga ggtttcttgg tattgcgcgt ttctcttcct tgctgactct ccgaatggcc     60
atggactcgt cgcttcaggc ccgcctgttt cccggtctcg ctatcaagat ccaacgcagt    120
aatggtttaa ttcacagtgc caatgtaagg actgtgaact tggagaaatc ctgtgtttca    180
gtggaatggg cagaaggagg tgccacaaag ggcaaagaga ttgattttga tgatgtggct    240
gcaataaacc cagaactctt acagcttctt cccttacatc cgaaggacaa tctgcccttg    300
caggaaaatg taacaatcca gaaacaaaaa cggagatccg tcaactccaa aattcctgct    360
ccaaaagaaa gtcttcgaag ccgctccact cgcatgtcca ctgtctcaga gcttcgcatc    420
acggctcagg agaatgacat ggaggtggag ctgcctgcag ctgcaaactc ccgcaagcag    480
ttttcagttc ctcctgcccc cactaggcct tcctgccctg cagtggctga aataccattg    540
aggatggtca gcgaggagat ggaagagcaa gtccattcca tccgtggcag ctcttctgca    600
aaccctgtga actcagttcg gaggaaatca tgtcttgtga aggaagtgga aaaaatgaag    660
aacaagcgag aagagaagaa ggcccagaac tctgaaatga gaatgaagag agctcaggag    720
tatgacagta gttttccaaa ctgggaattt gcccgaatga ttaaagaatt tcgggctact    780
ttggaatgtc atccacttac tatgactgat cctatcgaag agcacagaat atgtgtctgt    840
gttaggaaac gcccactgaa taagcaagaa ttggccaaga aagaaattga tgtgatttcc    900
attcctagca agtgtctcct cttggtacat gaacccaagt tgaaagtgga cttaacaaag    960
tatctggaga accaagcatt ctgctttgac tttgcatttg atgaaacagc ttcgaatgaa   1020
gttgtctaca ggttcacagc aaggccactg gtacagacaa tctttgaagg tggaaaagca   1080
acttgttttg catatggcca gacaggaagt ggcaagacac atactatggg cggagacctc   1140
tctgggaaag cccagaatgc atccaaaggg atctatgcca tggcctcccg ggacgtcttc   1200
ctcctgaaga atcaaccctg ctaccggaag ttgggcctgg aagtctatgt gacattcttc   1260
gagatctaca atgggaagct gtttgacctg ctcaacaaga aggccaagct gcgcgtgctg   1320
```

-continued

```
gaggacggca agcaacaggt gcaagtggtg gggctgcagg agcatctggt taactctgct   1380
gatgatgtca tcaagatgct cgacatgggc agcgcctgca gaacctctgg gcagacattt   1440
gccaactcca attcctcccg ctcccacgcg tgcttccaaa ttattcttcg agctaaaggg   1500
agaatgcatg gcaagttctc tttggtagat ctggcaggga atgagcgagg cgcagacact   1560
tccagtgctg accggcagac ccgcatggag ggcgcagaaa tcaacaagag tctcttagcc   1620
ctgaaggagt gcatcagggc cctgggacag aacaaggctc acaccccgtt ccgtgagagc   1680
aagctgacac aggtgctgag ggactccttc attggggaga actctaggac ttgcatgatt   1740
gccacgatct caccaggcat aagctcctgt gaatatactt taaacaccct gagatatgca   1800
gacagggtca aggagctgag cccccacagt gggcccagtg gagagcagtt gattcaaatg   1860
gaaacagaag agatggaagc ctgctctaac ggggcgctga ttccaggcaa tttatccaag   1920
gaagaggagg aactgtcttc ccagatgtcc agctttaacg aagccatgac tcagatcagg   1980
gagctggagg agaaggctat ggaagagctc aaggagatca tacagcaagg accagactgg   2040
cttgagctct ctgagatgac cgagcagcca gactatgacc tggagacctt tgtgaacaaa   2100
gcggaatctg ctctggccca gcaagccaag catttctcag ccctgcgaga tgtcatcaag   2160
gccttacgcc tggccatgca gctggaagag caggctagca gacaaataag cagcaagaaa   2220
cggccccagt gacgactgca aataaaaatc tgtttggttt gacacccagc ctcttccctg   2280
gccctcccca gagaactttg ggtacctggt gggtctaggc agggtctgag ctgggacagg   2340
ttctggtaaa tgccaagtat gggggcatct gggcccaggg cagctgggga gggggtcaga   2400
gtgacatggg acactccttt tctgttcctc agttgtcgcc ctcacgagag gaaggagctc   2460
ttagttaccc ttttgtgttg cccttctttc catcaagggg aatgttctca gcatagagct   2520
ttctccgcag catcctgcct gcgtggactg gctgctaatg gagagctccc tggggttgtc   2580
ctggctctgg ggagagagac ggagccttta gtacagctat ctgctggctc taaaccttct   2640
acgcctttgg gccgagcact gaatgtcttg tactttaaaa aaatgtttct gagacctctt   2700
tctactttac tgtctcccta gagtcctaga ggatccctac tgttttctgt tttatgtgtt   2760
tatacattgt atgtaacaat aaagagaaaa aataaaaaaa aaaaaaaaaa aaaaaaaaaa   2820
aaaaa                                                               2825
```

<210> SEQ ID NO 41
<211> LENGTH: 6257
<212> TYPE: DNA
<213> ORGANISM: Human

<400> SEQUENCE: 41

```
gcggctgcgc actgggcgct ctcgcccgag aagccgcagt ctcgagagcg tcaacgaggt     60
gtttcggtag tctctggcca tcctttctgc gcacccggtg tcgctgggct gcaccccggg    120
cggggacgtc cgccgggcac gggagggggc caagatgccg atcaataaat cagagaagcc    180
agaaagctgc gataatgtga aggttgttgt taggtgccgg cccctcaatg agagagagaa    240
atcaatgtgc tacaaacagg ctgtcagtgt ggatgagatg aggggaacta tcactgtaca    300
taagactgat tcttccaatg aacctccaaa gacatttact tttgatactg tttttggacc    360
agagagtaaa caacttgatg tttataactt aactgcaaga cctattattg attctgtact    420
tgaaggctac aatgggacta tttttgcata tggacaaacc ggaacaggca aaacttttac    480
catggaaggt gttcgagcta ttcctgaact tagaggaata attcccaatt catttgctca    540
catatttggt catattgcaa aagcggaggg tgatacaaga tttttggttc gagtgtctta    600
```

-continued

```
tttggaaata tataatgaag aagttcgtga ccttttgggc aaggatcaga cacaaaggtt    660
agaggttaaa gaaagacctg atgtgggagt ttatatcaaa gatttatcag cttatgtggt    720
aaataatgct gatgatatgg atagaattat gacgctaggc cacaaaaatc gttctgttgg    780
tgcaactaat atgaacgaac atagttcccg ttcccatgcc atctttacaa ttactataga    840
atgcagtgaa aaaggcattg atggtaacat gcatgtcagg atggggaagc tccatcttgt    900
agatcttgct ggttcagaaa gacaggcaaa aactggagct actggacagc gcctaaagga    960
agctacaaaa atcaatcttt cactttccac ccttggtaat gtaatttctg ccttggttga   1020
tggaaaaagc actcatgtgc cttatcgtaa ctctaaactg actcgtcttc ttcaggattc   1080
cttaggagga aattcaaaaa ccatgatgtg tgcaaatatt gggccagcag attacaatta   1140
tgatgaaact atcagtacat tacggtatgc caatcgtgct aagaatatta aaaataaagc   1200
tagaattaat gaagatccaa aggatgcttt gctgcgtcag ttccagaaag aaatagaaga   1260
actgaaaaag aagcttgaag aaggagaaga aatatcaggc tctgatatca gtgggtcaga   1320
ggaagatgat gatgaagagg gtgaggttgg agaagatgga gagaaaagga aaaaaagaag   1380
gggaaaaaag aaagtctccc cagacaagat gattgaaatg caagcaaaaa ttgatgagga   1440
gagaaaagca cttgaaacaa agctcgacat ggaagaagaa gaaagaaaca aggctagagc   1500
tgaattagag aaacgggaaa aagatcttct taaagcccaa caagagcatc agtctttgct   1560
ggaaaaatta tctgccctgg aaaagaaggt aattgttggt ggggttgact tgttggccaa   1620
agctgaggaa caagagaaac ttcttgaaga atctaacatg gaactggaag aaaggaggaa   1680
aagagcagag caacttcgca gagaacttga ggaaaaagag caagaacgct tggatattga   1740
agaaaaatat accagtttgc aagaggaagc acagggaaag accaagaagt taaagaaagt   1800
ttggactatg ctgatggctg caaagtcaga gatggctgat ctccaacaag aacatcagag   1860
ggaaattgaa ggcctactgg agaacattcg gcaacttagc cgggagcttc gacttcagat   1920
gcttattatt gataacttta tacctcggga ttatcaggaa atgattgaaa actatgtcca   1980
ttggaatgaa gacataggag aatggcagct aaaatgtgtt gcttatacag gaaataacat   2040
gaggaagcaa accccagtac ctgataaaaa ggagaaagat ccctttgagg tggacctttc   2100
tcacgtgtat cttgcctata ctgaggagag tctgcgtcag tctttgatga aactagaaag   2160
accacgaact tcaaagggga aagcaaggcc aaagacaggg agaagaaagc gttctgcaaa   2220
gcctgaaact gtaattgact ctttactgca gtaaatgtta cagacttaaa gtcacaataa   2280
aaattagtga tattctcatg cctggacaaa atctttaatt aaaacagtga agacttctct   2340
ataatttcaa ttaatggaag ttgtagatca atgaataaga ctggaaataa taatttgctt   2400
aagaactttt agtctacata tattaatata acattaaaat tgtacaactg gtgattgttc   2460
aaattgttgt actactactc ttcaattgta ctgtgcaggg aagttggggg aacagttcat   2520
actatagaga gttacagttt agatgtatgt gtaaatcgat tagctattta tccaactact   2580
gtatatttag gtaactagaa tttcaaaata gaaaaaaaaa aactgtgtcc tgttttgcac   2640
atagaaagaa gcagatcaga ttgtcctatg ttgcgctgtt atatatgaat gtttggactg   2700
tacatctaaa gaatgattcc gtcctaacac ccacccagcc tgtttgaaca cattctaatt   2760
gtctaacatt tgttgcattt taagtatgag atgactgatc ttatgaatgt tttgtagaaa   2820
atgttataat ttaacagtct ttgcgagtat acatgttttt taacaagttg aaaatgtttc   2880
atctgaacct ttcctaactt ttttttgcca gtttgagttc aaatcaaata caccttaagt   2940
tctggtttca tgttctcttg aaacattgaa ttgtacgtaa atataaagga tctactgttg   3000
```

-continued

```
cggaaaatta agaagctaaa tactgctcag ttatctttgc ctgcgtgtat atttttaaaa   3060
attcactctg aagtgttatg gatgcttttc tttgagttct aaattttggt gggaattact   3120
ttatgtctcc cagttaagaa gagtctccat tttccagaaa atacagctaa gcaagaaaaa   3180
tatcttttaa atactttgcc tttaaaacac ttttttattt tgtttttcta ttttaaaaat   3240
aaaatattat tttctgaatt tcttctattg ggtaatccag ttagaccata ttcctctaca   3300
aataaaaact atgttgattt catagtaaag taagttgtaa tagagataat tattttttc    3360
tgttgttagc tgcttatgaa acttttattg tattttttta aagttatgct actcctggcc   3420
gggcatggtg gctcacgcct gtaatcccag cactttggga ggccgaggca cgtggatcac   3480
ttgatgtcag gagttcgaga ccagcctggc taacatggtg aaaccctgtc tccagtacaa   3540
atacaataat tagctgggtg tggtggcgca cacctgtaat cccagctact tgggaggctg   3600
aggcaggaga atcacttgaa cctgggaggc ggaggttgca gtgagctgag atggcatcac   3660
tgcactccag cctgggtgac agggtgacac tccacctcaa aaaataaaaa taaaataaaa   3720
ataaagttat gctactccta aaccacttaa tatatgtttt gtggttttca aaattatgta   3780
atcagccctg aaacacattg gttgaaaata ttttgagact ttataagtta gtatttatta   3840
aattaatatt attttaataa gttttgttaa atcctagttt aaatgacaaa gctgtgtata   3900
gagtaggggt gagtgaaggt ggagtactct tgaggtggcg ataaaaatgt acccataaat   3960
ttaaagtcca ttctgtaatt ggaatactga atgtcctgtg tgtggtgaac attttctagg   4020
tgattagaat tgcatttcac tggctgcatt tgtttgtggt atgtaagata gctagaaatt   4080
tattacttaa ctctgtgggg cattgtttag atactgtgaa gagttgaggt aaatatgtgt   4140
cttgtaaaag ctttgtgtga tcagaatatt ttggtaatta taaaatgttt ttgatgatac   4200
acatttaact ctgttagtaa ttactctaaa gaaatcttaa ttttaccagt ttaaaaaaaa   4260
cgcttctttt taaaagttca tgtttctaac ctttaacaat tcagttaata ggaaaggagt   4320
aactttttaaa tcaagcttta aaacatggaa atttaagcca gtatgttaga tatttttttct  4380
atcccaccct accatgataa taaaaataaa tctataaaaa gtcaaaataa aaagccgatc   4440
tataaaaagt caattgagaa gttctaaaag caggctacta tagcaggggt gtttgttttt   4500
tgtttggaga cggagtctgg ctctattacc taggctggag tgcagtggga caatctcggc   4560
tcactgtaac ctctgtctct tcagcctcct gagttgctgg aactacagct gtatgccatc   4620
atgctcggct aatttttgta tttttttgta gagatggggt tttgccatgt tgcccgggcc   4680
tgtcttgaac tcctagagct taagtgatcc acccgcctca ggctcccgaa gtgctgggat   4740
tacaggcatg attataggcc tgagccacca caccccgcct actatagcag tttttttaaaa  4800
aaagcattat gttaaaactg attataccag atggacatta aatatccatc tcagaaatac   4860
caaaatttga tacataagcc tggcctgaat atcttttttt tttttttgag acggagtctt   4920
actctgtcgc ccaggctgga gtgcagtggc gcgatctcgg ctcactgcaa cctctgcctc   4980
ctgggttcaa gggattctcc tgcctcagcc tcttgagtag ctgggattac aggtttgcgc   5040
caccacaccc agctaatttt tgtatttttt ttttagtaga gaccgggttt caccatgttg   5100
gccaggctgg tctcacctga ctttgtgatc cgcccgcctc agcctcccaa agtgctggga   5160
ttacaggtgt gagccaccac gcctggcctc aagcctggtc tgaatatcta tatgcaaata   5220
tgggacactg acttcagagc tattcattta gctccagtca tagcaattct gtagtttcct   5280
cacatttact gtgtctttgt ccacaaatga aatatgttgt aaggtcagtg ttaatttcgt   5340
gagacgatat agatgaacac acttgctcat tttttgaaat aaatatgcag atttaaaatg   5400
```

-continued agtggcacat atatataaat aggttattga atgggtattc tcttttccct ttaatttaaa 5460
aagtgatatt tatttattaa aaggagcatt ggtagaatta ttggtttata gtatcttctt 5520
taataatcct tacaattaca tatactaata ggatgttaaa attatcatcg tgtttcctat 5580
ttgtgtttag attcttataa agcatgagat gagtaatcaa gggaagggtc gcatctccat 5640
gtttgcccca tgaatagaat ccatttgaca agccatttca tttcctttct ggagaaaggg 5700
agttgttttt tttttctttt tacagcaaaa atttaaggtt ttattggggg agggggtggt 5760
gctacttcct ctgtaacatg tttttaaaac tatgattatg gtttttggtt gtttttttgtt 5820 ttgtttgttt ccttttagtc tgtttttaat atccttcccc ttaactctta aggaaagtct 5880
tctttcctac agggctgtga attaaggaat gggtagcgtt tacatttaag tacaccaatg 5940
tctgcccaat ttcctaatgt atacatttgt tttattttaa attatttttt gttcttaaaa 6000
atactagaag aaaacataga tgtttctagt gcctttgaac ttatactgta gtctgactaa 6060
tttaatgaat aacttcagta gcattactat aatactgtat gctggccaaa attacaaatt 6120
acagtttgtt gcatcagttt caaaagccat gctttcattg tattttatgt ataaattgta 6180
tttgttcaag ttgtatatat tggtattgta tgtatacatg cagcatggtt aaataagaat 6240
aaaaatcttt tacctaa 6257

<210> SEQ ID NO 42
<211> LENGTH: 6103
<212> TYPE: DNA
<213> ORGANISM: Human

<400> SEQUENCE: 42
atccggggca gcggggaatg gctgagccag gggttcgccg cccccgccgc cgccgccgcc 60
gccgccgccg ccgccgccgc ccgctttcgg ctcgggcctc aggaccgtag catcctgaga 120
cattttgaat tgacacttct caagatttga ctggatcaga gttcatcatg tcaaagttga 180
aaagctcaga gtcagtcagg gtggtggttc gctgtcggcc catgaatggc aaggaaaagg 240
ctgcttcgta tgacaaagtg gtggatgtgg atgttaagct ggggcaggtg tctgtgaaga 300
accccaaagg gacggcccat gaaatgccca agaccttcac ctttgatgcc gtctatgact 360
ggaatgccaa gcagtttgaa ctgtacgatg agacgttccg accacttgtt gactctgtcc 420
tgcaaggttt caatggaacc atttttgcct atggacaaac tgggacagga aaaacctaca 480
ccatggaagg aatccgtggt gaccctgaaa aaagaggagt cattcctaac tcatttgacc 540
atatcttcac ccacatctct cgatcccaga atcaacaata cctggtcagg gcttcttact 600
tagagatcta ccaggaggag atccgagatt tgctctcaaa ggatcagacc aaaaggcttg 660
agctcaaaga gaggcctgac acaggagtgt atgtgaaaga cctgtcttcc tttgtcacca 720
agagtgtgaa ggagatagag catgtgatga atgtggggaa ccagaaccgt tctgtcggtg 780
ctaccaacat gaacgagcac agctcgcgtt ctcatgcaat tttcgttatc actattgagt 840
gcagcgaggt gggcctcgat ggtgaaaacc acatccgtgt aggaaaattg aaccttgtag 900
atcttgctgg cagcgaacgg caagccaaga ccggcgcaca aggggagaga ttaaaagaag 960
ctaccaagat caacctctcc ctttccgctt tgggtaatgt catctctgct ctagtggacg 1020
gcaaaagcac tcacattcca tatcgggact caaagcttac caggctcctc caagattccc 1080
ttggtggcaa tgccaagact gtgatggtgg ccaacgtggg gcctgcctct tacaacgtag 1140
aagagactct gaccactctg cgatatgcca accgtgccaa aaacattaag aacaaaccaa 1200
gggtcaatga ggaccccaag gatgccctcc ttcgagaatt ccaggaagag attgctcggc 1260

-continued

```
tcaaggccca gctggaaaaa cggtccattg gtaggaggaa gaggcgagag aagcggaggg   1320
aaggtggtgg cagtggtggg ggtggggaag aggaggagga ggagggagaa gagggtgagg   1380
aggaagggga tgataaggat gattactggc gggaacagca agaaaaactg gagattgaga   1440
agcgggccat tgtagaggat cacagcttgg ttgcagagga gaagatgagg ctgctgaagg   1500
agaaagagaa aaagatggag gacctgcggc gggagaagga tgctgccgag atgctgggcg   1560
ccaagatcaa ggccatggag agtaagttgc ttgttggagg aaaaaatata gtagatcata   1620
cgaatgaaca gcagaaaatc ctggagcaga aacgacagga aattgcagag cagaaacgtc   1680
gagaaagaga aatccagcaa cagatggaaa gtcgagatga ggagaccttg gaacttaaag   1740
agacatacag ctcattgcag caagaggtgg acatcaagac caaaaaactc aaaaagctct   1800
tctccaagct tcaggcagtg aaggctgaga tccatgacct ccaagaagaa cacatcaagg   1860
agcgccaaga gctagagcag actcagaatg agctcaccag ggagctgaaa ctcaagcatc   1920
ttattataga aaactttatc cctctggaag aaaaaagtaa aattatgaat agagccttct   1980
ttgatgaaga ggaagatcat tggaaactac atcctataac cagactggag aaccagcaga   2040
tgatgaagcg gccagtctca gccgtgggat ataagagacc attgagccag cacgcaagaa   2100
tgtccatgat gattcgtcca gaggcccgat atagggcaga aaacattgtg ctgttagagc   2160
tggacatgcc cagccggacc accagagact atgagggtcc agccattgcc cccaaggtcc   2220
aggctgcatt ggatgcggct ctgcaggatg aagatgagat acaggtggat gcatcatcat   2280
ttgaaagcac tgcaaataag aaatccaagg ccaggcctaa aagtggaagg aagtcgggat   2340
cctcctcctc ttcctcagga acccctgcat ctcagcttta tccacagtct cgggggctgg   2400
ttccaaagta aagccagctt ctcctctccc agggcggaaa cagcatttgc cttctgagag   2460
aagagactag caaaaagctg cagagaggat tcggcccaaa ctcagaactg ttcccctgag   2520
gagaagcggt ggcctctttg cagatcaacc aacttaatct ggttgaacgt gctgttccta   2580
atctggcact cagcccctct gggaaacatc ttttaattag catctcagaa atgcatgggt   2640
aaggtaaagt gcgatagttc aagtggaaag caagagaatg accagtgacc ttgcttcctt   2700
ccccccttgcc ttcttctccc ccttcccctg tgctcccttt ctctcctctc tccttttcta   2760
gcctgttctt tacatggggc tcccttcttg ttgaacaata gggcagaatc aggagtcacc   2820
ttagcaggac cacatctttg gagcctcggg ataaaatgac agtgaggttg aaaagtgaaa   2880
accctagaac ttgaataggt gcctgttctt gtagggagaa atgagaaatc gcatttggat   2940
ccaggcccca ggtgggcacc atcagcagtc ttgcttccat gcacctcagt aagaagtgga   3000
tctgcctttg ggacctgctc agtgaggaaa tctcttccaa tttctgcttc tgaatgattc   3060
aatgttggga gcaatagaaa taacattccc tttgccttct ctgagtgttt agggaaatag   3120
cttctttaaa acctcaaaac catgaccatc ctgtcaaaga cctaagtctg taagctggtg   3180
ccatgtccat acaccatgtc actttactct tcatttgtca ccatcttttc ccatgcacgc   3240
atactctgaa catccttgtg tgggcccatc ctctgcatcc agagcatgct ctgcagtggg   3300
cctgttttgt ggaagaaagg aggctgtctc tgccttctct gatgggactg gagttgaggg   3360
aaggagctgt attgtggcac ttctgaattc cccgttttgt tccatattgg tatagagagc   3420
agaagagtag ctaggcagat gcagagatgg agacatgaga ctcagtgcag tgggcaggga   3480
agacataaca gatggaagca aaggaatcct gcctgccttc agcagagaat tcaccgaatc   3540
ctagaactgt ggctccctcc aggcagagcc taagatgctg gtgaagaata gctgtgtgat   3600
tgaataggct caaaggagag ttcagaattc ccatttacat attactagtt tggtttgtaa   3660
```

gttttagttc cttgtattat tgagattcag agcttcattt tatgttggtc attaggtgaa 3720
tattactcat tttccctcaa gagaagctca taagtgtgtg tgggtgtgag agcacgatgg 3780
tgcctgtgtt ctgtgaatgt gtccatatgt gtctgtaaga gagacagaga ccaagaactt 3840
gcccaatttt agaaatacac taatgtgcag ttgttgcctt ttgtctgtat tgaaggccca 3900
ttgaatgact aatccaggct ggaagcattc ccatgtgggt gtctgagtcc atgagccaag 3960
cctgagggga cagtgagtct ccaggtctgc cacactggtg caccttgctg gcacggtgcc 4020
tcaggaaggt ggcgactcag gtgggccttg agttatattt taactcagct gctcagttcc 4080
cagggcacat ttctggatca gaacccatgg gaaacaggag gtactaagtg caatgtctta 4140
gcattctgca aaatggagat ctgttgtcca gcggcttatc tcctttttag taacccttct 4200
ttctgaaccc agggcccttt tcagccttcc ctcatatttt cttgagatca aactttactt 4260
ctttcttatt tactaagaat ttgcctgttt gaataagaac aaaacgctaa ggtgggtagc 4320
ctaagctgat tttctgctgg ttacacgtgt ctctcacacc acatttcctc aaagctaatc 4380
tgaattctgt aggctaaaaa tattcatgta gcaaatctga gaattgaaaa ctgcagataa 4440
ccggccgggt atggtgactc atgcctgtaa tcctagcact ttgggaggcc gaggtgggtg 4500
gaccacctga ggttaggact tcaagaccag cctggccaac atggtgaaac cccatctgta 4560
ctaaaaatac aaaaatttgc ctggtgtggt ggtgcatgcc tctagtccta gctactcggg 4620
aggctgaggc acgagaatca cttgaacctg ggaggcggag gttgcagtga gtcgagataa 4680
cactactgca ttccagcctg ggtgacagag tgagactcca cctcaaaaaa aaaaaaaaaa 4740
aaaaaaaaaa cagaaagaaa gaaaaagaaa actgcagata accctataca ttaatactgg 4800
tatctcgagg tgactcttct gaccaagggt ggttaagtga cacatagaac ttttctaaga 4860
gaagacagac aagttgacag gcatgccttg tactcagctg tgttcatgtg gtggtctgtg 4920
gaaagaaaag aagactcatt tggaaatgaa gctgtccctt tccaagcagt ctctggtgct 4980
tttcttctct caaaatggat ccgataaata tttgaataga gcagattgta gaatgtcgtg 5040
ctgtcaccag aaagctgctg ttttgggttc tgcattgagc caaatatgta gaggacctac 5100
caagcccact gagggactag gttttcatgt ctctagtcat acctagaatg ttctgagccg 5160
tctgagggcc ttcatgccgg cagcagctag caaagccaga aagcaagtct aacaggatct 5220
aagatgacca tcaggagaag gagtttgaga ctgtgtatgc aaccccccaat agacccccctt 5280
ttactctgat ctggagaatg tatctggctt catattttca agtcacatgt ctctcagacc 5340
cctggattca gaacccaagg ccacaaatca taggcatgaa gcactttctt aagactgacc 5400
taacgctgga ttatttcccg tccaatgcct gcatgctgct tgaattgctc cacccacacc 5460
tccatgacca agggcgccag agtgctgcaa ctggggcgtg ggccgctctc tgcttttcct 5520
gtctgactct gacaagtcct ccctcactga atgtagaatc gttgccaagt ttctgagaag 5580
tgtcgattcc ctgttaacat ggatatcagt tctgcctcac atttcccact tgaggttgag 5640
gcgtactgga gacaacacct cagaccatct gaaccccatc agtggacgaa aatggggctg 5700
ttaatatact ctaaaagcca tactaaaaat gctctgaggg aactggctaa gaatagtggg 5760
cctggtgatt gtctatcacg caaggctttg ttttgtactg ttcagaaatc tgtcaccttt 5820
ctgcctgccc ttgtttcctg aatgaaatgc ttctggggtt atttatgaaa ggagtgatcc 5880
tggggcaggc aggaggcagt gggcttcatg gctccttgaa gttattactg atcttgacct 5940
tctctttggc tacctttaga caaagaatac gccaatcaat acttggggct ctaagtttta 6000
caattgatat ttatttgtat catctctttg tctaggaatg taaaagtgat tctaaactaa 6060
gatgtgtaat aaaaatcaat cagatttatt gtacctacaa aaa 6103

<210> SEQ ID NO 43
<211> LENGTH: 5401
<212> TYPE: DNA
<213> ORGANISM: Human

<400> SEQUENCE: 43
tcactctcgc tgccgctgct ccgccccatc cccttctgtt tttctctctc attctccagt 60
ggcggcggcg gggaaggcgg aggcagaggc agcagcagcc gcgctggctg caatgaatga 120
tcccccagct tgggggGagg actccaggtg agcctctgcc ctcgggaggc ccgggacccc 180
cggccgccca cgaccggcag cccacgctat ggatccctag aggaaggagg agaagacagc 240
tcgccgccca cccccatccc attttcctct tcctttatct cattgttgcc gaagctgttt 300
acggcagcgc tccctctgct ccagcatggg gcgggctccg ggcacggctg ctcggcaggc 360
gctgctcccg cggcgactgg gggattctgc ctaattcacc tcccagccgg tgcagagagg 420
accggagagc ggtggaggcc cggactgcag cagcgttggg gccacctccc agcgtcccca 480
ccctaggagg ctgcatgcgg attgaagagc tgcgcctggg ggctgggccg gccccgctga 540
tcccgaccta gcgagcagga tagcaggacc gcccaggctg cggaggggct cgggggcagg 600
aaggtcagag cagcaagatg gccagtaaga ccaaggccag cgaggccctc aaggtggtgg 660
cccggtgccg ccccctcagc aggaaggagg aggctgctgg tcacgagcag atcctgacca 720
tggacgtgaa actgggccag gtgaccctgc ggaacccccg cgccgccccg ggggagctgc 780
ccaagacctt cacctttgac gccgtgtatg atgccagctc caagcaggcc gacctgtatg 840
acgaaaccgt gaggcccctg atagactccg tgctccaggg tttcaatggc acggtgtttg 900
cctatggcca gacgggcact ggcaagacct ataccatgca ggggacctgg gtggagcccg 960
agctgcgcgg ggtcatcccg aatgcctttg agcacatctt cacccacatc tcccgctccc 1020
agaaccaaca gtacctggtc cggcctcct atttggagat ctaccaggaa gagattcgag 1080
acctgctctc caaggagccg ggcaagaggc tagagctgaa agagaacccc gagactggcg 1140
tctacatcaa ggacctctcc tccttcgtca ccaagaatgt caaggagatt gagcatgtga 1200
tgaacctggg gaaccagacc cgggctgtgg gcagcaccca catgaatgag gtcagctccc 1260
gctcccatgc catcttcatc atcactgtgg agtgcagcga acgtggctct gatggccagg 1320
accacatccg agtgggcaag ctcaacctcg tggacctggc tggcagcgag aggcagaaca 1380
aggcaggccc caacacagcg ggaggggcag ccacaccatc ctcgggtggc ggtggtggcg 1440
gtggaggcag tggtggtggt gctggtggag agaggcctaa ggaagcctcc aaaatcaacc 1500
tctcattatc tgccctgggc aacgtgattg ctgccctggc gggcaacagg agcacccaca 1560
ttccctaccg ggactccaag ctgacccggc tgctccagga ctccctgggg gggaatgcca 1620
agaccatcat ggtagccaca ctggggccag cttctcacag ctacgatgag agcctctcca 1680
ccttgcgctt tgccaaccga gccaagaaca tcaagaacaa gccccgggtg aacgaggacc 1740
ccaaggacac actgctgcgg gaattccaag aggagattgc ccgcctgaag gcccagctgg 1800
agaagagggg gatgctgggg aagcggcccc ggaggaagag cagccgcagg aagaaggccg 1860
tgtccgcccc gcctgggtac cctgagggcc cagtgattga ggcctgggtg gcagaagagg 1920
aggatgacaa caacaacaac caccgcccgc cccagcccat cctggagtca gccttggaga 1980
agaacatgga gaattacctg caggaacaga aggagcggct ggaggaggag aaggcagcca 2040
tccaggatga ccgcagcctg gtgagcgagg agaagcagaa gctgctggag gagaaggaga 2100

```
agatgctgga ggacctgcgg cgggaacagc aggccacaga gctgcttgcg gccaagtaca   2160
aggccatgga gagcaagctc ctcatcgggg gcaggaacat catggatcac accaacgaac   2220
agcagaagat gttggaactg aagaggcagg agattgccga gcagaaacgt cgtgagcggg   2280
agatgcagca ggagatgatg ctccgggacg aggagactat ggagctccgg ggcacctaca   2340
catccctgca gcaggaggtg gaggtcaaaa ccaagaaact caagaagctc tacgccaagc   2400
tgcaggcggt gaaggcggag atccaggacc agcatgatga gtatatccgc gtgcggcagg   2460
acctggagga ggcgcagaac gagcagaccc gcgaactcaa gctcaagtac ctaatcatcg   2520
agaacttcat cccgccggag gagaagaaca agatcatgaa ccggcttttc ctggactgtg   2580
aggaggagca gtggaagttc cagccactgg tgccagccgg cgtcagtagc agccagatga   2640
agaagcggcc aacatctgca gtgggctaca agaggcctat cagccagtat gctcgggttg   2700
ccatggcaat ggggtcccac cccaggtaca gggctgaaaa cataatgttt ctggagttgg   2760
atgtgtcccc tccagctgtc tttgagatgg aattctctca cgaccaagaa caagaccctc   2820
gtgcgctaca catggagagg ctcatgcgat tggacagctt tctggaaaga ccttccacgt   2880
ctaaagtccg aaagtccaga tcctggtgcc agagtcctca gcggcctcca ccttccacca   2940
cacatgcctc cctggcctct gcttctctgc gccctgcaac agtggcggac catgagtgac   3000
aaccatcacg tcaggctgcc catccaatag actcctggga tggggcagcc aaccctggct   3060
catctcatct gccgcttggt gcgtgtgcgt gtgcgtgcat gtgcgtgtgc gtgtgtgcag   3120
gggtgagaat ctggcagatg gtgcctctgc ctgctcttct tcgcctcctt tatttaattc   3180
atgttattta ttcgcggagc tctgttcgtg ttggggagat gccctcgcct gagccgtctg   3240
ggcctaccgt ggtcactgcg tagcctcttt ttcttctgac ttgagagctc ccccagtcag   3300
atctcaggct tgtccccctg tcagctgcct ccagaaggga aggtagccag tgcctgagaa   3360
gacagtccct tttctaccca ccgcactcca taacctccat cttctcccac actgatggcg   3420
agcagcccct gagcactttc tggactgggg agactgcttg gtgttccctg aggacaagag   3480
acatcctgac agtgttgggc atctgctccc cgtggacaca gccccactct ccactttctg   3540
agcctcagac aacctcattc agcctcttgg gctccttttc aaggacatta ataacctcac   3600
caacatagct catgcccttc agctttgaca agaactcacg gcttcccaaa ctctgctttc   3660
tgcccacctt ggatgggaac tgtggaccaa gcaattacca tcgccttgga acctgcagga   3720
aatggaacag caattgagac aacttgaaca gtcatcaacg gaagtccctc cactggattc   3780
ctttgtttct gtcccctccg aggagtcatt ttggtcgaca ggctctcaag gcaactcccc   3840
attttcaaga ggctgctcct gcctgcttcg atcatttctc cctgcagctg cctagacccc   3900
gttcacagtg ggaggagtca atgtcattct acccctcgct aaacgaagat attaacatct   3960
attgcttttt cccttcatct gtcacaggaa acagaagccc aggcacaatc ttttccagct   4020
ttgcctgtta cccctgtttc tgaattgcat ctttaaggta ttattttgtt gacaatagat   4080
cctttattca ctagttacgc aaattggttc ctagggggat actccttacc ttcctttgtg   4140
atggcccaaa atgtctctag gtatctcaag tgataagtaa atttctacaa aaaaaaatgg   4200
ttaatgttca ttgactggct ttttaagtgt atattttgga ggacgggtga agaggtcata   4260
acgaaagcaa gcgagtgaat taggatttca aagtgcccta atagtgtgag tctccagttc   4320
ctagaatatg aagagtgctg tcgttggggt gaaaccatga gactgacaga tctgcctgaa   4380
atggggggtg tgggaggtgg tggcgggggt tattctcttt ccttcaggaa atgaaccctt   4440
cttacatcat tcaagttctg ctctgaggat caagcttggg tctgatttaa ctcagcgaca   4500
```

```
ctgtcatttc tgcttcatta ctggactaga gggttgagcc acccacttgc catttgctcc   4560
tgtccttcca ggaaatcaca attttcatca gagcccaaga gattatttga gactcaggat   4620
tcagatcaga ggttcgactg tggctgggac aggagttgtg tgtagaaatt caccaggtgg   4680
cctgagcgca gggggacctc cagggctgcg ttgagcagcc tctcccactg acctctttct   4740
cgtttgtgga caaagcagca cgtatcacct cattcatcac ttggacacat cgcctttgca   4800
ttgtcttgtc acacctccct cacagtctta tagcacaata tacccaaatc agccccccca   4860
gtccgagggc tgggcccaag gtatggtcgg aggaggagct cctgcctgcg gttttgtgta   4920
tgtgtgtatg tgtgtgcgtg tttgtgtgcg tgtttacctc cacaggggac actctacact   4980
cagtgtaaga tctgctggga acagggccac caggagtggc tggatctcag tctctctgtc   5040
tctctttctc tccttttcct tttggtgtat caaatatttg attgacaaag taagggcctt   5100
gattaggacc aaattctcgt gtgttgctat ggtctttatt taggacaaca attaacaatg   5160
cagtggccca ttcttgtcac tctacacata tgactatacg ggacatatgt aatatataaa   5220
tatatatata aaacattccc ctctgtcccc ttggcttcgg atggaggcct ttctgttgag   5280
ctgaaatgca cctgcagctg ggtgctgcca gcagcttgca ggccccagcc ctgttccaat   5340
caatgcagtt gacaataaag gaatgagtat cgtcacggaa aaaaaaaaaa aaaaaaaaaa   5400
a                                                                   5401
```

<210> SEQ ID NO 44
<211> LENGTH: 4348
<212> TYPE: DNA
<213> ORGANISM: Human

<400> SEQUENCE: 44

```
gggaggccca gggagaacgg ggaagggaca tttagtttga gacggtgctg agataggatc     60
atgaaggaag aggtgaaggg aattcctgta agagtggcgc tgcgttgtcg ccctctggtc    120
cccaaagaga ttagcgaggg ctgccagatg tgcctttcct tcgtgcccgg agagcctcag    180
gtggtggttg gtacagataa atccttcacc tacgattttg tatttgatcc ctctactgaa    240
caggaagaag tcttcaatac agcagtagcg ccactcataa aaggtgtatt taaaggatat    300
aatgcaacgg tcctggccta tggcagact ggctctggaa aaacctattc aatgggaggt    360
gcatatactg cagagcaaga gaatgaacca acagttgggg ttattcctag ggtaatacaa    420
ctgctcttca aagaaattga taaaaagagt gactttgaat ttactctgaa agtgtcttac    480
ttagagattt acaatgaaga aattttggat cttctatgtc catctcgtga gaaagctcaa    540
ataaatatac gagaggatcc taaggaaggc ataaagattg tgggactcac tgagaagact    600
gttttggttg ccttggatac tgtttcctgt ttggaacagg gcaacaactc taggactgtg    660
gcctccacgg ctatgaactc ccagtcgtcc cgatctcatg ccatctttac aatctcctta    720
gagcaaggaa agaaaagtga caagaatagc agctttcgct ccaagctgca tcttgtagac    780
ctcgctggat cagaaagaca gaagaaaacc aaggctgaag gggatcgtct aaaagagggt    840
attaatatta accgaggcct cctatgcttg ggaaatgtaa tcagtgctct tggagatgac    900
aaaaagggtg gctttgcgcc ctacagagat tccaagttga ctcgactgct tcaagattct    960
ctaggaggta atagccatac tcttatgata gcctgtgtga gtcctgctga ctccaatcta   1020
gaggaaacat taaatacccct tcgctatgct gacagagcaa gaaaaatcaa gaacaaacct   1080
attgttaata ttgatcccca gacagctgaa cttaatcatc taaagcaaca ggtacaacag   1140
ctacaagtct tgttgctaca ggcccatgga ggtaccctgc ctggatctat aactgtggaa   1200
```

-continued

```
ccatcagaga atctacaatc cctgatggag aagaatcagt ccctggtaga ggagaatgaa   1260
aaattaagtc gtggtctgag cgaggcagct ggtcagacag cccagatgtt ggagaggatc   1320
atttggacag agcaagcgaa tgaaaaaatg aacgccaagc tagaagagct caggcagcat   1380
gcggcctgca aactggatct tcaaaagcta gtggagactt tggaagacca ggaattgaaa   1440
gaaaatgtag agataatttg taacctgcag caattgatta cccagttatc ggatgaaact   1500
gttgcttgca tggctgcagc cattgatact gcggtggagc aagaagccca agtagaaacc   1560
agtccagaga cgagcaggtc ttctgacgct tttaccactc agcatgctct ccgtcaagcg   1620
cagatgtcta aggagctggt tgagttgaat aaagcgcttg cactgaaaga ggccctggct   1680
aggaagatga ctcagaatga cagccaactg cagcctattc agtaccaata ccaggataac   1740
ataaaagagc cagaattaga agtcatcaat ctgcaaaagg aaaaggaaga attggttctt   1800
gaacttcaga cagcaaagaa ggatgccaac caagccaagt tgagtgagcg ccgccgcaaa   1860
cgtctccagg agctggaggg tcaaattgct gatctgaaga agaaactgaa tgagcagtcc   1920
aaacttctga aactaaagga atccacagag cgtactgtct ccaaactgaa ccaggagata   1980
cggatgatga aaaaccagcg ggtacagtta atgcgtcaaa tgaaagaaga tgctgagaag   2040
tttagacagt ggaagcagaa aagagacaaa gaagtaatac agttaaaaga acgagaccgt   2100
aagaggcaat atgagctgct gaaacttgaa agaaacttcc agaaacaatc caatgtgctc   2160
agacgtaaaa cggaggaggc agcagctgcc aacaagcgtc tcaaggatgc tctccagaaa   2220
caacgggagg ttgcagataa gcggaaagag actcagagcc gtggaatgga aggcactgca   2280
gctcgagtga agaattggct tggaaacgaa attgaggtta tggtcagtac tgaggaagcc   2340
aaacgccatc tgaatgacct ccttgaagat agaaagatcc tggctcaaga tgtggctcaa   2400
ctcaaagaaa aaaaggaatc tggggagaat ccacctccta aactccggag gcgtacattc   2460
tcccttactg aagtgcgtgg tcaagtttcg gagtcagaag attctattac aaagcagatt   2520
gaaagcctag agactgaaat ggaattcagg agtgctcaga ttgctgacct acagcagaag   2580
ctgctggatg cagaaagtga agacagacca aaacaacgct gggagaatat tgccaccatt   2640
ctggaagcca agtgtgccct gaaatatttg attggagagc tggtctcctc caaaatacag   2700
gtcagcaaac ttgaaagcag cctgaaacag agcaagacca gctgtgctga catgcagaag   2760
atgctgtttg aggaacgaaa tcattttgcc gagatagaga cagagttaca agctgagctg   2820
gtcagaatgg agcaacagca ccaagagaag gtgctgtacc ttctcagcca gctgcagcaa   2880
agccaaatgg cagagaagca gttagaggaa tcagtcagtg aaaaggaaca gcagctgctg   2940
agcacactga agtgtcagga tgaagaactt gagaaaatgc gagaagtgtg tgagcaaaat   3000
cagcagcttc tccgagagaa tgaaatcatc aagcagaaac tgaccctcct ccaggtagcc   3060
agcagacaga aacatcttcc taaggatacc cttctatctc cagactcttc ttttgaatat   3120
gtccagccta agccaaaacc ttctcgtgtt aaagaaaagt tcctggagca aagcatggac   3180
atcgaggatc taaaatattg ttcagagcat tctgtgaatg agcatgagga tggtgatggt   3240
gatgatgatg agggggatga cgaggaatgg aagccaacaa aattagttaa tgtgtccagg   3300
aagaacatcc aagggtgttc ctgcaagggc tggtgtggaa acaagcaatg tgggtgcagg   3360
aagcaaaagt cagactgtgg tgtggactgt tgctgtgacc ccacaaagtg tcggaaccgc   3420
cagcaaggca aggatagctt gggcactgtt gaacggaccc aggattcaga aagctccttc   3480
aaactggagg atcctaccga ggtgacccca ggattgagct tctttaatcc cgtctgtgcc   3540
acccccaata gcaagatcct gaaagagatg tgcgatgtgg agcaggtgct gtcaaagaag   3600
```

actcccccag ctccctcccc ttttgacctc ccagagttga aacatgtagc aacagaatac 3660
caagaaaaca aggctccagg gaagaaaaag aaacgggctc tggccagcaa caccagcttc 3720
ttctctggct gctcccctat cgaagaagag gcccactgaa gttggagtca tcatctctac 3780
ccccagtctg gcttgggaga tgctttcagg ttgcagccag aaggggtttt ttaaatgact 3840
tctctggatt tcaggtttct tgctgttgaa aaaaggaaca aagcgttact gaaaagaagg 3900
taacctttgt tggatgtggg ccttagcctc caggtccaga ctactactct atgttctcca 3960
gaagggtgct aagtcaccta ctgaagagag aaccaactga ctttcctatt gactcatcag 4020
gaaccagtcc tcagtctggt caagttgttt cttatttgtg agcagttcag gctatctcct 4080
gatggggatg aggccaaggc tttcttatct tttggttgtc tctgcttaat ggaggagcct 4140
ggcctaggat ggaggcctgg cttagatctt tcattccacc tcaggaatga ggttgtgatc 4200
tttcctgtcc tgaccctctc tgaattatgt ttcaatagta ctcttgattg tctgccatgt 4260
tgttgaagca aatgaattat ttttaaatgt taagtaagta aataaacctt agcccgtctt 4320 ttttttttt ttttttttt tttttttt 4348

<210> SEQ ID NO 45
<211> LENGTH: 4125
<212> TYPE: DNA
<213> ORGANISM: Human

<400> SEQUENCE: 45
tttgaaactt ggcggttaaa gctccggctg ggcaggggcg gcgggagacc ccgggtgaac 60
ggggaaggga catttagttt gagacggtgc tgagatagga tcatgaagga agaggtgaag 120
ggaattcctg taagagtggc actgcgttgt cgccctctgg tccccaaaga gattagcgag 180
ggctgccaga tgtgcctttc cttcgtgccc ggggagactc aggtggtggt tggtactgat 240
aaatccttca cctacgattt tgtgtttgac ccctgtactg agcaggaaga agtcttcaat 300
aaagcagtag cgccgctcat aaaaggcata tttaaaggat ataatgcaac ggtcctggcc 360
tatgggcaga ctggctctgg aaaaacctat tcaatgggag gtgcatacac tgcggagcag 420
gagaatgaac caacagttgg cattattcct agggtaatac aactgctctt caaagaaatt 480
gatcaaaaga gtgactttga atttactctg aaagtgtctt acttagagat ttacaatgaa 540
gaaattttgg atcttctatg cccatctcgt gagaaagctc aaataaatat acgggaggat 600
cctaaggaag gcataaagat tgtgggactc actgagaaga ctgttttagt tgccttggat 660
actgtttcct gtttggagca gggcaacaac tctaggactg tggcctccac agctatgaac 720
tcccagtcgt cccgatctca tgccatcttt acaatctcct tagagcaagg aaagaaaagt 780
gacaagaata gcagctttcg ctccaagctg catcttgtag acctcgctgg atcagaaaga 840
cagaagaaaa ccaaggctga aggggatcgt ctaaaagagg gtattaatat taaccgaggc 900
ctcctatgct tgggaaatgt aatcagtgct cttggagatg acaaaaaggg tagctttgtg 960
ccctacagag attccaagtt aactcgactg ctgcaagatt ctctaggagg taacagccac 1020
actcttatga tagcctgtgt gagtcctgct gactccaatc tagaggaaac attaagtacc 1080
cttcgctatg ctgacagagc aagaaaaatc aagaacaaac ctattgttaa tattgatccc 1140
cacacagctg aacttaatca tctaaagcaa caggtacaac agctacaagt cttgttgcta 1200
caagcccatg gaggtaccct gcctggatct ataaatgcag aaccatcaga gaatctacaa 1260
tccctgatgg agaagaatca gtccctggta gaggagaatg aaaaattaag tcgttgtctg 1320
agcaaggcag ctggtcagac agcccagatg ttggagagga tcattttgac agagcaagtg 1380

```
aatgaaaaac tgaacgccaa gctagaagag ctcaggcagc atgcggcctg caagctggat   1440
cttcaaaagc tagtggagac tttggaagac caggaattga aagaaaatgt agagataatt   1500
tgtaacctgc agcaactgat tacccagtta tcagatgaaa ctgttgcttg cacggctgca   1560
gccattgata ctgcggtaga agaagaagct caagtggaaa ccagtccaga gacaagcagg   1620
tcttctgacg cttttaccac tcagcatgct ctccatcaag ctcagatgtc taaggaggtg   1680
gttgagttga ataacgccct tgcactgaaa gaggccctag ttaggaagat gactcagaac   1740
gacaaccaac tacagcccat tcagtttcaa taccaggata acataaaaaa tctagaatta   1800
gaagtcatca atctgcaaaa ggaaaaggaa gaattggttc gtgaacttca gacagcaaag   1860
aagaatgcca accaagccaa gctgagtgag caccgtcgca aacttctcca ggagctggag   1920
ggtcaaatag ctgatctgaa gaagaaactg aatgagcagt ccaaacttct gaaactaaag   1980
gaatccacag agcgtactgt ctccaaactg aaccaggaga tacggatgat gaaaaaccag   2040
cgggtacagt taatgcgtca aatgaaagag gatgctgaga agtttagaca gtggaagcag   2100
aaaagagaca aagaagtaat acagttaaaa gaacgagacc gtaagaggca atatgagctg   2160
ctgaaacttg aaagaaactt ccagaaacaa tccaatgtgc tcagacgtaa aacggaggag   2220
gcagcagctg ccaacaagcg tctcaaggat gctctccaga aacaacggga ggttgcagat   2280
aagcggaaag agactcagag ccgtggaatg gaaggcactg cagctcgagt gaggaattgg   2340
cttggaaatg aaattgaggt tatggtcagt actgaggaag ccaaacgcca tctgaatgac   2400
ctccttgaag acagaaagat cctggctcag gatgtggttc aactcaaaga aaaaaaggaa   2460
tctcgggaga atccacctcc taaactccgg aagtgtacat tctccctttc tgaggtgcat   2520
ggtcaagttt tggagtcaga agattgtatt acaaaacaga ttgaaagcct agagactgaa   2580
atggaactca ggagtgctca gattgctgac ctacagcaga agctgctgga tgcagaaagt   2640
gaagataggc caaaacaatg ctgggagaat attgccacca ttctggaagc caagtgtgcc   2700
ctgaaatatt tgattggaga gctggtctcc tccaaaatac atgtcaccaa acttgaaaac   2760
agcctgagac agagcaaggc cagctgtgct gacatgcaga agatgctatt tgaggaacaa   2820
aatcattttt ctgagataga gacagagtta caagctgagc tggtcagaat ggagcaacag   2880
caccaagaga aggtgctata ccttgtcagc cagctgcagg aaagccaaat ggcagagaag   2940
cagttagaga aatcagccag tgaaaaggaa ccacagttgg tgagcacact gcagtgtcag   3000
gatgaagaac ttgagaagat gcgagaagtg tgtgagcaaa atcagcagct tctccaagag   3060
aatgaaatca tcaagcagaa actgatcctc ctccaggtag ccagcagaca gaaacatctt   3120
cctaatgata cccttctatc tccagactct tcttttgaat atatcccacc taagccaaaa   3180
ccttctcgtg ttaaagaaaa gtttctggag caaagcatgg acatcgagga tctaaaatat   3240
tgttcagagc attctgtgaa tgagcatgaa gatggtgatg gtgatggcga cagtgatgag   3300
ggggatgatg aggaatggaa gccaacaaaa ttagtcaagg tgtccaggaa gaacatccaa   3360
gggtgttcct gcaagggctg gtgtgggaac aagcagtgtg ggtgcaggaa gcaaaagtca   3420
gactgtggtg tggactgtag ctgtgacccc acaaagtgtc ggaaccgcca gcaaggcaag   3480
gatagcttgg gcactgttga acagacccag gattccgaag gctccttcaa actggaggat   3540
cctaccgagg tgaccccagg attgagcttc tttaaccctg tctgtgccac ccccaatagc   3600
aagatcctga aagagatgtg tgacatggag caggtgctgt caaagaagac tgctccagct   3660
ccctcccctt ttgacctccc agagtcgaaa catggagcaa cagaatacca acaaaataag   3720
cctccaggga agaaaaagaa acgagctctg gctagcaaca ccagcttctt ctctggctgc   3780
```

```
tcccctattg aagaagaggc ccactgaagt tggagtcatc atctctaccc ccaatctggc   3840
ttgggagatg ctttccagtt gcagccagaa ggggtttttt aaatgacttc tctggatttc   3900
aggtttcttg ccgttgaaaa aaaggaacaa agcattacta aaaagaaggt aacctttgtt   3960
ggatgttgtc cctcagtctc catccccaga ctactgctct ctgctctcta gaaggctgct   4020
aaaccacctg ctgaagagag aaccaacaga ctttcctaat gactactcag gaaccagtcc   4080
tcagtatgat caagttcctt cttatttgtg agcagttcag gctat                   4125
```

<210> SEQ ID NO 46
<211> LENGTH: 3897
<212> TYPE: DNA
<213> ORGANISM: Human

<400> SEQUENCE: 46

```
acgcccaggt cgcccgcatc ccgctgccgc aggagagaga cagcgcgccc cggccctgct     60
ccccaggctt cgcccgggcg ccctcaactc tgtccccaga gactgagcac ctgtcctccg    120
cctcggcctc tgctgagagc cctctcctct ggagcacaca ccacccctgc agcccaagaa    180
gagtcccagc cccacgccgg ctaccaccat ggcggagacc aacaacgaat gtagcatcaa    240
ggtgctctgc cgattccggc ccctgaacca ggctgagatt ctgcggggag acaagttcat    300
ccccatttc caaggggacg acagcgtcgt tattgggggg aagccatatg tttttgaccg    360
tgtattcccc ccaaacacga ctcaagagca agtttatcat gcatgtgcca tgcagattgt    420
caaagatgtc cttgctggct acaatggcac catttttgct tatggacaga catcctcagg    480
gaaaacacat accatggagg gaaagctgca cgaccctcag ctgatgggaa tcattcctcg    540
aattgcccga gacatcttca accacatcta ctccatggat gagaaccttg agttccacat    600
caaggtttct tactttgaaa tttacctgga caaaattcgt gaccttctgg atgtgaccaa    660
gacaaatctg tccgtgcacg aggacaagaa ccgggtgcca tttgtcaagg gttgtactga    720
acgctttgtg tccagcccgg aggagattct ggatgtgatt gatgaaggga aatcaaatcg    780
tcatgtggct gtcaccaaca tgaatgaaca cagctctcgg agccacagca tcttcctcat    840
caacatcaag caggagaaca tggaaacgga gcagaagctc agtgggaagc tgtatctggt    900
ggacctggca gggagtgaga aggtcagcaa gactggagca gagggagccg tgctggacga    960
ggcaaagaat atcaacaagt cactgtcagc tctgggcaat gtgatctccg cactggctga   1020
gggcactaaa agctatgttc catatcgtga cagcaaaatg acaaggattc tccaggactc   1080
tctcgggggga aactgccgga cgactatgtt catctgttgc tcaccatcca gttataatga   1140
tgcagagacc aagtccaccc tgatgtttgg gcagcgggca aagaccatta agaacactgc   1200
ctcagtaaat ttggagttga ctgctgagca gtggaagaag aaatatgaga aggagaagga   1260
gaagacaaag gcccagaagg agacgattgc gaagctggag gctgagctga gccggtggcg   1320
caatggagag aatgtgcctg agacagagcg cctggctggg gaggaggcag ccctgggagc   1380
cgagctctgt gaggagaccc ctgtgaatga caactcatcc atcgtggtgc gcatcgcgcc   1440
cgaggagcgg cagaaatacg aggaggagat ccgccgtctc tataagcagc ttgacgacaa   1500
ggatgatgaa atcaaccaac aaagccaact catagagaag ctcaagcagc aaatgctgga   1560
ccaggaagag ctgctggtgt ccacccgagg agacaacgag aaggtccagc gggagctgag   1620
ccacctgcaa tcagagaacg atgccgctaa ggatgaggtg aaggaagtgc tgcaggccct   1680
ggaggagctg gctgtgaact atgaccagaa gtcccaggag gtggaggaga agagccagca   1740
gaaccagctt ctggtggatg agctgtctca gaaggtggcc accatgctgt ccctggagtc   1800
```

tgagttgcag cggctacagg aggtcagtgg acaccagcga aaacgaattg ctgaggtgct 1860
gaacgggctg atgaaggatc tgagcgagtt cagtgtcatt gtgggcaacg gggagattaa 1920
gctgccagtg gagatcagtg gggccatcga ggaggagttc actgtggccc gactctacat 1980
cagcaaaatc aaatcagaag tcaagtctgt ggtcaagcgg tgccggcagc tggagaacct 2040
ccaggtggag tgtcaccgca agatggaagt gaccgggcgg gagctctcat cctgccagct 2100
cctcatctct cagcatgagg ccaagatccg ctcgcttacg gaatacatgc agagcgtgga 2160
gctaaagaag cggcacctgg aagagtccta tgactccttg agcgatgagc tggccaagct 2220
ccaggcccag gaaactgtgc atgaagtggc cctgaaggac aaggagcctg acactcagga 2280
tgcagatgaa gtgaagaagg ctctggagct gcagatggag agtcaccggg aggcccatca 2340
ccggcagctg gcccggctcc gggacgagat caacgagaag cagaagacca ttgatgagct 2400
caaagaccta aatcagaagc tccagttaga gctagagaag cttcaggctg actacgagaa 2460
gctgaagagc gaagaacacg agaagagcac caagctgcag gagctgacat ttctgtacga 2520
gcgacatgag cagtccaagc aggacctcaa gggtctggag gagacagttg cccgggaact 2580
ccagaccctc cacaaccttc gcaagctgtt cgttcaagac gtcacgactc gagtcaagaa 2640
aagtgcagaa atggagcccg aagacagtgg ggggattcac tcccaaaagc agaagatttc 2700
ctttcttgag aacaacctgg aacagcttac aaaggttcac aaacagctgg tacgtgacaa 2760
tgcagatctg cgttgtgagc ttcctaaatt ggaaaaacga cttagggcta cggctgagag 2820
agttaaggcc ctggagggtg cactgaagga ggccaaggag ggcgccatga aggacaagcg 2880
ccggtaccag caggaggtgg accgcatcaa ggaggccgtt cgctacaaga gctcgggcaa 2940
acggggccat tctgcccaga ttgccaaacc cgtccggcct ggccactacc cagcatcctc 3000
acccaccaac ccctatggca cccggagccc tgagtgcatc agttacacca acagcctctt 3060
ccagaactac cagaatctct acctgcaggc cacacccagc tccacctcag atatgtactt 3120
tgcaaactcc tgtaccagca gtggagccac atcttctggc ggccccttgg cttcctacca 3180
gaaggccaac atggacaatg gaaatgccac agatatcaat gacaatagga gtgacctgcc 3240
gtgtggctat gaggctgagg accaggccaa gcttttccct ctccaccaag agacagcagc 3300
cagctaatct cccacaccca cggctgcata cctgcacttt cagtttctaa gagggactga 3360
ggcctcttct cagcatgctg caaacctgtg gtctctgata ctaactccct ccccaacccc 3420
tgttgttgga ctgtactatg tttgatgtct tctcttactt actctgtatc tctttgtact 3480
ctgtatctat atatcaaaag ctgctgctat gtctctcttc tgtcttattc tcaagtatct 3540
actgatgtat ttagcaattt caaagcatag tctaccttcc ttatttgggg caatagggag 3600
gagggtgaat gtttcttctt tctcatctac tcgtctcaca ctgagtggtg ttagtcactg 3660
agtagaggtc acagagatga caaaaggaaa aatgggagct agagggttgt gacccttcat 3720
acacacacgc acgcacgcac acaaacatgc acacacgcat gcacacacac aaagccttaa 3780
gcagaagaat gtcttagcat catgagacag agaaatagac tcttcctccc tcctctttca 3840
catatagcac aggggaaggt aaaatggaag ggctgctaat tgagacatat aattttc 3897

<210> SEQ ID NO 47
<211> LENGTH: 3688
<212> TYPE: DNA
<213> ORGANISM: Human

<400> SEQUENCE: 47
ccagcccccg cagtccgccc agaccgtaaa gggggacgct gaggagccgc ggacgctctc 60

```
cccggtgccg ccgccgctgc cgccgccatg gctgccatga tggatcggaa gtgagcatta    120
gggttaacgg ctgccggcgc cggctcttca agtcccggct ccccggccgc ctccacccgg    180
ggaacgcgag cgcggcgcag ctgactgctg cctctcacgg ccctcgcgac cacaagccct    240
caggtccggc gcgttccctg caagactgag cggcggggag tggctcccgg ccgcggcccc    300
ggctgcgaga aagatggcgg acctggccga gtgcaacatc aaagtgatgt gtcgcttcag    360
acctctcaac gagtctgaag tgaaccgcgg cgacaagtac atcgccaagt ttcagggaga    420
agacacggtc gtgatcgcgt ccaagcctta tgcatttgat cgggtgttcc agtcaagcac    480
atctcaagag caagtgtata atgactgtgc aaagaagatt gttaaagatg tacttgaagg    540
atataatgga acaatatttg catatggaca aacatcctct gggaagacac acacaatgga    600
gggtaaactt catgatccag aaggcatggg aattattcca agaatagtgc aagatatttt    660
taattatatt tactccatgg atgaaaattt ggaatttcat attaaggttt catattttga    720
aatatatttg gataagataa gggacctgtt agatgtttca aagaccaacc tttcagttca    780
tgaagacaaa aaccgagttc cctatgtaaa ggggtgcaca gagcgttttg tatgtagtcc    840
agatgaagtt atggatacca tagatgaagg aaaatccaac agacatgtag cagttacaaa    900
tatgaatgaa catagctcta ggagtcacag tatatttctt attaatgtca aacaagagaa    960
cacacaaacg gaacaaaagc tgagtggaaa actttatctg gttgatttag ctggtagtga   1020
aaaggttagt aaaactggag ctgaaggtgc tgtgctggat gaagctaaaa acatcaacaa   1080
gtcactttct gctcttggaa atgttatttc tgctttggct gagggtagta catatgttcc   1140
atatcgagat agtaaaatga caagaatcct tcaagattca ttaggtggca actgtagaac   1200
cactattgta atttgctgct ctccatcatc atacaatgag tctgaaacaa aatctacact   1260
cttatttggc caaagggcca aaacaattaa gaacacagtt tgtgtcaatg tggagttaac   1320
tgcagaacag tggaaaaaga agtatgaaaa agaaaaagaa aaaaataaga tcctgcggaa   1380
cactattcag tggcttgaaa atgagctcaa cagatggcgt aatggggaga cggtgcctat   1440
tgatgaacag tttgacaaag agaaagccaa cttggaagct ttcacagtgg ataaagatat   1500
tactcttacc aatgataaac cagcaaccgc aattggagtt ataggaaatt ttactgatgc   1560
tgaaagaaga aagtgtgaag aagaaattgc taaattatac aaacagcttg atgacaagga   1620
tgaagaaatt aaccagcaaa gtcaactggt agagaaactg aagacgcaaa tgttggatca   1680
ggaggagctt ttggcatcta ccagaaggga tcaagacaat atgcaagctg agctgaatcg   1740
ccttcaagca gaaaatgatg cctctaaaga agaagtgaaa gaagttttac aggccctaga   1800
agaacttgct gtcaattatg atcagaagtc tcaggaagtt gaagacaaaa ctaaggaata   1860
tgaattgctt agtgatgaat tgaatcagaa atcggcaact ttagcgagta tagatgctga   1920
gcttcagaaa cttaaggaaa tgaccaacca ccagaaaaaa cgagcagctg agatgatggc   1980
atctttacta aaagaccttg cagaaatagg aattgctgtg ggaaataatg atgtaaagca   2040
gcctgaggga actggcatga tagatgaaga gttcactgtt gcaagactct acattagcaa   2100
aatgaagtca gaagtaaaaa ccatggtgaa acgttgcaag cagttagaaa gcacacaaac   2160
tgagagcaac aaaaaaatgg aagaaaatga aaaggagtta gcagcatgtc agcttcgtat   2220
ctctcaacat gaagccaaaa tcaagtcatt gactgaatac cttcaaaatg tggaacaaaa   2280
gaaaagacag ttggaggaat ctgtcgatgc cctcagtgaa gaactagtcc agcttcgagc   2340
acaagagaaa gtccatgaaa tggaaaagga gcacttaaat aaggttcaga ctgcaaatga   2400
agttaagcaa gctgttgaac agcagatcca gagccataga gaaactcatc aaaaacagat   2460
```

cagtagtttg agagatgaag tagaagcaaa agcaaaactt attactgatc ttcaagacca 2520
aaaccagaaa atgatgttag agcaggaacg tctaagagta gaacatgaga agttgaaagc 2580
cacagatcag gaaaagagca gaaaactaca tgaacttacg gttatgcaag atagacgaga 2640
acaagcaaga caagacttga agggtttgga agagacagtg gcaaaagaac ttcagacttt 2700
acacaacctg cgcaaactct ttgttcagga cctggctaca agagttaaaa agagtgctga 2760
gattgattct gatgacaccg gaggcagcgc tgctcagaag caaaaaatct cctttcttga 2820
aaataatctt gaacagctca ctaaagtgca caaacagttg gtacgtgata atgcagatct 2880
ccgctgtgaa cttcctaagt tggaaaagcg acttcgagct acagctgaga gagtgaaagc 2940
tttggaatca gcactgaaag aagctaaaga aaatgcatct cgtgatcgca aacgctatca 3000
gcaagaagta gatcgcataa aggaagcagt caggtcaaag aatatggcca gaagagggca 3060
ttctgcacag attgctaaac ctattcgtcc cgggcaacat ccagcagctt ctccaactca 3120
cccaagtgca attcgtggag gaggtgcatt tgttcagaac agccagccag tggcagtgcg 3180
aggtggagga ggcaaacaag tgtaatcgtt tatacatacc cacaggtgtt aaaaagtaat 3240
cgaagtacga agaggacatg gtatcaagca gtcattcaat gactataacc tctactccct 3300
tgggattgta gaattataac ttttaaaaaa aatgtataaa ttatacctgg cctgtacagc 3360
tgtttcctac ctactcttct tgtaaactct gctgcttccc aacacaacta gagtgcaatt 3420
ttggcatctt aggagggaaa aaggacagtt tacaactgtg gccctattta ttacacagtt 3480
tgtctatcgt gtcttaaatt tagtctttac tgtgccaagc taactctacc ttataggact 3540
gtactttttg tattttttgt gtatgtttat tttttaatct cagtttaaat tacctagcta 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaa 3688

<210> SEQ ID NO 48
<211> LENGTH: 6927
<212> TYPE: DNA
<213> ORGANISM: Human

<400> SEQUENCE: 48
gatggctgag cgcgcaggag cccgggaggt ctgagccggg cgaggctcgc tccctgcgca 60
tcgcctcctc cgcccgccgc gtggtcgcgg gcaggtgggc cggggggcgc tgggcagggg 120
cggggcaggg ccagggcagg ccggtctgca gccggagggg ccggagcgga gaagctgccc 180
accttcccgg gctcggagcg gccggggctg ctcagccggc cgggctcgcg atgacctgct 240
gagaagcgtc gtcggaggct gcaggaggcg gcctagctgt gggcggtgca gctcgcggcc 300
tcctccctcg tcgttcccgg ccccggcccc ccacccatcc ccgtgccccc tccctaccgc 360
cggccgagat ggcggatcca gccgaatgca gcatcaaagt gatgtgccgg ttccggcccc 420
tcaacgaagc ggagatcctc cgcggggaca aattcatccc caaatttaaa ggcgatgaga 480
ccgtggtgat cgggcaaggg aagccatatg tcttcgacag agtgctacct cccaacacga 540
cccaagagca ggtttacaat gcatgtgcga agcaaattgt caaagatgtc cttgaaggtt 600
ataacgggac gatttttgcg tatgggcaga cttcatcagg aaaaacccac accatggagg 660
ggaagctgca tgacccccag ctcatgggga tcatcccacg aattgcccat gatatctttg 720
accatatcta ctccatggat gagaacctgg agtttcacat aaaggtttcc tattttgaga 780
tctacttgga caaaataagg gacttacttg atgtatccaa gaccaacttg gctgttcatg 840
aagataaaaa cagagtcccg tatgtaaagg ggtgcactga gcggtttgtg tcgagccctg 900

-continued

```
aggaagtcat ggatgtaata gatgaaggca aagcaaaccg acacgtggct gtgacaaaca    960
tgaatgaaca cagctctaga agtcacagta tcttcctgat aaatattaaa caagagaatg   1020
tagagactga aaaaaaactc agtgggaaac tttatttggt tgatttggct gggagcgaaa   1080
aggtcagcaa aactggtgcc gagggagctg ttcttgacga agctaaaaat atcaataagt   1140
ctttgtctgc tcttggaaat gtgatctctg ctttggcaga agggacaaaa acacatgtgc   1200
cataccggga cagcaagatg actcggattc ttcaggactc tttgggtggg aactgcagaa   1260
ccaccatcgt catttgctgt tctccttctg tcttcaatga ggctgagacc aagtccacac   1320
tgatgttcgg acagagagct aagaccatca agaatacagt ctctgtgaac ctagaactga   1380
cagcagaaga atggaagaag aaatatgaaa aagagaaaga gaaaaacaag actttgaaga   1440
atgttatcca gcatctggag atggagctaa acaggtggag gaatggagaa gctgtgcctg   1500
aggatgaaca gatcagtgcc aaggaccaga agaacctgga gccttgtgat aacaccccca   1560
tcatagacaa tattgctcct gttgttgctg gcatctctac agaggagaaa gagaagtacg   1620
atgaggagat ctccagtctc tacagacaac tggatgacaa ggatgatgaa attaaccagc   1680
agagccagct ggctgaaaag ctgaagcaac agatgttgga tcaggatgag cttttagctt   1740
ccacaagaag agactatgag aagatacagg aggagctgac acgtctccag attgaaaatg   1800
aggcagccaa ggatgaggtg aaagaagttc tccaggccct ggaggagctg gctgtcaatt   1860
atgaccagaa atcacaggaa gtggaggata agacccgggc caatgagcag ctgacagacg   1920
agctggccca gaaaacgact acattgacaa ccacacagag agagctgagc cagctacaag   1980
agcttagcaa ccaccagaag aaaagggcaa ctgagatcct gaatttgctg ttgaaagatc   2040
tgggggagat aggtggaatt attggcacca atgatgtgaa aactttggca gatgtgaatg   2100
gagtcattga ggaggagttt accatggccc gcctgtacat cagcaagatg aagtcagagg   2160
tcaagtccct ggtgaaccgc agcaaacagc tcgagagcgc ccagatggac tccaacagga   2220
agatgaatgc cagcgagcgg gagctggcag cctgccagct gctcatctcc cagcacgaag   2280
ccaagatcaa gtctctgaca gactacatgc agaacatgga acagaagagg aggcagctag   2340
aagagtccca ggactcgctc agcgaagagc tggcaaagct ccgagcccag gaaaaaatgc   2400
acgaagtcag cttccaggat aaggagaagg aacatctgac gcggttgcag gatgctgaag   2460
aaatgaagaa ggcgctggag cagcagatgg agagccaccg ggaagctcac cagaagcagc   2520
tgtccagact ccgagacgaa attgaggaga agcagaaaat cattgatgag attcgggatt   2580
tgaatcagaa actgcaactg gaacaggaga agcttagttc tgattataac aagctgaaaa   2640
tagaggacca agagagagaa atgaagctgg aaaagctctt attgctcaac gataaaaggg   2700
aacaagccag agaagacctc aaagggctgg aggagacagt gtctagagaa ttgcagacac   2760
tgcacaacct tcggaaactc tttgtccagg atctgaccac ccgagttaaa aaaagtgtgg   2820
agttggacaa cgatgatgga gggggcagtg ctgcccagaa gcagaaaatt tccttcttgg   2880
agaataacct ggagcagctc accaaagttc acaagcagct ggtccgggac aacgcagacc   2940
tgcgctgtga actgcccaag ctggagaagc ggctgcgtgc cacggcggag cgcgtcaagg   3000
ctctggagag cgcgctgaag gaggccaagg agaacgccat gcgggaccgt aagcgctacc   3060
agcaggaggt ggatcgtatc aaggaggccg tgcgggccaa gaacatggcc agaagggccc   3120
attcagccca gatcgccaag cccatccgcc ccggacacta cccggcctca tctccaacgg   3180
ccgtccatgc cattcgaggg ggaggaggca gctcttcaaa ttccactcac taccagaaat   3240
aaatacaaaa tatgactcca cgtagcatgt caaggactac attaatcacc aattccttta   3300
```

-continued tttttccccc cctacagttt ccattttttt tttatacttg cttactccag ccatctgcag 3360
tacaccagtt tcaggtcttt tgagctgtgt agagtttctg tgtgtacaga tgtgtgctcg 3420
gacttttctc tttttgagaa atctgaagga gatggttgca gaagatccac ttactactga 3480
gaaccattac caccgactcg gcctccgggg tgttgggtgg tttctgggtg gttcctggag 3540
cctcctctgg gcagtgcact gtcccatctg tacgccctaa tgtgccattc cctagagggg 3600
aacaaccaag tgccgtggag gcagatgatc atggtctgcc tcaactgtct ggtttcctgt 3660
aaaataaaca cattgtttta tatttttagg gaacaaaaag tgctgctata gggttcaaag 3720
ttttccttct gaacactttt ccgaaacaaa ttaccccaaa gacacatttt gaatatcctg 3780
gtcacatctt tggatctgta aaatatacct tttagtatgg cacctgttaa aatgcaaagc 3840
aaatttcttt ggggcagaaa aacaatctga cagtagcagt gtagaatttg ttcattcaaa 3900
tacatctgtg taaatgcaaa aagtcataaa attcacctcc gagctgcttg cttttgaacc 3960
tgcagcaact agtcttagcc ggcccggttt gaacatcgtt ctttcagaag tgctgaaaat 4020
gctgcaaagt tggataagtg gaaatgtggc tgcccctctc ctcactactt cctctctgat 4080
cgttctgaag cttgcattgg gaatggctgc tttctctaac cattttcagc ttgagtgggt 4140
attgctgaag aaatccaaca tcattccagc agttgaaaaa ggaagccttc gggagaaagt 4200
gcttgtcaaa attttgttct ttgtgcttgt gtatgagtaa gttgccatga ataagttatt 4260
attttaaccc ataattggcg actgtttata tgaattcttt ctttggcacc aaataggttt 4320
catcttctta ggcacaatta gaaaaaatcc acatagatgg atattttaca tttagttatt 4380
gctttatcca aatacatgaa tctaaagctg aatcaaccct tacttccagt tgtgcttatt 4440
aagaagatca atttccaagt agtaaagttt tcagggaaac tgactgtgct gctatttgtt 4500
ttgacaaatt tgggggtaag tcaatgacaa ccaaaccaat ctcggtggaa actcctatcc 4560
tatcatgttg tgtgcccaag atgagtgagc tggcactgtg ccctgaagct ttcaccactg 4620
taatgaaata tatgccaggg gagactttgg gcttttctca tgactgtgtg ggtcgaaggt 4680
agctcaagtg tgtgtgtgtg tgtgtgtgtg tgtgtgtgtg tgtgtgtgta tgtgtgtaaa 4740
gtgctaagaa ctgtgcattg acatccaaac atttcttgta caaaatttcc ctagcaaagc 4800
aaacctgctt tgacttaatt tatttgttaa atgttgcact ttgtttatgt atgttttgtt 4860
tttggtgggg aataaggaga gagaggacga caaattctat tgaagtattt attttgtgaa 4920
gatggcaatt ttgcatttgt ttaaattttt ttcattcttt aattttgtta tcagtgccag 4980
cccaatatac ctgctctacc attatttgcg gtctgataaa agggtccttg tggggcaggt 5040
tttgcaaagc ttatcaggta ataacatatg ccacataacc ttgttgatat gtttgcttct 5100
gatttgggaa gctaaacatt ggtgtttgag aggattgcca attattaatt gtcattacca 5160
ctactctcca ttactttttg tttggaaatt gaacaaaggt cagtaatggt ttttggctct 5220
tgttaatatc catcataaaa tagattgttt tagattcttt ccagggtgat ttttccctgg 5280
gtaccccgtt tctacttcta aagaattgct tggcactttc atgtttcaaa gggaaacatt 5340
cgcttgtagt tccattttac ttgatctcta caagggactg acaacatttg ctttattttt 5400
attcacagag aaagttggct ttgatgtctc ttaaagataa ttctgctagt tgctgatcag 5460
ccagtcagtt cacctagctt caatctttat aggacttcta atctaatttt cctatagtgt 5520
gactaaaagg gaggcaaatt attggaacgg attattcaaa tggatcctta aatattgcta 5580
tgtataataa gccagttatt atatcaggac catgttctct gtaggccact ttctaaaaaa 5640
gccacatatg tgcaattttc aggtttttag actattgctc cctgtacttt aaatgtaaaa 5700

```
accacacttc tgaacaacta agctcatgaa tatgattttg gttatatgca gcttttgact   5760
agcatgtatt gtgtcttttt ctcctctatg aataatttta tatttcatgc tacttcttga   5820
aagtttactc tttgatgctc taagagaaca gccagatggt ttatatgaat aatctttatc   5880
tgcaggatgg tggattggta aattaggaga atgttgtttg agatatcaag atttatgtct   5940
gggaactaaa atatataatg ccaaatgtgt ttttgtcaat tactagagaa ttctgtgcaa   6000
acatatcatc tcttcaaatg ctgcacactt tgcttttgtt aaacagcagg tagtagacag   6060
aacaataaca gtttcgcgtt aagactttta aaggaaatag aatcgtgatt aagaaatcag   6120
aatttataga tatattggga taaatgaaga aataaaaatg tttgtctaga atgtagcatc   6180
tagtgacttt ttaaagccct aacgtttaca taaagaagct ctagttctta tagaaataac   6240
aaagcaaata aaagttctta acaatcccct ctttcgaagt gcattttttt aaagcagggc   6300
aggagacatt tggactctag ctatatgaca tactgggaaa ggcagagggt ggagggaaga   6360
tttcacttca ttgtctagcc cagaatcttg agcaagctaa agaaaccatc ataatctaaa   6420
attgcttcat ttaacactaa caatttagac tttttaaacc aagcattgaa taatggctgg   6480
ataactgccg aagtaagcgc cgctccatga agtctgctta cttatttaaa aattgtgtat   6540
cagttttaaa tactgttcat tgtgtgcaga tataagggga atagggcatt ctgtagaatt   6600
atacatgtct agtttgtaaa gtgtgtcctg tgtactgcag atgtgtgttc tctgggcttt   6660
atgtatctgt acagtagctt tcacattaaa aaaattgtgg acaaacttgt ccggggggtt   6720
tgaggggaga atggtggttt atatcaataa cgatgctgta ctatagtcca tgtaacaaaa   6780
gatctggaag tcaccctcct ctggcccacg gaaaatttgg gtaatcttct aggttctaaa   6840
atgaagatgt atgggtactc tggcagactg catgttgtat aatttgaaaa atactaaaag   6900
tggaaaataa aattgaatta aactttg                                      6927
```

```
<210> SEQ ID NO 49
<211> LENGTH: 2469
<212> TYPE: DNA
<213> ORGANISM: Human

<400> SEQUENCE: 49

ggggtgcaga gcgttacagt gacagaggca ttatcccaag gacactgtca tacatttttg     60
aacagttaca aaaggacagc agcaaaatat atacaacaca catttcctat ttggaaatct    120
acaatgaatg tggttatgat cttttggatc caagacatga agcctccagt ttggaagatt    180
tgccgaaagt gacaatactg gaggatcctg atcagaacat tcacctgaaa aacttgactc    240
tccatcaggc aaccacagag gaagaagctc tgaatttgct ttttttagga gacaccaacc    300
gaatgattgc agagactcct atgaaccaag cttcaacccg ttcccactgc attttcacca    360
ttcatttgtc aagcaaggaa ccaggatctg caactgtacg acatgccaaa ctccatctgg    420
ttgacctggc tggttcagag cgagttgcaa agactggagt agggggccat cttctaacag    480
aggccaagta tatcaacttg tcactacatt acttagaaca ggttatcatt gccctttcag    540
aaaagcaccg ttcgcacatt ccttatagaa actccatgat gaccagtgtc ctaagagaca    600
gtttgggagg gaactgcatg acaactatga ttgcaacact ctccttggag aaaaggaatc    660
ttgatgagtc tatatcaacc tgcagatttg cacagcgagt ggcactcata aagaatgaag    720
ctgttcttaa tgaagaaatt aaccccagat tagtgattaa acgcctacaa aaggaaatcc    780
aggaactgaa ggatgaactg gccatggtca ctggggagca gaggacagag gcactcacag    840
aagcagagct ccttcagctg gaaaaactaa taacatcctt tttggaagac caggattcag    900
```

acagtagatt agaggttggc gcggatatgc gtaaagttca tcactgtttt catcatttaa 960
agaaactatt gaatgacaag aagatccttg aaaacaatac agtctcctct gaaagcaaag 1020
accaagattg tcaagaacca ttaaaagaag aagaatatag aaagctacga gatattctga 1080
aacagagaga taacgaaatc aatatcctgg tcaacatgtt aaaaaaagaa aagaagaaag 1140
ctcaggaggc tctccacttg gctggcatgg atagacgtga attcagacag tcccagagcc 1200 caccccttccg cctaggaaac ccagaagaag gtcaaagaat gcgactatcc tcagctccct 1260
cacaggccca ggacttcagc attttgggga aaagatccag tttgctccac aagaaaatag 1320
gaatgagaga ggaaatgtca ttaggatgcc aggaggcttt tgaaatcttc aagagggacc 1380
acgctgacag cgttaccatc gatgacaaca aacagattct gaaacagaga ttttctgaag 1440
ccaaggccct gggagaaagt ataaatgaag caagaagtaa aattggtcac ctgaaggaag 1500
aaatcaccca gcggcatata cagcaagtag ccctaggaat ctcggaaaac atggccgtgc 1560
ctctgatgcc agaccagcag gaggagaagc tgcgatcaca actggaggaa gaaaagagaa 1620
ggtataaaac aatgttcact cgcctgaaag ccctgaaggt ggagatcgag cacttgcagc 1680
tgctcatgga caaagccaag gtgaagctac agaaagagtt tgaagtctgg tgggcagagg 1740
aggccaccaa cctgcaggta aattctccag cagtgaattc actcgatcac acgaagccat 1800
ttctccagac atctgactcc cagcatgaat ggtcccaact cctctctaac aaaagtgatg 1860
tgaatgccag gaaaatcctg ccctcgcctt gccccagtcc acacagccag aaacagagca 1920
gcaccagcac cccactggaa gacagcatcc ccaagaggcc agtgtcgtcc atccctctca 1980
ccggagacag ccagacggac tcggacatca tcgccttcat caaggccaga cagagcattc 2040
tgcagaagca atgtttggga agcaattgaa tttccaggaa atatccatcc atgaattatg 2100
ccagcaagaa cgaagcacag atgaaggcag cgcccctcac ttgctctggc ttcagaagtg 2160
aactatgggc tgctgggagc aactagtgac tttgattccc atggagggga ctgtgtttct 2220
ttaaggatgc tgacctggag gccaccgaga ggctggggct ggggctgacc acaacatcct 2280
tcctgtggtt gctggagctg ctggcagggc caggcaaggc cagagtgcta ggggcagggt 2340
gaaggcttca gctcactgtt gtagtgacgt tttgtgtaga tctttataag cttttgagaa 2400
tgtgaaatag caccatcaaa atataatgtc agaggatgct cacaccagtg aaaaaaaaaa 2460
aaaaaaaaa 2469

<210> SEQ ID NO 50
<211> LENGTH: 3121
<212> TYPE: DNA
<213> ORGANISM: Human

<400> SEQUENCE: 50
gcgccctgag ctccgcctcc gggcccgata gcggcatcga gagcgcctcc gtcgaggacc 60
aggcggcgca gggggccggc gggcgaaagg aggatgaggg ggcgcagcag ctgctgaccc 120
tgcagaacca ggtggcgcgg ctggaggagg agaaccgaga ctttctggct gcgctggagg 180
acgccatgga gcagtacaaa ctgcagagcg accggctgcg tgagcagcag gaggagatgg 240
tggaactgcg gctgcggtta gagctggtgc ggccaggctg ggggggcctg cggctcctga 300
atggcctgcc tcccgggtcc tttgtgcctc gacctcatac agcccccctg gggggtgccc 360
acgcccatgt gctgggcatg gtgccgcctg cctgcctccc tggagatgaa gttggctctg 420
agcagagggg agagcaggtg acaaatggca gggaggctgg agctgagttg ctgactgagg 480
tgaacaggct gggaagtggc tcttcagctg cttcagagga ggaagaggag gaggaggagc 540

```
cgcccaggcg gaccttacac ctgcgcagaa ataggatcag caactgcagt cagagggcgg    600
gggcacgccc agggagtctg ccagagagga agggcccaga gctttgcctt gaggagttgg    660
atgcagccat tccagggtcc agagcagttg gtgggagcaa ggcccgagtt caggcccgcc    720
aggtccccc tgccacagcc tcagagtggc ggctggccca ggcccagcag aagatccggg    780
agctggctat caacatccgc atgaaggagg agcttattgg cgagctggtc cgcacaggaa    840
aggcagctca ggccctgaac cgccagcaca gccagcgtat ccgggagctg gagcaggagg    900
cagagcaggt gcgggccgag ctgagtgaag gccagaggca gctgcgggag ctcgagggca    960
aggagctcca ggatgctggc gagcggtctc ggctccagga gttccgcagg agggtcgctg   1020
cggcccagag ccaggtgcag gtgctgaagg agaagaagca ggctacggag cggctggtgt   1080
cactgtcggc ccagagtgag aagcgactgc aggagctcga gcggaacgtg cagctcatgc   1140
ggcagcagca gggacagctg cagaggcggc ttcgcgagga gacggagcag aagcggcgcc   1200
tggaggcaga aatgagcaag cggcagcacc gcgtcaagga gctggagctg aagcatgagc   1260
aacagcagaa gatcctgaag attaagacgg aagagatcgc ggccttccag aggaagaggc   1320
gcagtggcag caacggctct gtggtcagcc tggaacagca gcagaagatt gaggagcaga   1380
agaagtggct ggaccaggag atggagaagg tgctacagca gcggcgggcg ctggaggagc   1440
tgggggagga gctccacaag cgggaggcca tcctggccaa gaaggaggcc ctgatgcagg   1500
agaagacggg gctggagagc aagcgcctga gatccagcca ggccctcaac gaggacatcg   1560
tgcgagtgtc cagccggctg gagcacctgg agaaggagct gtccgagaag agcgggcagc   1620
tgcggcaggg cagcgcccag agccagcagc agatccgcgg ggagatcgac agcctgcgcc   1680
aggagaagga ctcgctgctc aagcagcgcc tggagatcga cggcaagctg aggcagggga   1740
gtctgctgtc ccccgaggag gagcggacgc tgttccagtt ggatgaggcc atcgaggccc   1800
tggatgctgc cattgagtat aagaatgagg ccatcacatg ccgccagcgg gtgcttcggg   1860
cctcagcctc gttgctgtcc cagtgcgaga tgaacctcat ggccaagctc agctacctct   1920
catcctcaga gaccagagcc ctcctctgca agtattttga caaggtggtg acgctccgag   1980
aggagcagca ccagcagcag attgccttct cggaactgga gatgcagctg gaggagcagc   2040
agaggctggt gtactggctg gaggtggccc tggagcggca gcgcctggag atggaccgcc   2100
agctgaccct gcagcagaag gagcacgagc agaacatgca gctgctcctg cagcagagtc   2160
gagaccacct cggtgaaggg ttagcagaca gcaggaggca gtatgaggcc cggattcaag   2220
ctctggagaa ggaactgggc cgttacatgt ggataaacca ggaactgaaa cagaagctcg   2280
gcggtgtgaa cgctgtaggc cacagcaggg gtggggagaa gaggagcctg tgctcggagg   2340
gcagacaggc tcctggaaat gaagatgagc tccacctggc acccgagctt ctctggctgt   2400
cccccctcac tgagggggcc ccccgcaccc gggaggagac gcgggacttg gtccacgctc   2460
cgttaccctt gacctggaaa cgctcgagcc tgtgtggtga ggagcagggg tcccccgagg   2520
aactgaggca gcgggaggcg gctgagcccc tggtggggcg ggtgcttcct gtgggtgagg   2580
caggcctgcc ctggaacttt gggcctttgt ccaagccccg gcgggaactg cgacgagcca   2640
gcccggggat gattgatgtc cggaaaaacc ccctgtaagc cctcggggca gaccctgcct   2700
tggagggaga ctccgagcct gctgaaaggg gcagctgcct gttttgcttc tgtgaagggc   2760
agtccttacc gcacacccta aatccaggcc ctcatctgta ccctcactgg gatcaacaaa   2820
tttgggccat ggcccaaaag aactggaccc tcatttaaca aataatatg caaattccca    2880
ccacttactt ccatgaagct gtggtaccca attgccgcct tgtgtcttgc tcgaatctca   2940
```

ggacaattct ggtttcaggc gtaaatggat gtgcttgtag ttcaggggtt tggccaagaa 3000
tcatcacgaa agggtcggtg gcaaccaggt tgtggtttaa atggtcttat gtatataggg 3060
gaaactggga gactttagga tcttaaaaaa ccatttaata aaaaaaaatc tttgaaggga 3120
c 3121

<210> SEQ ID NO 51
<211> LENGTH: 2510
<212> TYPE: DNA
<213> ORGANISM: Human

<400> SEQUENCE: 51
ggaggtggtt tcggttgcgg cagtcgcgtc ccgggagcgt cgctgcctgg tgaacgctag 60
aatgggtact aggaaaaaag ttcatgcatt tgtccgtgtc aaacccaccg atgactttgc 120
tcatgaaatg atcagatacg gagatgacaa aagaagcatt gatattcact taaaaaaaga 180
cattcggaga ggagttgtca ataaccaaca gacagactgg tcgtttaagt tggatggagt 240
tcttcacgat gcctcccagg acttggttta tgagacagtt gcaaaggatg tggtttctca 300
ggccctcgat ggctataatg gcaccatcat gtgttatggg cagacgggag ctggcaagac 360
atacaccatg atgggggcaa ctgagaatta caagcaccgg gggatcctcc ctcgtgccct 420
gcagcaggtt tttaggatga tcgaagaacg ccccacacat gccatcactg tgcgtgtttc 480
ctacttggaa atctataatg agagcctgtt tgatctcctg tccactctgc cctatgttgg 540
accctcagtc acaccaatga ccatcgtgga aaaccctcaa ggagtcttca ttaagggctt 600
gtcagttcac ctcacaagtc aggaggagga tgcattcagc ctcctttttg agggtgagac 660
caacaggatt atagcctccc acactatgaa caaaaactct tccagatcac actgcatttt 720
caccatctac ttagaggccc attcccggac cttatcagag gaaaagtaca tcacttccaa 780
aattaacttg gtggatctgg caggctcaga gaggctgggg aagtctgggt ctgagggcca 840
agtcctgaag gaagccacct acatcaacaa atcgctctca ttcctggagc aggccatcat 900
tgcccttggg gaccagaagc gggaccacat cccctttcgg cagtgcaagc tcacccacgc 960
tctgaaggac tcgttagggg gaaactgcaa tatggtcctc gtgacaaaca tctatggaga 1020
agctgcccag ttagaagaaa cgctatcttc actgagattt gccagcagga tgaagctagt 1080
caccactgag cctgccatca atgaaaagta tgatgctgag agaatggtca agaacctgga 1140
gaaggaacta gcactactca agcaggagct ggctatccat gacagcctga ccaaccgcac 1200
ctttgtgacc tatgacccca tggatgaaat ccagattgct gagatcaact cccaggtgcg 1260
gaggtacctg gaggggacac tggacgagat cgacataatc agccttagac agatcaagga 1320
ggtgttcaac cagttccggg tggttctgag ccaacaggaa caggaagtgg agtccacttt 1380
gcgcaggaag tacaccctca ttgacaggaa tgactttgca gccatttctg ctatccagaa 1440
ggcggggctt gtggatgttg atggccacct agtgggtgag cctgaaggac aaaactttgg 1500
actcggagtc gccccttttct ctaccaaacc tgggaagaaa gccaagtcca agaagacatt 1560
caaagagcca ctcaggcccg acaccccacc ctccaaacca gtggcctttg aggagtttaa 1620
gaatgagcaa ggtagtgaga tcaaccgaat tttcaaagaa aacaaatcca tcttgaatga 1680
acggaggaaa agggccagcg agaccacaca gcacatcaat gccatcaagc gggagattga 1740
tgtgaccaag gaggccctga atttccagaa gtcactacgg gagaagcaag gcaagtacga 1800
aaacaagggg ctgatgatca tcgatgagga agaattcctg ctgatcctca agctcaaaga 1860
cctcaagaag cagtaccgca gcgagtacca ggacctgcgt gacctcaggg ctgagatcca 1920

```
gtattgccag cacctagtgg atcagtgtcg ccaccgcctg ctcatggaat ttgacatctg   1980

gtacaatgag tcctttgtca tccctgagga catgcagatg gcactgaagc caggcggcag   2040

catccggcca ggcatggtcc ctgtgaacag gattgtgtct ctgggagaag atgaccagga   2100

caaattcagc cagctgcagc agagggtgct tcctgagggc cctgattcca tctccttcta   2160

caatgccaaa gtcaagatag agcagaagca taattacttg aaaaccatga tgggcctcca   2220

gcaggcacat agaaaataga acctcatcgc cagtacctta aaggacaaga ccagcaactc   2280

ccacctactg tagtggagct gctcaaccac ctgcccagag ctgcagcccc ctgtactcca   2340

atgctgggac ccagcacagc gaacacattt ggcctgcatg ttgggaggag catcctccaa   2400

ggacaacctt gctcatctcc acagagcact ttgggtttta attcactgtc ttatatgcag   2460

ggacaggata aaataacttt ctagtttgga cttttaaaaa aaaaaaaaaa              2510


<210> SEQ ID NO 52
<211> LENGTH: 8630
<212> TYPE: DNA
<213> ORGANISM: Human

<400> SEQUENCE: 52

taaatttaaa ggcggggcgg cctgtgagcc ctgaagtgcc ggccgcggag ggtcctggcc     60

attttcctgg gaccagttca gcctgatagg atggcggagg aaggagccgt ggccgtctgc    120

gtgcgagtgc ggccgctgaa cagcagagaa gaatcacttg gagaaactgc ccaagtttac    180

tggaaaactg acaataatgt catttatcaa gttgatggaa gtaaatcctt caattttgat    240

cgtgtctttc atggtaatga aactaccaaa aatgtgtatg aagaaatagc agcaccaatc    300

atcgattctg ccatacaagg ctacaatggt actatatttg cctatggaca gactgcttca    360

ggaaaaacat ataccatgat gggttcagaa gatcatttgg gagttatacc cagggcaatt    420

catgacattt tccaaaaaat taagaagttt cctgataggg aatttctctt acgtgtatct    480

tacatggaaa tatacaatga aaccattaca gatttactct gtggcactca aaaaatgaaa    540

cctttaatta ttcgagaaga tgtcaatagg aatgtgtatg ttgctgatct cacagaagaa    600

gttgtatata catcagaaat ggctttgaaa tggattacaa agggagaaaa gagcaggcat    660

tatggagaaa caaaaatgaa tcaaagaagc agtcgttctc ataccatctt taggatgatt    720

ttggaaagca gagagaaggg tgaaccttct aattgtgaag gatctgttaa ggtatcccat    780

ttgaatttgg ttgatcttgc aggcagtgaa agagctgctc aaacaggcgc tgcaggtgtg    840

cggctcaagg aaggctgtaa tataaatcga agcttattta ttttgggaca agtgatcaag    900

aaacttagtg atggacaagt tggtggtttc ataaattatc gagatagcaa gttaacacga    960

attctccaga attccttggg aggaaatgca aagacacgta ttatctgcac aattactcca   1020

gtatcttttg atgaaacact tactgctctc cagtttgcca gtactgctaa atatatgaag   1080

aatactcctt atgttaatga ggtatcaact gatgaagctc tcctgaaaag gtatagaaaa   1140

gaaataatgg atcttaaaaa acaattagag gaggtttctt tagagacgcg ggctcaggca   1200

atggaaaaag accaattggc ccaacttttg gaagaaaaag atttgcttca gaaagtacag   1260

aatgagaaaa ttgaaaactt aacacggatg ctggtgacct cttcttccct cacgttgcaa   1320

caggaattaa aggctaaaag aaaacgaaga gttacttggt gccttggcaa aattaacaaa   1380

atgaagaact caaactatgc agatcaattt aatataccaa caaatataac aacaaaaaca   1440

cataagcttt ctataaattt attacgagaa attgatgaat ctgtctgttc agagtctgat   1500

gttttcagta acactcttga tacattaagt gagatagaat ggaatccagc aacaaagcta   1560
```

ctaaatcagg agaatataga aagtgagttg aactcacttc gtgctgacta tgataatctg 1620
gtattagact atgaacaact acgaacagaa aaagaagaaa tggaattgaa attaaaagaa 1680
aagaatgatt tggatgaatt tgaggctcta gaaagaaaaa ctaaaaaaga tcaagagatg 1740
caactaattc atgaaatttc gaacttaaag aatttagtta agcatgcaga agtatataat 1800
caagatcttg agaatgaact cagttcaaaa gtagagctgc ttagagaaaa ggaagaccag 1860
attaagaagc tacaggaata catagactct caaaagctag aaaatataaa aatggacttg 1920
tcatactcat tggaaagcat tgaagaccca aaacaaatga agcagactct gtttgatgct 1980
gaaactgtag cccttgatgc caagagagaa tcagcctttc ttagaagtga aaatctggag 2040
ctgaaggaga aaatgaaaga acttgcaact acatacaagc aaatggaaaa tgatattcag 2100
ttatatcaaa gccagttgga ggcaaaaaag aaaatgcaag ttgatctgga gaaagaatta 2160
caatctgctt ttaatgagat aacaaaactc acctccctta tagatggcaa agttccaaaa 2220
gatttgctct gtaatttgga attggaagga aagattactg atcttcagaa agaactaaat 2280
aaagaagttg aagaaaatga agctttgcgg gaagaagtca ttttgctttc agaattgaaa 2340
tctttacctt ctgaagtaga aaggctgagg aaagagatac aagacaaatc tgaagagctc 2400
catataataa catcagaaaa agataaattg ttttctgaag tagttcataa ggagagtaga 2460
gttcaaggtt tacttgaaga aattgggaaa acaaaagatg acctagcaac tacacagtcg 2520
aattataaaa gcactgatca agaattccaa aatttcaaaa cccttcatat ggactttgag 2580
caaaagtata agatggtcct tgaggagaat gagagaatga atcaggaaat agttaatctc 2640
tctaaagaag cccaaaaatt tgattcgagt ttgggtgctt tgaagaccga gctttcttac 2700
aagacccaag aacttcagga gaaaacacgt gaggttcaag aaagactaaa tgagatggaa 2760
cagctgaagg aacaattaga aaatagagat tctacgctgc aaactgtaga aagggagaaa 2820
acactgatta ctgagaaact gcagcaaact ttagaagaag taaaaacttt aactcaagaa 2880
aaagatgatc taaaacaact ccaagaaagc ttgcaaattg agagggacca actcaaaagt 2940
gatattcacg atactgttaa catgaatata gatactcaag aacaattacg aaatgctctt 3000
gagtctctga aacaacatca agaaacaatt aatacactaa aatcgaaaat ttctgaggaa 3060
gtttccagga atttgcatat ggaggaaaat acaggagaaa ctaaagatga atttcagcaa 3120
aagatggttg gcatagataa aaaacaggat ttggaagcta aaaataccca aacactaact 3180
gcagatgtta aggataatga gataattgag caacaaagga agatattttc tttaatacag 3240
gagaaaaatg aactccaaca aatgttagag agtgttatag cagaaaagga acaattgaag 3300
actgacctaa aggaaaatat tgaaatgacc attgaaaacc aggaagaatt aagacttctt 3360
ggggatgaac ttaaaaagca acaagagata gttgcacaag aaaagaacca tgccataaag 3420
aaagaaggag agctttctag gacctgtgac agactggcag aagttgaaga aaaactaaag 3480
gaaaagagcc agcaactcca agaaaaacag caacaacttc ttaatgtaca agaagagatg 3540
agtgagatgc agaaaaagat taatgaaata gagaatttaa agaatgaatt aaagaacaaa 3600
gaattgacat tggaacatat ggaaacagag aggcttgagt tggctcagaa acttaatgaa 3660
aattatgagg aagtgaaatc tataaccaaa gaaagaaaag ttctaaagga attacagaag 3720
tcatttgaaa cagagagaga ccaccttaga ggatatataa gagaaattga agctacaggc 3780
ctacaaacca aagaagaact aaaaattgct catattcacc taaaagaaca ccaagaaact 3840
attgatgaac taagaagaag cgtatctgag aagacagctc aaataataaa tactcaggac 3900
ttagaaaaat cccataccaa attacaagaa gagatcccag tgcttcatga ggaacaagag 3960

-continued

```
ttactgccta atgtgaaaga agtcagtgag actcaggaaa caatgaatga actggagtta   4020
ttaacagaac agtccacaac caaggactca acaacactgg caagaataga aatggaaagg   4080
ctcaggttga atgaaaaatt tcaagaaagt caggaagaga taaaatctct aaccaaggaa   4140
agagacaacc ttaaaacgat aaaagaagcc cttgaagtta aacatgacca gctgaaagaa   4200
catattagag aaactttggc taaaatccag gagtctcaaa gcaaacaaga acagtcctta   4260
aatatgaaag aaaaagacaa tgaaactacc aaaatcgtga gtgagatgga gcaattcaaa   4320
cccaaagatt cagcactact aaggatagaa atagaaatgc tcggattgtc caaaagactt   4380
caagaaagtc atgatgaaat gaaatctgta gctaaggaga aagatgacct acagaggctg   4440
caagaagttc ttcaatctga aagtgaccag ctcaaagaaa acataaaaga aattgtagct   4500
aaacacctgg aaactgaaga ggaacttaaa gttgctcatt gttgcctgaa agaacaagag   4560
gaaactatta atgagttaag agtgaatctt tcagagaagg aaactgaaat atcaaccatt   4620
caaaagcagt tagaagcaat caatgataaa ttacagaaca agatccaaga gatttatgag   4680
aaagaggaac aatttaatat aaaacaaatt agtgaggttc aggaaaaagt gaatgaactg   4740
aaacaattca aggagcatcg caaagccaag gattcagcac tacaaagtat agaaagtaag   4800
atgctcgagt tgaccaacag acttcaagaa agtcaagaag aaatacaaat tatgattaag   4860
gaaaaagagg aaatgaaaag agtacaggag gcccttcaga tagagagaga ccaactgaaa   4920
gaaaacacta aagaaattgt agctaaaatg aaagaatctc aagaaaaaga atatcagttt   4980
cttaagatga cagctgtcaa tgagactcag gagaaaatgt gtgaaataga acacttgaag   5040
gagcaatttg agacccagaa gttaaacctg gaaaacatag aaacggagaa tataaggttg   5100
actcagatac tacatgaaaa ccttgaagaa atgagatctg taacaaaaga aagagatgac   5160
cttaggagtg tggaggagac tctcaaagta gagagagacc agctcaagga aaaccttaga   5220
gaaactataa ctagagacct agaaaaacaa gaggagctaa aaattgttca catgcatctg   5280
aaggagcacc aagaaactat tgataaacta agagggattg tttcagagaa aacaaatgaa   5340
atatcaaata tgcaaaagga cttagaacac tcaaatgatg ccttaaaagc acaggatctg   5400
aaaatacaag aggaactaag aattgctcac atgcatctga aagagcagca ggaaactatt   5460
gacaaactca gaggaattgt ttctgagaag acagataaac tatcaaatat gcaaaaagat   5520
ttagaaaatt caaatgctaa attacaagaa aagattcaag aacttaaggc aaatgaacat   5580
caacttatta cgttaaaaaa agatgtcaat gagacacaga aaaaagtgtc tgaaatggag   5640
caactaaaga aacaaataaa agaccaaagc ttaactctga gtaaattaga aatagagaat   5700
ttaaatttgg ctcagaaact tcatgaaaac cttgaagaaa tgaaatctgt aatgaaagaa   5760
agagataatc taagaagagt agaggagaca ctcaaactgg agagagacca actcaaggaa   5820
agcctgcaag aaaccaaagc tagagatctg gaaatacaac aggaactaaa aactgctcgt   5880
atgctatcaa aagaacacaa agaaactgtt gataaactta gagaaaaaat ttcagaaaag   5940
acaattcaaa tttcagacat tcaaaaggat ttagataaat caaaagatga attacagaaa   6000
aagatccaag aacttcagaa aaaagaactt caactgctta gagtgaaaga agatgtcaat   6060
atgagtcata aaaaaattaa tgaaatggaa cagttgaaga agcaatttga ggcccaaaac   6120
ttatctatgc aaagtgtgag aatggataac ttccagttga ctaagaaact tcatgaaagc   6180
cttgaagaaa taagaattgt agctaaagaa agagatgagc taaggaggat aaaagaatct   6240
ctcaaaatgg aaagggacca attcatagca accttaaggg aaatgatagc tagagaccga   6300
cagaaccacc aagtaaaacc tgaaaaaagg ttactaagtg atggacaaca gcaccttacg   6360
```

```
gaaagcctga gagaaaagtg ctctagaata aaagagcttt tgaagagata ctcagagatg   6420
gatgatcatt atgagtgctt gaatagattg tctcttgact tggagaagga aattgaattc   6480
caaaaagagc tttcaatgag agttaaagca aacctctcac ttccctattt acaaaccaaa   6540
cacattgaaa aactttttac tgcaaaccag agatgctcca tggaattcca cagaatcatg   6600
aagaaactga agtatgtgtt aagctatgtt acaaaaataa aagaagaaca acatgaatcc   6660
atcaataaat ttgaaatgga ttttattgat gaagtggaaa agcaaaagga attgctaatt   6720
aaaatacagc accttcaaca agattgtgat gtaccatcca gagaattaag ggatctcaaa   6780
ttgaaccaga atatggatct acatattgag gaaattctca aagatttctc agaaagtgag   6840
ttccctagca taaagactga atttcaacaa gtactaagta ataggaaaga aatgacacag   6900
tttttggaag agtggttaaa tactcgtttt gatatagaaa agcttaaaaa tggcatccag   6960
aaagaaaatg ataggatttg tcaagtgaat aacttcttta ataacagaat aattgccata   7020
atgaatgaat caacagagtt tgaggaaaga agtgctacca tatccaaaga gtgggaacag   7080
gacctgaaat cactgaaaga gaaaaatgaa aaactattta aaaactacca aacattgaag   7140
acttccttgg catctggtgc ccaggttaat cctaccacac aagacaataa gaatcctcat   7200
gttacatcaa gagctacaca gttaaccaca gagaaaattc gagagctgga aaattcactg   7260
catgaagcta aagaaaagtgc tatgcataag gaaagcaaga ttataaagat gcagaaagaa   7320
cttgaggtga ctaatgacat aatagcaaaa cttcaagcca aagttcatga atcaaataaa   7380
tgccttgaaa aaacaaaaga gacaattcaa gtacttcagg acaaagttgc tttaggagct   7440
aagccatata aagaagaaat tgaagatctc aaaatgaagc ttgtgaaaat agacctagag   7500
aaaatgaaaa atgccaaaga atttgaaaag gaaatcagtg ctacaaaagc cactgtagaa   7560
tatcaaaagg aagttataag gctattgaga gaaaatctca gaagaagtca acaggcccaa   7620
gatacctcag tgatatcaga acatactgat cctcagcctt caaataaacc cttaacttgt   7680
ggaggtggca gcggcattgt acaaaacaca aaagctctta ttttgaaaag tgaacatata   7740
aggctagaaa aagaaatttc taagttaaag cagcaaaatg aacagctaat aaaacaaaag   7800
aatgaattgt taagcaataa tcagcatctt tccaatgagg tcaaaacttg gaaggaaaga   7860
acccttaaaa gagaggctca caaacaagta acttgtgaga attctccaaa gtctcctaaa   7920
gtgactggaa cagcttctaa aaagaaacaa attacaccct ctcaatgcaa ggaacggaat   7980
ttacaagatc ctgtgccaaa ggaatcacca aaatcttgtt tttttgatag ccgatcaaag   8040
tctttaccat cacctcatcc agttcgctat tttgataact caagtttagg cctttgtcca   8100
gaggtgcaaa atgcaggagc agagagtgtg gattctcagc caggtccttg gcacgcctcc   8160
tcaggcaagg atgtgcctga gtgcaaaact cagtagactc ctctttgtca cttctctgga   8220
gatccagcat tccttatttg gaaatgactt tgtttatgtg tctatccctg gtaatgatgt   8280
tgtagtgcag cttaatttca attcagtctt tactttgcca ctagagttga aagataaggg   8340
aacaggaaat gaatgcattg tggtaattta gaatggtgat agcaatacct tcttcttgca   8400
tatggtaata cttttaaaag ttgaattgtt ttatttattt gtatattttg taaagaataa   8460
agttattgaa agaaatgtaa agttatctac atgacttagc atattccaaa gcataataca   8520
tacattaata taaaacatca ttttattaac aaaattgtaa atgtttttaa taccttacac   8580
attcaataaa tgtttagtag ttctgaatca ccaaaaaaaa aaaaaaaaaa              8630
```

<210> SEQ ID NO 53
<211> LENGTH: 4908

<212> TYPE: DNA
<213> ORGANISM: Human

<400> SEQUENCE: 53
acctgcgtgc agtcggtcct ccaggccacg cagcgcccga gagtaccagg gagactccgg 60
cccctgtcgg cgccaagccc ctccgcccct cacagcgccc aggtccgcgg ccgggccttg 120 atttttggc ggggaccgtc atggcgtcgc agccaaattc gtctgcgaag aagaaagagg 180
agaaggggaa gaacatccag gtggtggtga gatgcagacc atttaatttg gcagagcgga 240
aagctagcgc ccattcaata gtagaatgtg atcctgtacg aaaagaagtt agtgtacgaa 300
ctggaggatt ggctgacaag agctcaagga aaacatacac ttttgatatg gtgtttggag 360
catctactaa acagattgat gtttaccgaa gtgttgtttg tccaattctg gatgaagtta 420
ttatgggcta taattgcact atctttgcgt atggccaaac tggcactgga aaaactttta 480
caatggaagg tgaaaggtca cctaatgaag agtatacctg ggaagaggat cccttggctg 540
gtataattcc acgtaccctt catcaaattt ttgagaaact tactgataat ggtactgaat 600
tttcagtcaa agtgtctctg ttggagatct ataatgaaga gctttttgat cttcttaatc 660
catcatctga tgtttctgag agactacaga tgtttgatga tccccgtaac aagagaggag 720
tgataattaa aggtttagaa gaaattacag tacacaacaa ggatgaagtc tatcaaattt 780
tagaaaaggg ggcagcaaaa aggacaactg cagctactct gatgaatgca tactctagtc 840
gttcccactc agttttctct gttacaatac atatgaaaga aactacgatt gatggagaag 900
agcttgttaa aatcggaaag ttgaacttgg ttgatcttgc aggaagtgaa aacattggcc 960
gttctggagc tgttgataag agagctcggg aagctggaaa tataaatcaa tccctgttga 1020
ctttgggaag ggtcattact gcccttgtag aaagaacacc tcatgttcct tatcgagaat 1080
ctaaactaac tagaatcctc caggattctc ttggagggcg tacaagaaca tctataattg 1140
caacaatttc tcctgcatct ctcaatcttg aggaaactct gagtacattg gaatatgctc 1200
atagagcaaa gaacatattg aataagcctg aagtgaatca gaaactcacc aaaaaagctc 1260
ttattaagga gtatacggag gagatagaac gtttaaaacg agatcttgct gcagcccgtg 1320
agaaaaatgg agtgtatatt tctgaagaaa attttagagt catgagtgga aaattaactg 1380
ttcaagaaga gcagattgta gaattgattg aaaaaattgg tgctgttgag gaggagctga 1440
atagggttac agagttgttt atggataata aaaatgaact tgaccagtgt aaatctgacc 1500
tgcaaaataa aacacaagaa cttgaaacca ctcaaaaaca tttgcaagaa actaaattac 1560
aacttgttaa agaagaatat atcacatcag ctttggaaag tactgaggag aaacttcatg 1620
atgctgccag caagctgctt aacacagttg aagaaactac aaaagatgta tctggtctcc 1680
attccaaact ggatcgtaag aaggcagttg accaacacaa tgcagaagct caggatattt 1740
ttggcaaaaa cctgaatagt ctgtttaata atatggaaga attaattaag gatggcagct 1800
caaagcaaaa ggccatgcta gaagtacata agaccttatt tggtaatctg ctgtcttcca 1860
gtgtctctgc attagatacc attactacag tagcacttgg atctctcaca tctattccag 1920
aaaatgtgtc tactcatgtt tctcagattt ttaatatgat actaaaagaa caatcattag 1980
cagcagaaag taaaactgta ctacaggaat tgattaatgt actcaagact gatcttctaa 2040
gttcactgga aatgatttta tccccaactg tggtgtctat actgaaaatc aatagtcaac 2100
taaagcatat tttcaagact tcattgacag tggccgataa gatagaagat caaaaaaagg 2160
aactagatgg ctttctcagt atactgtgta acaatctaca tgaactacaa gaaaatacca 2220
tttgttcctt ggttgagtca caaaagcaat gtggaaacct aactgaagac ctgaagacaa 2280

-continued taaagcagac ccattcccag gaactttgca agttaatgaa tctttggaca gagagattct 2340
gtgctttgga ggaaaagtgt gaaaatatac agaaaccact tagtagtgtc caggaaaata 2400
tacagcagaa atctaaggat atagtcaaca aaatgacttt tcacagtcaa aaattttgtg 2460
ctgattctga tggcttctca caggaactca gaaattttaa ccaagaaggt acaaaattgg 2520
ttgaagaatc tgtgaaacac tctgataaac tcaatggcaa cctggaaaaa atatctcaag 2580
agactgaaca gagatgtgaa tctctgaaca caagaacagt ttatttttct gaacagtggg 2640
tatcttcctt aaatgaaagg gaacaggaac ttcacaactt attggaggtt gtaagccaat 2700
gttgtgaggc ttcaagttca gacatcactg agaaatcaga tggacgtaag gcagctcatg 2760
agaaacagca taacattttt cttgatcaga tgactattga tgaagataaa ttgatagcac 2820
aaaatctaga acttaatgaa accataaaaa ttggtttgac taagcttaat tgctttctgg 2880
aacaggatct gaaactggat atcccaacag gtacgacacc acagaggaaa agttatttat 2940
acccatcaac actggtaaga actgaaccac gtgaacatct ccttgatcag ctgaaaagga 3000
aacagcctga gctgttaatg atgctaaact gttcagaaaa caacaaagaa gagacaattc 3060
cggatgtgga tgtagaagag gcagttctgg ggcagtatac tgaagaacct ctaagtcaag 3120
agccatctgt agatgctggt gtggattgtt catcaattgg cggggttcca tttttccagc 3180
ataaaaaatc acatggaaaa gacaaagaaa acagaggcat taacacactg gagaggtcta 3240
aagtggaaga aactacagag cacttggtta caaagagcag attacctctg cgagcccaga 3300
tcaaccttta attcacttgg gggttggcaa ttttattttt aaagaaaact taaaaataaa 3360
acctgaaacc ccagaacttg agccttgtgt atagatttta aaagaatata tatatcagcc 3420
gggcgcggtg gctcatgcct gtaatcccag cactttggga ggctgaggcg ggtggattgc 3480
ttgagcccag gagtttgaga ccagcctggc caacgtggca aaacctcgtc tctgttaaaa 3540
attagccggg cgtggtggca cactcctgta atcccagcta ctggggaggc tgaggcacga 3600
gaatcacttg aacccaggaa gcggggttgc agtgagccaa aggtacacca ctacactcca 3660
gcctgggcaa cagagcaaga ctcggtctca aaaacaaaat ttaaaaaaga tataaggcag 3720
tactgtaaat tcagttgaat tttgatatct acccattttt ctgtcatccc tatagttcac 3780
tttgtattaa attgggtttc atttgggatt tgcaatgtaa atacgtattt ctagtttca 3840
tataaagtag ttcttttata acaaatgaaa agtatttttc ttgtatatta ttaagtaatg 3900
aatatataag aactgtactc ttctcagctt gagcttaaca taggtaaata tcaccaacat 3960
ctgtccttag aaaggaccat ctcatgtttt ttttcttgct atgacttgtg tattttcttg 4020
catcctccct agacttccct atttcgcttt ctcctcggct cactttctcc ctttttattt 4080
ttcaccaaac catttgtaga gctacaaaac ctatcctttc ttattttcag tagtcagaat 4140
tttatctaga aatcttttaa cacctttta gtggttattt ctaaaatcac tgtcaacaat 4200
aaatctaacc ctagttgtat ccctccttta agtatttaaa acttgttgcc ccaaatgtga 4260
aagcatttaa ttcctttaag aggcctaact cattcaccct gacagagttc acaaaaagcc 4320
cactttagag tatacattgc tattatggga gaccacccag acatctgact aatggctctg 4380
tgccacactc caagacctgt gccttttaga gaagctcaca atgatttaag gactgtttga 4440
aacttccaat tatgtctata atttatattc ttttgtttac atgatgaaac tttttgttgt 4500
tgcttgtttg tatataatac aatgtgtaca tgtatctttt tctcgattca aatcttaacc 4560
cttaggactc tggtattttt gatctggcaa ccatatttct ggaagttgag atgtttcagc 4620
ttgaagaacc aaaacagaag gaatatgtac aaagaataaa ttttctgctc acgatgagtt 4680

```
tagtgtgtaa agtttagaga catctgactt tgatagctaa attaaaccaa accctattga   4740

agaattgaat atatgctact tcaagaaact aaattgatct cgtagaatta tcttaataaa   4800

ataatggcta taatttctct gcaaaatcag atgtcagcat aagcgatgga taatacctaa   4860

taaactgccc tcagtaaatc catggttaat aaatgtggtt tctacatt                4908
```

<210> SEQ ID NO 54
<211> LENGTH: 2024
<212> TYPE: DNA
<213> ORGANISM: Human

<400> SEQUENCE: 54

```
ggaagacatc aggatgtacc atctgccctt ctgtcggacc ccagggtacg tcccatgagc     60

gcggccgagc tgcgtcgagg gcagcagagc gtgctgcact gctcagggac ccggactctg    120

cagtttctcc tgcactgttt tcacctttgg ccagacgggc tctgggaaga cctacaccct    180

gactggaccc cctccccagg gggagggggt gcctgtaccc cccagcctgg ctggcatcat    240

gcagaggacc ttcgcctggc tgttggaccg cgtgcagcac ctgggtgccc ctgtcaccct    300

tcgcgcctct tatctggaga tctacaatga gcaggttcgg gacttgctga gcctggggtc    360

tccccggccc ctccctgttc gctggaacaa gactcggggc ttctatgtgg agcagctgcg    420

ggtggtggaa tttgggagtc tggaggccct gatggaactt ttgcaaacgg gtctcagccg    480

tcgaaggaac tcagcccaca ccctgaacca ggcctccagc cgaagccatg ccctgctcac    540

cctttacatc agccgtcaaa ctgcccagca gatgccttct gtggaccctg gggagccccc    600

tgttggtggg aagctgtgct ttgtggacct ggcaggcagt gagaaggtag cagccacggg    660

atcccgtggg gagctgatgc ttgaggctaa cagcatcaac cgaagcctgc tggccctggg    720

tcactgcatc tccctgctgc tggacccaca gcggaagcag agccacatcc ctttccggga    780

cagcaagctc accaagttgc tggcagactc actgggaggg cgcggggtca ccctcatggt    840

ggcctgcgtg tccccctcag cccagtgcct tcctgagact ctcagcaccc tgcgatatgc    900

aagccgagct cagcgggtca ccacccgacc acaggccccc aagtctcctg tggcaaagca    960

gccccagcgt ttggagacag agatgctgca gctccaggag gagaaccgtc gcctgcagtt   1020

ccagctggac caaatggact gcaaggcctc agggctcagt ggagcccggg tggcctgggc   1080

ccagcggaac ctgtacggga tgctacagga gttcatgcta gagaatgaga ggctcaggaa   1140

agaaaagagc cagctgcaga atagccgaga cctggcccag aatgagcagc gcatcctggc   1200

ccagcaggtc catgcactag agaggcgtct cctctctgcc tgctaccatc accagcaggg   1260

tcctggcctg accccaccgt gtccctgctt gatggcccca gctcccccctt gccatgcact   1320

gccacccctc tactcctgcc cctgctgcca catctgccca ctgtgtcgag tgcccctggc   1380

ccactgggcc tgcctgccag gggagcacca cctgccccag gtgttggacc ctgaggcctc   1440

aggtggcagg cccccatctg cccggccccc accctgggca cccccatgca gccctggctc   1500

tgccaagtgc ccaagagaga ggagtcacag tgactggact cagacccgag tcctggcaga   1560

gatgttgacg gaggaggagg tggtaccttc tgcacctccc ctgcctgtga ggcccccgaa   1620

gacatcacca gggctcagag gtggggccgg ggttccaaac ctggcccaga gactggaggc   1680

cctcagagac cagattggca gctccctgcg acgtggccgc agccagccac cctgcagtga   1740

gggcgcacgg agcccaggcc aagtcctccc tccccattga aggccaagtg ggaacccagg   1800

agactgctgt gtgacctcag actgggctcc acactcttgg gcttcagtct gcccatctgc   1860

tgaatggaga cagcagctgc tactccacct gcagctgggc taggggcggg gactgggggt   1920
```

gctatttagg ggaacaaggg gattcaggag aaaccaggca gcaggggatg aaatacatga 1980
ataaagagag gcatcagctc caaaaaaaaa aaaaaaaaaa aaaa 2024

<210> SEQ ID NO 55
<211> LENGTH: 5878
<212> TYPE: DNA
<213> ORGANISM: Human

<400> SEQUENCE: 55
ccgggcgagc gcagccaaca tgtcggatac caaggtaaaa gttgccgtcc gggtccggcc 60
catgaaccga cgagaactgg aactgaacac caagtgcgtg gtggagatgg aagggaatca 120
aacggtcctg caccctcctc cttctaacac caaacaggga gaaaggaaac ctcccaaggt 180
atttgccttt gattattgct tttggtccat ggatgaatct aacactacaa aatacgctgg 240
tcaagaagtg gttttcaagt gccttgggga aggaattctt gaaaaagcct ttcaggggta 300
taatgcgtgt atttttgcat atggacagac aggttcggga aaatcctttt ccatgatggg 360
ccatgctgag cagctgggcc ttattccaag gctctgctgt gctttattta aaaggatctc 420
tttggagcaa aatgagtcac agacctttaa agttgaagtg tcctatatgg aaatttataa 480
tgagaaagtt cgggatcttt tagaccccaa agggagtaga cagtctctta aagttcgaga 540
acataaagtt ttgggaccat atgtagatgg tttatctcaa ctagctgtca ctagttttga 600
ggatattgag tcattgatgt ctgagggaaa taagtctcga acggtagctg ctaccaacat 660
gaacgaagaa agcagccgct cccatgctgt gttcaacatc ataatcacac agacacttta 720
tgacctgcag tctgggaatt ccggggagaa agtcagtaag gtcagcttgg tagacctggc 780
gggtagcgaa agagtatcta aaacaggagc tgcaggagag cgactgaaag aaggcagcaa 840
cattaacaaa tcgcttacaa ccttggggtt ggttatatca tcactggctg accaggcagc 900
tggcaagggt aaaagcaaat ttgtgcctta tcgagattca gtcctcactt ggctgcttaa 960
ggacaacttg gggggcaaca gccaaacctc tatgatagcc acaatcagcc cagccgcaga 1020
caactatgaa gagaccctct ccacattaag atatgcagac cgagccaaaa ggattgtgaa 1080
ccatgctgtt gtgaatgagg accccaacgc aaaagtgatc cgagaactgc gggaggaagt 1140
cgagaaactg agagagcagc tctctcaggc agaggccatg aaggcccctg aactgaagga 1200
gaagctcgaa gagtctgaaa agctgataaa agaactaaca gtgacttggg aagagaagct 1260
gagaaaaaca gaagagatag cacaggaaag acaacgacaa cttgaaagca tggggatttc 1320
cctggagatg tccggtatca aggtggggga tgacaaatgc tacttagtca atctgaatgc 1380
agaccctgct cttaacgaac ttctggttta ttatttaaag gatcacacca gggtgggtgc 1440
agatacctct caagatatcc agctttttgg cataggaatt cagcctcagc actgtgagat 1500
tgacattgca tctgatggag acgtcactct cactccaaaa gaaaatgcaa ggtcctgtgt 1560
gaacggcacc cttgtgtgca gtaccaccca gctgtggcat ggtgaccgaa tcctatgggg 1620
aaataatcac tttttttagaa taaacttacc taagaggaaa cgtcgagatt ggttgaaaga 1680
ctttgaaaaa gaaacgggcc cgccagagca tgacctggat gcagccagtg aggcttcctc 1740
tgaaccagac tataactatg aatttgcaca gatggaagtt atcatgaaaa ccctgaatag 1800
taatgaccca gttcaaaatg tggttcaggt cctggagaaa caatacctag aagaaaagag 1860
aagtgcccta gaggagcagc ggctcatgta tgagcgggaa ctggagcaac tccgccagca 1920
gctctccccc gacaggcagc cacagagtag cggccctgac cgcctggcct acagcagcca 1980
gacagcgcag cagaaggtga cccagtgggc agaagagagg gatgaactct tccgacaagg 2040

```
cctggcaaaa ctgcgagagc agctggttaa agctaatacc ttggtgaggg aagcaaactt   2100
cctggctgag gaaatgagca aactcaccga ttaccaagtg actcttcaga tccctgctgc   2160
aaacctcagt gccaatagga agagaggtgc aatagtgagt gaaccagcta tccaagtgag   2220
gaggaaagga aagagcaccc aagtgtggac cattgagaag ctggagaata aattaattga   2280
catgagagac ctttaccaag aatggaagga aaaagttcct gaggcaaaga gactctacgg   2340
aaaacgaggt gacccttcct atgaagctca agaaaatcac aacctcatcg gggtggcgaa   2400
tgtattcttg gaatgcctct tctgtgatgt gaaacttcag tatgcagtcc ctatcatcag   2460
ccagcagggg gaggttgcag ggcgtctcca cgtggaagtg atgcgtgtta caggagctgt   2520
tccagagcgt gtggtggagg atgactcttc ggagaattcc agtgaaagtg ggagccttga   2580
agtcgtagac agcagcgggg aaatcattca ccgagtcaaa aagctgacat gtcgggtaaa   2640
aattaaagaa gcaacggggc tgcccttaaa cctctcaaat tttgtcttct gtcaatacac   2700
attctgggac cagtgtgagt ctacggtggc tgccccggtg gtggaccccg aggtgccttc   2760
accacagtcc aaggatgccc agtacacagt ggccttctcc cactgtaagg actatgtggt   2820
gaatgtaaca gaagaatttc tggagttcat ttcagatgga gcactggcca ttgaagtatg   2880
gggccaccgg tgtgctggaa atggcagctc catctgggag gtcgattctc ttcatgctaa   2940
gacaagaaca ctgcatgaca ggtggaatga agtaacgcga agaatagaaa tgtggatctc   3000
catattagaa ttgaatgagt taggagagta tgctgcagtg gaacttcatc aggcaaaaga   3060
tgtcaacaca ggaggcatct ttcaacttag acagggtcat tcccgtagag tacaagtcac   3120
ggtgaaacct gtgcagcatt cagggacact gccacttatg gttgaagcca tcctgtcagt   3180
atccatcggc tgtgtaactg ccaggtccac caaactccaa agagggctgg acagttacca   3240
gagagatgat gaggatggtg atgatatgga tagttatcag gaagaagact taaactgcgt   3300
aagggagagg tggtcagatg cactcattaa acgacgagaa tacctggatg aacagataaa   3360
aaaagtcagc aataaaacag agaaaacaga ggacgatgtg gagcgggaag cccagcttgt   3420
ggagcagtgg gtagggctga ctgaggaaag gaatgctgtg ctggtgccag ccccaggcag   3480
tgggattcct ggggcacctg ccgactggat cccacctcct ggaatggaaa cccacatacc   3540
agttctcttc ctcgatttga atgcggatga ccccagtgcc aatgagcagc ttgttggccc   3600
ccatgcatcc ggcgtgaact ccatcctgcc caaggagcat ggcagtcagt ttttctacct   3660
gcccatcata aagcacagtg atgatgaggt ttcagccaca gcctcttggg attcctcggt   3720
gcatgattct gttcacttga atagggtcac accacagaat gaaaggattt acctaattgt   3780
gaaaaccaca gttcaactca gccaccctgc tgctatggag ttagtattac gaaaacgaat   3840
tgcagccaat atttacaaca aacagagttt cacgcagagt ttgaagagga gaatatccct   3900
gaaaaatata ttttattcct gtggtgtaac ctatgaaata gtatccaata taccaaaggc   3960
aactgaggag atagaggacc gggaaacgct ggctctcctg gcagcaagga gtgaaaacga   4020
aggcacatca gatggggaga cgtacattga gaagtacact cgaggcgtgc tgcaggtgga   4080
aaacattctg agtcttgaac ggctccggca ggccgtcaca gtcaaagaag cactttccac   4140
caaagcccgg cacattcgga ggagcctcag tacaccaaat gttcataatg tctcttccag   4200
ccgaccggac ctttctggct ttgatgaaga tgacaagggt tggccagaga accagttgga   4260
catgtctgac tatagctcca gttaccaaga tgtagcatgt tatggaactt tacccaggga   4320
ttctcctcga aggaataaag aaggttgtac atcagagact cctcatgcct taaccgtcag   4380
cccttttaaa gcattctctc ctcagccacc aaagtttttc aagcccctaa tgcctgtaaa   4440
```

agaggagcat aagaaaagga tagccctgga agcaaggcct cttctaagcc aggagagcat 4500
gcctccacct caggcacata accctggctg cattgtaccc tcaggaagca atggcagcag 4560
catgccagta gaacacaata acaaacgtga gaagaagatt gactctgagg aggaagaaaa 4620
tgagctggaa gctattaaca ggaagctaat aagttcacag ccttatgtac ctgtggagtt 4680
tgctgacttc agtgtttaca atgccagctt ggagaacagg gaatggtttt cctctaaagt 4740
agatctgtca aactcacggg tcttggagaa agaagtgtcc cgtagcccta ccaccagcag 4800
tattaccagt ggctactttt cccacagtgc ctccaatgcc accctgtctg acatggtggt 4860
cccttctagt gacagctcag accagctggc cattcagacg aaggatgcag actccaccga 4920
gcactccaca ccatcgcttg tgcatgattt caggccgtcc tcaaacaaag agttgacaga 4980
agtcgaaaaa ggcttggtaa aggacaagat aattgtggtg ccactcaagg aaaacagtgc 5040
cttagccaaa gggagcccat catcccagag catccctgag aaaaactcca aatcactgtg 5100
caggactggc tcatgttcag aactagatgc ctgccccagc aaaattagcc agccagccag 5160
gggattctgc cccagggagg tgacggtaga acacaccacc aacatccttg aagaccattc 5220
tttcacagaa tttatgggag tgtcagaggg aaaagatttt gatggtttga cagattcttc 5280
tgctggagag ctttccagta ggaggagtct accaaataaa acaggcggca agactgtctc 5340
cgatgggctc caccacccca gccagctgca ttccaagtta gagaatgacc aggtaataat 5400
tccagaggca gccttttggg ttctgtgctg tcaatgagta tgtctaactg tatgtcaacc 5460
ccagaggccc ttcaccgcaa caacttggta ggaaagattc atccagttgt ttgtgacggc 5520
aaagatgagc ccacagagaa gcaggctcac ttcctgcaca gctgtctctg tcggagagca 5580
agtctgtttt gggaactaga acgcaattgt gaaattataa gaccagtgga tttttttacc 5640
tggcacatgg gttggtgttg aatgaagtgt tcagatggat aaggatcaat ctcatattca 5700
ttccctggga tgtttagtta ccagttttcc caaagtgttc tggtagcatc taccatattt 5760
catcaaatct gtgattcctt tgattattat atgaaccatt attttatgta tcattaagaa 5820
aaaatactgc caattaaact ctgtcatatc aaaaaaaaaa aaaaaaaaaa aaaaaaaa 5878

<210> SEQ ID NO 56
<211> LENGTH: 8743
<212> TYPE: DNA
<213> ORGANISM: Human

<400> SEQUENCE: 56
cagacggaag ccgaacgagt tcctcggcgg ctgcaggatg gggactcca aagtgaaagt 60 ggcggtgcgg atacgaccca tgaaccggcg agagactgac ttgcatacca aatgtgtggt 120
ggatgtggat gcaaacaagg ttattcttaa tcctgtaaat acgaatcttt ccaaaggaga 180
tgcccggggc cagccgaagt gttttgctta tgatcattgt ttctggtcta tggatgaatc 240
tgtcaaagaa aagtatgcag gtcaagatat tgttttcaag tgccttggag agaatatcct 300
gcagaatgct tttgatggct acaatgcatg tatctttgcc tatggacaga ctggctctgg 360
aaaatcttat accatgatgg gcacagctga ccaacctgga ttaatcccaa gactttgcag 420
tggactcttt gaacgaactc agaaagagga aaatgaagaa cagagtttta aagtagaagt 480
gtcctacatg gaaatttata atgaaaaagt tcgagacctt cttgatccca aaggaagccg 540
tcagacgttg aaagtcagag agcatagtgt gttgggacct tatgtcgacg gactttctaa 600
actggctgcc acaagctaca aggatattga gtcgttgatg tctgagggta acaaatctcg 660
cactgttgct gcaaccaaca tgaacgagga gagtagccga tcccatgcag ttctcaaaat 720

-continued

```
caccctcaca catactctct acgatgcgaa gtctgggaca tctggagaga aagtgggcaa    780
actcagcctg gtggatttag ctggcagtga acgagcaacg aagacaggcg ctgcagggga    840
caggctgaag gaagggagca acattaacga gtccctcaca accctcggtc tggttatctc    900
agctcttgca gatcagagtg ctggcaaaaa caagaataaa tttgttccat atcgtgactc    960
agttctcacc tggctgctca aagacagcct cgggggtaac agcaagaccg ccatggtggc   1020
tactgtgagt cctgcagctg ataactatga tgaaaccctc tcaactctgc ggtatgcaga   1080
tcgagccaag cacattgtaa acaacgctgt ggtgaatgag gaccctaatg cccgaattat   1140
ccgggacctc cgggaagaag ttgagaaact ccgggagcag ctgaccaaag cagaggcaat   1200
gaaatctcca gagctaaagg accggctgga agaatctgag aagctaatcc aggaaatgac   1260
tgtgacctgg gaggagaaat taaggaaaac ggaggagatt gcacaggaac gacagaaaca   1320
gcttgagagt cttggaatat ctcttcagtc ttcgggaatc aaagttgggg atgataaatg   1380
cttccttgtg aatctgaatg ctgacccagc tctgaatgag cttctggtgt actatttaaa   1440
ggaacataca ttgatagggt cagcaaattc ccaagatatc caactgtgcg gcatgggaat   1500
tcttcctgaa cactgtatta tagacatcac gtcagaaggc caggttatgc tgactcctca   1560
gaagaacacc agaacatttg taaatgggtc atctgtctcc agtccaatac agctacacca   1620
tggggacagg atattatggg gaaacaatca tttcttcaga ctcaatttgc ctaaaaagaa   1680
aaagaaagca gaacgagagg atgaggacca ggatccctcc atgaagaacg agaatagttc   1740
tgagcagctg gatgtagacg gagactcctc cagcgaggtg tccagtgaag ttaactttaa   1800
ttacgaatac gcacagatgg aggtcaccat gaaggccctg ggcagcaatg atccgatgca   1860
gtccatatta aacagcctag aacaacagca tgaagaagaa aaacgatctg cactggagcg   1920
ccagaggctt atgtatgagc acgaattgga gcagctccgg agaaggctgt ctcctgagaa   1980
gcagaactgc cggagcatgg acaggttttc tttccactcg cccagcgctc agcaacgctt   2040
aagacagtgg gctgaggaga gagaagcaac gttgaataac agcctgatga ggctgaggga   2100
acaaattgtt aaggccaatc tattggtgag agaagctaat tacattgctg aggagctgga   2160
taaaagaaca gaatacaaag ttaccctaca gattccagcc tccagcctgg atgccaacag   2220
gaagcgaggc tctcttctta gtgagcctgc aatccaggtg agaagaaaag gaaaaggaaa   2280
gcagatttgg tctttggaaa aactggacaa caggctgttg gatatgagag acctttatca   2340
ggagtggaaa gagtgtgaag aagataaccc agtaatacga tcatacttca aacgtgctga   2400
tccattctat gatgagcagg aaaatctcag tctcattggg gtggccaatg tcttcctcga   2460
gtcacttttc tatgatgtga agttacaata cgctgttccc atcatcaacc agaaaggaga   2520
ggtggcaggt cggctgcacg tggaggtgat gcgactcagt ggtgatgttg gggagaggat   2580
cgcaggaggc gatgaggtgg cagaggtccc ctttgagaag gagacccagg agaacaaact   2640
ggtgtgcatg gttaaaatcc tgcaagctac tgggttgcca cagcatctgt cccactttgt   2700
gttctgcaaa tacagcttct gggatcaaca ggagccggtg attgtcgctc ctgaagtgga   2760
cacctcctcc tcttccgtca gcaaggagcc gcactgcatg gttgtctttg atcattgcaa   2820
tgagttttct gttaacatca ccgaagactt tatcgagcat ctttccgaag gagcattggc   2880
aattgaagta tatggacata aaataaacga tccccggaaa aaccccgccc tgtgggattt   2940
gggaatcatc caagcaaaga cacgtagtct tcgggacaga tggagtgaag tgaccaggaa   3000
attggaattc tgggttcaaa tcttggaaca gaatgagaat ggtgaatact gccctgtaga   3060
agtgatttct gcaaaggatg tcccaacagg aggaatcttc cagctccggc aggggcagtc   3120
```

-continued

```
ccggagagtt caagtcgaag tgaagtcagt gcaggaatct gggactttac cactgatgga   3180
agaatgtata ctgtctgttg gcattggatg tgtcaaagtt agaccgctca gagcccccag   3240
aacacatgag accttccatg aggaagagga agacatggac agctaccagg atcgagattt   3300
agagagactt cgtagaaaat ggctaaatgc attaacaaaa cgtcaggagt acttggatca   3360
acaattgcaa aagcttgtca gtaaacgtga taaaacagag gatgatgctg accgtgaagc   3420
gcagcttctg gagatgcggt tgaccctaac tgaggagagg aacgcggtga tggtcccctc   3480
tgctggcagt ggtattccag gggccccagc agaatggacc ccagtacctg ggatggagac   3540
acacattcct gttatattcc tggacttaaa tgctgatgat ttcagctctc aggataatct   3600
tgatgaccca gaagctggtg gatgggatgc gaccttgact ggggaagaag aagaggagtt   3660
ctttgaattg cagattgtga agcagcatga tggggaggtg aaagcagaag cctcctggga   3720
ctccgcggtg catggctgcc ctcagctcag caggggcacg cccgtggacg agcggttgtt   3780
cctgatcgtg cgcgtgacgg tccagctcag ccaccctgct gacatgcaac tggtgttacg   3840
caagagaatc tgtgtcaatg ttcacggccg ccagggtttt gcacagagtc tcctaaaaaa   3900
gatgtctcat cgaagttcta ttcctggctg tggagtgact tttgaaattg tctccaatat   3960
tccagaggat gcccagggag tggaagaacg ggaagcatta gcaagaatgg cagccaatgt   4020
tgaaaaccca gcttctgctg actcggaggc ttatattgaa aagtacctca ggagcgtgct   4080
ggctgtagaa aacctcctga ctttagatcg tctgcgccag gaagttgcag tgaaggaaca   4140
gttaacagga aaaggaaagt tgagcaggag gagtatcagt tctccaaatg tgaacagatt   4200
gtctggaagc cgacaagatc tcattccatc atacagtcta ggcagcaaca agggccggtg   4260
ggaaagtcag caggatgtat cccaaaccac agtttccaga ggaatagctc ctgcccccgc   4320
cctctctgtt tctccccaaa ataaccattc tccagatcca ggactcagta accttgcagc   4380
atcctacttg aatcctgtca aatccttcgt gccgcaaatg ccaaagctcc tcaagtctct   4440
ctttcccgtc cgcgatgaga agaggggcaa gcggccgtct cccctcgcac accagcccgt   4500
gccccgcatc atggtgcagt cagccagccc ggacatcagg gtgaccagga tggaggaggc   4560
tcagccggag atgggccctg acgtgctggt gcagacgatg gggggccccgg ccttgaagat   4620
ctgcgacaaa cctgccaaag tgccttcccc accgcctgtc atagctgtca cagcggtcac   4680
cccggctccg gaggcacagg acgggccccc cagcccccctg agtgaagcct ctagcgggta   4740
cttctcccac agcgtctcca ccgcgaccct gtcggacgcc ctgggccccg gcctggacgc   4800
tgcggccccg ccggggtcca tgcccaccgc ccctgaggcc gagcccgagg cgcccatcag   4860
ccaccccccca ccgcccacgg ccgtccccgc cgaggagccc cctggccccc agcagctcgt   4920
gagccccggt cgggagcgcc ccgacctcga ggcccccggcg cccggctccc cgttccgcgt   4980
ccggagggtg cgggcctcgg agttgcgctc cttctcgcgc atgctggctg gggaccccgg   5040
ctgctccccg ggggccgagg ggaatgcgcc ggccccgggc gccgggggac aggccctggc   5100
ctctgattcc gaggaagctg acgaggtccc ggagtggctc cgagagggcg agttcgtcac   5160
cgtgggcgcc cacaaaacgg gcgtggtgag atacgtgggg cctgccgact tccaagaggg   5220
cacgtgggtc ggcgtggagc tcgacctgcc ctcaggtaag aatgacggtt ccatcggcgg   5280
gaagcagtac ttcaggtgta accctggcta cgggctgctg gtcaggccca gccgggtccg   5340
cagggccacg ggccctgtgc ggcggcgcag cacaggactc cggctgggtg cccccgaggc   5400
ccgccggagc gccaccctct cgggctccgc caccaacctg gcctcgctga cagctgccct   5460
ggccaaggcc gacaggagcc acaagaaccc tgagaaccgg aaatcctggg ccagctgagc   5520
```

-continued cgctgcctta gggcgaactt ttctgggggt gcccggcccc ttttgagccc tgccagtgac 5580
agccctgagg agccaggagc ccggtggccc cttccccagg ggcagggcga tgaatgcttt 5640
ttgcacgaca cagggctggt gacctccctg ggcctctgga agctttgttt cttctgtacc 5700
cgggtaaagt gggggcctca actgtgcctc ctccggtgga tggaaggttc tgggtgcccg 5760
caggggctgg gggatgctag gactgagacc ctgggtggtg cagcgcctgg tgatcttgct 5820
gtgtgcctgt gcctggggcc ttatgttgct ctttctatca tttccattct ggtggcccca 5880
ctaatgtctt aacctaaacc ataattgtaa ccagtgcctt tcctccccac tggagggcaa 5940
gcccccccac ccacccagga tgtcctggct cactccgcaa gccccccagc ctcccaccct 6000
ggtcccagtt tcccgcaaag tgcctctggg ggaccccca gcctcccacc ctggtcccag 6060
gttccacaag tgcctctgga gggccctggg ctctggcaga tggtcctggt gccccagacg 6120
ggggccgagg gcctgagccc ccccatccct cctctgccag ggtttcttag cggtttctct 6180
gtggatgttt tggcatcttt agacacctgg aaagtctctt atgtttgccg tttattccct 6240
tcacagaagg cttggaatgt atttatttat atttattttt tcaaaatccg aaatcatttg 6300
cgagccgcaa tcgtcgtctg cctgtgtggg ggggcccagg gcctgccttg cacgttgcag 6360
cctctctggc cattgcagag ctgctggcct cctgcccagg tggagggtcc tggggacggc 6420
agaggataaa gccccctcct cacatccctc tattgcggat ccacagtggc cttactctta 6480
acttggatga gagcaaaaac ctgggagaat gatgtgcttc tgtagtcggt gacaaaggaa 6540
gaggcattgc tactttattt ggtgcacttt tggtttctag gaaggtcttt gggtcatttt 6600
aacttctcgg caactcccag actctcagag tgtggggctg gggcctggcg gctgggctgg 6660
tgcagggagt gtgctggtta gtctccagac cctcacagca gccacgcccc caggcccacc 6720
gtgcatggtg tgggcgggac agccggaagc ttccggggtg gcctccacct cctggctggg 6780
gcacttatgc tcccagagcc tttggtgcca ggtttgtggg atgggggtta gcgtctatgt 6840
gtggaaggcc accaatctag ggacaggagt cctgggtcaa gattcacaca gccacccttg 6900
gagctggttt ctagttctca catttagtca acatctagaa agcgctgcgg aaggctctgg 6960
ttctctaggg acttgaaggc gccaacagag tagtctccat ggtgggcctg tcccagccct 7020
ggctgcgagg acaggttgtc tttctctccc cagttggcga gggacacgaa ggctgcggcc 7080
gggctggcag agggcccggc ccctgggggg aggcactcct ccagggctct ccctgtcctt 7140
agccgatttt gagggaaccc tgtggcacct gtccctggat gaagagctgt cacctctgcc 7200
ttgcccttta actcaacccg cttcccagca cagcggcttt ctttttaaaa cctgtttcac 7260
tgagaagttt gtttttgggt ccgctggtgt cactatggcc tgggtgagag gccagcactg 7320
ctgctgccct gaggggaaac gcctgggccg tgtagtgggg acgctctggg aatggtggcg 7380
gacgggcagc gtgggtggga cctggcactt cgtggtggct gagccatcca cccagcagcg 7440
gcctcctgta gcaccatatt gggaaagtcc tgggggacgt gtgtgtcgtg ctttttacca 7500
tcggtttgac ttacagtgga gtagaacgag ccagagttcc tgacttgagc aggtggattt 7560
gggcccaggc cctgttcact cttgcttctc ggtgcggact aatgtcagct tgtggctggg 7620
aaagagggat gtgcagtgac gtggtcacca aggcagtgag ccccgctgac cccgggccag 7680
cacttggcag gcaggaggtg cggtctccag agtggtgggc cagggcgggc tggcctccgt 7740
cttctatctt cttttcttgc ctccctgacc agcagactca cctcccaaga acgcctgccc 7800
gcccacccgc cttaggactc ccgatgcgct cctggaaggc cccaggagtg gcaccttagt 7860
gtgggtcggc ccgcagatgg cacccaaggc cgggaagggc agtaactgca cacgcggcgc 7920
tgtcagagat gggggtgggg gatgcttctg ggggccctgc ctccccattg tgtgcccaga 7980
acatccctgg ccccaccccg ccacttccct cgggccctta tgaaggactg aggctccagg 8040
gtgagaaggc tcacttctgc cccaggcact gcgtccagca gcagagggga caggggggcag 8100 gtgtgtgact gggttcctgg gtacccaggc ctgaccagag ggagcgggag ggcagaggtg 8160
aggaggggga agatgtttct gggcctacca aggttcaaca agagaacgga gctgggaatg 8220
tgactgctgg agcctgagag gtggaggagt tctgatcccc cgttacttcc tagcattttc 8280
tcctcttgcc ttaaaagttc cctgtatgtg aaacgggaag tcctgagagt gtgtgttggt 8340
ggctgtgcgc acgcacacaa gacgggagtc accctgtgct tcctgcccaa gatactgacc 8400
cattgaaccc ccaaagcatc tttctctcca caaagtccgt ggtgccttcc tggtgggctg 8460
cagacactaa tggtgttggg gggtcttgga acagcttctc tatgtgtgga ttcgtgtaaa 8520
tgcgaagagt tcacatataa agaagtgact ttgattctgt gattatattg atttggtaca 8580
cagtaaatgg gagtttaaaa aatccaaaga ctctaatgac ttgtaaagac tctaatgatt 8640
tgtatcatgt aatgaactaa accacctgta attttgtacc atatgtgtct ttccatcaaa 8700
tgaccaacag cttctcaata aaaccagacc atttctcacc tgc 8743

<210> SEQ ID NO 57
<211> LENGTH: 6586
<212> TYPE: DNA
<213> ORGANISM: Human

<400> SEQUENCE: 57
ctggggagcc ggcgctggag gtggtgagtg gcgtggggac tgtgtcgagg gggtccccaa 60
ggtgccggac cctgcggagg ggcgaagttt cggcactggg gagggcgtgc ggacgctttc 120
cctacaggcg accactgctc tgcgggcggg tggtcttagc tccagtcccc cattcagttc 180
ctcagcattc caggtcggcg gcgaaggggt ccccgaacga agggcgcaag gcagcgtctc 240
tgctgggacc gggaagccgg acttcagggc ctctcggccc gtgggcttct ccccgagtct 300
ccccgagtcg gttggcatta agagtttagc agatactttc agaaatggat acataagaaa 360
tggctggaaa tcaaatgaat gtccaaagaa gagcttaggg tcttagtaac attctttttt 420
aaaataactg tctgccaaaa tgtcattaca cagtactcat aatagaaata acagcggtga 480
tattcttgat attccttctt cccaaaatag ttcatcactg aatgccctca cccacagtag 540
ccgacttaag ctgcatttga agtcggatat gtcagaatgt gaaaatgatg atccattatt 600
gagatctgca ggtaaagtca gagacataaa tagaacttat gttatttctg ccagtagaaa 660
aacagcagac atgcccctta cccctaatcc tgtaggtaga ttggcacttc agaggagaac 720
tacaaggaac aaagaatcat ctttgcttgt tagtgagttg gaagacacaa ctgaaaaaac 780
agcagaaaca cgtcttacat tacaacgtcg tgctaaaaca gattctgcag aaaagtggaa 840
aacagctgaa atagattctg tcaaaatgac actgaatgtg ggaggtgaaa cagaaaataa 900
tggtgtttct aaggaaagta gaacaaatgt aaggattgta aataatgcta aaaactcttt 960
tgttgcctct tctgtacctt tagatgaaga tccacaggtc attgaaatga tggctgataa 1020
gaaatacaaa gaaacatttt ctgcccccag tagagcaaat gaaaatgttg cacttaagta 1080
ctcaagtaat agaccaccca ttgcttccct gagtcagact gaagttgtta gatcaggaca 1140
cttgacaacg aaacctactc agagcaagtt ggatatcaaa gtgttgggaa caggaaactt 1200
gtatcataga agtattggga aggaaattgc aaaaacttca aataaatttg ggagcttaga 1260
aaaaagaaca cctacaaaat gtacaacaga acacaaactg acaacaaagt gcagcctgcc 1320

-continued

```
tcagcttaag agcccagctc catcaatact gaagaataga atgtctaacc ttcaagttaa   1380
acaaagacca aaaagttcct ttcttgcaaa taaacaggaa agatccgcag aaaatacaat   1440
tcttcccgaa gaagaaactg tagttcagaa cacctctgca ggaaaagacc ccttaaaagt   1500
agagaatagt caagtgacag tggcagtacg cgtaagacct ttcaccaaga gagagaagat   1560
tgaaaaagca tcccaggtag tcttcatgag tgggaaagaa ataactgtgg aacaccctga   1620
cacgaaacaa gtttataatt ttatttatga tgtttcattc tggtcttttg atgaatgtca   1680
tcctcactac gctagccaga caactgtcta tgagaagcta gcagcaccac tcctagaaag   1740
agccttcgaa ggcttcaata cctgtctttt tgcttatggt cagactggct ctggaaaatc   1800
atatacgatg atgggattta gtgaagaacc aggaataatt ccaagatttt gtgaagatct   1860
tttttctcaa gtagccagaa aacaaaccca agaggtcagc tatcacattg aaatgagctt   1920
ctttgaagta tataatgaaa aaattcacga ccttctggtt tgtaaagatg aaaatgggca   1980
gagaaagcaa ccactgagag tgagggaaca tcctgtttat ggaccatatg ttgaagcact   2040
gtcaatgaac attgtcagtt cttacgctga tatccagagt tggctagaat tgggaaataa   2100
acaaagagct actgctgcta ctggtatgaa tgataaaagt tcccgatctc attcagtttt   2160
caccctggtg atgacccaga ccaagacaga atttgtggaa ggggaagaac acgatcacag   2220
aataacaagt cgaattaacc taatagatct ggcaggcagt gagcgctgct ctacggctca   2280
cactaatgga gatcgactaa aggaaggtgt gagtattaat aagtccttgc taactttggg   2340
aaaagttata tctgcacttt cggaacaagc aaaccaaagg agtgttttta ttccttatcg   2400
tgaatctgtt cttacatggc tgttaaaaga aagtctgggt ggaaattcaa aaactgcaat   2460
gattgctacg attagtcccg ctgccagcaa catagaagaa acattaagca cacttagata   2520
tgctaaccaa gcccgtttaa tagtcaacat tgctaaagta aatgaagata tgaacgctaa   2580
gttaattaga gaattgaagg cagaaattgc aaagctaaaa gctgctcaga gaaacagtcg   2640
gaatattgac cctgaacgat acaggctctg tcggcaagaa ataacatcct taagaatgaa   2700
actgcatcaa caggagagag acatggcaga aatgcaaaga gtgtggaaag aaaagtttga   2760
acaagctgaa aaaagaaaac ttcaagaaac aaaagagtta cagaaagcag gaattatgtt   2820
tcaaatggac aatcatttac caaaccttgt taatctgaat gaagatccac aactatctga   2880
gatgctgcta tatatgataa aagaaggaac aactacagtt ggaaagtata aaccaaactc   2940
aagccatgat attcagttat ctggggtgct gattgctgat gatcattgta ctatcaaaaa   3000
ttttggtggg acagtgagta ttatcccagt tggggaagca aagacatatg taaatggaaa   3060
acatattttg gaaatcacag tattacgtca tggtgatcga gtgattcttg gtggagatca   3120
ttattttaga tttaatcatc cagtagaagt ccagaaagga aaaaggccat ctggaagaga   3180
tactcctata agtgagggtc caaaagactt tgaatttgca aaaaatgagt tgctcatggc   3240
acagagatca caacttgaag cagaaataaa agaggctcag ttgaaggcaa aggaagaaat   3300
gatgcaagga atccagattg caaaagaaat ggctcagcaa gagctttctt ctcaaaaagc   3360
tgcatatgaa agcaaaataa aagcactgga agcagaactg agagaagagt ctcaaaggaa   3420
aaaaatgcag gaaataaata accagaaggc taatcacaaa attgaggaat tagaaaaggc   3480
aaagcagcat cttgaacagg aaatatatgt caacaaaaag cgattagaaa tggagacatt   3540
ggctacaaaa caggctttag aagaccatag catccgccat gcaagaattc tggaagcttt   3600
agaaactgaa aagcaaaaaa ttgctaaaga agtacaaatt ctacagcaga atcggaataa   3660
tagggataaa acttttacag tgcagacaac ttggagctct atgaaactct caatgatgat   3720
```

-continued

```
tcaggaagcc aatgctatca gcagcaaatt gaaaacatac tatgtttttg gcagacatga   3780
tatatcagat aaaagtagtt ctgacacttc tattcgggtt cgtaacctga aactaggaat   3840
ctcaacattc tggagtctgg aaaagtttga atctaaactt gcagcaatga aagaacttta   3900
tgagagtaat ggtagtaaca ggggtgaaga tgccttttgt gatcctgaag atgaatggga   3960
acccgacatt acagatgcac cagtttcttc actttctaga aggaggagta ggagtttgat   4020
gaagaacaga agaatttctg gttgtttaca tgacatacaa gtccatccaa ttaagaattt   4080
gcattcttca cattcatcag gtttaatgga caaatcaagc actatttact caaattcagc   4140
agagtccttt cttcctggaa tttgcaaaga attgattggt tcttcgttag atttttttgg   4200
acagagttat gatgaagaaa gaactatagc agacagccta attaatagtt ttcttaaaat   4260
ttataatggg ctatttgcca tttccaaggc tcatgaagaa caagatgaag aaagtcaaga   4320
taacttgttt tcttctgatc gagcaatcca gtcacttact attcagactg catgtgcttt   4380
tgagcagcta gtagtgctaa tgaaacactg gctgagtgat ttactgcctt gtaccaacat   4440
agcaagactt gaggatgagt tgagacaaga agttaaaaaa ctgggaggct acttacagtt   4500
atttttgcag ggatgctgtt tggatatttc atcaatgata aaagaggctc aaaagaatgc   4560
aatccaaatt gtacaacaag ctgtaaagta tgtggggcag ttagcagttc tgaaagggag   4620
caagctacat tttctagaaa acggtaacaa taaagctgcc agtgtccagg aggaattcat   4680
ggatgctgtt tgtgatggtg taggcttagg aatgaagatt ttattagatt ctggactgga   4740
aaaagcaaaa gaacttcagc atgaactctt taggcagtgt acaaaaaatg aggttaccaa   4800
agaaatgaaa actaatgcca tgggattgat tagatctctt gaaaacatct ttgctgaatc   4860
gaaaattaaa agtttcagaa ggcaagtaca agaagaaaac tttgaatacc aagatttcaa   4920
gaggatggtt aatcgtgctc cagaattctt aaagttaaaa cattgcttag agaaagctat   4980
tgaaattatt atttctgcac tgaaaggatg ccatagtgat ataaatcttc tccagacttg   5040
tgttgaaagt attcgcaact tggccagtga tttttacagt gacttcagtg tgccttctac   5100
ttctgttggc agctatgaga gtagagtaac tcacattgtc caccaggaac tagaatctct   5160
agctaagtct ctcctctttt gttttgaatc tgaagaaagc cctgatttgt tgaaaccctg   5220
ggaaacttat aatcaaaata ccaaagaaga acaccaacaa tctaaatcaa gcgggattga   5280
cggcagtaag aataaaggtg taccaaagcg tgtctatgag ctccatggct catccccagc   5340
agtgagctca gaggaatgca cacccagtag gattcagtgg gtgtgaatac tgatgtgtag   5400
gcacttttat gaccacccat gaaagaaaaa gaacacttgc tcggtaattt tctttatgca   5460
ggagagttta agagaaatca gcacagatat ttcaaaaaag tccatgtctt tttatcttta   5520
aaatatctat ttatcaaagg ccagacacag tggctcacgc ctgtaatccc agcactttgg   5580
gaggcgggca gatcacaagg tcaggagttt gagaccggcc tggccaacat ggtgaaaccc   5640
cgtctctact aaaaatacaa aaatttgctg ggcatggtgg cgcgtgcctg taatcccagc   5700
tactaggggg gctgaggcag gaggatcgct tgaacctgag aggcagaggt tgcagtgagc   5760
caagatcatg ccactttact ccagtctgag caacagaacg agacttagtc aaaataaata   5820
aataaataag taaataaata aataaataaa atatctttta tctttaaagt gtttaacatt   5880
ggtatactgt ctgtagttgg ttcattagtc gtttataaag ggttattttc tcatgagtgg   5940
aaacctgaac aatcagttac ctttgtgcct atgccttctc tctcctcaga cagctgggat   6000
gtttatggtg aaatggcctg tacaagttta actaagacaa cttaacttgc attgttaatc   6060
aaaaattctt ttctcaaagg gttaactggt tgccattttg aatagtatgt tcaagggtgt   6120
```

```
agcttcctgt ttctttccaa attataagta gctacctaaa tatagtataa ttatatatta   6180

ataatatggc ttgctggcac agtagtttac cctgttatct gtgtttcata atgggggctg   6240

tatgaatatt atttaaaact aataaaatgt tgccagaatt atactaaact gttggatgag   6300

attaggagat cagaggctgg accttctctt gataatgctt gttttgttaa aggtataatg   6360

aaataatttg tatatgattt gatgaagatt aaagaccctt attttccaca gctttaaaaa   6420

aaaacctttta tttatgatca agtaataaag ataatattct acttgtggga tcttacatta   6480

tggaaatagt ttgacgtttt tgacctcaag agtatgtata atttgaagag atactttgta   6540

actatgcttg ggtgatattg agcagttcct aaagaataat tcattt                  6586
```

<210> SEQ ID NO 58
<211> LENGTH: 4775
<212> TYPE: DNA
<213> ORGANISM: Human

<400> SEQUENCE: 58

```
cagtcgcgcg cggtgcagtc gggaggtgga ggcaccggct gcattgtttt cgggatcgag     60

gggtgagggc gctatggcac ccggctgcaa aactgagtta cgcagcgtga caaatggtca    120

gtctaaccaa ccaagtaatg aaggtgatgc catcaaagtt tttgtgcgaa ttcgtcctcc    180

tgcagaaaga tctgggtcag ctgatggaga gcagaactta tgcttatctg tgctgtcctc    240

cacgagtctc cggctgcact ccaaccctga gcccaagacc ttcacgtttg atcatgttgc    300

agatgtggat accactcagg aatctgtatt tgcaactgtg gctaaaagca ttgtggagtc    360

ttgcatgagc ggttataatg gtaccatctt tgcatatgga cagactggct cagggaagac    420

atttactatg atgggaccat ctgaatctga taatttttct cataacctga gaggagtaat    480

cccacgaagt tttgaatatt tgttttcctt aattgatcgt gaaaaagaaa aggctggagc    540

tggaaagagt ttcctttgta agtgttcctt tattgaaatc tacaacgagc agatatatga    600

tctactggac tctgcatcgg ctggactgta cttaagggag catatcaaga agggagtctt    660

tgttgttggt gcggtggagc aggtggtaac ctcagctgct gaagcctatc aggtgctgtc    720

tggaggatgg aggaatagac gtgtggcatc aacatcaatg aacagagaat cgtctaggtc    780

tcatgccgtc tttacaatta caatagagtc aatggagaaa agtaatgaga ttgtgaatat    840

acggacctcc ctactcaacc tggtggattt agcaggatct gaaaggcaaa aagataccca    900

tgcagaaggg atgagattga aggaagcagg taacataaat cgatcattga gctgcctggg    960

ccaagtgatt acagcacttg tcgacgtggg taatggaaaa cagagacatg tttgctacag   1020

agactccaaa cttaccttct tactacggga ttcccttgga ggtaatgcca aaacagccat   1080

aattgcaaat gttcatcctg gatccaggtg ttttggggaa accctatcaa cacttaactt   1140

tgctcaaaga gccaagctga ttaaaaacaa ggcagtagta aatgaagaca cccaaggaaa   1200

tgtgagccag ctccaagctg aagtgaagag gctcaaagaa caactggcgg agcttgcttc   1260

aggacagaca ccaccagaaa gcttcctgac cagagacaaa aagaagacta actatatgga   1320

gtatttccag gaagcaatgt tattctttaa gaaatctgaa caggaaaaga agtctctgat   1380

agaaaaagtt acccaattag aagacctcac cctcaaaaag gaaaaattta ttcaatctaa   1440

taaaatgatt gtgaaattcc gagaggatca aataatacgc ttggaaaagc tccacaagga   1500

atcccgggga ggttttctgc ctgaggagca ggatcgtttg ctctcagaat taaggaatga   1560

gattcaaact ctgcgagaac aaatagagca ccaccccaga gttgcaaagt atgctatgga   1620

aaatcattcc ctcagggagg agaatagaag actgagatta ttagagcctg tgaaaagagc   1680
```

```
tcaagaaatg gatgcccaga ccattgcaaa actagaaaaa gctttctctg aaataagtgg   1740
catggagaaa agtgacaaaa atcagcaagg attttcacct aaagctcaga aagagccatg   1800
tttgtttgca aacactgaga agttaaaagc acaactcctg caaattcaga cagagctgaa   1860
taattcaaag caagaatatg aagaattcaa agaacttact aggaaaaggc agctagaatt   1920
ggaatcagag cttcagtctt tgcaaaaagc gaaccttaat cttgaaaacc ttttggaagc   1980
aacaaaagcc tgcaagcggc aagaagtttc tcagctgaat aaaattcatg ctgaaacact   2040
taagattata actacaccaa ccaaggccta ccaacttcat tcccgaccag taccaaaatt   2100
aagccctgaa atgggaagct ttggctctct atacactcag aattctagca tattagataa   2160
tgatatatta aatgagccag ttcctcctga gatgaatgaa caagcttttg aggccatttc   2220
tgaagagctt agaacagtgc aggaacaaat gagtgctctt caagccaaac tggatgaaga   2280
agagcataaa aacctaaagc ttcagcagca tgttgacaaa ctggaacatc attctaccca   2340
aatgcaggag cttttctcat cagaaagaat tgattggacc aaacagcagg aagagcttct   2400
ctcacagttg aatgtccttg aaaagcagct tcaagagact caaactaaaa atgacttttt   2460
gaaaagtgag gtacatgacc tgcgagtagt ccttcattct gctgacaagg agctttcttc   2520
agtgaaattg gaatatagtt cattcaaaac gaatcaggag aaagaattca acaaactttc   2580
tgaaagacac atgcatgtac agcttcaatt agataatctc aggttagaaa acgaaaagct   2640
gcttgagagc aaagcctgcc tacaggattc ctatgacaac ttacaagaaa taatgaaatt   2700
tgagattgac caactttcaa gaaacctcca aaacttcaaa aaagaaaatg aaactctgaa   2760
atctgatctg aataatttga tggagcttct tgaggcagaa aaagaacgca ataacaaatt   2820
atcattacag tttgaagaag ataaagaaaa cagttctaaa gaaatcttaa aagttcttga   2880
ggctgtacgt caggagaaac agaaagagac ggccaagtgt gagcagcaga tggcaaaagt   2940
acagaaacta gaagagagct tgcttgctac tgaaaaagtg atcagttccc tggaaaagtc   3000
tagagattct gataagaaag ttgtagctga cctcatgaac cagatccagg agctaagaac   3060
atcggtctgt gagaaaacag aaactataga caccctgaaa caagaactga aggacataaa   3120
ttgcaaatac aactctgctt tggttgacag agaagagagc agagtgttga tcaagaagca   3180
ggaagtggat attctggatc tgaaagaaac ccttaggctg agaatacttt ctgaggacat   3240
agagagggat atgctctgtg aggacctggc tcatgccact gagcagctga acatgctcac   3300
agaggcctca aaaaaacact cggggctgct gcagtctgcc caggaagaac tgaccaagaa   3360
ggaagccctg attcaggaac ttcagcacaa gctaaaccaa aagaaagagg aagtagaaca   3420
gaagaagaat gaatataact tcaaaatgag gcaactagaa catgtgatgg attctgctgc   3480
tgaggatccc cagagtccta agacaccacc tcactttcaa acacatttgg caaaactcct   3540
ggaaacacaa gaacaagaga tagaagatgg aagagcctct aagacttctt tggaacacct   3600
tgtaacaaag ctaaatgaag acagagaagt caaaaatgct gaaatcctca gaatgaagga   3660
gcagttgcgt gaaatggaaa acctacgcct ggaaagtcag cagttaatag agaaaaactg   3720
gctcctgcaa ggtcagctgg atgatattaa aagacaaaag gaaaacagtg atcagaatca   3780
tccagataat caacagctga agaatgaaca agaagaaagt atcaaagaaa gacttgcaaa   3840
aagtaaaata gttgaagaaa tgctgaaaat gaaagcagac ctagaagaag tccaaagtgc   3900
cctttacaac aaagagatgg aatgccttag aatgactgat gaagtcgaac gaacccaaac   3960
tttggagtct aaagcattcc aggaaaaaga acaactgaga tcaaagctgg aagaaatgta   4020
tgaagaaaga gagagaacat cccaggagat ggaaatgtta aggaagcagg tggagtgtct   4080
```

tgctgaggaa aatggaaagt tggtaggtca ccaaaatttg catcagaaga ttcagtacgt 4140
agtgcgacta aagaaggaaa atgtcaggct tgctgaggag acagaaaagt tgcgtgccga 4200
aaatgtattt ttaaaagaaa agaaaagaag tgaatcttga ggattccggt cagctaccta 4260
ggcatcacct tgtttgaaga tgtttcttct cttttacaag taagacctac tcctggccac 4320
ttaggagagc tgaatttatg gaccttaatt attaaatgtt tataaggtgg tggtaaccac 4380
ctcaagtttc tgatgaacat tctgcatcca tatacaccct gtgacagtca gcagtctgct 4440
attaagtggc ctacttcaag gctttgaatc aacttaaggg aaaacctttt gtctttgtaa 4500
aaataaaagc ctgtagctaa ggtttacagt ggacattagc cagatcattt tcttcttaga 4560
ttatgccata atctcctttg attcttatgg aagttctaac aatatatggt ggttccaaca 4620
cctgcagtga gtttaatgac tgacttagta gcaggtacaa gaagcaaact tgttaatata 4680
gattattttt gtattcttac tttaggtatt ttacttgagc attttccatg actgtaaata 4740
aagccatttt ttaagataaa aaaaaaaaaa aaaaa 4775

<210> SEQ ID NO 59
<211> LENGTH: 2469
<212> TYPE: DNA
<213> ORGANISM: Human

<400> SEQUENCE: 59
ttatcaaatg ctttttcaac aatagtttaa atgatcatat ggtttttgtc cttcattctg 60
ttgacatgat gtatcacatt cattgatttg catatgttga gtcatccttg catccctagg 120
ataaattcca cttggtcacg ataaatgatc tttttttct tttttttttt ttttttttgt 180
gagactgagt ctcactctgt cgcccaggct ggagtgcagt ggtgcaatct tggcttaccg 240
caacctccat cttctgggtt caagtgattc tcctgcctca gcctcccaag tagctgggac 300
tacaggtttt ccaggattta gggatggaag tactgtctgg agttgccaaa ggctataaca 360
tatgcctttt tgcttatgga cagacaggct ctgggaagac atataccatg ctgggcaccc 420
cagcctctgt tgggttgaca ccacggatat gtgagggtct cttcgtcagg gagaaagact 480
gtgcctcact gccttcctcc tgtaggataa aagtaagttt tctagaaatc tataatgaac 540
gggtgcggga tctgttgaag caatctggtc aaaaaaagtc ctataccctg cgggtcaggg 600
agcatccaga gatggggccc tatgtacaag gtttatctca acatgtagtt accaattata 660
agcaagtaat ccaactcttg gaggagggaa ttgcaaacag aatcacagca gccacccatg 720
ttcatgaggc cagcagcaga tcccacgcca ttttcacgat ccactacacg caggcaatcc 780
tggagaacaa cctcccttct gaaatggcta gcaagatcaa ccttgtggac ctagcaggca 840
gcgaaagagc agatcccagt tactgtaagg accgcattgc tgaaggagcc aatatcaaca 900
agtcccttgt gactctagga attgtcatct ccaccttagc ccagaactcc caagttttca 960
gcagctgcca gagcctcaac agctcagtca gcaatggtgg tgacagtggg atccttagct 1020
ctccttctgg gaccagcagt ggaggggcac cctcccgaag gcagtcttat atcccatacc 1080
gagactctgt gttgacctgg ctgctgaagg acagccttgg aggcaactct aaaaccatca 1140
tggttgccag tgagtgggat gccagagctg gacctgtgtt gggactggta ctctatctca 1200
gagaaagggc catggcccca gtgagtggga tgccagagct ggatctgtgt tgggactggt 1260
actctatctc agagaaaggg ccatggcccc agtgagtggg atgccagagc tggatctgtg 1320
ttgggactgg tactctatct cagagaaagg gccatgacca cctaggtttc tcatttcatc 1380
aggggtctta tacagcatgg gcagtagtaa caaggcaagt gattaagagc tgggatggat 1440
gggctggcat gtttttaaac tttctccttc tacctcagcg gtgtctcctg cacacactag 1500
ctacagtgag accatgagca cactgagata tgcatccagt gccaaaaaca ttatcaacaa 1560
gccacgagta aatgagatag accagctgac taaagactgg acccagaagt ggaatgattg 1620
gcaggccctc atggagcatt acagtgtgga catcaacagg aggagggctg gggtggtcat 1680
cgactccagc ctgccacact tgatggcctt ggaggatgat gtgctcagca caggtgttgt 1740
gctctatcat ctcaaggtga ggaggctagt gtatcctttt cttcctaagc cactggttcc 1800
agaggtcaag gagggaaaag ctaggagcag cagccatgtt actgtgaatt gaaatcaaga 1860
cagatgctac agagctgcct tcaggtttgc tctcaggaaa cgtctacctg acaaattgtg 1920
atctgttttg ccttcgtatg tatagagcag aagactggaa atcagaacaa ttgtttttca 1980
actgctgcta ctgttgttct tatgtaactt acttttgttc tctttgcctt aatttcctca 2040
ttttaaagta agaatgatgc ttatcatatt ccttttctgg cttagtgaag catagggta 2100 tagtcatgga gagtgaaacc ctaacctcaa gataaccatt agtgctccta aactctacaa 2160
atacagactg ctcaaaggtg gctttcaggt tgggcgcggt ggctcacacc tgtaatctca 2220
gcactttggg aggctgaggc gggcggatca cttggggtcg ggagttcggg accatcctgg 2280
ccaacatggt gaaaccccac ctctgctggg aatacaaggg ttagccgggc gtggtggtgg 2340
gagcctgtaa tcccagctac ttgggaggct ggggcgggag aatcacttgg acccaggagg 2400
tggaggttgc ggtgagctga gatcgcgcca ctgcgctcca gcctgggtga caaagtaaga 2460
ctctgtctc 2469

<210> SEQ ID NO 60
<211> LENGTH: 5282
<212> TYPE: DNA
<213> ORGANISM: Human

<400> SEQUENCE: 60
gcaggtgggg ccgccgcgga actccaggtc cggccgggag cagaggggcg ggggcgagag 60
ggaagtgggc gggagccgcg atctgagtag ccagcgtcgc cggcgaccgc ggagttctgg 120
gctagtggga ccccgcgcgg gctggttcgg gatgagcgat ggcatcggtc aaggtggccg 180
tgagggtccg gcccatgaat cgcagggaaa aggacttgga ggccaagttc attattcaga 240
tggagaaaag caaaacgaca atcacaaact taaagatacc agaaggaggc actggggact 300
caggaagaga acggaccaag accttcacct atgacttttc tttttattct gctgatacaa 360
aaagcccaga ttacgtttca caagaaatgg ttttcaaaac cctcggcaca gatgtcgtga 420
agtctgcatt tgaaggttat aatgcttgtg tctttgcata tgggcaaact ggatctggaa 480
agtcatacac tatgatggga aattcaggag attctggctt aatacctcgg atctgtgaag 540
gactcttcag tcggataaat gaaaccacca gatgggatga agcttctttt cgaactgaag 600
tcagctactt agaaatttat aacgaacgtg tgagagatct acttcggcgg aagtcatcta 660
aaaccttcaa tttgagagtc cgtgagcatc ccaaagaagg cccttatgtt gaggatttat 720
ccaaacattt agtacagaat tatggtgacg tagaagaact tatggatgcg ggcaatatca 780
accggaccac cgcagcgact gggatgaacg acgtcagtag caggtctcat gccatcttca 840
ccatcaagtt cactcaggct aaatttgatt ctgaaatgcc atgtgaaacc gtcagtaaga 900
tccacttggt tgatcttgcc ggaagtgagc gtgcagatgc caccggagcc accggggtta 960
ggctaaagga agggggaaat attaacaagt ccccttgtgac tctggggaac gtcatttctg 1020
ccttagctga tttatctcag gatgctgcaa atactcttgc aaagaagaag caagttttcg 1080

```
tgccttacag ggattctgtg ttgacttggt tgttaaaaga tagccttgga ggaaactcta   1140
aaactatcat gattgccacc atttcacctg ctgatgtcaa ttatggagaa accctaagta   1200
ctcttcgcta tgcaaataga gccaaaaaca tcatcaacaa gcctaccatt aatgaggatg   1260
ccaacgtcaa acttatccgt gagctgcgag ctgaaatagc cagactgaaa acgctgcttg   1320
ctcaagggaa tcagattgcc ctcttagact cccccacagc tttaagtatg gaggaaaaac   1380
ttcagcagaa tgaagcaaga gttcaagaat tgaccaagga atggacaaat aagtggaatg   1440
aaacccaaaa tattttgaaa gaacaaactc tagccctcag gaaagaaggg attggagttg   1500
ttttggattc tgaactgcct catttgattg gcatcgatga tgaccttttg agtactggaa   1560
tcatcttata tcatttaaag gaaggtcaga catacgttgg tagagacgat gcttccacgg   1620
agcaagatat tgttcttcat ggccttgact tggagagtga gcattgcatc tttgaaaata   1680
tcggggggac agtgactctg ataccccctga gtgggtccca gtgctctgtg aatggtgttc   1740
agatcgtgga ggccacacat ctaaatcaag gtgctgtgat tctcttggga agaaccaata   1800
tgtttcgctt taaccatcca aaggaagccg ccaagctcag ggagaagagg aagagtggcc   1860
ttctgtcctc cttcagcttg tccatgaccg acctctcgaa gtcccgtgag aacctgtctg   1920
cagtcatgtt gtataacccc ggacttgaat ttgagaggca acagcgtgaa gaacttgaaa   1980
aattagaaag taaaaggaaa ctcatagaag aaatggagga aaagcagaaa tcagacaagg   2040
ctgaactgga gcggatgcag caggaggtgg agacccagcg caaggagaca gaaatcgtgc   2100
agctccagat tcgcaagcag gaggagagcc tcaaacgccg cagcttccac atcgagaaca   2160
agctaaagga tttacttgcg gagaaggaaa aatttgaaga ggagaggctg agggaacagc   2220
aggaaatcga gctgcagaag aagagacaag aagaagagac ctttctccgc gtccaagaag   2280
aactccaacg actcaaagaa ctcaacaaca acgagaaggc tgagaagttt cagatatttc   2340
aagaactgga ccagctccaa aaggaaaaag atgaacagta tgccaagctt gaactggaaa   2400
aaaagagact agaggagcag gagaaggagc aggtcatgct cgtggcccat ctggaagagc   2460
agctccgaga gaagcaggag atgatccagc tcctgcggcg tggggaggta cagtgggtgg   2520
aagaggagaa gagggacctg gaaggcattc gggaatccct cctgcgggtg aaggaggctc   2580
gtgccggagg ggatgaagat ggcgaggagt tagaaaaggc tcaactgcgt ttcttcgaat   2640
tcaagagaag gcagcttgtc aagctagtga acttggagaa ggacctggtt cagcagaaag   2700
acatcctgaa aaaagaagtc caagaagaac aggagatcct agagtgttta aaatgtgaac   2760
atgacaaaga atctagattg ttggaaaaac atgatgagag tgtcacagat gtcacggaag   2820
tgcctcaaga tttcgagaaa ataaagccag tggagtacag gctgcaatat aaagaacgcc   2880
agctacagta cctcctgcag aatcacttgc caactctgtt ggaagaaaag cagagagcat   2940
ttgaaattct tgacagaggc cctctcagct tagacaacac tctttatcaa gtagaaaagg   3000
aaatggaaga aaaagaagaa cagcttgcac agtaccaggc caatgcaaac cagctgcaaa   3060
agctccaagc cacctttgaa ttcactgcca acattgcacg tcaggaggaa aaagtgagga   3120
aaaaggaaaa ggagattttg gagtccagag agaagcagca gagagaggcg ctggagcggg   3180
ccctggccag gctggagagg agacattctg cgctgcagag gcactccacc ctgggcatgg   3240
agattgaaga gcagaggcag aaacttgcca gtctgaacag tggcagcaga gagcagtcag   3300
ggctccaggc tagcctggag gctgagcagg aagccctgga gaaggaccag gagaggttag   3360
aatatgaaat ccagcagctg aaacagaaga tttatgaggt cgatggtgtt caaaaagatc   3420
atcatgggac cctggaaggg aaggtggctt cttccagctt gccagtcagt gctgaaaaat   3480
```

```
cacacctggt tcccctcatg gatgccagga tcaatgctta cattgaagaa gaagtccaaa   3540
gacgccttca ggatttgcat cgtgtgatta gtgaaggctg cagtacatct gcagacacga   3600
tgaaggataa tgagaaactt cacaatggca ccattcaacg taaactaaaa tatgagcgga   3660
tggtttctcg ctctttgggc gcaaatccag atgacctgaa ggacccaatt aaaattagta   3720
tcccacgcta cgtcctctgc gggcaaggaa aggatgcaca cttcgagttt gaggtcaaga   3780
ttactgtcct agatgagaca tggactgtat tcaggcgtta cagtcgtttt cgagaaatgc   3840
ataaaacatt gaagttaaag tatgcagagc ttgctgccct tgaatttgct ccaaagaaac   3900
tatttggaaa taaggatgaa cgtgtgattg ctgagagacg aagtcactta gagaaatacc   3960
tcagggactt tttcagcgtg atgctccagt ccgcaacatc tcccctccac atcaacaaag   4020
tgggactgac tctctcgaaa cataccattt gtgagttttc accattcttc aagaaaggag   4080
tctttgacta cagcagccac gggacggggt agagccagga gtgatggagg aaccaccaca   4140
gcagtgcctt ctcgtcgaag cgggctccga tgcagggcag ctcccccatg cgaggatccg   4200
ggtctgcctc ctcctgctga agacagacat gcagcagcgg gcccgggcca cctcacgttt   4260
ccatacctag tgcctgagtt tggggatggg atgctctgcc tgctgatgtg gccctgacag   4320
gcagccgtta ccgttccatt gcggttgaac gtggcctttt cccacagtgc ttccttctca   4380
ctgcgcagca aagttcgtcc cctgtggcaa gatagatgtg gttgggccat cgtgggttcc   4440
ctgagcccag ccagcctggg acctcccaaa gtgggtggct taccagacca cccttaaatg   4500
actttcatct ggtttcctct ttcaccaaaa tatactcgta tttttatat ttcttccatg    4560
tggctggcta tattccaaga aaagcatttt aaattatttc attgtatttt tttcttttt    4620
tccctcattt gaatcagaac ttttatataa aacccaaaca ctgatgttta cacagaattt   4680
catattctgc aaaagggatt ttttgatcca atcatgactg tagtcttcca tgcttgacaa   4740
attggatgta gacaacatta cttaaaactt ctataaatcc ctacaattag gatatttatt   4800
taaccttgaa tattcaagaa cattctccca aatctaaatg gctactgtgc attcttgagc   4860
tttttctgct aagcacaaaa tgaacgcaaa gctaaatgca tatttttaag tattattcac   4920
attttttgtt acagaatcta ttggatcttt ggctggaaaa ctagaattta tagcagttta   4980
ttaatgatac cttaaattac tcaggactta atgtagcatt gcacttctgt gtacagtaaa   5040
actgctttgt tttactaaag agaaaaatgt gagtggaaaa aatatgtatg tgttatatac   5100
tcaaatgtat ataattctat ctatagattt atatatgtat acattctgta cagtagttcc   5160
atcaaaatat gtaataattc acaccaattt tattaaatgt atttgctttt tcaaaattta   5220
aattgagctg ctatcaatat taaatgaagt tatggcatct aaaaaaaaaa aaaaaaaaaa   5280
aa                                                                  5282
```

<210> SEQ ID NO 61
<211> LENGTH: 3968
<212> TYPE: DNA
<213> ORGANISM: Human

<400> SEQUENCE: 61

```
gggcggctcc gggctcgggt tctgcggcgg cgcctgcagc gcggatcccc cacgtccccg     60
ctcgggccgg gcctcagaaa cgggcgagcc cgggcgcggg aggaagcggc ggccccggct    120
cgggtcctgc gacgcccagc tcccctcggg gcgccccccg aggggtcccc gccccccgcc    180
gcggccccgc ccctgcctca aggccccgcc ccccgtggcc ggcgctggcc ccgcccccttg   240
gcccgggctg ctgggagtcc ccggcggggc gggggtcagc tctggtcccg ttggtcctgg    300
```

```
gcgcggcgcc atggcctccg aggcggtgaa ggttgtcgtg cgctgccgtc ccatgaacca    360
gcgggagcga gagctgcgct gccagcccgt ggtgactgtg gactgcgcgc gcgcccagtg    420
ctgcatccag aacccgggcg ccgccgacga gccgcccaag cagttcacct tcgacggcgc    480
ctaccacgtg gaccacgtca ccgagcagat ctacaacgag atcgcctatc cgctggtgga    540
gggcgtcact gagggctaca atggcaccat ctttgcctac ggccagacag gcagcgggaa    600
gtccttcacc atgcagggcc tgccggatcc gccctcccag agaggcatca tccccagggc    660
cttcgagcac gtgttcgaga gcgtccagtg tgcagagaac actaagttcc tggtccgggc    720
ctcctacctg gagatctaca atgaagatgt ccgggacctc cttggggctg acaccaagca    780
gaagctggag ctgaaggagc acccagagaa gggcgtgtac gtgaaggggc tgtccatgca    840
cacggtgcac agcgtggccc agtgtgagca catcatggag actggctgga agaaccgttc    900
ggtcggctac acgctgatga acaaggattc ctcacgctcg cactccatct tcaccatcag    960
catcgagatg tctgccgtgg atgagcgggg caaggaccac ctccgggcgg gcaagctgaa   1020
cctggtggac ctggcgggca gcgagcggca gtccaagacc ggggccacgg gcgagcggct   1080
caaggaggcc accaagatca acctgtcgct ctcggcactg ggcaatgtca tctcggcgct   1140
ggtggacggg cgctgtaagc acgtccccta ccgtgactcg aagctgacgc ggctgctgca   1200
ggactcactg ggcggcaaca ccaagacgct catggtggcc tgcctgtcgc ctgcggacaa   1260
caactacgat gagacactca gcacgctgcg ctacgccaac cgggccaaga acatcaggaa   1320
caagccgcgc atcaatgagg accccaagga tgcgctgctt cgcgagtacc aggaggagat   1380
caagaagctc aaggccatcc tgacacagca gatgagcccc agcagcctgt cagccctgct   1440
gtccaggcag gtgcccccag accctgtgca ggtggaggag aagctgttgc cccaacctgt   1500
gatccagcat gacatggagg ccgagaagca gctgatccgg gaggagtatg aagagcgcct   1560
ggcccggctg aaagccgact ataaggccga gcaggagtct cgggccaggc tggaggaaga   1620
catcactgcc atgcgcaact catatgacgt caggctgtcc acgctggagg agaacctgcg   1680
gaaggagaca gaggctgtcc tgcaggtggg agtcctctac aaggctgagg tcatgtccag   1740
ggctgagttt gccagcagcg ctgagtaccc gcctgctttt cagtatgaga cagtggtgaa   1800
acccaaggtc ttctccacga ctgacactct gcccagtgac gatgtctcca agactcaggt   1860
ttcctccagg tttgcggagc tgcccaaggt ggaaccctcc aaatctgaga tttctctggg   1920
ctccagtgag tcatcctcgc tcgaagaaac ctctgtgtcc gaggctttcc ctgggcctga   1980
ggagccctcc aacgtggagg tctccatgcc cactgaggag tccaggagca gatacttcct   2040
ggatgagtgc ctcgggcagg aggccgctgg gcacctgctg gggggaacaga actacctccc   2100
gcaagaggag ccgcaggagg tgcccctgca ggggttacta ggcctgcagg acccgtttgc   2160
cgaggtggaa gccaagctgg ccagactctc ctccaccgtg gccaggacag atgcacccca   2220
ggcagacgtc cccaaggtcc ctgtgcaggt ccctgcgccg acagacctgc tggagcccag   2280
tgatgccagg cccgaagccg aggcggctga tgacttcccg cccaggcctg aggtagatct   2340
ggcctcggaa gtggccttag aggtggtgcg gacagcagag cctggcgtgt ggttggaggc   2400
tcaggccccg gtggccctgg tggctcagcc tgagcccctg ccggccacag ctggtgtgaa   2460
gagggagagc gtgggcatgg aggtggcagt gctgactgat gacccgctgc ccgttgtgga   2520
ccagcagcag gtgctggccc gtctgcagct gttggagcag caggttgtgg gtggagagca   2580
ggccaagaac aaggacctga aggagaagca caagcggcgc aagcgctacg cagacgagcg   2640
caggaagcag ctggtggctg ccctgcagaa ctcggatgag gacagcgggg actgggtgct   2700
```

```
gcttaacgtc tacgactcca tccaggagga agtgcgggcc aagagcaagc tgctggagaa   2760
gatgcagagg aagcttcggg cagcagaggt ggagatcaaa gatctgcagt ccgagtttca   2820
gctggagaag atcgattact tggccaccat ccgccggcag gagcgtgact ccatgctctt   2880
gcagcagctc ctggagcagg tgcagcccct gattcgcagg gactgtaact acagcaacct   2940
ggagaagatt ctgcgtgagt cctgctggga cgaagataac ggcttctgga agatcccaca   3000
tcccgtcatc acaaaaacca gcctcccagt agcagtttca actgggccac agaacaaacc   3060
agcccgcaaa acctctgcag cagacaatgg cgagccgaac atggaggagg accgctacag   3120
gctcatgctc agtcggagca acagtgaaaa cattgccagc aactacttcc gatctaagtg   3180
ggccagccag atcctcagca cagacgccag gaagagcctc acacatcaca actcgccacc   3240
aggcctcagc tgcccactca gcaacaactc tgccatccca cccacccagg cccctgaaat   3300
gccccagccc cggcccttcc gcctcgagtc cctcgacatc cctttcacca aggccaagcg   3360
taagaaaagc aaaagcaact ttggcagtga gcctctgtga gcacagctgc ttgccattgc   3420
ctgccttata ggcatgtaga gactgccagg ccctcccagg gcagccccaa ccaggtctcc   3480
tcccacctgc cacacagcgc tccggggcct gagggctccc tcagccctgg gaagacacat   3540
tcccttccct gttccccaga gagcccacct ctgccctggg caggagcccc tcggaggctg   3600
tatagtcctc cttagagagg cctgctccag ctgttcatac cacatcagtg tttccgtctg   3660
ctcacctgcc acagagccca cacccatgcc caccagtgtt ggtctttgcc tcaaagcctg   3720
agacctgctt cacggccttc accagccctg atggagaggg cagcagctgc cacgtggagg   3780
aagctcaata tcagctggga aggaactgtg cctctgtctg actggcccca cttcctaagc   3840
actgccctgc cccatggggt ggcacagggg tcccacagca ggtcttcctg cactgcccac   3900
ccctggctgg tctgtggccc aaggaaggcc actccacatt aagctgccca ataaactgct   3960
tttaagat                                                            3968
```

<210> SEQ ID NO 62
<211> LENGTH: 3379
<212> TYPE: DNA
<213> ORGANISM: Human

<400> SEQUENCE: 62

```
ctggcctggg cctgaagtga gtgagaggca catgaagaga agtattcaag tatttataca     60
gataggaatc aagataatca acaatgtctg tcactgagga agacctgtgc caccatatga    120
aagtagtagt tcgtgtacgt ccggaaaaca ctaaagaaaa agcagctgga tttcataaag    180
tggttcatgt tgtggataaa catatcctag tttttgatcc caaacaagaa gaagtcagtt    240
ttttccatgg aaagaaaact acaaatcaaa atgttataaa gaaacaaaat aaggatctta    300
aatttgtatt tgatgctgtt tttgatgaaa cgtcaactca gtcagaagtt tttgaacaca    360
ctactaagcc aattcttcgt agttttttga atggatataa ttgcacagta cttgcctatg    420
gtgccactgg tgctgggaag acccacacta tgctaggatc agctgatgaa cctggagtga    480
tgtatctaac aatgttacac ctttacaaat gcatggatga gattaaagaa gagaaaatat    540
gtagtactgc agtttcatat ctggaggtat ataatgaaca gattcgtgat ctcttagtaa    600
attcagggcc acttgctgtc cgggaagata cccaaaaagg ggtggtcgtt catggactta    660
ctttacacca gcccaaatcc tcagaagaaa ttttacattt attggataat ggaaacaaaa    720
acaggacaca acatcccact gatatgaatg ccacatcttc tcgttctcat gctgttttcc    780
aaatttactt gcgacaacaa gacaaaacag caagtatcaa tcaaaatgtc cgtattgcca    840
```

```
agatgtcact cattgacctg gcaggatctg agcgagcaag tacttccggt gctaagggga    900
cccgatttgt agaaggcaca aatattaata gatcactttt agctcttggg aatgtcatca    960
atgccttagc agattcaaag agaaagaatc agcatatccc ttacagaaat agtaagctta   1020
ctcgcttgtt aaaggattct cttggaggaa actgtcaaac tataatgata gctgctgtta   1080
gtccttcctc tgtattctac gatgacacat ataacactct taagtatgct aaccgggcaa   1140
aggacattaa atcttctttg aagagcaatg ttcttaatgt caataatcat ataactcaat   1200
atgtaaagat ctgtaatgag cagaaggcag agattttatt gttaaaagaa aaactaaaag   1260
cctatgaaga acagaaagcc ttcactaatg aaaatgacca agcaaagtta atgatttcaa   1320
accctcagga aaaagaaatc gaaaggtttc aagaaatcct gaactgcttg ttccagaatc   1380
gagaagaaat tagacaagaa tatctgaagt tggaaatgtt acttaaagaa aatgaactta   1440
aatcattcta ccaacaacag tgccataaac aaatagaaat gatgtgttct gaagacaaag   1500
tagaaaaggc cactggaaaa cgagatcata gacttgcaat gttgaaaact cgtcgctcct   1560
acctggagaa aaggagggag gaggaattga agcaatttga tgagaatact aattggctcc   1620
atcgtgtcga aaaagaaatg ggactcttaa gtcaaaacgg tcatattcca aaggaactca   1680
agaaagatct tcattgtcac catttgcacc tccagaacaa agatttgaaa gcacaaatta   1740
gacatatgat ggatctagct tgtcttcagg aacagcaaca caggcagact gaagcagtat   1800
tgaatgcttt acttccaacc ctaagaaaac aatattgcac attaaaagaa gccggcctgt   1860
caaatgctgc ttttgaatct gacttcaaag agatcgaaca tttggtagag aggaaaaaag   1920
tggtagtttg ggctgaccaa actggcgaac aaccaaagca aaacgatcta cccgggattt   1980
ctgttcttat gacctttca caacttggac cagttcagcc tattccttgt tgctcatctt   2040
caggtggaac taatctggtt aagattccta cagaaaaaag aactcggaga aaactaatgc   2100
catctccctt gaaaggacag catactctaa agtctccacc atctcaaagt gtgcagctca   2160
atgattctct tagcaaagaa cttcagccta ttgtatatac accagaagac tgtagaaaag   2220
cttttcaaaa tccgtctaca gtaaccttaa tgaaaccatc atcatttact acaagttttc   2280
aggctatcag ctcaaacata aacagtgata attgtctgaa aatgttgtgt gaagtagcta   2340
tccctcataa tagaagaaaa gaatgtggac aggaggactt ggactctaca tttactatat   2400
gtgaagacat caagagctcg aagtgtaaat tacccgaaca agaatcacta ccaaatgata   2460
acaaagacat tttacaacgg cttgatcctt cttcattctc aactaagcat tctatgcctg   2520
taccaagcat ggtgccatcc tacatggcaa tgactactgc tgccaaaagg aaacggaaat   2580
taacaagttc tacatcaaac agttcgttaa ctgcagacgt aaattctgga tttgccaaac   2640
gtgttcgaca agataattca agtgagaagc acttacaaga aaacaaacca acaatggaac   2700
ataaaagaaa catctgtaaa ataaatccaa gcatggttag aaaatttgga agaaatattt   2760
caaaaggaaa tctaagataa atcacttcaa aaccaagcaa aatgaagttg atcaaatctg   2820
cttttcaaag tttatccaat accctttcaa aaatatattt aaaatctttg aaagaagacc   2880
catcttaaag ctaagtttac ccaagtactt tcagcaagca gaaaaatgaa actctttgtt   2940
ttcttctttt gtgttctaaa aaaataaaat ttcaaaagaa aaggttgtct tttaagtttt   3000
ttaaatattt gttgcctttt aaaatccctg agtgtaagtt accatggtgg cagcttagtt   3060
ttactatgcc acaacaagtt gactaggaca ttttagtaaa tggtagtgag ttaaattatc   3120
tttattattt tttaaaaata agaatttaga agtggtaaaa ttatggccca agatgtattt   3180
ggttctctat tatgttttga tacattattt taatcatata tatgactttc cttttcaaaa   3240
```

atactttaat gtacaagtgt aaatatatgt gcccataaaa tcattgtaaa tattatttag 3300
tcatcacaaa taaaatattg tcccttgcta cttgatatat taaagatgta gattttaaag 3360
tgaaaaaaaa aaaaaaaaa 3379

<210> SEQ ID NO 63
<211> LENGTH: 2095
<212> TYPE: DNA
<213> ORGANISM: Human

<400> SEQUENCE: 63
agctagcagc tggcggacgc gacccggagg cggtgggggt gcggctgagc catgcccggt 60
ggcgcggcct gagcccctcc acctgctgca atcatgaagg acagcgggga ctccaaggac 120
cagcaactca tggtggcgct tcgggtccgg cccatcagcg tggcagagct ggaggaagga 180
gctaccctca tcgcccataa agtggatgag cagatggtgg ttctcatgga cccaatggag 240
gatcccgacg acatcctgcg ggcgcatcgc tcccgggaga agtcctacct gttcgacgtg 300
gcctttgact tcaccgccac ccaggagatg gtgtatcagg ccaccaccaa gagcctcatc 360
gagggcgtca tctcaggcta caatgccact gtctttgcct atggccccac aggctgtggg 420
aaaacctaca ccatgctggg cacagaccag gagcctggca tctatgttca gaccctcaac 480
gacctcttcc gtgccatcga ggagaccagc aatgacatgg agtatgaggt ctccatgtcc 540
tacctggaga tctacaatga gatgatccgg gacctgctga acccctccct gggctacctg 600
gagctgcggg aggactctaa gggggtgatc caggtggccg gcatcaccga agtctccacc 660
atcaatgcca aggagatcat gcagctgctg atgaagggga accggcagag gacccaggag 720
cccacggccg ccaaccagac gtcctcccgc tcccacgcgg tactgcaggt gaccgtgcgc 780
cagcgcagcc gggtcaagaa catcttgcag gaggtgcggc agggccgcct gttcatgatc 840
gacctggctg gctcagagcg cgcctcgcag acacagaatc gtgggcagcg tatgaaggag 900
ggggcccaca tcaaccgctc actgctggca ctgggcaact gcatcaacgc cctgagcgac 960
aagggtagca acaagtacat caactatcgc gacagcaagc tcacccggct cctgaaggac 1020
tctctgggag gaaacagccg cacagtgatg atcgctcaca tcagtcctgc gagcagtgcc 1080
ttcgaggagt cccggaacac cctgacctac gccggccggg ccaagaacat taagactagg 1140
gtgaagcaga acctcctgaa cgtctcctac cacatcgccc agtacaccag catcatcgct 1200
gacctgcggg gcgagatcca gcgactcaag cgcaagattg atgagcagac tgggcggggc 1260
caggcccggg gccggcagga tcggggtgac atccgccaca tccaagctga ggtccagctg 1320
cacagcgggc agggtgagaa ggctggcatg ggacagcttc gggagcagct cgccagcgcc 1380
ttccaggagc agatggatgt gcggaggcgc ctgctggagc tggagaaccg cgccatggag 1440
gtccagattg acacctcccg acacctgctc accatcgccg gctggaagca cgagaagtcc 1500
cgctgggccc tcaaatggcg ggaggagcag cgaaaggagt gctacgctaa ggacgacagc 1560
gagaaggact cagacacagg tgatgaccaa ccagacatcc tggagccacc cgaggtggcc 1620
gcagcccggg agagcattgc agccctggtg gacgagcaga agcaactgcg caagcagaag 1680
gtgtccaggg tttgggggga caaggagagt gggtttaggg gacagggtga gcaggtttga 1740
gaggcaaggc ggaggggcca gggtgggggt agccgtgaga cttgggaact caggccacaa 1800
atcctgtgtg actttgctaa gctctttaac ttctctatgc gtcacattcc ccacctgtaa 1860
aatgggagca gtccatggtg cagccctcat ggggttgctg ggaagattac ataaatgcct 1920
ggcacatacc aaggactcaa aaaatggtaa ctaatgttat aattagggtt tttcaggctg 1980

-continued ggcacagtga ctcacacctg taatctcagc acgttgggaa gttgaggtag gcagatcact 2040
tgaggccagg agttcgagac cagcctggcc aacatggcga aatcccgtct ttacc 2095

<210> SEQ ID NO 64
<211> LENGTH: 2972
<212> TYPE: DNA
<213> ORGANISM: Human

<400> SEQUENCE: 64
tcttcggacc taggctgccc tgccgtcatg tcgcaaggga tcctttctcc gccagcgggc 60
ttgctgtccg atgacgatgt cgtagtttct cccatgtttg agtccacagc tgcagatttg 120
gggtctgtgg tacgcaagaa cctgctatca gactgctctg tcgtctctac ctccctagag 180
gacaagcagc aggttccatc tgaggacagt atggagaagg tgaaagtata cttgagggtt 240
aggcccttgt taccttcaga gttggaacga caggaagatc agggttgtgt ccgtattgag 300
aatgtggaga cccttgttct acaagcaccc aaggactcgt ttgccctgaa gagcaatgaa 360
cggggaattg gccaagccac acacaggttc accttttccc agatctttgg gccagaagtg 420
ggacaggcat ccttcttcaa cctaactgtg aaggagatgg taaaggatgt actcaaaggg 480
cagaactggc tcatctatac atatggagtc actaactcag ggaaaaccca cacgattcaa 540
ggtaccatca aggatggagg gattctcccc cggtccctgg cgctgatctt caatagcctc 600
caaggccaac ttcatccaac acctgatctg aagcccttgc tctccaatga ggtaatctgg 660
ctagacagca agcagatccg acaggaggaa atgaagaagc tgtccctgct aaatggaggc 720
ctccaagagg aggagctgtc cacttccttg aagaggagtg tctacatcga aagtcggata 780
ggtaccagca ccagcttcga cagtggcatt gctgggctct cttctatcag tcagtgtacc 840
agcagtagcc agctggatga aacaagtcat cgatgggcac agccagacac tgccccacta 900
cctgtcccgg caaacattcg cttctccatc tggatctcat tctttgagat ctacaacgaa 960
ctgctttatg acctattaga accgcctagc caacagcgca agaggcagac tttgcggcta 1020
tgcgaggatc aaaatggcaa tccctatgtg aaagatctca actggattca tgtgcaagat 1080
gctgaggagg cctggaagct cctaaaagtg ggtcgtaaga accagagctt tgccagcacc 1140
cacctcaacc agaactccag ccgcagtcac agcatcttct caatcaggat cctacacctt 1200 caggggggaag gagatatagt ccccaagatc agcgagctgt cactctgtga tctggctggc 1260
tcagagcgct gcaaagatca gaagagtggt gaacggttga aggaagcagg aaacattaac 1320
acctctctac acaccctggg ccgctgtatt gctgcccttc gtcaaaacca gcagaaccgg 1380
tcaaagcaga acctggttcc cttccgtgac agcaagttga ctcgagtgtt ccaaggtttc 1440
ttcacaggcc gaggccgttc ctgcatgatt gtcaatgtga atccctgtgc atctacctat 1500
gatgaaactc ttcatgtggc caagttctca gccattgcta gccagcttgt gcatgcccca 1560
cctatgcaac tgggattccc atccctgcac tcgttcatca aggaacatag tcttcaggta 1620
tcccccagct tagagaaagg ggctaaggca gacacaggcc ttgatgatga tattgaaaat 1680
gaagctgaca tctccatgta tggcaaagag gagctcctac aagttgtgga agccatgaag 1740
acactgcttt tgaaggaacg acaggaaaag ctacagctgg agatgcatct ccgagatgaa 1800
atttgcaatg agatggtaga acagatgcaa cagcgggaac agtggtgcag tgaacatttg 1860
gacacccaaa aggaactatt ggaggaaatg tatgaagaaa aactaaatat cctcaaggag 1920
tcactgacaa gtttttacca agaagagatt caggagcggg atgaaaagat tgaagagcta 1980
gaagctctct tgcaggaagc cagacaacag tcagtggccc atcagcaatc agggtctgaa 2040

```
ttggccctac ggcggtcaca aaggttggca gcttctgcct ccacccagca gcttcaggag   2100
gttaaagcta aattacagca gtgcaaagca gagctaaact ctaccactga agagttgcat   2160
aagtatcaga aaatgttaga accaccaccc tcagccaagc ccttcaccat tgatgtggac   2220
aagaagttag aagagggcca gaagaatata aggctgttgc ggacagagct tcagaaactt   2280
ggtgagtctc tccaatcagc agagagagct tgttgccaca gcactggggc aggaaaactt   2340
cgtcaagcct tgaccacttg tgatgacatc ttaatcaaac aggaccagac tctggctgaa   2400
ctgcagaaca acatggtgct agtgaaactg gaccttcgga agaaggcagc atgtattgct   2460
gagcagtatc atactgtgtt gaaactccaa ggccaggttt ctgccaaaaa gcgccttggt   2520
accaaccagg aaaatcagca accaaaccaa caaccaccag ggaagaaacc attccttcga   2580
aatttacttc cccgaacacc aacctgccaa agctcaacag actgcagccc ttatgcccgg   2640
atcctacgct cacggcgttc ccctttactc aaatctgggc cttttggcaa aaagtactaa   2700
ggctgtgggg aaagagaaga gcagtcatgg ccctgaggtg ggtcagctac tctcctgaag   2760
aaataggtct cttttatgct ttaccatata tcaggaatta tatccaggat gcaatactca   2820
gacactagct tttttctcac ttttgtatta taaccaccta tgtaatctca tgttgttgtt   2880
ttttttttatt tacttatatg atttctatgc acacaaaaac agttatatta aagatattat   2940
tgttcacatt ttttattgaa aaaaaaaaaa aa                                 2972
```

<210> SEQ ID NO 65
<211> LENGTH: 6319
<212> TYPE: DNA
<213> ORGANISM: Human

<400> SEQUENCE: 65

```
attgtttgaa tttgaaaacg gtaacatcgc agtgctgctc gcgggtctgg ctagtcaggc     60
gaagtttgca gaatggaatc taattttaat caagagggag tacctcgacc atcttatgtt    120
tttagtgctg acccaattgc aaggccttca gaaataaatt tcgatggcat taagcttgat    180
ctgtctcatg aattttcctt agttgctcca aatactgagg caaacagttt cgaatctaaa    240
gattatctcc aggtttgtct tcgaataaga ccatttacac agtcagaaaa agaacttgag    300
tctgagggct gtgtgcatat tctggattca cagactgttg tgctgaaaga gcctcaatgc    360
atccttggtc ggttaagtga aaaaagctca gggcagatgg cacagaaatt cagtttttcc    420
aaggtttttg gcccagcaac tacacagaag gaattctttc agggttgcat tatgcaacca    480
gtaaaagacc tcttgaaagg acagagtcgt ctgattttta cttacgggct aaccaattca    540
ggaaaaacat atacatttca agggacagaa gaaaatattg gcattctgcc tcgaactttg    600
aatgtattat ttgatagtct tcaagaaaga ctgtatacaa agatgaacct taaaccacat    660
agatccagag aatacttaag gttatcatca gaacaagaga aagaagaaat tgctagcaaa    720
agtgcattgc ttcggcaaat taaagaggtt actgtgcata atgatagtga tgatactctt    780
tatggaagtt taactaactc tttgaatatc tcagagtttg aagaatccat aaaagattat    840
gaacaagcca acttgaatat ggctaatagt ataaaaattt ctgtgtgggt ttctttcttt    900
gaaatttaca atgaatatat ttatgactta tttgttcctg tatcatctaa attccaaaag    960
agaaagatgc tgcgcctttc ccaagacgta aagggctatt cttttataaa agatctacaa   1020
tggattcaag tatctgattc caaagaagcc tatagacttt taaaactagg aataaagcac   1080
cagagtgttg ccttcacaaa attgaataat gcttccagta gaagtcacag catattcact   1140
gttaaaatat tacagattga agattctgaa atgtctcgtg taattcgagt cagtgaatta   1200
```

```
tctttatgtg atcttgctgg ttcagaacga actatgaaga cacagaatga aggtgaaagg   1260
ttaagagaga ctgggaatat caacacttct ttattgactc tgggaaagtg tattaacgtc   1320
ttgaagaata gtgaaaagtc aaagtttcaa cagcatgtgc ctttccggga aagtaaactg   1380
actcactatt ttcaaagttt ttttaatggt aaagggaaaa tttgtatgat tgtcaatatc   1440
agccaatgtt atttagccta tgatgaaaca ctcaatgtat tgaagttctc cgccattgca   1500
caaaaagttt gtgtcccaga cactttaaat tcctctcaag agaaattatt tggacctgtc   1560
aaatcttctc aagatgtatc actagacagt aattcaaaca gtaaaatatt aaatgtaaaa   1620
agagccacca tttcatggga aaatagtcta gaagatttga tggaagacga ggatttggtt   1680
gaggagctag aaaacgctga agaaactcaa aatgtggaaa ctaaacttct tgatgaagat   1740
ctagataaaa cattagagga aaataaggct ttcattagcc acgaggagaa aagaaaactg   1800
ttggacttaa tagaagactt gaaaaaaaaa ctgataaatg aaaaaaagga aaaattaacc   1860
ttggaattta aaattcgaga agaagttaca caggagttta ctcagtattg ggctcaacgg   1920
gaagctgact ttaaggagac tctgcttcaa gaacgagaga tattagaaga aaatgctgaa   1980
cgtcgtttgg ctatcttcaa ggatttggtt ggtaaatgtg acactcgaga agaagcagcg   2040
aaagacattt gtgccacaaa agttgaaact gaagaagcta ctgcttgttt agaactaaag   2100
tttaatcaaa ttaaagctga attagctaaa accaaaggag aattaatcaa aaccaaagaa   2160
gagttaaaaa agagagaaaa tgaatcagat tcattgattc aagagcttga gacatctaat   2220
aagaaaataa ttacacagaa tcaaagaatt aaagaattga taaatataat tgatcaaaaa   2280
gaagatacta tcaacgaatt tcagaaccta aagtctcata tggaaaacac atttaaatgc   2340
aatgacaagg ctgatacatc ttctttaata ataaacaata aattgatttg taatgaaaca   2400
gttgaagtac ctaaggacag caaatctaaa atctgttcag aaagaaaaag agtaaatgaa   2460
aatgaacttc agcaagatga accaccagca aagaaagggt ctatccatgt tagttcagct   2520
atcactgaag accaaaagaa aagtgaagaa gtgcgaccga acattgcaga aattgaagac   2580
atcagagttt tacaagaaaa taatgaagga ctgagagcat ttttactcac tattgagaat   2640
gaacttaaaa atgaaaagga agaaaaagca gaattaaata aacagattgt tcattttcag   2700
caggaacttt ctctttctga aaaaaagaat ttaactttaa gtaaagaggt ccaacaaatt   2760
cagtcaaatt atgatattgc aattgctgaa ttacatgtgc agaaaagtaa aaatcaagaa   2820
caggaggaaa agatcatgaa attgtcaaat gagatagaaa ctgctacaag aagcattaca   2880
aataatgttt cacaaataaa attaatgcac acgaaaatag acgaactacg tactcttgat   2940
tcagtttctc agatttcaaa catagatttg ctcaatctca gggatctgtc aaatggttct   3000
gaggaggata atttgccaaa tacacagtta gaccttttag gtaatgatta tttggtaagt   3060
aagcaagtta aagaatatcg aattcaagaa cccaataggg aaaattcttt ccactctagt   3120
attgaagcta tttgggaaga atgtaaagag attgtgaagg cctcttccaa aaaaagtcat   3180
cagattgagg aactggaaca acaaattgaa aaattgcagg cagaagtaaa aggctataag   3240
gatgaaaaca atagactaaa ggagaaggag cataaaaacc aagatgacct actaaaagaa   3300
aaagaaactc ttatacagca gctgaaagaa gaattgcaag aaaaaaatgt tactcttgat   3360
gttcaaatac agcatgtagt tgaaggaaag agagcgcttt cagaacttac acaaggtgtt   3420
acttgctata aggcaaaaat aaaggaactt gaaacaattt tagagactca gaaagttgaa   3480
tgtagtcatt cagccaagtt agaacaagac attttggaaa aggaatctat catcttaaag   3540
ctagaaagaa atttgaagga atttcaagaa catcttcagg attctgtcaa aaacaccaaa   3600
```

-continued

```
gatttaaatg taaaggaact caagctgaaa gaagaaatca cacagttaac aaataatttg   3660
caagatatga aacatttact tcaattaaaa gaagaagaag aagaaaccaa caggcaagaa   3720
acagaaaaat tgaaagagga actctctgca agctctgctc gtacccagaa tctgaaagca   3780
gatcttcaga ggaaggaaga agattatgct gacctgaaag agaaactgac tgatgccaaa   3840
aagcagatta agcaagtaca gaaagaggta tctgtaatgc gtgatgagga taaattactg   3900
aggattaaaa ttaatgaact ggagaaaaag aaaaaccagt gttctcagga attagatatg   3960
aaacagcgaa ccattcagca actcaaggag cagttaaata atcagaaagt ggaagaagct   4020
atacaacagt atgagagagc atgcaaagat ctaaatgtta aagagaaaat aattgaagac   4080
atgcgaatga cactagaaga acaggaacaa actcaggtag aacaggatca agtgcttgag   4140
gctaaattag aggaagttga aaggctggcc acagaattgg aaaaatggaa ggaaaaatgc   4200
aatgatttgg aaaccaaaaa caatcaaagg tcaaataaag aacatgagaa caacacagat   4260
gtgcttggaa agctcactaa tcttcaagat gagttacagg agtctgaaca gaaatataat   4320
gctgatagaa agaaatggtt agaagaaaaa atgatgctta tcactcaagc gaaagaagca   4380
gagaatatac gaaataaaga gatgaaaaaa tatgctgagg acagggagcg ttttttttaag   4440
caacagaatg aaatggaaat actgacagcc cagctgacag agaaagatag tgaccttcaa   4500
aagtggcgag aagaacgaga tcaactggtt gcagctttag aaatacagct aaaagcactg   4560
atatccagta atgtacagaa agataatgaa attgaacaac taaaaaggat catatcagag   4620
acttctaaaa tagaaacaca aatcatggat atcaagccca aacgtattag ttcagcagat   4680
cctgacaaac ttcaaactga acctctatcg acaagttttg aaatttccag aaataaaata   4740
gaggatggat ctgtagtcct tgactcttgt gaagtgtcaa cagaaaatga tcaaagcact   4800
cgatttccaa aacctgagtt agagattcaa tttacacctt tacagccaaa caaaatggca   4860
gtgaaacacc ctggttgtac cacaccagtg acagttaaga ttcccaaggc tcggaagagg   4920
aagagtaatg aaatggagga ggacttggtg aaatgtgaaa ataagaagaa tgctacaccc   4980
agaactaatt tgaaatttcc tatttcagat gatagaaatt cttctgtcaa aaaggaacaa   5040
aaggttgcca tacgtccatc atctaagaaa acatattctt tacggagtca ggcatccata   5100
attggtgtaa acctggccac taagaaaaaa gaaggaacac tacagaaatt tggagacttc   5160
ttacaacatt ctccctcaat tcttcaatca aaagcaaaga agataattga aacaatgagc   5220
tcttcaaagc tctcaaatgt agaagcaagt aaagaaaatg tgtctcaacc aaaacgagcc   5280
aaacggaaat tatacacaag tgaaatttca tctcctattg atatatcagg ccaagtgatt   5340
ttaatggacc agaaaatgaa ggagagtgat caccagatta tcaaacgacg acttcgaaca   5400
aaaacagcca aataaatcac ttatggaaat gtttaatata aattttatag tcatagtcat   5460
tggaacttgc atcctgtatt gtaaatataa atgtatatat tatgcattaa atcactctgc   5520
atatagattg ctgttttata catagtataa ttttaattca ataaatgagt caaaatttgt   5580
atatttttat aaggcttttt tataatagct tctttcaaac tgtatttccc tattatctca   5640
gacattggat cagtgaagat cctaggaaag aggctgttat tctcatttat tttgctatac   5700
aggatgtaat aggtcaggta tttggtttac ttatatttaa caatgtctta tgaatttttt   5760
ttactttatc tgttatacaa ctgattttac atatctgttt ggattatagc taggatttgg   5820
agaataagtg tgtacagatc acaaaacatg tatatacatt atttagaaaa gatctcaagt   5880
ctttaattag aatgtctcac ttattttgta aacattttgt gggtacatag tacatgtata   5940
tatttacggg gtatgtgaga tgttttgaca caggcatgca atgtgaaata cgtgtatcat   6000
```

```
ggagaatgag gtatccatcc cctcaagcat ttttcctttg aattacagat aatccaatta   6060

cattctttag atcatttaaa aatatacaag taagttatta ttgattatag tcactctatt   6120

gtgctatcag atagtagatc attcttttta tcttatttgt ttttgtaccc attaaccatc   6180

cccacctccc cctgcaaccg tcagtaccct taccagccac tggtaaccat tcttctactc   6240

tgtatgccca tgaggtcaat tgattttatt tttagatccc ataaataaat gagaacatgc   6300

agtctttgtc aaaaaaaaa                                                6319
```

<210> SEQ ID NO 66
<211> LENGTH: 6335
<212> TYPE: DNA
<213> ORGANISM: Human

<400> SEQUENCE: 66

```
gcccaacatg gctggagcgc ggcggaggtg agccggccgc ccgcccgcag acgccccagc     60

ctactgcgcc cgagtcccgc ggccccagtg gcgcctcagc tctgcggtgc cgaggcccaa    120

cggctcgatc gctgcccgcc gccagcatgt tgggcgcccc ggacgagagc tccgtgcggg    180

tggctgtcag aataagacca cagcttgcca aagagaagat tgaaggatgc catatttgta    240

catctgtcac accaggagag cctcaggtct tcctagggaa agataaggct tttacttttg    300

actatgtatt tgacattgac tcccagcaag agcagatcta cattcaatgt atagaaaaac    360

taattgaagg ttgctttgaa ggatacaatg ctacagtttt tgcttatgga caaactggag    420

ctggtaaaac atacacaatg ggaacaggat ttgatgttaa cattgttgag gaagaactgg    480

gtattatttc tcgagctgtt aaacaccttt ttaagagtat tgaagaaaaa aaacacatag    540

caattaaaaa tgggcttcct gctccagatt ttaaagtgaa tgcccaattc ttagagctct    600

ataatgaaga ggtccttgac ttatttgata ccactcgtga tattgatgca aaaagtaaaa    660

aatcaaatat aagaattcat gaagattcaa ctggaggaat ttatactgtg ggcgttacaa    720

cacgtactgt gaatacagaa tcagagatga tgcagtgttt gaagttgggt gctttatccc    780

ggacaactgc cagtacccag atgaatgttc agagctctcg ttcacatgcc atttttacca    840

ttcatgtgtg tcaaaccaga gtgtgtcccc aaatagatgc tgacaatgca actgataata    900

aaattatttc tgaatcagca cagatgaatg aatttgaaac cctgactgca aagttccatt    960

ttgttgatct cgcaggatct gaaagactga agcgtactgg agctacaggc gagagggcaa   1020

aagaaggcat ttctatcaac tgtggacttt tggcacttgg caatgtaata agtgccttgg   1080

gagacaagag caagagggcc acacatgtcc cctatagaga ttccaagcta acaagactac   1140

tacaggattc cctcgggggt aatagccaaa caatcatgat agcatgtgtc agcccttcag   1200

acagagactt tatggaaacg ttaaacaccc tgaaatacgc caatcgagct agaaatatca   1260

agaataaggt gatggtcaat caggacagag ctagtcagca aatcaatgca cttcgtagtg   1320

aaatcacacg acttcagatg gagctcatgg agtacaaaac aggtaaaaga ataattgacg   1380

aagagggtgt ggaaagcatc aatgacatgt ttcatgagaa tgctatgcta cagactgaaa   1440

ataataacct gcgtgtaaga attaaagcca tgcaagagac ggttgatgca ttgaggtcca   1500

gaattacaca gcttgttagt gatcaggcca accatgttct tgccagagca ggtgaaggaa   1560

atgaggagat tagtaatatg attcatagtt atataaaaga aatcgaagat ctcagggcaa   1620

aattattaga aagtgaagca gtgaatgaga accttcgaaa aaacttgaca agagccacag   1680

caagagcgcc atatttcagc ggatcatcaa ctttttctcc taccatacta tcctcagaca   1740

aagaaaccat tgaaattata gacctagcaa aaaaagattt agagaagttg aaaagaaaag   1800
```

```
aaaagaggaa gaaaaaaagt gtggctggta aagaggataa tacagacact gaccaagaga   1860
agaaagaaga aaagggtgtt tcggaaagag aaaacaatga attagaagtg gaagaaagtc   1920
aagaagtgag tgatcatgag gatgaagaag aggaggagga ggaggaggaa gatgacattg   1980
atgggggtga aagttctgat gaatcagatt ctgaatcaga tgaaaaagcc aattatcaag   2040
cagacttggc aaacattact tgtgaaattg caattaagca aaagctgatt gatgaactag   2100
aaaacagcca gaaaagactg cagactctga aaaagcagta tgaagagaag ctaatgatgc   2160
tgcaacataa aattcgggat actcagcttg aaagagacca ggtgcttcaa aacttaggct   2220
cggtagaatc ttactcagaa gaaaaagcaa aaaaagttag gtctgaatat gaaaagaaac   2280
tccaagccat gaacaaagaa ctgcagagac ttcaagcagc tcaaaaagaa catgcaaggt   2340
tgcttaaaaa tcagtctcag tatgaaaagc aattgaagaa attgcagcag gatgtgatgg   2400
aaatgaaaaa aacaaaggtt cgcctaatga aacaaatgaa agaagaacaa gagaaagcca   2460
gactgactga gtctagaaga aacagagaga ttgctcagtt gaaaaaggat caacgtaaaa   2520
gagatcatca acttagactt ctggaagccc aaaaaagaaa ccaagaagtg gttctacgtc   2580
gcaaaactga agaggttacg gctcttcgtc ggcaagtaag acccatgtca gataaagtgg   2640
ctgggaaagt tactcggaag ctgagttcat ctgatgcacc tgctcaggac acaggttcca   2700
gtgcagctgc tgtcgaaaca gatgcatcaa ggacaggagc ccagcagaaa atgagaattc   2760
ctgtggcgag agtccaggcc ttaccaacgc cggcaacaaa tggaaacagg aaaaaatatc   2820
agaggaaagg attgactggc cgagtgttta tttccaagac agctcgcatg aagtggcagc   2880
tccttgagcg cagggtcaca gacatcatca tgcagaagat gaccatttcc aacatggagg   2940
cagatatgaa tagactcctc aagcaacggg aggaactcac aaaaagacga gagaaacttt   3000
caaaaagaag ggagaagata gtcaaggaga atggagaggg agataaaaat gtggctaata   3060
tcaatgaaga gatggagtca ctgactgcta atatcgatta catcaatgac agtatttctg   3120
attgtcaggc caacataatg cagatggaag aagcaaagga agaaggtgag acattggatg   3180
ttactgcagt cattaatgcc tgcaccctta cagaagcccg atacctgcta gatcacttcc   3240
tgtcaatggg catcaataag ggtcttcagg ctgcccagaa agaggctcaa attaaagtac   3300
tggaaggtcg actcaaacaa acagaaataa ccagtgctac ccaaaaccag ctcttattcc   3360
atatgttgaa agagaaggca gaattaaatc ctgagctaga tgctttacta ggccatgctt   3420
tacaagatct agatagcgta ccattagaaa atgtagagga tagtactgat gaggatgctc   3480
ctttaaacag cccaggatca gaaggaagca cgctgtcttc agatctcatg aagctttgtg   3540
gtgaagtgaa acctaagaac aaggcccgaa ggagaaccac cactcagatg gaattgctgt   3600
atgcagatag cagtgaacta gcttcagaca ctagtacagg agatgcctcc ttgcctggcc   3660
ctctcacacc tgttgcagaa gggcaagaga ttggaatgaa tacagagaca agtggtactt   3720
ctgctaggga aaaagagctc tctcccccac ctggcttacc ttctaagata ggcagcattt   3780
ccaggcagtc atctctatca gaaaaaaaaa ttccagagcc ttctcctgta acaaggagaa   3840
aggcatatga gaaagcagaa aaatcaaagg ccaaggaaca aaagcactca gattctggaa   3900
cttcagaggc tagtctttca cctccttctt ccccaccaag ccggccccgt aatgaactga   3960
atgtttttaa tcgtcttact gtttctcagg gaaacacatc agttcagcag gataagtctg   4020
atgaaagtga ctcctctctc tcggaggtac acagatcctc cagaaggggc ataatcaacc   4080
catttcctgc ttcaaaagga atcagagctt ttccacttca gtgtattcac atagctgaag   4140
ggcatacaaa agctgtgctc tgtgtggatt ctactgatga tctcctcttc actggatcaa   4200
```

```
aagatcgtac ttgtaaagta tggaatctgg tgactgggca ggaaataatg tcactggggg   4260
gtcatcccaa caatgtcgtg tctgtaaaat actgtaatta taccagtttg gtcttcactg   4320
tatcaacatc ttatattaag gtgtgggata tcagagattc agcaaagtgc attcgaacac   4380
taacgtcttc aggtcaagtt actcttggag atgcttgttc tgcaagtacc agtcgaacag   4440
tagctattcc ttctggagag aaccagatca atcaaattgc cctaaaccca actggcacct   4500
tcctctatgc tgcttctgga aatgctgtca ggatgtggga tcttaaaagg tttcagtcta   4560
caggaaagtt aacaggacac ctaggccctg ttatgtgcct tactgtggat cagatttcca   4620
gtggacaaga tctaatcatc actggctcca aggatcatta catcaaaatg tttgatgtta   4680
cagaaggagc tcttgggact gtgagtccca cccacaattt tgaacccct cattatgatg    4740
gcatagaagc actaaccatt caaggggata acctatttag tgggtctaga gataatggaa   4800
tcaagaaatg ggacttaact caaaaagacc ttcttcagca agttccaaat gcacataagg   4860
attgggtctg tgccctggga gtggtgccag accacccagt tttgctcagt ggctgcagag   4920
ggggcatttt gaaagtctgg aacatggata cttttatgcc agtgggagag atgaagggtc   4980
atgatagtcc tatcaatgcc atatgtgtta attccaccca catttttact gcagctgatg   5040
atcgaactgt gagaatttgg aaggctcgca atttgcaaga tggtcagatc tctgacacag   5100
gagatctggg ggaagatatt gccagtaatt aaacatgaat gaagataggt tgtaaactga   5160
atgctgtgat aatactctgt attctttatg gaaaatgttg tcctgtactt actaggcaaa   5220
acgtatgaat cggattaact ggaaaatata tctgaattca actgctgact ataaatggta   5280
ttctaataaa attgtgtact atcctgtgtg cttagtttta agatcaacca atagatatat   5340
atcctacaat tgatatattg ctttattcac acttttattg tggctgaatt tttgtgccta   5400
tctataaaac acactttcaa attatttgaa ttaccaagac gtctgctttt gtgacagtca   5460
gaaaacacac ctggaatacg atgcagccca ccattaactc attcatgtag tttattcaag   5520
tgatttatgt atttaaacta aatattgaaa atgttagtca aattgtggtt tgcttgtcag   5580
gtatttatat cagtctgtag tggattccca aatttcaaag ctcttttaat gtaatggaca   5640
aaaataagat atgagaatat tattgatgaa ttttcataag gtggaattga tcttaatcta   5700
ctaacagaga agggtagaca gtttgtgtta aatgttggca tttacttgta ttgaccaaag   5760
ttttgcagct ctactatatt ctgtgctcag gactaaaatg ctgttaattt ttttttttt    5820
ttccagtgct gtgcatatat tctgtgatgg gaaacattgt tgatgtccta acagaaatat   5880
attttgatct attttcctat ggagttgttt ctattatgac catttaattt tgtttttatt   5940
taatagtagt atttccttcc cttttatcta atttttttata tgctgctaaa tatattttaa  6000
atatactatg tttgcgaacc ttggtagcta tgatgagagc tattatcatc tgtggtggga   6060
aaagctatgt aaataggtag attgtataga gagactatct tgtgttgtgc ctgtatgaat   6120
ttttaaaagt tgttgactgg attttgcaaa aggatgtata atatttctgt ctgctcagaa   6180
tattaatttg taaattctgc aagtttaatt tttatgtaga tggtataaca tttgaaaata   6240
ttgtcttatg tgatttttc ccctgaaaat atttgcttgt aaatgaaaac ttagctaggg    6300
cttaaataaa catgttgcta tgaaattaaa aaaaa                              6335
```

<210> SEQ ID NO 67
<211> LENGTH: 2097
<212> TYPE: DNA
<213> ORGANISM: Human

<400> SEQUENCE: 67

```
gggcgggccc aaggagggag tggaatggcc gcgggcggct cgacgcagca gaggcgacgc      60

gagatggcgg cagcttcagc ggcggcgatc tcaggagctg gtcgctgtcg gctaagcaag     120

attggagcta ctcgtcgtcc acctccagct cgcgtaaggg tggctgtgcg actgcggcca     180

tttgtggatg gaacagcggg agcaagtgat ccccctgtg tgcggggcat ggacagctgc      240

tctctagaga ttgctaactg gaggaaccac caggagactc tcaaatacca gtttgatgcc     300

ttctatgggg agaggagtac tcagcaggac atctatgcag gttcagtgca gcccatccta     360

aggcacttgc tggaagggca gaatgccagt gtgcttgcct atggacccac aggagctggg     420

aagacgcaca caatgctggg cagcccagag caacctgggg tgatcccgcg ggctctcatg     480

gacctcctgc agctcacaag ggaggagggt gccgagggcc ggccatgggc cctttctgtc     540

accatgtctt acctagagat ctaccaggag aaggtattag acctcctgga ccctgcttcg     600

ggagacctgg taatccgaga agactgccgg gggaatatcc tgattccggg tctctcccag     660

aagcccatca gtagctttgc tgattttgag cggcacttcc tgccagccag tcgaaatcgg     720

actgtaggag ccacccggct caaccagcgc tcctcccgca gtcatgctgt gctcctggtc     780

aaggtggacc agcgggaacg tttggcccca tttcgccagc gagagggaaa actctacctg     840

attgacttgg ctgggtcaga ggacaaccgg cgcacaggca acaagggcct tcggctaaaa     900

gagagtggag ccatcaacac ctccctgttt gtcctgggca aagtggtaga tgcgctgaat     960

cagggcctcc ctcgtgtacc ttatcgggac agcaagctca ctcgcctatt gcaggactct    1020

ctgggtggct cagcccacag tatccttatt gccaacattg cccctgagag acgcttctac    1080

ctagacacag tctccgcact caactttgct gccaggtcca aggaggtgat caatcggcct    1140

tttaccaatg agagcctgca gcctcatgcc ttgggacctg ttaagctgtc tcagaaagaa    1200

ttgcttggtc caccagaggc aaagagagcc cgaggccctg aggaagagga gattgggagc    1260

cctgagccca tggcagctcc agcctctgcc tcccagaaac tcagcccct acagaagcta    1320

agcagcatgg acccggccat gctggagcgc ctcctcagct tggaccgtct gcttgcctcc    1380

caggggagcc agggggcccc tctgttgagt accccaaagc gagagcggat ggtgctaatg    1440

aagacagtag aagagaagga cctagagatt gagaggctta agacgaagca aaaagaactg    1500

gaggccaaga tgttggccca gaaggctgag gaaaaggaga accattgtcc cacaatgctc    1560

cggcccccttt cacatcgcac agtcacaggg gcaaagcccc tgaaaaaggc tgtggtgatg    1620

cccctacagc taattcagga gcaggcagca tccccaaatg ccgagatcca catcctgaag    1680

aataaaggcc ggaagagaaa gctggagtcc ctggatgccc tagagcctga ggagaaggct    1740

gaggactgct gggagctaca gatcagcccg gagctactgg ctcatgggcg ccaaaaaata    1800

ctggatctgc tgaacgaagg ctcagcccga gatctccgca gtcttcagcg cattggcccg    1860

aagaaggccc agctaatcgt gggctggcgg gagctccacg gcccttcag ccaggtggag     1920

gacctggaac gcgtggaggg cataacgggg aaacagatgg agtccttcct gaaggcaaac    1980

atcctgggtc tcgccgccgg ccagcgctgt ggcgcctcct gaccgtcgtc tcctcactcc    2040

gccttttcaa atttttgtat aaccccgtgt tgtgtaaata cagtttttgc tccggtg       2097
```

<210> SEQ ID NO 68
<211> LENGTH: 3324
<212> TYPE: DNA
<213> ORGANISM: Human

<400> SEQUENCE: 68

```
gcagagcacc gcgccttagc cgcgaagttc tagttcttgc tgccggtcct aacgtcccgc      60
```

-continued agtcttcgcc agccagccgt cccgcatgcg cgtttgggcg gcgtggagcc tgctgccatg 120
aagtcagcga gagctaagac accccggaaa cctaccgtga aaaaagggtc ccaaacgaac 180
cttaaagacc cagttggggt atactgtagg gtgcgcccac tgggctttcc tgatcaagag 240
tgttgcatag aagtgatcaa taatacaact gttcagcttc atactcctga gggctacaga 300
ctcaaccgaa atggagacta taaggagact cagtattcat ttaaacaagt atttggcact 360
cacaccaccc agaaggaact ctttgatgtt gtggctaatc ccttggtcaa tgacctcatt 420
catggcaaaa atggtcttct ttttacatat ggtgtgacgg gaagtggaaa aactcacaca 480
atgactggtt ctccagggga aggagggctg cttcctcgtt gtttggacat gatctttaac 540
agtatagggt catttcaagc taaacgatat gttttcaaat ctaatgatag gaatagtatg 600
gatatacagt gtgaggttga tgccttatta gaacgtcaga aaagagaagc tatgcccaat 660
ccaaagactt cttctagcaa acgacaagta gatccagagt ttgcagatat gataactgta 720
caagaattct gcaaagcaga agaggttgat gaagatagtg tctatggtgt atttgtctct 780
tatattgaaa tatataataa ttacatatat gatctattgg aagaggtgcc gtttgatccc 840
ataaaaccca aacctccaca atctaaattg cttcgtgaag ataagaacca taacatgtat 900
gttgcaggat gtacagaagt tgaagtgaaa tctactgagg aggcttttga agtttttctgg 960
agaggccaga aaaagagacg tattgctaat acccatttga atcgtgagtc cagccgttcc 1020
catagcgtgt tcaacattaa attagttcag gctcccttgg atgcagatgg agacaatgtc 1080
ttacaggaaa aagaacaaat cactataagt cagttgtcct tggtagatct tgctggaagt 1140
gaaagaacta accggaccag agcagaaggg aacagattac gtgaagctgg taatattaat 1200
cagtcactaa tgacgctaag aacatgtatg gatgtcctaa gagagaacca aatgtatgga 1260
actaacaaga tggttccata tcgagattca aagttaaccc atctgttcaa gaactacttt 1320
gatggggaag gaaaagtgcg gatgatcgtg tgtgtgaacc ccaaggctga agattatgaa 1380
gaaaacttgc aagtcatgag atttgcggaa gtgactcaag aagttgaagt agcaagacct 1440
gtagacaagg caatatgtgg tttaacgcct gggaggagat acagaaacca gcctcgaggt 1500
ccagttggaa atgaaccatt ggttactgac gtggttttgc agagttttcc acctttgccg 1560
tcatgcgaaa ttttggatat caacgatgag cagacacttc caaggctgat tgaagcctta 1620
gagaaacgac ataacttacg acaaatgatg attgatgagt ttaacaaaca atctaatgct 1680
tttaaagctt tgttacaaga atttgacaat gctgttttaa gtaaagaaaa ccacatgcaa 1740
gggaaactaa atgaaaagga gaagatgatc tcaggacaga aattggaaat agaacgactg 1800
gaaaagaaaa acaaaacttt agaatataag attgagattt tagagaaaac aactactatc 1860
tatgaggaag ataaacgcaa tttgcaacag gaacttgaaa ctcagaacca gaaacttcag 1920
cgacagtttt ctgacaaacg cagattagaa gccaggttgc aaggcatggt gacagaaacg 1980
acaatgaagt gggagaaaga atgtgagcgt agagtggcag ccaaacagct ggagatgcag 2040
aataaactct gggttaaaga tgaaaagctg aaacaactga aggctattgt tactgaacct 2100
aaaactgaga agccagagag accctctcgg gagcgagatc gagaaaaagt tactcaaaga 2160
tctgtttctc catcacctgt gcctttactc tttcaacctg atcagaacgc accaccaatt 2220
cgtctccgac acagacgatc acgctctgca ggagacagat gggtagatca taagcccgcc 2280
tctaacatgc aaactgaaac agtcatgcag ccacatgtcc ctcatgccat cacagtatct 2340
gttgcaaatg aaaaggcact agctaagtgt gagaagtaca tgctgaccca ccaggaacta 2400
gcctccgatg gggagattga aactaaacta attaagggtg atatttataa aacaaggggt 2460

-continued ggtggacaat ctgttcagtt tactgatatt gagactttaa agcaagaatc accaaatggt 2520
agtcgaaaac gaagatcttc cacagtagca cctgcccaac cagatggtgc agagtctgaa 2580
tggaccgatg tagaaacaag gtgttctgtg gctgtggaga tgagagcagg atcccagctg 2640
ggacctggat atcagcatca cgcacaaccc aagcgcaaaa agccatgaac tgacagtccc 2700
agtactgaaa gaacattttc atttgtgtgg atgatttctc gaaagccatg ccagaagcag 2760
tcttccaggt catcttgtag aactccagct ttgttgaaaa tcacggacct cagctacatc 2820
atacactgac ccagagcaaa gctttcccta tggttccaaa gacaactagt attcaacaaa 2880
ccttgtatag tatatgtttt gccatattta atattaatag cagaggaaga ctcctttttt 2940
catcactgta tgaatttttt ataatgtttt tttaaaatat atttcatgta tacttataaa 3000
ctaattcaca caagtgtttg tcttagatga ttaaggaaga ctatatctag atcatgtctg 3060
atttttattt gtgacttctc cagccctggt ctgaatttct taaggtttta taaacaaatg 3120
ctgctattta ttagctgcaa gaatgcactt tagaactatt tgacaattca gactttcaaa 3180
ataaagatgt aaatgactgg ccaataataa ccattttagg aaggtgtttt gaattctgta 3240
tgtatatatt cactttctga catttagata tgccaaaaga attaaaatca aaagcactaa 3300
gaaataaaaa aaaaaaaaaa aaaa 3324

<210> SEQ ID NO 69
<211> LENGTH: 1270
<212> TYPE: DNA
<213> ORGANISM: Human

<400> SEQUENCE: 69
gttagccaag attacaatga aggactactc caaattagga gtccatgaca tgaacgaccg 60
caaacgtctc ttccaactta tcaaaattat taagattatg caagaagaag ataaagcagt 120
cagtatccca gagcgtcatc ttcagacaag cagcctgcgc atcaaatctc aggaattaag 180
atctggccct cgcagacagc tgaattttga ttctcctgct gacaataaag acagaaatgc 240
cagcaatgat gggtttgaaa tgtgcagttt atcagatttc tctgcaaatg aacagaagtc 300
cacttaccta aaagtgctag aacacatgct accagatgat tcccagtacc atacaaaaac 360
aggaattctg aatgccacag ctggtgattc ctatgtgcaa acagaaatca gcacttcact 420
cttttcacca aattaccttt ctgcaatact gggggattgt gatattccca ttattcaaag 480
aatctctcat gtttcagggt ataactatgg aatcccccat tcttgtatca ggtaataaat 540
tttatctttc tttcttttga gggaaagtag cctcaggcaa gggcaggcct ctccttcatg 600
tccagcagac agcatctact ccttatttat agtaaatgaa tataacagaa attatcatga 660
acagcatttg catcaataat aggaatacct ggatgtggga aaattaatga gaaattggga 720
ctttctaggt gggagaaaga tgatattgtt catgtacatc agaacagctg ctacttgcca 780
ggatctgtag cagatctgtt tctattgttt attatagcgt aacatgatac atctagtaca 840
tctgtgaaag tgaaatagtt aacccttcta cagtggagaa aaaaattaca caatccacag 900 gacttttta aggttatcaa attcacttaa cccaaccagg agacttaaag atgctttgtt 960
aaaaaacaag ggcatgtagt ttaattaagt aggtctttgg ggcagttagt tcacctacac 1020
acattgaaat atgatcctaa ttttgagtgc tttctacaat ttcaaccccg gaaaaaacag 1080
ataattttgg tgattacaaa cagtaagaca ttgttggtgg agatgagagt ttgagagtca 1140
gggtgacaat aagttatttt tacctagtgt ttcgagttag aatttgaaat aaggtcccta 1200
agaggtgaaa taacaagtaa tccctagtac taacaatggt ataataggaa atatgttctt 1260
ttaatcttgt 1270

<210> SEQ ID NO 70
<211> LENGTH: 1354
<212> TYPE: DNA
<213> ORGANISM: Human

<400> SEQUENCE: 70
ttgtttacaa aaacaggcgg caggctgggg ttggtggggc ttgtgtttaa ttaacgcagc 60
acacaaagtc ttatgacgtc gttttactct tttctctcag gaaacaattc tggtgaaatg 120
tgatcgtcct ggccaccctc tgattgataa gacatatcat tttgaaagat atactggcct 180
tcccagctga catggacctc aggtcagctt cagcgtgaga agcaggccag gcctgggtct 240
ggagccgtcc tggccttccc agatgacatg gacctcaggt cagcttcagc gtgagaagca 300
ggccaggcct gggtctggag ccgtcctggc cttcccagat gacatggacc tcagggttta 360
tggtccagca gagtctcaga gcgcggtctt tggagatgtg tgccccctac tcacttctct 420
cttggatggg tacaatgttt gtgttatggc gtatggacag acgggcagcg gaaagagcta 480
taccatgctg ggacgccatt cggacgacgg ccctgttctg ccgcttgacc cacagagtga 540
cttaggaatt atccctagag tggctgagga gctcttcagg ctcattttgg aaaatacctc 600
aagaagccca aaggttgaag tctccatagt ggaagtttac aataatgaca tttttgacct 660
tctggccaaa gacagcattg cagcagtgtc gggggtcaag cgtgaggtgg tgacagccaa 720
ggatggacgg acagaggttg cgctgctggc ctctgaggct gtcggcagcg cctcgaaact 780
gatggagctc gttcatggag gtctgcagct cagggcgaag caccccaccc tggtgcacgc 840
ggattcctcc aggtctcacc tgataattac ggtgactcta accacagcct cctgctctga 900
cagcactgca gaccaagcct gcagtgccac cctccccagg gagcaaacag aggcaggaag 960
ggcaggaagg agccgcagag cttctcaagg ggccttggct ccacagctgg ttcctgggaa 1020
ccccgcaggg catgcggagc aggtgcaggc tcgactacag ctcgtggact cggccggcag 1080
cgagtgcgtt ggaggcgatg cgaagttact ggtgattctc tgcatttctc ccagccagag 1140
gcacctggca cagacgttgc agggcctggg tttcgggatc cgagctcggc aagtccagcg 1200
aggccctgcc cgaaagaagc cgcccagctc ccaaacggag gggaagagga ggccggattg 1260
aatgcattaa caagtttttc tcctaaaact gtgtttcttg tccttgcttt ataatgcata 1320
tgtgcttaga aataaacagg tttcacgtgg actc 1354

<210> SEQ ID NO 71
<211> LENGTH: 7237
<212> TYPE: DNA
<213> ORGANISM: Human

<400> SEQUENCE: 71
atggcgctgc cccagccgcc cgagccgccc cgcggcgcgc cccgcaaggc tcccagcctg 60
ctggagatgg gggcgctctg cctggactcg gagatcatcc tgggcttcac cagccacctc 120
ctgcggcgac gaggcaaggt ccggcgcacg cccgcaggac ctcccgcttc ccgggcggca 180
cggcgcgcac acccacttgc gggcacacgc gcggctgtaa agacacgtgc cgttcgcaga 240
cgcgccgagg cacagatacg ccggcgcggt cgctgcccgg ctcgaggcgc acaccgcggc 300
gacactaacc cacgcgcgac agttagacct aaagtggccc gcgacacgca gagctctgcg 360
aacttccgag cggctgggcc gggccatggg ggcgcctcgg ggccggatca cgtagccgcg 420
gcgcccccgg agagccagcg tggccgggag cgcctgccgg gctcttcccg cgccccggcc 480

-continued

```
atggtcggcc gcggcgtccc tctgtgcgct gcgcagcccg cggtggccga gggcggcccg    540
gcccgcgagc cgccgccgct gctggaggtg tccccccgaa agaggctacc cgccgggccc    600
gaccaggacc catgcggcag ccgccctgct cccgaaggcg ccggggccgg cccagagcag    660
ggccactcgg ccggcggagg cggctggtgc cgccactgcc acacgaagct ggtggagctc    720
aagcgacagg cgtggaagct ggtcagcggg cccgggacca ccctccggga tccttgcctc    780
tctgccctgc ttctcgacaa gctaccagca cctggggccc tgccagcctg tcgcccagag    840
gccgagcgcc gctgtgacgt ctgcgccaca cacctgcagc agctcacacg ggaggccatg    900
cacctgctgc aggcccctgc cagccatgag gaccttgacg ccccccatgg aggccccagc    960
ctcgcacccc ccagcaccac gaccagctcg agggacacgc caggaccagc gggtcctgca   1020
gggaggcagc caggacgagc tgggccagac aggaccaagg ggctggcctg gtcccccggg   1080
cccagtgtcc aggtgtctgt agcacctgcg ggtcttggag ggcgctgag cacggtcacc   1140
atccaggccc agcagtgcct ggagggcatg tggagtgtct cgcgggtcaa cagcttcctc   1200
ccgccggcgt gcctggccga ggcagcggtg gcggccgtgg cggtggcaga cacggtccga   1260
gaatgccccc ccgtggccgg ccctgatggc ttgtcgaagg cctggggccg tggtggagtc   1320
tgcacgtcag ccctggtcac ccccaccccg ggctcggtgg ggggctccac aggcccctca   1380
gctgcagcct ccttcttcat aagggctatg cagaagctca gcctggcctc caagaggaag   1440
aagccccacc cgccaccgcc tccagccacc cgcggcacct ccacctaccc caccgacttc   1500
agcggggtcc tgcagctgtg gccgcccccg gcgccccct gcctgctcag ggccgcctcc   1560
aagaccaagg acaaccctgg cagcatcggg aaggtgaagg ttatgctgcg gatctggccc   1620
gcacaggggg cccagcgctc ggccgaggcc atgtccttcc tgaaggtgga ccctcggaag   1680
aagcaggtga tcctctacga tcccgccgcc ggtcccccag gcagcgcagg cccccggcga   1740
gccgccactg ctgcagttcc caagatgttt gccttcgatg ccgtcttccc ccaggactcc   1800
gagcaggccg aagtctgctc ggggaccgtg gccgacgtgc tccagtcggt ggtcagtggg   1860
gctgatggct gcattttttc ctttggccac atgagcctgg gcaagtcgta caccatgatc   1920
gggaaggaca gctcacccca gagcctgggc atcgtgccct gcgccatctc ctggctcttc   1980
aggctcatcg aggagcgcag ggagaggacg ggcacccgct tctccgtccg ggtctcagcc   2040
gtggaggtgt gcgggcgcga ccagagcctg cgggacctgc tggccgaggt ggcccctggc   2100
agcctccagg acacccagtc tccgggagtg tacctgcggg aggaccccgt gtgtggggcg   2160
cagctccaga accaaagcga gctgcgggca cccacggccg agaaggcggc tttctacctg   2220
gatgcggccc tggcggcccg cagcaccagc cgagcgggct gtggcgagga cgcccgacgc   2280
agctcccaca tgttgttcac gctgcacgtc taccagtacc gcatggagaa gtgcggccgg   2340
ggaggaatgt ccggaggccg cagccgcctg cacctcatcg acctgggcag ctgtgaggcg   2400
gcggctggca gggccgggga ggctgctggg ggtcccctgt gtctgtccct gtcggccctg   2460
ggcagcgtca tcttggccct ggtcaacgga gccaagcatg tgccgtatcg ggaccacagg   2520
ctcaccatgc tgctgcgtga atccctggcc accgctggct gccgcaccac catgatcgcc   2580
cacgtgtcgg atgcgccagc ccagcacgca gagacactca gcaccgtgca gctcgccgcc   2640
cgcatccacc gcctgcgcag gaagaaggcc aagtacgcct ccagctcctc tggcggggag   2700
agctcctgtg aggaaggccg ggcccgtcgg cccccgcacc tgcggccctt ccacccacgc   2760
actgtggccc tggaccccga ccgcacgcct ccctgcctgc ccggtgaccc cgattactcc   2820
tccagcagcg agcagtcctg tgacacggtc atctacgtgg ggcccggtgg ggcggcgctg   2880
```

```
tcagaccggg agctcaccga caacgaaggt ccgcctgact tcgtgcccat catccctgcc   2940
ctgagccgcc accggccctc caagggtccc cgagacgcag accacttccg ctgcagcacc   3000
ttcgcggagc tgcaggagcg gctggaatgc atggacggca acgagggtcc ctcaggaggt   3060
ccaggtggca ccgacggagc tcaggccagc cccgcccgag gggccggaa gccctcgcca   3120
ccagaggctg catcccccag gaaggccgtg ggcaccccga tggctgccag cacccctcga   3180
ggcagttctg gtccagacac ccaccagggt accctgagc cctgcaaggc cattgtctgg   3240
ggtgaccaga gagaggacag cagcgcttgg cctgagctgc tggtcccgga aaaggctgca   3300
gtgagtggag gcaggaggcc actgcccagc ccggctcccc cacctcctca gttgctggaa   3360
gcctgcagag ccccagaaga gcctgggga gggggcactg atggagtggc acggacccct   3420
cccgtgggca tgagtgggca ggtggctggg tccccgatgc ttcctggggc cacctgcccc   3480
cgcctggctg ctggcagtcg ctgtccggag cggggcctgc tcaccaccac agtgaccctg   3540
cagcggccag tggagctcaa cggcgaggac gagctggtgt tcacggtggt ggaggagctg   3600
tccctgggg cgcttgccgg agctgggcgg cccaccagcc tggctagctt cgacagtgac   3660
tgctccctgc gggccctggc ctcggggtcc cggccagtca gcatcatcag cagcatcaat   3720
gatgagtttg acgcctacac ctctcaggcc cctgaggggg ggcccctgga gggggcagcc   3780
tgggccggca gcagtcacgg ctcctccatc agctcctggc tcagcgaggt cagcgtctgc   3840
actgccgaca gccgtgaccc cacgccgcag ccccgcttca gccccgactc gctggcaggg   3900
cttgaccctg gggcccccc tgccctggat ggttccctgg gggatggaag ctctgggttc   3960
ctggggccag acagacctga cagtcctggg ccaacctggg gtccgtgccc tggggaagtg   4020
gctgcagtgg ccccatcccg acccggcagg gagccccagg ccgggccctc gcggtgggca   4080
tccgcagccc agaccatcca ctccagcctc ccccggaaac cgaggactgc ctctgccacc   4140
acccgtgtgg gctgtgctcg cctgggccag agcccacctg gccgtggagg cctgtttgag   4200
gacccatggc tgctccgggt aggggagtgt gatacccagg cagcttctgc tggcagggcc   4260
cccagcccca cacttggctc cccccggctg cctgaggccc aggtgatgct agcctgtgcc   4320
cagagagtgg tggacgggtg tgaggtggca gccagggcgg cccgcaggcc agaggctgtg   4380
gctcggatcc caccgctgcg gaggggtgcc accacgctgg gtgtgacaac gccagctgtg   4440
tcctggggag atgctcccac ggaggtggtg gcctgctcgg ggagcctgaa ggcctccccc   4500
accagcaaga agggtctggc tcccaaggcg ggcttcctcc cgaggcccag tggggcggcc   4560
cccccggccc cacccacgcg gaagtccagc ctggagcaga ggagcagccc ggcctcggcc   4620
cctccgcatg ctgtgaaccc ggcgcgggtc ggggctgctg ctgtccttcg aggggaggag   4680
gagcccagac ccagcagccg ggctgaccac tctgtcccca gggccacgtc cagcctgaag   4740
gcccgggcca gcaaggtaga agcagcacac cgtcttgccg gacacgcgtc tctggagcgg   4800
tacgaaggcc tggcgcacag cagcagcaag ggccgggaag cccctgggcg gcctccccgg   4860
gctgtaccca agctgggtgt gccaccctcc agccccacac acggtccagc tcccgcctgt   4920
aggagcggcg cagccaaggc tgtgggggcc cccaagcccc ctgttggtgg aggcaagggc   4980
cgtggcctag tggctggtgg gtcgcgggct ctggggcctt cggtgaagct gtctacggcc   5040
tctgtgacgg gcaggagccc tggcggccct gtggccggtc ccagagcagc cccacgggcc   5100
gggcccagtg tcggggcgaa ggctggccgg ggtaccgtca tgggcacaaa gcaggcgctc   5160
cgggctgctc acagccgcgt ccatgagctg tcagccagtg gagccccggg ccgaggtggc   5220
tcctcgtggg gctcggcgga ctcagacagc ggccatgaca gcggcgtgaa cgtgggggag   5280
```

gagcggccac ccacgggccc ggccctgccc tccccctaca gcaaggtgac cgccccacgg 5340
cggccccagc gctacagcag cggccatggc agcgacaaca gcagcgtgct gagtggagag 5400
ctgccgcccg ccatgggccg caccgccctt ttccaccaca gcggtggcag cagtggctat 5460
gagagcctgc ggcgcgacag cgaggccacc ggcagcgcct cctccgcccc tgactccatg 5520
agcgagagtg gggctgcctc ccaggcgcc cgcacccgca gcctcaagtc ccccaagaag 5580
agggccacag gtctgcagcg gcggcgcctg attcccgccc cactgcccga caccactgcc 5640
ctgggccgta agcccagcct ccccgggcag tgggtggacc tgccccgcc cctggctggc 5700 tccctgaagg agccgttcga gatcaaggtg tacgagatcg atgacgtgga gcgccttcag 5760
cggccccgcc ccaccccgag ggaggccccc acccagggtc tggcgtgcgt cagtacaagg 5820
ctgcggctgg cggagcgcag gcagcagcgg ctgcgggagg tgcaggccaa gcacaagcac 5880
ctgtgtgagg agctggccga gacccagggc cggctgatgc tggagcctgg ccgctggctg 5940
gagcagtttg aggtggaccc ggagctggag cccgagtcgg ccgagtacct ggcggccctg 6000
gagcgagcca cggcggccct ggagcagtgc gtgaacctgt gcaaggcgca cgtcatgatg 6060
gtcacctgct tcgacatcag cgttgcagcc agtgctgcca tcccggggcc gcaggaggtg 6120
gacgtctgag gctgggcgcc ggacaagagg agggggcgtg cagcgggctg gaggacggga 6180
cgtgggacgg agcgaggatg tggtgggggc tgcgggggga ggatgcggag gggtttctgt 6240
gcaggacggg agtctcagag aggagacgga gtgtggggga gggagggccg gccacgcggt 6300
ggacagagcg agggtgccag ggtgaccaga agaccgtcac cacccgacag caacgcaagt 6360
gcctttgacc ttgatttgga cttttctccc ttttgcattt ggtgctacag acttgagaca 6420
ccagcagaag ttgtgttcag cccggccccg ctgcgcctgt ccgggccggg gctggcgccg 6480
gttgtgtttg tgtccacctt gccttctttg cagccaagca gtttttgtgg agtggagtgg 6540
gacttacctg cacgccccag gggtctttca ggattcagga tgacttttct tttacaatgg 6600
tttcctctcg gcagagcccg ggttgtgggg gatctgtgtg gggttctcaa cgcagatcca 6660
tcctggggtc tcccgggcag ggatggctga cctcgagtcc cctcccttcc cgagaacccg 6720
ctctgtcccg agggcagcta acaagggctg agccccaggt acaggttgcc tcttccacgg 6780
caggaatttt taccaaaacc acaagcaaaa aacaaaacag accaccacga ccaacaacaa 6840
agatgggggg tagggttttg taaaggttct gttaggttca tatttttata tcattttgcc 6900
cataaatgcg gaatttgccg tgggaatttg aagacaaatg atctatgttt ttatggtttt 6960
ctagggaagg tgttctgggg gccgggctct ctccagctgt gggaggcctg ctccctctgg 7020
ggggcaccct gggcagggtg ggggggcctt gggaggcgct tcttgccaaa tgcagacgag 7080
gggtgagcct gccagcgttt gcgacgtccc cgcacgacag gctcatactt tctgaggatc 7140
gtgcatagca taggacgtct gaacctttgt acaaatgtgt agatgacatc ttgctacagc 7200
ttttatttgt gaattaaaga tgcatcgatg gttccca 7237

<210> SEQ ID NO 72
<211> LENGTH: 2571
<212> TYPE: DNA
<213> ORGANISM: Human

<400> SEQUENCE: 72
tcctgagatg gccccagatc tgcaagagac atttgagaga agctatttat tagcagacgt 60
gaagaaatgg attctgcact tgattattta gccatgactt atcaatgatg atggattgga 120
aagcagtagc tgcccagaag ttaaatctgt cttctaaaaa gaagaaacat cggccttcca 180

-continued

```
cttcttccgc tgccgaacca ccgctctttg caaccagctt cagtgggatt ctgcagacct    240
cccctccccc agccccaccc tgcctgctga gggctgtcaa caaggtgaag gacaccccgg    300
ggctgggcaa ggtgaaagtc atgcttcgca tctgttccac cttggctcga gatacttcag    360
aatccagctc tttcttaaag gtggacccac ggaagaagca gatcaccttg tacgatcccc    420
tgacttgtgg aggtcaaaat gccttccaaa agagaggcaa ccaggttcct ccaaagatgt    480
ttgccttcga tgcagttttt ccacaagacg cttctcaggc tgaagtgtgt gcaggcaccg    540
tggcagaggt gatccagtct gtggtcaacg gggcagatgg ctgcgtgttc tgtttcggcc    600
acgccaaact gggaaaatcc tacaccatga tcggaaagga tgattccatg cagaacctgg    660
gcatcattcc ctgtgccatc tcttggctct tcaagctcat aaacgaacgc aaggaaaaga    720
ccggcgcccg tttctcagtc cgggtttccg ccgtggaagt gtgggggaag gaggagaacc    780
tgcgggacct gctgtcggag gtggccacgg gcagcctgca ggacggccag tccccgggcg    840
tgtacctctg tgaggacccc atctgcggca cgcagctgca gaaccagagc gagctgcggg    900
cccccaccgc agagaaggct gccttttttcc tggatgccgc cattgcctcc cgcaggagcc    960
accaacagga ctgtgatgag gacgaccacc gcaactcaca cgtgttcttc acactgcaca   1020
tctaccagta ccggatggag aagagcggga aagggggaat gtctggaggt cgcagccgcc   1080
tgcatctcat tgatctcggc agctgtgtga aagctcttag caaaaatcga gaaggaggct   1140
cagggctgtg tctctcgctg tctgctctgg gcaatgtcat cctggctctc gtcaatggca   1200
gcaaacacat tccatacaaa gagagcaagc tcgccatgtt gctgcgggag tctctgggga   1260
acatgaactg ccgtaccacc atgatcgcgc acatctcggc cgcggtcggg agctacgcgg   1320
agaccctgtc caccatccag attgcatcga gagtcttgag gatgaagaaa aagaagacga   1380
agtacacatc cagctcgtcc ggcggggaga gctcctgcga agaaggccgc atgcgcaggc   1440
ccacccagct gagacccttc cacaccaggg ccacggtgga ccctgacttc cccatcgctc   1500
acctgtccag cgaccccgac tactcctcca gcagcgagca gtcctgcgac accgtcatct   1560
acatcgggcc caacggcacg gccctctctg acaaggagct caccgacaac gagggccccc   1620
cagactttgt ccctatcgtg ccagccctgc agaagacccg gggcgacagc cggcccgcag   1680
aggcaggaga ggctgcagcc ggcaagtcag aaagggactg cctgaagtgc aacacgtttg   1740
ccgagctgca ggagaggctg gactgcatcg acggcagcga ggagcccagc agctttcctt   1800
tcgaagaact gcctgctcag tttgggccag agcaggcaag cagaggcccc cggttaagcc   1860
aagcagcggg ggcaagccca ctctctgagt ctgataagga agataatggg tccgaaggtc   1920
agctgaccaa cagagaaggc cctgaactcc cagcctccaa gatgcagagg agtcactcac   1980
ctgtgcccgc cgcggcaccc gcccacagcc ccagcccggc ctcacccagg agcgtcccgg   2040
gcagcagtag ccagcacagc gcctccccac tcgtgcagag ccccagcctc cagagcagcc   2100
gggagagcct caactcctgc ggcttcgtgg aaggcaagcc caggcccatg ggctcccccc   2160
ggctgggcat cgccagcctg tccaagacct cggagtacaa gccacccagc tctccttccc   2220
agagatgcaa agtctacacc cagaaggggg tcctgccgtc tcccgcccca ctgcctccct   2280
cgagcaagga ttccggcgtg gcgtctaggg agtccttgct gcagcccgag gtgcgtacgc   2340
cccggttgg aatgagcccc caggttttga aaaaatccat gtctgctggg agcgaagggt   2400
tcccggaaac tcctgtcgat gatgagcagc aggcagctac tccttcagag tccaagaagg   2460
agatcctgag caccacgatg gtgacggtgc agcagccact ggagctgaac ggtgaggacg   2520
agctggtgtt cacgctggtg gaggagctga ccatcagcgg ggtcctggac a            2571
```

<210> SEQ ID NO 73
<211> LENGTH: 2702
<212> TYPE: DNA
<213> ORGANISM: Human

<400> SEQUENCE: 73

```
gcggcgacgt ccacgcattt tctgacgtag cgagcgacgg cggggagccg agcggaagtc     60

cagcactatt gccgctagag gaggggaggg gtgagaagca taagtggcac cggaagtgga    120

attaatccgc ctacctctcc tgcgcctgcg aaacagaaaa gacaaggcgc ctgtcgggcg    180

gggtgtggct tcgggtggcg gagaacgctg cgattggccc tcggctgtgg cgacagcgac    240

gattggtccc tgcgtgcaga gcgcggtgag agtgggtggt ggccgttgga attcaaaagt    300

ggcgggtgtg gcgcggggct ggtagcggcc ggagccgtgc gagttctcta ccctgcttcg    360

cgagcgggcg agagaacgcg agtcccagga tccccggcac ccagttctct tccactgcat    420

tcccccggcg cgtgtgggac cgaggtggac atggatccgc agaggtcccc cctattggaa    480

gtaaagggga acatagaact gaagagacct ctgattaagg ccccttccca gctgcctctc    540

tcaggaagca gactcaagag gaggcctgac cagatggaag atggcctgga gcctgagaag    600

aaacggacaa gaggcctggg tgcaacgacc aaaattacca catcccaccc aagagttcca    660

tccctcacta cagtgccaca gacacaaggc cagaccacag ctcaaaaagt ttccaagaag    720

acaggacccc ggtgttccac agctattgcc acagggttga agaaccagaa gccagttcct    780

gctgttcctg tccagaagtc tggcacatca ggtgttcctc ccatggcagg agggaagaaa    840

cccagcaaac gtccagcctg ggacttaaag ggtcagttat gtgacctaaa tgcagaacta    900

aaacggtgcc gtgagaggac tcaaacgttg gaccaagaga accagcagct tcaggaccag    960

ctcagagatg cccagcagca ggtcaaggcc ctggggacag agcgcacaac actggagggg   1020

catttagcca aggtacaggc ccaggctgag cagggccaac aggagctgaa gaacttgcgt   1080

gcttgtgtcc tggagctgga agagcggctg agcacgcagg agggcttggt gcaagagctt   1140

cagaaaaaac aggtggaatt gcaggaagaa cggagggggac tgatgtccca actagaggag   1200

aaggagagga ggctgcagac atcagaagca gccctgtcaa gcagccaagc agaggtggca   1260

tctctgcggc aggagactgt ggcccaggca gccttactga ctgagcggga agaacgtctt   1320

catgggctag aaatggagcg ccggcgactg cacaaccagc tgcaggaact caagggcaac   1380

atccgtgtat tctgccgggt ccgccctgtc ctgccggggg agcccactcc acccccctggc   1440

ctcctcctgt ttccctctgg ccctggtggg ccctctgatc ctccaacccg ccttagcctc   1500

tcccggtctg acgagcggcg tgggaccctg agtggggcac cagctccccc aactcgccat   1560

gatttttcct ttgaccgggt attcccacca ggaagtggac aggatgaagt gtttgaagag   1620

attgccatgc ttgtccagtc agccctggat ggctatccag tatgcatctt tgcctatggc   1680

cagacaggca gtggcaagac cttcacaatg gagggtgggc ctgggggaga cccccagttg   1740

gaggggctga tccctcgggc cctgcggcac ctcttctctg tggctcagga gctgagtggt   1800

cagggctgga cctacagctt tgtagcaagc tacgtagaga tctacaatga gactgtccgg   1860

gacctgctgg ccactggaac ccggaagggt caagggggcg agtgtgagat tcgccgtgca   1920

gggccaggga gtgaggagct cactgtcacc aatgctcgat atgtccctgt ctcctgtgag   1980

aaagaagtgg acgccctgct tcatctggcc cgccagaatc gggctgtggc ccgcacagcc   2040

cagaatgaac ggtcatcacg cagccacagt gtattccagc tacagatttc tggggagcac   2100

tccagccgag gcctgcagtg tggggccccc ctcagtcttg tggacctggc cgggagtgag   2160
```

cgacttgacc ccggcttagc cctcggcccc ggggagcggg aacgccttcg ggaaacacag 2220
gccattaaca gcagcctgtc cacgctgggg ctggttatca tggccctgag caacaaggag 2280
tcccacgtgc cttaccggaa cagcaaactg acctacctgc tgcagaactc tctgggtggt 2340
agtgctaaga tgctcatgtt tgtgaacatt tctccactgg aagagaacgt ctccgagtcc 2400
ctcaactctc tacgctttgc ctccaaggtg aaccagtgtg ttattggtac tgctcaggcc 2460
aacaggaagt gaagacggat ccagatctgt gtgtgtgtgt gtgtgtgtgt gtgtgtgtgt 2520
gtgtgtgtgt gtgtgtccct atgtctatgt atcgggtgag ggtgggaggg gttgctggag 2580
ggtgctttat tgggtggagg gcaccatgtc ccagggctat caaataaaga atagtttggt 2640
ttttttttta aataaaggtt ttattagcat ttgcccaaga aggcagatac tttcatatct 2700
gt 2702

<210> SEQ ID NO 74
<211> LENGTH: 3309
<212> TYPE: DNA
<213> ORGANISM: Human

<400> SEQUENCE: 74
cgccgagtct gggcgcgggg acgcggggcg gcgcgaagcg gggccctctg ccgccccgcg 60
ctcccatgta cgccttttac tcgttgctca tctacatctt ctacagcctc ttccgcaggg 120
atggtggcgc cgcggcggcc gcggagcccg gggaccccgc ccagagagcc cgcaagcccc 180
ggggtcgccg gcgcccagac ctgcccgcgc cagagctgtg gaccgagctg accggcctgg 240
ccgccagctc cgagcctgag gatgggtcgg aaggcgcagc cgagggtcgc gcggccgcgg 300
tgtccctgga agaggcccta ctgcgcctcg ccgagttcct ctccgtccag ctgggggcgg 360
aagagagctg cgggggcccg gcggacctgg gccagtctgg cgaggtcccc tcactgttga 420
cagtgaccag tcagctcttg gcccttctgg catggcttcg aagccccagg gggaggcagg 480
ccctgctcca ggggactcag ccagcccctc gggtccggcc cccctctcca gatggatcca 540
catcccaaga agaaagccct tcccacttca ccgcagtccc aggcgagcca ctgggggatg 600
agacccaggg acagcagccc ctccagttgg aggaggatca gagggcgtgg cagcggctgg 660
agcagctcat cctgggacag ctggaggagc tgaagcagca gctggaacag caggaggagg 720
agttgggtcg actgcgcctg ggcgtggggg cgacggactc agagaaaagg gttcagcatc 780
tgactctgga gaacgaggcc ctgaagcaga gcctgagtct catgcgggac ctcctgctgc 840
actggggccc cgggcccccc atcagggctc cgcaggagga ggcggaggca ttgctagagc 900
tccagggccg gcttcaggag gcccaagaca ccacagaagc cctccgagcc cagctggggg 960
tgcaggaggt gcagctgcag ggccttcaag ggccctcca gcagctccag caggagacgg 1020
agcagaactg caggcgtgag ctacagcaga tgcatgggca gctggcagga cttcgggcac 1080
ggatggccag cctgcgtcag ggctgcgggg acctccgagg tttggtcagc acctttaccc 1140
agagctgtca gggttcgctg agtgaggccc ggggccaggt gtcctgggcc ttgggggcac 1200
tgtcatctgg agggcctggc actcagctcc ctgaggggca gcaagggccc ccagccggat 1260
gcccagggcg gctgccagaa ctcaagggaa atatccgtgt gctgtgtcgg ctgaggccag 1320
ggacatcttc tagccttgtg agtgtggagc ctggcccagg gggcaccgtc accacctgct 1380
accgggggcg ccatcgtcga ttccgcctag actgggtctt ccctccagac gccagccagg 1440
aggaggtctt cagagagctg gaacctgcgg tgctgtcctg cctccgaggc tacagcgtct 1500
gcatcttcac ctatggccag acaggcaccg ggaagaccta cagcatggag ggccctcctg 1560
aggaccccgg catagttcct agggcgctgc agtcgctgtt ccgggagatg ggggccggcc 1620
ggcagcaccg ggtgacactc agcatggtgg agatctacaa tgaggctgtc agggacctcc 1680
ttgctccagg gcctcccgag cgcctggccg tgaggcaggg cccagaaggc cagggcggga 1740
tccaggtggc tggcctcacc cactgggacg tgcccaacct ggagacattg caccagatgc 1800
tgaaactggg gaggagcaac cgggccaccg ccgccaccgc catgaaccag cgcagctccc 1860
gctcgcatgc cctggtcacg ctgacgctgc gcgcggcgtc tccaccgcgc gctccaggca 1920
ccgcaggcac gctgcacctg gtggacctgg cgggatccga acgcgcacgg aaggcagggg 1980
cggccggccc gccgcgggga gacccagacg gcgcccggcg cctgcgggag gcccagacca 2040
taaaccgctc gctgctggcg ctaggaggcg tgatggccgc actgcgggcc caccggccgc 2100
acgtgccctt ccgcgactcg cagctcacgc gactgctgca gccggcgctg ggcccaggca 2160
ccaccgcggt gctgctgctg caggtgggcg ccggggcggg gcaggtgtgt gcgtgccggt 2220
cgccgcccac ccgggcccgc ccacccgcgc ctcttgcccg cagatctcca cgcggccgga 2280
ggatctcggg gagacagtct gctccctcaa gttcgccgac cgagtgggtc aagtggagct 2340
ggggccagcc cggcgccgca gggtcccgcg ctcctccggg acgccttctt ccctcagcac 2400
cgacactccg ctcaccggga ccccctgcac ccctacgccg tcccctggca gtcctccatg 2460
ccccagtccc gacaacggct cgggctcggc tctcgcgccc gcagagggcc tgcccctcta 2520
gtcctgggtc gcggccctgc ccatggggtc tcaggccagg tctctgctgg cagaggcggt 2580
agtaaagtcc ctgtaccccg tctcccaggg cacaagctcc ctagcctctt tggatccatt 2640
gcccctgagc tcccagagtc acccctccac ctccgcagcc agtgaagtgt gttgtgcctg 2700
ctgaagtgat cacccccgc ccccagccct gcatcaggcc acaggtcttg gctttctcct 2760
tatcaccatt tgctgttatc acggcacaca gcagggaatc ccaggccccc ccgccaagtg 2820
gttacccaag tcaccactcc tgacccaaaa atcaggcatg gcattaaaac gttgcaaatt 2880
cctttactgt tatcccccc accaccagga ccatgtaggg tgcagtcttt actccctaac 2940
ccgtttcccg aaaaaggtgc tacctccttt ccagacagat gagagagggc aggacttcag 3000
gctggatcca ccactgggct ctccctcccc cagcctggag cacgggaggg gaggtgacgg 3060
ctggtgactg atggatgggt agtgggctga gaagagggga ctaggaaggg ctattccagg 3120
ctcagccctg ctcctgcagc tttgccgctg agtgtaggaa aaacaggcat gacagaccag 3180
ggtgagggtt gtgcccagct gggccacggc catgcgtggg gtggcccaat aaacaccgtg 3240
gactcccaaa aaaaaaaaaa aaaaaaaaaa aaaaaaaaaa aaaaaaaaaa aaaaaaaaaa 3300
aaaaaaaaa 3309

<210> SEQ ID NO 75
<211> LENGTH: 3366
<212> TYPE: DNA
<213> ORGANISM: Human

<400> SEQUENCE: 75
gcccgagtta atcatttcct gtggaaagtg tgcgggaggg gcgcgagcgg gctggccgag 60
gaggaggcgg cggcgtggag ctgcctcctg ccggcgggcc gggccgggcc gagccccggg 120
cgctgcggcg acgcctggat cctgcctccg ccaggccggc tgcctggtgc cccgaggagg 180
ctgctgagcc ccaggccatg gtcccctctc gcaggacgtg gaacctggga gccacgccct 240
cgctgcgggg cctgtggaga gtgggccggg ccccggagcc cgagccgggg atggctcgcc 300
ccgccccagc cccagccagc ccggccgccc gcccttttccc acacaccggc ccggggaggt 360

-continued

```
tgagaactgg gcgtggaaaa gataccccag tctgcggtga cgaggactcc agtgcccgaa    420
gtgcagctcg cccagcccta gctcagtgcc gagcccttag cgtggactgg gctggccccg    480
gaagccccca cgggctctac ctgaccctgc aggtagaaca cctgaaggag aagctcatta    540
gccaggccca ggaagtgagc cgactgcgat ctgagctggg gggcaccgac ttggagaagc    600
accgggacct gctgatggtg gagaatgagc gactgaggca ggagatgcgg cgctgtgagg    660
ccgagctgca agagctgcgc acaaagccag caggtccctg cccaggttgt gagcacagcc    720
aggagagcgc ccagctccgt gacaagctgt cccagctgca gctggagatg gcggaaagca    780
aaggcatgct gtcagagctg aacctagagg tgcagcagaa gaccgaccgg ctggctgagg    840
tggagctgcg actcaaggac tgcctggctg agaaggcaca ggaggaggag cggcttagtc    900
ggcgcctgcg tgacagccac gagaccattg ccagcctgcg ggcccagtcc ccacctgtca    960
agtatgtcat caagacagtg gaggtggagt cgtccaagac caagcaggcc ctcagcgagt   1020
cccaggcccg gaaccagcac ctgcaggagc aggtggctat gcagaggcag gtgctgaagg   1080
agatggaaca gcagctgcag agctcacacc agctgaccgc gcggctccgg gcgcagattg   1140
ccatgtacga gtcagagctg gagcgggccc atgggcagat gctggaggag atgcagtccc   1200
tggaagagga caagaaccgg gccattgagg aggcctttgc cagagcccag gtggagatga   1260
aggctgtgca cgagaatcta gcaggcgtcc ggaccaactt gctgaccttg cagccggcac   1320
tgcggaccct caccaacgac tacaatgggc tcaagcggca ggtgcgcggc ttcccactgc   1380
tgctgcagga ggccctcagg agtgtcaagg ccgagatagg ccaggccatc gaggaggtca   1440
acagcaacaa ccaggagctg ctgcgcaagt accgccgcga gctgcagctg cgtaagaagt   1500
gccacaatga gctcgtgcgg ctgaaaggga acatccgagt gattgctcgt gtccggccag   1560
tcaccaaaga ggatggggaa ggacctgagg ccaccaatgc tgtgactttc gatgccgacg   1620
acgactccat catccacctg ctgcacaagg gcaagcctgt gtccttcgag ctggacaagg   1680
tcttctcccc acaggcctcg cagcaggacg tgttccagga ggtgcaggcc ctggtcacct   1740
cttgcattga tggcttcaat gtctgcatct ttgcgtacgg ccagacgggc gccggcaaga   1800
cgtacacgat ggaggggacc gctgagaacc caggtatcaa ccagcgggcc ctgcagctgc   1860
tcttctccga ggtgcaggag aaggcgtctg actgggagta caccatcacc gtcagcgctg   1920
cggagatcta caatgaggtc ctcagggacc tgctagggaa agagcctcag gaaaaactgg   1980
agatccggct gtgcccagac ggcagtgggc agctgtatgt accagggctg actgagttcc   2040
aagtgcagag cgtggacgac atcaacaagg tgtttgagtt tggccacact aatcgcacga   2100
ccgagttcac caacctgaac gagcacagct cccgctcgca cgcgctgctc atcgtgacgg   2160
tgcgaggcgt ggactgcagc acaggcctcc gcaccacggg gaagctgaac ctggtggact   2220
tggctggctc ggagcgcgtg ggcaagtcgg gggccgaggg cagccgcctg cgggaggcgc   2280
agcacatcaa caagtcgctg tcggctctgg gggacgtcat tgctgccctg cgctcccgcc   2340
agggccacgt gcccttccgc aactccaagc tcacctacct gctgcaggat tcgcttagtg   2400
gtgacagcaa gaccctcatg gtggtacagg tgtccccccgt ggagaagaac actagcgaga  2460
cgctctattc cctcaagttt gctgagaggg tgcgctctgt ggagctgggg cctgggctac   2520
gcagggcaga gcttgggtcc tggtcaagcc aggagcatct agagtgggag ccggcttgtc   2580
agacgccaca gccctcggca cgggcccact cagcccccag ctctgggacc agtagccgcc   2640
ctggatccat ccggaggaag ctgcagccct cggggaagtc gcggccactg cctgtgtgac   2700
ggatgtgacc ccgctgggcc tgaagctggg ccctcactgg cctgtccctg ctgcagcgcc   2760
```

aggacccccg gaggtagagg cgagagtgga ggctcttctt ctgccccgtc tcccctcaaa 2820
gatgagaaac atgttcagaa ggaaacggtg tctctcggct gtggctctga gtgcaaattg 2880
catgggcgga aaggcggggg tggctgctct tcctggcagg cctgggccat cagcgaactg 2940
ggccccgtga ggagggcggg agtgtggagg agggtgggcc tctcacccag gctttctcgg 3000
cccctctcct cagcttgcag agctggccag ccccctcctt agggggtggg cgaggagcct 3060
ctgggcagac ccaagaacca tggggactgg ggtgggttgg tggcaccaat ggcagccctc 3120
cccgcccctc tccttcaagg agggttcccg cagctggggg gtgtgcggag gcgcatggcc 3180
tcccgccacg gggccgtgct gtgtttatgg ctggcagagg cagccagcgg gtgggggatt 3240
ctgctgctcg ctcacctgcc tggctcgctg gtctctcgaa ttttcttccc tctgaaatcc 3300
tatttaagaa cttttggaag cttagccatt tttacttatt aaaataaaag aagccttttt 3360
acacaa 3366

<210> SEQ ID NO 76
<211> LENGTH: 3219
<212> TYPE: DNA
<213> ORGANISM: Human

<400> SEQUENCE: 76
ggggagagtg ctgatcactc tcggggacca ggacatagac ctgtcgccat cgtttgtcat 60
cttcctgtcc acccgggatc caactgtcga gttcccacca gatctctgtt cccgggttac 120
ttttgtaaac ttcacagtta cccgtagcag tttacaaagc cagtgtctaa atgaagtact 180
taaagcagaa agacctgatg tggacgagaa acgatctgat cttcttaaac ttcaagggga 240
atttcagctc cgtttgcgtc agctggaaaa atctctacta caagctctga acgaggtgaa 300
agggcgcatt ttggatgacg acacgatcat aaccactctg gagaacctga agagagaggc 360
tgcagaggtc accaggaaag ttgaggagac ggacattgtc atgcaggagg tggagaccgt 420
gtcccagcag tacctcccgc tctccaccgc ctgcagcagc atctacttca ccatggagtc 480
cctcaagcag atacacttct tgtaccagta ctccctccag tttttcctgg acatttatca 540
caacgtccta tacgagaacc cgaacctgaa gggtgtcacc gaccacacac agcgcctgtc 600
cattataaca aaggacctct tccaggtggc gtttaaccga gtggctcgag gcatgctgca 660
tcaggaccac attacctttg ccatgctgct ggcaagaatc aaactgaagg gcaccgtggg 720
ggagcccacc tacgatgcag aattccagca cttcttgaga ggaaatgaga ttgtcctgag 780
tgctggctcc acccccagga tccagggcct gactgtggag caggcggagg cggtggtgag 840
gctgagctgc cttcccgcgt ttaaggactt gattgcaaag gttcaggcag acgagcaatt 900
tggcatctgg ctggacagca gctccccgga gcagactgtg ccctacctct ggagtgaaga 960
aacacctgca acacccattg gccaggccat ccaccgcctg ctcctgatcc aggctttccg 1020
gcccgatcgc ctgttggcca tggcccacat gtttgtttca acaaaccttg ggagtctttt 1080
catgtccatc atggagcagc cgctcgacct gacccacatt gtgggcacag aggtgaagcc 1140
caacactcct gtcttaatgt gctctgtgcc tggttatgat gccagtggac atgtcgagga 1200
ccttgcagcc gagcagaaca cgcagatcac ttcaattgca atcggctctg cagaaggctt 1260
taaccaagca gataaggcaa taaacaccgc tgtaaagtcg ggcaggtggg tgatgctgaa 1320
gaatgtgcat ctggccccag ggtggctgat gcagctggag aagaagttgc attccctgca 1380
gccgcatgcc tgcttccgac tcttcctcac catggagatc aaccccaagg tgcctgtgaa 1440
tctgctccgt gcgggccgca tctttgtgtt cgagccaccg ccaggggtga aggccaacat 1500

```
gctgaggacg ttcagcagca ttcccgtctc acggatatgc aagtctccca acgagcgtgc   1560

ccgcttgtac ttcctgctgg cctggtttca tgcgatcatc caagaacgct tacgatacgc   1620

accactgggg tggtcaaaga agtatgaatt tggagagtct gacctgcggt cagcttgcga   1680

tacggtggac acgtggctgg atgacacggc caagggcagg cagaacatct caccggataa   1740

gatcccgtgg tctgcactaa agaccttaat ggcccagtcc atttatggcg ggcgcgtgga   1800

caacgagttt gaccagcgtc tgctcaacac cttcctggag cgcctgttca caaccaggag   1860

tttcgacagt gagtttaagc tggcatgcaa ggtcgacgga cataaagaca ttcaaatgcc   1920

agatggcatc aggcgagagg agtttgtgca gtgggtggag ttgctccccg acacccagac   1980

gccctcctgg ctgggcctgc ccaacaacgc cgagagagtc ctccttacca cacagggtgt   2040

ggacatgatc agtaaaatgc tgaagatgca gatgttggag gatgaggacg acctggccta   2100

cgcagagact gagaagaaga cgaggacaga ctccacgtcc gacgggcgcc ctgcctggat   2160

gcggacactg cacaccaccg cgtccaactg gctgcacctc atcccccaga cgctgagcca   2220

cctcaagcgc accgtggaga atatcaagga tcctttgttc aggttctttg agagagaagt   2280

gaagatgggc gcaaagctgc ttcaggacgt tcgccaggac cttgcagatg tcgtccaggt   2340

gtgcgaagga aagaagaagc agaccaacta cttgcgcacg ctgatcaacg agctagtgaa   2400

agggatcttg cctcggagct ggtcccacta cacggtgcct gccggcatga ccgtcatcca   2460

gtgggtgtcc gacttcagcg agaggatcaa acagctgcag aacatctcac tggcagctgc   2520

atctggtggc gccaaggagc taaagaacat ccacgtgtgc ctgggtggcc tgttcgtgcc   2580

tgaggcgtac atcactgcca ccaggcagta tgtggcccag gccaacagct ggtccctgga   2640

ggagctctgc ctggaagtca acgtcaccac ctcacagggc gccacccttg acgcttgcag   2700

cttcggagtc acgggtttga aacttcaagg ggccacgtgc aacaacaaca agctgtcact   2760

gtccaatgcc atctcaaccg cccttcccct gacgcagctg cgctgggtca agcagacaaa   2820

caccgagaag aaggccagtg tggtaacctt acctgtctac ctgaacttca cccgtgcaga   2880

cctcatcttc accgtggact tcgaaattgc tacaaaggag gatcctcgca gcttctacga   2940

gcggggtgtc gcagtcttgt gcacagagta aacttttcta gctgcccctt tctgtaatag   3000

tgaaagttgg tatttaacat ttattcattt ttaaaatatt tggaaggtct gagcttgtga   3060

aaagaaagtg gttggtctga ggttggagga agctgaatgg aatctgacgg ttgggagtgg   3120

tggaaattgg aaggatacca ggaggtattt gggaaggcca atggcgtggc tcctttgagg   3180

aaataaaaca ctaagcatga aaaaaaaaaa aaaaaaaaa                           3219
```

<210> SEQ ID NO 77
<211> LENGTH: 43
<212> TYPE: DNA
<213> ORGANISM: Artificial Sequence
<220> FEATURE:
<223> OTHER INFORMATION: Primers

<400> SEQUENCE: 77

```
gcgtaatacg actcactata ggggcaggcc cagcccatcc cct                        43
```

<210> SEQ ID NO 78
<211> LENGTH: 43
<212> TYPE: DNA
<213> ORGANISM: Artificial Sequence
<220> FEATURE:
<223> OTHER INFORMATION: Primers

<400> SEQUENCE: 78
gcgtaatacg actcactata ggctcactcg ccttcgagag ata 43

<210> SEQ ID NO 79
<211> LENGTH: 43
<212> TYPE: DNA
<213> ORGANISM: Artificial Sequence
<220> FEATURE:
<223> OTHER INFORMATION: Primers

<400> SEQUENCE: 79
gcgtaatacg actcactata ggcttgctag gagaagggaa gac 43

<210> SEQ ID NO 80
<211> LENGTH: 43
<212> TYPE: DNA
<213> ORGANISM: Artificial Sequence
<220> FEATURE:
<223> OTHER INFORMATION: Primers

<400> SEQUENCE: 80
gcgtaatacg actcactata ggaaggatac ccagaaccct cac 43

<210> SEQ ID NO 81
<211> LENGTH: 43
<212> TYPE: DNA
<213> ORGANISM: Artificial Sequence
<220> FEATURE:
<223> OTHER INFORMATION: Primers

<400> SEQUENCE: 81
gcgtaatacg actcactata gggagatcag gtccgaaatg ctg 43

<210> SEQ ID NO 82
<211> LENGTH: 43
<212> TYPE: DNA
<213> ORGANISM: Artificial Sequence
<220> FEATURE:
<223> OTHER INFORMATION: Primers

<400> SEQUENCE: 82
gcgtaatacg actcactata ggccagagaa ctttgggtac ctg 43

<210> SEQ ID NO 83
<211> LENGTH: 43
<212> TYPE: DNA
<213> ORGANISM: Artificial Sequence
<220> FEATURE:
<223> OTHER INFORMATION: Primers

<400> SEQUENCE: 83
gcgtaatacg actcactata gggtgatatt ctcatgcctg gac 43

<210> SEQ ID NO 84
<211> LENGTH: 43
<212> TYPE: DNA
<213> ORGANISM: Artificial Sequence
<220> FEATURE:
<223> OTHER INFORMATION: Primers

<400> SEQUENCE: 84
gcgtaatacg actcactata gggggcggaa acagcatttg cct 43

<210> SEQ ID NO 85
<211> LENGTH: 43
<212> TYPE: DNA
<213> ORGANISM: Artificial Sequence
<220> FEATURE:
<223> OTHER INFORMATION: Primers

<400> SEQUENCE: 85
gcgtaatacg actcactata ggcaatagac tcctgggatg ggg 43

<210> SEQ ID NO 86
<211> LENGTH: 43
<212> TYPE: DNA
<213> ORGANISM: Artificial Sequence
<220> FEATURE:
<223> OTHER INFORMATION: Primers

<400> SEQUENCE: 86
gcgtaatacg actcactata ggccccagtc tggcttggga gat 43

<210> SEQ ID NO 87
<211> LENGTH: 43
<212> TYPE: DNA
<213> ORGANISM: Artificial Sequence
<220> FEATURE:
<223> OTHER INFORMATION: Primers

<400> SEQUENCE: 87
gcgtaatacg actcactata gggttggagt catcatctct acc 43

<210> SEQ ID NO 88
<211> LENGTH: 43
<212> TYPE: DNA
<213> ORGANISM: Artificial Sequence
<220> FEATURE:
<223> OTHER INFORMATION: Primers

<400> SEQUENCE: 88
gcgtaatacg actcactata ggctcttact tactctgtat ctc 43

<210> SEQ ID NO 89
<211> LENGTH: 43
<212> TYPE: DNA
<213> ORGANISM: Artificial Sequence
<220> FEATURE:
<223> OTHER INFORMATION: Primers

<400> SEQUENCE: 89
gcgtaatacg actcactata gggtaatcga agtacgaaga gga 43

<210> SEQ ID NO 90
<211> LENGTH: 43
<212> TYPE: DNA
<213> ORGANISM: Artificial Sequence
<220> FEATURE:
<223> OTHER INFORMATION: Primers

<400> SEQUENCE: 90
gcgtaatacg actcactata gggactccac gtagcatgtc aag 43

<210> SEQ ID NO 91
<211> LENGTH: 43
<212> TYPE: DNA
<213> ORGANISM: Artificial Sequence
<220> FEATURE:
<223> OTHER INFORMATION: Primers

<400> SEQUENCE: 91
gcgtaatacg actcactata gggccagcaa gaacgaagca cag 43

<210> SEQ ID NO 92
<211> LENGTH: 43
<212> TYPE: DNA
<213> ORGANISM: Artificial Sequence
<220> FEATURE:
<223> OTHER INFORMATION: Primers

<400> SEQUENCE: 92
gcgtaatacg actcactata ggagattcct ttttctaacc tgt 43

<210> SEQ ID NO 93
<211> LENGTH: 43
<212> TYPE: DNA
<213> ORGANISM: Artificial Sequence
<220> FEATURE:
<223> OTHER INFORMATION: Primers

<400> SEQUENCE: 93
gcgtaatacg actcactata ggagtacctt aaaggacaag acc 43

<210> SEQ ID NO 94
<211> LENGTH: 43
<212> TYPE: DNA
<213> ORGANISM: Artificial Sequence
<220> FEATURE:
<223> OTHER INFORMATION: Primers

<400> SEQUENCE: 94
gcgtaatacg actcactata ggcacttctc tggagatcca gca 43

<210> SEQ ID NO 95
<211> LENGTH: 43
<212> TYPE: DNA
<213> ORGANISM: Artificial Sequence
<220> FEATURE:
<223> OTHER INFORMATION: Primers

<400> SEQUENCE: 95
gcgtaatacg actcactata ggcttgaacc caggaagcgg ggt 43

<210> SEQ ID NO 96
<211> LENGTH: 43
<212> TYPE: DNA
<213> ORGANISM: Artificial Sequence
<220> FEATURE:
<223> OTHER INFORMATION: Primers

<400> SEQUENCE: 96
gcgtaatacg actcactata ggggccaagt gggaacccag gag 43

<210> SEQ ID NO 97
<211> LENGTH: 43
<212> TYPE: DNA
<213> ORGANISM: Artificial Sequence
<220> FEATURE:
<223> OTHER INFORMATION: Primers

<400> SEQUENCE: 97
gcgtaatacg actcactata gggtctaact gtatgtcaac ccc 43

<210> SEQ ID NO 98
<211> LENGTH: 43
<212> TYPE: DNA
<213> ORGANISM: Artificial Sequence
<220> FEATURE:
<223> OTHER INFORMATION: Primers

<400> SEQUENCE: 98
gcgtaatacg actcactata ggccctgagg agccaggagc ccg 43

<210> SEQ ID NO 99
<211> LENGTH: 43
<212> TYPE: DNA
<213> ORGANISM: Artificial Sequence
<220> FEATURE:
<223> OTHER INFORMATION: Primers

<400> SEQUENCE: 99
gcgtaatacg actcactata ggggcacttt tatgaccacc cat 43

<210> SEQ ID NO 100
<211> LENGTH: 43
<212> TYPE: DNA
<213> ORGANISM: Artificial Sequence
<220> FEATURE:
<223> OTHER INFORMATION: Primers

<400> SEQUENCE: 100
gcgtaatacg actcactata ggcctaggca tcaccttgtt tga 43

<210> SEQ ID NO 101
<211> LENGTH: 43
<212> TYPE: DNA
<213> ORGANISM: Artificial Sequence
<220> FEATURE:
<223> OTHER INFORMATION: Primers

<400> SEQUENCE: 101
gcgtaatacg actcactata gggtgggatg ccagagctgg atc 43

<210> SEQ ID NO 102
<211> LENGTH: 43
<212> TYPE: DNA
<213> ORGANISM: Artificial Sequence
<220> FEATURE:
<223> OTHER INFORMATION: Primers

<400> SEQUENCE: 102
gcgtaatacg actcactata ggggaggaac caccacagca gtg 43

<210> SEQ ID NO 103
<211> LENGTH: 43
<212> TYPE: DNA
<213> ORGANISM: Artificial Sequence
<220> FEATURE:
<223> OTHER INFORMATION: Primers

<400> SEQUENCE: 103
gcgtaatacg actcactata gggccttata ggcatgtaga gac 43

<210> SEQ ID NO 104
<211> LENGTH: 43
<212> TYPE: DNA
<213> ORGANISM: Artificial Sequence
<220> FEATURE:
<223> OTHER INFORMATION: Primers

<400> SEQUENCE: 104
gcgtaatacg actcactata ggccaagcaa aatgaagttg atc 43

<210> SEQ ID NO 105
<211> LENGTH: 43
<212> TYPE: DNA
<213> ORGANISM: Artificial Sequence
<220> FEATURE:
<223> OTHER INFORMATION: Primers

<400> SEQUENCE: 105
gcgtaatacg actcactata gggaggcaag gcggaggggc cag 43

<210> SEQ ID NO 106
<211> LENGTH: 43
<212> TYPE: DNA
<213> ORGANISM: Artificial Sequence
<220> FEATURE:
<223> OTHER INFORMATION: Primers

<400> SEQUENCE: 106
gcgtaatacg actcactata gggagcagtc atggccctga ggt 43

<210> SEQ ID NO 107
<211> LENGTH: 43
<212> TYPE: DNA
<213> ORGANISM: Artificial Sequence
<220> FEATURE:
<223> OTHER INFORMATION: Primers

<400> SEQUENCE: 107
gcgtaatacg actcactata gggtcatagt cattggaact tgc 43

<210> SEQ ID NO 108
<211> LENGTH: 43
<212> TYPE: DNA
<213> ORGANISM: Artificial Sequence
<220> FEATURE:
<223> OTHER INFORMATION: Primers

<400> SEQUENCE: 108
gcgtaatacg actcactata ggggttgtaa actgaatgct gtg 43

<210> SEQ ID NO 109
<211> LENGTH: 43
<212> TYPE: DNA
<213> ORGANISM: Artificial Sequence
<220> FEATURE:
<223> OTHER INFORMATION: Primers

<400> SEQUENCE: 109
gcgtaatacg actcactata ggcctcactc cgccttttca aat 43

<210> SEQ ID NO 110
<211> LENGTH: 43
<212> TYPE: DNA
<213> ORGANISM: Artificial Sequence
<220> FEATURE:
<223> OTHER INFORMATION: Primers

<400> SEQUENCE: 110
gcgtaatacg actcactata gggtcccagt actgaaagaa cat 43

<210> SEQ ID NO 111
<211> LENGTH: 43
<212> TYPE: DNA
<213> ORGANISM: Artificial Sequence
<220> FEATURE:
<223> OTHER INFORMATION: Primers

<400> SEQUENCE: 111
gcgtaatacg actcactata gggagggaaa gtagcctcag gca 43

<210> SEQ ID NO 112
<211> LENGTH: 43
<212> TYPE: DNA
<213> ORGANISM: Artificial Sequence
<220> FEATURE:
<223> OTHER INFORMATION: Primers

<400> SEQUENCE: 112
gcgtaatacg actcactata ggcagcaagt aagcagaaga ctc 43

<210> SEQ ID NO 113
<211> LENGTH: 43
<212> TYPE: DNA
<213> ORGANISM: Artificial Sequence
<220> FEATURE:
<223> OTHER INFORMATION: Primers

<400> SEQUENCE: 113
gcgtaatacg actcactata gggacaagag gagggggcgt gca 43

<210> SEQ ID NO 114
<211> LENGTH: 43
<212> TYPE: DNA
<213> ORGANISM: Artificial Sequence
<220> FEATURE:
<223> OTHER INFORMATION: Primers

<400> SEQUENCE: 114
gcgtaatacg actcactata gggggtacct accctcatga cct 43

<210> SEQ ID NO 115
<211> LENGTH: 43
<212> TYPE: DNA
<213> ORGANISM: Artificial Sequence
<220> FEATURE:
<223> OTHER INFORMATION: Primers

<400> SEQUENCE: 115
gcgtaatacg actcactata ggcggatcca gatctgtgtg tgt 43

<210> SEQ ID NO 116
<211> LENGTH: 43
<212> TYPE: DNA
<213> ORGANISM: Artificial Sequence
<220> FEATURE:
<223> OTHER INFORMATION: Primers

<400> SEQUENCE: 116
gcgtaatacg actcactata gggtctccca gggcacaagc tcc 43

<210> SEQ ID NO 117
<211> LENGTH: 43
<212> TYPE: DNA
<213> ORGANISM: Artificial Sequence
<220> FEATURE:
<223> OTHER INFORMATION: Primers

<400> SEQUENCE: 117
gcgtaatacg actcactata gggcctgaag ctgggccctc act 43

<210> SEQ ID NO 118
<211> LENGTH: 43
<212> TYPE: DNA
<213> ORGANISM: Artificial Sequence
<220> FEATURE:
<223> OTHER INFORMATION: Primers

<400> SEQUENCE: 118
gcgtaatacg actcactata gggccccttt ctgtaatagt gaa 43

<210> SEQ ID NO 119
<211> LENGTH: 43
<212> TYPE: DNA
<213> ORGANISM: Artificial Sequence
<220> FEATURE:
<223> OTHER INFORMATION: Primers

<400> SEQUENCE: 119
gcgtaatacg actcactata ggttgggaga cacatgtggg aac 43

<210> SEQ ID NO 120
<211> LENGTH: 43
<212> TYPE: DNA
<213> ORGANISM: Artificial Sequence
<220> FEATURE:
<223> OTHER INFORMATION: Primers

<400> SEQUENCE: 120
gcgtaatacg actcactata gggatgtctc ctcccttagt ctc 43

<210> SEQ ID NO 121
<211> LENGTH: 43
<212> TYPE: DNA
<213> ORGANISM: Artificial Sequence
<220> FEATURE:
<223> OTHER INFORMATION: Primers

<400> SEQUENCE: 121
gcgtaatacg actcactata ggaggggagg ggaatgactt atg 43

<210> SEQ ID NO 122
<211> LENGTH: 43
<212> TYPE: DNA
<213> ORGANISM: Artificial Sequence
<220> FEATURE:
<223> OTHER INFORMATION: Primers

<400> SEQUENCE: 122
gcgtaatacg actcactata ggggagtggg caaggtatgt aca 43

<210> SEQ ID NO 123
<211> LENGTH: 43
<212> TYPE: DNA
<213> ORGANISM: Artificial Sequence
<220> FEATURE:
<223> OTHER INFORMATION: Primers

<400> SEQUENCE: 123
gcgtaatacg actcactata ggaaccccac ccacggaaca act 43

<210> SEQ ID NO 124
<211> LENGTH: 43
<212> TYPE: DNA
<213> ORGANISM: Artificial Sequence
<220> FEATURE:
<223> OTHER INFORMATION: Primers

<400> SEQUENCE: 124
gcgtaatacg actcactata ggctctaggg agacagtaaa gta 43

<210> SEQ ID NO 125
<211> LENGTH: 43
<212> TYPE: DNA
<213> ORGANISM: Artificial Sequence
<220> FEATURE:
<223> OTHER INFORMATION: Primers

<400> SEQUENCE: 125
gcgtaatacg actcactata ggcaggctgg gtgggtgtta gga 43

<210> SEQ ID NO 126
<211> LENGTH: 43
<212> TYPE: DNA
<213> ORGANISM: Artificial Sequence
<220> FEATURE:
<223> OTHER INFORMATION: Primers

<400> SEQUENCE: 126
gcgtaatacg actcactata ggctgattct gccctattgt tca 43

<210> SEQ ID NO 127
<211> LENGTH: 43
<212> TYPE: DNA
<213> ORGANISM: Artificial Sequence
<220> FEATURE:
<223> OTHER INFORMATION: Primers

<400> SEQUENCE: 127
gcgtaatacg actcactata ggagaagatg gaggttatgg agt 43

<210> SEQ ID NO 128
<211> LENGTH: 43
<212> TYPE: DNA
<213> ORGANISM: Artificial Sequence
<220> FEATURE:
<223> OTHER INFORMATION: Primers

<400> SEQUENCE: 128
gcgtaatacg actcactata ggacatggca gacaatcaag agt 43

<210> SEQ ID NO 129
<211> LENGTH: 43
<212> TYPE: DNA
<213> ORGANISM: Artificial Sequence
<220> FEATURE:
<223> OTHER INFORMATION: Primers

<400> SEQUENCE: 129
gcgtaatacg actcactata ggaggaactt gatcatactg agg 43

<210> SEQ ID NO 130
<211> LENGTH: 43
<212> TYPE: DNA
<213> ORGANISM: Artificial Sequence
<220> FEATURE:
<223> OTHER INFORMATION: Primers

<400> SEQUENCE: 130
gcgtaatacg actcactata gggctatatg tgaaagagga ggg 43

<210> SEQ ID NO 131
<211> LENGTH: 43
<212> TYPE: DNA
<213> ORGANISM: Artificial Sequence
<220> FEATURE:
<223> OTHER INFORMATION: Primers

<400> SEQUENCE: 131
gcgtaatacg actcactata gggcacagtc ctataaggta gag 43

<210> SEQ ID NO 132
<211> LENGTH: 43
<212> TYPE: DNA
<213> ORGANISM: Artificial Sequence
<220> FEATURE:
<223> OTHER INFORMATION: Primers

<400> SEQUENCE: 132
gcgtaatacg actcactata gggatcatct gcctccacgg cac 43

<210> SEQ ID NO 133
<211> LENGTH: 43
<212> TYPE: DNA
<213> ORGANISM: Artificial Sequence
<220> FEATURE:
<223> OTHER INFORMATION: Primers

<400> SEQUENCE: 133
gcgtaatacg actcactata ggatggtgct atttcacatt ctc 43

<210> SEQ ID NO 134
<211> LENGTH: 43
<212> TYPE: DNA
<213> ORGANISM: Artificial Sequence
<220> FEATURE:
<223> OTHER INFORMATION: Primers

<400> SEQUENCE: 134
gcgtaatacg actcactata ggagcaagat ttagctggat ctt 43

<210> SEQ ID NO 135
<211> LENGTH: 43
<212> TYPE: DNA
<213> ORGANISM: Artificial Sequence
<220> FEATURE:
<223> OTHER INFORMATION: Primers

<400> SEQUENCE: 135
gcgtaatacg actcactata ggagcctggc tgagctactt ttc 43

<210> SEQ ID NO 136
<211> LENGTH: 43
<212> TYPE: DNA
<213> ORGANISM: Artificial Sequence
<220> FEATURE:
<223> OTHER INFORMATION: Primers

<400> SEQUENCE: 136
gcgtaatacg actcactata gggaagagcg gtgattcaga act 43

<210> SEQ ID NO 137
<211> LENGTH: 43
<212> TYPE: DNA
<213> ORGANISM: Artificial Sequence
<220> FEATURE:
<223> OTHER INFORMATION: Primers

<400> SEQUENCE: 137
gcgtaatacg actcactata ggtctaagga cagatgttgg tga 43

<210> SEQ ID NO 138
<211> LENGTH: 43
<212> TYPE: DNA
<213> ORGANISM: Artificial Sequence
<220> FEATURE:
<223> OTHER INFORMATION: Primers

<400> SEQUENCE: 138
gcgtaatacg actcactata ggaaccatga aaggagatgg gag 43

<210> SEQ ID NO 139
<211> LENGTH: 43
<212> TYPE: DNA
<213> ORGANISM: Artificial Sequence
<220> FEATURE:
<223> OTHER INFORMATION: Primers

<400> SEQUENCE: 139
gcgtaatacg actcactata ggtgacagag tttaattggc agt 43

<210> SEQ ID NO 140
<211> LENGTH: 43
<212> TYPE: DNA
<213> ORGANISM: Artificial Sequence
<220> FEATURE:
<223> OTHER INFORMATION: Primers

<400> SEQUENCE: 140
gcgtaatacg actcactata ggcagaggca ctttgcggga aac 43

<210> SEQ ID NO 141
<211> LENGTH: 43
<212> TYPE: DNA
<213> ORGANISM: Artificial Sequence
<220> FEATURE:
<223> OTHER INFORMATION: Primers

<400> SEQUENCE: 141
gcgtaatacg actcactata gggactaagt ctcgttctgt tgc 43

<210> SEQ ID NO 142
<211> LENGTH: 43
<212> TYPE: DNA
<213> ORGANISM: Artificial Sequence
<220> FEATURE:
<223> OTHER INFORMATION: Primers

<400> SEQUENCE: 142
gcgtaatacg actcactata gggcttcttg tacctgctac taa 43

<210> SEQ ID NO 143
<211> LENGTH: 43
<212> TYPE: DNA
<213> ORGANISM: Artificial Sequence
<220> FEATURE:
<223> OTHER INFORMATION: Primers

<400> SEQUENCE: 143
gcgtaatacg actcactata ggtctactcc ctcatcatct gga 43

<210> SEQ ID NO 144
<211> LENGTH: 43
<212> TYPE: DNA
<213> ORGANISM: Artificial Sequence
<220> FEATURE:
<223> OTHER INFORMATION: Primers

<400> SEQUENCE: 144
gcgtaatacg actcactata ggggaatata gccagccaca tgg 43

<210> SEQ ID NO 145
<211> LENGTH: 43
<212> TYPE: DNA
<213> ORGANISM: Artificial Sequence
<220> FEATURE:
<223> OTHER INFORMATION: Primers

<400> SEQUENCE: 145
gcgtaatacg actcactata gggtgcttag gaagtggggc cag 43

<210> SEQ ID NO 146
<211> LENGTH: 43
<212> TYPE: DNA
<213> ORGANISM: Artificial Sequence
<220> FEATURE:
<223> OTHER INFORMATION: Primers

<400> SEQUENCE: 146
gcgtaatacg actcactata ggtcttgggc cataatttta cca 43

<210> SEQ ID NO 147
<211> LENGTH: 43
<212> TYPE: DNA
<213> ORGANISM: Artificial Sequence
<220> FEATURE:
<223> OTHER INFORMATION: Primers

<400> SEQUENCE: 147
gcgtaatacg actcactata gggtaaagac gggatttcgc cat 43

<210> SEQ ID NO 148
<211> LENGTH: 43
<212> TYPE: DNA
<213> ORGANISM: Artificial Sequence
<220> FEATURE:
<223> OTHER INFORMATION: Primers

<400> SEQUENCE: 148
gcgtaatacg actcactata ggtagttact ggtctccact gcc 43

<210> SEQ ID NO 149
<211> LENGTH: 43
<212> TYPE: DNA
<213> ORGANISM: Artificial Sequence
<220> FEATURE:
<223> OTHER INFORMATION: Primers

<400> SEQUENCE: 149
gcgtaatacg actcactata ggctgtacac acttattctc caa 43

<210> SEQ ID NO 150
<211> LENGTH: 43
<212> TYPE: DNA
<213> ORGANISM: Artificial Sequence
<220> FEATURE:
<223> OTHER INFORMATION: Primers

<400> SEQUENCE: 150
gcgtaatacg actcactata ggatgaatga gttaatggtg ggc 43

<210> SEQ ID NO 151
<211> LENGTH: 43
<212> TYPE: DNA
<213> ORGANISM: Artificial Sequence
<220> FEATURE:
<223> OTHER INFORMATION: Primers

<400> SEQUENCE: 151
gcgtaatacg actcactata ggcaaggccg ccgtcgttgc cga 43

<210> SEQ ID NO 152
<211> LENGTH: 43
<212> TYPE: DNA
<213> ORGANISM: Artificial Sequence
<220> FEATURE:
<223> OTHER INFORMATION: Primers

<400> SEQUENCE: 152
gcgtaatacg actcactata gggaccaggg ctggagaagt cac 43

<210> SEQ ID NO 153
<211> LENGTH: 43
<212> TYPE: DNA
<213> ORGANISM: Artificial Sequence
<220> FEATURE:
<223> OTHER INFORMATION: Primers

<400> SEQUENCE: 153
gcgtaatacg actcactata ggtgtaggtg aactaactgc ccc 43

<210> SEQ ID NO 154
<211> LENGTH: 43
<212> TYPE: DNA
<213> ORGANISM: Artificial Sequence
<220> FEATURE:
<223> OTHER INFORMATION: Primers

<400> SEQUENCE: 154
gcgtaatacg actcactata gggcatgagc caccatgcct ggc 43

<210> SEQ ID NO 155
<211> LENGTH: 43
<212> TYPE: DNA
<213> ORGANISM: Artificial Sequence
<220> FEATURE:
<223> OTHER INFORMATION: Primers

<400> SEQUENCE: 155
gcgtaatacg actcactata ggtaagtccc actccactcc aca 43

<210> SEQ ID NO 156
<211> LENGTH: 43
<212> TYPE: DNA
<213> ORGANISM: Artificial Sequence
<220> FEATURE:
<223> OTHER INFORMATION: Primers

<400> SEQUENCE: 156
gcgtaatacg actcactata ggttagccag gcacggtggt gca 43

<210> SEQ ID NO 157
<211> LENGTH: 43
<212> TYPE: DNA
<213> ORGANISM: Artificial Sequence
<220> FEATURE:
<223> OTHER INFORMATION: Primers

<400> SEQUENCE: 157
gcgtaatacg actcactata gggtggatag ctagagggca cac 43

-continued

```
<210> SEQ ID NO 158
<211> LENGTH: 43
<212> TYPE: DNA
<213> ORGANISM: Artificial Sequence
<220> FEATURE:
<223> OTHER INFORMATION: Primers

<400> SEQUENCE: 158

gcgtaatacg actcactata gggtctggaa aggaggtagc acc                    43


<210> SEQ ID NO 159
<211> LENGTH: 43
<212> TYPE: DNA
<213> ORGANISM: Artificial Sequence
<220> FEATURE:
<223> OTHER INFORMATION: Primers

<400> SEQUENCE: 159

gcgtaatacg actcactata ggatgggtct tgggtctgcc cag                    43


<210> SEQ ID NO 160
<211> LENGTH: 43
<212> TYPE: DNA
<213> ORGANISM: Artificial Sequence
<220> FEATURE:
<223> OTHER INFORMATION: Primers

<400> SEQUENCE: 160

gcgtaatacg actcactata gggtgtctgt gaagggcccc aag                    43
```

INHIBITION OF MICROTUBULE PROTRUSION IN CANCER CELLS

The present invention is a USC §371 national stage filing of PCT International Application Serial No. PCT/US2007/063566, filed Mar. 8, 2007, which claims priority to U.S. Provisional Patent Application Ser. No. 60/780,468, filed Mar. 8, 2006, both of which are incorporated by reference herein in their entirety.

STATEMENT REGARDING FEDERALLY SPONSORED RESEARCH OR DEVELOPMENT

The present invention was developed at least in part with funds from the National Cancer Institute Howard Temin Career Award (K01-CA096555-01A1) and from the U.S. Army Grant No. W81XWH-05-1-0423. The United States Government has certain rights in the invention.

FIELD OF THE INVENTION

The present invention generally concerns at least the fields of cell biology, molecular biology, cancer, and medicine. In particular aspects, the present invention concerns the field of cancer therapy and/or prevention.

BACKGROUND OF THE INVENTION

Breast tumor cells can disseminate prior to significant primary tumor growth and remain dormant in distant tissues for extended periods of time (Naumov, MacDonald et al. 2001; Naumov, MacDonald et al. 2002; Schmidt-Kittler, Ragg et al. 2003). Survival, invasion and reemergence of such disseminated cells are primary determinants of tumor recurrence and patient death (Chambers, Groom et al. 2002). Detachment of epithelial cells from the extracellular matrix of their organ of origin causes cell rounding that leads rapidly to apoptotic cell death, a principle which is thought to limit metastatic spread (Frisch and Francis 1994; Reed 2003). In mammary epithelial cells, we have shown that apoptotic resistance allows cells to survive rounding, but additional genetic mutations are required for active tumor growth (Martin and Leder 2001; Martin, Ridgeway et al. 2004; Pinkas, Martin et al. 2004). Resistance to apoptosis by overexpression of survival proteins, like Bcl-2, prevents cell death during dissemination, but cell cycle arrest can still occur through activation of p53 (Nikiforov, Hagen et al. 1996; Nikiforov, Kwek et al. 1997). In solid tumors like breast cancer, detached cells generally remain arrested and must adhere to extracellular matrix in distant tissues to reinitiate growth (Naumov, MacDonald et al. 2001; Naumov, MacDonald et al. 2002). So while apoptotic resistance can promote extended bloodborne survival, additional mechanisms are required for tumor cells to escape blood vessels and successfully colonize distant tissues. (Naumov, MacDonald et al. 2001).

In vivo microscopy recently demonstrated that bloodborne tumor cells depend on tubulin polymerization to attach to the walls of capillary blood vessels (Korb, Schluter et al. 2004). However, any specific role for microtubules in this process remains unclear. Surprisingly, this recent study also showed that inhibiting actin polymerization greatly increased binding of tumor cells to blood vessel walls, even though actin depolymerization inhibits the actin-based invadopodia and podosomes that are well-known to affect the invasion of adherent tumor cells (Korb, Schluter et al. 2004). Bloodborne tumor cells therefore attach to capillary vessel walls via a cytoskeletal mechanism that is distinct from that of adherent cells, and is currently not well-characterized.

Recent genomic studies indicate that breast tumor cells may disseminate prior to significant primary tumor growth and remain dormant in distant tissues for extended periods of time (Schmidt-Kittler et al., 2003). Detachment of epithelial cells from the extracellular matrix of their organ of origin leads rapidly to apoptotic cell death, a principle which is thought to limit metastatic spread (Valentijn et al., 2004; Reddig and Juliano, 2005; Frisch and Francis, 1994). In mammary epithelial cells, apoptotic resistance will promote the survival of detached cells, but additional genetic mutations are required for active tumor growth (Pinkas et al., 2004; Martin et al., 2004). Resistance to apoptosis by overexpression of survival proteins, like Bcl-2, prevents cell death during dissemination, but cell cycle arrest can still occur through activation of p53 (Nikiforov et al., 1996; Nikiforov et al., 1997). Since these cells would survive but fail to actively grow, apoptotic resistance is one possible determinant of tumor dormancy (Townson et al., 2003).

However, evidence is accumulating that resistance to apoptotic cell death does not necessarily prevent early stress responses from occurring in cells. The apoptotically-resistant MDA-MB-231 cell line responds to hypoxic environments with increased invasiveness and the upregulation of cell surface $\alpha6\beta4$ integrin (Yoon et al., 2005). Lymphocytic cell lines that overexpress Bcl-2 still generate reactive oxygen species in response to TNF-$\alpha$, even though the later events in cell death are prevented (Liu et al., 2005). It is therefore important to consider whether apoptotically-resistant cells will truly remain dormant during the challenges of metastasis, or if they persistently respond to the challenging environment even though they are under a reduced threat of death.

Detachment of many adherent cell types from the extracellular matrix results in apoptotic cell death that arises from disrupted cell shape (see Valentijn et al, 2004; Reddig and Juliano, 2005 for review). In attached cells, tension generated by attachment of actin microfilaments to focal adhesions is counteracted by expansion of cytoplasmic microtubules to stabilize cell shape in a process termed tensegrity (Ingber, 2002; Wang et al., 2001). Disruption of this balance either by affecting cell attachment sites or directly inhibiting cytoskeletal structure induces rapid cell death (Chen et al., 1997; Martin and Leder, 2001). In order to survive detachment, epithelial cells must either avoid apoptosis or quickly reattach to adopt an appropriate cell shape. While tumor cells often develop resistance to apoptotic cell death, this phenomenon is rare in untransformed cells (Reed, 1999).

The present invention provides a long-felt solution to treating cancer, for example by preventing or reducing metastasis by targeting particular microtubule-associated structures heretofore unknown in the art.

SUMMARY OF EMBODIMENTS OF THE INVENTION

The present invention is directed to a system, methods, and compositions that relate to cancer therapy. In particular, embodiments of the present invention concern therapy that is related to microtubule protrusions in cancer cells, including in metastatic cancer cells, for example. In general embodiments of the invention, metastasis is inhibited or at least reduced in part by inhibition of the microtubule protrusion, for example by inhibition of a cellular mechanism required for establishment of a distant tumor.

It is described herein that mammary epithelial cell lines generate long and dynamic microtubule-driven protrusions of the plasma membrane after detachment. We also determine that detachment produces rapid detyrosination of α-tubulin, and the concentration of detyrosinated tubulin in protrusions. Full length α-tubulin contains a tyrosine residue at its c-terminus, and is termed Tyr-tubulin. Cleavage of this c-terminal tyrosine by a tubulin carboxypeptidase exposes a glutamic acid residue, yielding a detyrosinated form (Glu-tubulin) (Argarana, Arce et al. 1977; Argarana, Barra et al. 1978). Although this α-tubulin modification has been appreciated for thirty years, the identity of the gene encoding tubulin carboxypeptidase remains unknown. Glu-tubulin is post-translationally converted back to Tyr-tubulin, by a tubulin tyrosine ligase (TTL), which has recently been cloned in mice and humans (Erck, MacLeod et al. 2003). While microtubules containing Tyr-tubulin have a relatively short half-life, measured in minutes, Glu-tubulin is enriched in a more stable subset of microtubules (Webster, Gundersen et al. 1987). Microtubules containing Glu-tubulin can persist for hours and have been observed to remain for as long as 16 hours in nondividing cells (Webster, Gundersen et al. 1987). In breast tumor samples, increased levels of Glu-tubulin are associated with poor patient prognosis and an increased risk of cancer-related complications, but the mechanism for this effect is still unknown (Mialhe, Lafanechere et al. 2001).

The present invention relates to microtubule-based protrusions that promote reattachment of mammary epithelial cells to surfaces and each other, and may therefore allow detached cells to escape apoptosis by reattaching. Since this response persists in cells overexpressing Bcl-2 or Bcl-xL, it may promote the dormant dissemination of apoptotically-resistant tumor cells, even though they would not reinitiate growth until a much later time. Our data indicate that these microtubule protrusions do not necessarily originate from a tumor-specific mutation, since they are also observed in nontumorigenic mammary epithelial cell lines of both human and mouse origin. However, the persistence of this inherent microtubule response in apoptotically-resistant cells could have important consequences for the ability of disseminated tumor cells to efficiently adhere to new sites. The increased levels of Glu-tubulin upon detachment and its concentration in plasma membrane protrusions provide novel mechanisms to initiate microtubule-based tumor cell adhesion in blood vessels, and may explain why increased levels of Glu-tubulin in breast tumors predict poor patient survival.

The present invention generally concerns the previously unknown phenomenon that detached tumor cells generate microtubule protrusions that increase their ability to reattach to each other and/or surfaces. Because tumor cells become detached during spread through the blood or lymphatics, the generation of these protrusions is important for the ability of the tumor cells to spread metastatically to distant tissues and/or organs, in specific embodiments of the invention. In additional embodiments, such microtubule protrusions act to enhance tumor cell adhesion to vessel walls and/or allow tumor cells to avoid being crushed by size-restriction in capillaries. These protrusions increase in number and size per cell in more metastatic breast tumor cell lines. Protrusions also occur with a significantly higher frequency in populations of breast tumor cells with greater metastatic potential. In particular, death of cancer patients is most often caused by metastatic spread of the primary tumor through the bloodstream. However, large tumor cells are efficiently killed by shearing when they are pushed through small-diameter capillaries by blood pressure. The microtubule protrusions, in specific embodiments, help metastatic tumor cells avoid death by adhering to vessel walls and/or bracing against them before the size of the capillary becomes limiting. Inhibition of the function of these microtubule protrusions and/or inhibition of their production, for example, allows metastatic tumor cells to have a greater opportunity to be efficiently killed, such as by shearing through capillary beds, for example. In specific embodiments, the invention focuses on the role of these microtubule protrusions in the trapping and survival of tumor cells in distant capillary beds during metastatic spread.

Thus, in particular aspects of the invention, these microtubule protrusions are inhibited by one or more agents to specifically reduce the metastatic spread of tumors and tumor cells therein. In particular embodiments, an agent is delivered to an individual having cancer cells with one or more of the protrusions or is delivered to an individual at high risk for or susceptible to or suspected of having cancer cells with one or more of the protrusions. The agent is delivered such that it associates with at least one protrusion and thereby inhibits the function of the protrusion, degrades the protrusion, inhibits the activity of the protrusion, promotes degradation (such as an agent that promotes, facilitates or enhances ATP hydrolysis, for example) and/or prevents the protrusion from extending in length, for example. In alternative embodiments, the agent is delivered such that it associates with the cell and thereby inhibits the function of the protrusion, degrades the protrusion, inhibits the activity of the protrusion, promotes the degradation (such as an agent that facilitates or enhances ATP hydrolysis), and/or prevents the protrusion from extending in length. In additional or alternative embodiments, the agent may prevent the protrusion from being produced and/or prevent the protrusion from protruding (which may be referred to as extending) from the cell. The protrusion may be affected prior to extending from the cell, subsequent to extending from the cell, or is effective in either case. In certain aspects, the agent is selectively cytotoxic to detached cells, and in particular embodiments the agent kills apoptotic-resistant cells.

In embodiments of the invention, one or more components of a microtubule protrusion are inhibited, directly or indirectly. In particular aspects of the invention, the components comprise Glu-tubulin, kinesin and/or vimentin. Therefore, in specific embodiments of methods of the invention, one targets Glu-tubulin, kinesin and/or vimentin to inhibit one or more microtubule protrusions, for example from a cancer cell. In certain embodiments, the protrusions may be targeted by inhibiting Glu-tubulin, such as by one or more of the following, for example: 1) increasing activity and/or expression of tubulin tyrosine ligase (TTL), which postranslationally converts Glu-tubulin back to Tyr-tubulin; 2) inhibition of a carboxypeptidase that produces Glu-tubulin from Tyr-tubulin, such as by delivery of okadaic acid, 3-nitrotyrosine, 1-nor-okadone, Cantharidin, Phoslactomycin B (Fostriecin), DL-benzylsuccinic acid, Sodium orthovanadate, or a combination thereof, and in specific embodiments the carboxypeptidase is hAGBL3 (Rodriguez de la Vega et al., 2007). In certain embodiments, the protrusions may be targeted by inhibiting vimentin, such as by one or more of the following, for example: a dominant negative mutant, such as R113C and/or ΔC2B mutants; antisense or siRNA; and/or calyculin-A. In other embodiments, the protrusions may be targeted by inhibiting kinesin, such as by one or more of the following, for example: siRNA, including KIF5b siRNA, for example, lidocaine, and/or tetracaine.

In addition to, or alternative to, embodiments wherein one or more structural components of the microtubule protrusions are targeted, a regulatory molecule may be targeted that affects indirectly or directly the structural content of the microtubules. In specific cases, GSK-3b is not a structural component of microtubule protrusion, but a regulatory molecule. By phosphorylating APC and preventing it from binding microtubules, GSK-3b promotes microtentacle formation, in certain embodiments, but would not be a structural component (like Glu-tubulin, vimentin or kinesin).

In particular aspects, APC is a structural component, for example one that restricts microtubule protrusion extension. In specific embodiments, an agent is employed that enhances function of APC, such as, for example, lysophosphatidic acid (LPA) that can enhance the ability of APC to capture microtubules (Wen et al., 2004); and/or inhibition of GSK-3b, which enhances the function of APC by preventing phosphorylation.

In particular aspects of the invention, one or more methods of the invention employ inhibitors of one or more components of the microtubule protrusions and/or inhibitors of regulatory molecules and/or agents that enhance reduction of microtubule protrusions, and such compounds are delivered to the individual before and/or during and/or after surgery to prevent escape of residual cells during the wound healing that follows surgery. In particular embodiments, reduction of these microtentacles prevents tumor cells from successfully navigating the bloodstream. This could occur by preventing any attachment to the blood vessel wall (keeping the cells from invading distant tissues) or by causing them to fragment when passing through capillaries, for example.

Thus, as described above, in certain aspects of the invention, detyrosinated microtubule protrusions in detached cells promote reattachment. In fact, it is determined by the inventors that nontumorigenic mammary epithelial cell lines generate long and dynamic microtubule-driven protrusions of the plasma membrane in response to detachment. These protrusions promote reattachment of cells to surfaces and each other, and may therefore allow detached cells to escape apoptosis. Since this response persists in cells overexpressing Bcl-2 or Bcl-xL, it indicates that disseminated apoptotically-resistant cells are not as dormant as previously suspected. The data indicate that these microtubule protrusions do not necessarily originate from a tumor-specific mutation, but nevertheless have important consequences for the ability of tumor cells to efficiently adhere to new sites, in certain embodiments of the invention.

Time-lapse video microscopy of detached mammary epithelial cells detected the extension of long, dynamic protrusions of the plasma membrane, and the present inventors have characterized the cytoskeletal mechanism underlying this novel observation. Nontumorigenic mammary epithelial cell lines of both human and mouse origin produce such protrusions, indicating that it is likely an inherent characteristic of the untransformed cells. This response may be relatively short-lived, in specific embodiments, since mammary epithelial cells die by apoptosis within about 24 hours in suspension. However, cell lines that resist apoptosis through expression of either Bcl-2 or Bcl-xL will persistently form protrusions. Previous studies by the inventors indicate that such apoptotically-resistant cell lines will not form tumors in mice and lie dormant in distant tissues, in specific embodiments of the invention. Given the persistent motility response in these detached cells, they may not be as dormant as previously suggested. These protrusions can be inhibited with tubulin-depolymerizing agents such as colchicine, colcemid, vinblastine, vincristine, nocodazole and myoseverin, for example, but are enhanced by the actin-depolymerizing agent, Latrunculin-A or Cytochalasin-D. Immunofluorescence microscopy and Western blotting demonstrate that the protrusions are largely comprised of detyrosinated Glu-tubulin, a post-translationally modified form of tubulin that is found in stabilized microtubules. These microtubule processes can extend more than 3 times the cell diameter, and undergo a rapid probing motion more than once per second. Formation of these microtubule protrusions is necessary for efficient cell-cell and cell-substratum attachment. In particular embodiments of the invention, this inherent microtubule response in detached mammary epithelial cells provides at least some of the invasive characteristics of breast cancer, independent of any tumor-specific genetic alteration, for example.

In particular embodiments of the invention, a diagnostic application is employed. In certain aspects of the invention, the identification of one or more cells with microtubule protrusions is indicative of the presence of cancer, for example metastatic cancer. In fact, given that a higher incidence of protrusions is present in highly metastatic tumor cells, in specific embodiments this serves as a diagnostic test. In a specific embodiment, a sample is obtained from an individual at high risk for developing cancer, suspected of having cancer, known to have cancer, or at high risk for developing metastatic cancer, known to have metastatic cancer, or suspected of having metastatic cancer, for example. The sample is assayed for the presence of one or more protrusions on one or more cells.

The assay to detect cells with protrusions may comprise any suitable method and reagents to identify the presence of one or more protrusions, and in specific embodiments the assay comprises identifying distinguishing cell morphology. In additional embodiments, one or more cells may be assayed for the presence of one or more gene products particularly associated with the protrusions, such as the compositions thereof, including polypeptides, for example. In further embodiments, the expression of a polynucleotide encoding one or more gene products particularly associated with the compositions of the protrusions may be assayed. Thus, in specific embodiments the assay utilizes reagents such as nucleic acid, polypeptide, antibodies, small molecules, mixtures, combinations, and so forth. In specific embodiments, compositions such as RNA or DNA viruses are employed, such as for viral gene therapy, for example. Samples of any suitable kind may be obtained from the individual to assay for protrusions, although in specific embodiments the samples comprise blood; plasma; serum; tissue, including vessel tissue; bone; bone marrow; and so forth.

In other embodiments of the invention, there are methods and reagents for preventing cancer, including preventing metastatic cancer, for example. In particular aspects, the term "preventing" encompasses prevention from occurrence, delay of onset, reduction in intensity, reduction in prevalence, and/or reduction in recurrence, for example. In specific aspects of the invention, one or more agents of the invention are administered to an individual not known to have metastatic cancer, including one suspected of having cancer or one susceptible for developing cancer, including metastatic cancer. In certain cases, an agent of the invention is provided to an individual upon or soon after diagnosis of the cancer to prevent metastasis. In one exemplary embodiment, an individual with a primary tumor receives the agent of the invention before and/or at the time of surgery and/or treatment of the primary tumor, although in alternative embodiments the individual receives the agent of the invention subsequent to the time of surgery and/or other treatment of the primary tumor, or the individual receives the agent at both times. In animal models, surgery or photodynamic therapy of primary prostate tumors have been shown to actually increase the incidence of lung metastasis (since damage to the primary tumor induces wound healing, blood vessel growth, etc., that provides an opportunity for any surviving cells to escape the primary site)

(Momma et al., 1998). Thus, in certain embodiments of the invention, an individual is treated with an inhibitor of protrusions at the time of and/or prior to surgery or treatment so that any escaping cells would be more likely to be shredded in distant capillary beds.

Epithelial cells are important for biological barriers, in certain instances, for example, in skin and lung lining. Thus, in specific embodiments of the invention, the cancer cells related to the invention are epithelial cells and once they are circulating they are biologically driven to establish a barrier or become part of an existing barrier. More than 90% of human solid tumors arise as carcinomas from epithelial cells (Birchmeier, 1996), so how epithelial cells respond to detachment is relevant to the treatment of human cancers, in particular embodiments. Therefore, the epithelial cell employs a mechanism to search for other cells to include in a barrier, and in specific embodiments of the invention the microtubule protrusions are employed by the cell to establish a barrier or incorporate the cell into an existing barrier. In specific embodiments, the microtubule protrusions move to search for other cells to form the barrier, yet once they contact another cell, those protrusions then remain stationary on the contacted cell, at least temporarily.

In some aspects of the invention, cancer cells enter the bloodstream and become destroyed by pressure from the size of the capillary beds unless the cell can prevent reaching the capillary beds, yet this event is difficult to measure because it occurs rapidly. However, in certain embodiments of the invention, a signal associated with the cell, such as luciferase on a vector or genome in the cell, signifies the location of the cell and, if applicable, its subsequent destruction. For example, cancer cells that harbor luciferase are delivered to mice, luciferin substrate is delivered to the mice, and subsequent tracking of the signaling cells can be employed. The inventors demonstrate that when cancer cells with a high number of microtubule protrusions are injected into mice, one can observe them localizing within minutes to the lungs. In specific embodiments, luciferase cancer cells with lower numbers of microtubules push through the capillaries and retention in the lungs would be reduced. If tumor cells are treated with drugs that inhibit the microtubule protrusions before and/or during and/or after injection of the cells into the mice, then in certain embodiments fewer cells remain in the lungs and more tumor cells become fragmented by forced passage through narrow lung capillaries. The destruction of cells in the capillary beds may be observed by looking for cell fragments in blood downstream of the lung, for example. In embodiments wherein visualization of cells is desired, one may employ a signal that lasts longer than standard fluorescence, such as quantum dot, which utilizes fluorescence that essentially never fades.

In certain embodiments of the invention, the outer surface of cancer cells, such as tumor cells, is more flexible than a normal cell, and therefore the microtubule protrusions more easily protrude from the cell. In specific embodiments, this is the result of a weaker actin cortex in a cancer cell, and Glu-tubulin may be sufficient to sustain the protrusion, for example without vimentin and kinesin or considerably reduced levels of vimentin and kinesin. In these cases, it is preferable to target Glu-tubulin over vimentin and/or kinesin, although vimentin and/or kinesin may be targeted in addition to Glu-tubulin.

In particular aspects of the invention, a cancer cell is further defined as a detached cancer cell, and it may be from breast, prostate, pancreatic, colon, lung, brain, liver, ovarian, testicular, cervical, gall bladder, spleen, bone marrow, head and neck, stomach, kidney, or bone bladder, skin, oral, throat, esophageal, thyroid cancer, for example. In further specific embodiments, the individual has metastatic cancer, is suspected of having metastatic cancer, or is susceptible to metastatic cancer. In specific embodiments, the cell is an epithelial cancer, such as a carcinoma.

In an additional embodiment of the present invention, there is a method of preventing metastasis of cancer in an individual, comprising the step of administering to the individual one or more agents that target one or more microtubule protrusions from at least one cancer cell in the individual.

In another embodiment, there is a pharmaceutical composition comprising an agent that targets at least one component of a microtubule protrusion from a cell, and a pharmaceutically acceptable carrier.

In an additional embodiment, there is a kit comprising an agent that targets at least one component of a microtubule protrusion from a cell, wherein said kit is housed in a suitable container.

In another embodiment, there is a method of screening for an agent that targets at least one component of a microtubule protrusion from a cell, comprising the steps of: providing a microtubule protrusion from a cell or a component of the protrusion; and providing a candidate modulator, wherein when the candidate modulator associates with one or more components of the microtubule protrusion, said candidate modulator is the agent. The candidate modulator may be a small molecule, a nucleic acid, a polypeptide, a peptide, an antibody, or a mixture or combination thereof, for example. The method may occur in vitro or in vivo. In specific embodiments, the method further comprises manufacturing of the agent. In other specific embodiments, the agent is delivered to an individual with cancer, an individual at high risk or suspected of having cancer, or an individual susceptible to having metastatic cancer, for example.

In certain embodiments, the present invention provides that detyrosinated microtubule protrusions in suspended mammary epithelial cells promote reattachment.

The skilled artisan recognizes that while observations related to the invention are in breast tumor cell lines, this principle could be therapeutic for many different cancer types. Examples of other cancers for which the invention may be utilized include at least prostate, pancreatic, colon, lung, brain, liver, ovarian, testicular, cervical, gall bladder, spleen, bone marrow, head and neck, stomach, kidney, bone, bladder, skin, oral, throat, esophageal, thyroid and so forth. In particular aspects of the invention, the cancer is resistant to one or more cancer therapies, such as tamoxifen, cisplatin, bortezomib, doxorubicin, paclitaxel, letrozole, trastuzumab, vinblastine, raloxifene hydrochloride, irinotecan, gefitinib, fulvestrant, and so forth.

In an additional embodiment of the invention, there is a method of reducing the risk of a tumor cell from a first organ in an individual to establish a malignancy in a second organ in the individual, comprising delivering a therapeutically effective amount of an agent that targets one or more microtubule protrusions of the tumor cell. In a specific embodiment, the tumor cell releases from the tumor upon therapy for the tumor, such as upon surgery in the individual, for example. Releasing of the tumor cell from a primary tumor mass may be caused directly or indirectly upon utilizing the therapy. In further embodiments, the method may be further defined as the tumor cell releasing from the tumor upon excision of the tumor from the individual. In specific aspects, the tumor cell is released from a primary tumor mass during excision of at least part of the primary tumor mass from the individual. Therefore, in particular aspects this clarifies the difference between the primary tumor mass and the residual tumor cells left in the body (which would be at risk of spreading metastatically to distant tissues during wound healing). In particular cases, the method is further defined as the tumor cell releasing from the primary tumor mass during removal of the primary tumor mass from the individual and/or during therapy for the primary tumor mass for the individual. In other cases, the method is further defined as the tumor cell being one that remains in the body of the individual during removal of a primary tumor mass from the individual and/or during therapy for the primary tumor mass for the individual. In additional embodiments, the agent is delivered to the individual before, during, and/or after the surgery.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features that are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DESCRIPTION OF THE DRAWINGS

For a more complete understanding of the present invention, reference is now made to the following descriptions taken in conjunction with the accompanying drawings.

In FIG. 1A, human MCF10A or mouse EpH4 mammary epithelial cell lines produce protrusions of the plasma membrane when plated over agarose and photographed live (black arrows). Apoptosis becomes apparent in detached MCF10A and EpH4 cells after 24 hours of detachment and almost all cells are dead by 48 hours, as indicated by darkening and condensation of the cells. EpH4 cells that overexpress Bcl-2 (EpH4-Bcl2) remain largely viable at 48 hours and continue to produce protrusions. In FIG. 1B, EpH4 cells or those overexpressing Bcl-2 were placed in suspension for the indicated time in hours. Cleavage of PARP to a truncated form (ΔPARP), indicates that apoptosis is largely complete in EpH4 cells after 16 hours, while relatively few EpH4-Bcl2 cells die even after 24 hours. In FIG. 1C, EpH4 cells that produce protrusions (white arrows) continue to exclude propidium iodide, indicating an intact plasma membrane. Similar results were obtained with MCF10A cells.

In FIG. 2A, after 15 minutes of suspension, protrusions in EpH4 and MCF10A cells are quite small (Control, white arrows). Treatment with the actin depolymerizing agent, Cytochalasin-D, increased protrusions (white arrowheads) and this effect was even more pronounced with the actin inhibitor Latrunculin-A (LA, 5 μM). The microtubule depolymerizing agent, Colchicine (1 μM) prevented protrusions. The combination of LA and Colchicine (LA+Col) prevented protrusion formation, and those that did form appeared to be fragmented (black arrow). In FIG. 2B, populations of live, suspended cells were scored blindly for two or more protrusions longer than the cell radius. Each bar represents the mean+S.D. for three experiments in which at least 100 single cells were counted.

In FIG. 5A, cell lysates were immunoblotted to detect levels of modified tubulin isoforms in the cell populations. In FIG. 5B, modified α-tubulin isoforms were normalized to total α-tubulin and then compared relative to the levels in attached cells at time zero. Bars represent the mean+S.E.M. of four independent experiments. While Glu-tubulin increases significantly in response to detachment ($P<0.05$, t-test), none of the other tubulin forms increase significantly ($P>0.05$, t-test). Differences in Glu-tubulin upon detachment were also statistically-significant when compared to matched controls at time zero or one hour (black asterisks). LA treatment does not significantly increase cellular levels of Glu-tubulin in either attached or detached cells ($P>0.05$, t-test).

In FIG. 6A, EpH4-Bcl2 cells were suspended over agarose and treated with inhibitors as above. Following treatment, cells were plated into 0.3% methylcellulose media over agarose and the rate of cell-cell attachment was followed by Hoescht DNA staining. While LA-treated cells cluster similarly or even more tightly compared to control cells after 5 hours (black arrow), cells treated with tubulin polymerization inhibitors are significantly delayed in clustering. Similar results were found in three independent experiments. In FIG. 6B, EpH4-Bcl2 cells suspended over agarose for one hour in DMEM or DMEM containing LA (5 μM), Colchicine (1 μM), or the combination. Reattachment of these cells to either uncoated tissue culture plates or those pre-coated with laminin was followed by XTT cell viability assay. Values represent mean+S.D. of raw XTT values of three separate experiments. While actin depolymerization with LA does not affect cell-surface attachment, depolymerization of tubulin with colchicine significantly prevents initial cell attachment to either uncoated or laminin-coated plates.

FIG. 33 illustrates an exemplary Hs578t/Bt474 timecourse for an exemplary vimentin siRNA, Vim4.

DETAILED DESCRIPTION OF EMBODIMENTS OF THE INVENTION

I. Definitions

Figure 1:
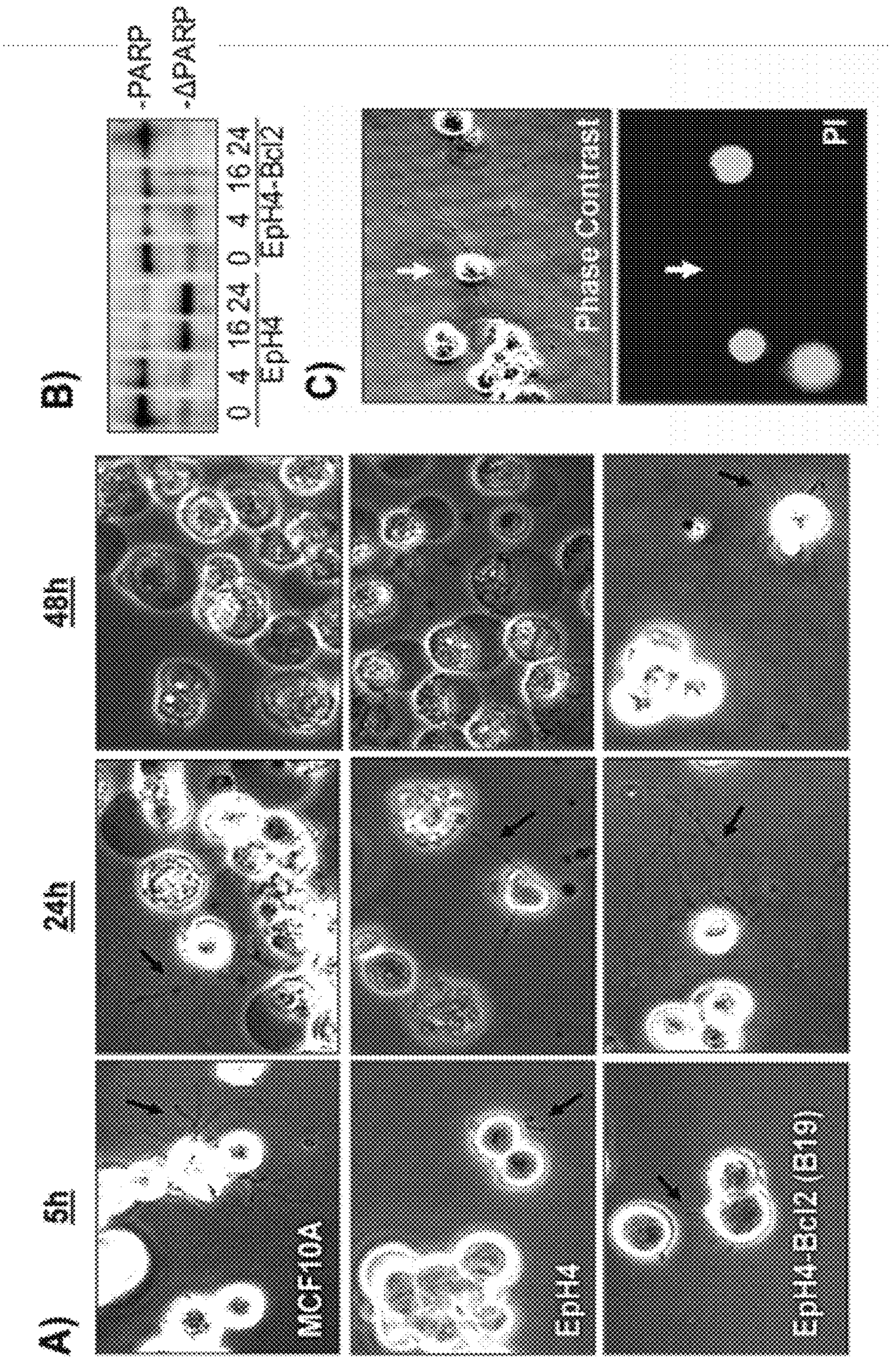
FIGS. 1A-1C show that detachment induces cellular protrusions in both normal and Bcl2-expressing mammary epithelial cells.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The term "detached cancer cell" as used herein refers to a cancer cell, such as a tumor cell, that has escaped its primary organ site, and now is present elsewhere in the body of the patient, such as residing elsewhere in the body of the patient, for example. In specific embodiments, the detached cancer cell is in the bloodstream.

The term "detyrosinated Glu-tubulin" as used herein refers to α-tubulin in which the carboxyl-terminal tyrosine residue has been removed and now exposes a glutamic acid residue at its carboxyl-terminus.

The term "distant tumor" as used herein refers to a tumor cell that has separated from its organ of origin and now resides elsewhere in the body.

The term "microtubule protrusion" as used herein refers to extensions of the plasma membrane in detached cells that are enriched in tubulin protein, for example Glu-tubulin and largely devoid of polymerized actin. When treated with inhibitors of actin depolymerization, there is enhancement of the protrusions, such as with the protrusions increasing in length, number per cell and frequency in a population, for example. This is in contrast to well-known invadopodia and podosomes associated with adherent tumor cells that are actin-based and inhibited by actin depolymerization.

II. Embodiments of the Present Invention

Breast tumor cells enter the bloodstream long before the development of clinically evident metastasis. However, the early presence of such bloodborne cells predicts poor patient outcome. Nearly 90% of human breast tumors arise as carcinomas from mammary epithelial cells, so it is important to characterize how these cells respond to the detached conditions that they would experience in the bloodstream. In the present invention, mammary epithelial cell lines produce long and dynamic protrusions of the plasma membrane when detached. Although human and mouse mammary epithelial cell lines die by apoptosis within 16 hours of detachment, this protrusive response persists for days in cells overexpressing either Bcl-2 or Bcl-xL, for example. Unlike actin-dependent invadopodia and podosomes, these protrusions are actually enhanced by actin depolymerization with Cytochalasin-D or Latrunculin-A. Immunofluorescence and Western blotting demonstrate that the protrusions are enriched in detyrosinated Glu-tubulin, a posttranslationally modified form of $\alpha$-tubulin that is found in stabilized microtubules. Video microscopy indicates that these protrusions promote cell-cell attachment, and inhibiting microtubule-based protrusions correlates with reduced extracellular matrix attachment. Since bloodborne metastasis depends on both cell-cell and cell-matrix attachment, microtubule-based protrusions in detached mammary epithelial cells provide a novel target that could influence the metastatic spread of breast tumors.

Thus, in specific aspects of the invention, there are methods and compositions associated with particular cancer cells that comprise one or more microtubule protrusions from the cell. In particular aspects of the invention, the microtubule protrusions are utilized by the cell to attach to an entity, such as a tissue, and including a blood vessel wall. Such attachment in certain aspects protects the cancer cell from the destruction caused by forcing it through a capillary vessel, and in additional aspects the attached cancer cell escapes through the vessel wall.

Thus, in some embodiments of the invention the microtubule protrusions are targeted to prevent attachment to a surface such as a blood vessel wall. In particular embodiments, an agent is delivered to an individual having cancer cells with one or more of the protrusions or is delivered to an individual susceptible to having cancer cells with one or more of the protrusions. The agent is delivered such that it associates with at least one protrusion and thereby inhibits the function of the protrusion, degrades the protrusion, inhibits the activity of the protrusion, promotes degradation (such as an agent that promotes, facilitates or enhances ATP hydrolysis) and/or prevents the protrusion from extending in length, for example. In alternative embodiments, the agent is delivered such that it associates with the cell and thereby inhibits the function of the protrusion, degrades the protrusion, inhibits the activity of the protrusion, promotes the degradation (such as an agent that facilitates or enhances ATP hydrolysis), and/or prevents the protrusion from extending in length. In additional or alternative embodiments, the agent may prevent the protrusion from being produced and/or prevent the protrusion from protruding (which may be referred to as extending) from the cell. The protrusion may be affected prior to extending from the cell, subsequent to extending from the cell, or is effective in either case. In certain aspects, the agent is selectively cytotoxic to detached cells, and in particular embodiments the agent kills apoptotic-resistant cells, for example.

Upon delivery of the agent to the individual, one or more protrusions from a cancer cell are affected, such as is described herein, and in particular embodiments the cell is a metastatic cancer cell, which in some cases is a detached cancer cell, such as from a tumor. In particular embodiments of the invention, metastatic cancer is prevented, is reduced in prevalence, is reduced in mass, or is delayed. In certain aspects of the invention, at least one symptom related to cancer is improved directly or indirectly because of the invention.

Cancer cells of the invention that may be targeted by methods and/or compositions of the invention may be of any suitable kind. In particular cases, the cancer cells are from a solid tumor. In specific aspects, the cancer cells are cells that are in a tumor, such as a primary tumor, for example, or that are released from a tumor, or that are left behind at a tumor site upon removal of at least part of the primary tumor mass. In specific embodiments, the tumor cells are not restricted to cells directly detaching from the primary tumor, but are residual cells remaining at the surgical or therapeutic site. Thus, the present invention not only kills cells that directly remain or escape during the procedure, but also cells that are missed entirely by the surgery or therapy. For example, increased metastasis due to wound healing can even be seen with localized therapies, such as photodynamic therapy, and does not have to be restricted to surgical approaches. The damage caused to local tissue by radiotherapy, photodynamic therapy, localized heating or other such approaches could free cells that could be destroyed by targeting microtubule protrusions. The tumor cells that evade therapy of any kind, including surgery, chemotherapy, immunotherapy, radiation, photodynamic therapy, and so forth, may be targets of the invention.

III. Therapeutic Agents of the Invention

In certain embodiments of the invention, an agent that targets microtubule protrusions is utilized to inhibit the function, activity, or production of the protrusion. Any suitable agent may be employed, although in specific aspects the agent comprises one or more small molecules; one or more polypeptides; one or more antibodies; one or more nucleic acids; including RNA, DNA; or a mixture or combination thereof, and so forth. In specific embodiments, RNA or DNA viruses are employed in the invention, such as for viral gene therapy, for example.

In particular embodiments, the agent affects the protrusion by inhibiting the function, activity, or synthesis of the protrusion, or by enhancing the degradation of the protrusion, for example. However, in some embodiments, the agent affects cells that are detached and at some point during the life of the cell comprised one or more protrusions.

In certain aspects, the agent of the invention comprises one or more inhibitors, and the inhibitors are administered to an individual in need thereof, such as an individual that has cancer, which may be metastatic cancer, in some embodiments, and the individual may be suspected to have metastatic cancer or may be susceptible to cancer including metastatic cancer, for example.

Although the agent may affect any composition of the microtubule protrusions directly or indirectly, exemplary targets are as follows.

A. Agents that Affect Detyrosinated Glu-Tubulin

In particular aspects of the invention, one or more agents that affect detyrosinated glu-tubulin (also referred to as alpha-tubulin, for example) is employed. In specific embodiments they comprise one or more inhibitors of detyrosinated glu-tubulin, although in alternative embodiments they comprise one or more agents that induce, initiate, or facilitate breakdown of the protrusions. Alpha-tubulin is detyrosinated by a yet unknown carboxypeptidase enzyme to form glu-tubulin. The counteracting enzyme, tubulin tyrosine ligase has been identified. The formation of detyrosinated glu-tubulin could be prevented by either inhibiting the action of the unknown carboxypeptidase, or by enhancing the activity of tubulin tyrosine ligase, or both, for example. Any inhibitor of detyrosinated glu-tubulin function or its synthesis may be employed, although in specific embodiments the inhibitor comprises an antibody; a small molecule compound; a hydrolyzable nucleotide triphosphate, such as ATP, GTP, and/or UTP, for example; one or more nucleic acids; including RNA, DNA; or a mixture or combination thereof, and so forth; or a mixture or combination thereof.

1. Inhibitors of Tubulin Carboxypeptidase

In certain embodiments of the invention, one or more inhibitors of tubulin carboxypeptidase are employed, such as the following: 1) 3-nitrotyrosine; 2) okadaic acid; 3) 1-norokadone; 4) cantharidin; 5) Phoslactomycin B (Fostriecin); 6) siRNA against hAGBL3; 7) chemical inhibitors specifically against hAGBL3 activity; 8) DL-benzylsuccinic acid; 9) Sodium orthovanadate, or combinations thereof.

2. Tubulin Depolymerizers

In certain embodiments of the invention, one or more depolymerizers of tubulin, such as one or more of the following: 1) Colchicine; 2) Vinblastine; 3) Vincristine; 4) Nocodazole; 5) Phomopsin A; 6) Vindesine; 7) Myoseverin; 8) Cytochalasin E; 9) Podophyllotoxin; 10) Etoposide; 11) Griseofulvin; or a combination thereof.

3. Tubulin Stabilizers

In certain embodiments of the invention, one or more stabilizers of tubulin are employed, such as to stop motion of the microtubule protrusions, such as one or more of the following: 1) Paclitaxel; 2) Docetaxel; 3) Epothilones, or a combination thereof.

B. Agents that Affect GSK-3

In particular aspects of the invention, one or more agents that affect GSK-3 is employed, and in specific aspects the one or more agents comprises an inhibitor of GSK-3. The inhibitor may act directly on GSK-3 or may act indirectly on another molecule that affects GSK-3. In some embodiments the compositions comprise one or more agents that induce, initiate, or facilitate breakdown of the protrusions. Any inhibitor of GSK-3 may be employed, although in specific embodiments the inhibitor comprises an antibody; agents such as those identified in U.S. Patent Publication No. US 2005/0026946, the entirety of which is incorporated by reference herein; $C_{16}H_{10}BrN_3O_2$ (GSK-3 Inhibitor IX (Cat. No. 361550; Calbiochem®, San Diego, Calif.); insulin, such as with lithium; SB-415286, such as with lithium (MacAulay et al., 2003; Coghlan et al., 2000); CT118637 (Dokken et al., 2005); GSK-3 Inhibitor 1—Calbiochem 361540; GSK-3 Inhibitor II—Calbiochem 361541; GSK-3 Peptide Inhibitor I—Calbiochem 361545; GSK-3 Peptide Inhibitor II—Calbiochem 361546; GSK-3 Inhibitor VII—Calbiochem 361548; GSK-3 Inhibitor VIII—Calbiochem 361549; GSK-3 Inhibitor XI—Calbiochem 361553; GSK-3 Inhibitor XII—Calbiochem 361554 and so forth.

In certain embodiments of the invention, one or more inhibitors of GSK-3b are employed, such as one or more of the following: 1) Lithium; 2) 4-Benzyl-2-methyl-1,2,4-thiadiazolidine-3,5-dione; 3) 2-Thio(3-iodobenzyl)-5-(1-pyridyl)-[1,3,4]-oxadiazole; 4) 2,4-Dibenzyl-5-oxothiadiazolidine-3-thione; 5) 2-Chloro-1-(4,5-dibromo-thiophen-2-yl)-ethanone; 6) α-4-Dibromoacetophenone; 7) N-(4-Methoxybenzyl)-N'-(5-nitro-1,3-thiazol-2-yl)urea; 8) (2'Z, 3'E)-6-Bromoindirubin-3'-oxime; 9) 3-(1-(3-Hydroxypropyl)-1H-pyrrolo[2,3-b]pyridin-3-yl]-4-pyrazin-2-yl-pyrrole-2,5-dione; 10) (5-Methyl-1H-pyrazol-3-yl)-(2-phenylquinazolin-4-yl)amine; 11) Purvalanol-A, or a combination thereof.

C. Agents that Affect Kinesin

In particular aspects of the invention, one or more agents that target kinesin is employed, and in specific aspects the one or more agents comprises an inhibitor of kinesin. The inhibitor may act directly on kinesin or may act indirectly on another molecule that affects kinesin. Any inhibitor of kinesin may be employed, although in specific embodiments the inhibitor comprises S-trityl-L-cysteine; 1,6,7,1',6',7'-Hexahydroxy-5,5'-diisopropyl-3,3'-dimethyl-[2,2'-binaphthalene]-8,8'-dicarboxaldehyde (also referred to as gossypol); 3-(5H-dibenzo[a,d]cyclohepten-5-ylidene)-N,N-dimethyl-1-1propanamine hydrochloride (also referred to as flexeril); 2-{[2-(4-{3-[2-(trifluoromethyl)-10H-phenothiazin-10-yl]propyl}-1-piperazinyl)ethyl]amino}-ethanol trihydrochloride; $K_6Mo_{18}O_{62}P_2$; 2,3,4,5-Tetrabromo-6-(3,6-dihydroxy-9H-xanthen-9-yl)-benzoic acid; 1,1,2,2-Tetra(3,5-dichloro-4-hydroxyphenyl)ethane; 10-Carboxy-1,2,3,4,5,6,7,8,13,13,14,14-dodecachloro-1,4,4a,4b,5,8,8a,8b-octahydro-11,sulfo-1,4:5,8-demethanotriphenylene; 2,2'-Dithiobis-(8-quinolinol); 8-[3-(2-Chloro-10H-phenothiazin-10-yl)propyl]-8-azabicyclo[3.2.1]octane-3-ol, compound with ethanesulfonic acid, or a mixture or combination thereof, for example. (See DeBonis et al., 2004, for example, which is incorporated by reference herein in its entirety).

D. Agents that Affect Adenomatous Polyposis Coli Protein (APC)

In some embodiments of the invention, one or more agents that affect APC are employed in the invention. APC is one of the targets of GSK-3b phosphorylation and regulates microtubule capture at the actin cortex (a network of actin filaments beneath the plasma membrane). The mutated form of APC that is found in cancers most often loses its microtubule binding domain. In some embodiments, if APC fails to capture microtubules at the actin cortex, the microtubules extend past the plasma membrane to produce the observed protrusions associated with the invention. Thus, in specific embodiments any compound or therapy targeting the restoration of APC function will inhibit the protrusions. In particular embodiments, the compound comprises protein, peptide, nucleic acid, including DNA, RNA, small molecule, or a mixture or combination thereof, and so forth.

E. Inhibitors of Vimentin

In certain embodiments of the invention, one or more inhibitors of vimentin, such as vimentin assembly, are utilized, such as the following: 1) Calyculin-A; 2) Ionomycin; 3) ProstagladinF (2a); 4) Vimentin siRNA; 5) bradykinin; 6) Bisindolymaleimide; 7) Estramustine; 8) Isoproterenol; 9) 8-Br-cAMP; 10) epinephrine; 11) forskolin; 12) Prostaglandin-E1, or combinations thereof.

F. Inhibitors of Kinesin

In certain embodiments of the invention, one or more inhibitors of kinesin, such as kinesin activity, are employed, such as the following: 1) Lidocaine; 2) Tetracaine; 3) S-Trityl-L-cysteine; 4) Monastrol; 5) Adociasulfate-2; 6) Terpendole-E; 7) siRNAs against specific kinesins, or a combination thereof.

G. Inhibitors of Src

In certain embodiments of the invention, one or more inhibitors of Src, such as Src activity, are employed, such as follows: 1) 4-amino-5-(4-chlorophenyl)-7-(t-butyl)pyrazolo[3,4-d]pyrimidine (PP2); 2) 4-(4'-Phenoxyanilino)-6,7-dimethoxyquinazoline; 3) Dasatinib; 4) Csk overexpression; 5) siRNA against Src, or a combination thereof.

H. Stabilizers of Actin

In certain embodiments of the invention, one or more stabilizers of actin, such as, for example, one or more of the following: 1) Jasplakinolide; 2) Phalloidin; 3) Dolastatin; 4) Chrondramides; 5) Doliculide, or a combination thereof.

IV. Antisense/siRNA Embodiments

TABLE I

List of human kinesin/dynein names, Genbank accession numbers and PCR primer sequences for PCR amplification of DNA templates for generating siRNA.

| Kinesin* | Other name** | GenBank ID | Family** | 5' primer | SEQ ID NO | 3' primer | SEQ ID NO |
|---|---|---|---|---|---|---|---|
| KIF 1A | HsATSV | NM_004321 | Kinesin-3 | GCGTAATACGACTCACTATAGGGGCAGGCCCAGCCCATCCCCT | 77 | GCGTAATACGACTCACTATAGGTTGGGAGACACATGTGGGAAC | 119 |
| KIF 1B | HsKIF1B | NM_015074 | Kinesin-3 | GCGTAATACGACTCACTATAGGCTCACTCGCCTTCGAGAGATA | 78 | GCGTAATACGACTCACTATAGGGATGTCTCCTCCCTTAGTCTC | 120 |
| KIF 1C | HsKIF1C | AB014606 | Kinesin-3 | GCGTAATACGACTCACTATAGGCTTGCTAGGAGAAGGGAAGAC | 79 | GCGTAATACGACTCACTATAGGAGGGGAGGGGAATGACTTATG | 121 |
| KIF 2A | HsKin2 | NM_004520 | Kinesin-13 | GCGTAATACGACTCACTATAGGAAGGATACCCAGAACCCTCAC | 80 | GCGTAATACGACTCACTATAGGGGAGTGGGCAAGGTATGTACA | 122 |
| KIF 2B | HsLOC8464 | NM_032559 | Kinesin-13 | GCGTAATACGACTCACTATAGGGAGATCAGGTCCGAAATGCTG | 81 | GCGTAATACGACTCACTATAGGAACCCCACCCACGGAACAACT | 123 |
| KIF 2C | MCAK | NM_006845 | Kinesin-13 | GCGTAATACGACTCACTATAGGCCAGAGAACTTTGGGTACCTG | 82 | GCGTAATACGACTCACTATAGGCTCTAGGGAGACAGTAAAGTA | 124 |
| KIF 3A | HsKIF3A | NM_007054 | Kinesin-2 | GCGTAATACGACTCACTATAGGGTGATATTCTCATGCCTGGAC | 83 | GCGTAATACGACTCACTATAGGCAGGCTGGGTGGGTGTTAGGA | 125 |
| KIF 3B | HsKIF3B | NM_004798 | Kinesin-2 | GCGTAATACGACTCACTATAGGGGGCGGAAACAGCATTTGCCT | 84 | GCGTAATACGACTCACTATAGGCTGATTCTGCCCTATTGTTCA | 126 |
| KIF 3C | HsKIF3C | NM_002254 | Kinesin-2 | GCGTAATACGACTCACTATAGGCAATAGACTCCTGGGATGGGG | 85 | GCGTAATACGACTCACTATAGGAGAAGATGGAGGTTATGGAGT | 127 |
| KIF 4A | HsKIF4 | AF071592 | Kinesin-4 | GCGTAATACGACTCACTATAGGCCCCAGTCTGGCTTGGGAGAT | 86 | GCGTAATACGACTCACTATAGGACATGGCAGACAATCAAGAGT | 128 |
| KIF 4B | — | AF241316 | Kinesin-4 | GCGTAATACGACTCACTATAGGGTTGGAGTCATCATCTCTACC | 87 | GCGTAATACGACTCACTATAGGAGGAACTTGATCATACTGAGG | 129 |
| KIF 5A | HsnKHC | NM_004984 | Kinesin-1 | GCGTAATACGACTCACTATAGGCTCTTACTTACTCTGTATCTC | 88 | GCGTAATACGACTCACTATAGGGCTATATGTGAAAGAGGAGGG | 130 |
| KIF 5B | HsuKHC | NM_004521 | Kinesin-1 | GCGTAATACGACTCACTATAGGGTAATCGAAGTACGAAGAGGA | 89 | GCGTAATACGACTCACTATAGGGCACAGTCCTATAAGGTAGAG | 131 |
| KIF 5C | HsxKHC | NM_004522 | Kinesin-1 | GCGTAATACGACTCACTATAGGGACTCCACGTAGCATGTCAAG | 90 | GCGTAATACGACTCACTATAGGGATCATCTGCCTCCACGGCAC | 132 |
| KIF 6 | — | BX649045 | | GCGTAATACGACTCACTATAGGGCCAGCAAGAACGAAGCACAG | 91 | GCGTAATACGACTCACTATAGGATGGTGCTATTTCACATTCTC | 133 |
| KIF 7 | HsKIF7 | NM_017576 | TBD | GCGTAATACGACTCACTATAGGAGATTCCTTTTTCTAACCTGT | 92 | GCGTAATACGACTCACTATAGGAGCAAGATTTAGCTGGATCTT | 134 |
| KIF 9 | HsKIF9 | NM_022342 | Orphan | GCGTAATACGACTCACTATAGGAGTACCTTAAAGGACAAGACC | 93 | GCGTAATACGACTCACTATAGGAGCCTGGCTGAGCTACTTTTC | 135 |
| KIF 10 | HsCENP-E | NM_001813 | Kinesin-7 | GCGTAATACGACTCACTATAGGCACTTCTCTGGAGATCCAGCA | 94 | GCGTAATACGACTCACTATAGGGAAGAGCGGTGATTCAGAACT | 136 |
| KIF 11 | HsKPS/Eg5 | NM_004523 | Kinesin-5 | GCGTAATACGACTCACTATAGGCTTGAACCCAGGAAGCGGGGT | 95 | GCGTAATACGACTCACTATAGGTCTAAGGACAGATGTTGGTGA | 137 |
| KIF 12 | HsKIF12 | NM_138424 | TBD | GCGTAATACGACTCACTATAGGGGCCAAGTGGGAACCCAGGAG | 96 | GCGTAATACGACTCACTATAGGAACCATGAAAGGAGATGGGAG | 138 |
| KIF13A | HsRBKIN1 | NM_022113 | Kinesin-3 | GCGTAATACGACTCACTATAGGGTCTAACTGTATGTCAACCCC | 97 | GCGTAATACGACTCACTATAGGTGACAGAGTTTAATTGGCAGT | 139 |
| KIF13B | HsGAKIN | AF279865 | Kinesin-3 | GCGTAATACGACTCACTATAGGCCCTGAGGAGCCAGGAGCCCG | 98 | GCGTAATACGACTCACTATAGGCAGAGGCACTTTGCGGGAAAC | 140 |
| KIF 14 | HUMORFW | D26361 | Kinesin-3 | GCGTAATACGACTCACTATAGGGGCACTTTTATGACCACCCAT | 99 | GCGTAATACGACTCACTATAGGGACTAAGTCTCGTTCTGTTGC | 141 |

TABLE I-continued

List of human kinesin/dynein names, Genbank accession numbers and PCR primer sequences for PCR amplification of DNA templates for generating siRNA.

| Kinesin* | Other name** | GenBank ID | Family** | 5' primer | SEQ ID NO | 3' primer | SEQ ID NO |
|---|---|---|---|---|---|---|---|
| KIF 15 | HsKip7 | AB035898 | Orphan | GCGTAATACGACTCACTATAGGCCTAGGCATCACCTTGTTTGA | 100 | GCGTAATACGACTCACTATAGGGCTTCTTGTACCTGCTACTAA | 142 |
| KIF16A | HsKIF16A | AK122666 | TBD | GCGTAATACGACTCACTATAGGGTGGGATGCCAGAGCTGGATC | 101 | GCGTAATACGACTCACTATAGGTCTACTCCCTCATCATCTGGA | 143 |
| KIF16B | HsJ777L9 | AY166853 | Kinesin-3 | GCGTAATACGACTCACTATAGGGGAGGAACCACCACAGCAGTG | 102 | GCGTAATACGACTCACTATAGGGGAATATAGCCAGCCACATGG | 144 |
| KIF 17 | HsKIAA1405 | XM_027915 | Kinesin-2 | GCGTAATACGACTCACTATAGGGCCTTATAGGCATGTAGAGAC | 103 | GCGTAATACGACTCACTATAGGGTGCTTAGGAAGTGGGGCCAG | 145 |
| KIF18 | HsDKFZp434 | NM_031217 | Kinesin-8 | GCGTAATACGACTCACTATAGGCCAAGCAAAATGAAGTTGATC | 104 | GCGTAATACGACTCACTATAGGTCTTGGGCCATAATTTTACCA | 146 |
| KIF19A | HsFLJ3730 | AK094619 | Orphan | GCGTAATACGACTCACTATAGGGAGGCAAGGCGGAGGGGCCAG | 105 | GCGTAATACGACTCACTATAGGGTAAAGACGGGATTTCGCCAT | 147 |
| KIF20A | HsRabK6/MKLP2 | NM_005733 | Kinesin-6 | GCGTAATACGACTCACTATAGGGAGCAGTCATGGCCCTGAGGT | 106 | GCGTAATACGACTCACTATAGGTAGTTACTGGTCTCCACTGCC | 148 |
| KIF20B | HsKlpMPP1 | NM_016195 | Orphan | GCGTAATACGACTCACTATAGGGTCATAGTCATTGGAACTTGC | 107 | GCGTAATACGACTCACTATAGGCTGTACACACTTATTCTCCAA | 149 |
| KIF21A | HsNYREN62 | NM_017641 | Kinesin-4 | GCGTAATACGACTCACTATAGGGGTTGTAAACTGAATGCTGTG | 108 | GCGTAATACGACTCACTATAGGATGAATGAGTTAATGGTGGGC | 150 |
| KIF 22 | HsKid | NM_007317 | Kinesin-10 | GCGTAATACGACTCACTATAGGCCTCACTCCGCCTTTTCAAAT | 109 | GCGTAATACGACTCACTATAGGCAAGGCCGCCGTCGTTGCCGA | 151 |
| KIF 23 | HsMKLP1 | NM_004856 | Kinesin-6 | GCGTAATACGACTCACTATAGGGTCCCAGTACTGAAAGAACAT | 110 | GCGTAATACGACTCACTATAGGGACCAGGGCTGGAGAAGTCAC | 152 |
| KIF 24 | — | NM_018278 | | GCGTAATACGACTCACTATAGGGAGGGAAAGTAGCCTCAGGCA | 111 | GCGTAATACGACTCACTATAGGTGTAGGTGAACTAACTGCCCC | 153 |
| KIF 25 | HsKlp6q27 | NM_005355 | unamed | GCGTAATACGACTCACTATAGGCAGCAAGTAAGCAGAAGACTC | 112 | GCGTAATACGACTCACTATAGGGCATGAGCCACCATGCCTGGC | 154 |
| KIF26A | HsKIAA1236 | XM_050278 | Orphan | GCGTAATACGACTCACTATAGGGACAAGAGGAGGGGGCGTGCA | 113 | GCGTAATACGACTCACTATAGGTAAGTCCCACTCCACTCCACA | 155 |
| KIF26B | HsLOC3489 | BC035896 | Orphan | GCGTAATACGACTCACTATAGGGGGTACCTACCCTCATGACCT | 114 | GCGTAATACGACTCACTATAGGTTAGCCAGGCACGGTGGTGCA | 156 |
| KIF C1 | HsCHO2 | XM_058039 | Kinesin-14 | GCGTAATACGACTCACTATAGGCGGATCCAGATCTGTGTGTGT | 115 | GCGTAATACGACTCACTATAGGGTGGATAGCTAGAGGGCACAC | 157 |
| KIF C2 | HsKIFC2 | NM_145754 | Kinesin-14 | GCGTAATACGACTCACTATAGGGTCTCCCAGGGCACAAGCTCC | 116 | GCGTAATACGACTCACTATAGGGTCTGGAAAGGAGGTAGCACC | 158 |
| KIF C3 | HsKIFC3 | NM_005550 | Kinesin-14 | GCGTAATACGACTCACTATAGGGCCTGAAGCTGGGCCCTCACT | 117 | GCGTAATACGACTCACTATAGGATGGGTCTTGGGTCTGCCCAG | 159 |
| DYNEIN | DHC1 | BC021297 | | GCGTAATACGACTCACTATAGGGCCCCTTTCTGTAATAGTGAA | 118 | GCGTAATACGACTCACTATAGGGTGTCTGTGAAGGGCCCCAAG | 160 |

*see reference Miki et al.
**see reference Lawrence et al.

Molecules directed against a transcript may be employed to inhibit the expression of the product, for example. The molecules may be of any suitable length, and in specific embodiments the molecules are antisense RNA molecules, for example that may be as long as the full length of an mRNA or shorter. In specific embodiments, siRNA is employed, which usually refers to shorter versions 21-23 bp in length. This shorter version usually helps the cell avoid mounting an antiviral response (interferon-based) to the dsRNA molecule. Since dsRNAs look a lot like some retroviruses, cells have an intricate system to shut the cell down (and even commit apoptosis) if a dsRNA that is too long appears in the cytoplasm. The shorter 21-23 bp fragment essentially elude this system, since the cell has probably decided that something this short cannot be a viral threat.

Antisense, including siRNA, molecules may be generated against any suitable polynucleotide to inhibit microtubule protrusions. In specific embodiments, exemplary sequences provided herein. In specific embodiments, the antisense, including siRNA, molecules may be directed against a 5' leader, exon, intron, splice junction, or 3' UTR, for example. They may be of any suitable length, although in specific embodiments they are 21, 22, or 23 base pairs in length.

For example, one may employ vimentin polynucleotides to obtain exemplary antisense or siRNA molecules: NM_003380 (SEQ ID NO:1), BC066956 (SEQ ID NO:2), BC030573 (SEQ ID NO:3), or BC000163 (SEQ ID NO:4). An exemplary GSK-3b polynucleotide to obtain exemplary antisense or siRNA molecules includes NM_002093 (SEQ ID NO:5). An exemplary c-Src polynucleotide to obtain exemplary antisense or siRNA molecules includes BC104847 (SEQ ID NO:6). Exemplary Fyn polynucleotides to obtain exemplary antisense or siRNA molecules include NM_153048 (SEQ ID NO:7), NM_153047 (SEQ ID NO:8), or NM_002037 (SEQ ID NO:9). An exemplary Fer polynucleotide to obtain exemplary antisense or siRNA molecules includes NM_005246 (SEQ ID NO:10). Exemplary Lck polynucleotides to obtain exemplary antisense or siRNA molecules includes NM_001042771 (SEQ ID NO:11) or NM_005356 (SEQ ID NO:12). An exemplary c-Yes polynucleotide to obtain exemplary antisense or siRNA molecules includes NM_005433 (SEQ ID NO:13). Exemplary Fgr polynucleotides to obtain exemplary antisense or siRNA molecules include NM_005248 (SEQ ID NO:14), NM_001042747 (SEQ ID NO:15), or NM_001042729 (SEQ ID NO:16). An exemplary Lyn polynucleotide to obtain exemplary antisense or siRNA molecules includes NM_002350 (SEQ ID NO:17). Exemplary Hck polynucleotides to obtain exemplary antisense or siRNA molecules include NM_002110 (SEQ ID NO:18) and AY893634 (SEQ ID NO:19). Exemplary Blk polynucleotides to obtain exemplary antisense or siRNA molecules include NM_001715 (SEQ ID NO:20), BC032413 (SEQ ID NO:21), or BC007371 (SEQ ID NO:22). Exemplary c-Abl polynucleotides to obtain exemplary antisense or siRNA molecules include NM_005157 (SEQ ID NO:23), NM_007313 (SEQ ID NO:24), NM_005158 (SEQ ID NO:25), or M14752 (SEQ ID NO:26). Exemplary hAGTPBP1 polynucleotides to obtain exemplary antisense or siRNA molecules include NM_015239 (SEQ ID NO:27) or BC060815 (SEQ ID NO:28). Exemplary hAGBL2 polynucleotides to obtain exemplary antisense or siRNA molecules include NM_024783 (SEQ ID NO:29), BC036234 (SEQ ID NO:30), or BC028200 (SEQ ID NO:31). An exemplary hAGBL3 polynucleotide to obtain exemplary antisense or siRNA molecules includes BC030651 (SEQ ID NO:32). Exemplary hAGBL4 polynucleotides to obtain exemplary antisense or siRNA molecules include NM_032785 (SEQ ID NO:33) or BC126383 (SEQ ID NO:34).

Exemplary kinesin polynucleotides sequences are provided, such as those that are suitable for targeting antisense or siRNA molecules against: KIF 1A (NM_004321; SEQ ID NO:35); KIF 1B (NM_015074; SEQ ID NO:36); KIF 1C (AB014606; SEQ ID NO:37); KIF 2A (NM_004520; SEQ ID NO:38); KIF 2B (NM_032559; SEQ ID NO:39); KIF 2C (NM_006845; SEQ ID NO:40); KIF 3A (NM_007054; SEQ ID NO:41); KIF 3B (NM_004798; SEQ ID NO:42); KIF 3C(NM_002254; SEQ ID NO:43); KIF 4A (AF071592; SEQ ID NO:44); KIF 4B (AF241316; SEQ ID NO:45); KIF 5A (NM_004984; SEQ ID NO:46); KIF 5B (NM_004521; SEQ ID NO:47); KIF 5C(NM_004522; SEQ ID NO:48); KIF 6 (BX649045; SEQ ID NO:49); KIF 7 (NM_017576; SEQ ID NO:50); KIF 9 (NM_022342; SEQ ID NO:51); KIF 10 (NM_001813; SEQ ID NO:52); KIF 11 (NM_004523; SEQ ID NO:53); KIF 12 (NM_138424; SEQ ID NO:54); KIF13A (NM_022113; SEQ ID NO:55); KIF13B (AF279865; SEQ ID NO:56); KIF 14 (D26361; SEQ ID NO:57); KIF 15 (AB035898; SEQ ID NO:58); KIF16A (AK122666; SEQ ID NO:59); KIF16B (AY166853; SEQ ID NO:60); KIF 17 (XM_027915; SEQ ID NO:61); KIF18 (NM_031217; SEQ ID NO:62); KIF19A (AK094619; SEQ ID NO:63); KIF20A (NM_005733; SEQ ID NO:64); KIF20B (NM_016195; SEQ ID NO:65); KIF21A (NM_017641; SEQ ID NO:66); KIF 22 (NM_007317; SEQ ID NO:67); KIF 23 (NM_004856; SEQ ID NO:68); KIF 24 (NM_018278; SEQ ID NO:69); KIF 25 (NM_005355; SEQ ID NO:70); KIF26A (XM_050278; SEQ ID NO:71); KIF26B (BC035896; SEQ ID NO:72); KIF C1 (XM_058039; SEQ ID NO:73); KIF C2 (NM_145754; SEQ ID NO:74); KIF C3 (NM_005550; SEQ ID NO:75); and DYNEIN (BC021297; SEQ ID NO:76).

V. Combination Therapy

In certain embodiments of the invention, an individual receiving cancer therapy of the present invention or an individual that will receive cancer therapy of the present invention also receives an additional cancer therapy. In some instances, the additional therapy targets the primary cancer in the individual, whereas in other instances the additional therapy targets cancer that has metastasized, or both. The inventive therapy may be used during the treatment of the primary tumor and thus be employed at the same time as an additional treatment for the cancer.

Thus, in certain embodiments of the invention, it is desirable to combine the inventive compositions with other agents effective in the treatment of hyperproliferative disease, such as anti-cancer agents. In particular embodiments, an anti-cancer agent includes a composition of the invention. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

More generally, these other compositions would be provided in a combined amount effective to kill or inhibit proliferation of the cell. This process may involve contacting the cells with the inventive agent and the additional agent(s) or multiple factor(s) at the same time. This may be achieved by contacting the cell with a single composition or pharmacological formulation that includes both agents, or by contacting the cell with two distinct compositions or formulations, at the same time, wherein one composition includes the agent of the invention and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with another therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that the inventive therapy could be used similarly in conjunction with chemotherapeutic, radiotherapeutic, or immunotherapeutic intervention, in addition to pro-apoptotic or cell cycle regulating agents, for example.

In one specific embodiment, localized heating may be employed as a therapy in addition to the inventive therapy, and in specific embodiments the localized heating facilitates directly or indirectly the release of a tumor cell from a primary tumor mass. One current tumor treatment is to use an approach such as focal ultrasound or heating of nanoparticles with magnetic fields to heat the local environment surrounding a tumor or the tumor cells themselves. Like focused radiation or laser-based photodynamic therapy, such a heat-based treatment could destroy most of a given tumor, but also promote the spread of the cells that survive the treatment (as can any cancer therapy, in particular aspects of the invention). The subsequent healing process (growth factors, motility stimulation and angiogenesis, for example) could also promote the spread of the tumor cells away from the primary site, similar to surgery. Thus, tissue-damaging types of treatments may be employed with the inventive therapy of inhibition of microtubule protrusions.

The inventive therapy may precede or follow the other agent treatment by intervals ranging from minutes to weeks. In embodiments where the other agent and agent of the invention are applied separately to the cell, one would generally ensure that a significant period of time did not expire between the time of each delivery, such that the agent and additional therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, wherein agent of the invention is "A" and the secondary agent, such as radio- or chemotherapy, for example, is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of the therapeutic agents of the present invention to an individual will follow general protocols for the administration of chemotherapeutics, taking into account the toxicity, if any, of the agent. It is expected that the treatment cycles would be repeated as necessary. It also is contemplated that various standard therapies, as well as surgical intervention, may be applied in combination with the described hyperproliferative cell therapy.

A. Chemotherapy

Cancer therapies also include a variety of combination therapies with both chemical- and radiation-based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with an agent of the invention. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, the additional treatment is a gene therapy in which a therapeutic polynucleotide is administered before, after, or at the same time as an agent of the invention. A variety of proteins are encompassed within the invention, some of which are described below.

1. Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

2. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK'S. One CDK, cyclin-dependent kinase 4 (CDK4), regulates progression through the G1. The activity of this enzyme may be to phosphorylate Rb at late G1. The activity of CDK4 is controlled by an activating subunit, D-type cyclin, and by an inhibitory subunit, the p16INK4 has been biochemically characterized as a protein that specifically binds to and inhibits CDK4, and thus may regulate Rb phosphorylation (Serrano et al., 1993; Serrano et al., 1995). Since the p16INK4 protein is a CDK4 inhibitor (Serrano, 1993), deletion of this gene may increase the activity of CDK4, resulting in hyperphosphorylation of the Rb protein. p16 also is known to regulate the function of CDK6.

p16INK4 belongs to a newly described class of CDK-inhibitory proteins that also includes p16B, p19, p21WAF1, and p27KIP1. The p16INK4 gene maps to 9p21, a chromosome region frequently deleted in many tumor types. Homozygous deletions and mutations of the p16INK4 gene are frequent in human tumor cell lines. This evidence suggests that the p16INK4 gene is a tumor suppressor gene. This interpretation has been challenged, however, by the observation that the frequency of the p16INK4 gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type p16INK4 function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

3. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., BclXL, BclW, BclS, Mcl-1, A1, Bfl-1) or counteract Bcl-2 function and promote cell death (e.g., Bax, Bak, Bik, Bim, Bid, Bad, Harakiri).

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VI. Pharmaceutical Preparations

Pharmaceutical compositions of the present invention comprise an effective amount of one or more agents of the invention and, optionally, additional agents, dissolved or dispersed in or provided with a pharmaceutically acceptable carrier, for example. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one agent of the invention or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The agent of the invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The agent of the invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include the agent of the invention, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the agent of the invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, one or more agents of the invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, an agent of the invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound agent of the invention may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VII. Screening For Modulators Of the Microtubule Protrusions

The present invention further comprises methods for identifying modulators of the microtubule protrusions from cancer cells or modulators of one or more components of the microtubule protrusions from cancer cells. These assays may comprise random screening of large libraries of candidate substances; alternatively, the assays may be used to focus on particular classes of compounds selected with an eye towards structural attributes that are believed to make them more likely to modulate the function of one or more microtubule protrusions or one or more components thereof.

By function, for example, it is meant that one may assay for the ability of a compound to inhibit at least partially the production, extension, and/or activity of one or more microtubule protrusions from one or more cancer cells, including one or more detached cancer cells. In alternative embodiments, one assays the promotion of degradation of the microtubule protrusions.

To identify a microtubule protrusion modulator, one generally will determine the function, presence, or both of one or more microtubule protrusions in the presence and absence of the candidate substance, a modulator defined as any substance that alters function, presence, or both. For example, a method generally comprises:

(a) providing a candidate modulator;

(b) admixing the candidate modulator with an isolated compound or cell, or a suitable experimental animal;

(c) measuring one or more characteristics of the compound, cell or animal in step (c); and (d) comparing the characteristic measured in step (c) with the characteristic of the compound, cell or animal in the absence of said candidate modulator, wherein a difference between the measured characteristics indicates that said candidate modulator is, indeed, a modulator of the compound, cell or animal.

Assays may be conducted in cell-free systems, in isolated cells, or in organisms including transgenic animals.

It will, of course, be understood that all of the screening methods of the present invention are useful in themselves notwithstanding the fact that effective candidates may not be found. The invention provides methods for screening for such candidates, not solely methods of finding them.

A. Modulators

As used herein the term "candidate substance" refers to any molecule that may potentially inhibit or enhance microtubule protrusion activity, function, or presence, but most preferably inhibit. The candidate substance may be a protein or fragment thereof, a small molecule, or even a nucleic acid molecule. It may prove to be the case that the most useful pharmacological compounds will be compounds that are structurally related to other microtubule inhibitors, GSK-3 inhibitors, vimentin inhibitors, kinesin inhibitors, APC-enhancers, or a combination thereof. Using lead compounds to help develop improved compounds is known as "rational drug design" and includes not only comparisons with known inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on the microtubule protrusion. Regardless of the type of inhibitor or activator identified by the present screening methods, the effect of the inhibition or activator by such a compound results in one or more modifications of the microtubule protrusion as compared to that observed in the absence of the added candidate substance.

B. In Vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

An exemplary technique for high throughput screening of compounds is described in WO 84/03564. Large numbers of small peptide test compounds are synthesized on a solid substrate, such as plastic pins or some other surface. Bound polypeptide is detected by various methods.

C. In Cyto Assays

The present invention also contemplates the screening of compounds for their ability to modulate a microtubule protrusion in cells. Various cell lines can be utilized for such screening assays, including cells specifically engineered for this purpose including, for example, breast cancer cell lines.

Depending on the assay, culture may be required. The cell is examined using any of a number of different physiologic assays. For example, high-content microscopic imaging could be used to record the presence of microtubule protrusions in high throughput assays, or cell-cell adhesion could be measured as a functional indication of protrusion activity, for example. Alternatively, molecular analysis may be performed, for example, looking at protein expression, mRNA expression (including differential display of whole cell or polyA RNA) and others.

D. In Vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

The present invention provides methods of screening for a candidate substance that modulates, such as at least inhibits partially, the function, production, or activity of one or more microtubule protrusions, for example from a cancer cell, including a detached cancer cell. In specific embodiments, the present invention is directed to a method for determining the ability of a candidate substance to inhibit or reduce metastasis of cancer cells, generally including the steps of: administering a candidate substance to the animal; and determining the ability of the candidate substance to interfere with one or more characteristics of a detached cancer cell comprising one or more microtubule protrusions.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

VIII. Kits of the Invention

Any of the compositions described herein may be comprised in a kit, and the kit itself and its reagents therein are housed in a suitable container. In a non-limiting example, an agent that inhibits the function or activity of a microtubule protrusion and/or that prevents production or extension of the protrusion may be comprised in a kit. In an additional example, the kit further comprises an additional agent, such as a pharmaceutically acceptable carrier, an additional cancer therapeutic agent, or both, for example. The kits will thus comprise, in suitable container means, the agent of the invention and, optionally, an additional cancer therapeutic agent.

The kits may comprise a suitably aliquoted agent, whether labeled or unlabeled, such as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one components in the kit, the kit also will generally comprise a second, third or other additional container into which the additional components may be separately placed. However, various combinations of components may be comprised in a vial. The kits of the present invention also will typically include a means for containing the agent, additional agent, carrier, or any other reagent containers in close confinement for commercial sale. Such containers may include injection or blow molded plastic containers into which the desired vials are retained.

When the components of the kit are provided in one and/or more liquid solutions, the liquid solution may be an aqueous solution, with a sterile aqueous solution being particularly preferred. The agent may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means, in some embodiments.

Irrespective of the number and/or type of containers, the kits of the invention may also comprise, and/or be packaged with, an instrument for assisting with the injection/administration and/or placement of the ultimate agent, such as within the body of an animal. Such an instrument may be a syringe, pipette, forceps, and/or any such medically approved delivery vehicle. In specific cases, the kit comprises one or more reagents for testing for cancer, such as by testing for one or more cancer cells that have one or more microtubule protrusions. The kit may also comprise one or more reagents for localization of cells with microtubule protrusions, such as a signal, including fluorescence, for example. Membrane stains, such as DiI or wheat-germ agglutinin conjugates with fluorescent dyes or quantum dots would serve as effective imaging agents for microtubule protrusions, for example.

IX. Examples

The following examples are provided for further illustration of the present invention, and do not limit the invention. The examples provided herein are for illustrative purposes only, and are in no way intended to limit the scope of the present invention. While the invention has been described in detail, and with reference to specific embodiments thereof, it will be apparent to one with ordinary skill in the art that various changes and modifications can be made in the specific embodiments which are disclosed and still obtain a like or similar result without departing from the spirit and scope of the invention. Experiments and exemplary procedures are described below which provide additional enabling support for the present invention.

Example 1

Exemplary Materials and Methods

This example provides exemplary materials and methods for use in the invention, although the skilled artisan is aware of other materials and methods that are sufficiently suitable.

Exemplary Cell Lines and Materials

MCF10A human mammary epithelial cells were kindly provided by Fred Miller and Robert Pauley of the Barbara Ann Karmanos Cancer Institute (Detroit. Mich.) and are a high-passage clone designated MCF10A1. MCF10A cells were grown in DMEM/F12 (Gibco) supplemented with 5% horse serum, insulin (5 μg/ml), EGF (20 ng/ml), hydrocortisone (500 ng/ml), penicillin-streptomycin (100 μg/ml each), and L-glutamine (2 mmol/L). EpH4 mouse mammary epithelial cells and those stably expressing pcDNA3.1-Bcl2 (B19) were previously described (Pinkas et al., 2004; Lopez-Barahona et al., 1995), and maintained in DMEM (Gibco) supplemented with 10% bovine calf serum, penicillin-streptomycin (100 μg/ml each), and L-glutamine (2 mmol/L). For all inhibitor and detachment studies, both MCF10A and EpH4 cells were treated in serum-free DMEM.

Immunofluorescence and Microscopy

EpH4 and B19 cells were suspended over 2% agarose coated plates to prevent attachment in either serum-free DMEM or media containing. Latrunculin-A (5 μM) to enhance protrusions. For co-staining of α-tubulin and actin, suspended cells were then centrifuged onto poly-L-lysine coated coverslips (280 g×5 min), fixed in 3.7% formaldehyde in PBS for 10 min, and permeablized with 0.1% Triton X-100 in PBS. Adhered cells were then stained for 1 hr at room temperature using FITC-conjugated anti-α-tubulin (1:200; Sigma), Alexa-594 phalloidin (1:100; Molecular Probes), and Hoescht 33342 (1:5000; Sigma).

For visualization of modified tubulin, untreated cells were grown on glass coverslips or suspended in the presence of 5 μM LA and centrifuged onto poly-L-lysine coated coverslips. Cells were fixed in ice-cold methanol for 10 min, permeablized in 0.25% Triton X-100 for 10 min, and blocked for 1 hr at room temperature in PBS containing 5% BSA and 0.5% NP40. Immunostaining for mouse monoclonal antibodies α-tubulin clone DM1A (1:2000; Sigma), tyrosinated tubulin clone TUB1A2 (1:2000; Sigma), and acetylated tubulin clone 611B1 (1:1000; Sigma) were incubated at room temperature for 1 hr in PBS containing 2% BSA and 0.5% NP40. Rabbit polyclonal anti-detyrosinated tubulin (Glu; 1:500, Chemicon) was incubated overnight at 4° C. Anti-IgG antibodies conjugated to Alexa-594 (1:1000; Molecular Probes) were used for secondary detection. Live and fixed cell images were collected using an Olympus CKX41 inverted fluorescent microscope (Melville, N.Y.) equipped with the Olympus F-View II 12-bit CCD digital camera system. Image acquisition and analysis was performed using the Olympus MicroSuite Five imaging software.

Western Blotting

Whole cell lysates were prepared from EpH4 cells that were scraped or suspended in the presence or absence of 5 μM Latrunculin-A. Cells were pelleted at 3000 rpm×5 min and resuspended in lysis buffer (2% SDS, 100 mM Tris-HCl (pH 6.8), 20% Glycerol, 20 mM DTT, 1 mM phenylmethylsulfonyl fluoride, 1% protease inhibitor cocktail (Sigma, P2714)), and then immediately boiled for 10 min. Protein concentration was measured using a Lowry based assay (Bio-Rad, Hercules, Calif.). The amount of 17.5 μg of protein from each sample was separated by SDS-PAGE on 10% polyacrylamide gels and then transferred to Immuno-Blot PVDF membranes (Bio-Rad, Hercules, Calif.). The membrane was blocked in 2% milk in TBS with 0.1% Tween for 1 hr at room temperature followed by an overnight incubation at 4° C. in monoclonal α-tubulin (1:1000), tyrosinated tubulin (1:1000), acetylated tubulin (1:1000), and polyclonal detyrosinated tubulin (1:1000) in 1% milk in TBST. Secondary antibodies to IgG conjugated to horseradish peroxidase were used (1:5000; GE Healthcare, Piscataway, N.J.) and visualized using ECL chemiluminescent detection kit.

Cell-Substratum Attachment Assay

Equivalent numbers of B19 cells were suspended over 6-well plates coated in 2% agarose in serum-free media containing 5 μM Latrunculin-A (LA; BioMol, Plymouth Meeting, Pa.), 100 μM colchicine (Col; Sigma, St. Louis, Mo.), 5 μg/ml nocodazole (Noc), or 1 μg/ml vinblastine (VinB; Sigma) for a duration of 1 hr at 37° C. Cells were collected by centrifugation (1000 rpm×5 min) and drug containing media was aspirated. Cells were resuspended in EpH4 serum-containing growth media and aliquoted out into 24 wells (8 timepoints×3 replicates) of a 96-well clear bottom black plate. After plating, cells were allowed to attach for duration of 15 min, 45 min, 1.5 hr, 2 hr, 3 hr, 4 hr, 5 hr, and 24 hr at which point the media was aspirated from the replicate wells, washed twice in PBS, and fresh growth media was replaced at each timepoint. After 24 hr, all wells were aspirated and cells were incubated in growth media containing Hoescht 33342 (1:5000) for 30 min at 37° C. to label all attached cells. Fluorescence was measured using a Biotek Synergy HT Multi-Detection Microplate Reader (Winooski, Vt.) at excitation wavelength 360 nm and an emission filter of 460 nm followed by subsequent analysis using the KC4 Data Analysis software. The percentage of cell attachment for each treatment exposure was calculated as the RFU at each timepoint divided by the RFU at 24 h (maximum attachment). The standard deviations of triplicates at each timepoint are shown.

Cell-Cell Attachment Assay

B19 cells were seeded onto 10 cm dishes until 80% confluency. The media was aspirated and cells were incubated in fresh growth media containing Hoescht 33342 (1:5000) for 30 min at 37° C. to label all attached cells. The cells were washed twice in PBS, detached by trypsinization, and an equivalent number of cells were resuspended in serum-free media containing 0.3% methylcellulose with either 5 μM Latrunculin A, 100 μM Colchicine, 1 μg/ml vinblastine, or 5 μg/ml nocodazole and plated over 2% agarose-coated 24-well plates. The progression of cell-cell adhesion over time was visualized by the EpiChemi3 Imaging System (UVP, Inc.; Upland, Calif.) using an excitation wavelength of 365 nm and a blue band pass filter. Images were obtained with an attached Hamamatsu CCD camera (Hamamatsu Photonics, Hamamatsu City, Japan) and analyzed with UVP Labworks Image Acquisition and Analysis Software v. 4.6.

Example 2

Characterization of Microtubule Protrusions and Inhibition Thereof

When detached from extracellular matrix, the nontumorigenic MCF10A human mammary epithelial cell line and EpH4 mouse mammary epithelial cell line produce protrusions of the plasma membrane (FIG. 1A, black arrows). Time-lapse video microscopy detects rapid motion in these protrusions and transient probing contact with surfaces. This response is short-lived, as EpH4 or MCF10A cells die efficiently by apoptosis within 24 hours following detachment (Pinkas et al., 2004; Martin and Leder, 2001), and complete cellular fragmentation by 48 hrs. terminates these protrusions (FIG. 1A). However, when EpH4 cells were used that overexpress Bcl-2 (B 19) and are highly resistant to apoptotic challenge (Pinkas et al., 2004), many of the cells remain intact after 48 hours and continue to generate protrusions (FIG. 1A). Similar resistance and protrusions are observed in EpH4 or MCF10A cells overexpressing either Bcl-2 or Bcl-xL (Martin et al., 2004; Martin and Leder, 2001), and apoptotically-resistant cells can continue to generate protrusions for at least seven days following detachment. Cells that produce protrusions exclude propidium iodide, indicating that the plasma membrane remains intact (FIG. 1B, white arrow).

Figure 2:
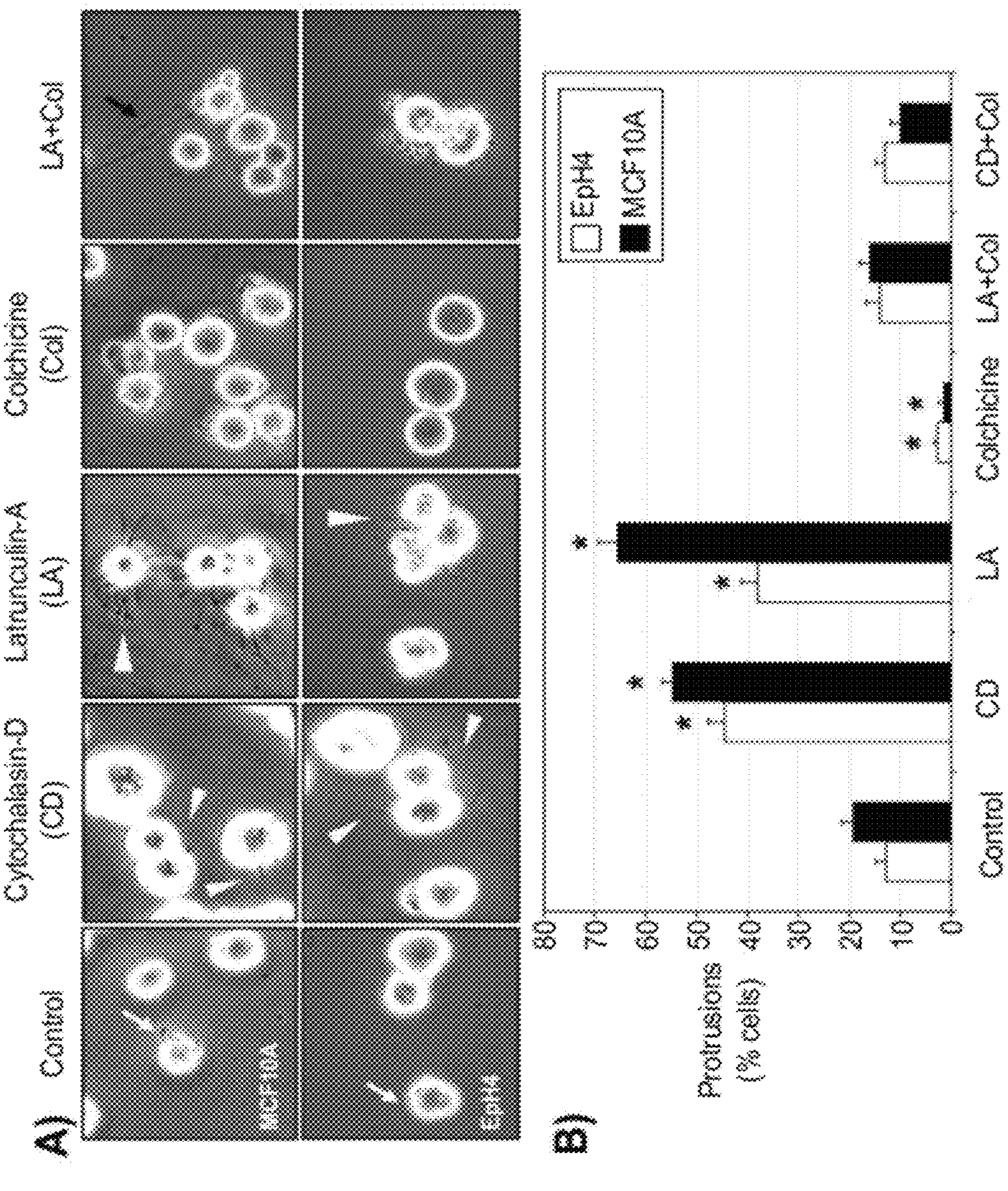
FIGS. 2A-2B show that cytoskeletal inhibitors affect cellular protrusions.
Figure 3:
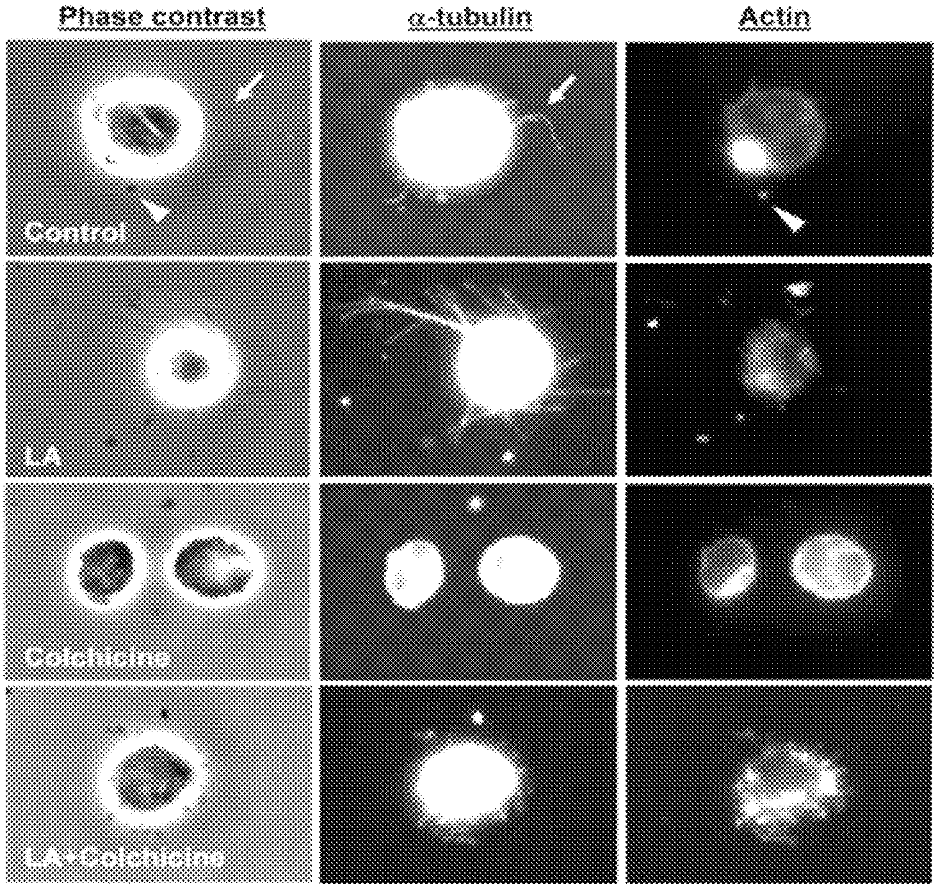
FIG. 3 shows that protrusions are microtubule-based. EpH4 cells were suspended in either DMEM (Control) or media containing 5 μM Latrunculin-A (LA), 1 μM Colchicine or the combination of both drugs for 30 minutes. Cells were then spun onto glass coverslips and fluorescently stained for α-tubulin (green) and polymerized actin (red). Protrusions that are difficult to see by phase contrast are easily discernible with immunostaining for α-tubulin (white arrows). Protrusions contain little polymerized actin, except at points of concentration, which are often at the end (arrowhead). Depolymerization of actin with LA strongly enhances the formation of microtubule protrusions.

In order to initially characterize the cytoskeletal mechanism underlying these protrusions, suspended cells were treated with inhibitors of actin and tubulin polymerization (FIG. 2). After 15 minutes of suspension, the protrusions in untreated EpH4 or MCF10A cells remain fairly short (FIG. 2, white arrows). These early protrusions can often be difficult to detect with phase-contrast microscopy, due to interfering light refraction from the plasma membrane. Despite an initial hypothesis that these protrusions were actin-driven, inhibition of actin polymerization with latrunculin-A (LA) significantly enhanced both the number and length of protrusions (FIG. 2, arrowheads). Inhibition of tubulin polymerization with colchicine prevented protrusions and led to a general blebbing of the plasma membrane. Simultaneous treatment with LA and colchicine generally blocked protrusions, and those that did form appeared fragmented into a "beads-on-a-string" morphology (FIG. 2, black arrow). These inhibitor results suggested that the protrusions were microtubule-driven and immunofluorescence of detached cells spun onto coverslips confirmed this hypothesis and the relative lack of actin filaments along the protrusions (FIG. 3). Protrusions were more easily visible with immunofluorescence than phase contrast microscopy (FIG. 3, white arrows). Although actin filament staining was generally low along the length of the protrusion, dense points of actin were often found at the end of protrusions (FIG. 3, arrowheads). The effect of LA to increase the number and length of microtubule protrusions was also evident with immunofluorescence.

Figure 4:
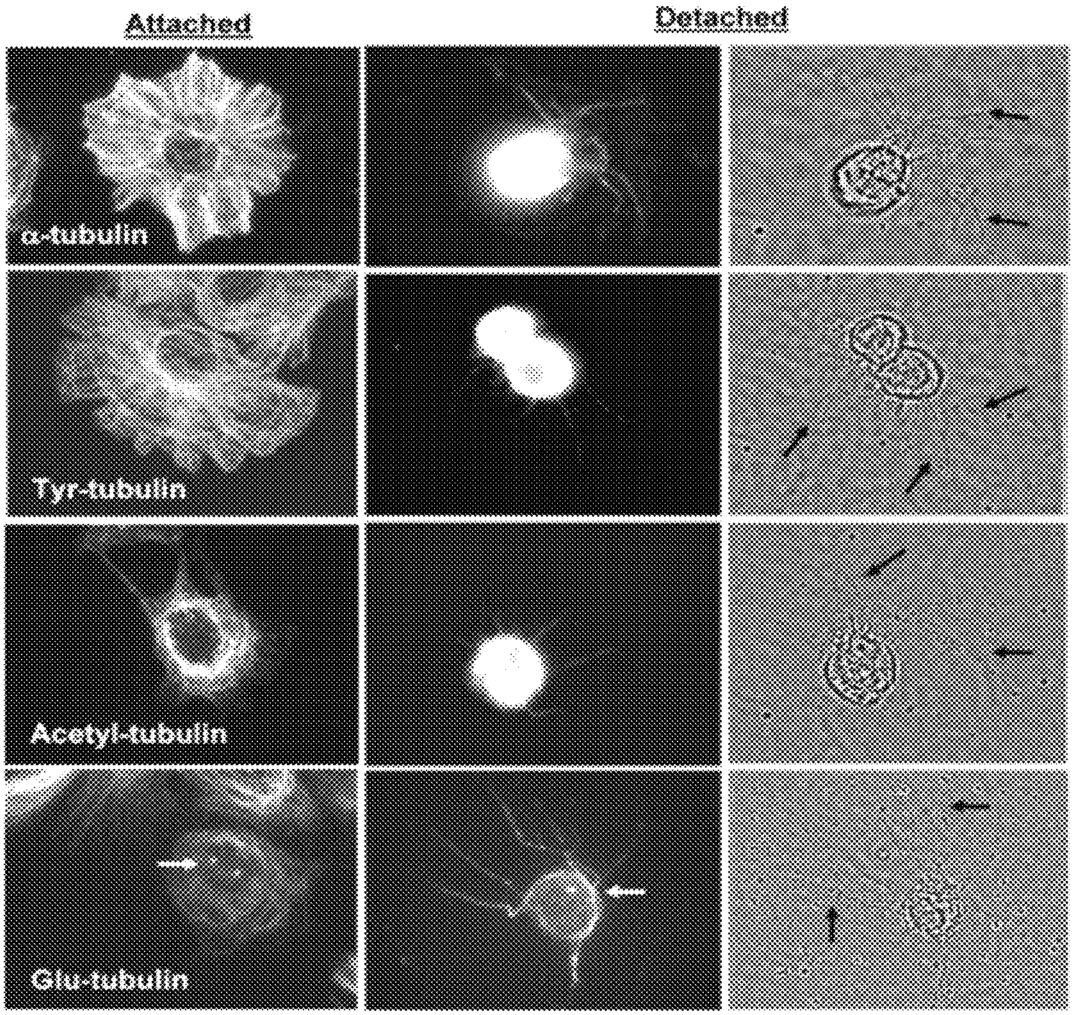
FIG. 4 demonstrates that protrusions are enriched in detyrosinated α-tubulin. EpH4-Bcl2 cells were grown on glass coverslips (Attached) or suspended over agarose for one hour in the presence of LA (5 μM) to enhance protrusion formation (Detached). Immunostaining for different posttranslationally-modified forms of tubulin indicates differential localization in attached and suspended cells. Full-length α-tubulin, Tyr-tubulin and Acetyl-tubulin localize predominantly to the cell body in detached cells rather than specifically along the extended protrusions visible by phase-contrast (black arrows). Detyrosinated α-tubulin (Glu-tubulin) is enriched in the protrusions relative to the cell body, and is also found in centrosomes (white arrows).

Posttranslationally-modified forms of α-tubulin are differentially localized between the cell body and protrusions, depending on the attachment state of the cells (FIG. 4). This and the remaining experiments were performed in EpH4 cells expressing Bcl-2 (B19) to prevent induction of apoptosis during the experiments, but similar results were observed in both MCF10A and EpH4 cells. Immunofluorescence with an antibody that recognizes all forms of α-tubulin shows staining throughout cytoplasmic microtubules in attached cells, and a relatively even distribution between the cell body and protrusions in detached cells. Full-length α-tubulin contains a tyrosine at its c-terminal end (Tyr-tubulin), and is generally found in microtubules which turnover with a half-life of minutes (Webster et al., 1987). This dynamic, tyrosinated tubulin is also found throughout cytoplasmic microtubules and specifically extends into lamellipodia in attached cells. In suspended cells, tyrosinated tubulin is mostly concentrated in the cell body and only weakly labels protrusions. Far fewer acetylated microtubules are found in attached cells, showing a mostly perinuclear localization. Acetylated tubulin is also found primarily in the cell body of detached cells, similar to tyrosinated tubulin. Tubulin which has been detyrosinated (Glu-tubulin) labels only a subset of cytoplasmic microtubules in attached cells, and is predominantly found in centrosomes (FIG. 4, white arrows). In detached cells, Glu-tubulin remains at the centrosome, but unlike the other forms of α-tubulin, Glu-tubulin is enriched in protrusions relative to the cell body.

Figure 5:
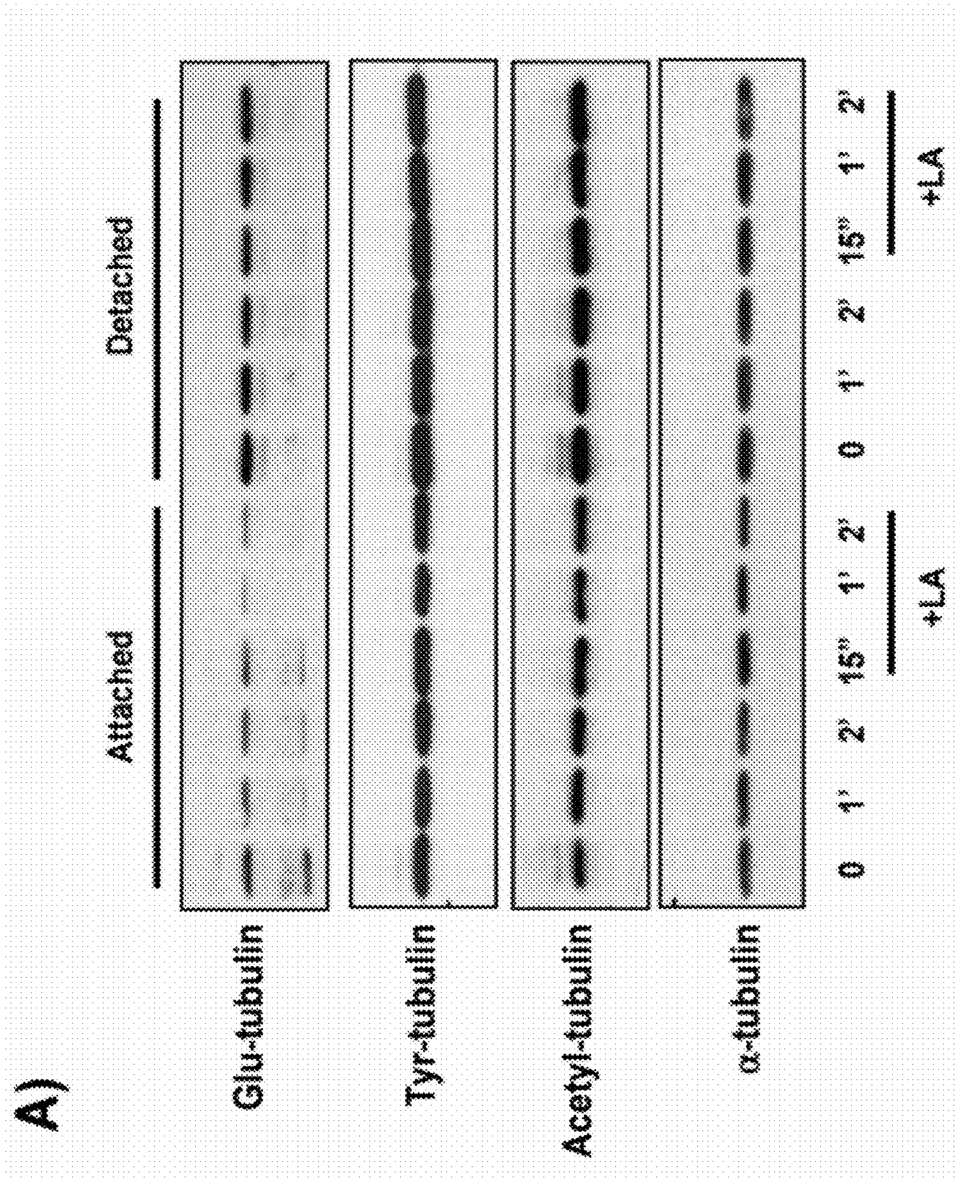
FIGS. 5A-5B show that cellular levels of Glu-tubulin increase in response to detachment. EpH4-Bcl2 cells were grown attached to tissue culture dishes or suspended over agarose for the indicated times in either the absence or presence of LA (5 μM).
Figure 5:
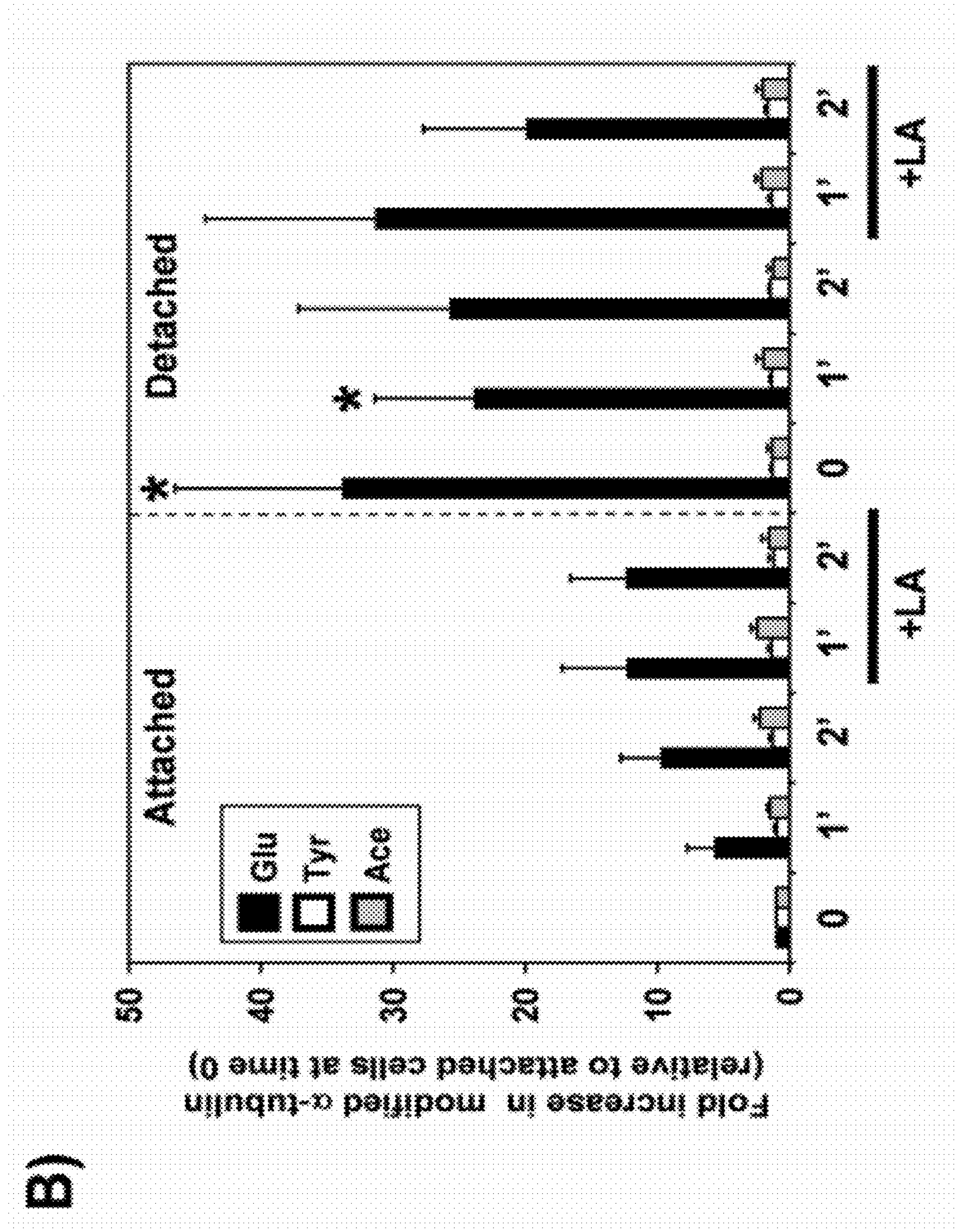

Measurement of cellular levels of modified α-tubulin shows that detyrosinated Glu-tubulin is increased in detached cells (FIG. 5). Immediately following detachment, levels of Glu-tubulin increase and remain elevated for at least 2 hours. However, the level of Glu-tubulin protein is not specifically increased by treatment with LA in either attached or suspended cells. The increased length and number of protrusions in response to LA may therefore reflect a decrease in an actin-dependent counteracting force, rather than a direct induction of protrusions. Total cellular levels of α-tubulin, tyrosinated or acetylated tubulin do not show a detachment-induced increase comparable to Glu-tubulin, and remain unaffected by LA treatment.

Figure 6:
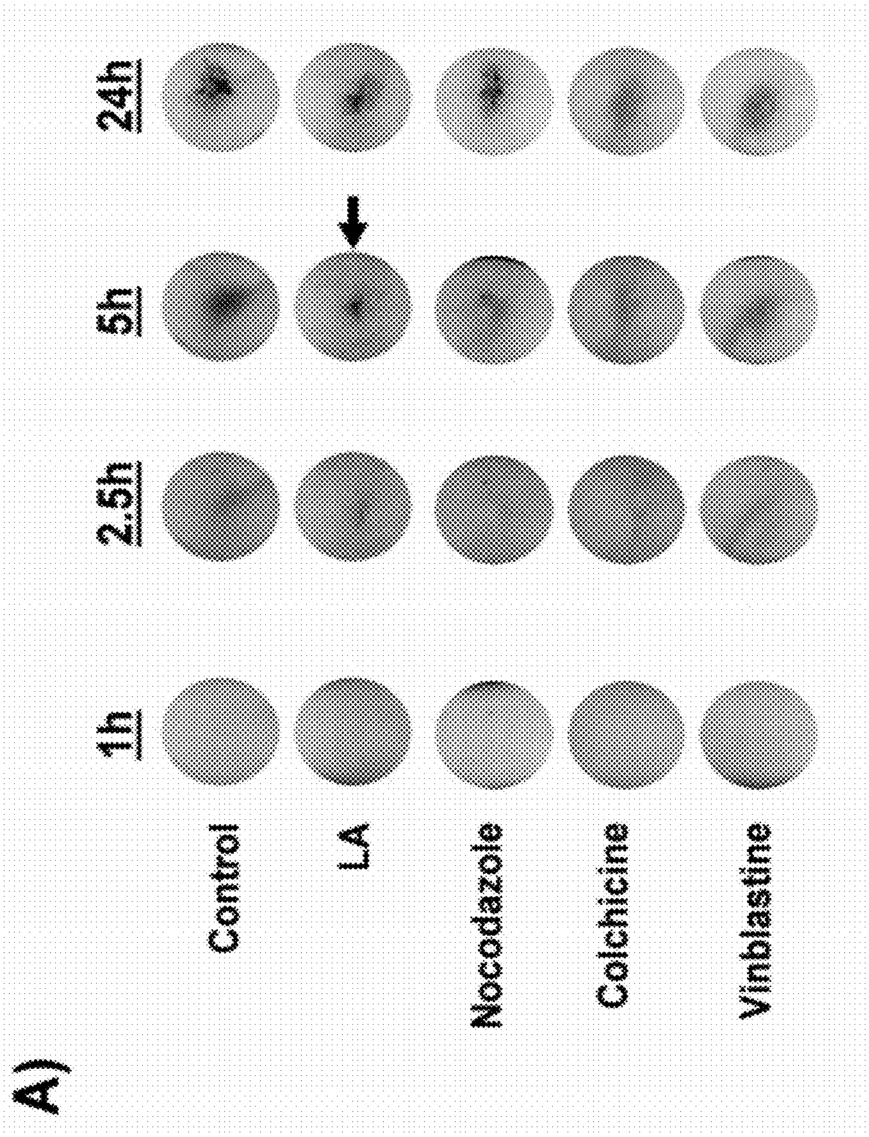
FIGS. 6A-6B demonstrates that microtubule protrusions are required for efficient cell attachment.
Figure 6:
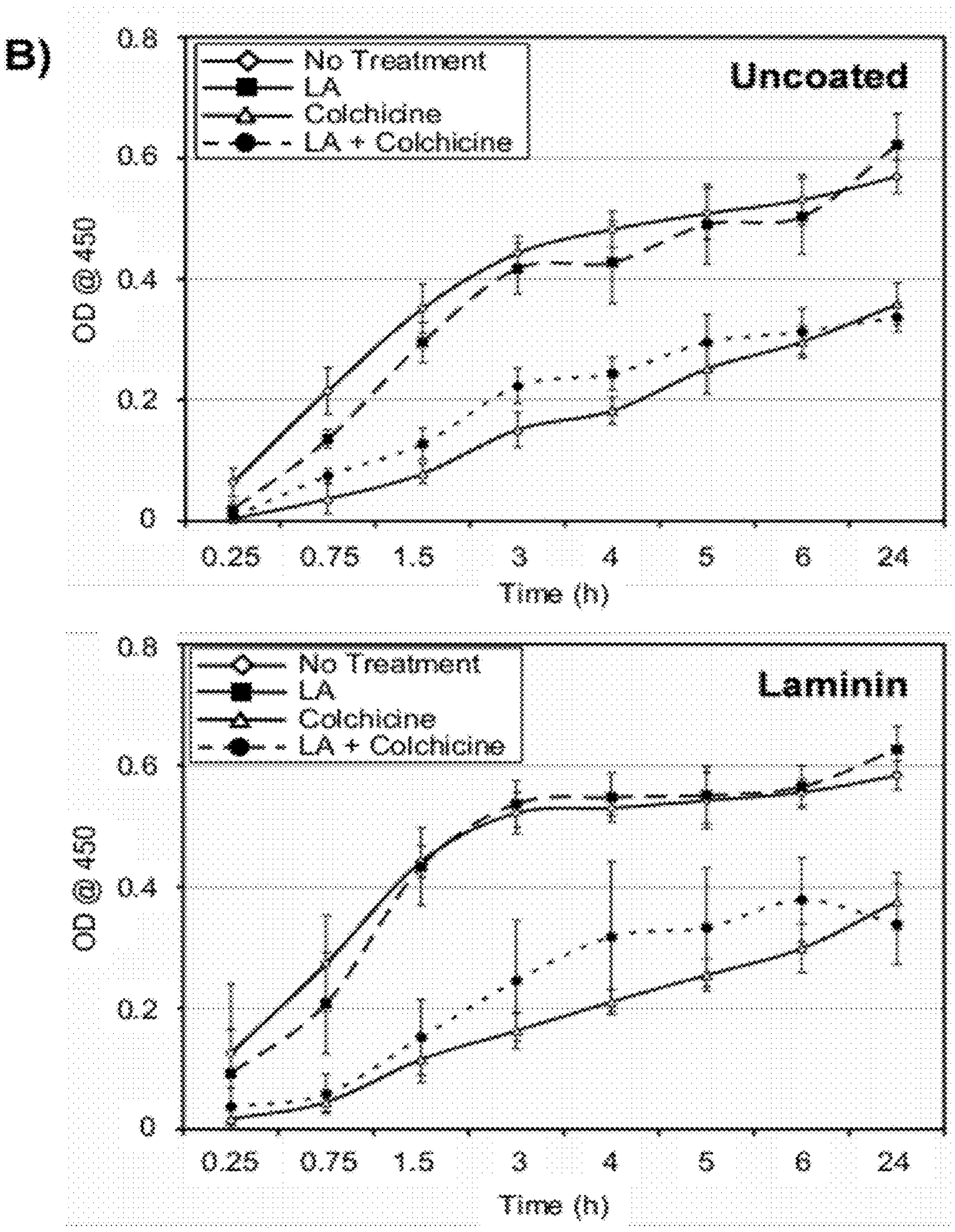

To determine if these microtubule protrusions influence the ability of cells to form attachments, the cells were treated with inhibitors of actin or tubulin polymerization and assessed both cell-cell and cell-substratum attachment (FIG. 6). Transient inhibition of actin polymerization with LA did not significantly affect attachment of cells to tissue culture surfaces, particularly at early time points (FIG. 6A). Treatment with LA did speed the rate at which cells bound to each other, with enhanced clustering by 5 hours compared to other conditions (FIG. 6B). Three different inhibitors of tubulin polymerization (nocodazole, colchicine and vinblastine) significantly delayed attachment of cells to tissue culture surfaces (FIG. 6A) and prevented efficient clustering of cells to each other (FIG. 6B). At this point, the results indicate that these microtubule protrusions simply facilitate contact between cells or with a surface without strictly depending on a specific receptor interaction. Induction of such nonspecific attachment activity in detached mammary epithelial cells could promote tumor cell dissemination, particularly when apoptotic resistance allows this response to continue for extended periods.

Example 3

Protrusions are Increased in Metastatic Breast Tumor Cell Lines

Figure 7:
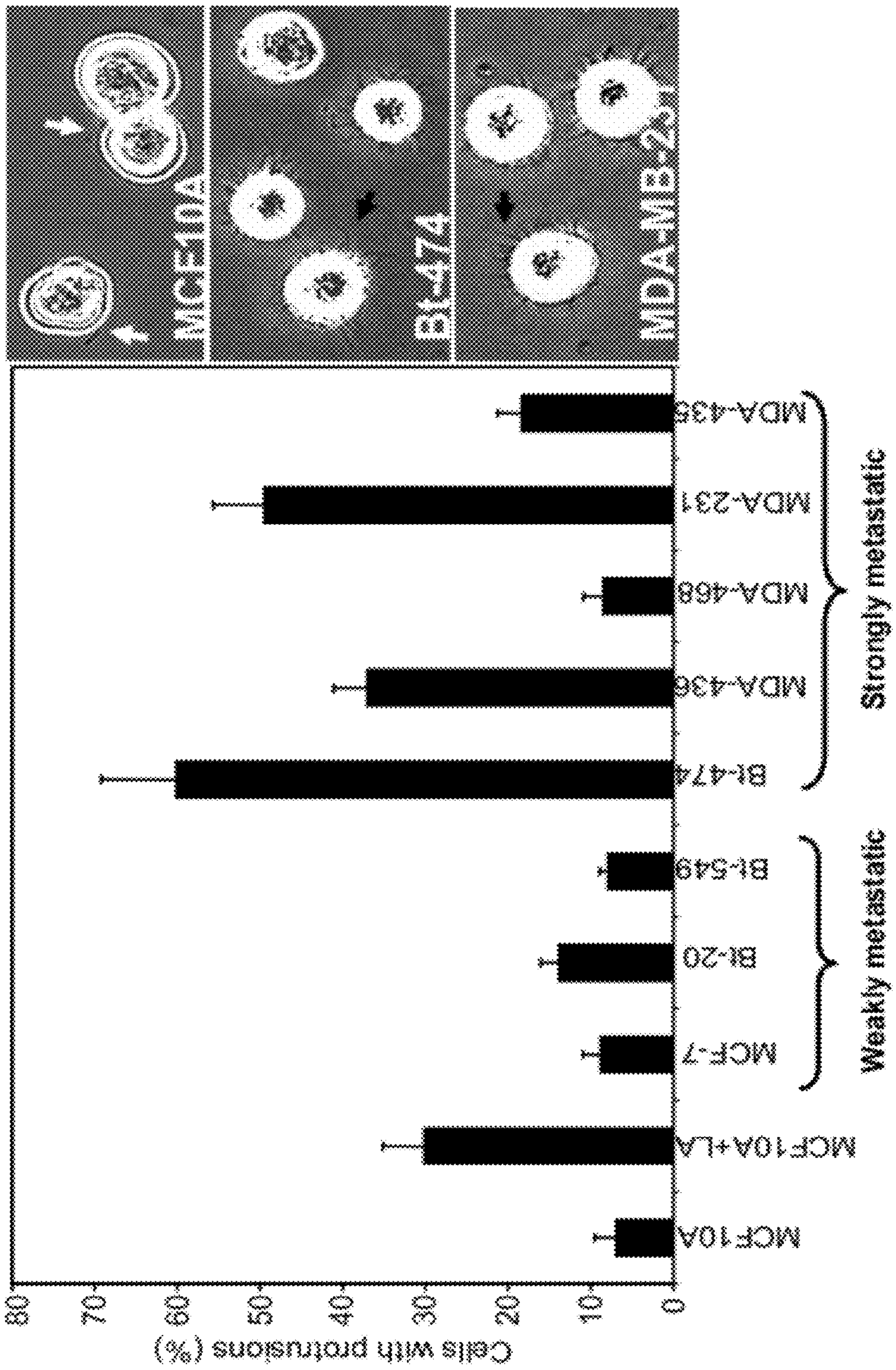
FIG. 7 demonstrates that metastatic breast tumor cell lines have more frequent and numerous protrusions.

FIG. 7 shows that metastatic breast tumor cell lines have more frequent and numerous protrusions. The nontumorigenic human mammary epithelial cell line (MCF10A) or the indicated human breast tumor cell lines were grown in suspension for 30-60 minutes, and protrusions were counted in random fields with phase-contrast microscopy. Values represent the mean±S.D. of three experiments in which at least 100 cells were counted. Treatment of MCF10A cells with the exemplary actin inhibitor, Latrunculin-A (LA, 5 mM), increases protrusions, as observed previously. Human tumor cell lines show high levels of protrusions even in the absence of LA treatment, indicating that depolymerization of actin is not required for tumor lines to produce microtubule protrusions. In addition to more frequent protrusions, metastatic tumor cell lines often displayed a greater number of protrusions per cell. This effect was most apparent in the highly metastatic but exemplary Bt-474 and MDA-MB-231 cells (pictured, black arrows). The exemplary MCF10A cells show far fewer and shorter protrusions at the same time point (pictured, white arrows). Such protrusions are not observed in attached cells.

Thus, in embodiments of the invention, tumor cells produce more protrusions and indicate kinesin motor proteins and Gsk-3b as at least some signaling pathways involved in protrusion generation.

Example 4

Chemical Inhibition of Microtubule Protrusions

Figure 8:
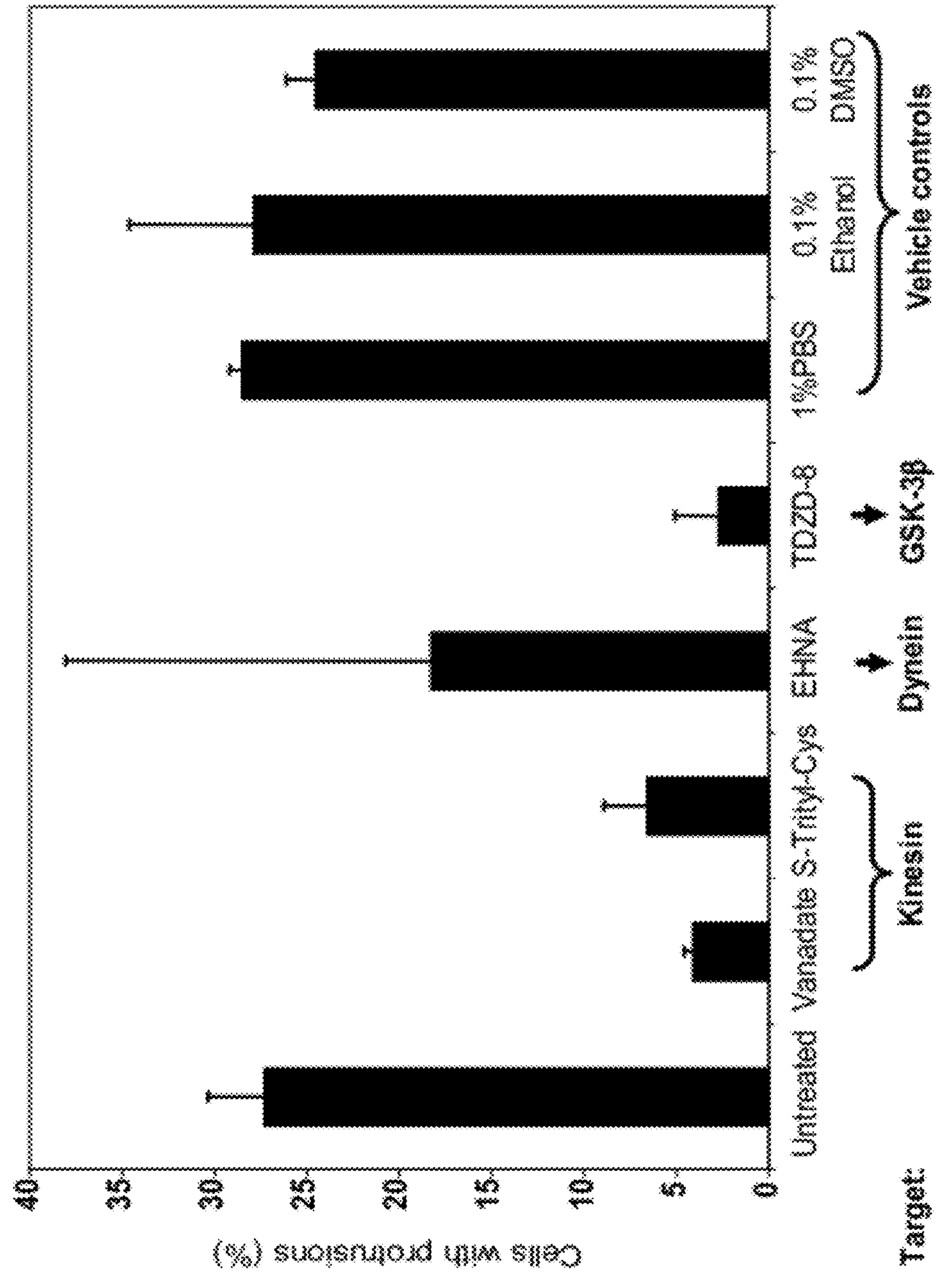
FIG. 8 demonstrates that protrusions can be reduced by chemical inhibition of specific signaling proteins.
Figure 9:
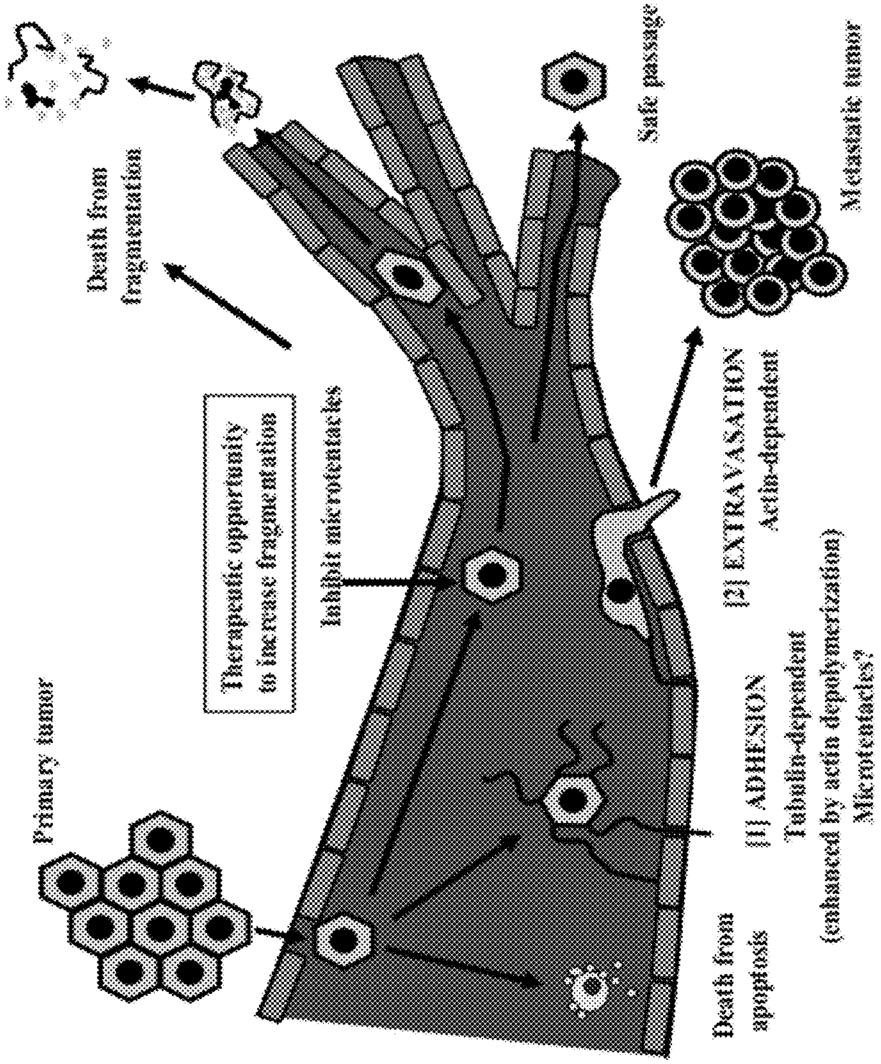
FIG. 9 illustrates how circulating tumor cells may become part of a metastatic tumor, in specific embodiments. In particular, circulating cells eventually get destroyed in the capillaries unless they adhere to the blood vessel walls.

MCF10A cells were placed into suspension in the presence of the indicated chemical inhibitors targeted at specific signaling pathways or the corresponding vehicle controls. Cells were then treated with the actin polymerization inhibitor, Latrunculin-A (LA, 5 μM) for one hour to enhance protrusions. FIG. 8 shows chemical inhibition of kinesin motor protein activity with sodium orthovanadate (1 mM) or S-Trityl-L-Cysteine (100 μM) significantly reduces protrusions. Inhibition of dynein motor proteins with EHNA (500 mM) also reduced protrusions, but these results were not statistically significant. The strongest inhibition of protrusions resulted from pretreatment of cells with a chemical inhibitor of glycogen-synthase-kinase-3β (TDZD-8, 20 μM). Treatment of cells with the corresponding vehicle controls (1% PBS, 0.1% ethanol, 0.1% DMSO) did not effect protrusions. These data indicate that there is kinesin and GSK-3b activity in the generation of microtubule protrusions in detached cells, in specific embodiments of the invention. Thus, protrusions can be reduced by chemical inhibition of specific signaling proteins.

Example 5

Detyrosinated Microtubule Protrusions in Suspected Mammary Epithelial Cells Promote Reattachment Breast tumor cells can disseminate prior to significant primary tumor growth and remain dormant in distant tissues for extended periods of time (Naumov et al., 2002; Naumov et al., 2001; Schmidt-Kittler et al., 2003). Survival, invasion and reemergence of such disseminated cells are primary determinants of tumor recurrence and patient death (Chambers et al., 2002). Detachment of epithelial cells from the extracellular matrix of their organ of origin causes cell rounding that leads rapidly to apoptotic cell death, a principle which is thought to limit metastatic spread (Frisch and Francis, 1994; Reed, 2003). In mammary epithelial cells, the inventors have shown that apoptotic resistance allows cells to survive rounding, but additional genetic mutations are required for active tumor growth (Pinkas et al., 2004; Martin and Leder, 2001; martin et al., 2004). Resistance to apoptosis by overexpression of survival proteins, like Bcl-2, prevents cell death during dissemination, but cell cycle arrest can still occur through activation of p53 (Nikiforov et al., 1996; Nikiforov et al., 1997). In solid tumors like breast cancer, detached cells generally remain arrested and must adhere to extracellular matrix in distant tissues to reinitiate growth (Naumov et al., 2002; Naumov et al., 2001). So while apoptotic resistance can promote extended bloodborne survival, additional mechanisms are required for tumor cells to escape blood vessels and successfully colonize distant tissues (Naumov et al., 2001).

In vivo microscopy recently demonstrated that bloodborne tumor cells depend on tubulin polymerization to attach to the walls of capillary blood vessels (Korb et al., 2004). However, any specific role for microtubules in this process remains unclear. Surprisingly, this recent study also showed that inhibiting actin polymerization greatly increased binding of tumor cells to blood vessel walls, even though actin depolymerization inhibits the actin-based invadopodia and podosomes that are well-known to affect the invasion of adherent tumor cells (Korb et al., 2004). Bloodborne tumor cells therefore attach to capillary vessel walls via a cytoskeletal mechanism that is distinct from that of adherent cells, and is currently not well-characterized.

As described herein, mammary epithelial cell lines generate long and dynamic microtubule-driven protrusions of the plasma membrane after detachment. We also determine that detachment produces rapid detyrosination of α-tubulin, and the concentration of detyrosinated tubulin in protrusions. Full length α-tubulin contains a tyrosine residue at its c-terminus, and is termed Tyr-tubulin. Cleavage of this c-terminal tyrosine by a tubulin carboxypeptidase exposes a glutamic acid residue, yielding a detyrosinated form (Glu-tubulin) (Argarana et al., 1977; Argarana et al., 1978). Although this α-tubulin modification has been appreciated for nearly thirty years, the identity of the gene encoding tubulin carboxypeptidase remains unknown. Glu-tubulin is postranslationally converted back to Tyr-tubulin, by a tubulin tyrosine ligase (TTL), which has recently been cloned in mice and humans (Erck et al., 2003). While microtubules containing Tyr-tubulin have a relatively short half-life, measured in minutes, Glu-tubulin is enriched in a more stable subset of microtubules (Webster et al., 1987). Microtubules containing Glu-tubulin can persist for hours and have been observed to remain for as long as 16 hours in nondividing cells (Webster et al., 1987). In breast tumor samples, increased levels of Glu-tubulin are associated with poor patient prognosis and an increased risk of cancer-related complications, but the mechanism for this effect is still unknown (Mialhe et al., 2001).

Microtubule-based protrusions promote reattachment of mammary epithelial cells to surfaces and each other, and may therefore allow detached cells to escape apoptosis by reattaching. Since this response persists in cells overexpressing Bcl-2 or Bcl-xL, it may promote the dormant dissemination of apoptotically-resistant tumor cells, even though they would not reinitiate growth until a much later time. The data indicate that these microtubule protrusions do not necessarily originate from a tumor-specific mutation, since they are also observed in nontumorigenic mammary epithelial cell lines of both human and mouse origin.

However, the persistence of this inherent microtubule response in apoptotically-resistant cells could have important consequences for the ability of disseminated tumor cells to efficiently adhere to new sites. The increased levels of Glu-tubulin upon detachment and its concentration in plasma membrane protrusions provide novel mechanisms to initiate microtubule-based tumor cell adhesion in blood vessels, and may explain why increased levels of Glu-tubulin in breast tumors predict poor patient survival.

Example 6

Exemplary Microscopy and Other Studies of Microtubule Protrusions

Figure 10:
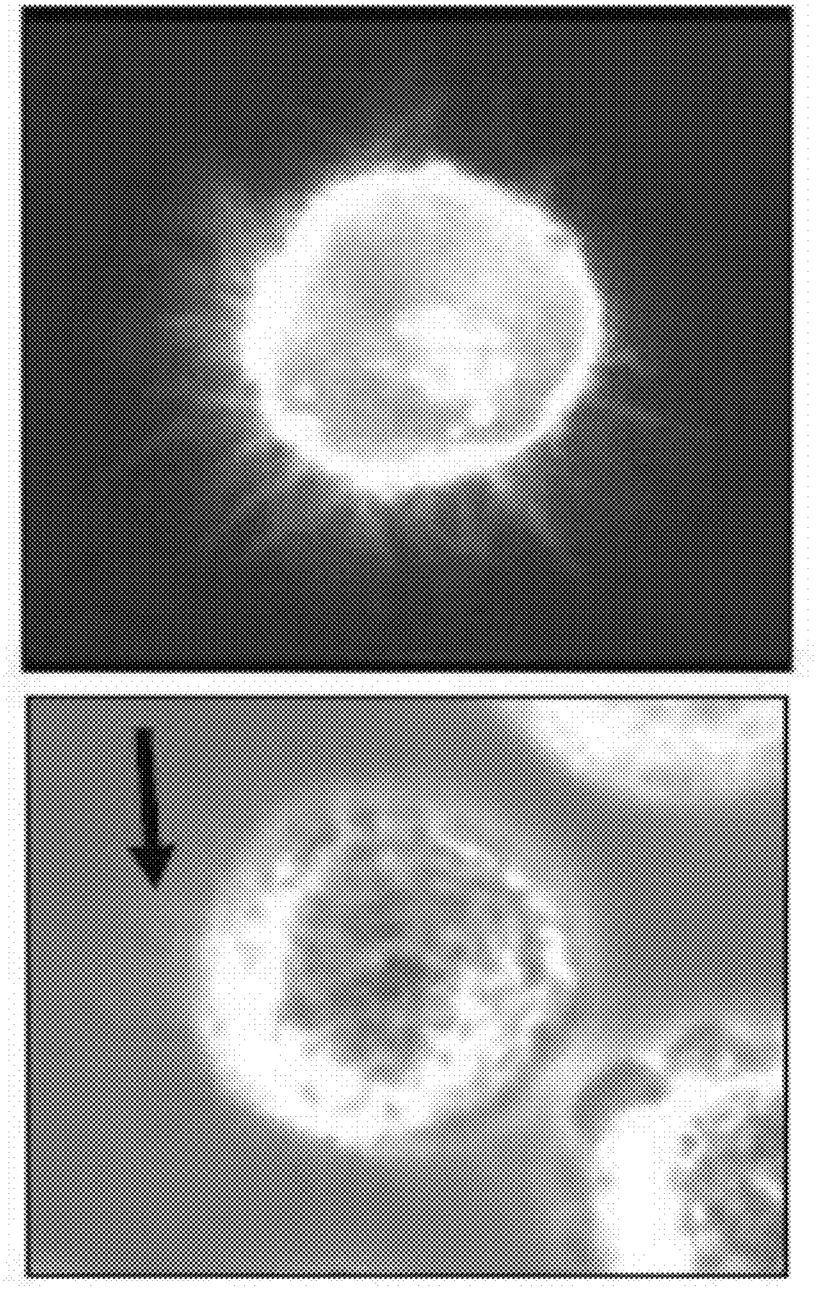
FIG. 10 shows GFP-membrane expression provides high-contrast protrusion imaging.

FIG. 10 shows that microtubule protrusions can be quite difficult to observe by phase-contrast microscopy. Transfection of a membrane-targeted GFP protein greatly enhances the visibility of protrusions. Differences in protrusion thickness and visibility by phase-contrast may be due to coalignment of other filaments with Glu-tubulin (such as vimentin). Vimentin may serve as a completely separate therapeutic target to reduce protrusions and promote fragmentation of circulating tumor cells.

Figure 11:
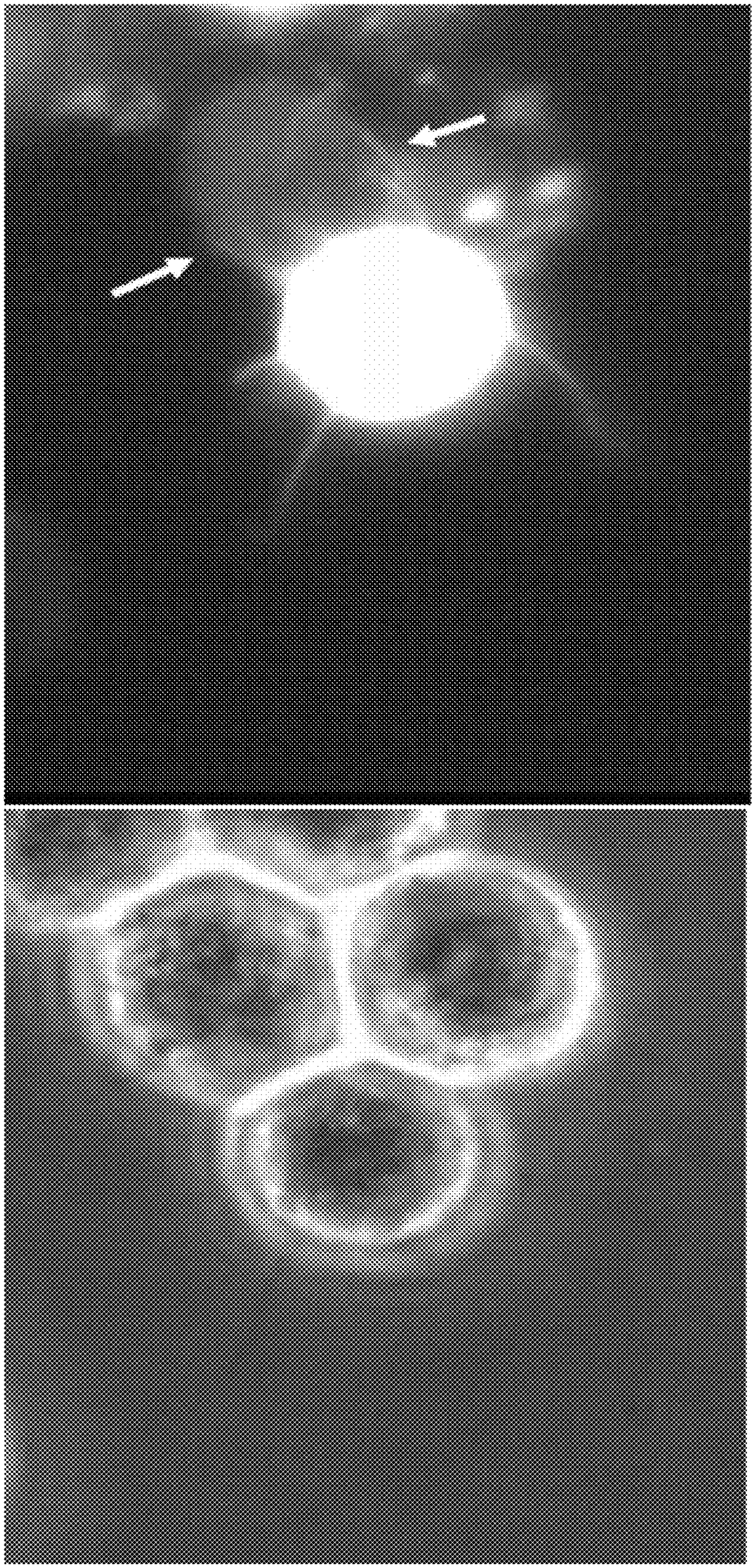
FIG. 11 shows that microtubule protrusions mediate binding to adjacent cells. GFP labeling of protrusions allows them to be observed in cell clusters, where not all cells express GFP (white arrows).

FIG. 11 shows that GFP labeling of protrusions allows them to be observed in cell clusters (where not all cells express GFP). Using this method, the inventors have shown that protrusions from one cell wrap around adjacent cells (white arrows). This provides an explanation for the role of protrusions in cell-cell adhesion.

Figure 12:
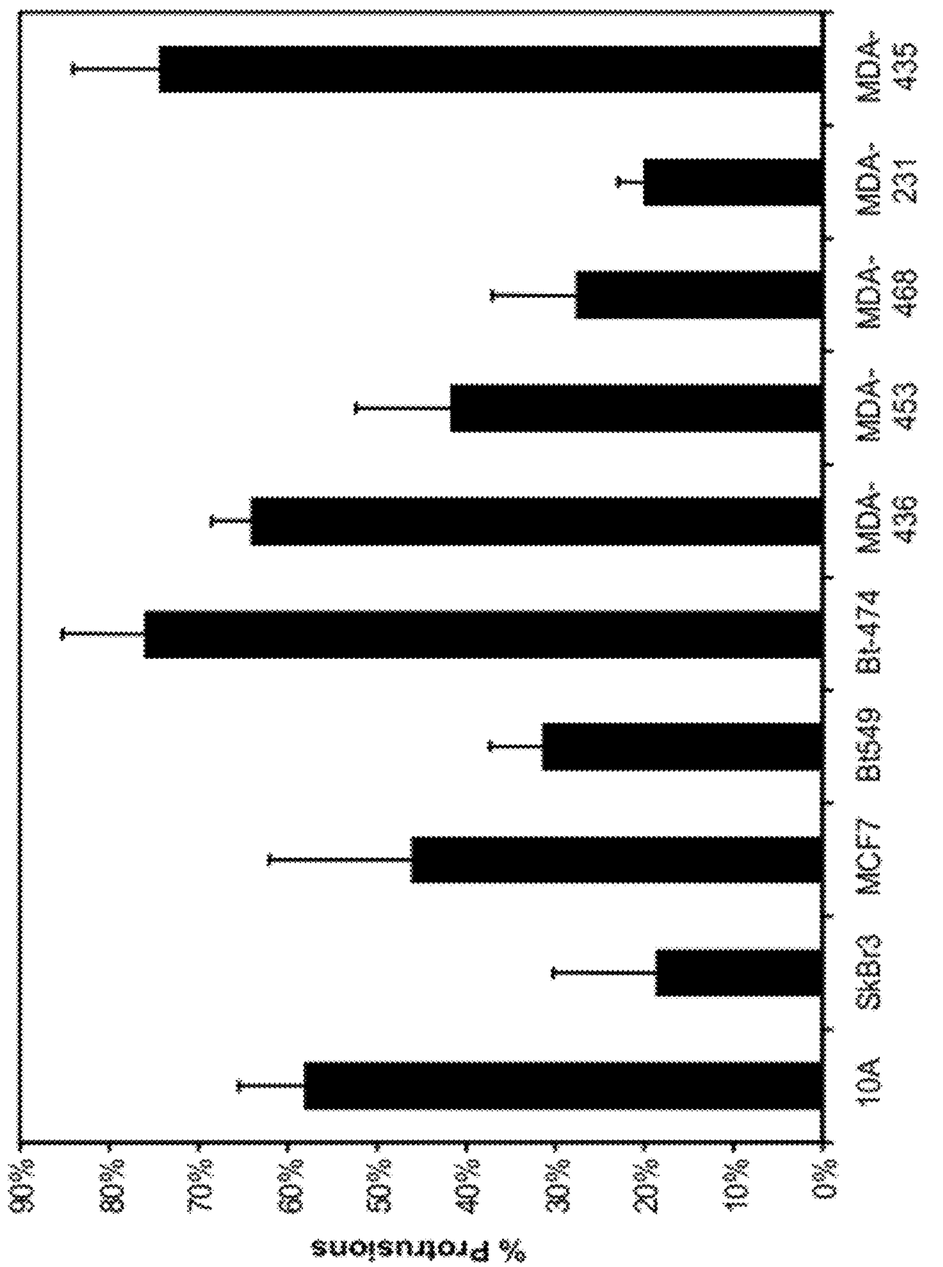
FIG. 12 shows that GFP-membrane labeling identifies variations in protrusion frequency. GFP labeling of protrusions allows detection of protrusions that were previously not visible by phase-contrast microscopy. Bars represent mean+S.D. for three experiments in which the indicated breast tumor cell lines were transfected with GFP-membrane and at least 100 cells were scored blindly for protrusions.

FIG. 12 shows GFP labeling of protrusions also allows detection of protrusions that were previously not visible by phase-contrast microscopy. While this newer data does not match exactly with older phase-contrast data, in particular embodiments it is a more accurate way to measure these novel protrusions. Using GFP-membrane, MCF10A cells have far higher protrusion levels than we measured previously. However, there are still distinct differences between tumor cells lines. SkBr3 has very low protrusion counts, while the metastatic breast tumor cell lines (Bt-474, MDA-436 and MDA-435) have very high counts. These tumor cell lines may be used as examples of low and high protrusion-producing cells to identify the molecular structures underlying protrusions.

Figure 13:
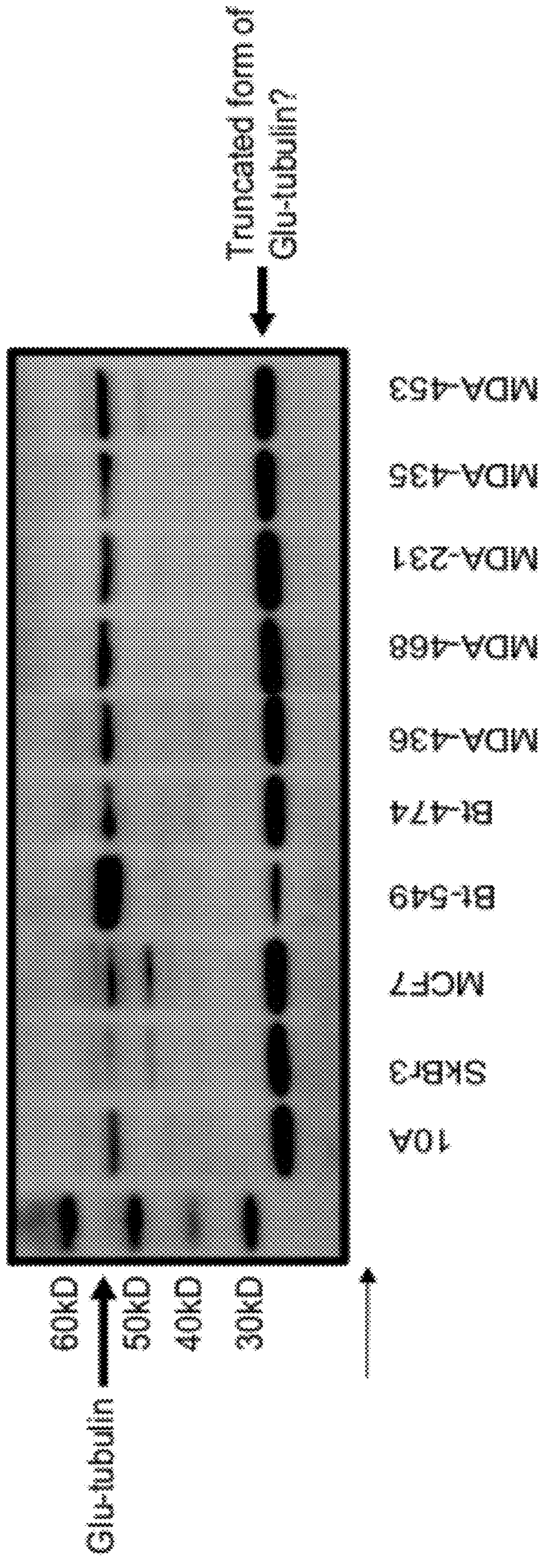
FIG. 13 demonstrates that lower Glu-tubulin levels correlate with lower protrusion frequency. Western blotting for levels of Glu-tubulin shows that the SkBr3 cell line, which has the lowest protrusion counts also has the lowest levels of Glu-tubulin.

FIG. 13 shows that western blotting for levels of Glu-tubulin shows that the SkBr3 cell line, which has the lowest protrusion counts also has the lowest levels of Glu-tubulin. In general, cell lines with higher protrusion counts have higher Glu-tubulin levels (Bt-474, MDA-436, MDA-435), but there are some exceptions that are not yet completely understood (MDA-231 and Bt-549). These two cell lines have higher levels of Glu-tubulin, but fairly low protrusion counts. Interestingly, the Bt-549 cell line results suggest that the lower band on our gel (~25 kDa) is a truncated form of Glu-tubulin that has not yet been reported in the literature. Note that the increased levels of 52 kDa Glu-tubulin result in a diminishment of the 25 kDa band. This indicates that the two bands come from the same pool of Glu-tubulin protein. In certain embodiments, the shorter form plays a role in protrusion generation, whereas in alternative embodiments the shorter form does not play a role in protrusion generation.

Figure 14:
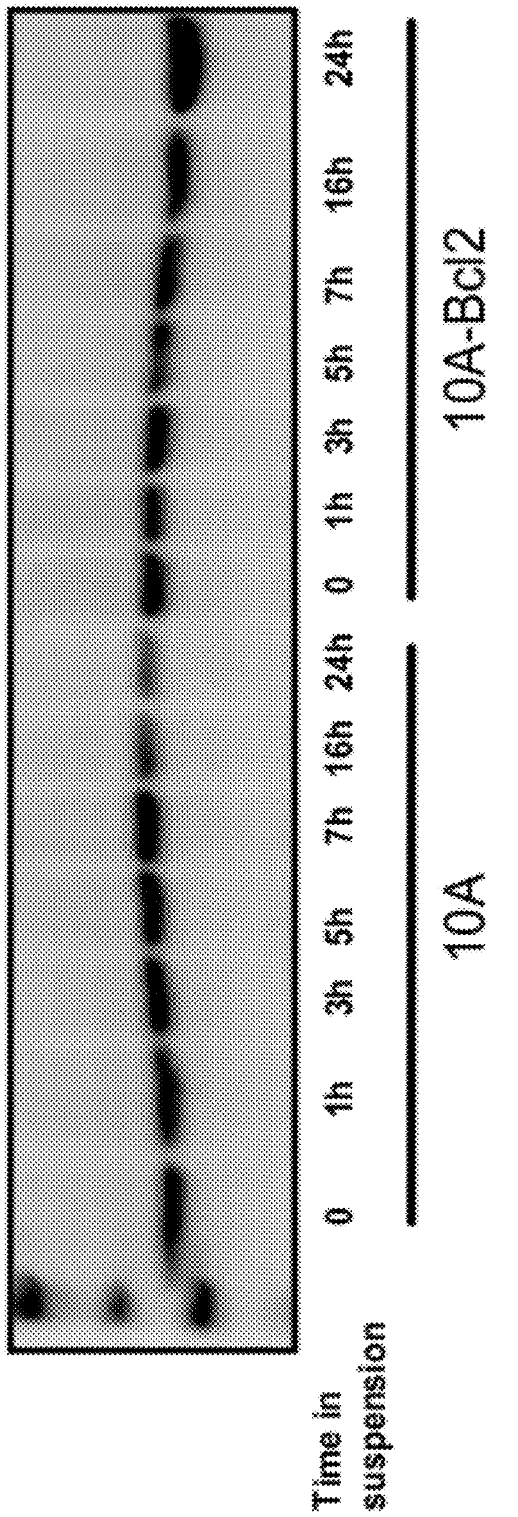
FIG. 14 demonstrates that increases in Glu-tubulin persist in apoptotically-resistant cells. Western blotting shows that Glu-tubulin levels increase in MCF10A cells during suspension, but begin to diminish by 16 hours. Glu-tubulin levels remain high in cells that overexpress Bcl-2 and resist apoptosis (10A-Bcl2).

FIG. 14 provides western blotting that shows that Glu-tubulin levels increase in MCF10A cells during suspension, but start to diminish by 16 hrs. This reduction likely reflects the beginning of apoptotic cell death in the MCF10A cells. When apoptosis is inhibited by Bcl-2 (10A-Bcl2 stable cell line), then the increase in Glu-tubulin continues and is strongest after 24 hrs. This indicates that apoptotically-resistant cells will continue to respond to detachment by upregulating proteins involved in invasion. In this way, circulating tumor cells may become more invasive without a specific mutation, but simply as a result of detaching from their home organ.

Targeting such persistent changes in circulating tumor cells provides novel therapeutic embodiments.

Figure 15:
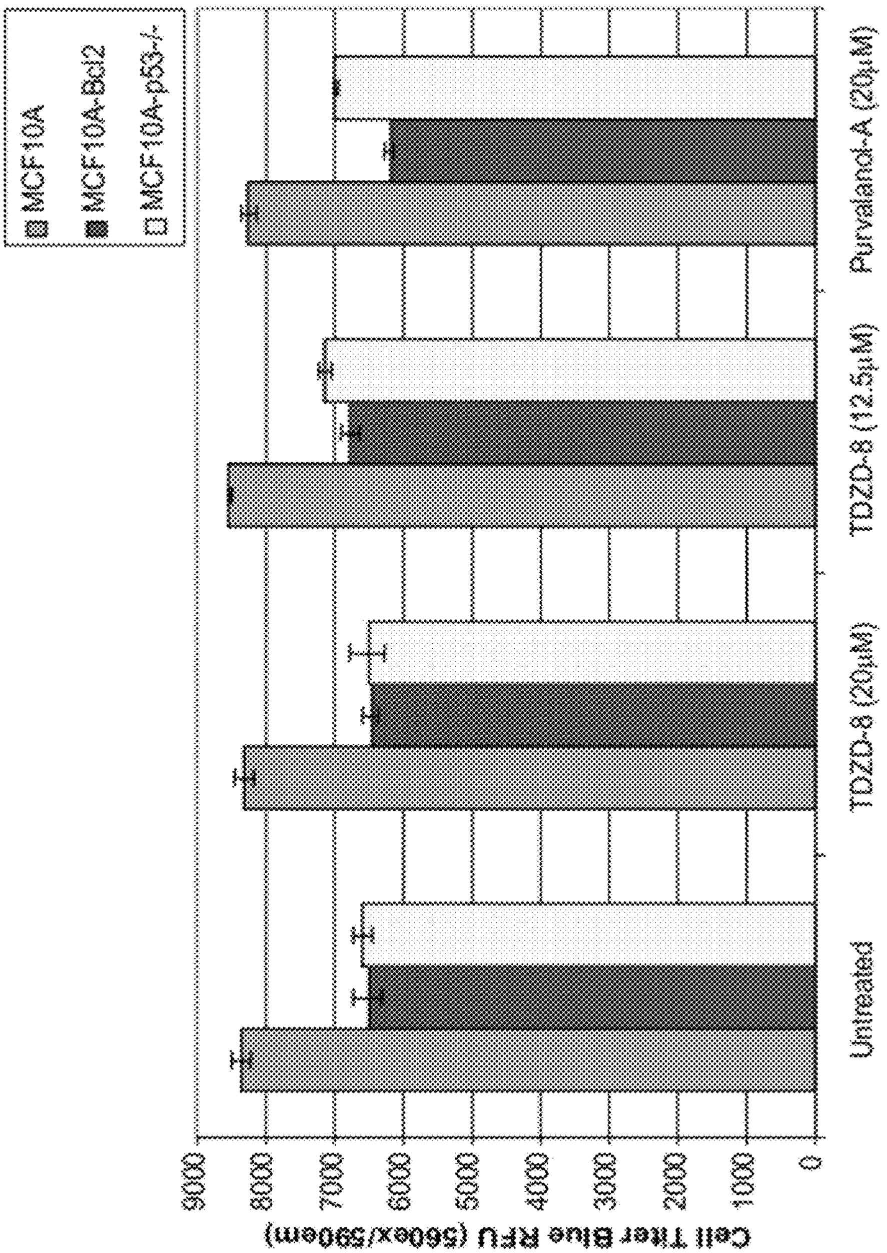
FIG. 15 demonstrates that chemical inhibition of GSK-3β is not toxic to cells.

FIG. 15 demonstrates treatment with the indicated concentrations of the GSK-3b inhibitors (TDZD-8 or Purvalanol-8) for 2 hours did not reduce cell viability significantly. Treatment with TDZD-8 did reduce protrusion frequency significantly with one hour of treatment. These results indicate that the reduced protrusion frequency is not caused simply by nonspecific cell death.

Figure 16:
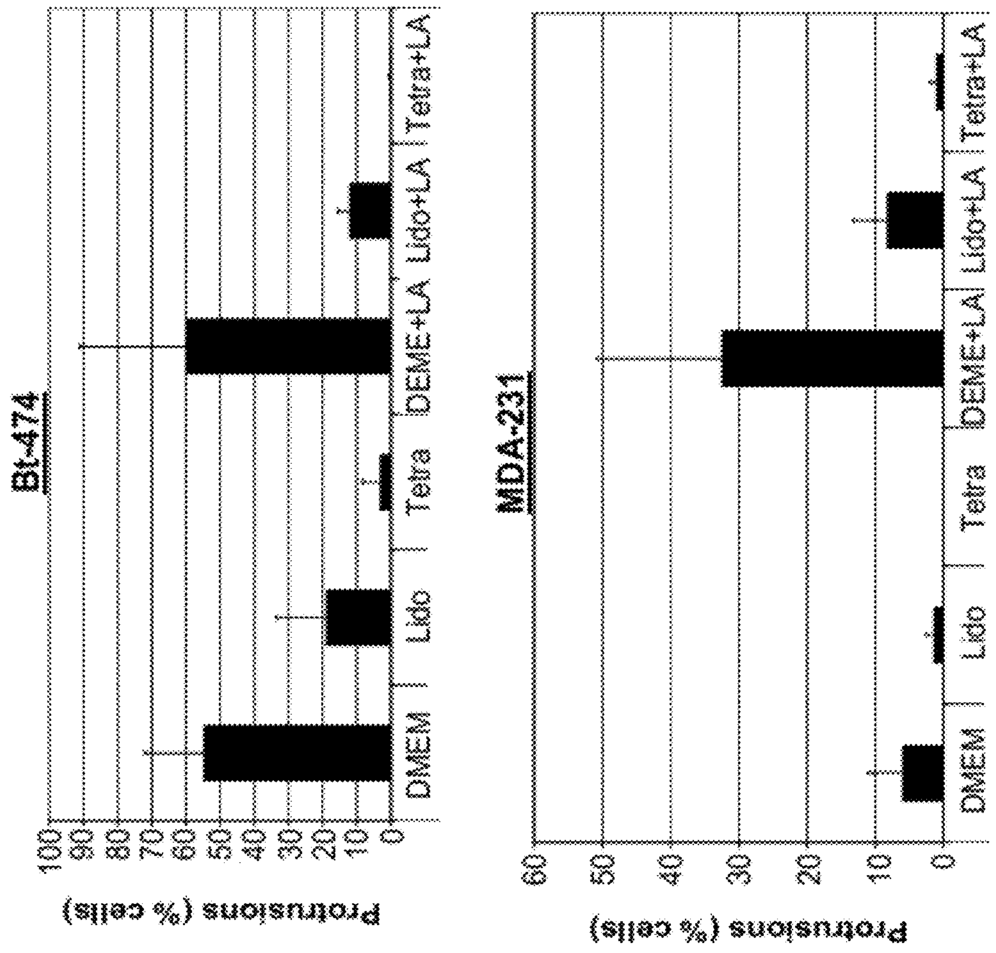
FIG. 16 shows that kinesin inhibition with local anesthetics reduces protrusions in breast tumor cells.

FIG. 16 shows that two breast tumor cell lines (Bt-474, MDA-231) were transfected with GFP-membrane for 24 hours to image protrusions. Cells were then pretreated with local anesthetics that inhibit kinesin motor protein function (Lidocaine—50 mM or Tetracaine—2.5 mM). Cells were then suspended in DMEM culture media with or without 5 mM Latrunculin-A (LA) to induce protrusions by depolymerizing actin. Protrusions that result with or without LA were inhibited significantly by Lidocaine or Tetracaine. Bars represent mean+S.D. of at least three blindly counted experiments.

Figure 17:
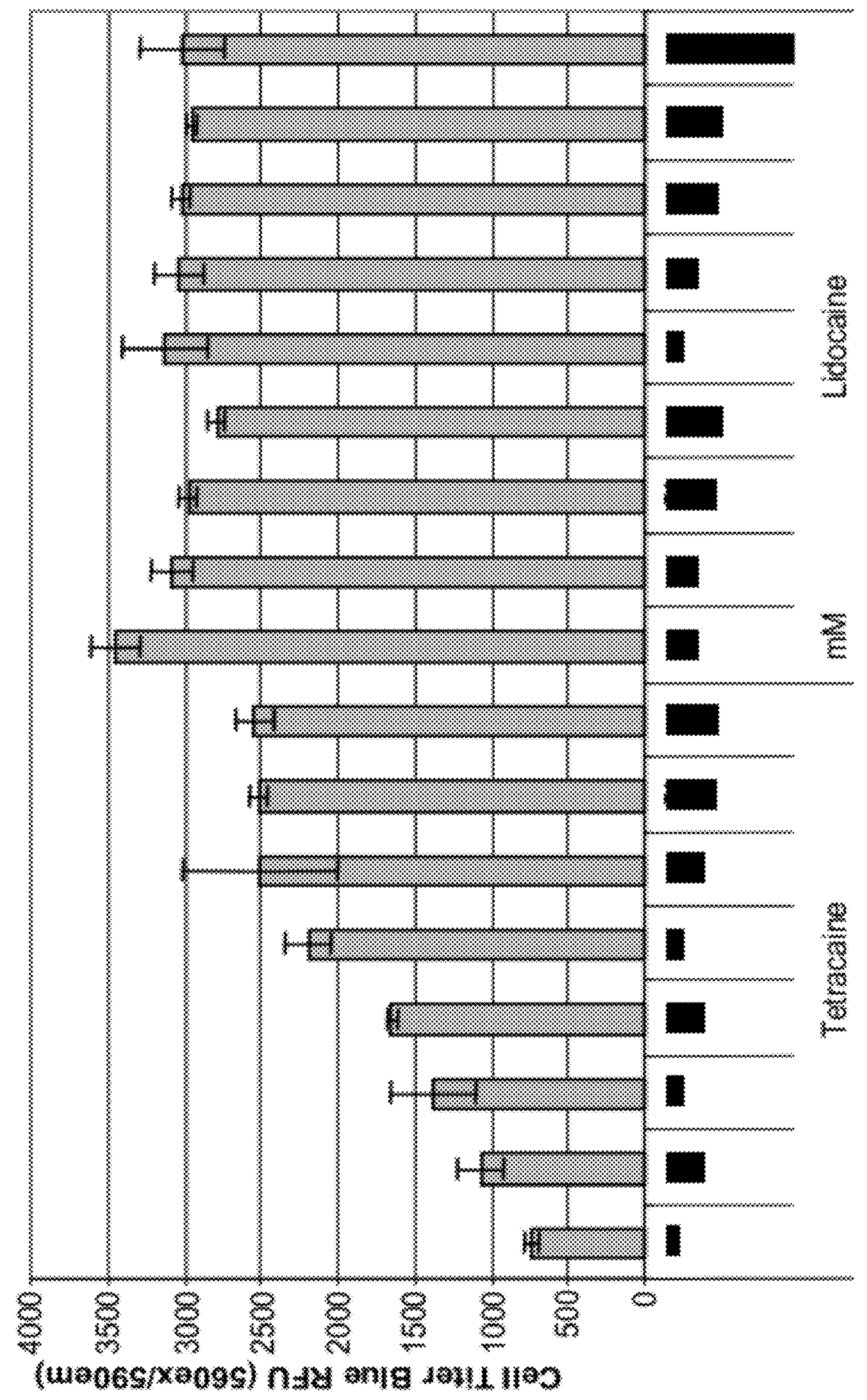
FIG. 17 demonstrates that lidocaine is not cytotoxic at higher concentrations and tetracaine is cytotoxic at higher concentrations.

FIG. 17 demonstrates that MCF10A cells were treated for two hours with the indicated concentrations of the local anesthetics Tetracaine or Lidocaine. Lidocaine was not toxic to cells even at 50 mM. Tetracaine did show significant cell toxicity at 3 mM and above. Both anesthetics reduced protrusions significantly at sub-toxic doses (Tetracaine-2.5 mM, Lidocaine 50 mM). These results suggest that kinesin inhibition can reduce protrusions without causing nonspecific cell death. However, tetracaine concentrations will have to be monitored carefully to ensure that cytotoxicity is not responsible for any effects observed.

Figure 18:
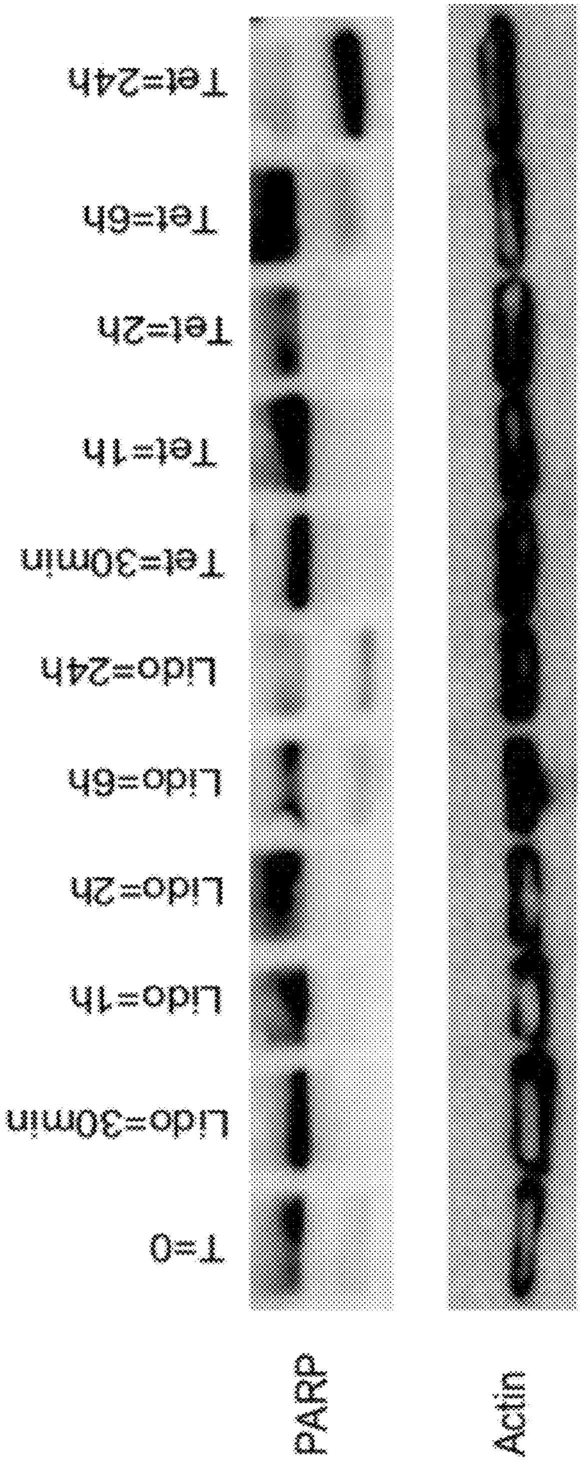
FIG. 18 shows that local anesthetics do not induce apoptosis until after 6 hours of treatment. Cleavage of PARP protein indicates apoptosis.

In FIG. 18, MCF10A cells were treated for the indicated times with Lidocaine (50 mM) or Tetracaine (2.5 mM). Cell lysates were Western blotted for PARP cleavage as an indication of cell death or beta-actin as a loading control. Apoptosis in response to either Lidocaine or Tetracaine is not detectable until 6 hours. Each of these compounds cause reduced protrusions with only one hour of treatment, therefore the effect on protrusions is likely not the result of apoptosis.

Figure 19:
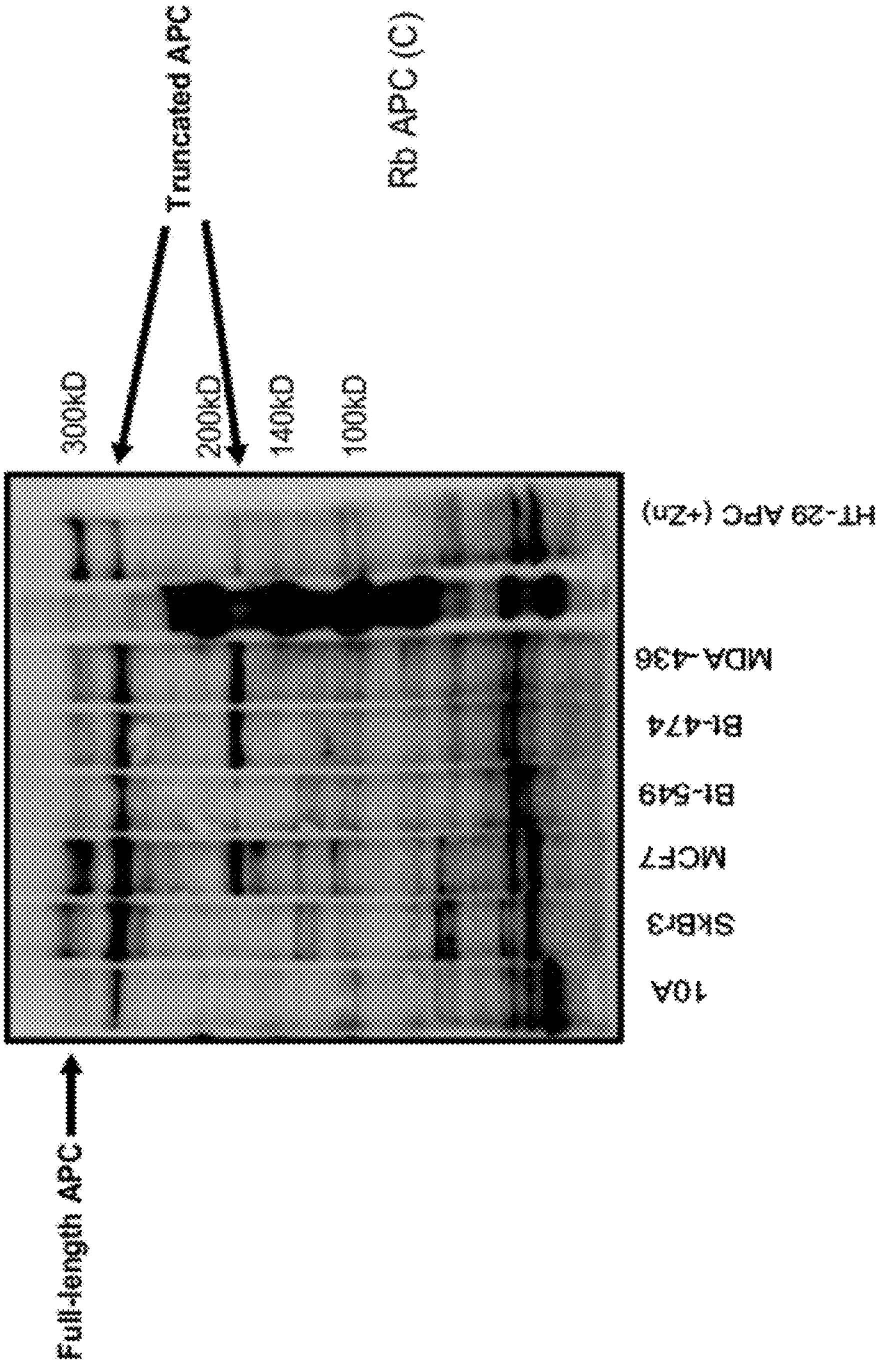
FIG. 19 demonstrates that truncated APC expression (~170 kDa) correlates with increased protrusions.

In FIG. 19, lysates from human breast tumor cell lines were Western blotted for expression of APC protein. Full-length APC migrates at 300 kDa, while HT-29 cells are known to also have truncated forms of roughly 250 kDa and 170 kDa. Addition of Zn to the culture media inducibly expresses full-length APC in this HT-29 cell line. Cell lines with relatively high levels of protrusions (MCF-7, Bt-474 and MDA-436) show higher expression of the 170 kDa truncated form of APC. In specific embodiments, truncated APC acts as a dominant negative protein that prevents full-length APC from efficiently capturing microtubules at the actin cortex underlying the plasma membrane. This provides more evidence that loss of APC function contributes to the generation of microtubule protrusions.

Figure 20:
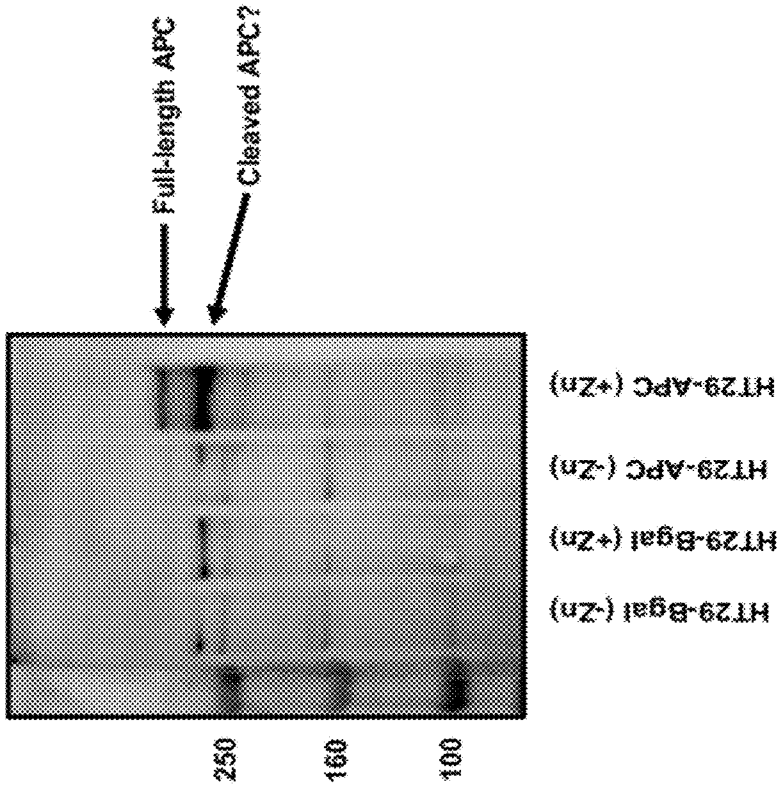
FIG. 20 shows inducible full-length (~300 kDa) APC expression in exemplary HT-29 cells. Increased levels of ~250 kDa form after induction may indicate that cleavage of full-length APC occurs.

FIG. 20 provides western blotting from stable HT-29 human colon cancer cell lines to identify full-length APC. Human HT-29 cell lines that stably express either beta-galactosidase (HT29-Bgal) or full-length APC (HT29-APC) were grown in the presence or absence of Zn++ (100 μM, 48 hours) to induce gene expression. Inducible expression of full-length APC is observed at ~300 kDa in the far-right lane. HT-29 cells also express truncated form of APC at approximately 250 kDa and 170 kDa. While full-length APC is known to be 300 kDa, the increase in the 250 kDa band with inducible expression indicates that posttranslational cleavage of APC occurs, in specific embodiments.

Figure 21:
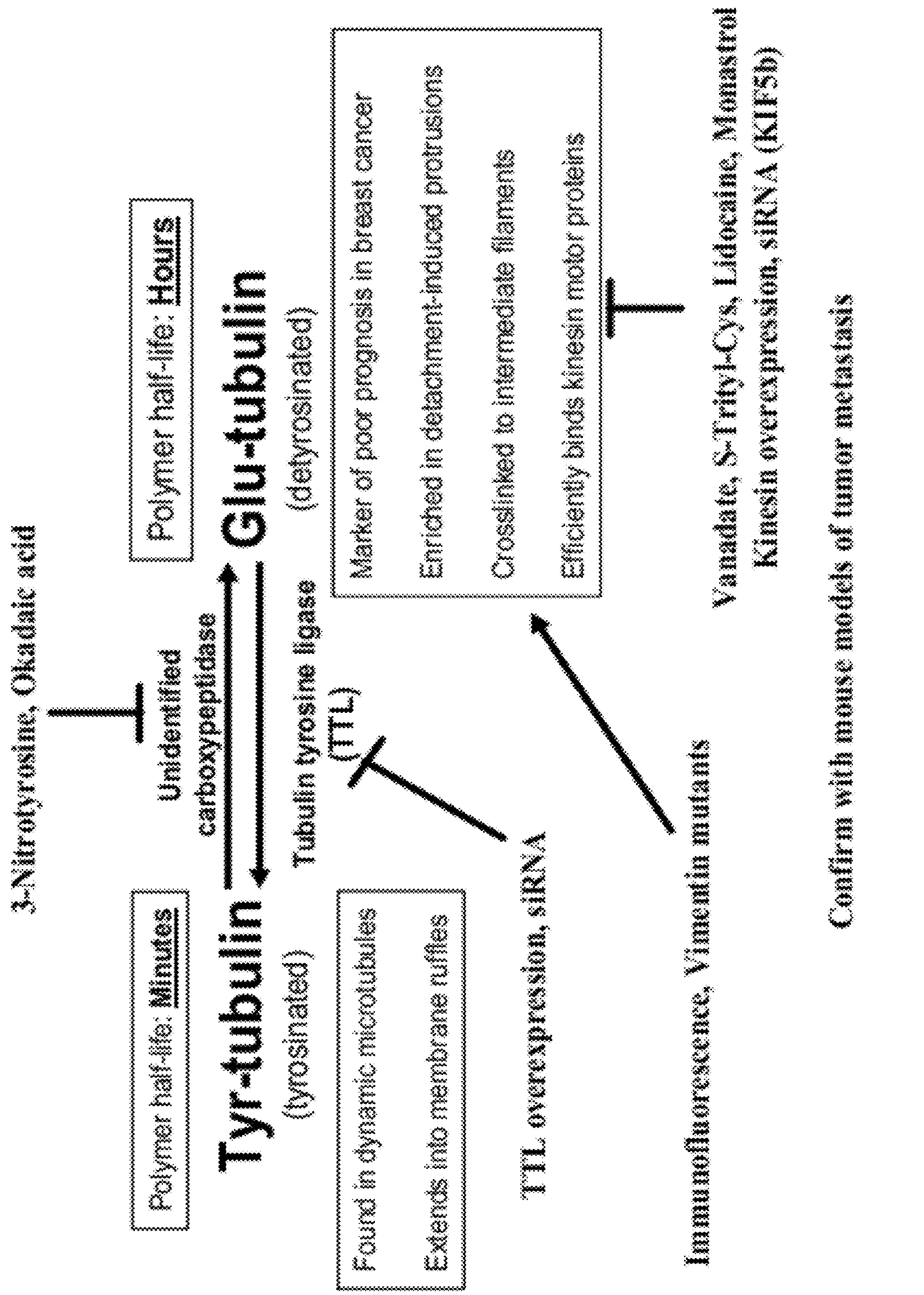
FIG. 21 illustrates an exemplary strategy to provide and/or identify therapeutic targets in protrusions.
Figure 22:
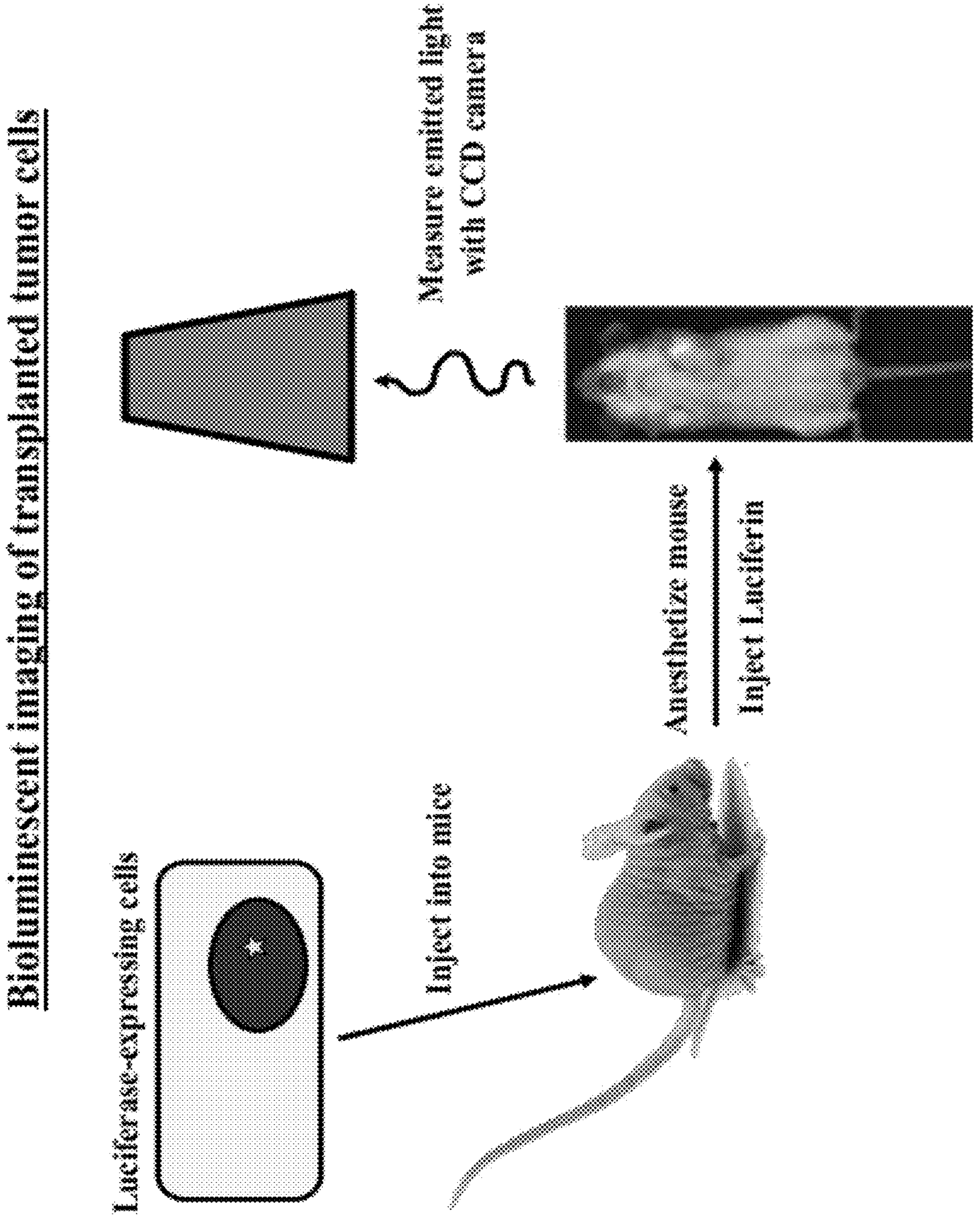
FIG. 22 shows bioluminescent imaging of transplanted tumor cells.
Figure 23:
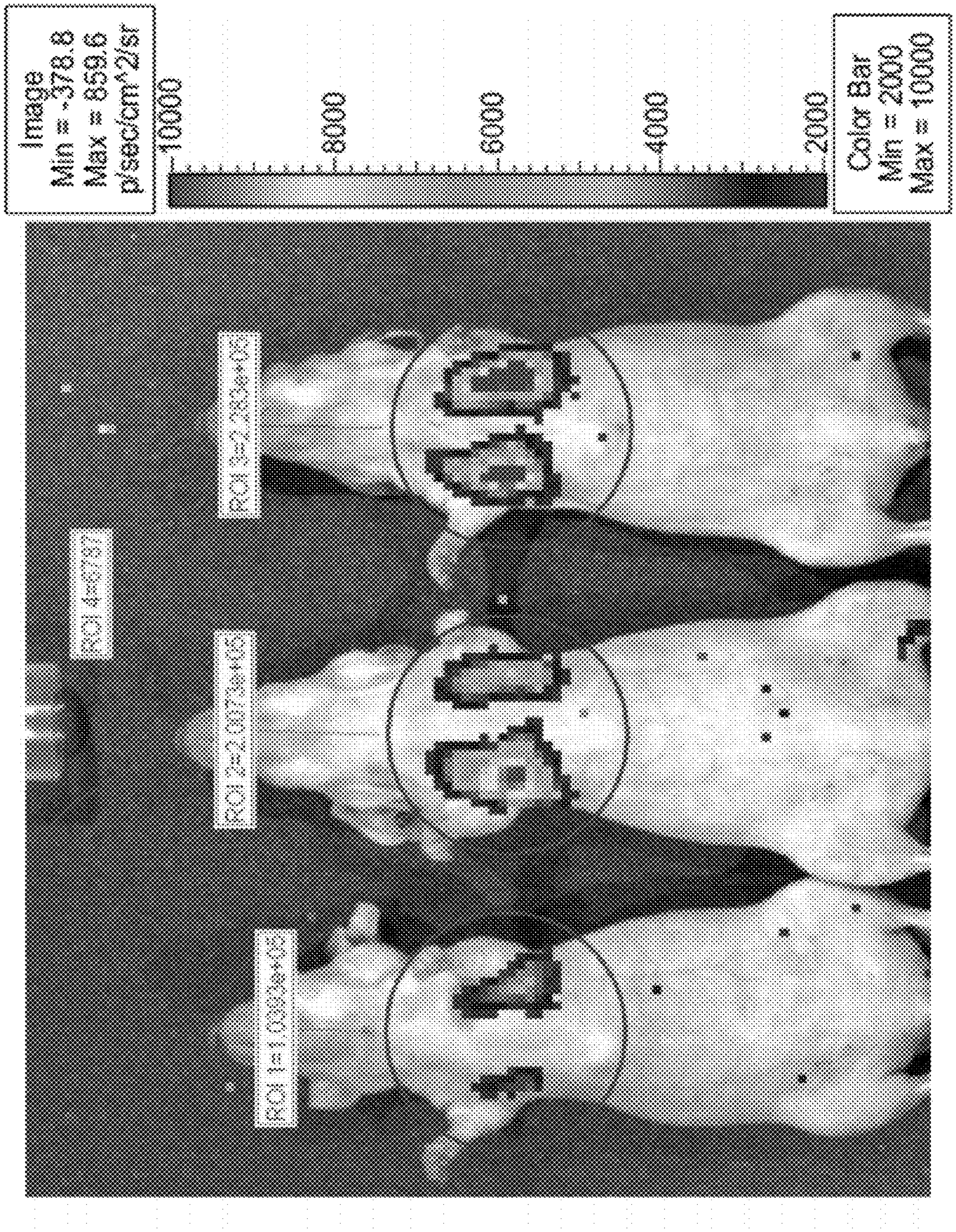
FIG. 23 shows imaging the trapping of circulating breast tumor cells in the lungs of living mice (15 minutes post injection into the tail vein).

In FIG. 21, there is an exemplary strategy to identify specific therapeutic targets in protrusions. FIG. 22 shows exemplary bioluminescent imaging of transplanted tumor cells. In FIG. 23, $1\times10^6$ EpH4-Bcl2 cells were injected via the tail vein into nude mice. These cells stably express firefly luciferase, which allows them to be imaged while circulating in the bloodstream of living mice by injecting luciferin and imaging the light generated from the cells. This imaging is performed using an Xenogen IVIS-200 imaging system. Since epithelial cells are generally too large to fit through capillary beds, they are efficiently trapped in the first capillary bed they encounter. For most circulating tumor cells, this first capillary bed is in the lung. The efficient trapping of the circulating breast tumor cells in the lung is evident with bioluminescence imaging.

Figure 24:
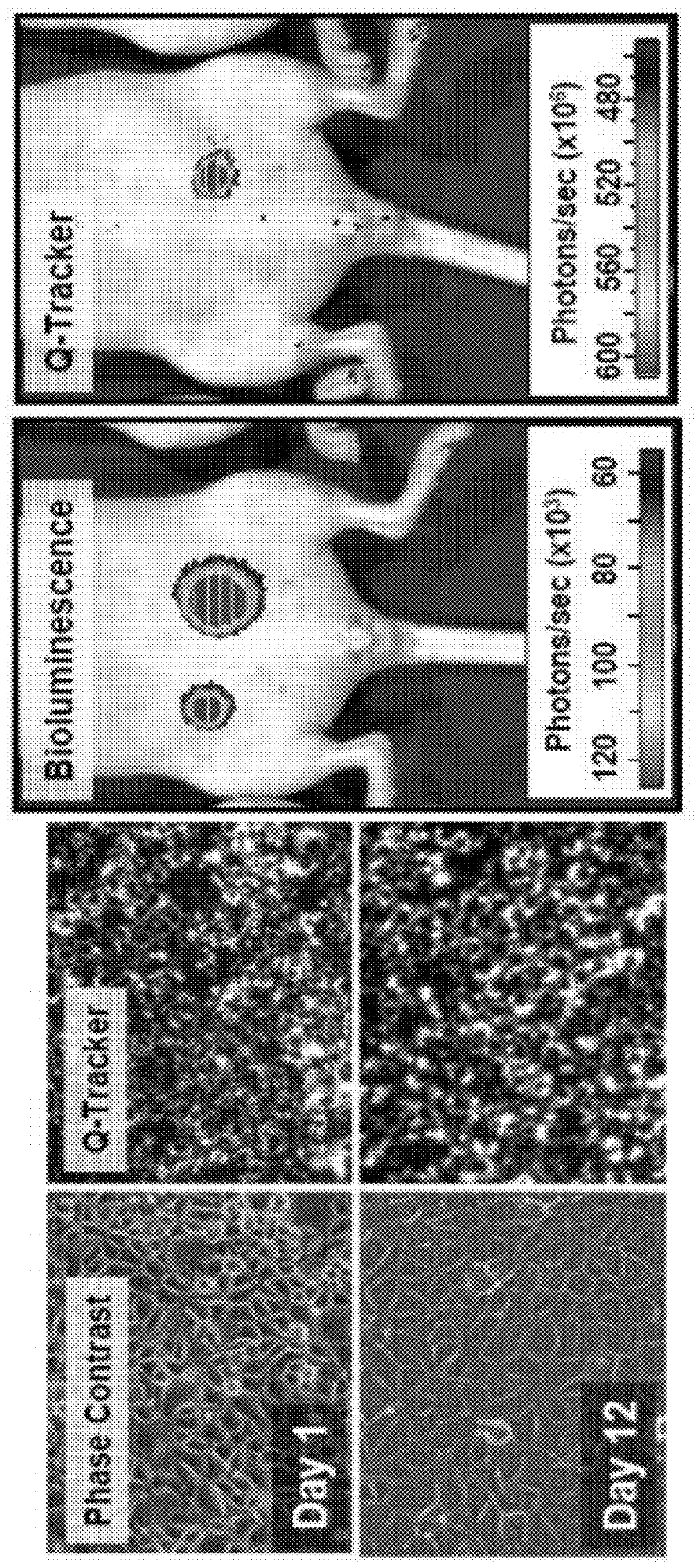
FIG. 24 shows combined fluorescence/bioluminescence imaging (cell division-fragmentation).

FIG. 24 provides exemplary combined fluorescence and bioluminescence imaging of EpH4 cells to gauge dormant cell division in vivo. Incubation of EpH4 cells with QTracker-605, a quantum dot-based cellular labeling reagent (Invitrogen), leads to efficient fluorescent labeling in the cytoplasm. This fluorescent label persists for at least 12 days in nondividing monolayers of cells, but is lost in dividing cells (not shown). Subcutaneous injection of EpLuc cells labeled with QTracker (right) or unlabeled control cells (left) shows that combined bioluminescence and fluorescence images can identify tumor cell locations and allow for independent measurement of cell division. This technique may be employed to identify therapeutic opportunities in dormant tumor cells. This technique can also be used to measure tumor cell fragmentation in lung capillaries by measuring the time-frame of decreased fluorescence and the emergence of quantum-dot fragments in the blood downstream of the lung.

Therefore, the invention provides at least the following: 1) protrusions based on Glu-tubulin promote cell adhesion; 2) tumor cell lines show higher levels of Glu-tubulin and protrusions; 3) inhibition of kinesin motor protein activity can reduce protrusions, and a) toxicity does not explain the effect on protrusions; b) Lidocaine and Tetracaine are known to reduce metastasis, via unclear mechanism; and c) kinesins were not previously implicated in metastatic repression by anesthetics; 4) inhibiting GSK-3b can also reduce protrusions, yet toxicity does not explain effect on protrusions; 5) truncated APC correlates with increased protrusions, and in specific embodiments truncated APC acts as a dominant negative; also, since GSK-3b inhibits MT binding by APC, reducing GSK-3b may promote recapture of MTs; 6) one can measure cancer cell trapping in lungs of living mice (Xenogen IVIS-200); and 7) combined fluorescence/bioluminescence imaging quantitatively measures fragmentation of circulating tumor cells.

Example 7

Exemplary Vimentin Embodiments

Figure 25:
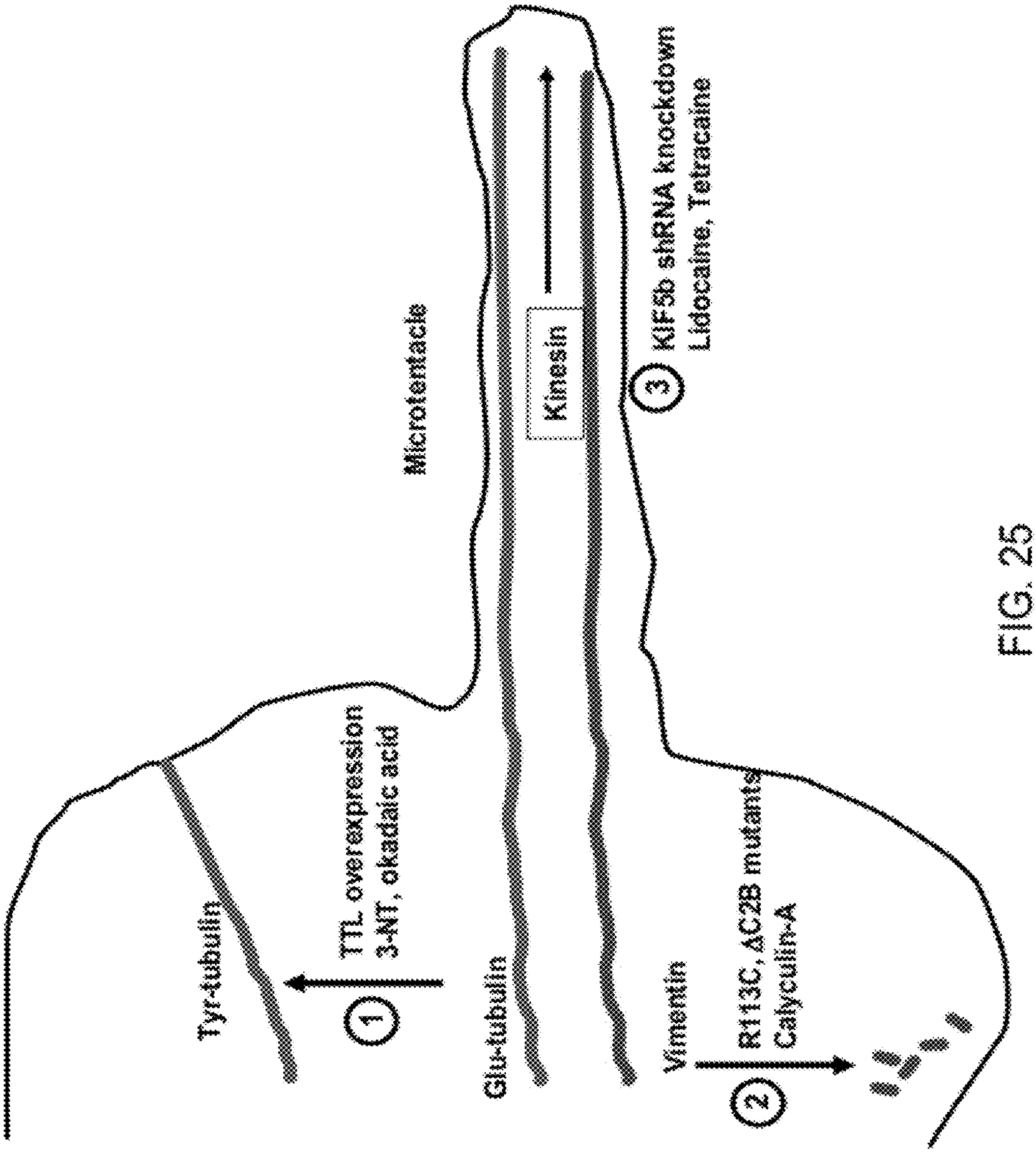
FIG. 25 shows an exemplary structural schematic of a microtubule protrusion, wherein the protrusion is comprised of Glu-tubulin utilizing a kinesin-based mechanism for its interaction with vimentin.

In specific embodiments of the invention, vimentin is targeted to inhibit one or more microtubule protrusions. FIG. 25 shows an exemplary structural schematic of a microtubule protrusion, wherein the protrusion is comprised of Glu-tubulin utilizing a kinesin-based mechanism for its interaction with vimentin. In embodiments of the invention, microtubule protrusions are comprised of aligned Glu-tubulin microtubules and vimentin intermediate filaments. Intermediate filaments are far more resilient and can bear more compressive stress than microtubules. However, vimentin depends on kinesin motor proteins to transport it outward from the cell center to align with Glu-microtubules.

In certain embodiments, for the maximum microtentacle strength, all of these systems are employed. Therefore, in specific cases of the invention, disruption of at least one of them, and in some cases two of them or all three, may serve as a therapeutic target. The following specific embodiments may apply in the invention: 1) formation of Glu-microtubules are prevented with overactivation of tubulin tyosine ligase (TTL) and/or chemical inhibitors of tubulin carboxypeptidase (3-NT or okadaic acid, for example), for example; 2) vimentin assembly is prevented by structural vimentin mutants (R113C or DC2B, for example) or chemical inhibitors (Calyculin-A or ionomycin, for example), for example; and/or 3) kinesin motor activity is prevented through siRNA or shRNA knockdown of specific kinesins (such as KIF5b) and/or through chemical inhibition of kinesin activity (Lidocaine, Tetracaine, S-Trityl-Cysteine, for example), for example. Additional exemplary inhibitors for Glu-tubulin, vimentin and kinesin also exist and further examples are provided elsewhere herein. Inhibition of any single component is useful, in specific embodiments of the invention, but inhibition may also be more effective with combined inhibitors to target more than one component or one component by more than one means. In specific cases for the invention, use of more than one inhibitor has additive effects, whereas in alternative specific cases use of more than one inhibitor has synergistic effects. Combination therapy may also inhibit microtubule protrusions more selectively, allowing lower dosages of each individual therapy and thereby reducing detrimental side effects.

Figure 26:
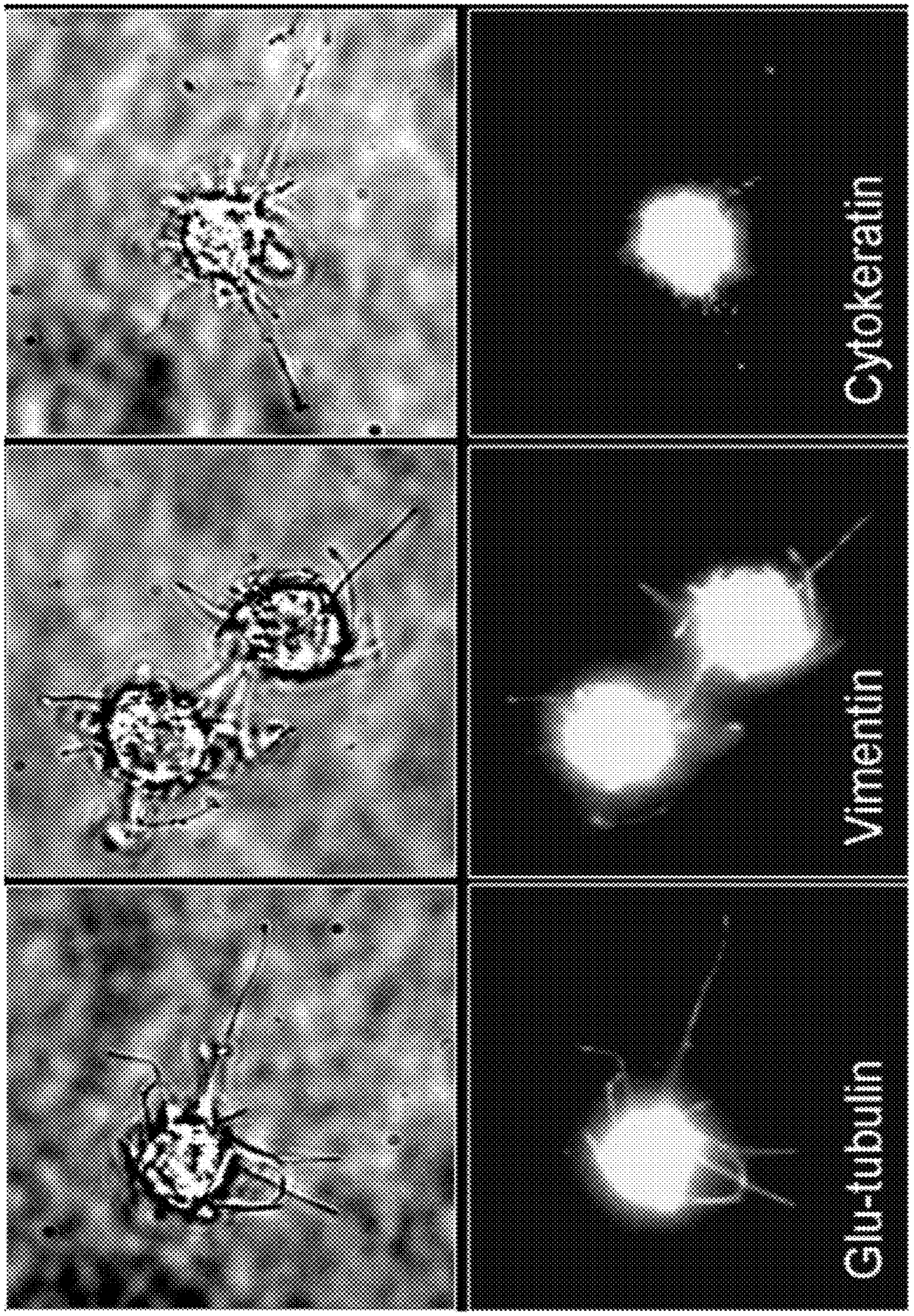
FIG. 26 illustrates that at least some microprotrusions are enriched in Glu-tubulin and vimentin, in specific embodiments.
Figure 27:
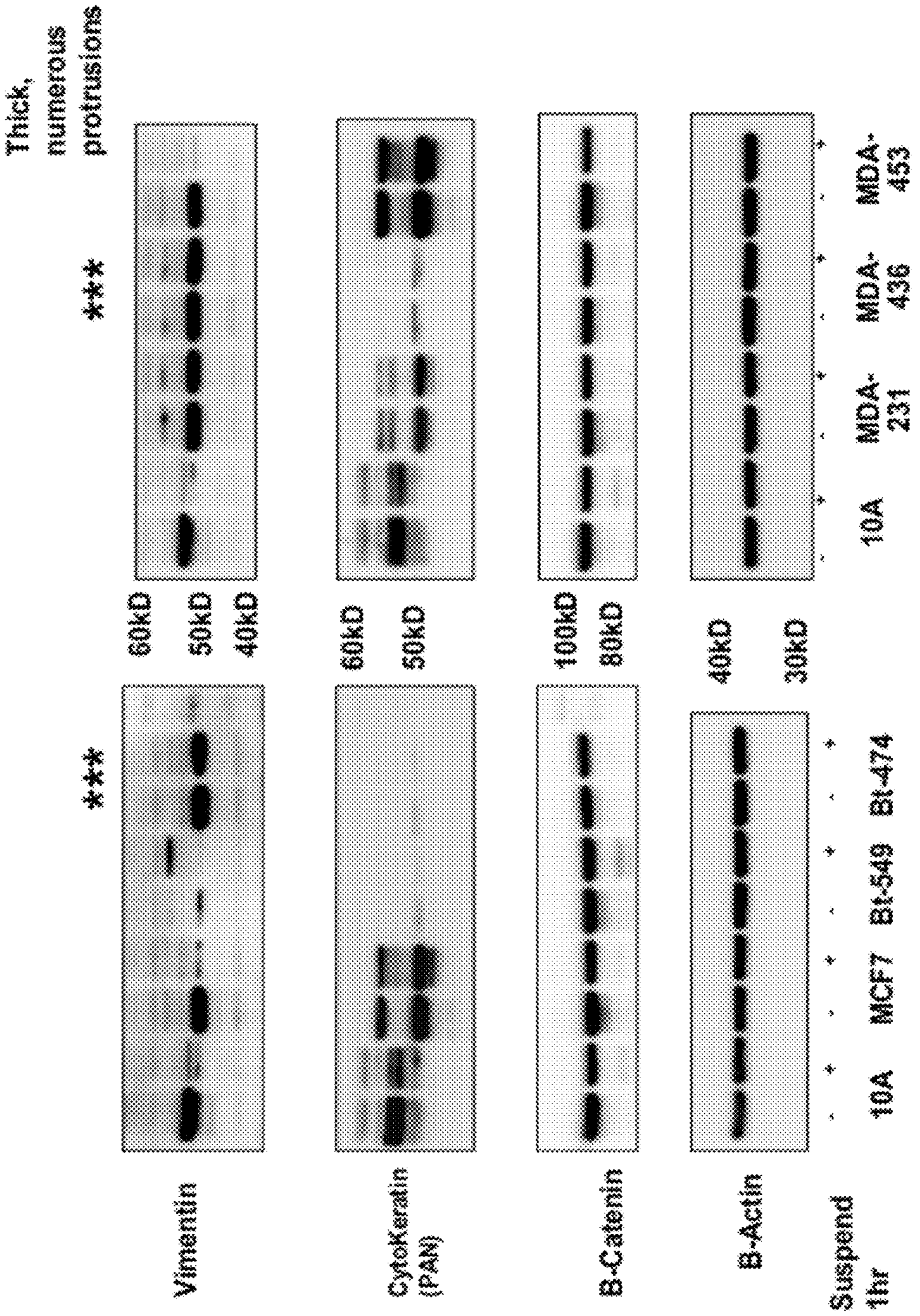
FIG. 27 demonstrates that numerous, thick protrusions correlate with high vimentin and low cytokeratin (***, Bt-474 and MDA-436), and that persistence of vimentin in suspension also correlates.
Figure 28:
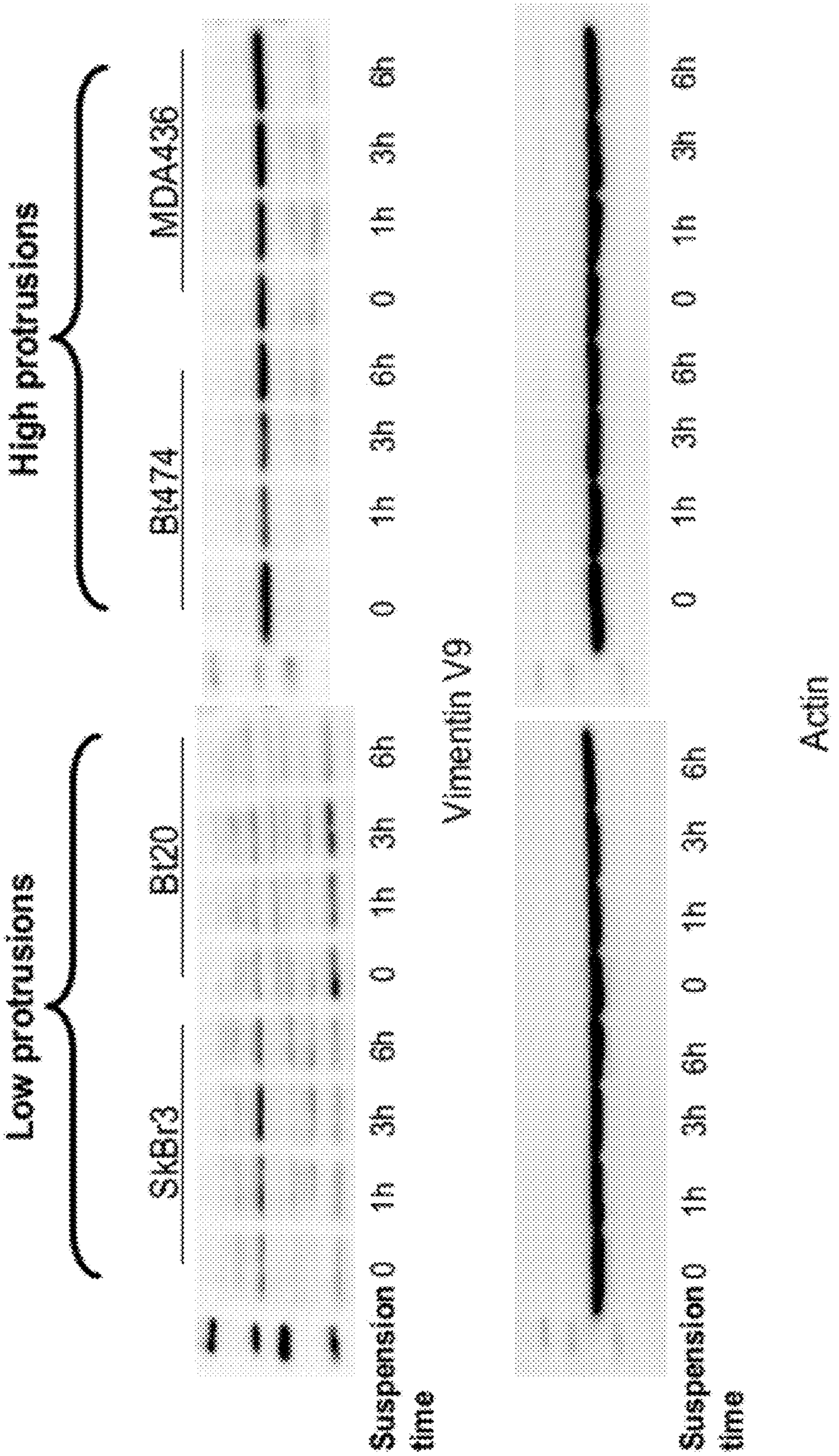
FIG. 28 shows that there are increased vimentin levels and stability in cell lines with high protrusions.
Figure 29:
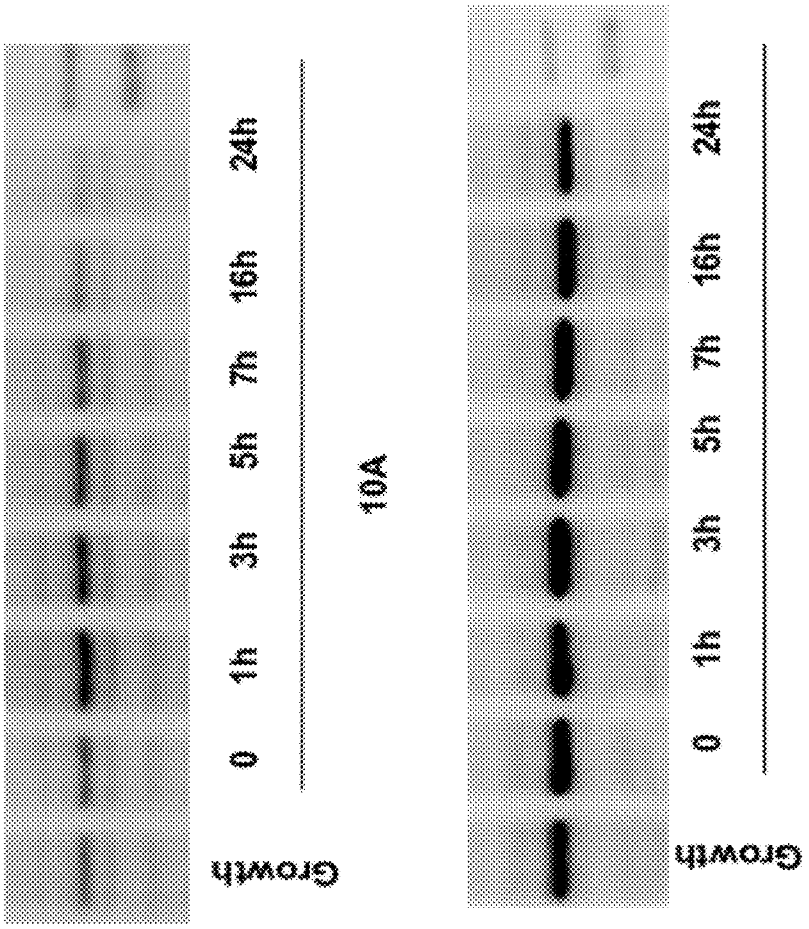
FIG. 29 shows that vimentin increases persist in apoptotically-resistant cells.
Figure 30:
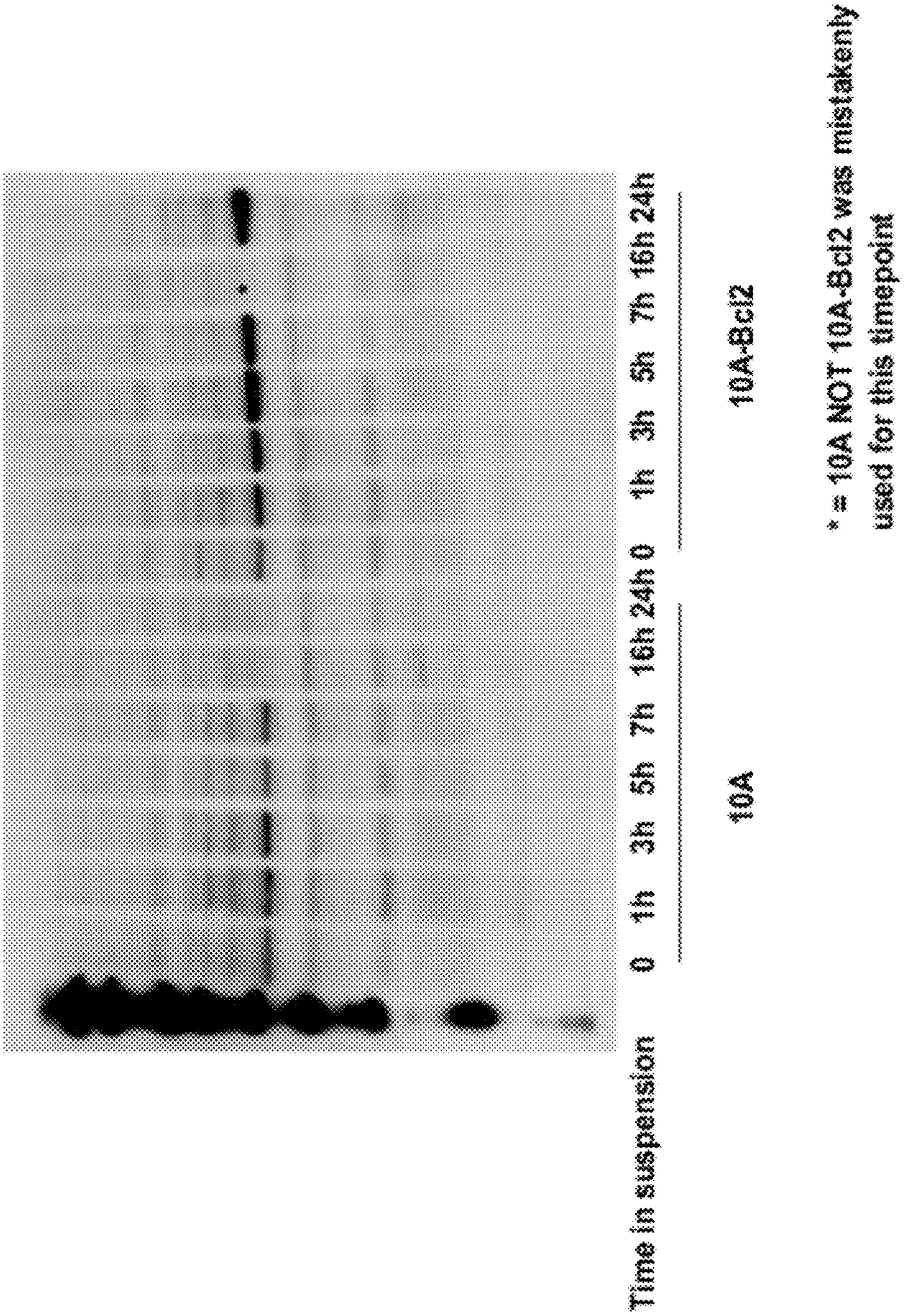
FIG. 30 shows that suspension increases vimentin levels, which persist in apoptotically-resistant cells.

FIG. 26 illustrates that at least some microprotrusions are enriched in Glu-tubulin and vimentin, in specific embodiments. FIG. 27 demonstrates that numerous, thick protrusions correlate with high vimentin and low cytokeratin, and that persistence of vimentin in suspension also correlates. FIG. 28 shows that there are increased vimentin levels and stability in cell lines with high protrusions. FIG. 29 shows that vimentin increases persist in apoptotically-resistant cells. FIG. 30 shows that suspension increases vimentin levels, which persist in apoptotically-resistant cells.

Figure 31:
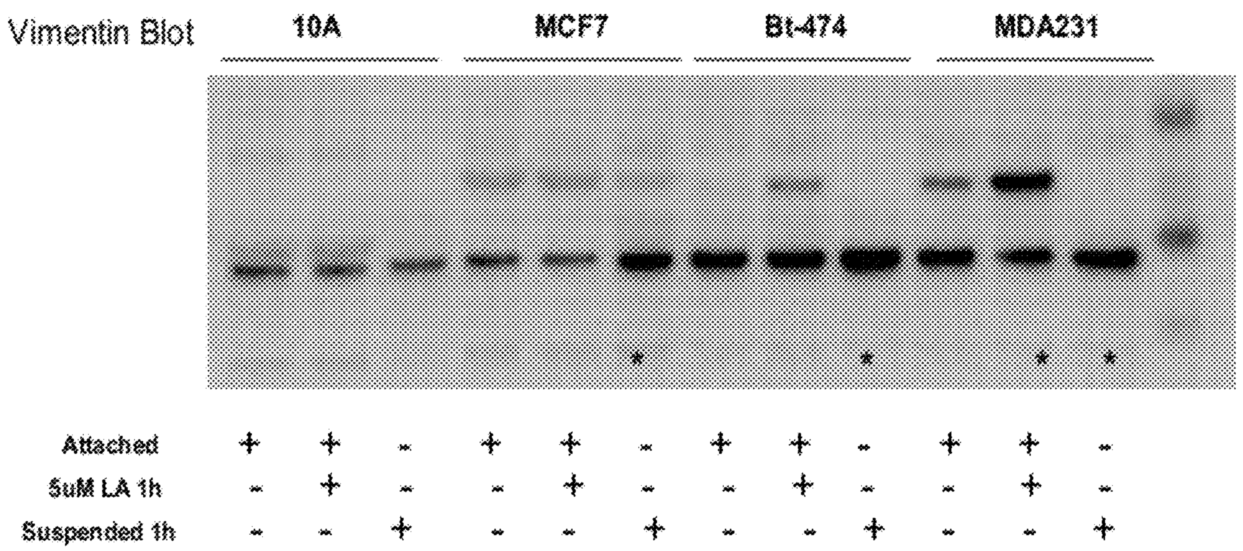
FIG. 31 provides an exemplary vimentin blot for different cell lines, in the presence or absence of LA and suspended for one hour or not.
Figure 32:
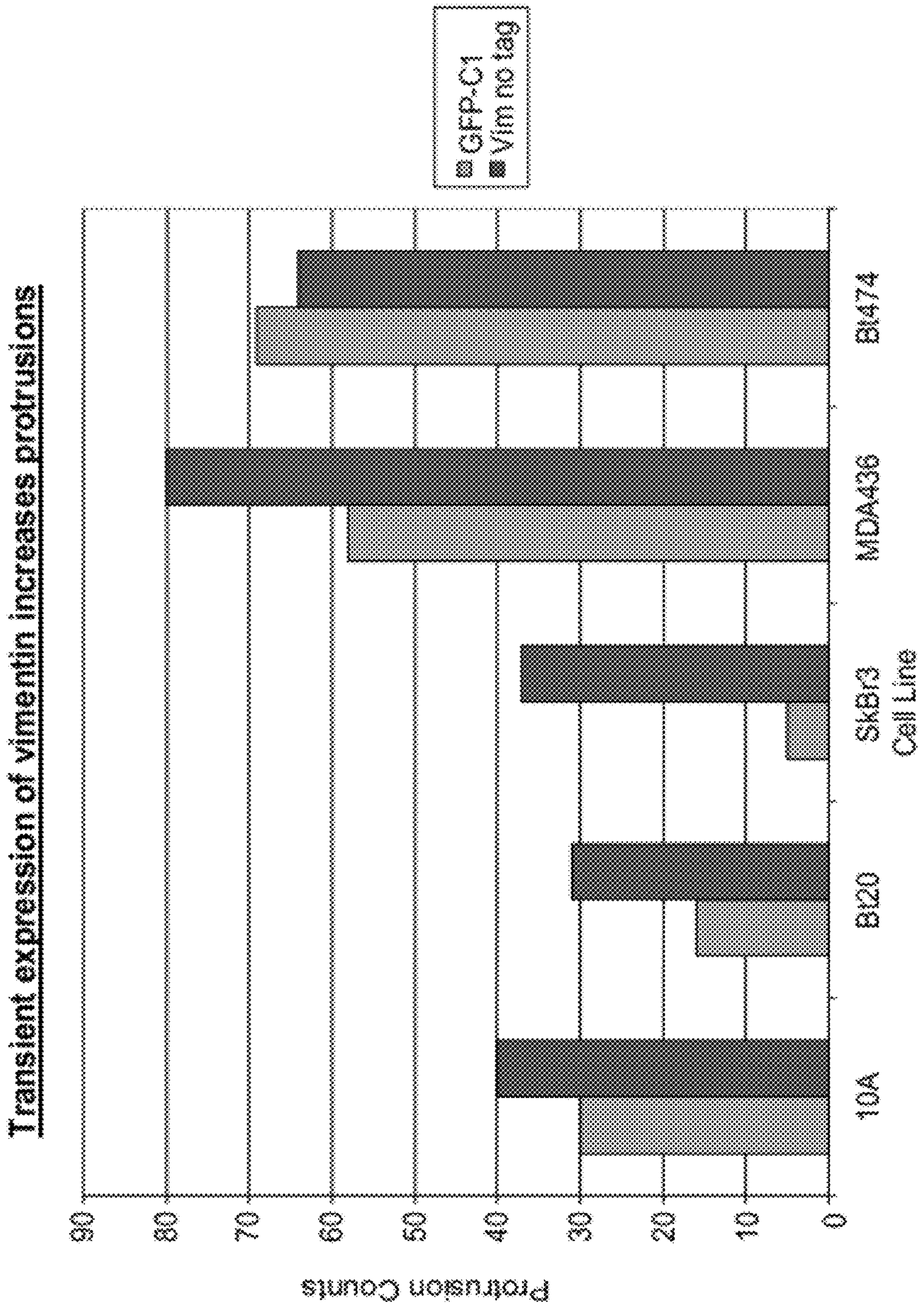
FIG. 32 demonstrates that transient expression of vimentin increases protrusions.
Figure 34:
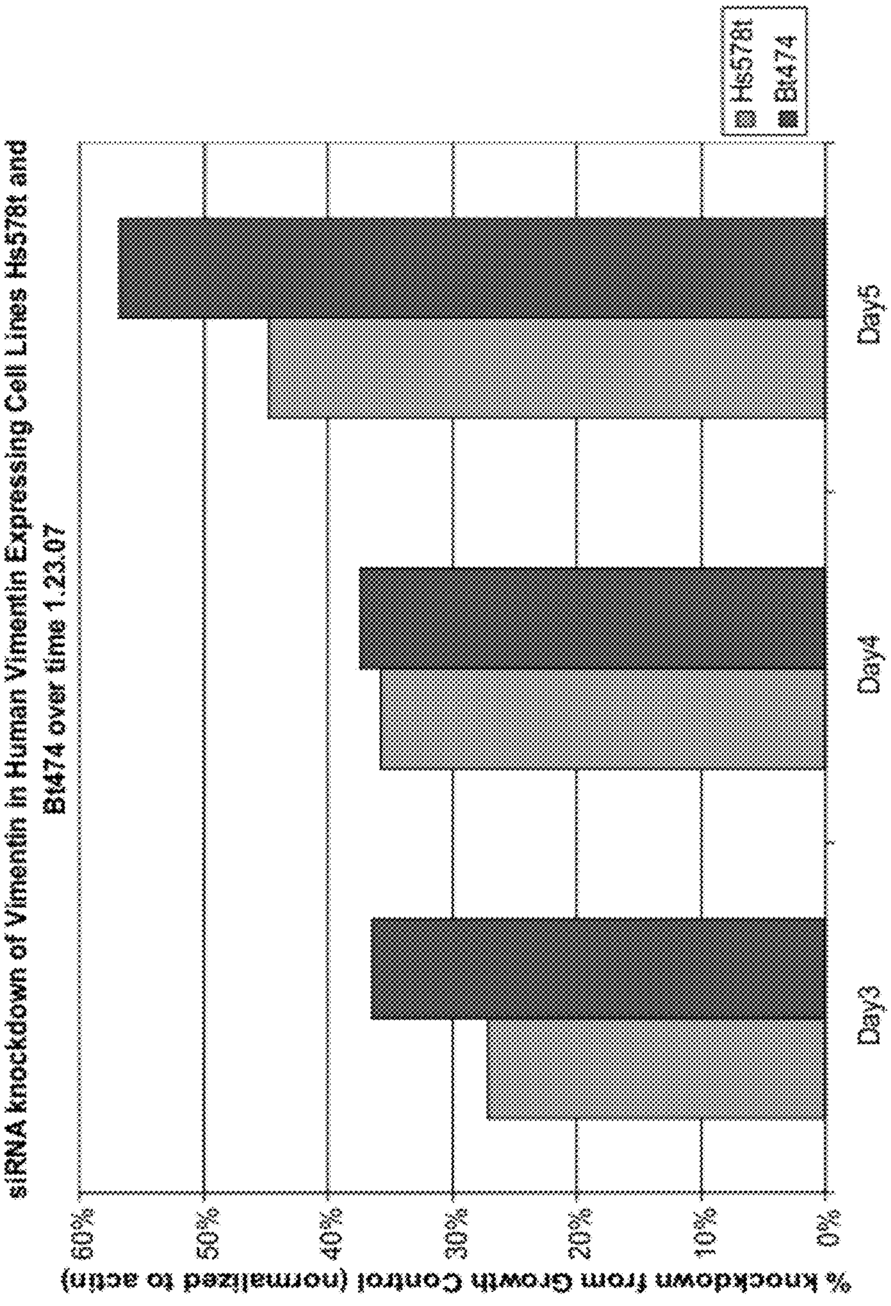
FIG. 34 shows siRNA knockdown of vimentin in exemplary human vimentin-expressing cell lines HS578t and Bt 474 over time.

FIG. 31 demonstrates an exemplary vimentin blot is provided for different cell lines, in the presence or absence of LA and suspended for one hour or not. FIG. 32 demonstrates that transient expression of vimentin increases protrusions. FIG. 33 illustrates an exemplary Hs578t/Bt474 timecourse for siRNA Vim4. FIG. 34 shows siRNA knockdown of vimentin in human vimentin-expressing cell lines HS578t and Bt 474 over time.

Figure 35:
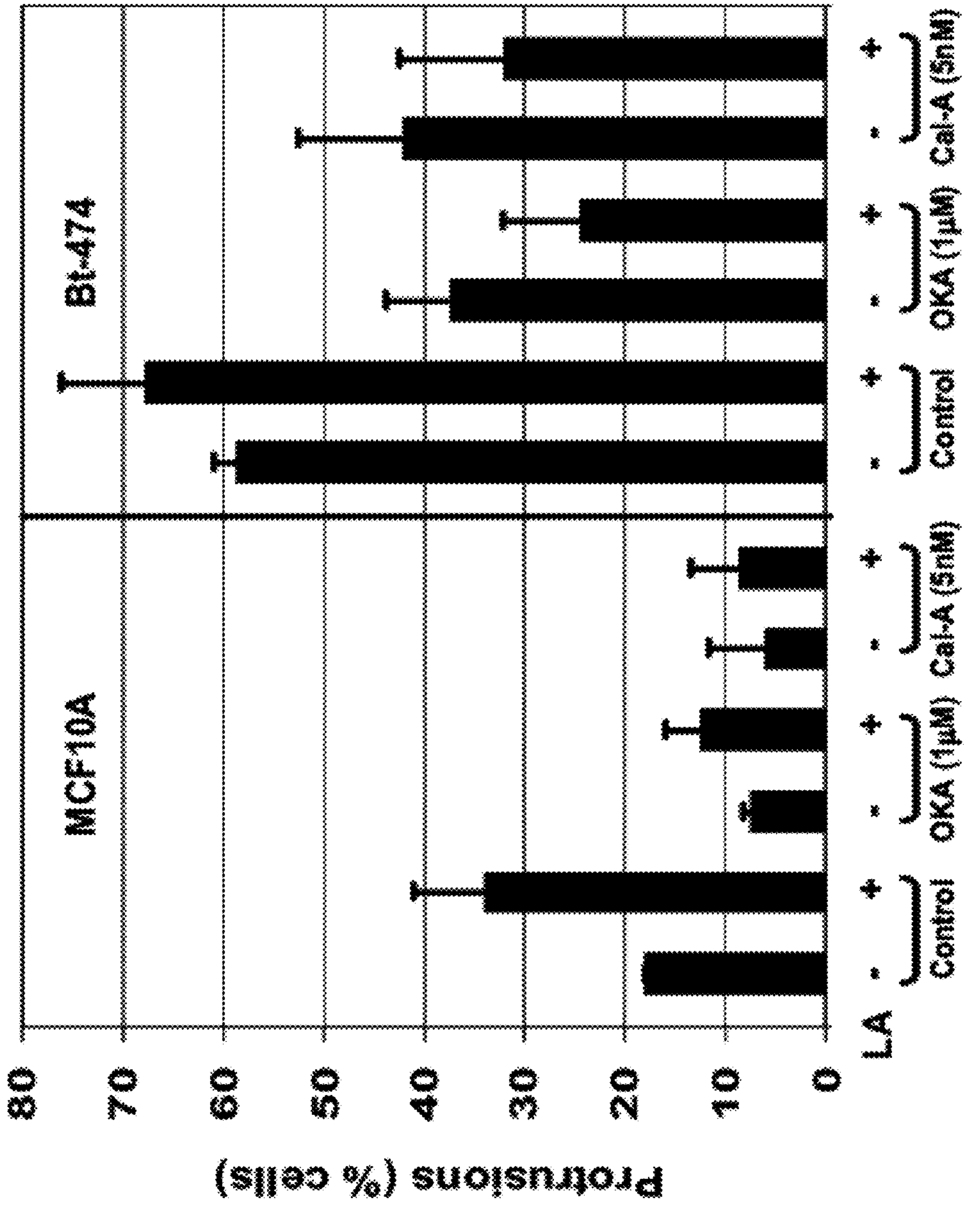
FIG. 35 demonstrates that pretreatment with okadaic acid or calyculin-A reduces microtentacles.

In FIG. 35, cells were pretreated for 1 h with DMEM media alone (Control) or the indicated concentrations of either Okadaic Acid (OKA) to inhibit tubulin carboxypeptidase or Calyculin-A (Cal-A) to promote vimentin disassembly. Cells were then suspended by trypsinization with or without addition of Latrunculin-A (LA) to enhance microtentacle frequency. Both Okadaic acid and Calyculin-A reduce microtentacles significantly, even when enhanced by LA. These data indicate that Glu-tubulin and vimentin are structural components of microtentacles and that inhibition of these components can reduce microtentacles even when the actin cortical barrier is removed.

Figure 36:
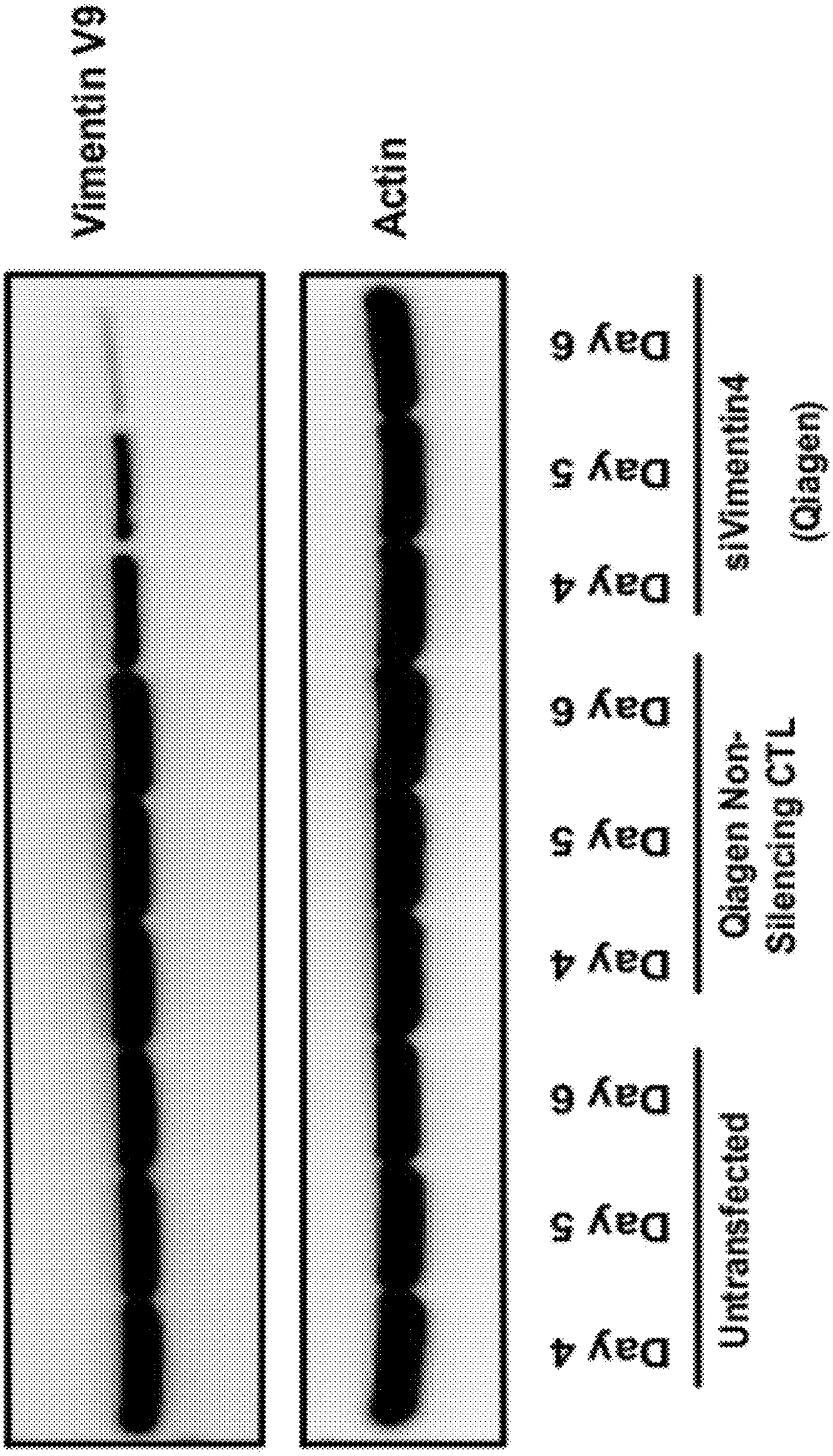
FIG. 36 shows that vimentin can be efficiently downregulated with siRNA.

In FIG. 36, Bt-474 cells were left untransfected or transfected with either Qiagen proprietry non-silencing control siRNA conjugated to Alexa-488 or siVim4 using HiPerfect protocol (6 ul of HiPerfect with 5 nM siRNA). At days indicated, protein lysates were collected in 150 uL or RIPA buffer and immunoblotted for either Vimentin expression with monoclonal V9 antibody or actin as a loading control.

Figure 37:
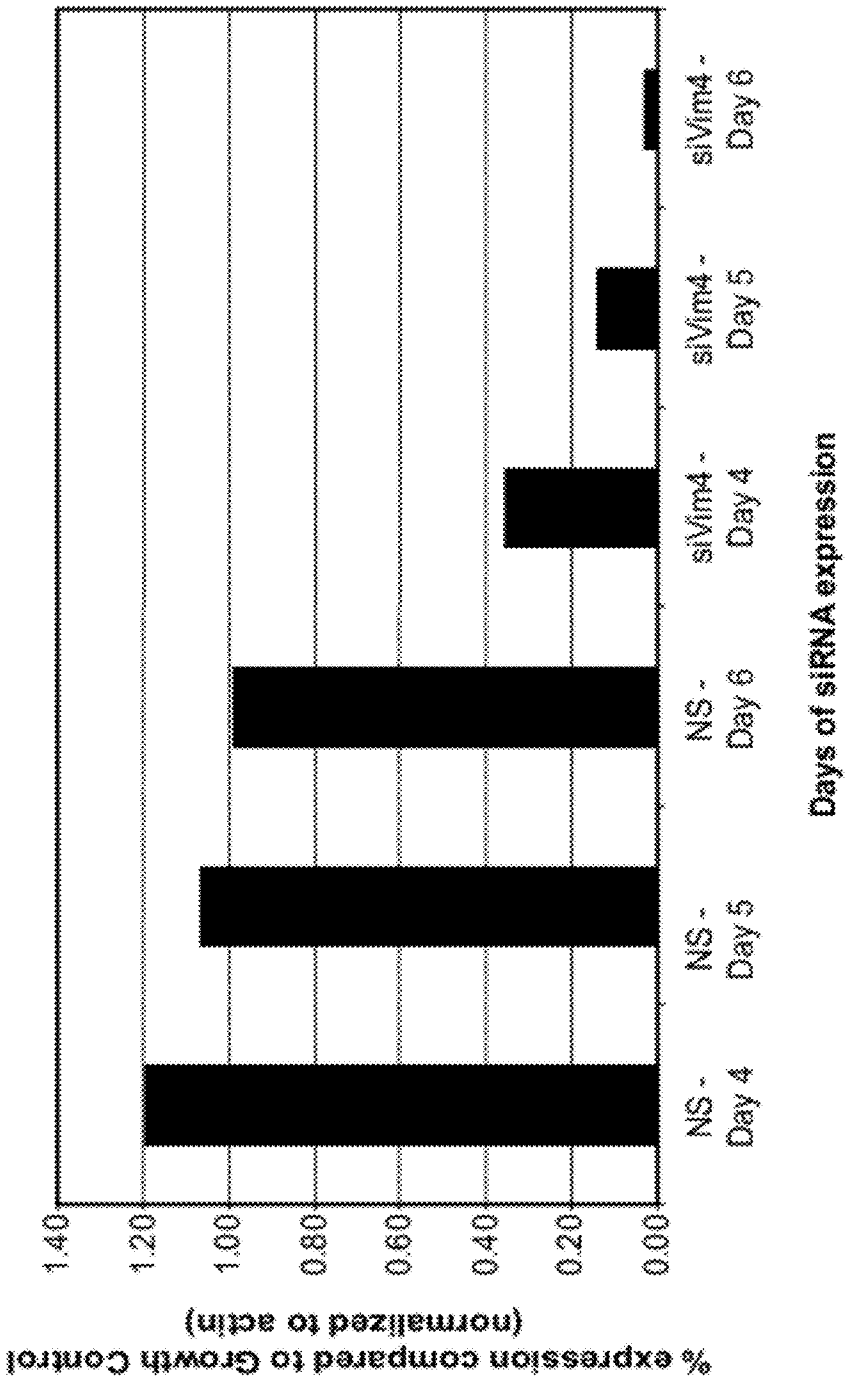
FIG. 37 provides demonstration of quantitation of siRNA-mediated vimentin downregulation.

In FIG. 37, quantitation of siRNA-mediated vimentin downregulation is provided. Vimentin-based chemiluminescent signal was normalized to that of actin for each sample. The amount of vimentin remaining after transfection of either the nonsilencing siRNA control (NS) or the vimentin siRNA (siVim4) was compared to the amount of vimentin in untransfected cells at each time point. Vimentin protein levels are reduced 97% by Day 6 with the siVim4 siRNA but not significantly altered by the nonsilencing control.

Figure 38:
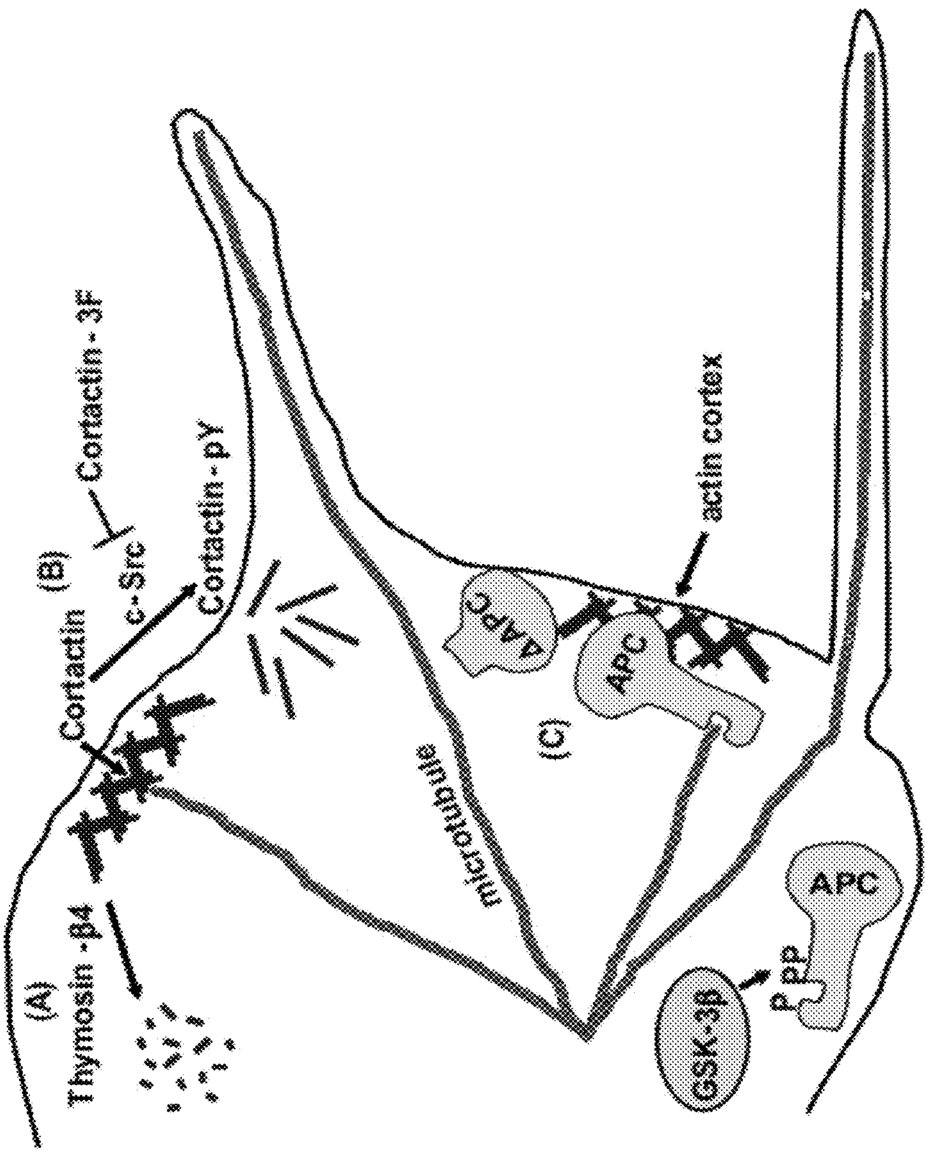
FIGS. 38A-38C provide an exemplary schematic showing interaction of microtentacles with the actin cortex. Truncation of APC in tumor cells (ΔAPC) or its phosphorylation by GSK-3b allow microtubules to extend past the actin cortex to produce microtentacles. Inhibiting Src family kinases may reduce microtentacles by increasing crosslinking in the actin cortex.

FIGS. 38A-38C show interaction of microtentacles with the actin cortex: Outward expansion of microtubules from the cell center is counteracted by contraction of the network of actin filaments that underlies the plasma membrane (actin cortex). In FIG. 38A, loss of actin polymerization in tumor through expression of proteins like Thymosin-b4 promotes microtubule protrusion extension (similar to observations with the chemical actin inhibitor, Latrunculin-A), in specific embodiments. Inhibiting the function of proteins like Thymosin-b4 serves to stabilize the actin cortex and/or prevent miocrotubule protrusions, in specific embodiments. In FIG. 38B, actin filaments are crosslinked in the cortex by a protein called cortactin. Phosphorylation of cortactin by c-Src prevents its ability to cross-link actin filaments and could loosen the actin cortex enough to promote microtubule protrusion extension. Inhibition of Src family kinases is a therapeutic target to reduce microtentacles. Abl tyrosine kinase can also phosphorylate Cortactin, and may therefore also be a therapeutic target (Boyle et al., 2007). In FIG. 38C, the tumor suppressor protein, adenomatous polyposis coli (APC) serves to capture microtubules at the actin cortex. The amino terminus of APC binds the actin cortex, and its carboxyl-terminus serves to capture microtubules. Mutations in APC that occur in tumors remove the microtubule binding domain. The resulting failure to capture microtubules at the cortex enhances microtubule protrusion extension, in specific embodiments. In addition, phosphorylation of APC by GSK-3b kinase prevents it from binding microtubules. Inhibition of GSK-3b enhances the ability of APC to capture microtubules and therefore reduce the extension of microtubule protrusions, in particular cases. Any other compound that would increase microtubule capture by APC is also useful.

Example 8

Significance of the Present Invention

Elevation of detyrosinated α-tubulin (Glu-tubulin) in detached mammary epithelial cells and its concentration in long cellular protrusions is interesting, given the apparent role of this modified form of tubulin in tumor progression. In breast tumor samples, increased levels of Glutubulin are associated with poor patient prognosis and an increased risk of cancer-related complications (Mialhe et al., 2001). Glu-tubulin is postranslationally converted back to Tyr-tubulin, by tubulin tyrosine ligase (TTL) (Erck et al., 2003). Reduced expression of TTL increases steady state levels of Glutubulin and promotes sarcoma growth (Lafanechere et al., 1998). Suppressed TTL expression is also observed in human breast tumors and neuroblastomas of poor prognosis (Lafanechere et al., 1998).

While microtubules containing Tyr-tubulin have a relatively short half-life, measured in minutes, Glu-tubulin is enriched in a more stable subset of microtubules (Webster et al., 1987). Microtubules containing Glu-tubulin can persist for hours and have been observed to remain for as long as 16 hours in nondividing cells (Webster et al., 1987). The observation that the microtubule protrusions of detached cells are enriched in Glu-tubulin is consistent with the stability and persistence of these protrusions. However, microtubules composed of Glu-tubulin are not inherently more stable in vitro (Skoufias and Wilson, 1998). Detyrosination itself is therefore not thought to directly alter the physical properties of tubulin polymers (Skoufias and Wilson, 1998), but how microtubules interact with other cellular systems. Glu-tubulin does interact preferentially with kinesin proteins (Kreitzer and Gundersen, 1999), which can transport capping proteins to the plus ends of microtubules to stabilize them (Carvalho et al., 2004). The results indicate that detachment induces an increase in the total cellular levels of Glu-tubulin and therefore may promote increased microtubule stabilization.

Interestingly, recent data from budding yeast that express only Glu-tubulin show that microtubules composed of Glu-tubulin do not attach to the actin cortex underlying the plasma membrane (Badin-Larcon et al., 2004). Detachment-induced increases in Glu-tubulin could promote plasma membrane protrusions of microtubules by preventing efficient capture at the actin cortex. The finding that depolymerization of actin with Latrunculin-A or Cytochalasin-D promotes the extension of microtubule protrusions is consistent with this hypothesis. Unlike detachment, Latrunculin-A did not increase Glutubulin levels. Therefore, our current model is that detachment increases stabilized microtubules enriched in Glu-tubulin, while decreased actin polymerization simply promotes extension of these microtubule protrusions.

Decreased levels of polymerized actin are observed in many different tumor types relative to their untransformed counterparts (Rao and Li, 2004). In addition, tumor cells often overexpress proteins that favor actin depolymerization, such as Thymosin-β4 (Cha et al., 2003; Wang et al., 2003) and Thymosin-β10 (Liu et al., 2004). Elevation of Thymosin-β4 decreases actin filaments in the cytoplasm and at the cortex (Wang et al., 2003) and is associated with metastatic progression of breast (Magdalena et al., 2000) and colon carcinoma (Wang et al., 2003). It is possible that widespread depolymerization of cellular actin by proteins such as Thymosin-β4 would enhance microtubule protrusions in a manner similar to Latrunculin-A or Cytochalasin-D, and promote metastasis. Evidence implicating decreased biophysical tension of the actin cortex with the metastatic progression of mammary epithelial cells is especially interesting support for this hypothesis (Guck et al., 2005). Extension of microtubule-rich axons at sites of actin cortical instability in neuronal cell lines also supports this proposed mechanism (Etienne-Manneville, 2004; Bradke and Dotti, 1999; Baorto et al., 1992). Depolymerization of actin with Cytochalasin-D also promotes microtubule processes in chicken erythrocytes from day 2 embryos (Winckler and Solomon, 1991), again supporting the balanced opposition of actin compression and microtubule extension. Recent experiments in our lab indicate that the frequency of microtubule protrusions varies greatly between different human breast tumor cell lines and correlates roughly with metastatic potential. Although the protrusions in MCF10A and EpH4 cells responded similarly to cytoskeletal inhibitors, the protrusions in MCF10A cells were consistently longer and thicker (FIG. 8), indicating that there are additional determinants of protrusion structure that are yet to be identified.

These extended protrusions are particularly intriguing in light of recent evidence that a microtubule-based phenomenon regulates the ability of tumor cells to arrest in the capillaries of distant tissues (Korb et al., 2004). Using in vivo video microscopy, Korb et al demonstrate that initial adherence of intravenously-injected colon carcinoma cells to the walls of liver capillaries is inhibited by microtubule depolymerization (2004). Conversely, inhibition of actin polymerization actually increases binding of the colon carcinoma cells to the capillary wall. Although the reasons for these in vivo effects are not yet clear, both results are consistent with the mechanisms underlying the protrusions that we observe in detached mammary epithelial cells. Successful metastasis of circulating tumor cells also depends on homotypic aggregation (Glinsky et al., 2003), a process that has now been shown to involve extension of microtubule protrusions between adjacent cells.

Actin polymerization inhibitors did prevent efficient extravasation of tumor cells in vivo (Korb et al., 2004). Numerous studies have established that actin-based invadopodia and podosomes are important for tumor cell migration along and through extracellular matrix (see Yamaguchi et al. (2005) for review). Unlike the protrusions that we observe, invadopodia and podosomes are strongly inhibited by actin depolymerization and unaffected by tubulin depolymerization (Bourguignon et al., 1998; Spinardi et al., 2004). On the other hand, microtubule protrusions may be necessary for detached cells to efficiently engage new attachment sites, and are actually enhanced by actin depolymerization. Therefore, in specific embodiments microtubule protrusions promote initial attachment to capillary walls and homotypic aggregation, while actin-based motility is necessary for successful extravasation. To distinguish these microtubule-based structures from actin-based invadopodia and podosomes they have been termed tubulin microtentacles (Whipple et al., 2007).

Outside of this mechanism in tumor cells, detachment of untransformed cells also rapidly decreases polymerized actin (Mooney et al., 1995). Inward tension of actin microfilaments is counteracted by outward expansion of microtubules to stabilize attached cells, in a process termed tensegrity (Ingber, 2002). Residual expansion of microtubules in detached cells, which have lost this actin-mediated compression, could initiate microtubule protrusion formation, without the requirement for any abnormal alteration of the actin cytoskeleton.

The results showing that detached mammary epithelial cell lines of both human and mouse origin produce microtubule protrusions may indicate that it is a fairly general detachment response. Epithelial cells are tasked with maintaining barrier function in the body through the formation of continuous sheets (Mullin et al., 2005), and are particularly prone to apoptotic cell death when detached from the extracellular matrix (Frisch and Francis, 1994). The dynamic protrusions that we observe could provide a selective advantage by promoting cell survival and the maintenance of the epithelial barriers through reattachment. This aggressive reattachment response would normally be controlled through rapid apoptosis in detached cells. In contrast, the persistent microtubule protrusions that are observed in apoptotically-resistant cells could enhance tumor cell attachment at distant sites. Since apoptotic resistance does not directly influence the motility of mammary epithelial cells (Pinkas et al., 2004; Martin et al., 2004), any advantage would likely arise from the extended opportunity apoptotically-resistant cells have to produce such protrusions. Nearly 90% of human solid tumors arise as carcinomas from epithelial cells [41], so such an aggressive motility response to detachment could have broad implications for metastatic spread. In specific embodiments, the data predict that these protrusions would be enhanced by genetic alterations causing reduced actin polymerization, but this is not a strict requirement and could occur without a tumor-specific mutation, in certain aspects. Importantly, the persistence of these protrusions requires only apoptotic resistance which is not sufficient to induce primary breast tumor outgrowth (Pinkas et al., 2004; Martin et al., 2004). Enhanced attachment of cells via these microtubule protrusions could therefore occur prior to significant tumor outgrowth and promote early spread of bloodborne carcinoma cells to distant tissues.

Tumor cells that remain following surgery or ablative therapy against the primary tumor can gain increased access to the bloodstream and lymphatics during the wound healing that follows these treatments (Momma et al., 1998). It is possible that bloodborne dissemination of tumor cells at this stage serves to seed distant tissues with tumor cells that will recur in the patient, even many years later. In certain aspects of the invention, inhibiting tubulin microtentacles would reduce the persistent survival of these tumor cells by reducing their attachment and forcing fragmentation of the tumor cells in narrow capillaries, for example. For this reason, an important application of microtentacle-directed therapy would be to start treating patients prior to surgery and continue therapy from then forward so that cells escaping into the body during surgery are reduced in their ability to survive dissemination to distant tissues. Reducing microtentacles could increase shredding of bloodborne tumor cells in capillaries or reduce attachment of tumor cells in lymphatic vessels, for example.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

REFERENCES

All patents and publications cited herein are hereby incorporated by reference in their entirety herein. Full citations for the references cited herein are provided in the following list.

PATENTS AND PATENT APPLICATIONS

U.S. Patent Application Publication 2005/0026946
PCT Patent Application Publication WO 84/03564

PUBLICATIONS

Argarana, C. E., Arce, C. A., Barra, H. S., and Caputto, R. (1977). In vivo incorporation of [$^{14}$C]tyrosine into the C-terminal position of the alpha subunit of tubulin. Arch Biochem Biophys 180, 264-8.

Argarana, C. E., Barra, H. S., and Caputto, R. (1978). Release of [14C]tyrosine from tubulinyl-[$^{14}$C]tyrosine by brain extract. Separation of a carboxypeptidase from tubulintyrosine ligase. Mol Cell Biochem 19, 17-21.

Badin-Larcon, A. C., Boscheron, C., Soleilhac, J. M., Piel, M., Mann, C., Denarier, E., Fourest-Lieuvin, A., Lafanechere, L., Bornens, M., and Job, D. (2004). Suppression of nuclear oscillations in *Saccharomyces cerevisiae* expressing Glu tubulin. Proc Natl Acad Sci USA 101, 5577-82.

Badin-Larcon, A. C., Boscheron, C., Soleilhac, J. M., Piel, M., Mann, C., Denarier, E., Fourest-Lieuvin, A., Lafanechere, L., Bornens, M., and Job, D. Suppression of nuclear oscillations in *Saccharomyces cerevisiae* expressing Glu tubulin. Proc Natl Acad Sci USA 2004; 101: 5577-5582.

Baorto, D. M., Mellado, W., and Shelanski, M. L. (1992). Astrocyte process growth induction by actin breakdown. J Cell Biol 117, 357-67.

Birchmeier, C., Birchmeier, W., and Brand-Saberi, B. (1996). Epithelial-mesenchymal transitions in cancer progression. Acta Anat 156, 217-26.

Birchmeier, W. and Behrens, J. Cadherin expression in carcinomas: role in the formation of cell junctions and the prevention of invasiveness. Biochim Biophys Acta 1994; 1198: 11-26.

Bourguignon, L. Y., Gunja-Smith, Z., Iida, N., Zhu, H. B., Young, L. J., Muller, W. J., and Cardiff, R. D. (1998). CD44v(3, 8-10) is involved in cytoskeleton-mediated tumor cell migration and matrix metalloproteinase (MMP-9) association in metastatic breast cancer cells. J Cell Physiol 176, 206-15.

Boyle, S, N., Michaud, G. A., Schweitzer, B., Predki, P. F., and Koleske, A. J. A Critical Role for Cortactin Phosphorylation by Abl-Family Kinases in PDGF-Induced Dorsal-Wave Formation. Curr Biol 2007.

Califano, D., Monaco, C., Santelli, G., Giuliano, A., Veronese, M. L., Berlingieri, M. T., de Franciscis, V., Berger, N., Trapasso, F., Santoro, M., Viglietto, G., and Fusco, A. Thymosin beta-10 gene overexpression correlated with the highly malignant neoplastic phenotype of transformed thyroid cells in vivo and in vitro. Cancer Res 1998; 58: 823-828.

Carvalho, P., Gupta, M. L., Jr., Hoyt, M. A., and Pellman, D. (2004). Cell cycle control of kinesin-mediated transport of Bik1 (CLIP-170) regulates microtubule stability and dynein activation. Dev Cell 6, 815-29.

Carvalho, P., Gupta, M. L., Jr., Hoyt, M. A., and Pellman, D. Cell cycle control of kinesin-mediated transport of Bik1 (CLIP-170) regulates microtubule stability and dynein activation. Dev Cell 2004; 6: 815-829.

Cha, H. J., Jeong, M. J., and Kleinman, H. K. (2003). Role of thymosin beta4 in tumor metastasis and angiogenesis. J Natl Cancer Inst 95, 1674-80.

Cha, H. J., Jeong, M. J., and Kleinman, H. K. Role of thymosin beta4 in tumor metastasis and angiogenesis. J Natl Cancer Inst 2003; 95: 1674-1680.

Chambers, A. F., Groom, A. C., and MacDonald, I. C. (2002). Dissemination and growth of cancer cells in metastatic sites. Nat Rev Cancer 2, 563-72.

Chen, C. S., Mrksich, M., Huang, S., Whitesides, G. M., and Ingber, D. E. Geometric control of cell life and death. Science 1997; 276: 1425-1428.

DeBonis, S., Skoufias, D. A., Lebeau, L., Lopez, R., Robin, G., Margolis, R. L., Wade, R. H., Kozielski, F. In vitro screening for inhibitors of the human mitotic kinesin Eg5 with antimitotic and antitumor activities. Mol. Cancer. Therap. 2004; 3(9): 1079-1090.

Dokken, B. B., Sloniger, B. A., and Henriksen, E. J. Acute selective glycogen synthase kinase-3 inhibition enhances insulin signaling in prediabetic insulin-resistant rat skeletal muscle. Am J Physiol Endocrinol Metab 2005; 288: E1188-E1194.

Erck, C., MacLeod, R. A., and Wehland, J. (2003). Cloning and genomic organization of the TTL gene on mouse chromosome 2 and human chromosome 2q13. Cytogenet Genome Res 101, 47-53.

Erck, C., MacLeod, R. A., and Wehland, J. Cloning and genomic organization of the TTL gene on mouse chromosome 2 and human chromosome 2q13. Cytogenet Genome Res 2003; 101: 47-53.

Etienne-Manneville, S. (2004). Actin and microtubules in cell motility: which one is in control? Traffic 5, 470-7. 33. Bradke, F., and Dotti, C. G. (1999). The role of local actin instability in axon formation. Science 283, 1931-4.

Frisch, S. M. and Francis, H. Disruption of epithelial cell-matrix interactions induces apoptosis. J Cell Biol 1994; 124: 619-626.

Frisch, S. M., and Francis, H. (1994). Disruption of epithelial cell-matrix interactions induces apoptosis. J Cell Biol 124, 619-26.

Ghosh, J. C. and Altieri, D. C. Activation of p53-dependent apoptosis by acute ablation of glycogen synthase kinase-3b in colorectal cancer cells. Clin Cancer Res 2005; 11(12): 4580-4588.

Glinsky, V. V., Glinsky, G. V., Glinskii, O. V., Huxley, V. H., Turk, J. R., Mossine, V. V., Deutscher, S. L., Pienta, K. J., and Quinn, T. P. (2003). Intravascular metastatic cancer cell homotypic aggregation at the sites of primary attachment to the endothelium. Cancer Res 63, 3805-11.

Guck, J., Schinkinger, S., Lincoln, B., Wottawah, F., Ebert, S., Romeyke, M., Lenz, D., Erickson, H. M., Ananthakrishnan, R., Mitchell, D., Kas, J., Ulvick, S., and Bilby, C. (2005).

Guck, J., Schinkinger, S., Lincoln, B., Wottawah, F., Ebert, S., Romeyke, M., Lenz, D., Erickson, H. M., Ananthakrishnan, R., Mitchell, D., Kas, J., Ulvick, S., and Bilby, C. Optical deformability as an inherent cell marker for testing malignant transformation and metastatic competence. Biophys J 2005; 88: 3689-3698.

Infante, A. S., Stein, M. S., Zhai, Y., Borisy, G. G., and Gundersen, G. G. Detyrosinated (Glu) microtubules are stabilized by an ATP-sensitive plus-end cap. J. Cell Sci. 2000; 113:3907-3919.

Ingber, D. E. (2002). Cancer as a disease of epithelial-mesenchymal interactions and extracellular matrix regulation. Differentiation 70, 547-60.

Ingber, D. E. Cancer as a disease of epithelial-mesenchymal interactions and extracellular matrix regulation. Differentiation 2002; 70: 547-560.

Janmey, P. A., Euteneuer, U., Traub, P., and Schliwa, M. Viscoelastic properties of vimentin compared with other filamentous biopolymer networks. J Cell Biol 1991; 113: 155-160.

Kato, C., Miyazaki, K., Nakagawa, A., Ohira, M., Nakamura, Y., Ozaki, T., Imai, T., and Nakagawara, A. Low expression of human tubulin tyrosine ligase and suppressed tubulin tyrosination/detyrosination cycle are associated with impaired neuronal differentiation in neuroblastomas with poor prognosis. Int J Cancer 2004; 112: 365-375.

Kaufmann, M., Diebold, J., Arnholdt, H., Muller, P., Bischoff, J., Harich, D., Schlimok, G., Riethmuller, G., Eils, R., and Klein, C. A. (2003). From latent disseminated cells to overt metastasis: genetic analysis of systemic breast cancer progression. Proc Natl Acad Sci USA 100, 7737-42.

Kobayashi, T., Okada, F., Fujii, N., Tomita, N., Ito, S., Tazawa, H., Aoyama, T., Choi, S. K., Shibata, T., Fujita, H., and Hosokawa, M. Thymosin-beta4 regulates motility and metastasis of malignant mouse fibrosarcoma cells. Am J Pathol 2002; 160: 869-882.

Korb, T., Schluter, K., Enns, A., Spiegel, H. U., Senninger, N., Nicolson, G. L., and Haier, J. (2004). Integrity of actin fibers and microtubules influences metastatic tumor cell adhesion. Exp Cell Res 299, 236-47.

Kreitzer, G., Liao, G., and Gundersen, G. G. Detyrosination of tubulin regulates the interaction of intermediate filaments with microtubules in vivo via a kinesin-dependent mechanism. Mol Biol Cell 1999; 10: 1105-1118.

Lafanechere, L., Courtay-Cahen, C., Kawakami, T., Jacrot, M., Rudiger, M., Wehland, J., Job, D., and Margolis, R. L. (1998). Suppression of tubulin tyrosine ligase during tumor growth. J Cell Sci 111 (Pt 2), 171-81.

Liao, G. and Gundersen, G. G. Kinesin is a candidate for cross-bridging microtubules and intermediate filaments. Selective binding of kinesin to detyrosinated tubulin and vimentin. J Biol Chem 1998; 273: 9797-9803.

Liu, C. R., Ma, C. S., Ning, J. Y., You, J. F., Liao, S. L., and Zheng, J. (2004). Differential thymosin beta 10 expression levels and actin filament organization in tumor cell lines with different metastatic potential. Chin Med J (Engl) 117, 213-8.

Liu, G. Y., Hung, Y. C., Hsu, P. C., Liao, Y. F., Chang, W. H., Tsay, G. J., and Hung, H. C. Ornithine decarboxylase prevents tumor necrosis factor alpha-induced apoptosis by decreasing intracellular reactive oxygen species. Apoptosis 2005; 10: 569-581.

Lopez-Barahona, M., Fialka, I., Gonzalez-Sancho, J. M., Asuncion, M., Gonzalez, M., Iglesias, T., Bernal, J., Beug, H., and Munoz, A. Thyroid hormone regulates stromelysin expression, protease secretion and the morphogenetic potential of normal polarized mammary epithelial cells. Embo J 1995; 14: 1145-1155.

MacAulay, K., Hajduch, E., Blair, A. S., Coghlan, M. P., Smith, S. A., Hundal, H. S. Use of lithium and SB-415286 to explore the role of glycogen synthase kinase-3 in the regulation of glucose transport and glycogen synthase. Eur. J. Biochem. 2003; 270:3829-3838.

Magdalena, C., Dominguez, F., Loidi, L., and Puente, J. L. (2000). Tumour prothymosin alpha content, a potential prognostic marker for primary breast cancer. Br J Cancer 82, 584-90.

Maniotis, A. J., Chen, C. S., and Ingber, D. E. Demonstration of mechanical connections between integrins, cytoskeletal filaments, and nucleoplasm that stabilize nuclear structure. Proc Natl Acad Sci USA 1997; 94: 849-854.

Martin, S. S, and Leder, P. Human mcf10a mammary epithelial cells undergo apoptosis following actin depolymerization that is independent of attachment and rescued by bcl-2. Mol Cell Biol 2001; 21: 6529-6536.

Martin, S. S., Ridgeway, A. G., Pinkas, J., Lu, Y., Reginato, M. J., Koh, E. Y., Michelman, M., Daley, G. Q., Brugge, J. S., and Leder, P. (2004). A cytoskeleton-based functional 20 genetic screen identifies Bcl-xL as an enhancer of metastasis, but not primary tumor growth. Oncogene 23, 4641-5.

Mialhe, A., Lafanechere, L., Treilleux, I., Peloux, N., Dumontet, C., Bremond, A., Panh, M. H., Payan, R., Wehland, J., Margolis, R. L., and Job, D. (2001). Tubulin detyrosination is a frequent occurrence in breast cancers of poor prognosis. Cancer Res 61, 5024-7.

Momma T, Hamblin M R, Wu H C, Hasan T., Photodynamic therapy of orthotopic prostate cancer with benzoporphyrin derivative: local control and distant metastasis. Cancer Res. 1998 Dec. 1; 58(23):5425-31.

Mooney, D. J., Langer, R., and Ingber, D. E. (1995). Cytoskeletal filament assembly and the control of cell spreading and function by extracellular matrix. J Cell Sci 108, 2311-20.

Mullin, J. M., Agostino, N., Rendon-Huerta, E., and Thornton, J. J. (2005). Keynote review epithelial and endothelial barriers in human disease. Drug Discov Today 10, 395-408.

Naumov, G. N., MacDonald, I. C., Chambers, A. F., and Groom, A. C. (2001). Solitary cancer cells as a possible source of tumour dormancy? Semin Cancer Biol 11, 271-6.

Naumov, G. N., MacDonald, I. C., Weinmeister, P. M., Kerkvliet, N., Nadkarni, K. V., Nikiforov, M. A., Hagen, K., Ossovskaya, V. S., Connor, T. M., Lowe, S. W., Deichman, G. I., and Gudkov, A. V. (1996). p53 modulation of anchorage independent growth and experimental metastasis. Oncogene 13, 1709-19.

Nikiforov, M. A., Kwek, S. S., Mehta, R., Artwohl, J. E., Lowe, S. W., Gupta, T. D., Deichman, G. I., and Gudkov, A. V. (1997). Suppression of apoptosis by bcl-2 does not prevent p53-mediated control of experimental metastasis and anchorage dependence. Oncogene 15, 3007-12.

Pinkas, J., Martin, S. S., and Leder, P. (2004). Bcl-2-mediated cell survival promotes metastasis of EpH4 betaMEKDD mammary epithelial cells. Mol Cancer Res 2, 551-6.

Rao, J. and Li, N. Microfilament actin remodeling as a potential target for cancer drug development. Curr Cancer Drug Targets 2004; 4: 345-354.

Re, F., Zanetti, A., Sironi, M., Polentarutti, N., Lanfrancone, L., Dejana, E., and Colotta, F. Inhibition of anchorage-dependent cell spreading triggers apoptosis in cultured human endothelial cells. J Cell Biol 1994; 127: 537-546.

Reddig, P. J. and Juliano, R. L. Clinging to life: cell to matrix adhesion and cell survival. Cancer Metastasis Rev 2005; 24: 425-439.

Reed, J. C. (2003). Apoptosis-targeted therapies for cancer. Cancer Cell 3, 17-22.

Reed, J. C. Dysregulation of apoptosis in cancer. J Clin Oncol 1999; 17: 2941-2953.

Rodriguez de la Vega, M., Sevilla, R. G., Hermoso, A., Lorenzo, J., Tanco, S., Diez, A., Fricker, L. D., Bautista, J. M., and Aviles, F. X. Nna1-like proteins are active metallocarboxypeptidases of a new and diverse M14 subfamily. The FASEB Journal 2007; 20: 1-15.

Schmidt-Kittler, O., Ragg, T., Daskalakis, A., Granzow, M., Ahr, A., Blankenstein, T. J., Kaufmann, M., Diebold, J., Arnholdt, H., Muller, P., Bischoff, J., Harich, D., Schlimok, G., Riethmuller, G., Eils, R., and Klein, C. A. From latent disseminated cells to overt metastasis: genetic analysis of systemic breast cancer progression. Proc Natl Acad Sci USA 2003; 100: 7737-7742.

Skoufias, D. A., and Wilson, L. (1998). Assembly and colchicine binding characteristics of tubulin with maximally tyrosinated and detyrosinated alpha-tubulins. Arch Biochem Biophys 351, 115-22.

Spinardi, L., Rietdorf, J., Nitsch, L., Bono, M., Tacchetti, C., Way, M., and Marchisio, P. C. (2004). A dynamic podosome-like structure of epithelial cells. Exp Cell Res 295, 360-74.

Townson, J. L., Naumov, G. N., and Chambers, A. F. The role of apoptosis in tumor progression and metastasis. Curr Mol Med 2003; 3: 631-642.

Valentijn, A. J., Zouq, N., and Gilmore, A. P. Anoikis. Biochem Soc Trans 2004; 32: 421-425.

Wang, N., Naruse, K., Stamenovic, D., Fredberg, J. J., Mijailovich, S. M., Tolic-Norrelykke, I. M., Polte, T., Mannix, R., and Ingber, D. E. Mechanical behavior in living cells consistent with the tensegrity model. Proc Natl Acad Sci USA 2001; 98: 7765-7770.

Wang, W. S., Chen, P. M., Hsiao, H. L., Ju, S. Y., and Su, Y. (2003). Overexpression of the thymosin beta-4 gene is associated with malignant progression of SW480 colon cancer cells. Oncogene 22, 3297-306.

Wang, W. S., Chen, P. M., Hsiao, H. L., Wang, H. S., Liang, W. Y., and Su, Y. Overexpression of the thymosin beta-4 gene is associated with increased invasion of SW480 colon carcinoma cells and the distant metastasis of human colorectal carcinoma. Oncogene 2004; 23: 6666-6671.

Webster, D. R., Gundersen, G. G., Bulinski, J. C., and Borisy, G. G. (1987). Differential turnover of tyrosinated and detyrosinated microtubules. Proc Natl Acad Sci USA 84, 9040-4.

Wen, Y., Eng, C. H., Schmoranzer, J., Cabrera-Poch, N., Morris, E. J., Chen, M., Wallar, B. J., Alberts, A. S., and Gundersen, G. G. EB1 and APC bind to mDia to stabilize microtubules downstream of Rho and promote cell migration. Nat Cell Biol 2004; 6: 820-830.

Weterman, M. A., van Muijen, G. N., Ruiter, D. J., and Bloemers, H. P. Thymosin beta-10 expression in melanoma cell lines and melanocytic lesions: a new progression marker for human cutaneous melanoma. Int J Cancer 1993; 53: 278-284.

Wilson, S. M., Morris, V. L., Groom, A. C., and Chambers, A. F. (2002). Persistence of solitary mammary carcinoma cells in a secondary site: a possible contributor to dormancy. Cancer Res 62, 2162-8.

Winckler, B., and Solomon, F. (1991). A role for microtubule bundles in the morphogenesis of chicken erythrocytes. Proc Natl Acad Sci USA 88, 6033-7.

Yamaguchi, H., Wyckoff, J., and Condeelis, J. Cell migration in tumors. Curr Opin Cell Biol 2005; 17: 559-564.

Yamamoto, T., Gotoh, M., Kitajima, M., and Hirohashi, S. Thymosin beta-4 expression is correlated with metastatic capacity of colorectal carcinomas. Biochem Biophys Res Commun 1993; 193: 706-710.

Yoon, S. O., Shin, S., and Mercurio, A. M. Hypoxia stimulates carcinoma invasion by stabilizing microtubules and promoting the Rab11 trafficking of the alpha6beta4 integrin. Cancer Res 2005; 65: 2761-2769.

What is claimed is:

1. A method of inhibiting one or more microtubule protrusions from a cancer cell in an individual, comprising the steps of:

(a) obtaining a blood sample from the individual, (b) detecting at least one cancer cell in the blood sample, (c) detecting one or more microtubule protrusions on the cancer cell, and (d) delivering to the individual a therapeutically effective amount of an agent that inhibits tubulin, vimentin, kinesin, or GSK-3β in the individual, thereby inhibiting the one or more microtubule protrusions from a cancer cell in the individual.

2. The method of claim 1, wherein said agent inhibits production of said protrusion, inhibits extension of said protrusion, inhibits activity of said protrusion, or promotes degradation of said protrusion.

3. The method of claim 1, wherein the agent inhibits tubulin.

4. The method of claim 1, wherein the tubulin is further defined as detyrosinated Glu-tubulin.

5. The method of claim 3, wherein the agent that inhibits tubulin inhibits production of Glu-tubulin and/or increases production of Tyr-tubulin.

6. The method of claim 5, wherein the agent inhibits production of Glu-tubulin by inhibiting a carboxypeptidase that produces Glu-tubulin from Tyr-tubulin.

7. The method of claim 6, wherein the agent comprises an siRNA.

8. The method of claim 7, wherein the agent comprises an siRNA for hAGBL3.

9. The method of claim 1, wherein the cancer cell is further defined as a detached cancer cell.

10. The method of claim 1, wherein the cancer cell is from breast, prostate, pancreatic, colon, lung, brain, liver, ovarian, testicular, cervical, gall bladder, spleen, bone marrow, head and neck, thyroid, stomach, kidney, or bone cancer.

11. The method of claim 1, wherein the cancer cell is from breast cancer.

12. The method of claim 1, wherein the individual has metastatic cancer, is suspected of having metastatic cancer, or is susceptible to metastatic cancer.

13. The method of claim 1, further defined as targeting microtubule protrusions prior to, during and/or after surgery to reduce the ability of cancer cells that escape the primary site during surgery to colonize distant tissues.

14. The method of claim 13, wherein the cancer cell is further defined as a detached cancer cell.

15. A method of preventing metastasis of cancer in an individual, comprising the steps of:

(a) obtaining a blood sample from the individual, (b) detecting at least one cancer cell in the blood sample, (c) detecting one or more microtubule protrusions on the cancer cell, and (d) administering to the individual a therapeutically effective amount of one or more agents that inhibit tubulin, vimentin, kinesin, or GSK-3β in at least one cancer cell in the individual, thereby preventing metastasis of cancer in the individual.

16. A method of reducing the risk of a tumor cell from a first organ in an individual to establish a malignancy in a second organ in the individual, comprising:

(a) obtaining a blood sample from the individual, (b) detecting at least one tumor cell in the blood sample, (c) detecting one or more microtubule protrusions on the tumor cell, and (d) delivering a therapeutically effective amount of an agent that inhibits tubulin, vimentin, kinesin, or GSK-3β in the tumor cell, thereby reducing the risk of a tumor cell from a first organ in an individual to establish a malignancy in a second organ in the individual.

17. The method of claim 16, wherein the tumor cell releases from the tumor upon surgery in the individual.

18. The method of claim 17, further defined as the tumor cell releasing from a primary tumor mass upon excision of at least part of the primary tumor mass from the individual.

19. The method of claim 16, further defined as the tumor cell releasing from the primary tumor mass during removal of the primary tumor mass from the individual and/or during therapy for the primary tumor mass for the individual.

20. The method of claim 16, further defined as the tumor cell that remains in the body of the individual during removal of a primary tumor mass from the individual and/or during therapy for the primary tumor mass for the individual.

21. The method of claim 17, wherein the agent is delivered to the individual before, during, and/or after the surgery.

* * * * *

UNITED STATES PATENT AND TRADEMARK OFFICE

CERTIFICATE OF CORRECTION

PATENT NO. : 8,193,238 B2
APPLICATION NO. : 12/282014
DATED : June 5, 2012
INVENTOR(S) : Stuart Martin et al.

It is certified that error appears in the above-identified patent and that said Letters Patent is hereby corrected as shown below:

Column 1, lines 14-18, delete paragraph and insert:

--This invention was made with government support under Grant Number CA096555 awarded by the National Institutes of Health and Grant Number W81XWH-05-1-0423 awarded by the US Army. The government has certain rights in the invention.--

Signed and Sealed this
Fourteenth Day of August, 2012

David J. Kappos
*Director of the United States Patent and Trademark Office*